United States Patent
Wu et al.

(10) Patent No.: US 10,703,757 B2
(45) Date of Patent: Jul. 7, 2020

(54) COMPOUNDS AND METHODS FOR CDK8 MODULATION AND INDICATIONS THEREFOR

(71) Applicant: Plexxikon Inc., Berkeley, CA (US)

(72) Inventors: Guoxian Wu, Palo Alto, CA (US); Aaron Albers, Berkeley, CA (US); John Buell, San Francisco, CA (US); Elizabeth A. Burton, Berkeley, CA (US); Phuongly Pham, San Francisco, CA (US); Hannah Powers, Berkeley, CA (US); Songyuan Shi, Fremont, CA (US); Wayne Spevak, Berkeley, CA (US); Jeffrey Wu, Berkeley, CA (US); Jiazhong Zhang, Foster City, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/851,639

(22) Filed: Dec. 21, 2017

(65) Prior Publication Data
US 2018/0215763 A1    Aug. 2, 2018

Related U.S. Application Data

(60) Provisional application No. 62/438,682, filed on Dec. 23, 2016.

(51) Int. Cl.
| | |
|---|---|
| C07D 487/04 | (2006.01) |
| A61K 31/437 | (2006.01) |
| C07D 471/04 | (2006.01) |
| A61K 31/498 | (2006.01) |
| A61P 35/02 | (2006.01) |
| A61K 31/444 | (2006.01) |
| A61K 31/4545 | (2006.01) |
| A61K 31/46 | (2006.01) |
| A61K 31/4709 | (2006.01) |
| A61K 31/4985 | (2006.01) |
| A61K 31/506 | (2006.01) |
| A61K 31/5377 | (2006.01) |
| A61K 31/541 | (2006.01) |
| A61K 45/06 | (2006.01) |
| C07D 519/00 | (2006.01) |

(52) U.S. Cl.
CPC .......... *C07D 487/04* (2013.01); *A61K 31/437* (2013.01); *A61K 31/444* (2013.01); *A61K 31/4545* (2013.01); *A61K 31/46* (2013.01); *A61K 31/4709* (2013.01); *A61K 31/498* (2013.01); *A61K 31/4985* (2013.01); *A61K 31/506* (2013.01); *A61K 31/5377* (2013.01); *A61K 31/541* (2013.01); *A61K 45/06* (2013.01); *A61P 35/02* (2018.01); *C07D 471/04* (2013.01); *C07D 519/00* (2013.01)

(58) Field of Classification Search
CPC ... C07D 487/04; C07D 471/04; C07D 519/00
See application file for complete search history.

(56) References Cited

U.S. PATENT DOCUMENTS

| | | | |
|---|---|---|---|
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West et al. | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,759,475 B2 | 7/2010 | West | |
| 7,846,941 B2 | 12/2010 | Zhang et al. | |
| 7,863,288 B2 | 1/2011 | Ibrahim et al. | |
| 7,863,289 B2 | 1/2011 | Spevak et al. | |
| 7,872,018 B2 | 1/2011 | Ibrahim et al. | |
| 7,893,075 B2 | 2/2011 | Zhang et al. | |
| 7,947,708 B2 | 5/2011 | Ibrahim et al. | |

(Continued)

FOREIGN PATENT DOCUMENTS

| | | |
|---|---|---|
| EP | 1813613 | 8/2007 |
| WO | WO 2007/002325 | 1/2007 |

(Continued)

OTHER PUBLICATIONS

U.S. Appl. No. 16/058,945, filed Aug. 8, 2018, Wu.

(Continued)

*Primary Examiner* — Joseph R Kosack
(74) *Attorney, Agent, or Firm* — Sheppard Mullin Richter & Hampton LLP

(57) ABSTRACT

Disclosed are compounds of Formula I:

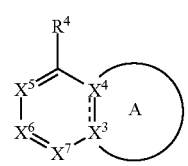

or a pharmaceutically acceptable salt, a solvate, a tautomer, an isomer or a deuterated analog thereof, wherein $R^4$, $X^3$, $X^4$, $X^5$, $X^6$, $X^7$ and Ring A are as described in any of the embodiments described in this disclosure; compositions thereof; and uses thereof.

38 Claims, No Drawings

(56) References Cited

U.S. PATENT DOCUMENTS

| | | |
|---|---|---|
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,676,748 B2 | 6/2017 | Wu et al. |
| 9,682,981 B2 | 6/2017 | Zhang et al. |
| 9,695,169 B2 | 7/2017 | Ibrahim |
| 9,718,847 B2 | 8/2017 | Zhang et al. |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 1,016,075 A1 | 12/2018 | Lin et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128390 A1 | 5/2014 | Lin et al. |
| 2014/0234254 A1 | 8/2014 | Xi |
| 2014/0303121 A1 | 10/2014 | Zhang et al. |
| 2014/0303187 A1 | 10/2014 | Wu et al. |
| 2015/0290205 A1 | 10/2015 | Ibrahim et al. |
| 2016/0176865 A1 | 6/2016 | Ibrahim et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2017/0362231 A1 | 12/2017 | Ibrahim et al. |
| 2018/0002332 A1 | 1/2018 | Ibrahim et al. |
| 2018/0030051 A1 | 2/2018 | Ibrahim et al. |
| 2018/0055828 A1 | 3/2018 | Bollag |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim |
| 2018/0111930 A1 | 4/2018 | Desai |
| 2018/0215763 A1 | 8/2018 | Wu et al. |
| 2018/0265508 A1 | 9/2018 | Lin |
| 2018/0305358 A1 | 10/2018 | Ibrahim et al. |
| 2018/0327403 A1 | 11/2018 | Ibrahim et al. |
| 2018/0354946 A1 | 12/2018 | Zhang et al. |
| 2019/0031654 A1 | 1/2019 | Ibrahim et al. |

FOREIGN PATENT DOCUMENTS

| | | |
|---|---|---|
| WO | WO 2007/013896 | 2/2007 |
| WO | WO 2008/129152 | 10/2008 |
| WO | WO 2010/003133 | 1/2010 |
| WO | WO 2010/111527 | 9/2010 |
| WO | WO 2010/129467 | 11/2010 |
| WO | WO 2012/109075 | 8/2012 |
| WO | WO 2014/093383 | 6/2014 |
| WO | WO 2015/050505 | 4/2015 |
| WO | WO 2015/100117 | 7/2015 |

OTHER PUBLICATIONS

U.S. Appl. No. 16/109,199, filed Aug. 22, 2018, Wu.
U.S. Appl. No. 16/123,612, filed Sep. 6, 2018, Desai et al.
U.S. Appl. No. 16/148,244, filed Oct. 1, 2018, Zhang et al.
U.S. Appl. No. 16/158,107, filed Oct. 11, 2018, Ibrahim et al.
U.S. Appl. No. 16/172,573, filed Oct. 26, 2018, Rezaei et al.
U.S. Appl. No. 16/219,730, filed Dec. 13, 2018, Ibrahim et al.
Collins, et al. The synthesis of 3-pyrazinyl-imidazo[1,2-a]pyridines from a vinyl ether. Tetrahedron Letters. (2010) 51:3528-3530.
International Search Report and Written Opinion dated Sep. 4, 2018 for PCT/US2017/068045. 26 pages.
Johnson, et al. Sequential C3 and C5 Direct C—H Arylation of Imidazo[1,2-a]pyrazines with (Hetero)aryl Bromides. Eur. J. Org. Chem. 2014, 1589-1593.
Katritzky, et al. Regiospecific synthesis of 3-substituted imidazo[1,2-a]pyridines, imidazo[1,2-a]pyrimidines, and imidazo[1,2-c]pyrimidine. J Org Chem. Jun. 13, 2003;68(12):4935-7.
U.S. Appl. No. 16/358,608, filed Mar. 19, 2019, Zhang et al.
U.S. Appl. No. 16/400,801, filed May 1, 2019, Ibrahim et al.
U.S. Appl. No. 16/441,610, filed Jun. 14, 2019, Ibrahim et al.
U.S. Appl. No. 16/510,617, filed Jul. 12, 2019, Ibrahim et al.
U.S. Appl. No. 16/510,764, filed Jul. 12, 2019, Ibrahim et al.
U.S. Appl. No. 16/510,757, filed Jul. 12, 2019, Ibrahim et al.
U.S. Appl. No. 16/563,656, filed Sep. 6, 2019, Zhang et al.
U.S. Appl. No. 16/687,015, filed Nov. 18, 2019, Zhang et al.

(56) References Cited

OTHER PUBLICATIONS

U.S. Appl. No. 16/684,198, filed Nov. 14, 2019, Desai et al.
U.S. Appl. No. 16/706,497, filed Dec. 6, 2019, Ibrahim et al.

COMPOUNDS AND METHODS FOR CDK8 MODULATION AND INDICATIONS THEREFOR

CROSS-REFERENCE TO RELATED APPLICATIONS

This application claims the benefit under 35 U.S.C. § 119(e) of U.S. Provisional Application 62/438,682, filed Dec. 23, 2016, which is hereby incorporated by reference in its entirety.

FIELD

The present invention relates to organic compounds useful for therapy in a mammals, and in particular for modulating CDK8 or Cyclin C for various diseases associated with the overexpression of CDK8 or Cyclin C.

BACKGROUND

CDK8 is a part of the 30+ protein Mediator complex, that bridges specific transcription factors with the general transcription machinery & RNA pol II. The CDK8 module consists of 4 proteins: CDK8, CyclinC, MED12, and MED13. MED12 and CyclinC are required for CDK8 kinase activity; MED13 is required to recruit the module to the small Mediator complex. The role of CDK8 on transcription is context-specific, depending on the specific biological context and the identity of the transcription factors with which it interacts. The role of CDK8 on transcription is context-specific, depending on the specific biological context and the identity of the transcription factors with which it interacts.

CDK8 expression is upregulated in tumors. CDK8 regulates β-catenin signaling, upregulated in many tumor types, including, but not limited to Colorectal (47-76%), gastric, pancreatic, and mH2A-deficient melanoma. CDK8 overexpression also has correlated with poor outcomes in colon-specific cancer, gastric cancer, breast cancer and, ovarian cancer. Correlation in CDK8 expression and disease states such as colon cancer, gastric cancer, colorectal cancer, ovarian cancer and melanoma. Dale et al. Nature Chemical Biology (Oct. 26, 2016), DOI: 10.1038/NCHEMBIO. 1952. CDK8 expression is also observed in breast cancer. Mallinger et al., Journal of Medicinal Chemistry (1980) DOI: 10.1021/acs.jmedchem. 5b01685.

It was found that CDK8 inhibitors were active against AML cell characterized by significantly higher levels of STAT5 S726 and STAT1 S727, and that this founding provides a rationale for the clinical development of CDK8 inhibitors as a personal therapeutic approach in AML. Rzymski et al. Oncotarget. 2017 May 16; 8(20): 33779-33795.

CDK8 has been identified as a negative regulator of IL-10 production during innate immune activation that suggests CDK8 inhibitors may warrant consideration as therapeutic agents for inflammatory disorders. Johannessen et al. Published Online: 14 Aug. 2017; DOI: 10.1038/NCHEMBIO.2458 Small-molecule studies identify CDK8 as a regulator of IL-10 in myeloid cells.

Aberrant expression of CDK8 is also associated with the regulation of malignant phenotype and with poor prognosis in human laryngeal squamous cell carcinoma. MingHua Li et al. Eur Arch Otorhinolaryngol (Feb. 20, 2017).

CDK8 also mediates immune surveillance of tumors. CDK8 directly phosphorylates serine 727 on STAT1 downstream of cytokine (e.g. IFNg) stimulation, constitutive in natural killer (NK cells). Inhibition of STAT1 phosphorylation in NK cells results in increased NK cell cytotoxicity towards tumor cells in vitro and in vivo, and thus, CDK8 may be helpful for the treatment of cancers associated with increased NK cell cytotoxicity, including, but not limited to lung cancer and lung cancer metastasis, breast cancer and breast cancer metastasis, and leukemia. CDK8 may also increase the effectiveness of chemotherapeutic agents.

Dysregulation of CDKs has been linked to pathological events and both proliferative and non-proliferative disease, including cancers, Alzheimer's disease (AD), Parkinson's disease, Stroke/ischemia, pain, traumatic brain injury, kidney disease, inflammation pathologies, type 2 diabetes, and various viral infections (HSV, HCMV, HPV, HIV).

Currently, there are no FDA approved CDK8 inhibitors. Accordingly, there is a substantial unmet need for novel CDK8 inhibitors.

SUMMARY

One embodiment of the disclosure relates to novel compounds, as described in any of the embodiments herein, or a pharmaceutically acceptable salt, a solvate, a tautomer, an isomer or a deuterated analog thereof, wherein these novel compounds can modulate CDK8.

Another embodiment of this disclosure relates to a compound of Formula I:

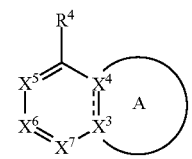

wherein $R^4$, $X^3$, $X^4$, $X^5$, $X^6$, $X^7$ and Ring A are as described in any of the embodiments described in this disclosure.

Other embodiments and sub-embodiments of Formula I are further described herein in this disclosure.

Another embodiment of the disclosure relates to a pharmaceutical composition comprising a compound according to Formula I or any embodiment and sub-embodiment of Formula I described herein in this disclosure, or a pharmaceutically acceptable salt, a solvate, a tautomer, an isomer or a deuterated analog of any of these compounds, and a pharmaceutically acceptable carrier or excipient.

Another embodiment of the disclosure relates to a pharmaceutical composition comprising a compound according to Formula I, or any embodiment of Formula I described herein in this disclosure, or a pharmaceutically acceptable salt, a solvate, a tautomer, an isomer or a deuterated analog of any of these compounds, and another therapeutic agent.

Another embodiment of this disclosure relates to a method for treating a subject with a disease or condition mediated by CDK8, said method comprising administering to the subject an effective amount of a compound according to Formula I, or any embodiment of Formula I described in this disclosure, or a pharmaceutically acceptable salt, a solvate, a tautomer, an isomer or a deuterated analog of any of these compounds, or a pharmaceutical composition of any of the compounds as described in this disclosure, wherein the disease or condition express aberrantly or otherwise CDK8, or activating mutations or translocations of any of the foregoing. In other embodiments of this embodiment, the disease or condition can be any one or more of the disease or conditions described in this disclosure. In other embodiments, the disease or condition is brain cancer, lung cancer, colon cancer, epidermoid cancel, squamous cell cancer, bladder cancer, gastric cancer, pancreatic cancer, breast cancer, head cancer, neck cancer, renal cancer, kidney cancer, liver cancer, ovarian cancer, prostate cancer, colorectal cancer, uterine cancer, rectal cancer, oesophageal cancer, testicular cancer, thyroid cancer, melanoma, uveal melanoma, acute myelogenous, leukemia, acute myeloid leukemia (AML), multiple myeloma, chronic myelogneous leukemia, myeloid cell leukemia, glioma, Kaposi's sarcoma, human laryngeal squamous cell carcinoma, inflammation, Alzheimer's disease, Parkinson's disease, dementia, amyloidosis, atherosclerosis, stroke/ischemia, pain, traumatic brain injury, kidney disease, inflammation pathologies, type 2 diabetes, or a viral infection. In other embodiments, the disease or condition is brain cancer, lung cancer, colon cancer, epidermoid cancel, squamous cell cancer, bladder cancer, gastric cancer, pancreatic cancer, breast cancer, head cancer, neck cancer, renal cancer, kidney cancer, liver cancer, ovarian cancer, prostate cancer, colorectal cancer, uterine cancer, rectal cancer, oesophageal cancer, testicular cancer, thyroid cancer, melanoma, acute myelogenous, leukemia, multiple myeloma, chronic myelogneous leukemia, myeloid cell leukemia, glioma, Kaposi's sarcoma, Alzheimer's disease, Parkinson's disease, dementia, amyloidosis, atherosclerosis, stroke/ischemia, pain, traumatic brain injury, kidney disease, inflammation pathologies, type 2 diabetes, or a viral infection.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I(a) of this disclosure, and all the embodiments thereof, are to be read from left to right, wherein the right hand side is directly attached to the parent structure as defined. However, if a point of attachment is shown on the left hand side of the chemical moiety (e.g., -alkyloxy-($C_1$-$C_{25}$)alkyl), then the left hand side of this chemical moiety is attached directly to the parent moiety as defined. It is assumed that when considering generic descriptions of compounds of the described herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e. $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —CH$_2$—, ethylene —CH$_2$CH$_2$—, propylene —CH$_2$CH$_2$CH$_2$—, and isopropylene —CH(CH$_3$)CH$_2$—, —CH$_2$CH(CH$_3$)—, —CH$_2$—(CH$_2$)$_2$CH$_2$—, —CH$_2$—CH(CH$_3$)CH$_2$—, —CH$_2$—C(CH$_3$)$_2$—CH$_2$—CH$_2$CH(CH$_3$)—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkenyl" refers to a linear monovalent hydrocarbon radical or a branched monovalent hydrocarbon radical having the number of carbon atoms indicated in the prefix and containing at least one double bond. For example, $C_2$-$C_6$ alkenyl is meant to include ethenyl, propenyl, and the like.

The term "alkenylene" refers to a linear monovalent hydrocarbon radical or a branched divalent hydrocarbon radical containing at least one double bond and having the number of carbon atoms indicated in the prefix.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkynylene" refers to a linear monovalent hydrocarbon radical or a branched monovalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers.

"Alkoxy" or "alkoxyl" refers to a —O-alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

The term "alkoxyalkyl" refers to an alkyl group substituted with one or more, such as one to three alkoxy groups.

"Alkylamino" refers to a —NH-alkyl group, where alkyl is as defined herein. Exemplary alkylamino groups include $CH_3NH-$, ethylamino, and the like. The term "aminoalkyl" refers to -alkylene-$NH_2$.

"Dialkylamino" refers to a —N(alkyl)(alkyl) group, where each alkyl is independently as defined herein. Exemplary dialkylamino groups include dimethylamino, diethylamino, ethylmethylamino, and the like. "Cycloalkylamino" denotes the group —$NR^{dd}R^{ee}$, where $R^{dd}$ and $R^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Amino" or "amine" denotes the group —$NH_2$.

"Cycloalkyl" or "Carbocycle" or "Carbocyclic" by itself, or as part of another substituent, unless otherwise stated, refers to saturated or unsaturated, non-aromatic monocyclic, or fused rings, such as bicyclic or tricyclic carbon ring systems, or cubane, having the number of carbon atoms indicated in the prefix or if unspecified having 3-10, also 3-8, and also 3-6, ring members per ring, such as cyclopropyl, cyclopentyl, cyclohexyl, 1-cyclohexenyl and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). The term "cycloalkenyl" refers to a cycloalkyl having at least one point of unsaturation.

"Cycloalkylalkyl" refers to an -(alkylene)-cycloalkyl group where alkylene as defined herein has the indicated number of carbon atoms or if unspecified having six or fewer, or four or fewer main chain carbon atoms; and cycloalkyl is as defined herein has the indicated number of carbon atoms or if unspecified having 3-10, also 3-8, and also 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

The term "cyano" refers to the group —CN. The term "cyanoalkyl" refers to an alkyl, as defined herein, that is substituted with 1, 2 or 3 cyano groups.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl and 2-naphthyl. The term "arylene" refers to a divalent aryl, wherein the aryl is as defined herein.

"Arylalkyl" or "aralkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

The term "haloalkyl" refers to an alkyl substituted by one to seven halogen atoms. Haloalkyl includes monohaloalkyl or polyhaloalkyl. For example, the term "$C_{1-4}$ haloalkyl" is meant to include trifluoromethyl, difluoromethyl, 2,2,2-trifluoroethyl, 4-chlorobutyl, 3-bromopropyl, and the like. Further, the term "haloalkylene" refers to an alkylene substituted by one to seven halogen atoms.

"Halogen" or "halo" refers to all halogens, that is, chloro (Cl), fluoro (F), bromo (Br), or iodo (I).

"Heteroatom" is meant to include oxygen (O), nitrogen (N), and sulfur (S).

"Heteroaryl" by itself, or as part of another substituent, refers to a monocyclic aromatic ring radical containing 5 or 6 ring atoms, or a bicyclic aromatic radical having 8 to 10 atoms, containing one or more, 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any of the heteroatoms is N.

"Heteroarylene" by itself or as part of another substituent, refers to a divalent heteroaryl, where the heteroaryl is as defined herein.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein.

"Heterocycloalkyl" refers to a saturated or unsaturated non-aromatic cycloalkyl group that contains from one to five heteroatoms selected from N, O, S (including S(O) and S(O)$_2$), or P (including phosphine oxide) wherein the nitrogen and sulfur atoms are optionally oxidized, and the nitrogen atom(s) are optionally quarternized, the remaining ring atoms being C, where one or two C atoms may optionally be replaced by a carbonyl. The heterocycloalkyl may be substituted with one or two oxo groups, and can includes sulfone and sulfoxide derivatives. The heterocycloalkyl may be a monocyclic, a fused bicyclic or a fused polycyclic ring system of 3 to 12, or 4 to 10 ring atoms, or 5 to 8 ring atoms in which one to five ring atoms are heteroatoms selected from —N═, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, benzofuranyl, pyrazolidinyl, morpholinyl, and the like. A heterocycloalkyl group can be attached to the remainder of the molecule through a ring carbon or a heteroatom. The terms "oxoheterocycloalkyl" and "dioxoheterocycloalkyl" refer to a heterocycloalkyl substituted with either one or two oxo groups, respectively. The "heterocycloalkenyl" refers to a heterocycloalkyl having at least one point of unsaturation.

"Heterocycloalkylalkyl" or "heterocyclylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein.

"Hydroxyl" or "hydroxy" refers to the group —OH. The term "hydroxyalkyl" or "hydroxyalkylene" refers to an alkyl group or alkylene group, respectively as defined herein, substituted with 1-5 hydroxy groups.

The term "—O—$C_1$-$C_6$ haloalkylene" refers to moiety wherein the point of attachment to the parent moiety is represented by the bond on the oxygen atom, and wherein haloalkylene is as defined herein.

The term "—S(O)$_2$—$C_1$-$C_4$ alkyl" refers to moiety wherein the point of attachment to the parent moiety is represented by the bond on the sulfur, and wherein —$C_1$-$C_4$ alkyl is as defined herein.

The term "—$C_0$-$C_4$ alkylene-C(O)—NH$_2$" refers to moiety wherein the point of attachment to the parent moiety is represented by the bond on the) —$C_0$-$C_4$ alkylene, and wherein —$C_0$-$C_4$ alkylene is as defined herein.

The term "—N(H)C(O)—$C_1$-$C_4$ alkyl" refers to moiety wherein the point of attachment to the parent moiety is represented by the bond on the nitrogen atom, and wherein) —$C_1$-$C_4$ alkyl is as defined herein.

The term "—O—$C_1$-$C_6$ hydroxyalkylene" refers to moiety wherein the point of attachment to the parent moiety is represented by the bond on the oxygen atom, and wherein $C_1$-$C_6$ haloalkyl is as defined herein.

A "bridged ring" or a "bridged compound" is a carbocyclic or heterocyclic compound additionally having two or more rings containing a bridge of one to four carbon atoms that connect two bridgehead atoms. For purposes of this disclosure, bridgehead atoms cannot be two adjacent atoms on any particular ring. For purposes of this disclosure, two bridgehead atoms in a bridged ring cannot the same atom on any particular ring. A bridged heterocyclic ring refers to a bridged compound having at least one heteroatom. The bridgehead atoms are part of the skeletal framework of the molecule. Bridged rings (or compounds) may be fully carbocyclic (all carbon skeletal atoms). Below is an example of a bridged ring showing each of the bridge and bridgehead atoms.

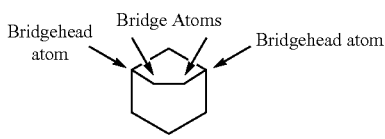

The term "oxo" refers to C(═O) or (O). In some embodiments, two possible points of attachment on a carbon form an oxo group.

A "spiro ring system" refers to two rings (carbocyclic rings, heterocyclic rings, or combinations thereof), wherein the spiro ring system is joined by one common spiro carbon atom.

A fused ring system refers to two rings (carbocyclic rings, heterocyclic rings, or combinations thereof) wherein the two rings are fused together by two adjacent carbon atoms that are shared between the two fused rings.

"Optional" or "Optionally" as used throughout the disclosure means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein in connection with compounds of the disclosure, the term "synthesizing" and like terms means chemical synthesis from one or more precursor materials.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. Such salts can be derived from pharmaceutically acceptable inorganic or organic bases and from pharmaceutically-acceptable inorganic or organic acids, depending on the particular substituents found on the compounds described herein.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

When compounds of the present disclosure contain relatively acidic functionalities, base addition salts can be obtained by contacting the neutral form of such compounds with a sufficient amount of the desired base (i.e. a primary, secondary, tertiary, quaternary, or cyclic amine; an alkali metal hydroxide; alkaline earth metal hydroxide; or the like), either neat or in a suitable inert solvent. The desired acid can be, for example, a pyranosidyl acid (such as glucuronic acid or galacturonic acid), an alpha-hydroxy acid (such as citric acid or tartaric acid), an amino acid (such as aspartic acid or glutamic acid), an aromatic acid (such as benzoic acid or cinnamic acid), a sulfonic acid (such as p-toluenesulfonic acid or ethanesulfonic acid), or the like. In some embodiments, salts can be derived from pharmaceutically acceptable acids such as acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, malonic, mandelic, oxalic, methanesulfonic, mucic, naphthalenesulfonic, nicotinic, nitric, pamoic, pantothenic, phosphoric, succinic, sulfuric, sulfamic, hydroiodic, carbonic, tartaric, p-toluenesulfonic, pyruvic, aspartic, benzoic, cinnamic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylsulfamic, cyclohexylaminosulfonic, quinic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

The term "deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. All isotopic variations of the compounds of the present disclosure, whether radioactive or not, are intended to be encompassed within the scope of the present disclosure. Examples of isotopes that can be incorporated into compounds of the disclosure include isotopes of hydrogen, carbon, nitrogen, oxygen, phosphorous, fluorine, and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Unless otherwise stated, when a position is designated specifically as "H" or "hydrogen," the position is understood to have hydrogen at its natural abundance isotopic composition or its isotopes, such as deuterium (D) or tritium ($^{3}H$). Certain isotopically-labeled compounds of the present disclosure (e.g., those labeled with $^{3}H$ and $^{14}C$) are useful in compound and/or substrate tissue distribution assays. Tritiated (i.e., $^{3}H$) and carbon-14 (i.e., $^{14}C$) and fluorine-18 ($^{18}F$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I(a) in vivo when such prodrug is administered to a subject. Prodrugs of a compound of Formula I(a) are prepared by modifying functional groups present in the compound of Formula I(a) in such a way, either in routine manipulation or in vivo, that the modifications may be cleaved in vivo to release the parent compound. Prodrugs may proceed from prodrug form to active form in a single step or may have one or more intermediate forms which may themselves have activity or may be inactive. Some prodrugs are activated enzymatically to yield the active compound, or a compound which, upon further chemical reaction, yields the active compound. Prodrugs include compounds of Formula I(a) wherein a hydroxy, amino, carboxyl or sulfhydryl group in a compound of Formula I(a) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I(a), and the like. Other examples of prodrugs include, without limitation, carbonates, ureides, solvates, or hydrates of the active compound. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth.

The term "carrier" is also meant to include microspheres, liposomes, miscelles, nanoparticles (naturally-equipped nanocarriers, for example, exosomes), and the like. It is known that exosomes can be highly effective drug carriers, and there are various ways in which drugs can be loaded into exosomes, including those techniques described in J Control Release. 2015 Dec. 10; 219: 396-405, the contents of which are incorporated by reference in its entirety.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." As another example, stereoisomers include geometric isomers, such as cis- or trans-orientation of substituents on adjacent carbons of a double bond. Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

"Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as those described herein. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 1 mM or less, 1 µM or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "modulate," "modulation," and the like refer to the ability of a compound to increase or decrease the function and/or expression of an enzyme, such as CDK8, where such function may include transcription regulatory activity and/or binding. Modulation may occur in vitro or in vivo. Modulation, as described herein, includes the inhibition, antagonism, partial antagonism, activation, agonism or partial agonism of a function or characteristic associated with CDK8, either directly or indirectly, and/or the upregulation or downregulation of the expression CDK8, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

As used herein, the terms "treat," "treating," "therapy," "therapies," and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

As used herein, the term "subject," "animal subject," and the like refers to a living organism including, but not limited to, human and non-human vertebrates, e.g. any mammal, such as a human, other primates, sports animals and animals of commercial interest such as cattle, horses, ovines, or porcines, rodents, or pets such as dogs and cats.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject.

Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

The ability of a compound to inhibit the function of CDK8 can be demonstrated in a biochemical assay, e.g., binding assay, or a cell-based assay.

As used herein, the term "CDK8 mediated disease or condition" refers to a disease or condition in which the biological function of CDK8 affects the development and/or course of the disease or condition, and/or in which modulation of CDK8 alters the development, course, and/or symptoms. These mutations attenuate the intrinsic activity of the receptor to different degrees and are models for the effect of modulation of CDK8 activity. A CDK8 mediated disease or condition includes a disease or condition for which CDK8 inhibition provides a therapeutic benefit, e.g. wherein treatment with CDK8 inhibitors, including compounds described herein, provides a therapeutic benefit to the subject suffering from or at risk of the disease or condition.

The term "CDK8 mediated disease or disorder" includes a disease associated with or that implicates CDK8 activity, for example, the overactivity of CDK8, and conditions that accompany with these diseases. The term "overactivity of CDK8" refers to either: 1) CDK8 expression in cells which normally do not express CDK8; 2) increased CDK8 expression leading to unwanted cell proliferation; or 3) mutations leading to constitutive activation of CDK8. Examples of an CDK8 mediated diseases or disorders include a disorder resulting from over stimulation of CDK8 or from abnormally high amount of CDK8 activity, due to abnormally high amount of CDK8. It is known that overactivity of CDK8 has been implicated in the pathogenesis of a number of diseases, including proliferative and non-proliferative disorders, including neoplastic disorders and cancers, neurodegenerative diseases, and viral diseases as described herein.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of CDK8, or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for CDK8," and terms of like import mean that a particular compound binds to CDK8 to a statistically greater extent than to other enzymes that may be present in a particular sample. Also, where biological activity other than binding is indicated, the term "specific for CDK8" indicates that a particular compound has greater biological effect associated with binding CDK8 than to other enzymes, e.g., enzyme activity inhibition. The specificity is also with respect to other biomolecules (not limited to CDK8 enzymes) that may be present in a particular sample.

The term "first line cancer therapy" refers to therapy administered to a subject as an initial regimen to reduce the number of cancer cells. First line therapy is also referred to as induction therapy, primary therapy and primary treatment. First-line therapy can be an administered combination with one or more agents. A summary of currently accepted approaches to first line treatment for certain disease can be found in the NCI guidelines for such diseases.

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy." A summary of the currently accepted approaches to second line treatment for certain diseases is described in the NCI guidelines for such diseases.

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

In addition, abbreviations as used herein have respective meanings as follows:

| | |
|---|---|
| ° C. | Degree Celsius |
| Ac | Acetyl |
| BOC | tert-Butoxycarbonyl |
| DEAE | Diethylaminoethyl |
| DMEM | Dulbecco's Modified Eagle's Medium |
| DMSO | Dimethylsulfoxide |
| FBS | Fetal bovine serum |
| HPLC | High Performance Liquid Chromatography |
| LCMS | Liquid Chromatography Mass Spectrometry |
| L-Trp | L-tryptophan |
| [M + H]+ or (MH)+ | Mass peak plus hydrogen |
| [M − H−]− or (MH)− | Mass peak minus hydrogen |
| MEM | Minimum essential medium |
| PBS | Phosphate buffered saline |

| | |
|---|---|
| TCA | Trichloroacetic acid |
| THF | Tetrahydrofuran |
| n-Bu | n-Butyl |
| Me | Methyl |
| MS | Mass spectrometry |
| ES | Electrospray ionization |
| N | Normal |
| IDO | indoleamine 2,3-dioxygenase |
| TDO | tryptophan-2,3-dioxygenase |
| DMEM | Dulbecco's Modified Eagle's Medium |
| IC$_{50}$ | Half minimal (50%) inhibitory concentration |
| ESI | Electrospray ionization |
| MS | Mass spectrometry |
| RP | Reverse phase |
| T3P | 1-Propanephosphonic anhydride |
| LC | Liquid chromatography |

II. Compounds

Embodiment 1 of this disclosure relates to a compound of I:

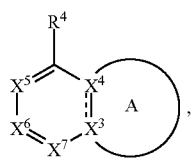

or a pharmaceutically acceptable salt, a solvate, a tautomer, an isomer, or a deuterated analog thereof, wherein:

Ring A, together with $X^3$, $X^4$ and the optional double bond connecting $X^3$ and $X^4$, is one of Rings A1, A2, A3 or A4:

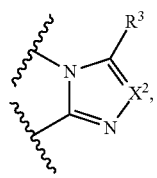

A1

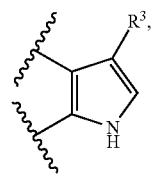

A2

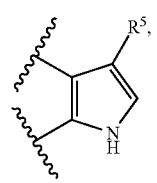

A3

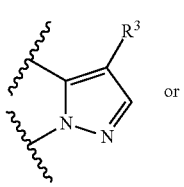

A4 or

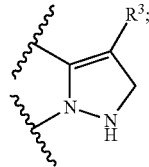

A5

$X^2$ is N or CH;

$X^5$, $X^6$ and $X^7$ are as defined in groups (G-A1), (G-A2), (G-A3) or (G-A4):

(G-A1): when Ring A is Ring A1, $X^5$ is $CR^5$, $X^6$ is N or CH, and $X^7$ is N or CH, provided that $X^6$ and $X^7$ are not both N;

(G-A2): when Ring A is Ring A2, $X^5$ is $CR^5$, $X^6$ is CH, and $X^7$ is N;

(G-A3): when Ring A is Ring A3, $X^5$ is $CR^3$, $X^6$ is CH, and $X^7$ is N;

(G-A4): when Ring A is Ring A4, $X^5$ is $CR^5$ or N, $X^6$ is CH, and $X^7$ is CH;

(G-A5): when Ring A is Ring A5, $X^5$ is $CR^5$ or N, $X^6$ is CH, and $X^7$ is CH;

$R^3$ is —B-L-T;

$R^4$ is one of (a)-(f):
(a) —X-heterocycloalkyl, wherein the heterocycloalkyl moiety of —X-heterocycloalkyl is substituted with 0-3 $R^7$ groups and 0-1 $R^8$ groups, wherein the heterocycloalkyl moiety of —X-heterocycloalkyl is saturated or unsaturated;
(b) —X-cycloalkyl, wherein the cycloalkyl moiety of —X-cycloalkyl is substituted with 0-3 $R^7$ groups and 0-1 $R^8$ groups, and wherein the cycloalkyl is saturated or unsaturated;
(c) aryl or heteroaryl, wherein the aryl or heteroaryl is substituted with 0-1 $R^{10}$ groups and 0-1 $R^{11}$ groups;
(d) alkynyl optionally substituted with $R^{12}$;
(e) alkoxy optionally substituted with 1-3 $R^{13a}$; or
(f) —N(H)($R^{15}$);

$R^5$ is hydrogen, halogen, —CN, or methyl optionally substituted with 1-3 halogens;

$R^6$ is H, alkyl, -alkylene-CN, cycloalkyl, heterocycloalkyl, heteroaryl, or aryl; each $R^7$ is independently alkyl, halogen, CN, hydroxyl, haloalkyl, cyanoalkyl, hydroxyalkyl optionally substituted with heteroaryl, provided that halogen and CN are not bonded to a heteroatom;

$R^8$ is CN, aryl, heterocycloalkyl, heteroaryl, —(CH$_2$)$_{0-3}$—C(O)—N(H)—R$^6$, —C(O)R$^6$, —(CH$_2$)$_{0-3}$C(O)OR$^6$, —(CH$_2$)$_{0-3}$S(O)$_2$R$^6$; or

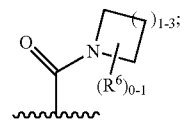

or $R^7$ and $R^8$, when both are attached to the same carbon atom of the saturated heterocycloalkyl, may join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 alkyl groups, and wherein the oxoheterocycloalkyl is optionally fused to an aryl or heteroaryl;

B is a bond, arylene, heteroarylene or heterocycloalkylene, wherein the arylene, heteroarylene or heterocycloalkylene are each substituted with 0-3 G1 groups and 0-1 G2 groups;

L is a bond, —C(O)—, —N(H)—, —N(H)S(O)₂—, —S(O)₂—N(H)—, —S(O)₂—, —S(O)₂—C₁-C₄ alkylene, —N(H)C(O)—C₁-C₄ alkylene, —N(H)C(O)OC₁-C₄ alkylene, —N(H)—(CH₂)₀₋₄—, C₁-C₄ alkylene-N(H)—C(O)—, —C₁-C₆ alkylene, —O—C₁-C₆ alkylene, —O—C₁-C₆ haloalkylene, —O—C₁-C₆ alkylene-O—, or —O—C₁-C₆ hydroxyalkylene;

T is heteroaryl, aryl, alkyl, cycloalkyl or heterocycloalkyl, wherein the heteroaryl, alkyl, cycloalkyl or heterocycloalkyl are each substituted with 0-3 G3 groups and 0-1 G4 groups;

or B-L is ethynylene and T is heteroaryl substituted with 0-3 G3 groups;

each G1 is independently halogen, —C₁-C₄ alkyl, alkoxy, —C₁-C₄haloalkyl, hydroxyl, or —C₁-C₄ hydroxyalkyl;

G2 is —C₀-C₄ alkylene-S(O)₂—C₁-C₄alkyl, —C₀-C₄ alkylene-C(O)—NH₂, or —N(H)C(O)—C₁-C₄ alkyl;

each G3 is independently halogen, —C₁-C₆alkyl, —C₁-C₆ alkoxy, —C₁-C₆ haloalkyl, hydroxyl, C₁-C₆ hydroxyalkyl, or —C₀-C₆ alkylene-CN;

G4, when attached to a carbon atom, is halogen, —C₁-C₆alkyl, —C₁-C₆ alkoxy, —C₁-C₆ haloalkyl, hydroxyl, —C₁-C₆ hydroxyalkyl, —C₀-C₆ alkylene-CN, —C₀-C₄ alkylene-S(O)₂—C₁-C₆ alkyl, —C₀-C₄ alkylene-N(H)—S(O)₂—C₁-C₄ alkyl, —C₀-C₄ alkylene-C(O)—NH₂, —C₀-C₄ alkylene-C(O)—N(H)—C₁-C₄ alkyl, —N(H)—C(O)—C₁-C₄ alkyl, —C₀-C₄ alkylene-C(O)—N(C₁-C₄ alkyl)₂, —C₁-C₆ alkylene-N—(C₁-C₄ alkyl)₂, —C₁-C₆ alkylene-N(H)—(C₁-C₄ alkyl), —C₁-C₆ alkylene-NH₂, —C₀-C₄ alkylene-heterocycloalkyl, —C₀-C₄ alkylene-C(O)O—C₁-C₆ alkyl, or —C₀-C₆ alkylene-cycloalkyl optionally substituted with CN, OH, —C₁-C₄alkyl, —C(O)O—C₁-C₄ alkyl, —C(O)OH, or halogen;

or G4, when attached to a nitrogen atom, is —C₁-C₆alkyl, —C₁-C₆alkylene-C₁-C₆ alkoxy, —C₁-C₆ haloalkyl, —C₁-C₆ hydroxyalkyl, —C₁-C₆ alkylene-CN, —C₁-C₄ alkylene-S(O)₂—C₁-C₆ alkyl, —C₁-C₃ alkyl-N(H)—S(O)₂—C₁-C₄ alkyl, —C₁-C₄ alkylene-C(O)—NH₂, —C₁-C₄ alkylene-C(O)—N(H)—C₁-C₄ alkyl, —C₁-C₄ alkylene-C(O)—N(C₁-C₄ alkyl)₂, —C₁-C₆ alkylene-N—(C₁-C₄ alkyl)₂, —C₁-C₆ alkylene-N(H)—(C₁-C₄ alkyl), —C₁-C₆ alkylene-NH₂, —C₀-C₄ alkylene-heterocycloalkyl, —C₀-C₄ alkylene-C(O)O—C₁-C₆ alkyl, —C₀-C₄ alkylene-C(O)OH, or —C₁-C₆ alkylene-cycloalkyl optionally substituted with CN, OH, C₁-C₄ alkyl, —C(O)O—C₁-C₄ alkyl, —C(O)OH, or halogen;

R⁹ is H, alkyl, hydroxyalkyl, or haloalkyl;

R¹⁰ is —NHS(O)₂-alkyl, —S(O)₂-alkyl, —S(O)₂-heterocycloalkyl, —S(O)₂—N(H)alkyl, —(CH₂)₀₋₂—C(O)NH—C₁-C₃alkyl, —(CH₂)₀₋₃—O-aryl-R⁹, -heteroaryl-R⁹, —(CH₂)₀₋₃—O-heteroaryl-R⁹, —C₁-C₄ alkylene-heterocycloalkyl, —C₁-C₄ alkylene-O-heterocycloalkyl, —O—C₁-C₄ alkylene-O—C₀-C₄ alkylene-heterocycloalkyl, —(CH₂)₀₋₃—NHC(O)O—C₁-C₄ alkylene-aryl, —C(O)—O-alkyl, —(CH₂)₀₋₃—N(C(O)-heteroaryl-R⁹, —(CH₂)₀₋₃—N(C(O)-aryl-R⁹, alkyl, alkenyl, alkynyl or CN;

R¹¹ is halogen, cycloalkyl, cycloalkenyl, or heterocycloalkyl;

R¹² is —C₁-C₆ alkylamino, -cycloalkylene-W, heterocycloalkylene-W, heteroaryl-W, —C₁-C₆ alkylene-C(O)NHR⁶, —C₁-C₆ alkylene —C(O)OR⁶, —C₁-C₆ hydroxyalkyl, —C₁-C₆ cyanoalkyl, —Z¹-alkylene-Z², —Z¹-haloalkylene-Z², or —Z¹-hydroxyalkylene-Z²;

each R¹³ᵃ is independently H, halogen, hydroxyl, alkyl, hydroxyalkyl, haloalkyl, CN, or heterocycloalkyl;

R¹⁵ is H, alkyl, haloalkyl, hydroxyalkyl, cyanoalkyl, heteroarylalkyl, heteroaryl optionally substituted with alkyl, or heterocycloalkyl;

W is H, halogen, hydroxyl, alkyl, hydroxyalkyl, haloalkyl, CN, or heterocycloalkyl;

X is a bond, —O—, or —N(H)—;

Z¹ is absent, —C₁-C₄ alkylene, or —C₁-C₄ haloalkylene; and

Z² is —C₁-C₄ alkoxyl optionally substituted with hydroxyl, —N(H)S(O)₂—C₁-C₄ alkyl, —N(H)—C(O)—C₁-C₄ alkyl, —N(H)—C(O)—C₁-C₄ haloalkyl, —C(O)—N(H)—C₁-C₄ alkyl, —C(O)—N(H)—C₁-C₄ haloalkyl, or phenyl.

Embodiment 1' of this disclosure relates to a compound of I:

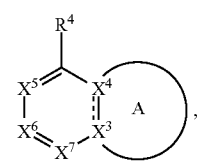

I or a pharmaceutically acceptable salt, a solvate, a tautomer, an isomer, or a deuterated analog thereof, wherein:

Ring A, together with X³, X⁴ and the optional double bond connecting X³ and X⁴, is one of Rings A1, A2, A3 or A4:

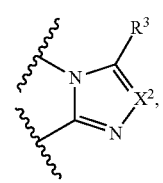

A1

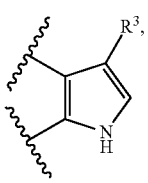

A2

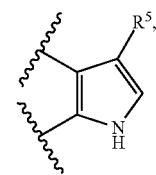

A3

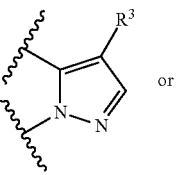

A4 or

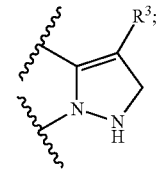

A5

$X^2$ is N or CH;

$X^5$, $X^6$ and $X^7$ are as defined in groups (G-A1), (G-A2), (G-A3) or (G-A4):

(G-A1): when Ring A is Ring A1, $X^5$ is $CR^5$, $X^6$ is N or CH, and $X^7$ is N or CH, provided that $X^6$ and $X^7$ are not both N;

(G-A2): when Ring A is Ring A2, $X^5$ is $CR^5$, $X^6$ is CH, and $X^7$ is N;

(G-A3): when Ring A is Ring A3, $X^5$ is $CR^3$, $X^6$ is CH, and $X^7$ is N;

(G-A4): when Ring A is Ring A4, $X^5$ is $CR^5$ or N, $X^6$ is CH, and $X^7$ is CH;

(G-A5): when Ring A is Ring A5, $X^5$ is $CR^5$ or N, $X^6$ is CH, and $X^7$ is CH;

$R^3$ is —B-L-T;

$R^4$ is one of (a)-(f):
(a) —X-heterocycloalkyl, wherein the heterocycloalkyl moiety of —X-heterocycloalkyl is substituted with 0-3 $R^7$ groups and 0-1 $R^8$ groups, wherein the heterocycloalkyl moiety of —X-heterocycloalkyl is saturated or unsaturated;
(b) —X-cycloalkyl, wherein the cycloalkyl moiety of —X-cycloalkyl is substituted with 0-3 $R^7$ groups and 0-1 $R^8$ groups, and wherein the cycloalkyl is saturated or unsaturated;
(c) aryl or heteroaryl, wherein the aryl or heteroaryl is substituted with 0-1 $R^{10}$ groups and 0-1 $R^{11}$ groups;
(d) alkynyl optionally substituted with $R^{12}$;
(e) alkoxy optionally substituted with 1-3 $R^{13a}$; or
(f) —N(H)($R^{15}$);

$R^5$ is hydrogen, halogen, —CN, or methyl optionally substituted with 1-3 halogens;

$R^6$ is H, alkyl, -alkylene-CN, cycloalkyl, heterocycloalkyl, heteroaryl, or aryl;

each $R^7$ is independently alkyl, halogen, CN, hydroxyl, haloalkyl, cyanoalkyl, hydroxyalkyl optionally substituted with heteroaryl, provided that halogen and CN are not bonded to a heteroatom;

$R^8$ is CN, aryl, heterocycloalkyl, heteroaryl, —(CH$_2$)$_{0-3}$—C(O)—N(H)—$R^6$, —C(O)$R^6$, —(CH$_2$)$_{0-3}$C(O)O$R^6$, —(CH$_2$)$_{0-3}$S(O)$_2R^6$; or

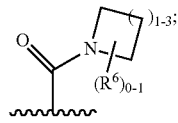

or $R^7$ and $R^8$, when both are attached to the same carbon atom of the saturated heterocycloalkyl, may join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 alkyl groups, and wherein the oxoheterocycloalkyl is optionally fused to an aryl or heteroaryl;

B is a bond, arylene, heteroarylene or heterocycloalkylene, wherein the arylene, heteroarylene or heterocycloalkylene are each substituted with 0-3 G1 groups and 0-1 G2 groups;

L is a bond, —C(O)—, —N(H)—, —N(H)S(O)$_2$—, —S(O)$_2$—N(H)—, —S(O)$_2$—, —S(O)$_2$—C$_1$-C$_4$ alkylene, —N(H)C(O)—C$_1$-C$_4$ alkylene, —N(H)C(O)OC$_1$-C$_4$ alkylene, —N(H)—(CH$_2$)$_{0-4}$—, C$_1$-C$_4$ alkylene-N(H)—C(O)—, —C$_1$-C$_6$ alkylene, —O—C$_1$-C$_6$ alkylene, —O—C$_1$-C$_6$ haloalkylene, —O—C$_1$-C$_6$ alkylene-O—, or —O—C$_1$-C$_6$ hydroxyalkylene;

T is heteroaryl, aryl, alkyl, cycloalkyl or heterocycloalkyl, wherein the heteroaryl, alkyl, cycloalkyl or heterocycloalkyl are each substituted with 0-3 G3 groups and 0-1 G4 groups;

or B-L is ethynylene and T is heteroaryl substituted with 0-3 G3 groups;

each G1 is independently halogen, —C$_1$-C$_4$ alkyl, alkoxy, —C$_1$-C$_4$haloalkyl, hydroxyl, or —C$_1$-C$_4$ hydroxyalkyl;

G2 is —C$_0$-C$_4$ alkylene-S(O)$_2$—C$_1$-C$_4$alkyl, —C$_0$-C$_4$ alkylene-C(O)—NH$_2$, or —N(H)C(O)—C$_1$-C$_4$ alkyl;

each G3 is independently halogen, —C$_1$-C$_6$alkyl, —C$_1$-C$_6$ alkoxy, —C$_1$-C$_6$ haloalkyl, hydroxyl, C$_1$-C$_6$ hydroxyalkyl, or —C$_0$-C$_6$ alkylene-CN;

G4, when attached to a carbon atom, is halogen, —C$_1$-C$_6$alkyl, —C$_1$-C$_6$ alkoxy, —C$_1$-C$_6$ haloalkyl, hydroxyl, —C$_1$-C$_6$ hydroxyalkyl, —C$_0$-C$_6$ alkylene-CN, —C$_0$-C$_4$ alkylene-S(O)$_2$—C$_1$-C$_6$ alkyl, —C$_0$-C$_4$ alkylene-N(H)—S(O)$_2$—C$_1$-C$_4$ alkyl, —C$_0$-C$_4$ alkylene-C(O)—NH$_2$, —C$_0$-C$_4$ alkylene-C(O)—N(H)—C$_1$-C$_4$ alkyl, —N(H)—C(O)—C$_1$-C$_4$ alkyl, —C$_0$-C$_4$ alkylene-C(O)—N(C$_1$-C$_4$ alkyl)$_2$, —C$_1$-C$_6$ alkylene-N—(C$_1$-C$_4$ alkyl)$_2$, —C$_1$-C$_6$ alkylene-N(H)—(C$_1$-C$_4$ alkyl), —C$_1$-C$_6$ alkylene-NH$_2$, —C$_0$-C$_4$ alkylene-heterocycloalkyl, —C$_0$-C$_4$ alkylene-C(O)O—C$_1$-C$_6$ alkyl, or —C$_0$-C$_6$ alkylene-cycloalkyl optionally substituted with CN, OH, —C$_1$-C$_4$alkyl, —C(O)O—C$_1$-C$_4$ alkyl, —C(O)OH, or halogen;

or G4, when attached to a nitrogen atom, is —C$_1$-C$_6$alkyl, —C$_1$-C$_6$ alkoxy, —C$_1$-C$_6$ haloalkyl, —C$_1$-C$_6$ hydroxyalkyl, —C$_1$-C$_6$ alkylene-CN, —C$_1$-C$_4$ alkylene-S(O)$_2$—C$_1$-C$_6$ alkyl, —C$_1$-C$_3$ alkyl-N(H)—S(O)$_2$—C$_1$-C$_4$ alkyl, —C$_1$-C$_4$ alkylene-C(O)—NH$_2$, —C$_1$-C$_4$ alkylene-C(O)—N(H)—C$_1$-C$_4$ alkyl, —C$_1$-C$_4$ alkylene-C(O)—N(C$_1$-C$_4$ alkyl)$_2$, —C$_1$-C$_6$ alkylene-N—(C$_1$-C$_4$ alkyl)$_2$, —C$_1$-C$_6$ alkylene-N(H)—(C$_1$-C$_4$ alkyl), —C$_1$-C$_6$ alkylene-NH$_2$, —C$_0$-C$_4$ alkylene-heterocycloalkyl, —C$_0$-C$_4$ alkylene-C(O)O—C$_1$-C$_6$ alkyl, —C$_0$-C$_4$ alkylene-C(O)OH, or —C$_1$-C$_6$ alkylene-cycloalkyl optionally substituted with CN, OH, C$_1$-C$_4$ alkyl, —C(O)O—C$_1$-C$_4$ alkyl, —C(O)OH, or halogen;

$R^9$ is H, alkyl, hydroxyalkyl, or haloalkyl;

$R^{10}$ is —NHS(O)$_2$-alkyl, —S(O)$_2$-alkyl, —S(O)$_2$-heterocycloalkyl, —S(O)$_2$—N(H)alkyl, —(CH$_2$)$_{0-2}$—C(O)NH—C$_1$-C$_3$alkyl, —(CH$_2$)$_{0-3}$—O-aryl-$R^9$, -heteroaryl-$R^9$, —(CH$_2$)$_{0-3}$—O-heteroaryl-$R^9$, —C$_1$-C$_4$ alkylene-heterocycloalkyl, —C$_1$-C$_4$ alkylene-O-heterocycloalkyl, —O—C$_1$-C$_4$ alkylene-O—C$_0$-C$_4$ alkylene-heterocycloalkyl, —(CH$_2$)$_{0-3}$—NHC(O)O—C$_1$-C$_4$ alkylene-aryl, —C(O)—O-alkyl, —(CH$_2$)$_{0-3}$—N(C(O)-heteroaryl-$R^9$, —(CH$_2$)$_{0-3}$—N(C(O)-aryl-$R^9$, alkyl, alkenyl, alkynyl or CN;

$R^{11}$ is halogen, cycloalkyl, cycloalkenyl, or heterocycloalkyl;

$R^{12}$ is —C$_1$-C$_6$ alkylamino, -cycloalkylene-W, heterocycloalkylene-W, heteroaryl-W, —C$_1$-C$_6$ alkylene-C(O)NH$R^6$, —C$_1$-C$_6$ alkylene —C(O)O$R^6$, —C$_1$-C$_6$ hydroxyalkyl, —C$_1$-C$_6$ cyanoalkyl, —Z$^1$-alkylene-Z$^2$, —Z$^1$-haloalkylene-Z$^2$, or —Z$^1$-hydroxyalkylene-Z$^2$;

each $R^{13a}$ is independently H, halogen, hydroxyl, alkyl, hydroxyalkyl, haloalkyl, CN, or heterocycloalkyl;

$R^{15}$ is H, alkyl, haloalkyl, hydroxyalkyl, cyanoalkyl, heteroarylalkyl, heteroaryl optionally substituted with alkyl, or heterocycloalkyl;

W is H, halogen, hydroxyl, alkyl, hydroxyalkyl, haloalkyl, CN, or heterocycloalkyl;

X is a bond, —O—, or —N(H)—;

$Z^1$ is absent, —C$_1$-C$_4$ alkylene, or —C$_1$-C$_4$ haloalkylene; and $Z^2$ is —C$_1$-C$_4$ alkoxyl optionally substituted with hydroxyl, —N(H)S(O)$_2$—C$_1$-C$_4$ alkyl, —N(H)—C(O)—

$C_1$-$C_4$ alkyl, —N(H)—C(O)—$C_1$-$C_4$ haloalkyl, —C(O)—N(H)—$C_1$-$C_4$ alkyl, —C(O)—N(H)—$C_1$-$C_4$ haloalkyl, or phenyl.

Embodiment 1(a) of this disclosure relates to the compound in Embodiment 1 or 1', wherein
Ring A, together with $X^3$, $X^4$ and the optional double bond connecting $X^3$ and $X^4$, is Ring A1.

Embodiment 1(b) of this disclosure relates to the compound in Embodiment 1 or 1', wherein
Ring A, together with $X^3$, $X^4$ and the optional double bond connecting $X^3$ and $X^4$, is Ring A2.

Embodiment 1(c) of this disclosure relates to the compound in Embodiment 1 or 1', wherein
Ring A, together with $X^3$, $X^4$ and the optional double bond connecting $X^3$ and $X^4$, is Ring A3.

Embodiment 1(d) of this disclosure relates to the compound in Embodiment 1 or 1', wherein
Ring A, together with $X^3$, $X^4$ and the optional double bond connecting $X^3$ and $X^4$, is Ring A4.

Embodiment 1(e) of this disclosure relates to the compound in any one of Embodiments 1, 1', 1(a), 1(b), 1(c), or 1(d), wherein:

B is a bond, arylene, heteroarylene or heterocycloalkylene, wherein the arylene, heteroarylene or heterocycloalkylene are each substituted with 0-3 G1 groups and 0-1 G2 groups;

L is a bond, —O—, —C(O)—, —N(H)—, —N(H)S(O)$_2$—, —S(O)$_2$—$C_1$-$C_4$ alkylene, —N(H)C(O)—$C_1$-$C_4$ alkylene, —N(H)C(O)O$C_1$-$C_4$ alkylene, —N(H)—(CH$_2$)$_{0-4}$—, —$C_1$-$C_6$ alkylene, —O—$C_1$-$C_6$ alkylene, —O—$C_1$-$C_6$haloalkylene, —O—$C_1$-$C_6$ alkylene-O—, or —O—$C_1$-$C_6$ hydroxyalkylene; and T is heteroaryl, aryl, alkyl, cycloalkyl or heterocycloalkyl, wherein the heteroaryl, alkyl, cycloalkyl or heterocycloalkyl are each substituted with 0-3 G3 groups and 0-1 G4 groups.

Embodiment 1(f) of this disclosure relates to the compound in any one of Embodiments 1, 1', 1(a), 1(b), 1(c), or 1(d), wherein:
or B-L is ethynylene and T is heteroaryl substituted with 0-3 G3 groups.

Embodiment 1(g) of this disclosure relates to the compound in any one of Embodiments 1, 1', 1(a), 1(b), 1(c), 1(d), 1(e), or 1(f) wherein:

$R^4$ is (a) —X-heterocycloalkyl, wherein the heterocycloalkyl moiety of —X-heterocycloalkyl is substituted with 0-3 $R^7$ groups and 0-1 $R^8$ groups, wherein the heterocycloalkyl moiety of —X-heterocycloalkyl is saturated or unsaturated.

Embodiment 1(h) of this disclosure relates to the compound in any one of Embodiments 1, 1', 1(a), 1(b), 1(c), 1(d), 1(e), or 1(f) wherein:

$R^4$ is (b) —X-cycloalkyl, wherein the cycloalkyl moiety of —X-cycloalkyl is substituted with 0-3 $R^7$ groups and 0-1 $R^8$ groups, and wherein the cycloalkyl is saturated or unsaturated.

Embodiment 1(i) of this disclosure relates to the compound in any one of Embodiments 1, 1', 1(a), 1(b), 1(c), 1(d), 1(e), or 1(f) wherein:

$R^4$ is (c) aryl or heteroaryl, wherein the aryl or heteroaryl is substituted with 0-1 $R^{10}$ groups and 0-1 $R^{11}$ groups.

Embodiment 1(j) of this disclosure relates to the compound in any one of Embodiments 1, 1', 1(a), 1(b), 1(c), 1(d), 1(e), or 1(f) wherein:

$R^4$ is (d) alkynylene optionally substituted with $R^{12}$.

Embodiment 1(k) of this disclosure relates to the compound in any one of Embodiments 1, 1', 1(a), 1(b), 1(c), 1(d), 1(e), or 1(f) wherein:

$R^4$ is (e) alkoxy optionally substituted with 1-3 $R^{13a}$.

Embodiment 2 of this disclosure relates to the compound Embodiments 1 or 1' having any one of Formula II(a)-II(g):

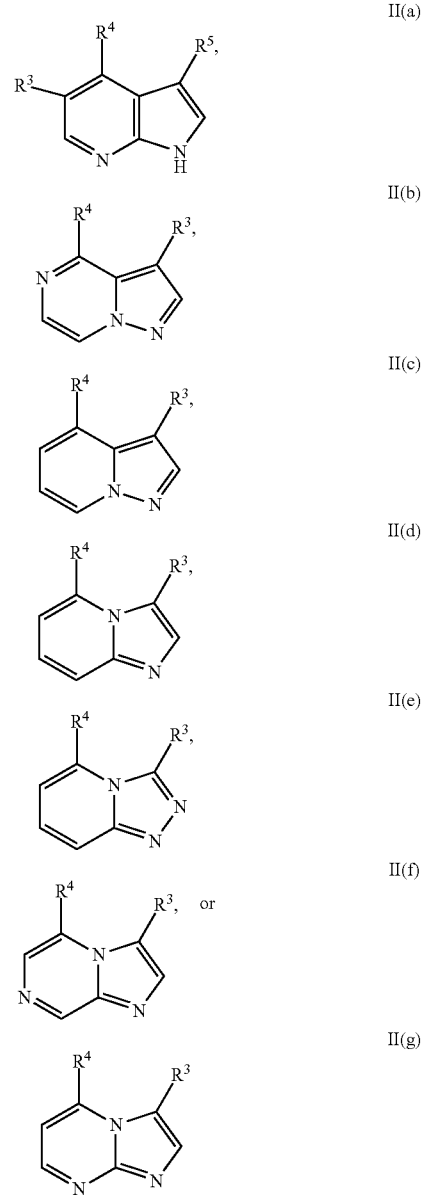

or a pharmaceutically acceptable salt, a solvate, a tautomer, an isomer, or a deuterated analog thereof.

Embodiment 3 of this disclosure relates to the compound in any one of Embodiments 1, 1', 1(a), 1(b), 1(c), 1(d), 1(e), 1(f) or 2, wherein:

$R^4$ is one of (a1)-(f):

(a1) saturated 5-6 membered heterocycloalkyl substituted with 0-3 $R^7$ groups, wherein the saturated heterocycloalkyl is further optionally substituted with one $R^8$ group;

(a2) heterocycloalkenyl (includes sulfone and sulfoxide derivatives in definition) substituted with 0-3 $R^7$ groups, wherein the heterocycloalkenyl is further optionally substituted with one $R^8$ group;

(b1) saturated $C_3$-$C_6$ cycloalkyl substituted with 0-3 $R^7$ groups, wherein the saturated $C_3$-$C_6$ cycloalkyl is further optionally substituted with one $R^8$ group;
(b2) $C_5$-$C_6$ cycloalkenyl substituted with 0-3 $R^7$ groups, wherein the cycloalkenyl is further optionally substituted with one $R^8$ group;
(c1) aryl or heteroaryl substituted with one $R^{10}$ group, wherein the aryl or heteroaryl is further optionally substituted with one $R^{11}$ group;
(d) —$C_2$-$C_3$ alkynylene substituted with $R^{12}$;
(e) —$C_1$-$C_6$ alkoxy optionally substituted with 1-3 $R^{13a}$; or
(f) —N(H)($R^{15}$);
$R^5$ is H, F, Br, Cl, or $CH_3$;
$R^6$ is H, —$C_1$-$C_6$ alkyl, —$C_1$-$C_6$ haloalkyl, —$C_1$-$C_6$ alkylene-CN, —$C_3$-$C_6$ cycloalkyl, 4-6 membered heterocycloalkyl, 5-6 membered heteroaryl, or phenyl;
each $R^7$ is independently —$C_1$-$C_6$ alkyl, halogen, CN, hydroxyl, —$C_1$-$C_6$ alkyl, —$C_1$-$C_6$ haloalkyl, —$C_1$-$C_6$ cyanoalkyl, or —$C_1$-$C_6$ hydroxyalkyl optionally substituted with heteroaryl, provided that halogen and CN are not bonded to a heteroatom;
$R^8$ is CN, phenyl, 5-6 membered heterocycloalkyl, heteroaryl, —$(CH_2)_{0-2}$—C(O)—N(H)—$R^6$, —C(O)$R^6$, —$(CH_2)_{0-2}$C(O)O$R^6$, —$(CH_2)_{0-2}$S(O)$_2R^6$; or

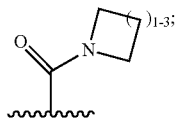

or $R^7$ and $R^8$, when both are attached to the same carbon atom of the saturated heterocycloalkyl, join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 —$C_1$-$C_6$ alkyl groups, and wherein the oxoheterocycloalkyl is optionally fused to an phenyl or 5-6 membered heteroaryl;
$R^{10}$ is —NHS(O)$_2$—$C_1$-$C_5$ alkyl, —S(O)$_2$—$C_1$-$C_5$ alkyl, —S(O)$_2$-5-6 membered heterocycloalkyl, —S(O)$_2$—N(H)$C_1$-$C_5$ alkyl, —$(CH_2)_{0-1}$—C(O)NH$_2$, —$(CH_2)_{0-1}$—O-phenyl, —$(CH_2)_{0-1}$—O-(5-6 membered)heteroaryl, —$(CH_2)_{0-1}$—NHC(O)O—$C_1$-$C_2$ alkylene-phenyl, —$(CH_2)_{0-1}$—N(C(O)-5-6 membered heteroaryl, —$(CH_2)_{0-1}$—N(C(O)-phenyl, —$C_1$-$C_5$ alkylene-(5-6 membered)heterocycloalkylalkyl, —$C_2$-$C_4$alkenyl-, or CN;
$R^{11}$ is H, $C_3$-$C_7$ cycloalkyl, $C_5$-$C_6$ cycloalkenyl or 5-6 membered heterocycloalkyl;
$R^{12}$ is 4-6 membered cycloalkylene-$R^{13a}$, —C(O)NH$R^6$, —$Z^1$—$(CH_2)_{1-2}$—$Z^2$, —$Z^1$—$(C_1$-$C_2)$haloalkylene-$Z^2$, or —$Z^1$—$(C_1$-$C_2)$hydroxyalkylene-$Z^2$;
each $R^{13a}$ is halogen, hydroxyl, —$C_1$-$C_3$ alkyl, —$C_1$-$C_3$ hydroxyalkyl, —$C_1$-$C_3$ haloalkyl or CN;
$R^{15}$ is H, —$C_1$-$C_6$ alkyl, —$C_1$-$C_6$ haloalkyl, —$C_1$-$C_6$ hydroxyalkyl, —$C_1$-$C_6$ cyanoalkyl, or heteroaryl-$C_1$-$C_6$ alkyl;
W is H, halogen, hydroxyl, —$C_1$-$C_6$ alkyl, —$C_1$-$C_6$ hydroxyalkyl, —$C_1$-$C_6$ haloalkyl, CN, or 5-6 membered heteroalkyl;
X is a bond or —O—;
$Z^1$ is absent, —$C_1$-$C_3$ alkylene, or —$C_1$-$C_3$ haloalkylene; and
$Z^2$ is —$C_1$-$C_3$ alkoxyl optionally substituted with hydroxyl, —N(H) S(O)$_2$—$C_1$-$C_3$ alkyl, —N(H)—C(O)—$C_1$-$C_3$ alkyl, —N(H)—C(O)—$C_1$-$C_3$ haloalkyl, —C(O)—N(H)—$C_1$-$C_3$ alkyl, —C(O)—N(H)—$C_1$-$C_3$ haloalkyl, or phenyl.

Embodiment 3(a) of this disclosure relates to the compound in any one of Embodiment 3, wherein:
$R^4$ is: (a1) saturated 5-6 membered heterocycloalkyl substituted with 0-1 $R^7$ groups, wherein the saturated heterocycloalkyl is further optionally substituted with one $R^8$ group.

Embodiment 3(b) of this disclosure relates to the compound in Embodiment 3, wherein:
$R^4$ is: (b1) cyclohexyl substituted with 0-1 $R^7$ group, wherein the saturated cyclohexyl is further optionally substituted with one $R^8$ group.

Embodiment 3(c) of this disclosure relates to the compound in Embodiment 3, wherein:
$R^4$ is: (b2) cyclohexenyl substituted with 0-1 $R^7$ groups, wherein the cycloalkenyl is further optionally substituted with one $R^8$ group.

Embodiment 3(d) of this disclosure relates to the compound in Embodiment 3, wherein:
$R^4$ is (c) phenyl, pyridyl or pyrazolyl, wherein the phenyl, pyridyl or pyrazolyl is optionally substituted with one $R^{10}$ group, and wherein the phenyl, pyridyl or pyrazolyl is further optionally substituted with one $R^{11}$ group.

Embodiment 3(e) of this disclosure relates to the compound in Embodiment 3, wherein:
$R^4$ is (d) ethynylene substituted with $R^{12}$.

Embodiment 3(f) of this disclosure relates to the compound in Embodiment 3, wherein:
(f) —N(H)($R^{15}$).

Embodiment 4 of this disclosure relates to the compound in any one of Embodiments 1, 1', 1(a), 1(b), 1(c), 1(d), 1(e), 1(f), 2 or 3, wherein $R^4$ is one of (a1)-(f):
(a1) saturated 5-6 membered heterocycloalkyl substituted with 0-1 $R^7$ groups, wherein the saturated heterocycloalkyl is further optionally substituted with one $R^8$ group;
(a2) unsaturated 5-6-membered N-substituted heterocycloalkyl substituted with 0-1 $R^7$ groups, wherein the six-membered N-substituted heterocycloalkyl is further optionally substituted with one $R^8$ group;
(b1) cyclohexyl substituted with 1 $R^7$ group, wherein the saturated cyclohexyl is further optionally substituted with one $R^8$ group;
(b2) cyclohexenyl substituted with 1 $R^7$ groups, wherein the cycloalkenyl is further optionally substituted with one $R^8$ group;
(c) phenyl, pyridyl or pyrazolyl, wherein the phenyl, pyridyl or pyrazolyl is optionally substituted with one $R^{10}$ group, and wherein the phenyl, pyridyl or pyrazolyl is further optionally substituted with one $R^{11}$ group;
(d) ethynylene substituted with $R^{12}$;
(e) —$C_1$-$C_{32}$ alkoxy optionally substituted with 1-2 $R^{13a}$; or
(f) —N(H)($R^{15}$);
$R^6$ is H, —$C_1$-$C_4$ alkyl, —$C_1$-$C_4$ haloalkyl, —$C_3$-$C_4$ cycloalkyl, 4-6 membered heterocycloalkyl, 5-6 membered heteroaryl, or phenyl;
each $R^7$ is independently —$C_1$-$C_4$ alkyl, fluoro, chloro, bromo, CN, hydroxyl, —$C_1$-$C_4$ haloalkyl, —$C_1$-$C_4$ cyanoalkyl, —$C_1$-$C_4$ hydroxyalkyl optionally substituted with heteroaryl, provided that fluoro, chloro, bromo, and CN are not bonded to a heteroatom;
$R^8$ is CN, phenyl, 5-6 membered heteroaryl, —C(O)—N(H)—$R^6$, —C(O)O$R^6$, —$(CH_2)_{0-1}$S(O)$_2R^6$; or

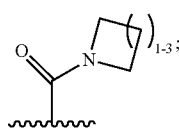

or R⁷ and R⁸, when both are attached to the same carbon atom of the saturated heterocycloalkyl, join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 —$C_1$-$C_4$ alkyl groups, and wherein the oxoheterocycloalkyl is optionally fused to an phenyl or 5-6 membered heteroaryl;

$R^{10}$ is —NHS(O)$_2$—$C_1$-$C_4$alkyl, —S(O)$_2$—$C_1$-$C_4$alkyl, —S(O)$_2$-5-6 membered heterocycloalkyl, —S(O)$_2$—N(H) $C_1$-$C_4$alkyl, —(CH$_2$)$_{0-1}$—C(O)NH$_2$, —(CH$_2$)$_{0-1}$—O-phenyl, —(CH$_2$)$_{0-1}$—O-(5-6 membered)heteroaryl, —(CH$_2$)$_{0-1}$—NHC(O)O—CH$_2$-phenyl, —(CH$_2$)$_{0-1}$—N(C(O)-5-6 membered heteroaryl, —(CH$_2$)$_{0-1}$—N(C(O)-phenyl, —$C_1$-$C_4$ alkylene-(5-6 membered)heterocycloalkylalkyl, —$C_2$-$C_4$alkenyl-, or CN;

$R^{11}$ is halogen, —$C_1$-$C_3$ alkyl $C_3$-$C_6$ cycloalkyl, $C_5$-$C_6$ cycloalkenyl or 5-6 membered heterocycloalkyl;

$R^{12}$ is 4-6 membered cycloalkylene-$R^{13a}$, —C(O)NHR⁶, —$Z^1$—(CH$_2$)$_{1-2}$—$Z^2$, —$Z^1$—($C_1$-$C_2$)haloalkylene-$Z^2$, or —$Z^1$—($C_1$-$C_2$)hydroxyalkylene-$Z^2$;

each $R^{13a}$ is F, Cl, hydroxyl, —$C_1$-$C_3$ alkyl, —$C_1$-$C_3$ hydroxyalkyl, —$C_1$-$C_3$ haloalkyl or CN;

$R^{15}$ is H, —$C_1$-$C_4$ alkyl, —$C_1$-$C_4$ haloalkyl, —$C_1$-$C_4$ hydroxyalkyl, —$C_1$-$C_4$ cyanoalkyl, heteroaryl-$C_1$-$C_4$ alkyl;

W is H, halogen, hydroxyl, —$C_1$-$C_6$ alkyl, —$C_1$-$C_6$ hydroxyalkyl, —$C_1$-$C_6$ haloalkyl, CN, or 5-6 membered heteroalkyl;

X is a bond;

$Z^1$ is absent, —$C_1$-$C_3$ alkylene, or —$C_1$-$C_3$ fluoroalkylene;

$Z^2$ is —$C_1$-$C_3$ alkoxyl, —N(H) S(O)$_2$—$C_1$-$C_3$ alkyl, —N(H)—C(O)—$C_1$-$C_3$ alkyl, —N(H)—C(O)—$C_1$-$C_3$ haloalkyl, —C(O)—N(H)—$C_1$-$C_3$ alkyl, —C(O)—N(H)—$C_1$-$C_3$ haloalkyl, or phenyl;

B is a bond, phenylene, 5-6 membered heteroarylene or 4-6 membered heterocycloalkylene, wherein the phenylene, 5-6 membered heteroarylene or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—N(H)—, —S(O)$_2$—, —S(O)$_2$—$C_1$-$C_3$ alkylene, N(H)C(O)—$C_1$-$C_3$ alkylene, —N(H)C(O)O $C_1$-$C_3$ alkylene, $C_1$-$C_4$ alkylene-N(H)—C(O)—, —N(H)—(CH$_2$)$_{0-3}$, —$C_1$-$C_5$ alkylene, —O—$C_1$-$C_5$ alkylene, —O—$C_1$-$C_5$haloalkylene, —O—$C_1$-$C_5$ alkylene-O—, or —O—$C_1$-$C_5$ hydroxyalkylene;

T is 5-10 membered heteroaryl, 6-10 membered aryl, $C_1$-$C_6$ alkyl, 3-6 membered cycloalkyl or 4-6 membered heterocycloalkyl; wherein the heteroaryl, —$C_1$-$C_6$ alkyl, 3-6 membered cycloalkyl or 4-6 membered heterocycloalkyl are each substituted with 0-3 G3 groups and 0-1 G4 groups;

or B-L is ethynylene and T is 5-10 membered heteroaryl substituted with 0-3 G3 groups;

each G1 is independently halogen, —$C_1$-$C_3$ alkyl, —$C_1$-$C_3$ alkoxy, —$C_1$-$C_3$ haloalkyl, hydroxyl, or $C_1$-$C_3$ hydroxyalkyl;

G2 is —$C_0$-$C_3$ alkylene-S(O)$_2$—$C_1$-$C_3$ alkyl, —$C_0$-$C_3$ alkylene-C(O)—NH$_2$, or —N(H)C(O)—$C_1$-$C_3$ alkyl;

each G3 is independently halogen, —$C_1$-$C_5$ alkyl, —$C_1$-$C_5$ alkoxy, —$C_1$-$C_5$ haloalkyl, hydroxyl, —$C_1$-$C_5$ hydroxyalkyl, or —$C_0$-$C_5$ alkylene-CN; and G4, when attached to a carbon atom, is halogen, —$C_1$-$C_5$ alkyl, —$C_1$-$C_5$ alkoxy, —$C_1$-$C_5$ haloalkyl, hydroxyl, —$C_1$-$C_5$ hydroxyalkyl, —$C_0$-$C_5$ alkylene-CN, —$C_0$-$C_3$ alkylene-S(O)$_2$—$C_1$-$C_3$ alkyl, —$C_0$-$C_3$ alkylene-N(H)—S(O)$_2$—$C_1$-$C_4$ alkyl, —$C_0$-$C_3$ alkylene-C(O)—NH$_2$, —$C_0$-$C_4$ alkylene-C(O)—N(H)—$C_1$-$C_2$ alkyl, —$C_1$-$C_4$ alkylene-N—($C_1$-$C_3$ alkyl)$_2$, —$C_1$-$C_4$ alkylene-N(H)—($C_1$-$C_3$ alkyl), —$C_1$-$C_4$ alkylene-NH$_2$, —$C_0$-$C_3$ alkylene-heterocycloalkyl, —$C_0$-$C_3$ alkylene-C(O)O—$C_1$-$C_4$ alkyl, or —$C_0$-$C_3$ alkylene-cycloalkyl optionally substituted with CN, OH, —$C_1$-$C_3$alkyl, —C(O)O—$C_1$-$C_3$ alkyl, —C(O)OH, or halogen;

or G4, when attached to a nitrogen atom, is-$C_1$-$C_6$alkyl, —$C_1$-$C_6$alkylene-$C_1$-$C_6$ alkoxy, —$C_1$-$C_6$ haloalkyl, —$C_1$-$C_6$ hydroxyalkyl, —$C_1$-$C_6$ alkylene-CN, —$C_1$-$C_3$ alkylene-S(O)$_2$—$C_1$-$C_3$ alkyl, —$C_1$-$C_3$ alkylene-N(H)—S(O)$_2$—$C_1$-$C_3$ alkyl, —$C_1$-$C_3$ alkylene-C(O)—NH$_2$, —$C_1$-$C_3$ alkylene-C(O)—N(H)$C_1$-$C_3$ alkyl, or —$C_1$-$C_5$ alkylene-cycloalkyl optionally substituted with CN, OH, $C_1$-$C_3$alkyl, —C(O)O—$C_1$-$C_3$ alkyl, —C(O)OH, or halogen.

Embodiment 4' of this disclosure relates to the compound in any one of Embodiments 1, 1', 1(a), 1(b), 1(c), 1(d), 1(e), 1(f), 2 or 3, wherein $R^4$ is one of (a1)-(f):

(a1) saturated 5-6 membered heterocycloalkyl substituted with 0-1 $R^7$ groups, wherein the saturated heterocycloalkyl is further optionally substituted with one $R^8$ group;

(a2) unsaturated 5-6-membered N-substituted heterocycloalkyl substituted with 0-1 $R^7$ groups, wherein the six-membered N-substituted heterocycloalkyl is further optionally substituted with one $R^8$ group;

(b1) cyclohexyl substituted with 1 $R^7$ group, wherein the saturated cyclohexyl is further optionally substituted with one $R^8$ group;

(b2) cyclohexenyl substituted with 1 $R^7$ groups, wherein the cycloalkenyl is further optionally substituted with one $R^8$ group;

(c) phenyl, pyridyl or pyrazolyl, wherein the phenyl, pyridyl or pyrazolyl is optionally substituted with one $R^{10}$ group, and wherein the phenyl, pyridyl or pyrazolyl is further optionally substituted with one $R^{11}$ group;

(d) ethynylene substituted with $R^{12}$;

(e) —$C_1$-$C_{32}$ alkoxy optionally substituted with 1-2 $R^{13a}$; or (f) —N(H)($R^{15}$);

$R^6$ is H, —$C_1$-$C_4$ alkyl, —$C_1$-$C_4$ haloalkyl, —$C_3$-$C_4$ cycloalkyl, 4-6 membered heterocycloalkyl, 5-6 membered heteroaryl, or phenyl;

each $R^7$ is independently —$C_1$-$C_4$ alkyl, fluoro, chloro, bromo, CN, hydroxyl, —$C_1$-$C_4$ haloalkyl, —$C_1$-$C_4$ cyanoalkyl, —$C_1$-$C_4$ hydroxyalkyl optionally substituted with heteroaryl, provided that fluoro, chloro, bromo, and CN are not bonded to a heteroatom;

$R^8$ is CN, phenyl, 5-6 membered heteroaryl, —C(O)—N (H)—R⁶, —C(O)OR⁶, —(CH$_2$)$_{0-1}$S(O)$_2$R⁶; or

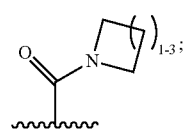

or R⁷ and R⁸, when both are attached to the same carbon atom of the saturated heterocycloalkyl, join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 —$C_1$-$C_4$ alkyl groups, and wherein the oxoheterocycloalkyl is optionally fused to an phenyl or 5-6 membered heteroaryl;

$R^{10}$ is —NHS(O)$_2$—$C_1$-$C_4$alkyl, —S(O)$_2$—$C_1$-$C_4$alkyl, —S(O)$_2$-5-6 membered heterocycloalkyl, —S(O)$_2$—N(H) $C_1$-$C_4$alkyl, —(CH$_2$)$_{0-1}$—C(O)NH$_2$, —(CH$_2$)$_{0-1}$—O-phenyl, —(CH$_2$)$_{0-1}$—O-(5-6 membered)heteroaryl, —(CH$_2$)$_{0-1}$—NHC(O)O—CH$_2$-phenyl, —(CH$_2$)$_{0-1}$—N(C(O)-5-6 membered heteroaryl, —(CH$_2$)$_{0-1}$—N(C(O)-phenyl, —$C_1$-$C_4$ alkylene-(5-6 membered)heterocycloalkylalkyl, —$C_2$-$C_4$alkenyl-, or CN;

$R^{11}$ is halogen, —$C_1$-$C_3$ alkyl $C_3$-$C_6$ cycloalkyl, $C_5$-$C_6$ cycloalkenyl or 5-6 membered heterocycloalkyl;

$R^{12}$ is 4-6 membered cycloalkylene-$R^{13a}$, —C(O)NHR$^6$, —$Z^1$—(CH$_2$)$_{1-2}$—$Z^2$, —$Z^1$—($C_1$-$C_2$)haloalkylene-$Z^2$, or —$Z^1$—($C_1$-$C_2$)hydroxyalkylene-$Z^2$;

each $R^{13a}$ is F, Cl, hydroxyl, —$C_1$-$C_3$ alkyl, —$C_1$-$C_3$ hydroxyalkyl, —$C_1$-$C_3$ haloalkyl or CN;

$R^{15}$ is H, —$C_1$-$C_4$ alkyl, —$C_1$-$C_4$ haloalkyl, —$C_1$-$C_4$ hydroxyalkyl, —$C_1$-$C_4$ cyanoalkyl, heteroaryl-$C_1$-$C_4$ alkyl;

W is H, halogen, hydroxyl, —$C_1$-$C_6$ alkyl, —$C_1$-$C_6$ hydroxyalkyl, —$C_1$-$C_6$ haloalkyl, CN, or 5-6 membered heteroalkyl;

X is a bond;

$Z^1$ is absent, —$C_1$-$C_3$ alkylene, or —$C_1$-$C_3$ fluoroalkylene;

$Z^2$ is —$C_1$-$C_3$ alkoxyl, —N(H) S(O)$_2$—$C_1$-$C_3$ alkyl, —N(H)—C(O)—$C_1$-$C_3$ alkyl, —N(H)—C(O)—$C_1$-$C_3$ haloalkyl, —C(O)—N(H)—$C_1$-$C_3$ alkyl, —C(O)—N(H)—$C_1$-$C_3$ haloalkyl, or phenyl;

B is a bond, phenylene, 5-6 membered heteroarylene or 4-6 membered heterocycloalkylene, wherein the phenylene, 5-6 membered heteroarylene or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—N(H)—, —S(O)$_2$—, —S(O)$_2$—$C_1$-$C_3$ alkylene, N(H)C(O)—$C_1$-$C_3$ alkylene, —N(H)C(O)O $C_1$-$C_3$ alkylene, $C_1$-$C_4$ alkylene-N(H)—C(O)—, —N(H)—(CH$_2$)$_{0-3}$, —$C_1$-$C_5$ alkylene, —O—$C_1$-$C_5$ alkylene, —O—$C_1$-$C_5$haloalkylene, —O—$C_1$-$C_5$ alkylene-O—, or —O—$C_1$-$C_5$ hydroxyalkylene;

T is 5-10 membered heteroaryl, 6-10 membered aryl, $C_1$-$C_6$ alkyl, 3-6 membered cycloalkyl or 4-6 membered heterocycloalkyl; wherein the heteroaryl, —$C_1$-$C_6$ alkyl, 3-6 membered cycloalkyl or 4-6 membered heterocycloalkyl are each substituted with 0-3 G3 groups and 0-1 G4 groups;

or B-L is ethynylene and T is 5-10 membered heteroaryl substituted with 0-3 G3 groups;

each G1 is independently halogen, —$C_1$-$C_3$ alkyl, —$C_1$-$C_3$ alkoxy, —$C_1$-$C_3$ haloalkyl, hydroxyl, or $C_1$-$C_3$ hydroxyalkyl;

G2 is —$C_0$-$C_3$ alkylene-S(O)$_2$—$C_1$-$C_3$ alkyl, —$C_0$-$C_3$ alkylene-C(O)—NH$_2$, or —N(H)C(O)—$C_1$-$C_3$ alkyl;

each G3 is independently halogen, —$C_1$-$C_5$ alkyl, —$C_1$-$C_5$ alkoxy, —$C_1$-$C_5$ haloalkyl, hydroxyl, —$C_1$-$C_5$ hydroxyalkyl, or —$C_0$-$C_5$ alkylene-CN; and G4, when attached to a carbon atom, is halogen, —$C_1$-$C_5$ alkyl, —$C_1$-$C_5$ alkoxy, —$C_1$-$C_5$ haloalkyl, hydroxyl, —$C_1$-$C_5$ hydroxyalkyl, —$C_0$-$C_5$ alkylene-CN, —$C_0$-$C_3$ alkylene-S(O)$_2$—$C_1$-$C_3$ alkyl, —$C_0$-$C_3$ alkylene-N(H)—S(O)$_2$—$C_1$-$C_4$ alkyl, —$C_0$-$C_3$ alkylene-C(O)—NH$_2$, —$C_0$-$C_3$ alkylene-C(O)—N(H)—$C_1$-$C_2$ alkyl, —$C_1$-$C_4$ alkylene-N—($C_1$-$C_3$ alkyl)$_2$, —$C_1$-$C_4$ alkylene-N(H)—($C_1$-$C_3$ alkyl), —$C_1$-$C_4$ alkylene-NH$_2$, —$C_0$-$C_3$ alkylene-heterocycloalkyl, —$C_0$-$C_3$ alkylene-C(O)O—$C_1$-$C_4$ alkyl, or —$C_0$-$C_3$ alkylene-cycloalkyl optionally substituted with CN, OH, —$C_1$-$C_3$alkyl, —C(O)O—$C_1$-$C_3$ alkyl, —C(O)OH, or halogen;

or G4, when attached to a nitrogen atom, is-$C_1$-$C_6$alkyl, —$C_1$-$C_6$ alkoxy, —$C_1$-$C_6$ haloalkyl, —$C_1$-$C_6$ hydroxyalkyl, —$C_1$-$C_6$ alkylene-CN, —$C_1$-$C_3$ alkylene-S(O)$_2$—$C_1$-$C_3$ alkyl, —$C_1$-$C_3$ alkylene-N(H)—S(O)$_2$—$C_1$-$C_3$ alkyl, —$C_1$-$C_3$ alkylene-C(O)—NH$_2$, —$C_1$-$C_3$ alkylene-C(O)—N(H) $C_1$-$C_3$ alkyl, or —$C_1$-$C_5$ alkylene-cycloalkyl optionally substituted with CN, OH, $C_1$-$C_3$alkyl, —C(O)O—$C_1$-$C_3$ alkyl, —C(O)OH, or halogen.

Embodiment 4(a) of this disclosure relates to the compound in Embodiment 4 or 4', wherein $R^4$ is:

(a1) saturated 5-6 membered heterocycloalkyl substituted with 0-1 $R^7$ groups, wherein the saturated heterocycloalkyl is further optionally substituted with one $R^8$ group.

Embodiment 4(b) of this disclosure relates to the compound in Embodiment 4 or 4', wherein $R^4$ is:

(a2) unsaturated 5-6-membered N-substituted heterocycloalkyl substituted with 0-1 $R^7$ groups, wherein the six-membered N-substituted heterocycloalkyl is further optionally substituted with one $R^8$ group.

Embodiment 4(c) of this disclosure relates to the compound in Embodiment 4 or 4', wherein $R^4$ is:

(b1) cyclohexyl substituted with 1 $R^7$ group, wherein the saturated cyclohexyl is further optionally substituted with one $R^8$ group.

Embodiment 4(d) of this disclosure relates to the compound in Embodiment 4 or 4', wherein $R^4$ is:

(b2) cyclohexenyl substituted with 1 $R^7$ groups, wherein the cycloalkenyl is further optionally substituted with one $R^8$ group.

Embodiment 4(e) of this disclosure relates to the compound in Embodiment 4 or 4', wherein $R^4$ is:

(c) phenyl, pyridyl or pyrazolyl, wherein the phenyl, pyridyl or pyrazolyl is optionally substituted with one $R^{10}$ group, and wherein the phenyl, pyridyl or pyrazolyl is further optionally substituted with one $R^{11}$ group.

Embodiment 4(f) of this disclosure relates to the compound in Embodiment 4 or 4', wherein $R^4$ is:

(d) ethynylene substituted with $R^{12}$.

Embodiment 4(g) of this disclosure relates to the compound in Embodiment 4 or 4', wherein $R^4$ is:

Embodiment 4(h) of this disclosure relates to the compound in Embodiment 4 or 4', wherein $R^4$ is:

B is a bond, phenylene, 5-6 membered heteroarylene or 4-6 membered heterocycloalkylene, wherein the phenylene, 5-6 membered heteroarylene or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—$C_1$-$C_3$ alkylene, —N(H)C(O)—$C_1$-$C_3$ alkylene, —N(H)C(O)O$C_1$-$C_3$ alkylene, —N(H)—(CH$_2$)$_{0-3}$—, —$C_1$-$C_5$ alkylene, —O—$C_1$-$C_5$ alkylene, —O—$C_1$-$C_5$haloalkylene, —O—$C_1$-$C_5$ alkylene-O—, or —O—$C_1$-$C_5$ hydroxyalkylene; and T is 5-10 membered heteroaryl, 6-10 membered aryl, $C_1$-$C_6$ alkyl, 3-6 membered cycloalkyl or 4-6 membered heterocycloalkyl; wherein the heteroaryl, —$C_1$-$C_6$ alkyl, 3-6 membered cycloalkyl or 4-6 membered heterocycloalkyl are each substituted with 0-3 G3 groups and 0-1 G4 groups.

Embodiment 4(i) of this disclosure relates to the compound in Embodiment 4 or 4', wherein $R^4$ is: B-L is ethynylene and T is 5-10 membered heteroaryl substituted with 0-3 G3 groups.

Embodiment 5 of this disclosure relates to the compound in any one of Embodiments 1, 1', 2, 3, 3(a). 3(b), 3(c), 3(d), 3(e), 3(f), 4, 4', 4(a), 4(b), 4(c), 4(d), 4(e), 4(f) or 4(g), wherein:

B is a bond, phenylene, 5-6 membered heteroarylene or 4-6 membered heterocycloalkylene, wherein the phenylene, 5-6 membered heteroarylene or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—C$_1$-C$_3$ alkylene, —N—(H)C(O)—C$_1$-C$_3$ alkylene, —N(H)C(O)OC$_1$-C$_3$ alkylene, —N(H)—(CH$_2$)$_{0-3}$—, —C$_1$-C$_4$ alkylene, —O—C$_1$-C$_4$ alkylene, —O—C$_1$-C$_4$ haloalkylene, —O—C$_1$-C$_4$ alkylene-O—, or —O—C$_1$-C$_4$ hydroxyalkylene;

T is 5-10 membered heteroaryl, 6-10 membered aryl, —C$_1$-C$_4$ alkyl, 3-6 membered cycloalkyl or 4-6 membered heterocycloalkyl; wherein the heteroaryl, C$_1$-C$_6$ alkyl, 3-6 membered cycloalkyl or 4-6 membered heterocycloalkyl are each substituted with 0-2 G3 groups and 0-1 G4 Groups;

each G1 is independently halogen, —C$_1$-C$_2$ alkyl, C$_1$-C$_2$ alkoxy, —C$_1$-C$_2$ fluoroalkyl, hydroxyl, or —C$_1$-C$_2$ hydroxyalkyl;

G2 is —S(O)$_2$—C$_1$-C$_2$ alkyl, —C$_0$-C$_2$ alkylene-C(O)—NH$_2$, or —N(H)C(O)—C$_1$-C$_2$ alkyl;

each G3 is independently halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, or —C$_0$-C$_4$ alkylene-CN; and G4, when attached to a carbon atom, is halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, or —C$_0$-C$_4$ alkylene-CN—C$_0$-C$_2$ alkylene-S(O)$_2$—C$_1$-C$_2$ alkyl, —N(H)—S(O)$_2$—C$_1$-C$_3$ alkyl, —C$_0$-C$_2$ alkylene-C(O)—NH$_2$, —C$_0$-C$_2$ alkylene-C(O)—N(H)—CH$_3$, —C$_1$-C$_3$ alkylene-N—(C$_1$-C$_2$ alkyl)$_2$, —C$_1$-C$_3$ alkylene-N(H)—(C$_1$-C$_2$ alkyl), —C$_1$-C$_3$ alkylene-NH$_2$, —C$_0$-C$_4$ alkylene-pyrrolidinyl, —C$_0$-C$_4$ alkylene-cyclopropyl, —C$_0$-C$_2$ alkylene-C(O)O—C$_1$-C$_3$ alkyl, —C$_0$-C$_2$ alkylene-cyclopropylene-OH, —C$_0$-C$_2$ alkylene-cyclopropylene-C(O)O—C$_1$-C$_4$ alkyl, —C$_0$-C$_2$ alkylene-cyclopropylene-C(O)OH, or —C$_0$-C$_2$ alkylene-cyclopropylene-CN;

or G4, when attached to a nitrogen atom, is-C$_1$-C$_5$ alkyl, —C$_1$-C$_5$alkylene-C$_1$-C$_5$ alkoxy, —C$_1$-C$_5$ haloalkyl, —C$_1$-C$_5$ hydroxyalkyl, —C$_1$-C$_5$ alkylene-CN, —C$_1$-C$_2$ alkylene-S(O)$_2$—C$_1$-C$_2$ alkyl, —C$_1$-C$_3$ alkylene-C(O)—NH$_2$, or, —C$_1$-C$_3$ alkylene-C(O)—N(H)C$_1$-C$_2$ alkyl, —C$_1$-C$_4$ alkylene-cyclopropyl, or —C$_1$-C$_4$ alkylene-cyclopropylene-CN.

Embodiment 5' of this disclosure relates to the compound in any one of Embodiments 1, 1', 2, 3, 3(a). 3(b), 3(c), 3(d), 3(e), 3(f), 4, 4', 4(a), 4(b), 4(c), 4(d), 4(e), 4(f) or 4(g), wherein:

B is a bond, phenylene, 5-6 membered heteroarylene or 4-6 membered heterocycloalkylene, wherein the phenylene, 5-6 membered heteroarylene or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—C$_1$-C$_3$ alkylene, —N—(H)C(O)—C$_1$-C$_3$ alkylene, —N(H)C(O)OC$_1$-C$_3$ alkylene, —N(H)—(CH$_2$)$_{0-3}$—, —C$_1$-C$_4$ alkylene, —O—C$_1$-C$_4$ alkylene, —O—C$_1$-C$_4$ haloalkylene, —O—C$_1$-C$_4$ alkylene-O—, or —O—C$_1$-C$_4$ hydroxyalkylene;

T is 5-10 membered heteroaryl, 6-10 membered aryl, —C$_1$-C$_4$ alkyl, 3-6 membered cycloalkyl or 4-6 membered heterocycloalkyl; wherein the heteroaryl, C$_1$-C$_6$ alkyl, 3-6 membered cycloalkyl or 4-6 membered heterocycloalkyl are each substituted with 0-2 G3 groups and 0-1 G4 Groups;

each G1 is independently halogen, —C$_1$-C$_2$ alkyl, C$_1$-C$_2$ alkoxy, —C$_1$-C$_2$ fluoroalkyl, hydroxyl, or —C$_1$-C$_2$ hydroxyalkyl;

G2 is —S(O)$_2$—C$_1$-C$_2$ alkyl, —C$_0$-C$_2$ alkylene-C(O)—NH$_2$, or —N(H)C(O)—C$_1$-C$_2$ alkyl;

each G3 is independently halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, or —C$_0$-C$_4$ alkylene-CN; and G4, when attached to a carbon atom, is halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, or —C$_0$-C$_4$ alkylene-CN—C$_0$-C$_2$ alkylene-S(O)$_2$—C$_1$-C$_2$ alkyl, —N(H)—S(O)$_2$—C$_1$-C$_3$ alkyl, —C$_0$-C$_2$ alkylene-C(O)—NH$_2$, —C$_0$-C$_2$ alkylene-C(O)—N(H)—CH$_3$, —C$_1$-C$_3$ alkylene-N—(C$_1$-C$_2$ alkyl)$_2$, —C$_1$-C$_3$ alkylene-N(H)—(C$_1$-C$_2$ alkyl), —C$_1$-C$_3$ alkylene-NH$_2$, —C$_0$-C$_4$ alkylene-pyrrolidinyl, —C$_0$-C$_4$ alkylene-cyclopropyl, —C$_0$-C$_2$ alkylene-C(O)O—C$_1$-C$_3$ alkyl, —C$_0$-C$_2$ alkylene-cyclopropylene-OH, —C$_0$-C$_2$ alkylene-cyclopropylene-C(O)O—C$_1$-C$_4$ alkyl, —C$_0$-C$_2$ alkylene-cyclopropylene-C(O)OH, or —C$_0$-C$_2$ alkylene-cyclopropylene-CN;

or G4, when attached to a nitrogen atom, is-C$_1$-C$_5$ alkyl, —C$_1$-C$_5$ alkoxy, —C$_1$-C$_5$ haloalkyl, —C$_1$-C$_5$ hydroxyalkyl, —C$_1$-C$_5$ alkylene-CN, —C$_1$-C$_2$ alkylene-S(O)$_2$—C$_1$-C$_2$ alkyl, —C$_1$-C$_3$ alkylene-C(O)—NH$_2$, or, —C$_1$-C$_3$ alkylene-C(O)—N(H)C$_1$-C$_2$ alkyl, —C$_1$-C$_4$ alkylene-cyclopropyl, or —C$_1$-C$_4$ alkylene-cyclopropylene-CN.

Embodiment 6 of this disclosure relates to the compound in any one of Embodiments 1, 1', 2, 3, 3(a), 3(b), 3(c), 3(d), 3(e), 3(f), 4, 4' 4(a), 4(b), 4(c), 4(d), 4(e), 4(f), 4(g), 5, or 5', wherein:

B and L are bonds, and T is a 9-10 membered bicyclic fused aryl, or a 9-10 membered bicyclic fused heteroaryl, wherein the bicyclic fused aryl or the bicyclic fused heteroaryl are each optionally substituted as defined in (i) or (ii):

(i) 1-3 substituents, each independently C$_1$-C$_2$ alkyl, halogen, C$_1$-C$_2$ haloalkyl, hydroxyl and C$_1$-C$_2$ hydroxyalkyl, or (ii) —C(O)-heterocycloalkyl optionally substituted with R$^{13b}$; and R$^{13b}$ H, alkyl, CN, hydroxyl, hydroxyalkyl or haloalkyl.

Embodiment 7 of this disclosure relates to the compound in any one of Embodiments 1, 1', 2, 3, 3(a), 3(b), 3(c), 3(d), 3(e), 3(f), 4, 4', 4(a), 4(b), 4(c), 4(d), 4(e), 4(f), 4(g), 5, 5' or 6, wherein:

B and L are bonds, and T is a naphthalenyl, isoquinolinyl, quinolinyl, isoindolyl, 1H-indazolyl, 2H-indazolyl, 1H-benzimidazolyl, 1,3-dihydro-2H-inden-2-one-5-yl, 2,3-dihydrobenzofuranyl, 2,3-dihydrobenzo[d]thiazolyl, benzothiophenyl, imidazo[1,2-a]pyridinyl, indolin-2-one, each optionally substituted as defined in (i) or (ii):

(i) 1-2 substituents, each independently —C$_1$-C$_2$ alkyl, halogen, —C$_1$-C$_2$ haloalkyl, hydroxyl and —C$_1$-C$_2$ hydroxyalkyl, or (ii) —C(O)-5-6 membered heterocycloalkyl optionally substituted with R$^{13b}$; and R$^{13b}$ is —C$_1$-C$_2$alkyl, —C$_1$-C$_2$ hydroxyalkyl or —C$_1$-C$_2$ fluoroalkyl.

Embodiment 8 of this disclosure relates to the compound in any one of Embodiments 1, 1', 1(a), 1(b), 1(c), 1(d), 1(e), 1(f), 2, 3, 4, 4', 4(h), 4(i), 5, 5', 6, or 7, wherein:

33

$R^4$ is:

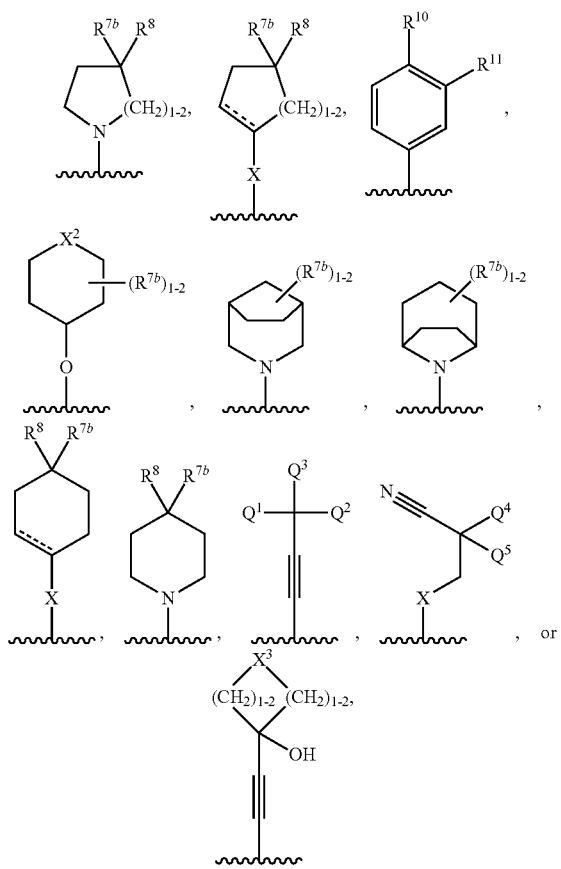

wherein:
≡≡≡≡ is a single or double bond;
X is a bond, —N(H)—, —O or —(C$_1$-C$_3$)alkylene;
$X^2$ is O, N($R^{17}$), S, S(O), S(O)$_2$;
$X^3$ is a —CH$_2$—, —N(H)—, or —O—;
$R^6$ is H, —(C$_1$-C$_4$)alkyl, —(C$_1$-C$_4$)haloalkyl, or —(C$_3$-C$_6$)cycloalkyl;
each $R^{7b}$ is independently H, —C$_1$-C$_4$ alkyl, fluoro, chloro, CN, hydroxyl, —C$_1$-C$_3$ haloalkyl, or —C$_1$-C$_3$ cyanoalkyl;
$R^8$ is CN, —(CH$_2$)$_{0-1}$—C(O)—N(H)—$R^6$, —(CH$_2$)$_{0-1}$—C(O)—NH$_2$, —(CH$_2$)$_{0-1}$C(O)O$R^6$, or

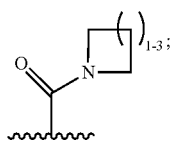

or $R^{7b}$ and $R^8$ join together, with the carbon to which they are attached, to form a 5-6 membered heterocycloalkyl, wherein the 5-6 membered heterocycloalkyl is substituted with one or two oxo groups, and further optionally substituted with 1-2 alkyl groups, wherein the 5-6 membered heterocycloalkyl is optionally fused to phenyl when the 5-6 membered heterocycloalkyl is a six membered ring;
$R^9$ is H, alkyl, or haloalkyl;
$R^{10}$ is —S(O)$_2$—N(H)alkyl, —O-phenyl, —(CH$_2$)$_2$-piperidine, or CN;

34

$R^{11}$ is H or heterocycloalkyl;
$R^{17}$ is H, C$_1$-C$_3$ alkyl, —C(O)C$_1$-C$_3$ alkyl, —C(O)—O—C$_1$-C$_3$ alkyl, or —C(O)NH$_2$;
$Q^1$ is —C$_1$-C$_4$ alkyl, —C$_1$-C$_4$ haloalkyl;
$Q^2$ is —C$_1$-C$_4$ alkyl, —C$_1$-C$_4$ haloalkyl;
or $Q^1$ and $Q^2$, together with carbon atom to which they are attached, is —C$_3$-C$_6$ cycloalkyl, or a 4-6 membered heterocycloalkyl; and
$Q^3$ is CN, OH, —C(O)NH$R^6$, —N(H)—S(O)$_2$—C$_1$-C$_3$ alkyl, —N(H)—C(O)—C$_1$-C$_3$ alkyl or phenyl.

Embodiment 8(a) of this disclosure relates to the compound in Embodiment 8, wherein:

$R^4$ is:

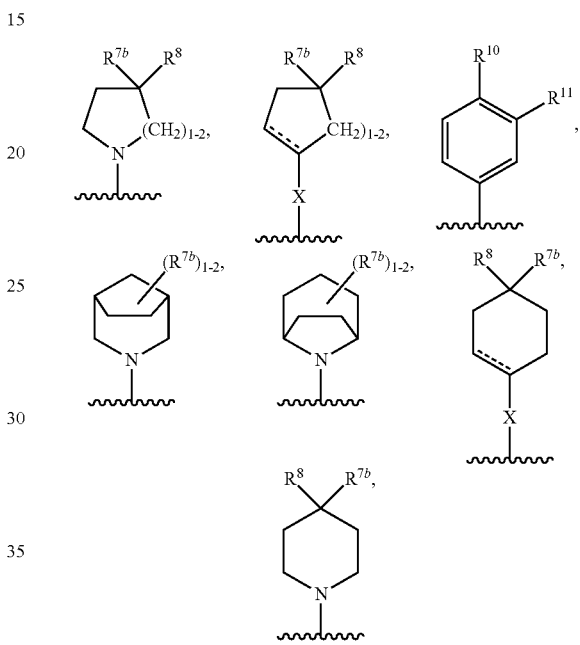

≡≡≡≡ is a single or double bond;
X is a bond;
$R^6$ is H, —(C$_1$-C$_4$)alkyl, —(C$_1$-C$_4$)haloalkyl, or —(C$_3$-C$_6$)cycloalkyl;
each $R^{7b}$ is independently H, —C$_1$-C$_4$ alkyl, fluoro, chloro, CN, hydroxyl, —C$_1$-C$_3$ haloalkyl, or —C$_1$-C$_3$ cyanoalkyl;
$R^8$ is CN, —(CH$_2$)$_{0-1}$—C(O)—N(H)—$R^6$, —(CH$_2$)$_{0-1}$—C(O)—NH$_2$, —(CH$_2$)$_{0-1}$C(O)O$R^6$, or

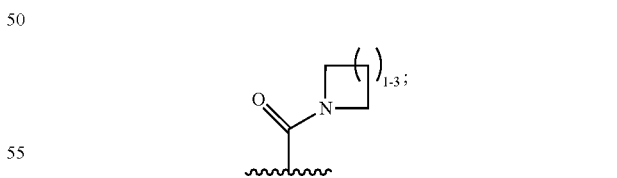

or $R^{7b}$ and $R^8$ join together, with the carbon to which they are attached, to form a 5-6 membered heterocycloalkyl, wherein the 5-6 membered heterocycloalkyl is substituted with one or two oxo groups, and further optionally substituted with 1-2 alkyl groups, wherein the 5-6 membered heterocycloalkyl is optionally fused to phenyl when the 5-6 membered heterocycloalkyl is a six membered ring;
$R^9$ is H, alkyl, or haloalkyl;
$R^{10}$ is —S(O)$_2$—N(H)alkyl, —O-phenyl, —(CH$_2$)$_2$-piperidine, or CN;

$R^{11}$ is H or heterocycloalkyl; and
$R^{17}$ is H, $C_1$-$C_3$ alkyl, —C(O) $C_1$-$C_3$ alkyl, —C(O)—O—$C_1$-$C_3$ alkyl, or —C(O)NH$_2$.

Embodiment 8(b) of this disclosure relates to the compound in Embodiment 8, wherein:
$R^4$ is:

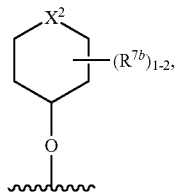

wherein:
$X^2$ is O, N($R^{17}$), S, S(O), S(O)$_2$;
each $R^{7b}$ is independently H, —$C_1$-$C_4$ alkyl, fluoro, chloro, CN, hydroxyl, —$C_1$-$C_3$ haloalkyl, or —$C_1$-$C_3$ cyanoalkyl; and
$R^{17}$ is H, $C_1$-$C_3$ alkyl, —C(O)—$C_1$-$C_3$ alkyl, —C(O)—O—$C_1$-$C_3$ alkyl, or —C(O)NH$_2$.

Embodiment 8(c) of this disclosure relates to the compound in Embodiment 8, wherein:
$R^4$ is:

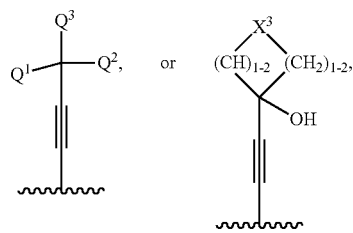

X is a bond, —N(H)—, —O— or —CH$_2$—;
$X^3$ is (CH$_2$)$_{1-3}$, O or N(H);
$Q^1$ is H, —$C_1$-$C_4$ alkyl, $C_1$-$C_4$ haloalkyl;
$Q^2$ is H, —$C_1$-$C_4$ alkyl, —$C_1$-$C_4$ haloalkyl;
or $Q^1$ and $Q^2$, together with carbon atom to which they are attached, is $C_3$-$C_6$ cycloalkyl, or a 4-6 membered heterocycloalkyl; and
$Q^3$ is CN, OH, —C(O)NHR$^6$, —N(H)—S(O)$_2$—$C_1$-$C_3$ alkyl, —N(H)—C(O)—$C_1$-$C_3$ alkyl or phenyl.

Embodiment 8(d) of this disclosure relates to the compound in Embodiment 8, wherein:
$R^4$ is:

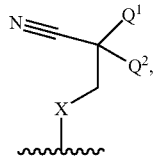

X is a bond, —N(H)—, —O— or —CH$_2$—;
$Q^1$ is H, —$C_1$-$C_4$ alkyl, $C_1$-$C_4$ haloalkyl; and
$Q^2$ is H, —$C_1$-$C_4$ alkyl, —$C_1$-$C_4$ haloalkyl;
or $Q^1$ and $Q^2$, together with carbon atom to which they are attached, is $C_3$-$C_6$ cycloalkyl, or a 4-6 membered heterocycloalkyl.

Embodiment 9 of this disclosure relates to the compound in any one of Embodiments 1, 1', 1(a), 1(b), 1(c), 1(d), 1(e), 1(f), 2, 3, 4, 4', 4(h), 4(i), 5, 5', 6, 7 or 8, wherein $R^4$ is:

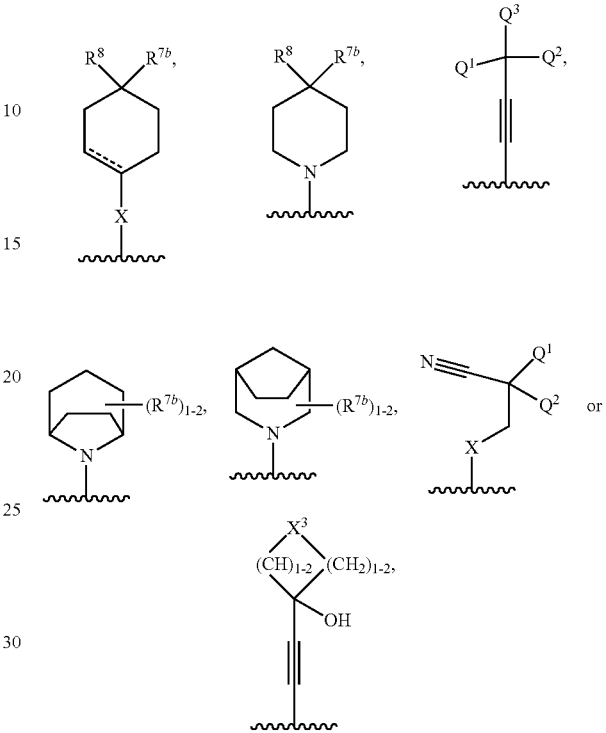

X is a bond, —N(H)—, —O— or —CH$_2$—;
$X^3$ is (CH$_2$)$_{1-3}$, O or N(H);
$Q^1$ is H, —$C_1$-$C_4$ alkyl, $C_1$-$C_4$ haloalkyl;
$Q^2$ is H, —$C_1$-$C_4$ alkyl, —$C_1$-$C_4$ haloalkyl;
or $Q^1$ and $Q^2$, together with carbon atom to which they are attached, is $C_3$-$C_6$ cycloalkyl, or a 4-6 membered heterocycloalkyl; and
$Q^3$ is CN, OH, —C(O)NHR$^6$, —N(H)—S(O)$_2$—$C_1$-$C_3$ alkyl, —N(H)—C(O)—$C_1$-$C_3$ alkyl or phenyl.

Embodiment 10 of this disclosure relates to the compound in any one of Embodiments 1, 1', 1(a), 1(b), 1(c), 1(d), 1(e), 1(f), 2, 3, 4, 4', 4(h), 4(i), 5, 5', 6, 7, 8 or 9, wherein $R^4$ is:

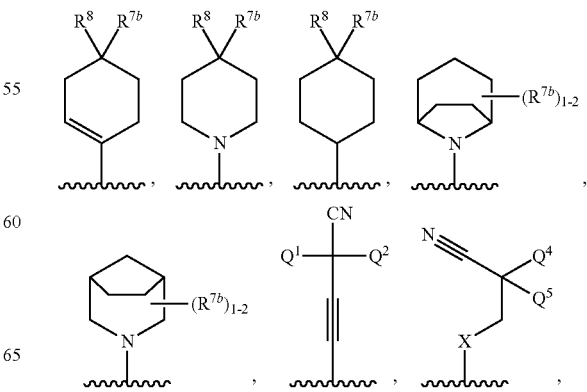

-continued

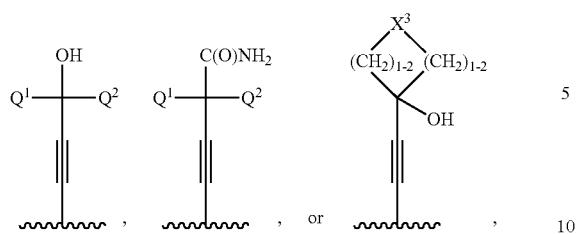

wherein

X is a bond, —N(H)—, —O— or —CH$_2$—;

X$^3$ is O or N(H);

Q$^1$ is —C$_1$-C$_4$ alkyl or —C$_1$-C$_4$ haloalkyl; and

Q$^2$ is —C$_1$-C$_4$ alkyl or —C$_1$-C$_4$ haloalkyl;

or Q$^1$ and Q$^2$, together with carbon atom to which they are attached, is —C$_3$-C$_6$ cycloalkyl, or a 4-6 membered heterocycloalkyl.

Embodiment 11 of this disclosure relates to the compound in any one of Embodiments 1, 1', 1(a), 1(b), 1(c), 1(d), 1(e), 1(f), 2, 3, 4, 4', 5, 5', 6, 7, 8, 9, or 10 wherein R$^4$ is:

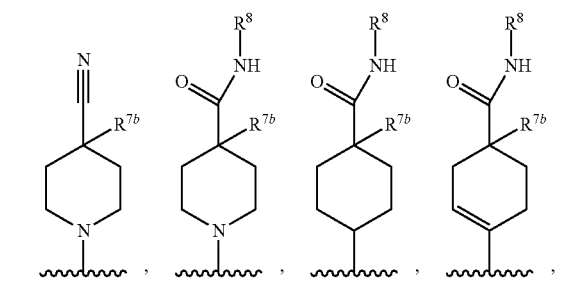

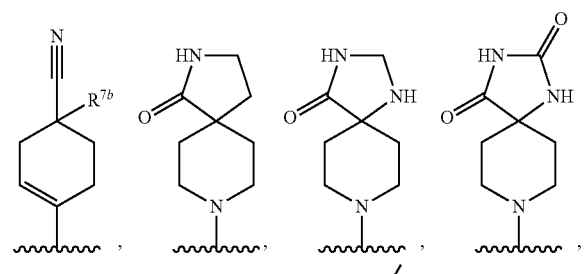

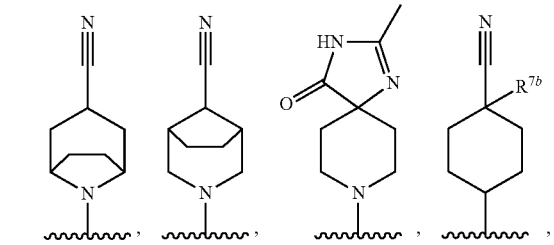

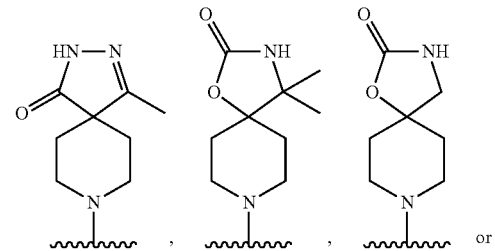

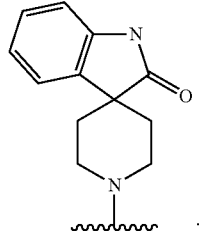

Embodiment 12 of this disclosure relates to the compound in any one of Embodiments 1, 1', 1(a), 1(b), 1(c), 1(d), 1(e), 1(f), 2, 3, 4, 4', 4(h), 4(i), 5, 5', 6, 7, 8, 9, 10 or 11, wherein R$^4$ is:

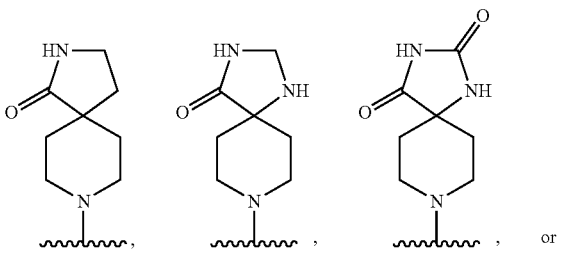

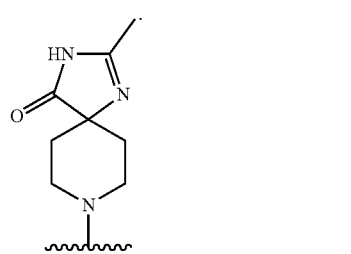

Embodiment 12(a) of this disclosure relates to the compound Embodiment 12, wherein R$^4$ is:

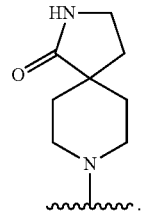 [SMILES: *N1CCC2(CCNC2=O)CC1]

Embodiment 12(b) of this disclosure relates to the compound Embodiment 12, wherein R$^4$ is:

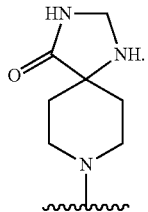 [SMILES: *N1CCC2(CC1)NCNC2=O]

Embodiment 12(c) of this disclosure relates to the compound Embodiment 12, wherein R$^4$ is:

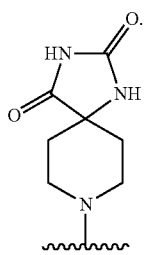 [SMILES: *N1CCC2(CC1)NC(=O)NC2=O]

Embodiment 12(d) of this disclosure relates to the compound Embodiment 12, wherein R⁴ is:

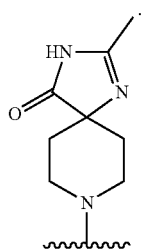

Embodiment 13 of this disclosure relates to the compound in any one of Embodiments 1, 1', 1(a), 1(b), 1(c), 1(d), 1(e), 1(f), 2, 3, 4, 4', 4(h), 4(i), 5, 5', 6, 7, 8, 9, 10 or 11, wherein R⁴ is:

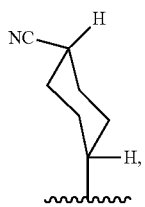 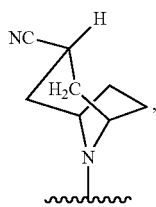 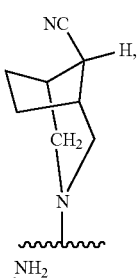

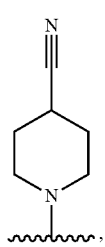, 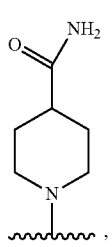, 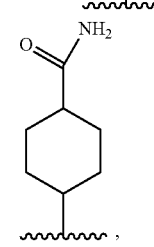, or

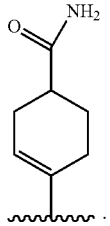

Embodiment 13(a) of this disclosure relates to the compound in Embodiment 13, wherein R⁴ is:

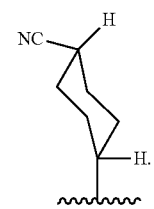

Embodiment 13(b) of this disclosure relates to the compound in Embodiment 13, wherein R⁴ is:

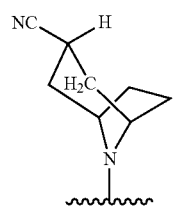

Embodiment 13(c) of this disclosure relates to the compound in Embodiment 13, wherein R⁴ is:

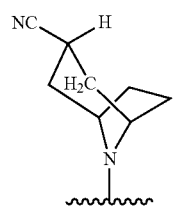

Embodiment 13(d) of this disclosure relates to the compound in Embodiment 13, wherein R⁴ is:

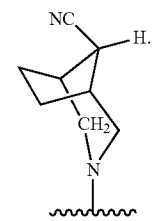

Embodiment 13(e) of this disclosure relates to the compound in Embodiment 13, wherein R⁴ is:

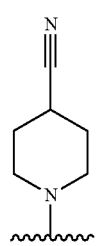

Embodiment 13(f) of this disclosure relates to the compound in Embodiment 13, wherein R⁴ is:

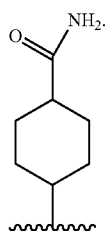

Embodiment 13(g) of this disclosure relates to the compound in Embodiment 13, wherein $R^4$ is:

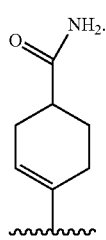

Embodiment 14 of this disclosure relates to the compound in any one of Embodiments 1, 1', 1(a), 1(b), 1(c), 1(d), 1(e), 1(f), 2, 3, 4, 4', 4(h), 4(i), 5, 5', 6, 7, 8, 9, 10, 11 or 13, wherein $R^4$ is:

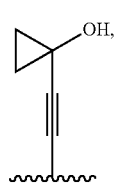 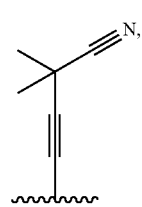  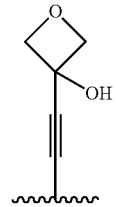

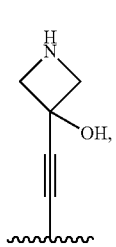 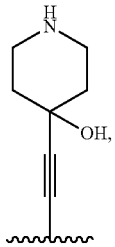 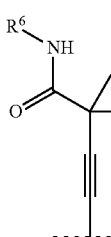 , or 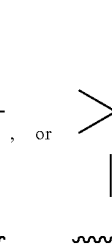 .

Embodiment 14(a) of this disclosure relates to the compound m Embodiment 14, wherein $R^4$ is:

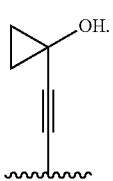 [SMILES: *C#CC1(O)CC1]

Embodiment 14(b) of this disclosure relates to the compound in Embodiment 14, wherein $R^4$ is:

Embodiment 14(c) of this disclosure relates to the compound in Embodiment 14, wherein $R^4$ is:

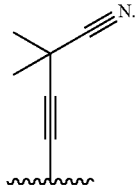 [SMILES: *C#CC(C)(C)C#N]

Embodiment 14(d) of this disclosure relates to the compound in Embodiment 14, wherein $R^4$ is:

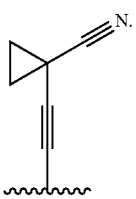 [SMILES: *C#CC1(C#N)CC1]

Embodiment 14(e) of this disclosure relates to the compound in Embodiment 14, wherein $R^4$ is:

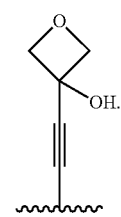 [SMILES: *C#CC1(O)COC1]

Embodiment 14(f) of this disclosure relates to the compound in Embodiment 14, wherein $R^4$ is:

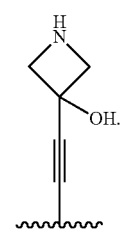 [SMILES: *C#CC1(O)CNC1]

Embodiment 14(g) of this disclosure relates to the compound in Embodiment 14, wherein $R^4$ is:

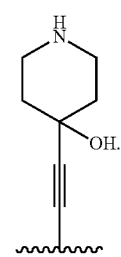 [SMILES: *C#CC1(O)CCNCC1]

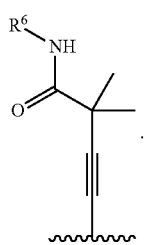
Embodiment 14(h) of this disclosure relates to the compound in Embodiment 14, wherein R⁴ is:
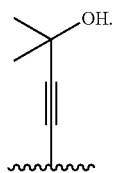 [SMILES: *C#CC(C)(C)O]
Embodiment 15 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g) or 14(h), wherein R³ is:
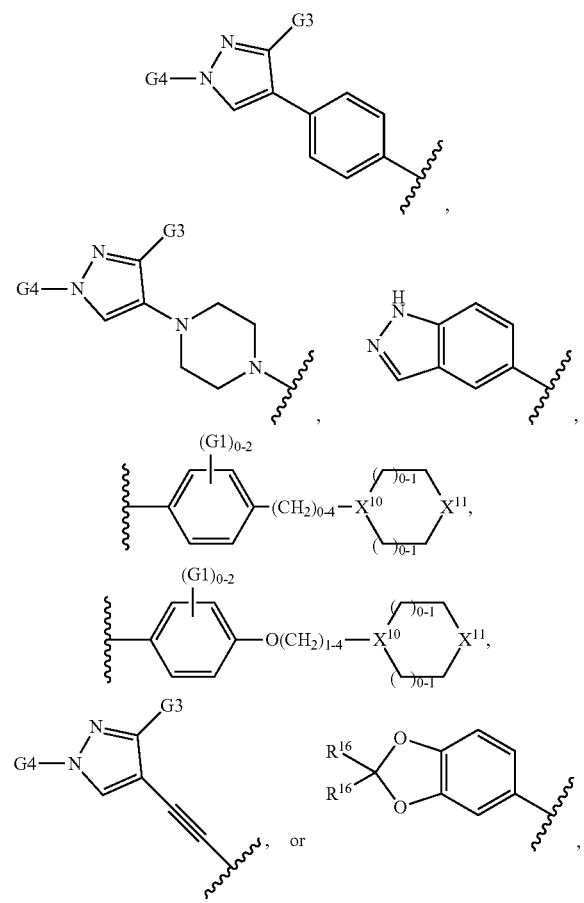
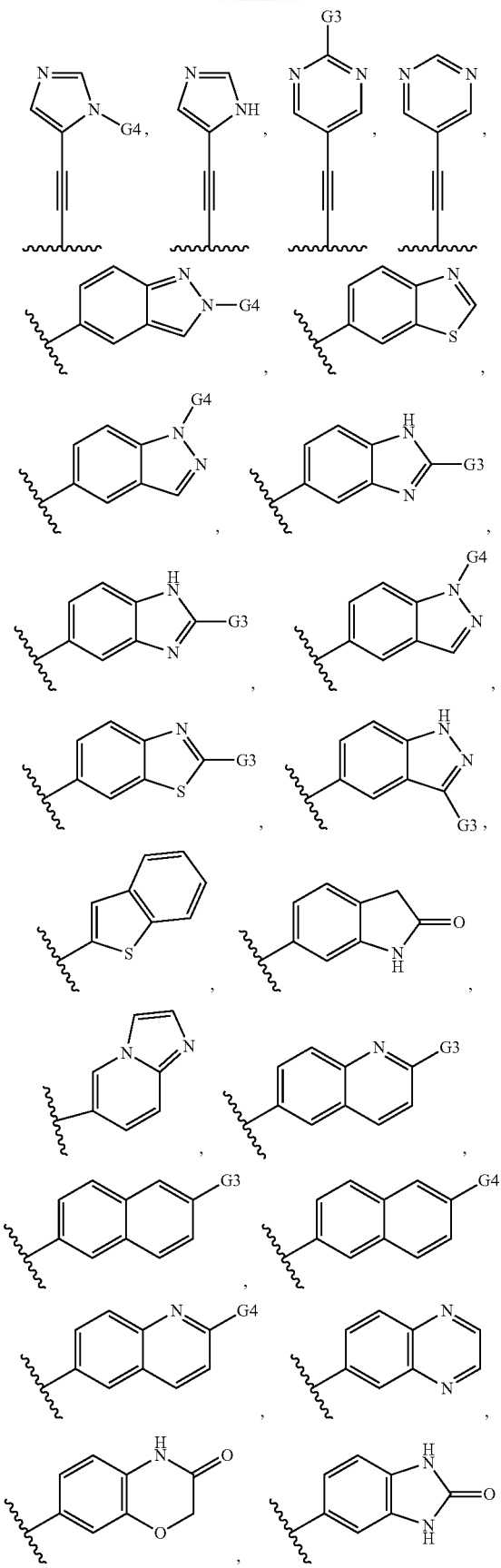

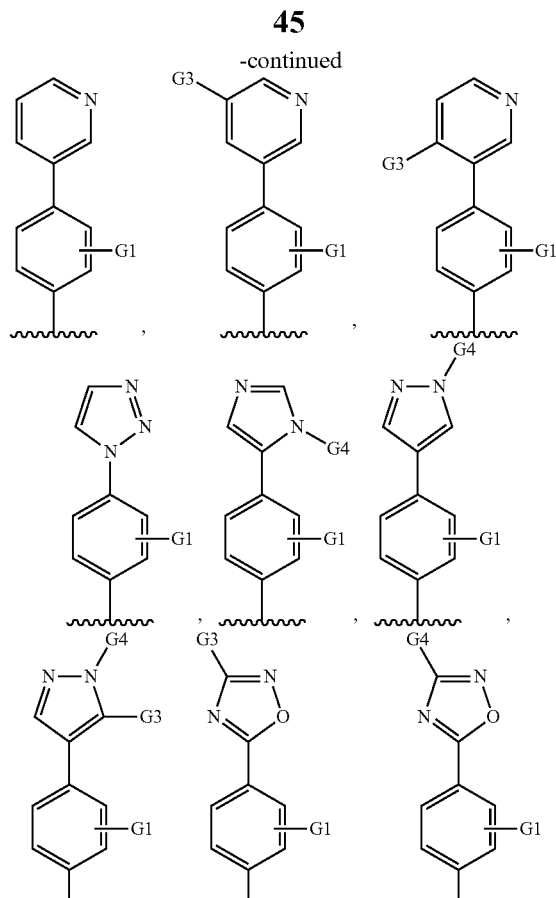

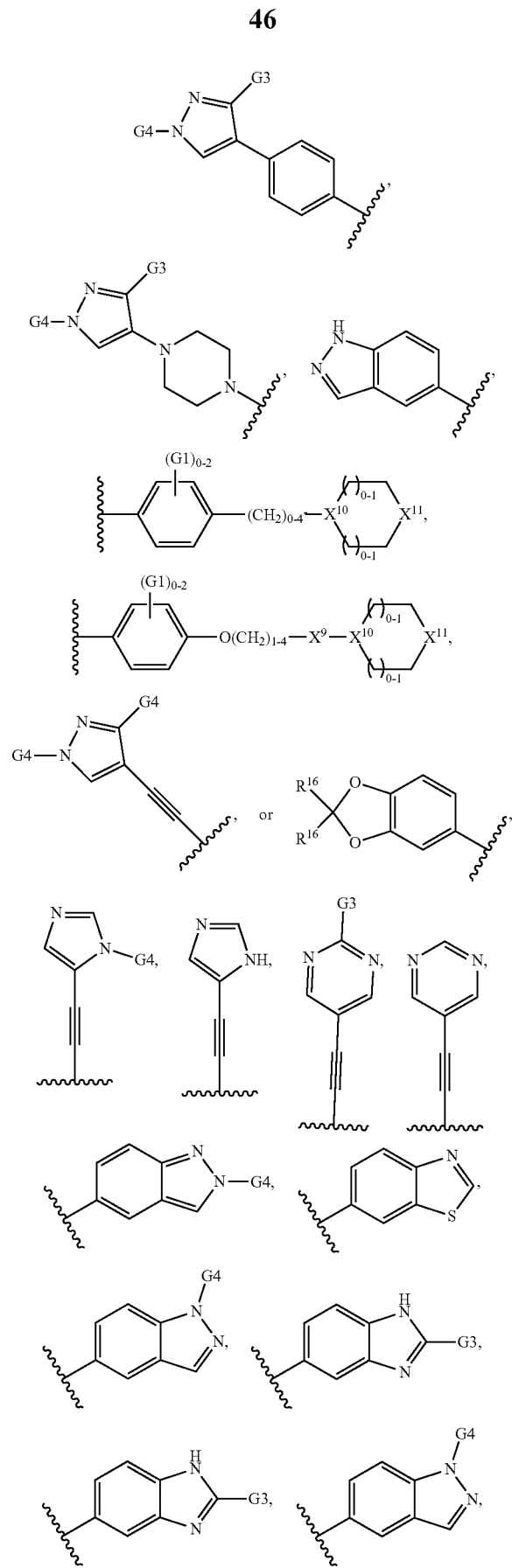

wherein:

G1 is H, CH₃, or F;

G3 is —CH₃, —CH₂F, CHF₂, —CF₃, —OCH₃, —CH₂—CH₂F, —(CH₂)₂—CN, —(CH₂)₃—CN, —(CH₂)₁₋₂C(CH₃)₂—CN, or —(CH₂)₁₋₂C(CH₃)₂—OH; and G4 is —CH₃, —CH₂F, CHF₂, —CF₃, —CH₂—CH₂F, —CH₂—CH₃, —CH₂—CHF₂, —CH₂—CF₃, —CH₂—CH₂—CH₂F, —(CH₂)₁₋₂C(CH₃)₂—OH; —C₁-C₄ alkylene-cyclopropyl, —C₁-C₄ alkylene-cyclopropylene-CN, —C₁-C₄ alkylene-cyclopropylene-OH, —C₁-C₅ alkylene-CN, or —(CH₂)₁₋₃N(CH₃)₂;

each R¹⁶ is H, halogen, (C₁-C₄)alkyl optionally substituted with halogen;

X⁹ is a bond or O;

X¹⁰ is CH, —C(CH₃)—, N; and

X¹¹ is —CH₂, NH, O, S, S(O), or S(O)₂.

Embodiment 15(a) of this disclosure relates to the compound of Embodiment-15, wherein G4 is —CH₃, —CH₂F, CHF₂, —CF₃, —CH₂—CH₂—CH₂F, —(CH₂)₁₋₂C(CH₃)₂—OH; —C₁-C₄ alkylene-cyclopropyl, —C₁-C₄ alkylene-cyclopropylene-CN, —C₁-C₄ alkylene-cyclopropylene-OH, —C₁-C₅ alkylene-CN, or —(CH₂)₁₋₃N(CH₃)₂.

Embodiment 15(b) of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g) or 14(h), wherein R³ is:

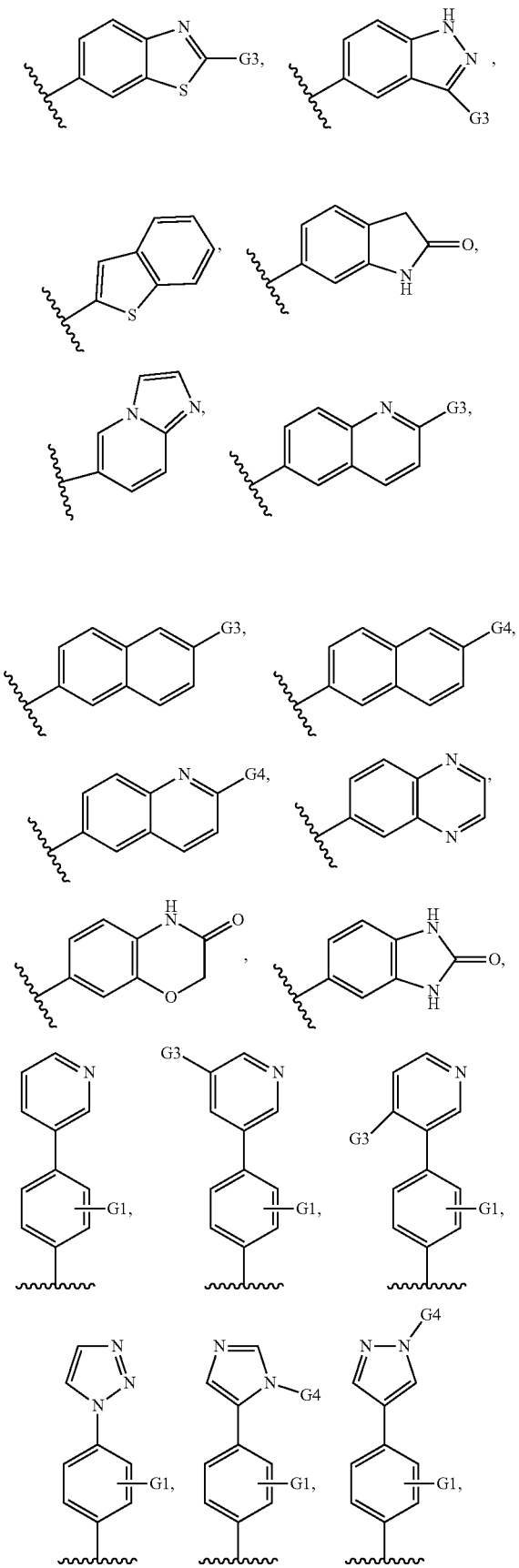

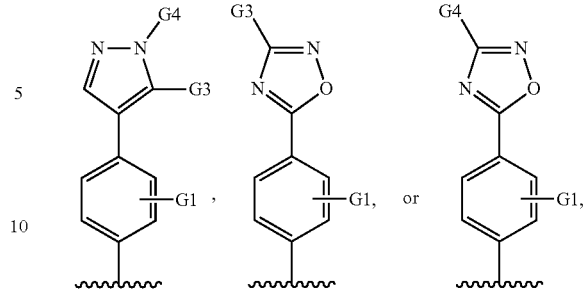

wherein

G1 is H, CH₃, or F;

G3 is —CH₃, —CH₂F, CHF₂, —CF₃, —OCH₃, —CH₂—CH₂F, —(CH₂)₂—CN, —(CH₂)₃—CN, —(CH₂)₁₋₂C(CH₃)₂—CN, or —(CH₂)₁₋₂C(CH₃)₂—OH; and G4 is —CH₃, —CH₂F, CHF₂, —CF₃, —CH₂—CH₂—CH₂F, —(CH₂)₁₋₂C(CH₃)₂—OH; —C₁-C₄ alkylene-cyclopropyl, —C₁-C₄ alkylene-cyclopropylene-CN, —C₁-C₄ alkylene-cyclopropylene-OH, —C₁-C₅ alkylene-CN, or —(CH₂)₁₋₃N(CH₃)₂;

each R¹⁶ is H, halogen, (C₁-C₄)alkyl optionally substituted with halogen;

X⁹ is a bond or O;

X¹⁰ is CH, —C(CH₃)—, N; and

X¹¹ is —CH₂, NH, O, S, S(O), or S(O)₂.

Embodiment 16 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), or 15(b), wherein R³ is:

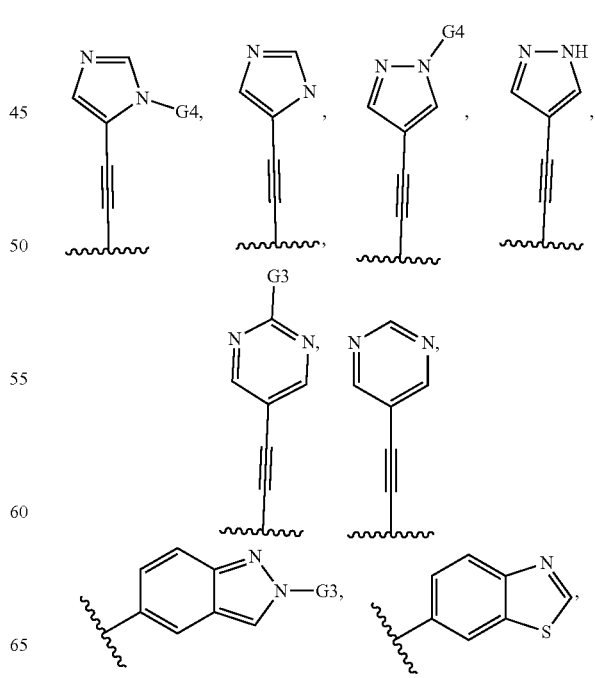

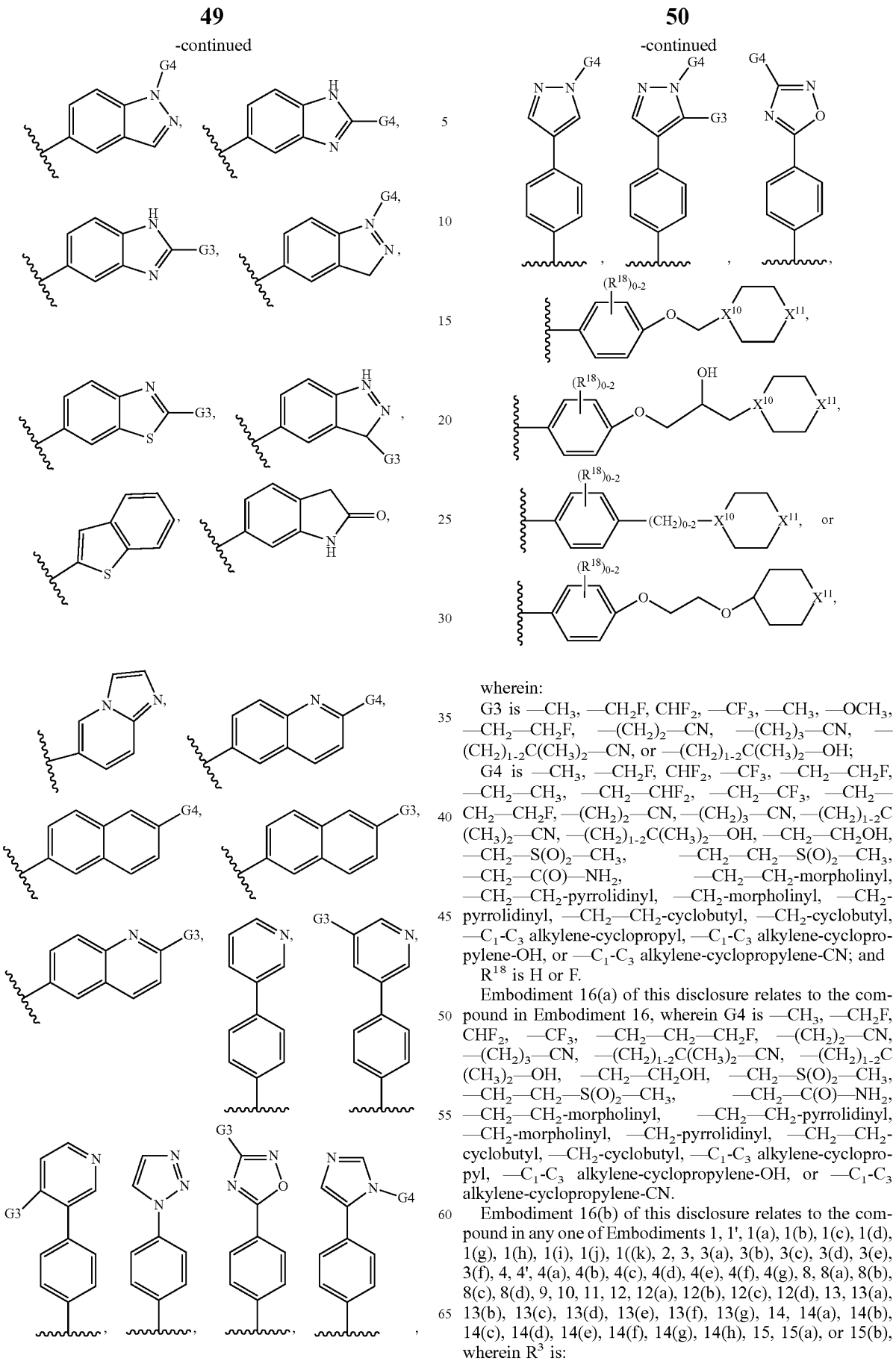

wherein:

G3 is —CH$_3$, —CH$_2$F, CHF$_2$, —CF$_3$, —CH$_3$, —OCH$_3$, —CH$_2$—CH$_2$F, —(CH$_2$)$_2$—CN, —(CH$_2$)$_3$—CN, —(CH$_2$)$_{1-2}$C(CH$_3$)$_2$—CN, or —(CH$_2$)$_{1-2}$C(CH$_3$)$_2$—OH;

G4 is —CH$_3$, —CH$_2$F, CHF$_2$, —CF$_3$, —CH$_2$—CH$_2$F, —CH$_2$—CH$_3$, —CH$_2$—CHF$_2$, —CH$_2$—CF$_3$, —CH$_2$—CH$_2$—CH$_2$F, —(CH$_2$)$_2$—CN, —(CH$_2$)$_3$—CN, —(CH$_2$)$_{1-2}$C(CH$_3$)$_2$—CN, —(CH$_2$)$_{1-2}$C(CH$_3$)$_2$—OH, —CH$_2$—CH$_2$OH, —CH$_2$—S(O)$_2$—CH$_3$, —CH$_2$—CH$_2$—S(O)$_2$—CH$_3$, —CH$_2$—C(O)—NH$_2$, —CH$_2$—CH$_2$-morpholinyl, —CH$_2$—CH$_2$-pyrrolidinyl, —CH$_2$-morpholinyl, —CH$_2$-pyrrolidinyl, —CH$_2$—CH$_2$-cyclobutyl, —CH$_2$-cyclobutyl, —C$_1$-C$_3$ alkylene-cyclopropyl, —C$_1$-C$_3$ alkylene-cyclopropylene-OH, or —C$_1$-C$_3$ alkylene-cyclopropylene-CN; and R$^{18}$ is H or F.

Embodiment 16(a) of this disclosure relates to the compound in Embodiment 16, wherein G4 is —CH$_3$, —CH$_2$F, CHF$_2$, —CF$_3$, —CH$_2$—CH$_2$—CH$_2$F, —(CH$_2$)$_2$—CN, —(CH$_2$)$_3$—CN, —(CH$_2$)$_{1-2}$C(CH$_3$)$_2$—CN, —(CH$_2$)$_{1-2}$C(CH$_3$)$_2$—OH, —CH$_2$—CH$_2$OH, —CH$_2$—S(O)$_2$—CH$_3$, —CH$_2$—CH$_2$—S(O)$_2$—CH$_3$, —CH$_2$—C(O)—NH$_2$, —CH$_2$—CH$_2$-morpholinyl, —CH$_2$—CH$_2$-pyrrolidinyl, —CH$_2$-morpholinyl, —CH$_2$-pyrrolidinyl, —CH$_2$—CH$_2$-cyclobutyl, —CH$_2$-cyclobutyl, —C$_1$-C$_3$ alkylene-cyclopropyl, —C$_1$-C$_3$ alkylene-cyclopropylene-OH, or —C$_1$-C$_3$ alkylene-cyclopropylene-CN.

Embodiment 16(b) of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), or 15(b), wherein R$^3$ is:

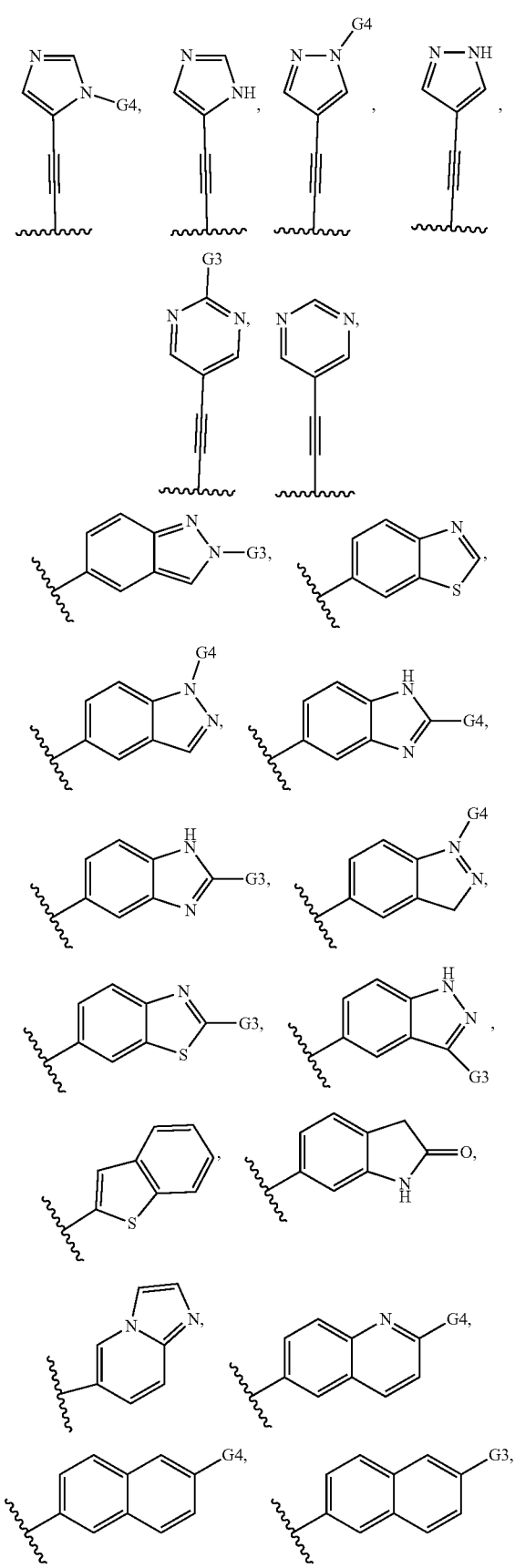

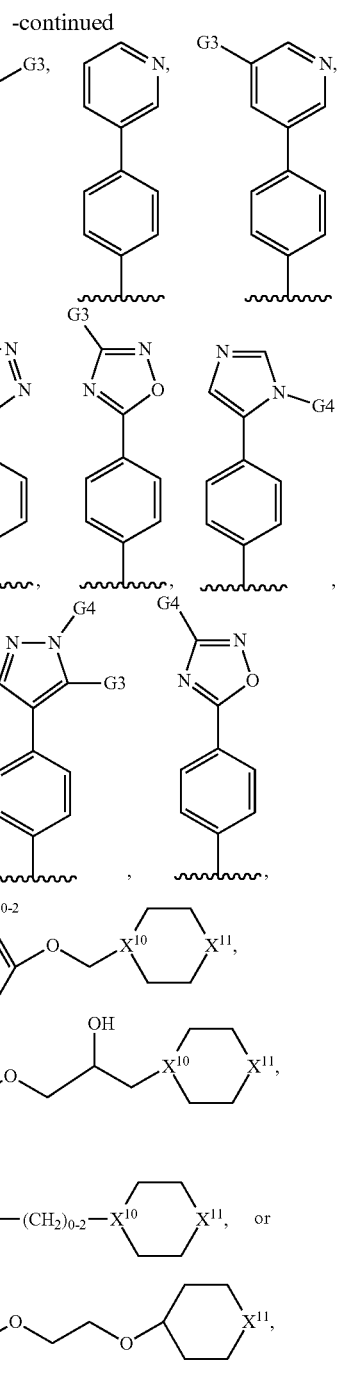

wherein:
G3 is —CH₃, —CH₂F, CHF₂, —CF₃, —CH₃, —OCH₃, —CH₂—CH₂F, —(CH₂)₂—CN, —(CH₂)₃—CN, —(CH₂)₁₋₂C(CH₃)₂—CN, or —(CH₂)₁₋₂C(CH₃)₂—OH;

G4 is —CH₃, —CH₂F, CHF₂, —CF₃, —CH₂—CH₂—CH₂F, —(CH₂)₂—CN, —(CH₂)₃—CN, —(CH₂)₁₋₂C(CH₃)₂—CN, —(CH₂)₁₋₂C(CH₃)₂—OH, —CH₂—CH₂OH, —CH₂—S(O)₂—CH₃, —CH₂—CH₂—S(O)₂—CH₃, —CH₂—C(O)—NH₂, —CH₂—CH₂-morpholinyl, —CH₂—CH₂-pyrrolidinyl, —CH₂-morpholinyl, —CH₂-pyrrolidinyl, —CH₂—CH₂-cyclobutyl, —CH₂-cyclobutyl, —C₁-C₃ alkylene-cyclopropyl, —C₁-C₃ alkylene-cyclopropylene-OH, or —C₁-C₃ alkylene-cyclopropylene-CN; and
R¹⁸ is H or F.

Embodiment 17 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), or 16(b), wherein $R^3$ is:

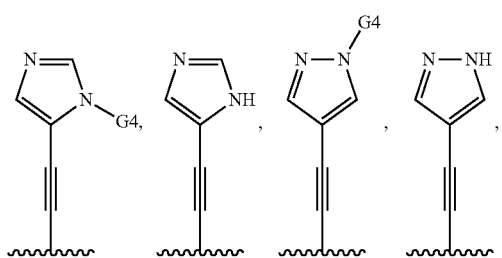

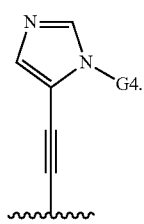

Embodiment 17(a) of this disclosure relates to the compound in Embodiment 17, wherein $R^3$ is:

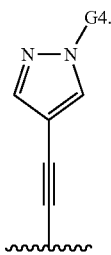

Embodiment 17(b) of this disclosure relates to the compound in Embodiment 17, wherein $R^a$ is:

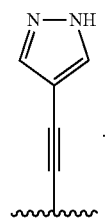

Embodiment 17(c) of this disclosure relates to the compound in Embodiment 17, wherein $R^3$ is:

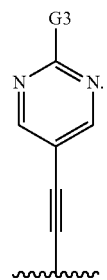

Embodiment 17(d) of this disclosure relates to the compound in Embodiment 17, wherein $R^3$ is:

Embodiment 17(e) of this disclosure relates to the compound in Embodiment 17, wherein $R^3$ is:

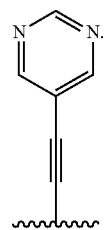 [SMILES: *C#Cc1cncnc1]

Embodiment 17(f) of this disclosure relates to the compound in Embodiment 17, wherein $R^3$ is:

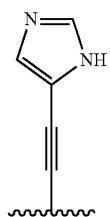

Embodiment 18 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 5, 5', 6, 7, 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), or 16(b) wherein $R^3$ is:

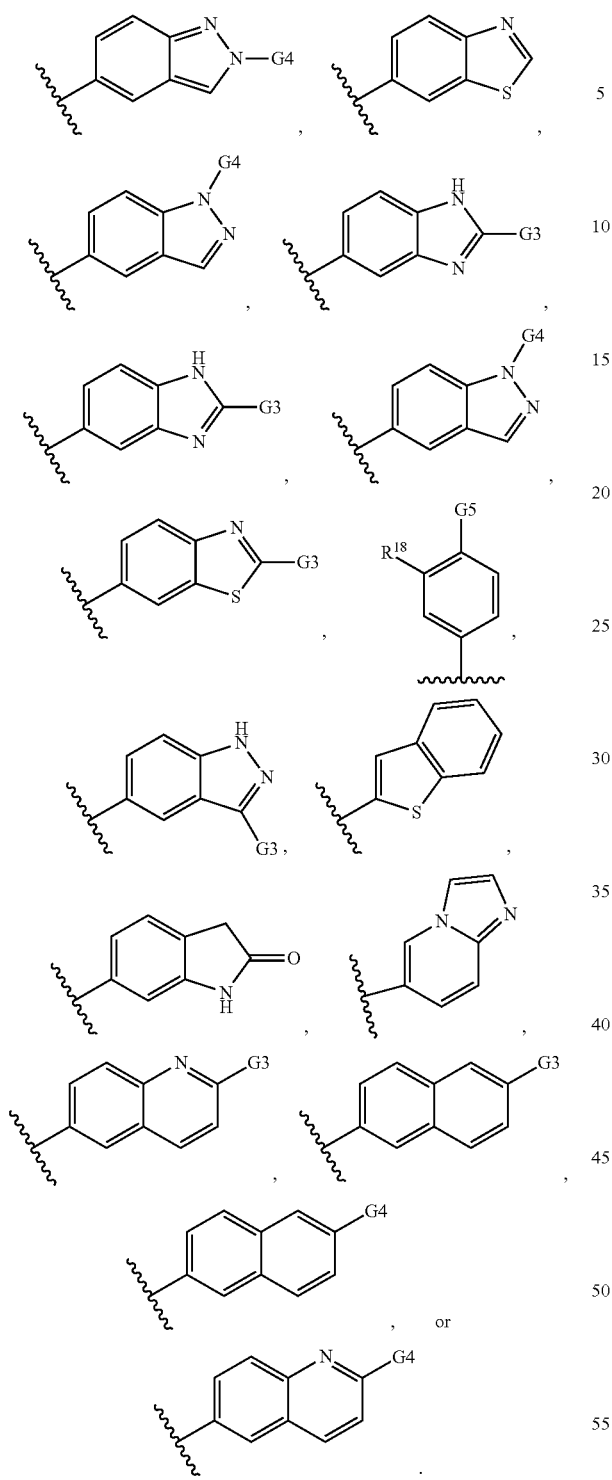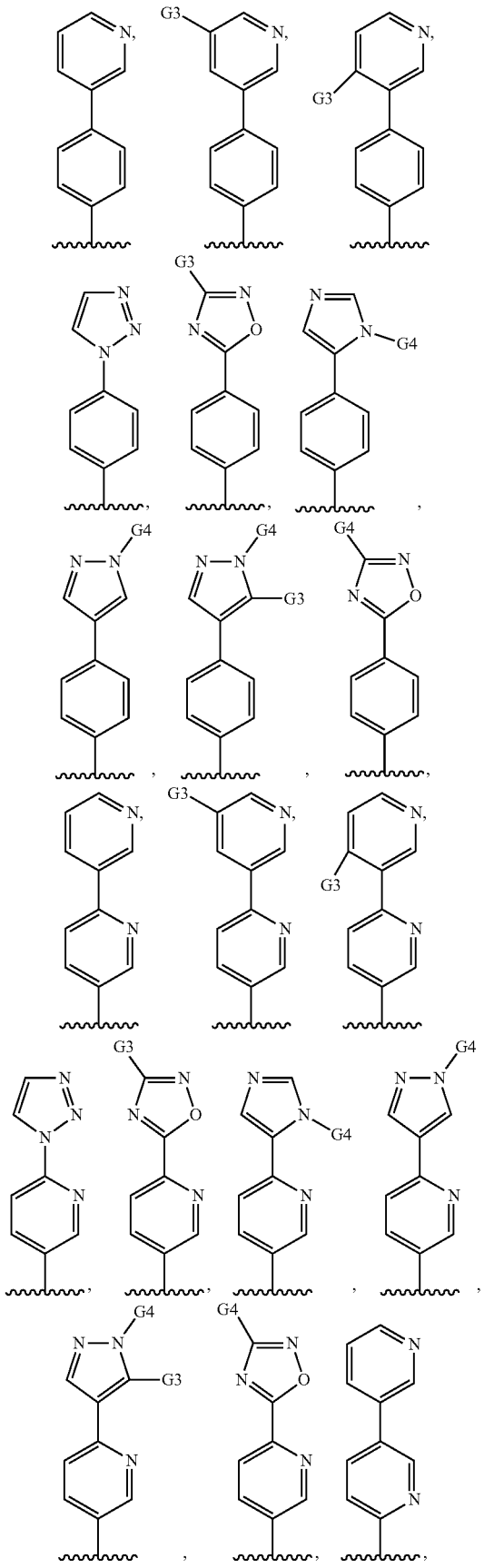
Embodiment 19 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), or 16(b), wherein $R^3$ is:

-continued
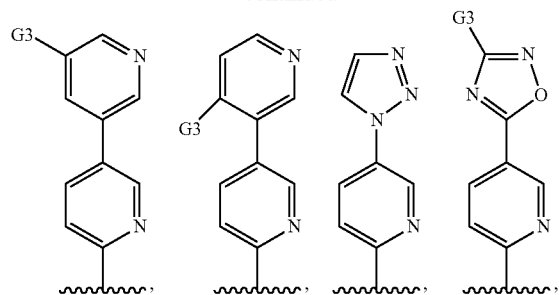
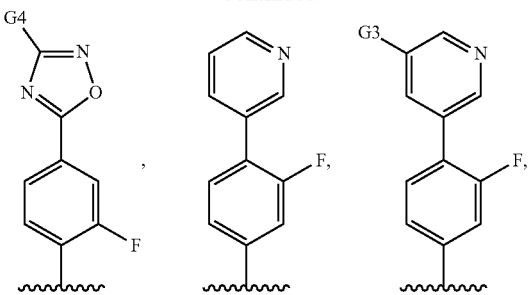
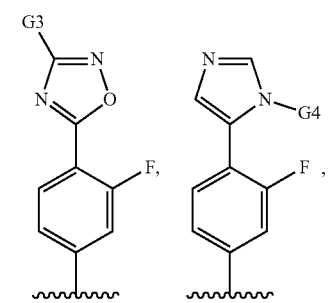
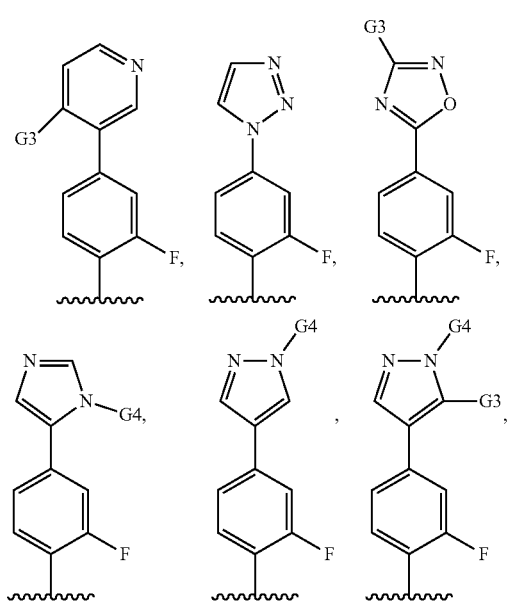
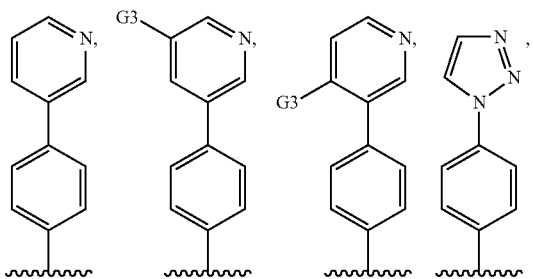
, or
Embodiment 19(a) of this disclosure relates to the compound in Embodiment 19, wherein $R^3$ is:

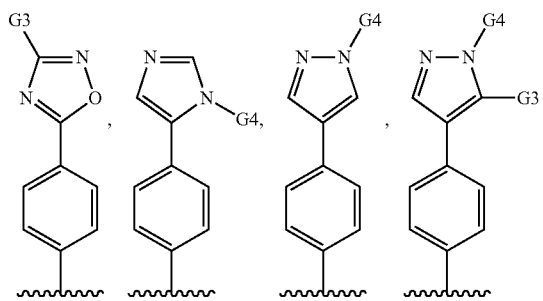
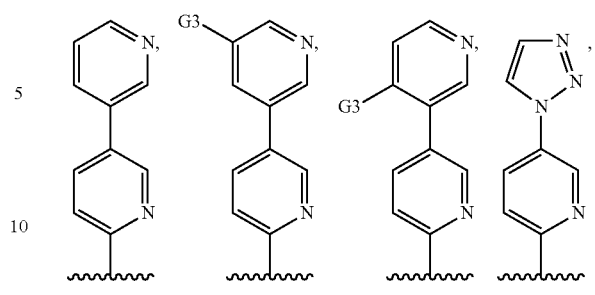
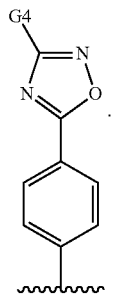
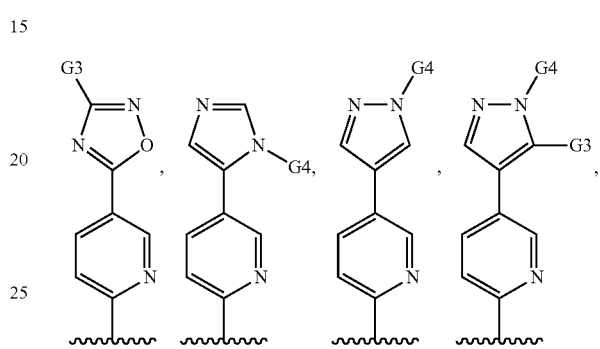
Embodiment 19(b) of this disclosure relates to the compound in Embodiment 19, wherein $R^3$ is:
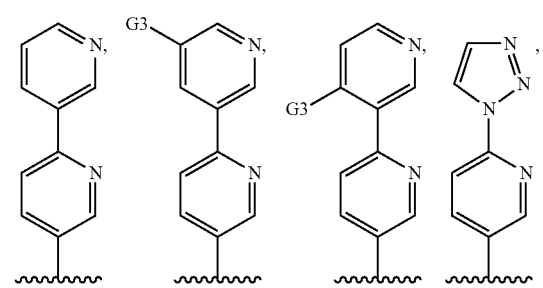
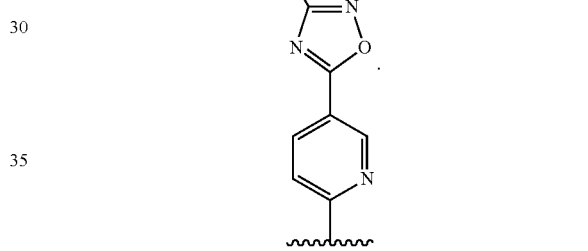
Embodiment 19(d) of this disclosure relates to the compound in Embodiment 19, wherein $R^3$ is:
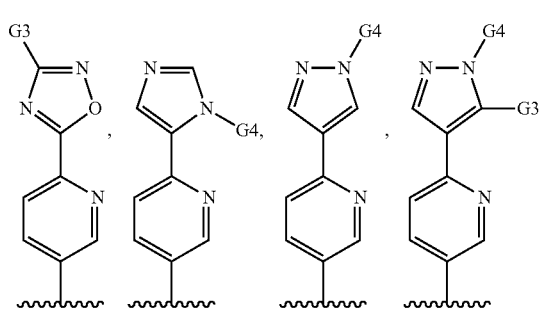
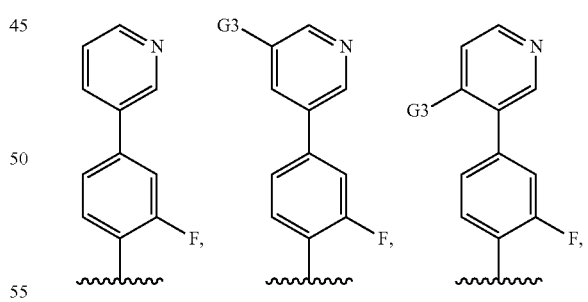

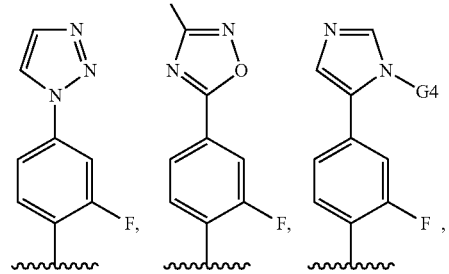
Embodiment 19(c) of this disclosure relates to the compound in Embodiment 19, wherein $R^3$ is:

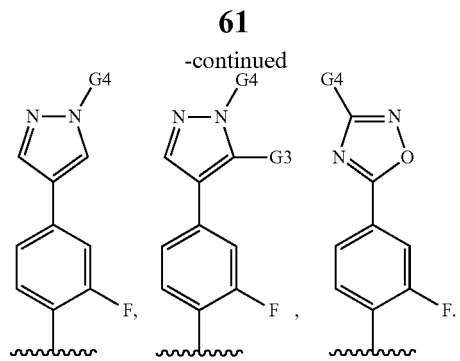
Embodiment 19(e) of this disclosure relates to the compound in Embodiment 19, wherein R³ is:
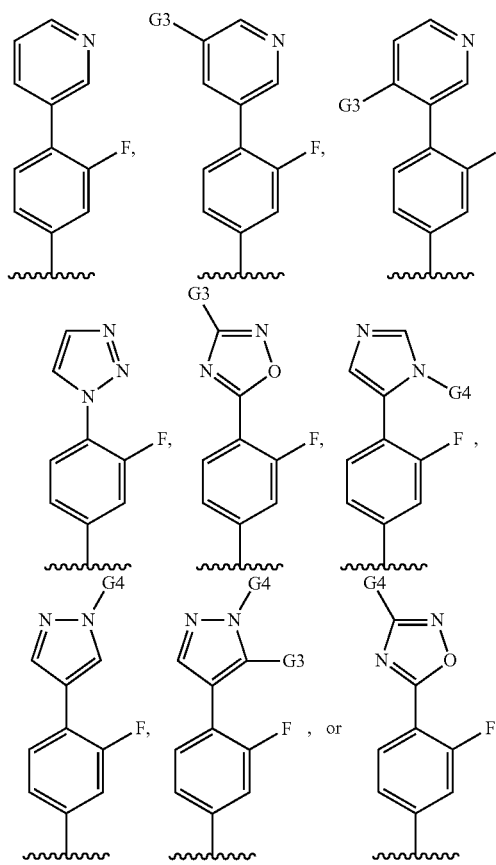
Embodiment 20 of this disclosure relates to the compound in any one of Embodiments 1, 1', 1(a), 1(b), 1(c), 1(d), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), or 16(b), wherein R³ is:
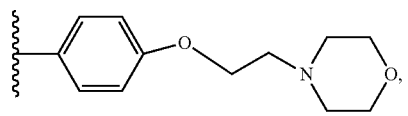
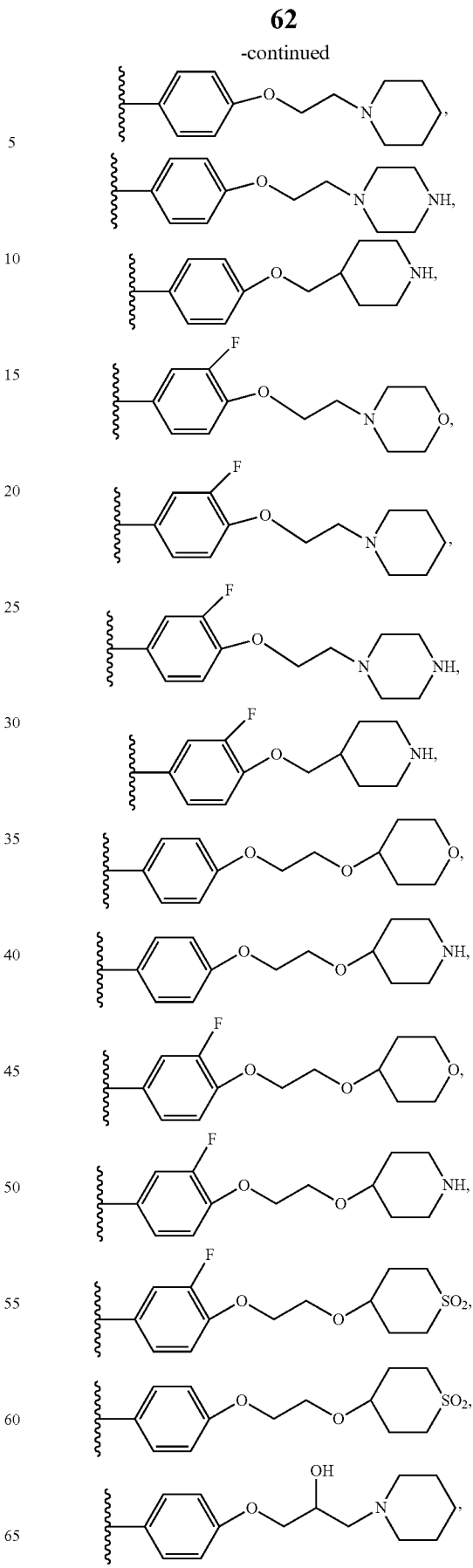

-continued
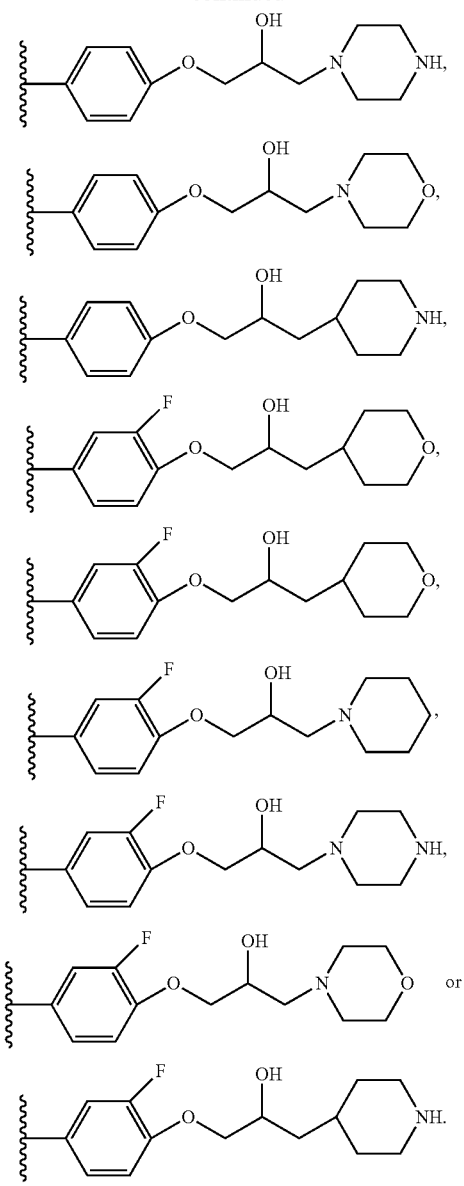
Embodiment 20(a) of this disclosure relates to the compound in Embodiment 20, wherein $R^3$ is:
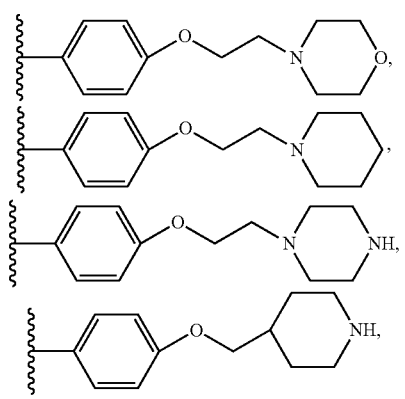
-continued
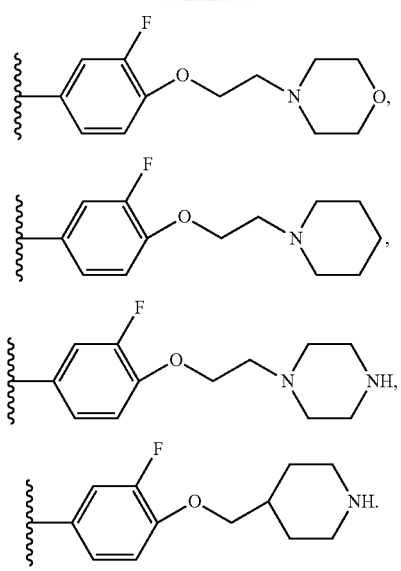
Embodiment 20(b) of this disclosure relates to the compound in Embodiment 20, wherein $R^3$ is:
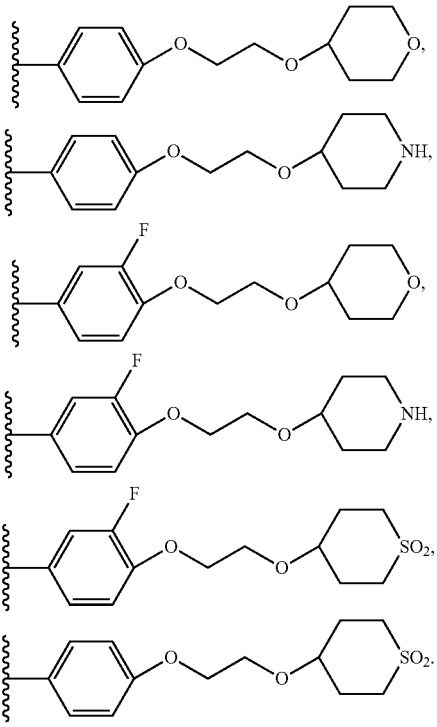
Embodiment 20(c) of this disclosure relates to the compound in Embodiment 20, wherein $R^3$ is:
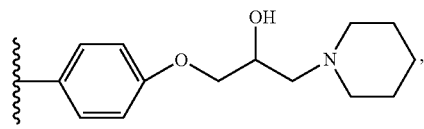

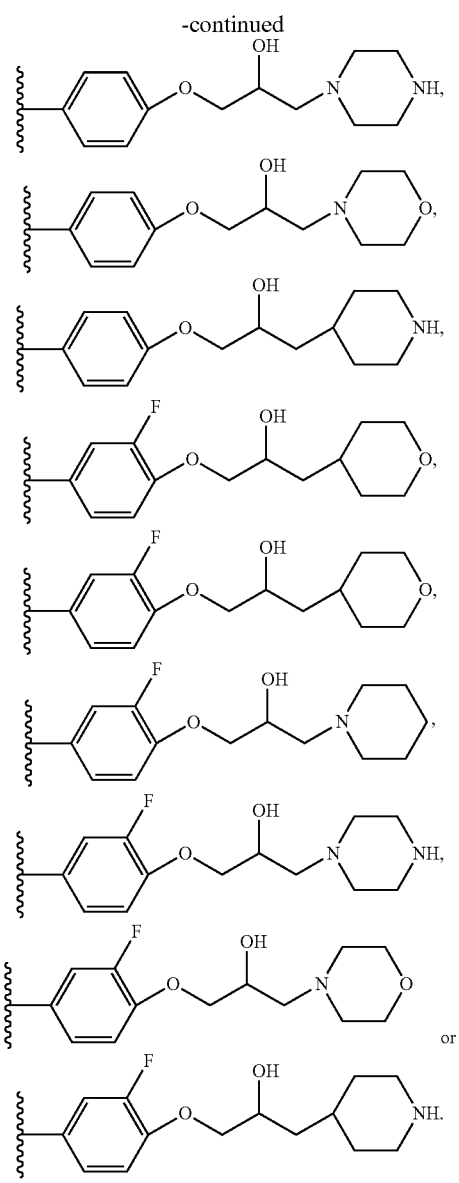

[0190] Embodiment 21 of this disclosure relates to the compound in any one of Embodiments 1, 1', 1(a), 1(b), 1(c), 1(d), 1(e), 1(f), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 4(h), 4(i), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), 16(b), 17, 17(a), 17(b), 17(c), 17(d), 17(e), 17(f), 19, 19(a), 19(b), 19(c), 19(d), 19(e), 20(a), 20(b) or 20(c) wherein G4 is —$CH_3$, —$CH_2F$, $CHF_2$, —$CF_3$, —$CH_{32}$—$CH_2$—$CH_2F$, —$(CH_2)_2$—CN, —$(CH_2)_3$—CN, —$(CH_2)C(CH_3)_2$—CN, —$CH_2$—C($CH_3)_2$—OH; —$C_1$-$C_3$ alkylene-cyclopropyl, —$CH_2$-cyclopropylene-OH, or —$CH_2$-cyclopropylene-CN.

Embodiment 21(a) of this disclosure relates to the compound in Embodiment 21, wherein G4 is —$CH_3$.

Embodiment 21(b) of this disclosure relates to the compound in Embodiment 21, wherein G4 is —$CH_2F$.

Embodiment 21(c) of this disclosure relates to the compound in Embodiment 21, wherein G4 is $CHF_2$.

Embodiment 21(d) of this disclosure relates to the compound in Embodiment 21, wherein G4 is —$CF_3$.

Embodiment 21(e) of this disclosure relates to the compound in Embodiment 21, wherein G4 is —$CH_3$—$CH_2$—$CH_2F$.

Embodiment 21(f) of this disclosure relates to the compound in Embodiment 21, wherein G4 is —$(CH_2)_2$—CN, —$(CH_2)_3$—CN.

Embodiment 21(g) of this disclosure relates to the compound in Embodiment 21, wherein G4 is —$(CH_2)C(CH_3)_2$—CN.

Embodiment 21(h) of this disclosure relates to the compound in Embodiment 21, wherein G4 is —$CH_2$—C($CH_3)_2$—OH.

Embodiment 21(i) of this disclosure relates to the compound in Embodiment 21, wherein G4 is —$C_1$-$C_3$ alkylene-cyclopropyl.

Embodiment 21(j) of this disclosure relates to the compound in Embodiment 21, wherein G4 is —$CH_2$-cyclopropylene-OH.

Embodiment 21(k) of this disclosure relates to the compound in Embodiment 21, wherein G4 is —$CH_2$-cyclopropylene-CN.

Embodiment 22 of this disclosure relates to the compound in selected from Table 1, or a pharmaceutically acceptable salt thereof.

In some embodiments of Embodiment 1, $R^4$ is (b) —X-cycloalkyl, wherein the cycloalkyl moiety of —X-cycloalkyl is substituted with 1-3 $R^7$ groups and 0-1 $R^8$ groups, and wherein the cycloalkyl is saturated or unsaturated.

Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, different crystal forms or polymorphs, and active metabolites.

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers as defined herein. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

In addition to the present formulae and compounds described herein, the disclosure also includes prodrugs (generally pharmaceutically acceptable prodrugs), active metabolic derivatives (active metabolites), and their pharmaceutically acceptable salts.

Unless specified to the contrary, specification of a compound herein includes pharmaceutically acceptable salts of such compound.

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae.

In some embodiments, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex can be formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

III. Formulations and Administration

Embodiment 23 of this disclosure relates to a pharmaceutical composition comprising a compound in one of Embodiments 1, 1', 1(a), 1(b), 1(c), 1(d), 1(e), 1(f), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 4(h), 4(i), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), 16(b), 17, 17(a), 17(b), 17(c), 17(d), 17(e), 17(f), 19, 19(a), 19(b), 19(c), 19(d), 19(e), 20, 20(a), 20(b), 20(c), 21, 21(a), 21(b), 21(c), 21(d), 21(e), 21(f), 21(g), 21(h), 21(i), 21(j), 21(k) or 22, and a pharmaceutically acceptable carrier. Embodiment 23(a) of this disclosure relates to a pharmaceutical composition comprising a compound in one of the embodiments described herein and a pharmaceutically acceptable carrier.

Embodiment 24 of this disclosure relates to a pharmaceutical composition of Embodiment 23, further comprising a second pharmaceutical agent. Embodiment 24(a) of this disclosure relates to a pharmaceutical composition of Embodiment 23(a), further comprising a second pharmaceutical agent.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, $21^{st}$ edition, Lippincott, Williams and Wilkins, Philadelphia, Pa., 2005 (hereby incorporated by reference herein).

Compounds of the present disclosure (i.e. any of the compounds described in Embodiments 1-22, including any of the subembodiments thereof) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

IV. Methods of Use

The methods and compounds will typically be used in therapy for human subjects. However, they may also be used to treat similar or identical indications in other animal subjects.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per dosage. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by CDK8 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in a compound in one of Embodiments 1-22, or a pharmaceutically acceptable salt, deuterated analog, a tautomer or an isomer thereof, and wherein the compound is administered on an empty stomach.

As used herein, the term CDK8 mediated disease or condition refers to a disease or condition in which the biological function of CDK8 affects the development and/or course of the disease or condition, and/or in which modulation of CDK8 alters the development, course, and/or symptoms. These mutations attenuate the intrinsic activity of the receptor to different degrees and are models for the effect of modulation of CDK8 activity. A CDK8 mediated disease or condition includes a disease or condition for which CDK8 inhibition provides a therapeutic benefit, e.g. wherein treatment with CDK8 inhibitors, including compounds described herein, provides a therapeutic benefit to the subject suffering from or at risk of the disease or condition.

Embodiment 26 of this disclosure relates to method for treating a subject with a disease or condition mediated by CDK8, said method comprising administering to the subject an effective amount of a compound in one of Embodiments 1, 1', 1(a), 1(b), 1(c), 1(d), 1(e), 1(f), 1(g), 1(h), 1(i), 1(j), 1((k), 2, 3, 3(a), 3(b), 3(c), 3(d), 3(e), 3(f), 4, 4', 4(a), 4(b), 4(c), 4(d), 4(e), 4(f), 4(g), 4(h), 4(i), 8, 8(a), 8(b), 8(c), 8(d), 9, 10, 11, 12, 12(a), 12(b), 12(c), 12(d), 13, 13(a), 13(b), 13(c), 13(d), 13(e), 13(f), 13(g), 14, 14(a), 14(b), 14(c), 14(d), 14(e), 14(f), 14(g), 14(h), 15, 15(a), 15(b), 16, 16(a), 16(b), 17, 17(a), 17(b), 17(c), 17(d), 17(e), 17(f), 19, 19(a), 19(b), 19(c), 19(d), 19(e), 20, 20(a), 20(b), 20(c), 21, 21(a), 21(b), 21(c), 21(d), 21(e), 21(f), 21(g), 21(h), 21(i), 21(j), 21(k) or 22, or a pharmaceutically acceptable salt, deuterated analog, a tautomer or an isomer thereof, or a pharmaceutical composition in one of claims 23-25, wherein the disease or condition express aberrantly or otherwise CDK8, or activating mutations or translocations of any of the foregoing.

Embodiment 27 of this disclosure relates to the method for treating a subject with a disease or condition according to Embodiment 26, wherein the disease or condition is brain cancer, lung cancer, colon cancer, epidermoid cancel, squamous cell cancer, bladder cancer, gastric cancer, pancreatic cancer, breast cancer, head cancer, neck cancer, renal cancer, kidney cancer, liver cancer, ovarian cancer, prostate cancer, colorectal cancer, uterine cancer, rectal cancer, oesophageal cancer, testicular cancer, thyroid cancer, melanoma, uveal melanoma, acute myelogenous, leukemia, acute myeloid leukemia, multiple myeloma, chronic myelogneous leukemia, myeloid cell leukemia, glioma, Kaposi's sarcoma, human laryngeal squamous cell carcinoma, inflammation, Alzheimer's disease, Parkinson's disease, dementia, amyloidosis, atherosclerosis, stroke/ischemia, pain, traumatic brain injury, kidney disease, inflammation pathologies, type 2 diabetes, or a viral infection.

Embodiment 27(a) of this disclosure relates to the method for treating a subject with a disease or condition according to Embodiment 27, wherein the disease or condition is FLT3-ITD acute myeloid leukemia.

Embodiment 27(b) of this disclosure relates to the method for treating a subject with a disease or condition according to Embodiment 27(a), wherein the method further comprises administering one or more FLT3 inhibitors. The FLT3 inhibitor can be administered before, after or simultaneously with the compound of this disclosure. Non-limiting examples of FLT3 inhibitors that can be employed in this embodiment include sorafenib, midostaurin, quizartib, gilteritinib, and. crenolanib. In another embodiment, the FLT3 inhibitor that is employed in this embodiment is quizartinib.

Embodiment 27(c) of this disclosure relates to a method for treatment of a disease or condition according to Embodiment 27, wherein the disease or condition is FLT3-ITD acute myeloid leukemia, and wherein the method further comprises administering one or more FLT3 inhibitors.

Embodiment 28 of this disclosure relates to the method for treating a subject with a disease or condition according to Embodiment 27, wherein the disease or condition is colorectal cancer, gastric cancer, pancreatic cancer, and melanoma, breast cancer, ovarian cancer, lung cancer, lung cancer metastasis, breast cancer metastasis, or leukemia.

Embodiment 29 of this disclosure relates to the method for treating a subject with a disease or condition according to Embodiment 27, wherein the viral infection is HSV, HCMV, HPV or HIV.

V. Combination Therapy

CDK8 modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In another embodiment, the present disclosure provides methods for treating a disease or condition mediated by CDK8 by administering to the subject an effective amount of a composition including any one or more compound(s) as described herein in combination with one or more other suitable therapies for treating the disease.

Embodiment 24 of this disclosure relates to the pharmaceutical composition according to Embodiment 23, further comprising a second pharmaceutical agent.

Embodiment 25 of this disclosure relates to the pharmaceutical composition according to Embodiment 24, wherein the second pharmaceutical agent: i) an alkylating agent (such as adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, or treosulfan); ii) an antibiotic (such as bleomycin, dactinomycin, daunorubicin, doxorubicin, epirubicin, idarubicin, menogaril, mitomycin, mitoxantrone, neocarzinostatin, pentostatin, or plicamycin); iii) an antimetabolite (such as azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, or trimetrexate); iv) an antibody therapy agent selected from alemtuzumab, bevacizumab, cetuximab, galiximab, gemtuzumab, pembrolizumab, nivolumab, durvalumab, panitumumab, pertuzumab, rituximab, tositumomab, trastuzumab, and 90 Y ibritumomab tiuxetan; v) a hormone or hormone antagonist (such as anastrozole, androgens, buserelin, diethylstilbestrol, exemestane, flutamide, fulvestrant, goserelin, idoxifene, letrozole, leuprolide, magestrol, raloxifene, tamoxifen, or toremifene); vi) a taxane (such as DJ-927, docetaxel, TPI 287, paclitaxel or DHA-paclitaxel); vii) a retinoid (such as alitretinoin, bexarotene, fenretinide, isotretinoin, or tretinoin); viii) an alkaloid (such as etoposide, homoharringtonine, teniposide, vinblastine, vincristine, vindesine, or vinorelbine); ix) an antiangiogenic agent (such as AE-941 (GW786034, Neovastat), ABT-510, 2-methoxyestradiol, lenalidomide, or thalidomide); x) a topoisomerase inhibitor (such as amsacrine, edotecarin, exatecan, irinotecan (also active metabolite SN-38 (7-ethyl-10-hydroxy-camptothecin)), rubitecan, topotecan, or 9-aminocamptothecin; xi) a kinase inhibitor [such as PI3K inhibitors (e.g. BEZ235, GDC-0941, XL147, XL765), Cdk4 inhibitors (e.g. PD-332991), Akt inhibitors, a Mek inhibitor (such as AS703026, AZD6244 (Selumetinib), AZD8330, BIX 02188, CI-1040 (PD184352), GSK1120212 (JTP-74057), PD0325901, PD318088, binimetinib, PD98059, RDEA119 (BAY 869766), TAK-733 or U0126-EtOH), an EGFR inhibitor, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib, cabozantinib, selumetinib, dovitinib, or vatalanib]; xii) a targeted signal transduction inhibitor (such as bortezomib, geldanamycin, or rapamycin); xiii) a biological response modifier (such as imiquimod, interferon-alpha, or interleukin-2); xiv) a chemotherapeutic agent (such as 3-amino-2-carboxyaldehyde thiosemicarbazone, mTOR inhibitors (such as sirolimus, temsirolimus, everolimus, deforolimus), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, or tiazofurin); xv) an Hsp90 inhibitor (e.g. geldanamycin, radicicol, tanespimycin); xvi) a famesyl-transferase inhibitors (e.g. tipifamib); xvii) an aromatase inhibitor (such as anastrozole, letrozole or exemestane); xviii) an IDO inhibitor; xix) a histone acetyltransferase (HAT) inhibitor; xx) histone deacetylase (HDAC) inhibitor; xxi) a sirtuin (SIRT) inhibitor; xxii) a BET inhibitor (such as BRD2, BRD3, BRD4 and/or BRDT); or xxiii) an antiangiogenic agent, (such as AE-941 (GW786034, Neovastat), enzalutamide, ABT-510, 2-methoxyestradiol, lenalidomide or thalidomide.

Embodiment 25(a) of this disclosure relates to the pharmaceutical composition of Embodiment 25, wherein the second pharmaceutical composition is: i) an alkylating agent, ii) an antibiotic; iii) an antimetabolite; iv) an antibody therapy agent; v) a hormone or hormone antagonist; vi) a taxane; vii) a retinoid; viii) an alkaloid; ix) an antiangiogenic agent; x) a topoisomerase inhibitor; xi) a kinase inhibitor; xii) a targeted signal transduction; xiii) a biological response modifier; xiv) a chemotherapeutic agent; xv) an Hsp90 inhibitor; xvi) a famesyltransferase inhibitors; xvii) an aromatase inhibitor; xviii) an IDO inhibitor; xix) a histone acetyltransferase (HAT) inhibitor; a xx) histone deacetylase (HDAC) inhibitor; xxi) a sirtuin (SIRT) inhibitor; xxii) a BET inhibitor; or xxiii) an antiangiogenic agent.

Embodiment 25(b) of this disclosure relates to a pharmaceutical composition according to Embodiment 24(a), wherein the second pharmaceutical agent is as described in Embodiment 25 or 25(a).

Bromodomains (e.g., BET proteins, such as BRD2, BRD3, BRD4, and/or BRDT), and e.g., diseases related to abnormal expression of bromodomains, including cell proliferative disorders, cancers, chronic autoimmune, inflammatory conditions, among others. Non-limiting examples of BET inhibitors include GSK1210151A and GSK525762.

The histone deacetylase inhibitors (HDAC inhibitors) are cytostatic agents that inhibit the proliferation of tumor cells in culture and in vivo by inducing cell cycle arrest, differentiation and/or apoptosis. HDAC inhibitors exert their anti-tumor effects via the induction of expression changes of oncogenes or tumour suppressor, through modulating that the acetylation/deactylation of histones and/or non-histone proteins such as transcription factors. Histone acetylation and deacetylation play important roles in the modulation of chromatin topology and the regulation of gene transcription. Non-limiting examples of HDAC inhibitors include vorinostat, romidepsin, chidamide, panobinostat, belinostat, valproic acid, mocetinostat, abexinostat, entinostat, resminostat, givinostat, and quisinostat. HDAC inhibitors have been used extensively in psychiatry and neurology as mood stabilizers and anti-epileptics. One example of this is valproic acid, marketed as a drug under the trade names Depakene, Depakote, and Divalproex. HDAC inhibitors are also being used as a mitigator for neurodegenerative diseases such as Alzheimer's disease and Huntington's disease In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, .gamma.-ray, or electron, proton, neutron, or .alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

VI. Kits

In another aspect, the present disclosure provides kits that include one or more compounds as described in any one of a compound in one of Embodiments 1-22, or a pharmaceutically acceptable salt, deuterated analog, a tautomer or an isomer thereof, or a pharmaceutical composition in one of Embodiments 23-25. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a an CDK8 mediated disease or condition; the kits described herein may include written instructions for use and/or other indication that the compound or composition is suitable or approved for administration to a mammal, e.g., a human, for an CDK8-mediated disease or condition; and the compound or composition may be packaged in unit dose or single dose form, e.g., single dose pills, capsules, or the like.

VII. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist, (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra-high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multi-well plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well-known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

VIII. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

IX. Manipulation of CDK8

Techniques for the manipulation of nucleic acids, such as, e.g., subcloning, labeling probes (e.g. random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the disclosure can be performed by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the present disclosure can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the present disclosure can also be provided in expression vectors and cloning vehicles, e.g., sequences encoding the polypeptides used to practice the methods of the present disclosure. Expression vectors and cloning vehicles used to practice the methods of the present disclosure can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors used to practice the methods of the present disclosure can include chromosomal, non-chromosomal and synthetic DNA sequences. Large numbers of suitable vectors are known to those of skill in the art, and are commercially available.

The nucleic acids used to practice the methods of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif 6435:10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the present disclosure can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids used to practice the methods of the present disclosure are administered in vivo for in situ expression of the peptides or polypeptides used to practice the methods of the disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, selected from baculoviridiae, parvoviridiae, picornoviridiae, herpesveridiae, poxviridae, adenoviridiae, or picomnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the present disclosure; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present disclosure also relates to use of fusion proteins, and nucleic acids encoding them. A polypeptide used to practice the methods of the present disclosure can be fused to a heterologous peptide or polypeptide, such as N-terminal identification peptides which impart desired characteristics, such as increased stability or simplified purification. Peptides and polypeptides used to practice the methods of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one aspect, a nucleic acid encoding a polypeptide used to practice the methods of the present disclosure is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll (1993) DNA Cell. Biol. 12:441-53.

The nucleic acids and polypeptides used to practice the methods of the present disclosure can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl) aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding polypeptides and peptides used to practice the methods of the present disclosure to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides used to practice the methods of the present disclosure can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the present disclosure. For example, in one aspect of the disclosure, a monitored parameter is transcript expression of a gene comprising a nucleic acid used to practice the methods of the present disclosure. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the present disclosure. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the present disclosure, any known array and/or method of making and using arrays can be incorporated in whole or in part, or variations thereof, as described, for example, in U.S. Pat. Nos. 6,277,628; 6,277, 489; 6,261,776; 6,258,606; 6,054,270; 6,048,695; 6,045, 996; 6,022,963; 6,013,440; 5,965,452; 5,959,098; 5,856, 174; 5,830,645; 5,770,456; 5,632,957; 5,556,752; 5,143, 854; 5,807,522; 5,800,992; 5,744,305; 5,700,637; 5,556, 752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The present disclosure also provides a transformed cell comprising a nucleic acid sequence used to practice the methods of the present disclosure, e.g., a sequence encoding a polypeptide used to practice the methods of the present disclosure, or a vector used to practice the methods of the present disclosure. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the present disclosure. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the present disclosure may or may not also include an initial methionine amino acid residue.

Cell-free translation systems can also be employed to produce a polypeptide used to practice the methods of the present disclosure. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/mL), 100 μM chloroquine, 10% NuSerum, DNA (0.4 mg/mL) in DMEM/F12 medium is then applied on the cells 10 mL volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO ProS. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/mL). Individual colonies of G418-resistant cells are isolated about 2-3 weeks later, clonally selected and then propagated for assay purposes.

EXAMPLES

The examples below depict the general synthetic procedure for the compounds described herein. Synthesis of the compounds described herein is not limited by these examples and schemes. One skilled in the art will know that other procedures can be used to synthesize the compounds described herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. Unless otherwise specified, intermediate compounds in the examples below, that do not contain a description of how they are made, are either commercially available to one skilled in the art, or can otherwise be synthesized by the skilled artisan using commercially available precursor molecules and synthetic methods known in the art.

The following Schemes and synthetic examples are intended to be illustrative and are not limiting or restrictive to the scope of the disclosure.

Example 1

Compound P-0357 and compound P-0432 are prepared in three or seven steps respectively from 5-bromo-4-fluoro-1H-pyrrolo[2,3-b]pyridine 1 as shown in Scheme 1.

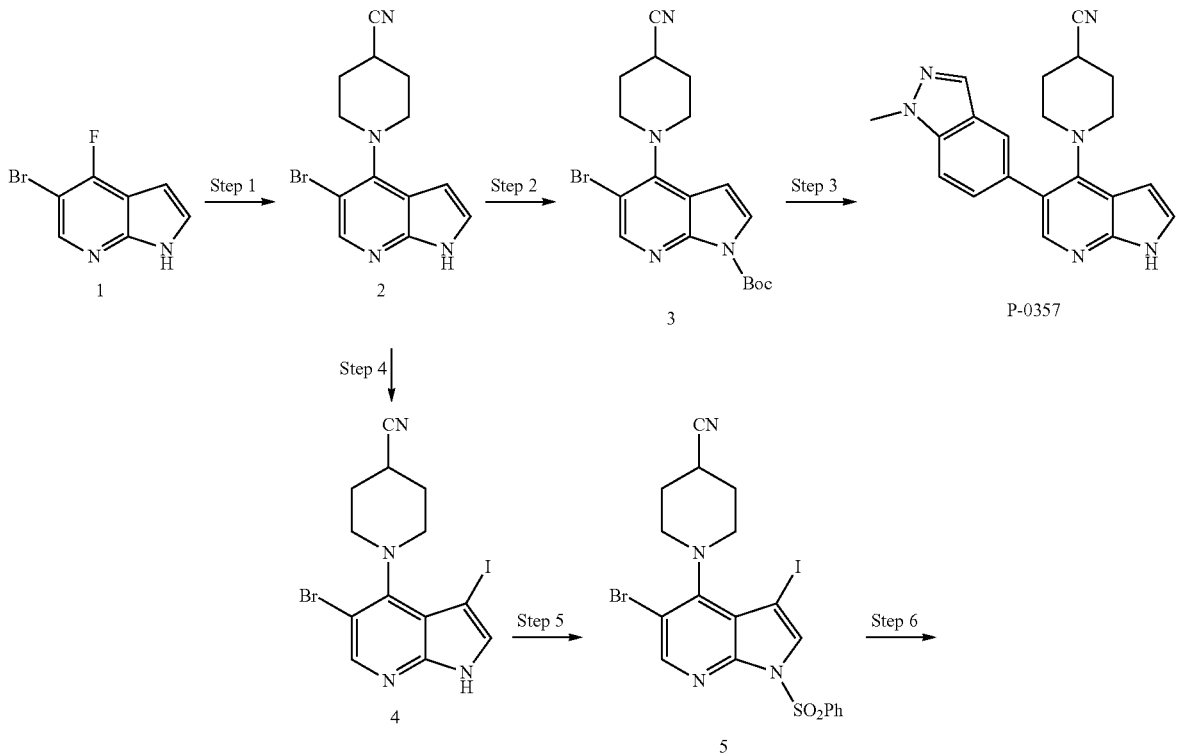

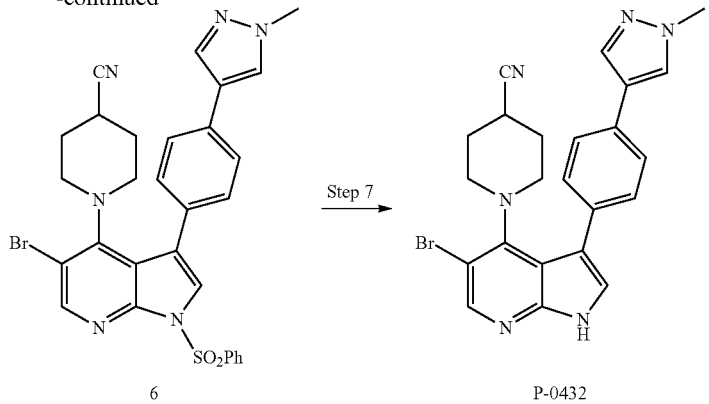

Step 1—Preparation of 1-(5-bromo-1H-pyrrolo[2,3-b]pyridin-4-yl)piperidine-4-carbonitrile 2

5-bromo-4-fluoro-1H-pyrrolo[2,3-b]pyridine (1, 1.00 g, 4.65 mmol) and tert-butyl 4-cyanopiperidine-1-carboxylate (1.17 g, 5.56 mmol) were dissolved in n-butanol (10 mL) and DIEA (1.59 mL, 9.13 mmol) in a 50 mL Teflon capped pressure vial and heated to 200° C. for 36 hours in an oil bath. Upon completion the solvent was removed under reduced pressure to give the crude product (2, 1.42 g).

Step 2—Preparation of tert-butyl 5-bromo-4-(4-cyanopiperidin-1-yl)-1H-pyrrolo[2,3-b]pyridine-1-carboxylate 3

1-(5-bromo-1H-pyrrolo[2,3-b]pyridin-4-yl)piperidine-4-carbonitrile (2, 1.42 g, 4.19 mmol) was dissolved in DCM (10 mL) and triethylamine (1.19 mL, 8.53 mmol). Tert-butoxycarbonyl tert-butyl carbonate (1.10 g, 5.04 mmol) and DMAP (0.0510 g, 0.417 mmol) were added and the mixture was stirred at 25° C. for two hours. Upon completion the reaction mixture was evaporated to dryness in the presence of silica gel and then purified by silica gel column chromatography eluting with a gradient of 0-70% ethyl acetate in hexane to give product (3, 1.62 g).

Step 3—Preparation of 1-[5-(1-methylindazol-5-yl)-1H-pyrrolo[2,3-b]pyridin-4-yl]piperidine-4-carbonitrile P-0357

Tert-butyl 5-bromo-4-(4-cyano-1-piperidyl)pyrrolo[2,3-b]pyridine-1-carboxylate (3, 0.070 g, 0.173 mmol) and 1-methyl-5-(4,4,5,5-tetramethyl-1,3,2-dioxaborolan-2-yl)indazole (0.067 g, 0.26 mmol) were dissolved in dioxane (5 mL). Methanesulfonato(tricyclohexylphosphino)(2'-methylamino-1,1'-biphenyl-2-yl)palladium(II) (0.010 g, 0.015 mmol) and 0.5 M K$_2$HPO$_4$ (1.04 mL) were added and the reaction vial was purged with nitrogen gas, sealed, then heated at 130° C. for 40 minutes. The reaction mixture was then poured over brine and extracted with ethyl acetate. The organic layers were combined, dried over anhydrous sodium sulfate, filtered and evaporated to dryness in the presence of silica gel. The material was purified by reverse-phase silica gel column chromatography eluting with a gradient of 0-30% acetonitrile in water to give product (P-0357). [M+H+]$^+$=357.0.

Step 4—Preparation of 1-(5-bromo-3-iodo-1H-pyrrolo[2,3-b]pyridin-4-yl)piperidine-4-carbonitrile 4

1-(5-bromo-1H-pyrrolo[2,3-b]pyridin-4-yl)piperidine-4-carbonitrile (2, 0.200 g, 0.660 mmol) was dissolved in DMF (5.1 mL) in a 20 mL scintillation vial. Then, 1-iodopyrrolidine-2,5-dione (0.180 g, 0.800 mmol) was added and the reaction mixture was allowed to stir at ambient temperature for 4 hours. The reaction mixture was poured over saturated aqueous sodium thiosulfate and extracted with ethyl acetate. The organic layers were combined, dried over anhydrous sodium sulfate, filtered, and then evaporated to dryness in the presence of silica gel. This material was purified by silica gel column chromatography eluting with a gradient of 0-100% ethyl acetate in hexane to give product (4, 0.174 g).

Step 5—Preparation of 1-[5-bromo-3-iodo-1-(p-tolylsulfonyl)pyrrolo[2,3-b]pyridin-4-yl]piperidine-4-carbonitrile 5

(5-bromo-3-iodo-1H-pyrrolo[2,3-b]pyridin-4-yl)piperidine-4-carbonitrile (4, 0.170 g, 0.394 mmol) and 4-methylbenzenesulfonyl chloride (0.090 g, 0.472 mmol) were dissolved in DCM (10 mL). DIEA (0.140 mL, 0.804 mmol) and DMAP (5.0 mg, 0.041 mmol) were added and the solution was allowed to stir at ambient temperature for 4 hours. The reaction was diluted with brine and extracted with ethyl acetate. The organic layers were combined, dried over anhydrous sodium sulfate, filtered, and then evaporated to dryness in the presence of silica gel. This material was purified by silica gel column chromatography eluting with a gradient of 0-100% ethyl acetate in hexanes to give product (5, 0.214 g).

Step 6—Preparation of 1-[5-bromo-3-[4-(1-methylpyrazol-4-yl)phenyl]-1-(p-tolylsulfonyl)pyrrolo[2,3-b]pyridin-4-yl]piperidine-4-carbonitrile 6

1-[5-bromo-3-iodo-1-(p-tolylsulfonyl)pyrrolo[2,3-b]pyridin-4-yl]piperidine-4-carbonitrile (5, 0.100 g, 0.171 mmol) and 1-methyl-4-[4-(4,4,5,5-tetramethyl-1,3,2-dioxaborolan-2-yl)phenyl]pyrazole (0.054 g, 0.19 mmol) were dissolved in dioxane (3 mL). Then, 1M aqueous potassium carbonate (0.34 mL) and 1,1'-bis(diphenylphosphino)ferrocene-palladium(II) dichloride dichloromethane complex (0.016 g, 0.020 mmol) were added and the reaction vial was purged with nitrogen gas, sealed and heated at 100° C. for 30 minutes. The reaction mixture was poured over anhydrous sodium sulfate, filtered, and then evaporated to dryness in the presence of silica gel. This material was purified by silica gel column chromatography eluting with a gradient of 30-100% ethyl acetate in hexane to give product (6, 0.032 g).

Step 7—Preparation of 1-[5-bromo-3-[4-(1-methyl-pyrazol-4-yl)phenyl]-H-pyrrolo[2,3-b]pyridin-4-yl]piperidine-4-carbonitrile P-0432

1-[5-bromo-3-[4-(1-methylpyrazol-4-yl)phenyl]-1-(p-tolylsulfonyl)pyrrolo[2,3-b]pyridin-4-yl]piperidine-4-carbonitrile (6, 0.030 g, 0.049 mmol) was dissolved in a mixture of THF (3 mL) and methanol (3 mL). Then, 3M aqueous lithium hydroxide (0.01 mL) was added and the solution was allowed to stir at 50° C. for 4 hours. The reaction mixture was poured over water and extracted with ethyl acetate. The organic layers were combined, dried over anhydrous sodium sulfate, filtered, and then evaporated to dryness. The resulting solid was sonicated in DCM and hexane then filtered to give product (P-0432). [M+H+]$^+$=463.0.

Example 2

Compound P-0133 is prepared in three steps from 5-chloro-4-iodo-1H-pyrrolo[2,3-b]pyridine 7 as shown in Scheme 2.

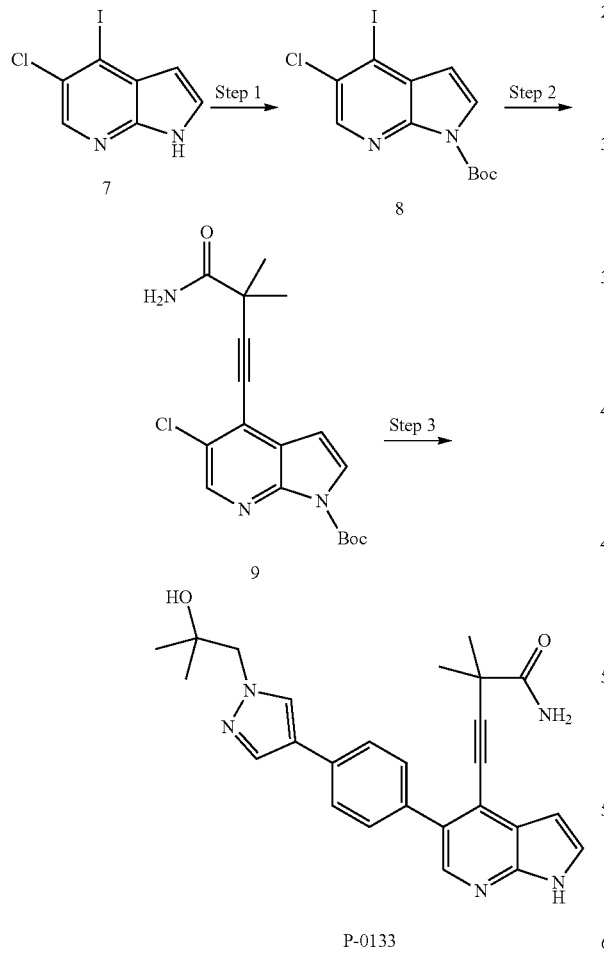

Scheme 2

P-0133

Step 1—Preparation of tert-butyl 5-chloro-4-iodo-1H-pyrrolo[2,3-b]pyridine-1-carboxylate 8

To a solution of 5-chloro-4-iodo-1H-pyrrolo[2,3-b]pyridine (7, 0.100 g, 0.359 mmol) in DCM (5 mL) was added tert-butoxycarbonyl tert-butyl carbonate, followed by DIEA (0.125 mL, 0.718 mmol) and DMAP (4.4 mg, 0.036 mmol). The reaction mixture was allowed to stir at ambient temperature for 2 hours. The reaction mixture was evaporated to dryness in the presence of silica gel and then purified by silica gel column chromatography eluting with a gradient of 0-60% ethyl acetate in hexane to give product (8, 115 mg).

Step 2—Preparation of tert-butyl 4-(4-amino-3,3-dimethyl-4-oxobut-1-yn-1-yl)-5-chloro-1H-pyrrolo[2,3-b]pyridine-1-carboxylate 9

Tert-butyl 5-chloro-4-iodo-pyrrolo[2,3-b]pyridine-1-carboxylate (8, 115 mg, 0.304 mmol) and 2-methylbut-3-yn-2-ol (0.051 mg, 0.456 mmol) were dissolved in diethylamine (5 mL). Copper(I) iodide (12 mg, 0.061 mmol), palladium (II) acetate (14 mg, 0.061 mmol), and triphenylphosphine (32.0 mg, 0.122 mmol) were added and the mixture was heated to 60° C. for 6 hours in an oil bath. The reaction mixture was poured over water and extracted with ethyl acetate. The organic layers were combined, washed with brine, dried over anhydrous sodium sulfate, filtered, and then evaporated to dryness in the presence of silica gel. This material was purified by silica gel column chromatography eluting with a gradient of 0-60% ethyl acetate in hexane to give product (9, 46 mg).

Step 3—Preparation of 4-[5-[4-[1-(2-hydroxy-2-methyl-propyl)pyrazol-4-yl]phenyl]-1H-pyrrolo[2,3-b]pyridin-4-yl]-2,2-dimethyl-but-3-ynamide P-0133

Tert-butyl 4-(4-amino-3,3-dimethyl-4-oxo-but-1-ynyl)-5-chloro-pyrrolo[2,3-b]pyridine-1-carboxylate (9, 46.0 mg, 0.127 mmol) and 2-methyl-1-[4-[4-(4,4,5,5-tetramethyl-1,3,2-dioxaborolan-2-yl)phenyl]pyrazol-1-yl]propan-2-ol (47.8 mg, 0.140 mmol) were dissolved in dioxane (3 mL). Methanesulfonato(tricyclohexylphosphino)(2'-methylamino-1,1'-biphenyl-2-yl)palladium(II) (8.6 mg, 0.013 mmol) and 0.5 M K$_2$HPO$_4$ (1.16 mL) were added and the vial was purged with nitrogen, sealed, then heated at 120° C. for 40 minutes. The reaction mixture was poured over anhydrous sodium sulfate, filtered, and then evaporated to dryness in the presence of silica gel. This crude material was purified by reverse-phase silica gel column chromatography eluting with a gradient of 0-50% acetonitrile in water to give product (P-0133,). [M+H+]$^+$=442.1.

Example 3

Compound P-0376 is prepared in two steps from 3-bromo-5-fluoroimidazo[1,2-a]pyridine 10 as shown in Scheme 3.

Scheme 3

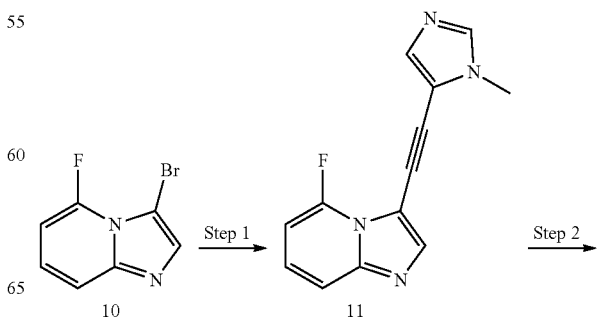

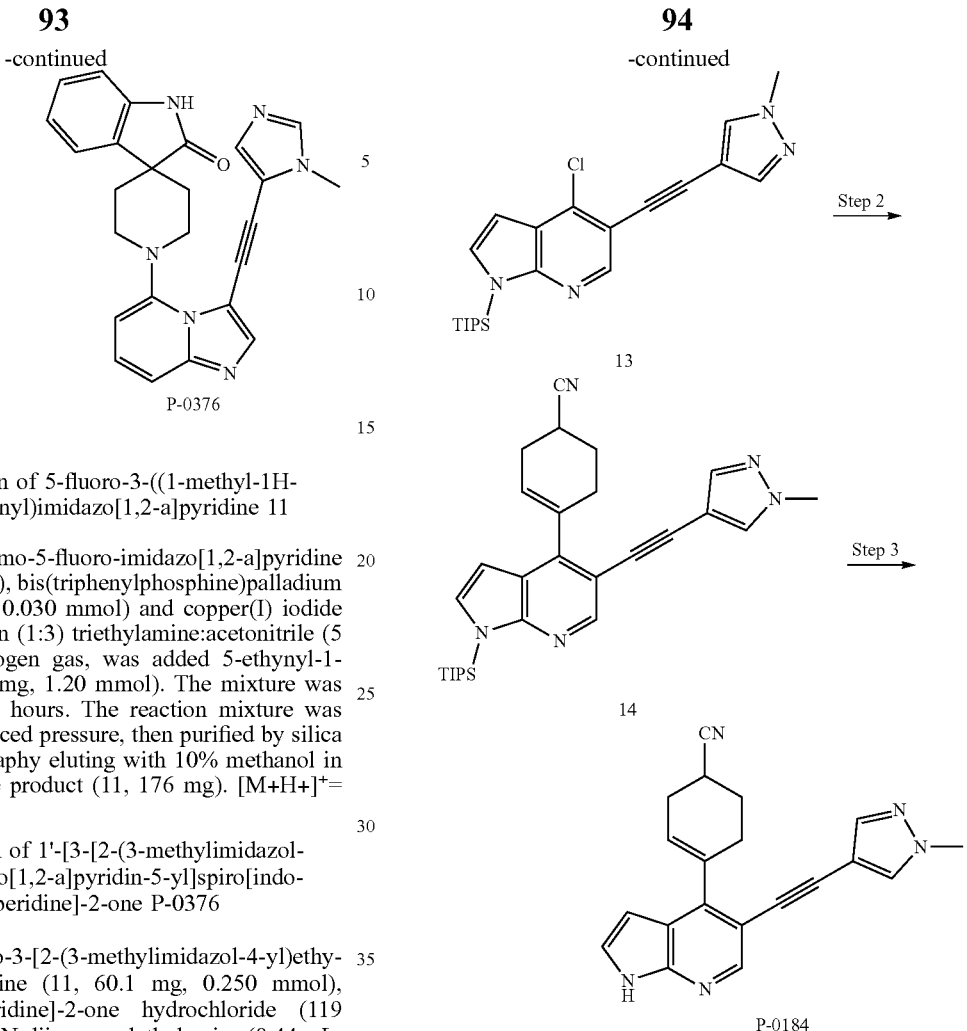

Step 1—Preparation of 5-fluoro-3-((1-methyl-1H-imidazol-5-yl)ethynyl)imidazo[1,2-a]pyridine 11

To a mixture of 3-bromo-5-fluoro-imidazo[1,2-a]pyridine (10, 215 mg, 1.00 mmol), bis(triphenylphosphine)palladium(II) dichloride (21 mg, 0.030 mmol) and copper(I) iodide (5.7 mg, 0.030 mmol) in (1:3) triethylamine:acetonitrile (5 mL), purged with nitrogen gas, was added 5-ethynyl-1-methyl-imidazole (127 mg, 1.20 mmol). The mixture was heated at 80° C. for 2 hours. The reaction mixture was concentrated under reduced pressure, then purified by silica gel column chromatography eluting with 10% methanol in ethyl acetate to provide product (11, 176 mg). [M+H+]$^+$= 241.2.

Step 2—Preparation of 1'-[3-[2-(3-methylimidazol-4-yl)ethynyl]imidazo[1,2-a]pyridin-5-yl]spiro[indoline-3,4'-piperidine]-2-one P-0376

A mixture of 5-fluoro-3-[2-(3-methylimidazol-4-yl)ethynyl]imidazo[1,2-a]pyridine (11, 60.1 mg, 0.250 mmol), spiro[indoline-3,4'-piperidine]-2-one hydrochloride (119 mg, 0.499 mmol) and N,N-diisopropylethylamine (0.44 mL, 2.5 mmol) in NMP (2 mL) was purged with nitrogen gas, and then heated in a microwave reactor at 220° C. for 1 hour. The reaction was allowed to cool and was diluted with ethyl acetate and extracted with water followed by brine. The organic layer was separated and was dried over anhydrous magnesium sulfate, filtered and concentrated under reduced pressure. The material was purified by silica gel column chromatography eluting with 10% methanol in ethyl acetate. The material obtained from chromatography was triturated with acetonitrile to provide product (P-0376). [M+H$^+$]$^+$= 423.30.

Example 4

Compound P-0184 is prepared in three steps from 4-chloro-5-iodo-1-(triisopropylsilyl)-1H-pyrrolo[2,3-b]pyridine 12 as shown in Scheme 4.

Step 1—Preparation of 4-chloro-5-((1-methyl-1H-pyrazol-4-yl)ethynyl)-1-(triisopropylsilyl)-1H-pyrrolo[2,3-b]pyridine 13

To a mixture of (4-chloro-5-iodo-pyrrolo[2,3-b]pyridin-1-yl)-triisopropyl-silane (12, 100 mg, 0.230 mmol), bis(triphenylphosphine)palladium(II) dichloride (4.8 mg, 0.0069 mmol) and copper(I) iodide (1.3 mg, 0.0069 mmol) in (1:3) triethylamine:acetonitrile (3.0 mL), purged with nitrogen gas, was added 4-ethynyl-1-methyl-pyrazole (29.3 mg, 0.276 mmol). The mixture was heated at 90° C. for 3 hours. The mixture was concentrated down under reduced pressure and purified by silica gel column chromatography eluting with 20% ethyl acetate in hexane to provide product (13, 55 mg). [M+H$^+$]$^+$=413.1.

Step 2—Preparation of 4-(5-((1-methyl-1H-pyrazol-4-yl)ethynyl)-1-(triisopropylsilyl)-1H-pyrrolo[2,3-b]pyridin-4-yl)cyclohex-3-ene-1-carbonitrile 14

A mixture of [4-chloro-5-[2-(1-methylpyrazol-4-yl)ethynyl]pyrrolo[2,3-b]pyridin-1-yl]-triisopropyl-silane (13, 55 mg, 0.13 mmol), 4-(4,4,5,5-tetramethyl-1,3,2-dioxaborolan-2-yl)cyclohex-3-ene-1-carbonitrile (34 mg, 0.15 mmol), methanesulfonato(tricyclohexylphosphino)(2'-methylamino-1,1'-biphenyl-2-yl)palladium(II) (8.9 mg, 0.013 mmol) in dioxane (2 mL) was purged with nitrogen gas, then 0.5 M aqueous K$_2$HPO$_4$ (0.8 mL) was added. The mixture was heated at 100° C. for 3 hours. The sample was diluted with ethyl acetate and dried over anhydrous magnesium sulfate. The solid was removed by filtration and the filtrate was concentrated under reduced pressure. The material was purified by silica gel column chromatography eluting with 50% ethyl acetate in hexane to provide product (14, 18 mg). [M+H$^+$]$^+$=484.3.

Step 3—Preparation of 4-[5-[2-(1-methylpyrazol-4-yl)ethynyl]-H-pyrrolo[2,3-b]pyridin-4-yl]cyclohex-3-ene-1-carbonitrile P-0184

A mixture of 4-[5-[2-(1-methylpyrazol-4-yl)ethynyl]-1-triisopropylsilyl-pyrrolo [2,3-b]pyridin-4-yl]cyclohex-3-ene-1-carbonitrile 14 (18 mg, 0.037 mmol) and 1M aqueous KOH (0.11 mL) in (1:1) THF:MeOH (1 mL) was allowed to stir at 50° C. for 3 hours. The reaction mixture was diluted with water and extracted with ethyl acetate. The organic layer was washed with brine and dried over anhydrous magnesium sulfate. The solid was removed by filtration and the filtrate was concentrated under reduced pressure. The sample was purified by silica gel column chromatography eluting with 100% ethyl acetate. This material was further purified by reverse phase silica gel column chromatography eluting with a gradient of acetonitrile in water with 0.1% formic acid to provide product (P-0184). [M+H$^+$]$^+$=328.2.

Example 5

Compound P-0130 is prepared in three steps from 4-chloropyrazolo[1,5-a]pyrazine 15 as shown in Scheme 5.

Scheme 5

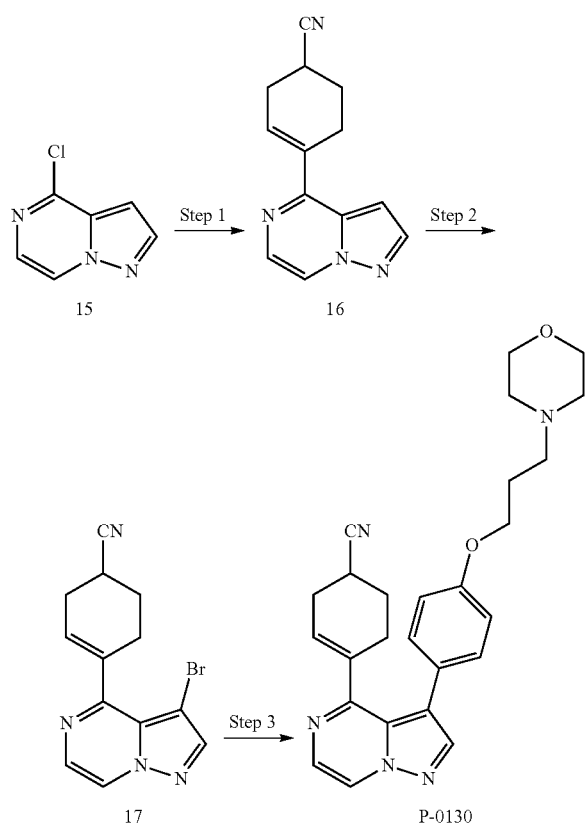

Step 1—Preparation of 4-(pyrazolo[1,5-a]pyrazin-4-yl)cyclohex-3-ene-1-carbonitrile 16

To a pressure vessel charged with 4-chloropyrazolo[1,5-a]pyrazine (15, 2.00 g, 13.0 mmol), 4-(4,4,5,5-tetramethyl-1,3,2-dioxaborolan-2-yl)cyclohex-3-ene-1-carbonitrile (3.20 g, 13.7 mmol), 1,1'-bis(diphenylphosphino)ferrocene-palladium(II) dichloride dichloromethane complex (0.99 g, 1.2 mmol) was added acetonitrile (32 mL) and 1M aqueous potassium carbonate (16 mL). The reaction mixture was allowed to stir at for 15 minutes. The reaction mixture was poured into water and extracted with ethyl acetate. The organic layer was washed with water, brine, and dried over anhydrous MgSO$_4$. The solids were removed by filtration and the filtrate was concentrated under reduced pressure. The crude material was purified by silica gel column chromatography eluting with a gradient of 0-80% ethyl acetate in dichloromethane to provide product (16, 2.02 g). [M+H$^+$]$^+$=225.2.

Step 2—Preparation of 4-(3-bromopyrazolo[1,5-a]pyrazin-4-yl)cyclohex-3-ene-1-carbonitrile 17

To 4-pyrazolo[1,5-a]pyrazin-4-ylcyclohex-3-ene-1-carbonitrile (16, 2.02 g, 9.01 mmol) in acetonitrile (50 mL) was added N-bromosuccinimide (1.7 g, 9.56 mmol). The reaction was allowed to stir at ambient temperature for 4 hours. The reaction mixture was poured into aqueous 1 M potassium carbonate and extracted with DCM. The organic layer was washed with water and brine, and then dried over anhydrous MgSO$_4$. The solids were removed by filtration and the filtrate was concentrated under reduced pressure to provide the product (17, 2.57 g) [M+H$^+$]$^+$=305.0.

Step 3—Preparation of 4-[3-[4-(3-morpholinopropoxy)phenyl]pyrazolo[1,5-a]pyrazin-4-yl]cyclohex-3-ene-1-carbonitrile P-0130

To 4-(3-bromopyrazolo[1,5-a]pyrazin-4-yl)cyclohex-3-ene-1-carbonitrile (17, 70 mg, 0.231 mmol), 4-[3-[4-(4,4,5,5-tetramethyl-1,3,2-dioxaborolan-2-yl)phenoxy]propyl]morpholine (110 mg, 0.317 mmol), and 1,1'-bis(diphenylphosphino)ferrocene-palladium(II) dichloride dichloromethane complex (30 mg, 0.039 mmol) in acetonitrile (3 mL) was added 1M aqueous potassium carbonate (1.5 mL). The reaction mixture was allowed to stir at for 15 minutes. The reaction mixture was poured into water and extracted with ethyl acetate. The organic layer was washed with water and brine, and then dried over anhydrous MgSO$_4$. The solids were removed by filtration and the filtrate was concentrated under reduced pressure. The material was purified by silica gel column chromatography eluting with a gradient of 0-100% ethyl acetate in hexane to provide product (P-0130). The fractions containing product were combined and concentrated under reduced pressure, dried under high vacuum overnight to provide the compound (23, 61 mg). [M+H$^+$]$^+$=444.6.

Example 6

Compound P-0117 is prepared in three steps from 4-chloropyrazolo[1,5-a]pyrazine 15 as shown in Scheme 6.

Scheme 6

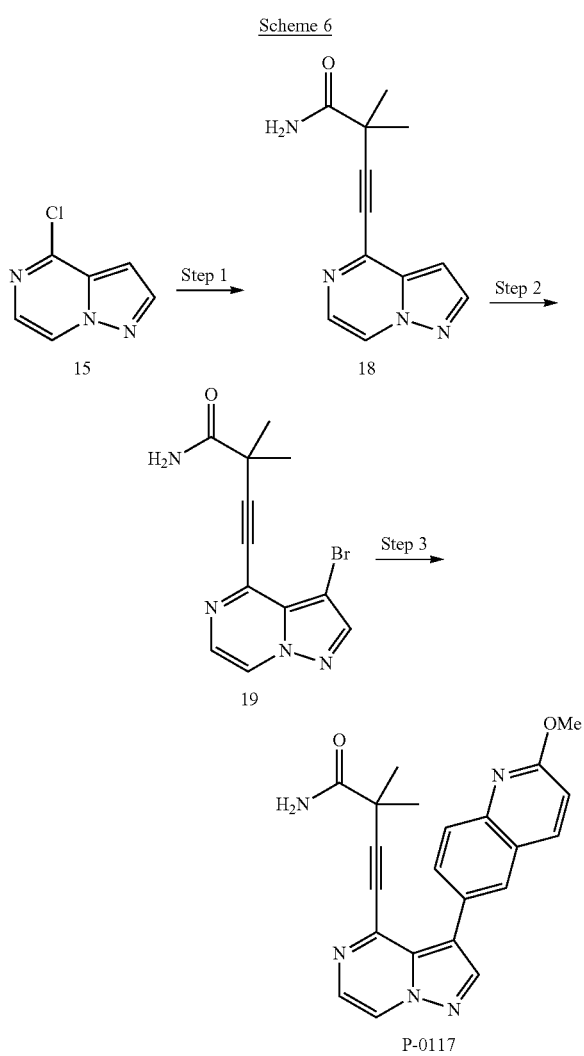 [SMILES: Clc1nccn2nccc12 ; CC(C)(C#Cc1nccn2nccc12)C(N)=O ; CC(C)(C#Cc1nccn2ncc(Br)c12)C(N)=O ; COc1ccc2cc(-c3cnn4ccnc(C#CC(C)(C)C(N)=O)c34)ccc2n1]

Step 1—Preparation of 2,2-dimethyl-4-(pyrazolo[1,5-a]pyrazin-4-yl)but-3-ynamide 18

To 4-chloropyrazolo[1,5-a]pyrazine (15, 1.50 g, 9.77 mmol), 2,2-dimethylbut-3-ynamide (1.30 g, 11.7 mmol), copper(I) iodide (186 mg, 0.977 mmol), triphenylphosphine (512 mg, 1.95 mmol) and Pd/C (5%, 1.04 g, 0.488 mmol) were added diisopropylamine (15 mL) and 1,4-dioxane (7.5 mL). The mixture was allowed to stir at 80° C. for 4 hours. The reaction was filtered through celite and then partitioned between ethyl acetate and water. The organic layer was dried over anhydrous magnesium sulfate, filtered and concentrated under reduced pressure. The material was purified solution phase of the reaction mixture was collected by filtration and concentrated to dryness under reduced pressure. The material was purified by silica gel column chromatography eluting with a gradient of 0-100% ethyl acetate in hexane to provide product (18, 2.1 g). [M+H$^+$]$^+$=229.2.

Step 2—Preparation of 4-(3-bromopyrazolo[1,5-a]pyrazin-4-yl)-2,2-dimethylbut-3-ynamide 19

To 2,2-dimethyl-4-(pyrazolo[1,5-a]pyrazin-4-yl)but-3-ynamide (18, 1.4 g, 6.1 mmol) dissolved in acetonitrile (50 mL) was added N-bromosuccinimide (1.09 g, 6.12 mmol). The reaction was allowed to stir at ambient temperature for 4 hours. The reaction mixture was poured into aqueous 1M potassium carbonate and extracted with DCM. The organic layer was washed with water and brine and then dried over anhydrous MgSO$_4$. The solids were removed by filtration and the filtrate was concentrated under reduced pressure. The residue was suspended in acetonitrile and the resulting solid material was collected by filtration to provide product (19, 1.08 g). [M+H$^+$]$^+$=306.9.

Step 3—Preparation of 4-[3-(2-methoxy-6-quinolyl)pyrazolo[1,5-a]pyrazin-4-yl]-2,2-dimethyl-but-3-ynamide P-0117

To 4-(3-bromopyrazolo[1,5-a]pyrazin-4-yl)-2,2-dimethylbut-3-ynamide (19, 70 mg, 0.228 mmol), 2-methoxy-6-(4,4,5,5-tetramethyl-1,3,2-dioxaborolan-2-yl)quinoline (85 mg, 0.298 mmol), and 1,1'-bis(diphenylphosphino)ferrocene-palladium(II) dichloride dichloromethane complex (30 mg, 0.039 mmol) in acetonitrile (3 mL) was added 1M aqueous potassium carbonate. The reaction mixture was allowed to stir at for 15 minutes. The reaction mixture was poured into water and extracted with ethyl acetate. The organic layer was washed with water and brine and then dried over anhydrous MgSO$_4$. The solids were removed by filtration and the filtrate was concentrated under reduced pressure. The material was purified by prep RP-HPLC eluting with a gradient of acetonitrile in water with 0.1% formic acid to provide product (P-0117). [M+H$^+$]$^+$=386.5.

Example 7

Compound P-0433 is prepared in three steps from 4-bromopyrazolo[1,5-a]pyridine 20 as shown in Scheme 7.

Scheme 7

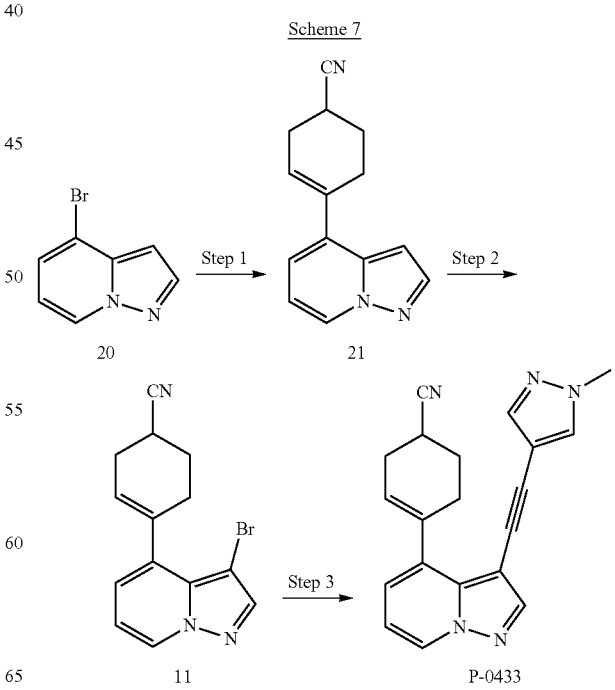

Step 1—Preparation of 4-(pyrazolo[1,5-a]pyridin-4-yl)cyclohex-3-ene-1-carbonitrile 21

To 4-bromopyrazolo[1,5-a]pyridine (20, 0.540 g, 2.74 mmol) in 1,4-dioxane (8 mL) was added by 4-(4,4,5,5-tetramethyl-1,3,2-dioxaborolan-2-yl)cyclohex-3-ene-1-carbonitrile (0.690 g, 2.96 mmol), 1,1'-bis(diphenylphosphino)ferrocene-palladium(II) dichloride dichloromethane complex (0.223 g, 0.274 mmol) and 1M aqueous potassium carbonate (4 mL). The reaction was allowed to stir at 100° C. for 30 minutes. The reaction mixture was poured into water and extracted with ethyl acetate. The organic layer was washed with water and brine and then dried over anhydrous $MgSO_4$. The solid was removed by filtration and the volatiles were removed under reduced pressure. The material was purified by silica gel column chromatography eluting with a gradient of 0-100% ethyl acetate in hexane to provide product (21, 520 mg). $[M+H^+]^+=224.2$.

Step 2—Preparation of 4-(3-bromopyrazolo[1,5-a]pyridin-4-yl)cyclohex-3-ene-1-carbonitrile 22

To 4-pyrazolo[1,5-a]pyridin-4-ylcyclohex-3-ene-1-carbonitrile (21, 0.520 g, 2.32 mmol) in acetonitrile (50 mL)) was added N-bromosuccinimide (0.539 g, 3.03 mmol). The reaction was allowed to stir at room temperature for 1 hour. The reaction mixture was poured into aqueous 1M potassium carbonate and extracted with dichloromethane. The organic layer was washed with water and brine and then dried over anhydrous $MgSO_4$. The solids were removed by filtration and the volatiles were removed under reduced pressure. The resulting crude material was purified by silica gel column chromatography eluting with a gradient of 0-100% ethyl acetate in hexane to provide product (22, 530 mg). $[M+H^+]^+=302.1$.

Step 3—Preparation of 4-[3-[2-(1-methylpyrazol-4-yl)ethynyl]pyrazolo[1,5-a]pyridin-4-yl]cyclohex-3-ene-1-carbonitrile P-0433

4-(3-bromopyrazolo[1,5-a]pyridin-4-yl)cyclohex-3-ene-1-carbonitrile (22, 35 mg, 0.12 mmol), 4-ethynyl-1-methylpyrazole (0.017 mL, 0.15 mmol), cesium carbonate (0.094 g, 0.29 mmol), tris(dibenzylideneacetone)dipalladium(0) (10 mg, 0.017 mmol), and tricyclohexylphosphine (10 mg, 0.035 mmol) were combined in acetonitrile (1 mL) and allowed to stir at 75° C. for 16 hours. The reaction mixture was filtered through celite and then partitioned between ethyl acetate and saturated aqueous ammonium chloride. The organic layer was separated, dried over anhydrous magnesium sulfate and filtered. The filtrate was concentrated under reduced pressure and purified by silica gel column chromatography eluting with a gradient of 0-10% ethyl acetate in hexane. The obtained product was further purified by reverse phase silica gel column chromatography eluting with a gradient of acetonitrile in water with 0.1% formic acid to provide product (P-0433). $[M+H^+]^+=328.2$.

Example 8

Compound P-0333 is prepared in five steps from 4-bromopyrazolo[1,5-a]pyridine 20 as shown in Scheme 8.

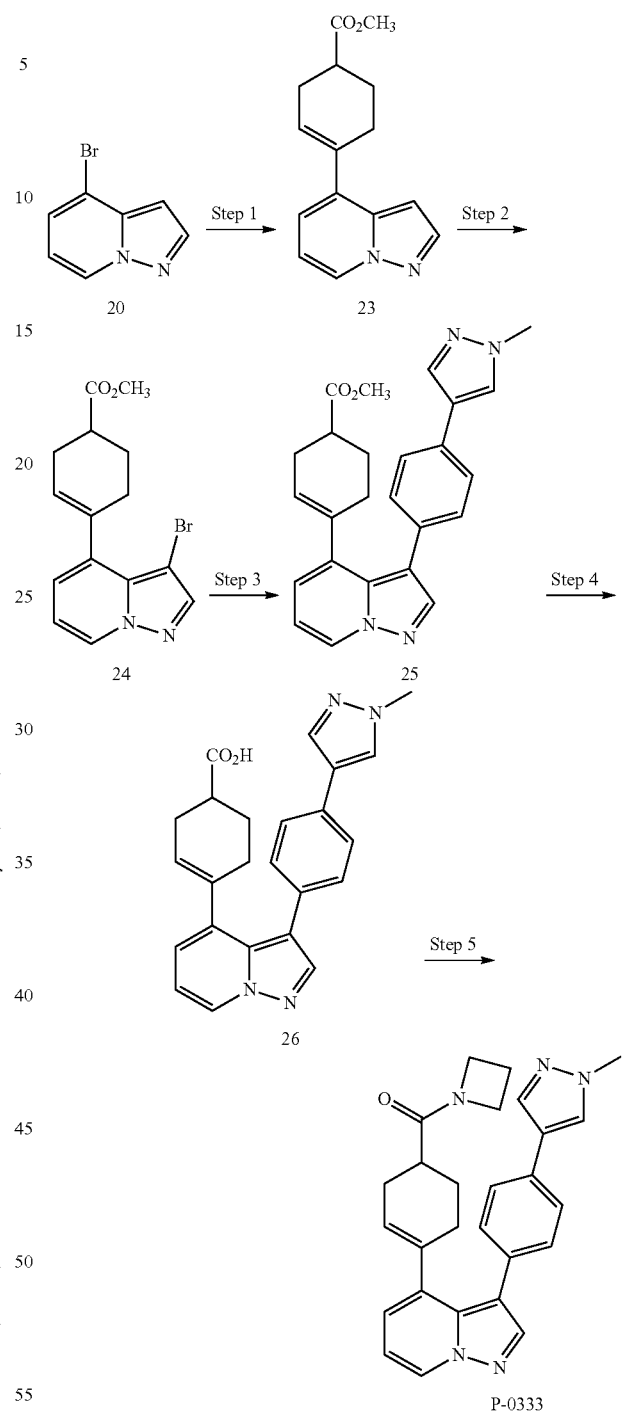

Scheme 8

Step 1—Preparation of methyl 4-(pyrazolo[1,5-a]pyridin-4-yl)cyclohex-3-ene-1-carboxylate 23

To a mixture 4-bromopyrazolo[1,5-a]pyridine (550 mg, 2.79 mmol), methyl 4-(4,4,5,5-tetramethyl-1,3,2-dioxaborolan-2-yl)cyclohex-3-ene-1-carboxylate (0.80 g, 3.0 mmol) and 1,1'-bis(diphenylphosphino)ferrocene-palladium(II) dichloride dichloromethane complex (0.22 g, 0.27 mmol) in dioxane (20 mL) was added 1M aqueous potassium carbonate (5 mL). The mixture was purged with nitrogen and was then allowed to stir at 120° C. for 1 hour. The reaction mixture was poured into water and extracted with ethyl acetate. The organic layer was washed with water and brine and then dried over anhydrous MgSO$_4$. The solid was removed by filtration and the volatiles were removed under reduced pressure. The crude material was purified by silica gel column chromatography to provide product (23, 680 mg). [M+H$^+$]$^+$=257.1.

Step 2—Preparation of methyl 4-(3-bromopyrazolo [1,5-a]pyridin-4-yl)cyclohex-3-ene-1-carboxylate 24

To a solution of methyl 4-pyrazolo[1,5-a]pyridin-4-ylcyclohex-3-ene-1-carboxylate (23, 300 mg, 1.17 mmol) in THF (30 mL) was added N-bromosuccinimide (200 mg, 1.12 mmol). The mixture was allowed to stir at room temperature for two hours. The reaction mixture was poured into water and extracted with ethyl acetate. The organic layer was collected, washed with brine, and dried over anhydrous sodium sulfate. After removal of the drying agent by filtration, the volatiles were removed under reduced pressure to provide product (24, 373 mg). [M+H$^+$]$^+$=336.7.

Step 3—Preparation of methyl 4-(3-(4-(1-methyl-1H-pyrazol-4-yl)phenyl)pyrazolo[1,5-a]pyridin-4-yl) cyclohex-3-ene-1-carboxylate 25

To a mixture of methyl 4-(3-bromopyrazolo[1,5-a]pyridin-4-yl)cyclohex-3-ene-1-carboxylate (24, 370 mg, 1.10 mmol), 1-methyl-4-[4-(4,4,5,5-tetramethyl-1,3,2-dioxaborolan-2-yl)phenyl]pyrazole (320 mg, 1.13 mmol) and 1,1'-bis(diphenylphosphino)ferrocene-palladium(II) dichloride dichloromethane complex (100 mg, 0.131 mmol) in acetonitrile (10 mL) was added 1M aqueous potassium carbonate (2 mL). The mixture was allowed to stir at 120° C. for 1 hour. The reaction mixture was poured into water and extracted with ethyl acetate. The organic layer was collected, washed with brine, and dried over anhydrous sodium sulfate. After removal of drying agent and solvent, the residue was purified by silica gel column chromatography to provide product (25, 68 mg). [M+H$^+$]$^+$=413.1.

Step 4—Preparation of 4-(3-(4-(1-methyl-1H-pyrazol-4-yl)phenyl)pyrazolo[1,5-a]pyridin-4-yl)cyclohex-3-ene-1-carboxylic acid 26

To a solution of methyl 4-[3-[4-(1-methylpyrazol-4-yl) phenyl]pyrazolo[1,5-a]pyridin-4-yl]cyclohex-3-ene-1-carboxylate (68 mg, 0.17 mmol) in THF (3 mL) was added 1M aqueous lithium hydroxide (2 mL). The mixture was allowed to stir at ambient temperature for 48 hours. The reaction mixture was concentrated and the residue was purified by prep RP-HPLC to provide compound product (26, 14 mg). [M+H$^+$]$^+$=399.3.

Step 5—Preparation of azetidin-1-yl-[4-[3-[4-(1-methylpyrazol-4-yl)phenyl]pyrazolo[1,5-a]pyridin-4-yl]cyclohex-3-en-1-yl]methanone P-0333

To 4-[3-[4-(1-methylpyrazol-4-yl)phenyl]pyrazolo[1,5-a] pyridin-4-yl]cyclohex-3-ene-1-carboxylic acid (11 mg, 0.028 mmol) in THF (5 mL) was added HBTU (11 mg, 0.029 mmol) followed by triethylamine (0.1 mL, 0.72 mmol). The suspension was allowed to stir at ambient temperature for 30 minutes. To this suspension was added azetidine (3 mg, 0.05 mmol). The reaction mixture was allowed to stir at ambient temperature overnight. The reaction mixture was poured into water and extracted with ethyl acetate. The organic layer was collected, washed with brine, and dried over anhydrous sodium sulfate. After removal of drying agent and solvent, the residue was purified by silica gel column chromatography to provide product (P-0333). [M+H$^+$]$^+$=438.20.

Example 9

Compound P-0217 is prepared in three steps from 4-(pyrazolo[1,5-a]pyridin-4-yl)cyclohex-3-ene-1-carbonitrile 21 as shown in Scheme 9.

Scheme 9

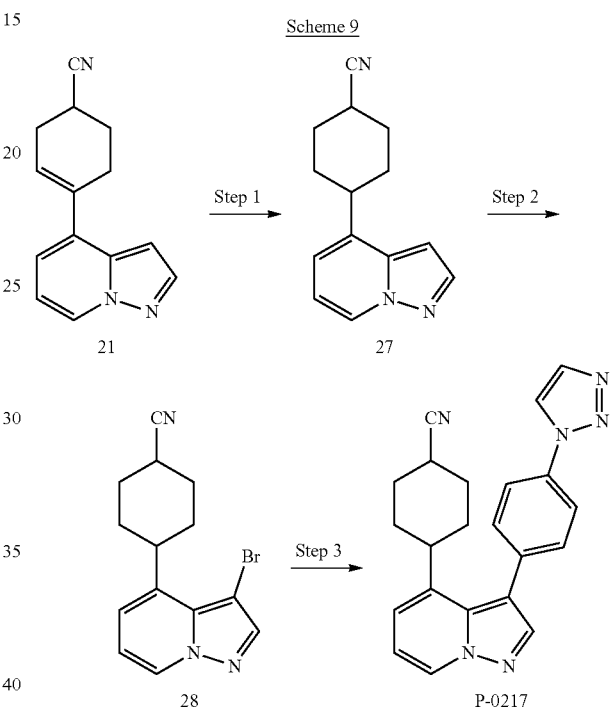

Step 1—Preparation of (1r,4r) and (1s,4s)-4-(pyrazolo[1,5-a]pyridin-4-yl)cyclohexane-1-carbonitrile 27

To a pressure vessel was added 4-pyrazolo[1,5-a]pyridin-4-ylcyclohex-3-ene-1-carbonitrile (21, 753 mg, 3.37 mmol), palladium hydroxide on carbon (20 wt pct loading dry basis, wet support, 119 mg, 11.9 mg palladium hydroxide, 0.085 mmol) and MeOH (60.0 mL). The reaction vessel was evacuated/filled with hydrogen and shaken at ambient temperature and 35 psi H$_2$ pressure for 8 hours. The reaction was filtered, giving a clear, colorless solution. The resultant solution was evaporated and purified by reverse phase flash column chromatography (C18, 0-100% CH$_3$CN (0.1% HCO$_2$H), H$_2$O (0.1% HCO$_2$H)), giving the product as a mixture of cis and trans isomers (27, 561 mg). [M+H$^+$]$^+$= 226.10 and 226.15.

Step 2—Preparation of (1r,4r) and (1s,4s)-4-(3-bromopyrazolo[1,5-a]pyridin-4-yl)cyclohexane-1-carbonitrile 28

To 4-pyrazolo[1,5-a]pyridin-4-ylcyclohexanecarbonitrile (27, 561 mg, 2.49 mmol) in acetonitrile (30.0 mL) cooled to 0° C. was added N-bromosuccinimide (444 mg, 2.49 mmol, in 3.0 mL CH₃CN, pre-chilled to 0° C.) dropwise, by syringe. The reaction was allowed to stir at 0° C. for 1 hour. The reaction was added to ethyl acetate and the organic fraction was washed with H$_2$O (1×100 mL) and 5 M NaCl (1×100 mL), dried over Na$_2$SO$_4$, filtered, and evaporated, giving the product as a mixture of cis and trans isomers (28, 757 mg). [M+H$^+$]$^+$=306.0 and 306.0.

Step 3—Preparation of (1r,4r) and (1s,4s)-4-[3-[4-(triazol-1-yl)phenyl]pyrazolo[1,5-a]pyridin-4-yl]cyclohexanecarbonitrile P-0217

To 4-(3-bromopyrazolo[1,5-a]pyridin-4-yl)cyclohexanecarbonitrile (28, 62 mg, 0.20 mmol), 1-[4-(4,4,5,5-tetramethyl-1,3,2-dioxaborolan-2-yl)phenyl]triazole (57.7 mg, 0.213 mmol), chloro(2-dicyclohexylphosphino-2',6'-dimethoxy-1,1'-biphenyl) [2-(2-aminoethylphenyl)]palladium(II) methyl-t-butyl ether adduct (15.7 mg, 0.021 mmol) was added 0.5 M aqueous potassium phosphate (0.600.0 mL) and CH$_3$CN (3.0 mL). The reaction vial was placed under N$_2$, sealed, and allowed to stir at 120° C. for 2 h. The reaction was diluted with ethyl acetate and the organic fraction was washed with H$_2$O followed by 5 M aqueous NaCl, dried over anhydrous sodium sulfate, filtered, evaporated, and purified by reverse phase flash column chromatography (C18, 0-100% CH$_3$CN (0.1% HCO$_2$H), H$_2$O (0.1% HCO$_2$H)), giving product as a mixture of cis and trans isomers (P-0217). [M+H$^+$]$^+$=369.5 and 369.5.

Example 10

Compound P-0185 is prepared in five steps from 4-bromopyrazolo[1,5-a]pyridine 27 as shown in Scheme 10.

Scheme 10

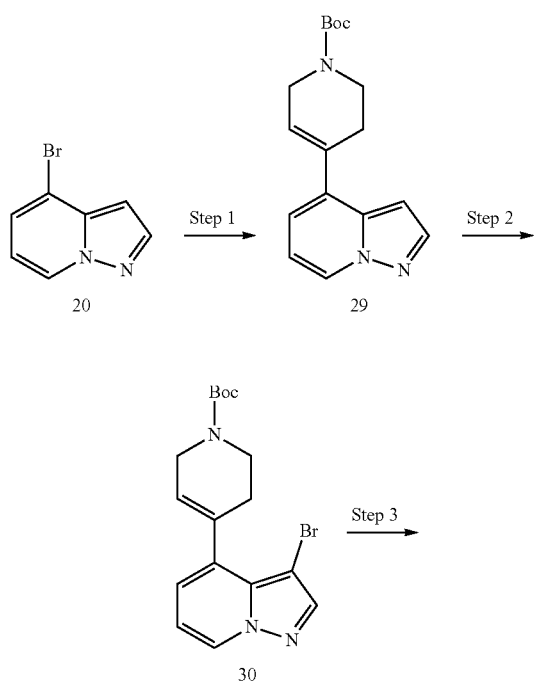

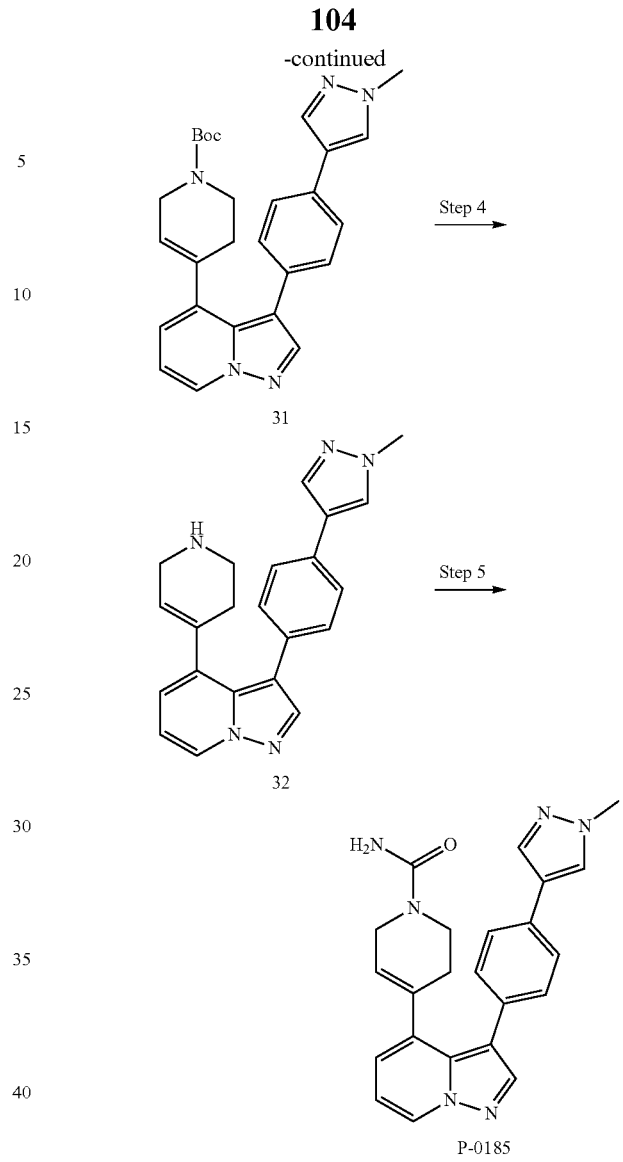

Step 1—Preparation of tert-butyl 4-(pyrazolo[1,5-a]pyridin-4-yl)-3,6-dihydropyridine-1(2H)-carboxylate 29

A mixture of 4-bromopyrazolo[1,5-a]pyridine (20) (502 mg, 2.55 mmol), tert-butyl 4-(4,4,5,5-tetramethyl-1,3,2-dioxaborolan-2-yl)-3,6-dihydro-2H-pyridine-1-carboxylate (867 mg, 2.81 mmol) and 1,1'-bis(diphenylphosphino)ferrocene-palladium(II) dichloride dichloromethane complex (208 mg, 0.255 mmol) in 1,4-dioxane (25 mL) was purged with nitrogen gas, followed by the addition of 2.5M K$_2$CO$_3$ (3.1 mL). The mixture was allowed to stir at 90° C. for 3 hours. The reaction was diluted with ethyl acetate, dried over anhydrous magnesium sulfate, filtered and concentrated under reduced pressure. The material was purified by silica gel column chromatography eluting with 30% ethyl acetate in hexane to provide product (29, 750 mg). [M+H$^+$]$^+$=300.2.

Step 2—Preparation of tert-butyl 4-(3-bromopyrazolo[1,5-a]pyridin-4-yl)-3,6-dihydropyridine-1(2H)-carboxylate 30

To tert-butyl 4-pyrazolo[1,5-a]pyridin-4-yl-3,6-dihydro-2H-pyridine-1-carboxylate (39, 750 mg, 2.51 mmol) in acetonitrile (50 mL) was added N-bromosuccinimide (0.21 mL, 2.51 mmol) and the reaction was allowed to stir at ambient temperature for 15 hours. The mixture was quenched with saturated aqueous sodium thiosulfate solution and then extracted with dichloromethane. The organic layer was washed with water followed by brine and dried over anhydrous magnesium sulfate. The solids were removed by filtration and the resulting filtrate was concentrated under reduced pressure. The material was purified by silica gel column chromatography eluting with 30% ethyl acetate in hexane to provide product (30, 778 mg). [M+H$^+$]$^+$= 380.0.

Step 3—Preparation of tert-butyl 4-(3-(4-(1-methyl-1H-pyrazol-4-yl)phenyl)pyrazolo[1,5-a]pyridin-4-yl)-3,6-dihydropyridine-1 (2H)-carboxylate 31

A mixture of tert-butyl 4-(3-bromopyrazolo[1,5-a]pyridin-4-yl)-3,6-dihydropyridine-1(2H)-carboxylate (30, 201 mg, 0.53 mmol), 1-methyl-4-[4-(4,4,5,5-tetramethyl-1,3,2-dioxaborolan-2-yl)phenyl]pyrazole (166 mg, 0.584 mmol), methanesulfonato(tricyclohexylphosphino)(2'-methyl-amino-1,1'-biphenyl-2-yl)palladium(II) (35 mg, 0.053 mmol) in 1,4-dioxane (5 mL) was purged with nitrogen gas, and then added 0.5 M K$_2$HPO$_4$ (2.00 mL) was added. The mixture was allowed to stir at 110° C. for 3 hours. The reaction was diluted with ethyl acetate and was dried over anhydrous magnesium sulfate. The solids were removed by filtration and the resulting filtrate was concentrated under reduced pressure. The sample was purified by silica gel column chromatography eluting with 100% ethyl acetate to provide product (31, 38 mg). [M+H$^+$]$^+$=456.3.

Step 4—Preparation of 3-(4-(1-methyl-1H-pyrazol-4-yl)phenyl)-4-(1,2,3,6-tetrahydropyridin-4-yl)pyrazolo[1,5-a]pyridine 32

To tert-butyl 4-[3-[4-(1-methylpyrazol-4-yl)phenyl]pyrazolo[1,5-a]pyridin-4-yl]-3,6-dihydro-2H-pyridine-1-carboxylate (31, 36 mg, 0.079 mmol) was added 25% TFA in dichloromethane (2 mL) and the reaction was allowed to stir at ambient temperature for 2 hours. The reaction was concentrated down under reduced pressure to provide product (32, 33 mg) as the TFA salt. [M+H$^+$]$^+$=356.2.

Step 5—Preparation of 4-[3-[4-(1-methylpyrazol-4-yl)phenyl]pyrazolo[1,5-a]pyridin-4-yl]-3,6-dihydro-2H-pyridine-1-carboxamide P-0185

To 3-[4-(1-methylpyrazol-4-yl)phenyl]-4-(1,2,3,6-tetrahydropyridin-4-yl) pyrazolo[1,5-a]pyridine; 2,2,2-trifluoroacetic acid (42, 33 mg, 0.070 mmol) and triethylamine (0.029 mL, 0.19 mmol) in dichloromethane (2 mL) was added slowly trimethylsilyl isocyanate (0.029 mL, 0.21 mmol). The reaction was allowed to stir at room temperature for 2 hours. The reaction was quenched with saturated aqueous sodium bicarbonate, extracted with ethyl acetate and washed with water followed by brine. The organic layer was dried over anhydrous magnesium sulfate, filtered and the filtrate was concentrated under reduced pressure. The material was purified by silica gel column chromatography eluting with 20% methanol in ethyl acetate to provide impure product that was further purified by reverse phase flash column chromatography (C18, 0-100% CH$_3$CN (0.1% HCO$_2$H), H$_2$O (0.1% HCO$_2$H)) to provide product (P-0185). [M+H$^+$]$^+$=399.1.

Example 11

Compound P-0304 is prepared in four steps from 3-bromo-5-fluoroimidazo[1,2-a]pyridine 13 as shown in Scheme 11.

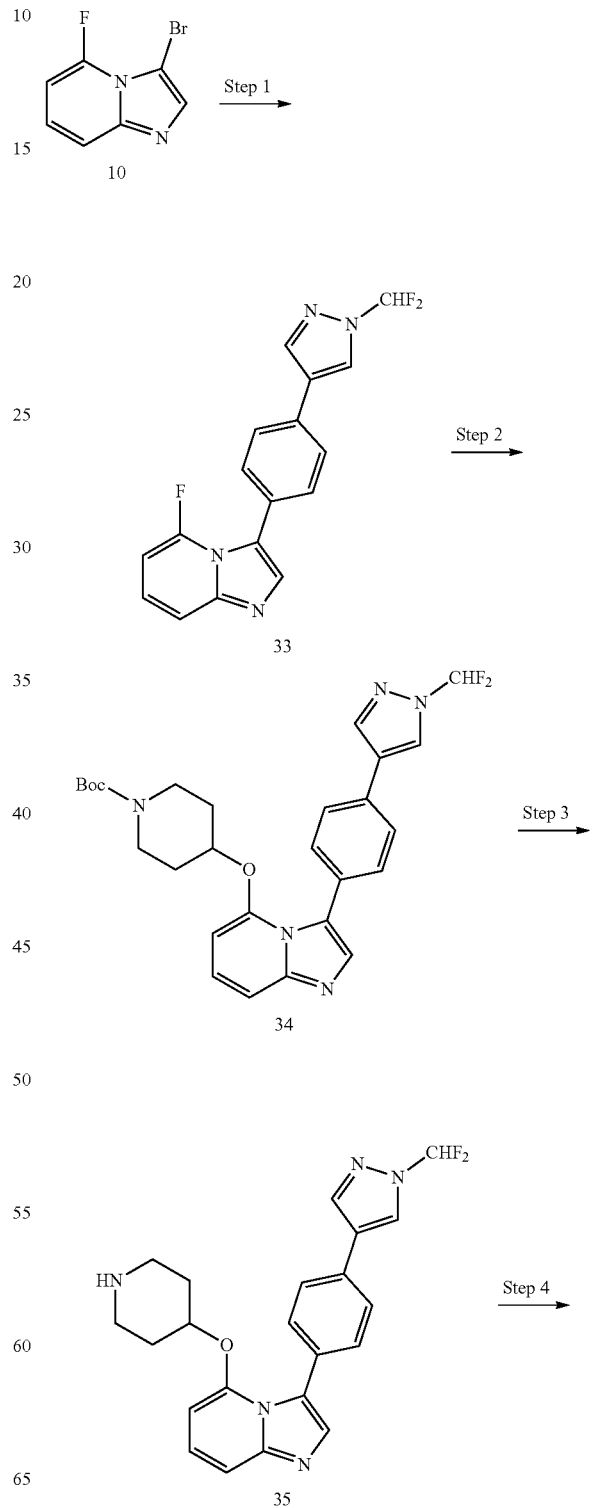

-continued

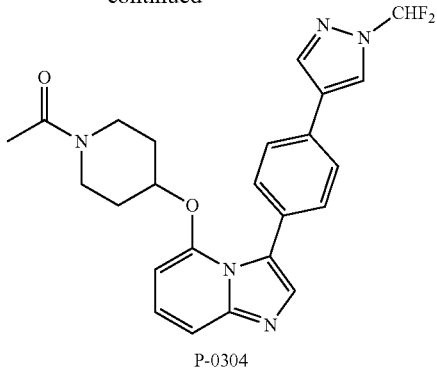

P-0304

Step 1—Preparation of 3-(4-(1-(difluoromethyl)-1H-pyrazol-4-yl)phenyl)-5-fluoroimidazo[1,2-a]pyridine 33

To 3-bromo-5-fluoro-imidazo[1,2-a]pyridine (10, 0.50 g, 2.3 mmol), 1-(difluoromethyl)-4-[4-(4,4,5,5-tetramethyl-1,3,2-dioxaborolan-2-yl)phenyl]pyrazole (0.80 g, 2.5 mmol), and 1,1'-bis(diphenylphosphino)ferrocene-palladium(II) dichloride dichloromethane complex (0.20 g, 0.25 mmol) in acetonitrile (8 mL) was added 1M potassium carbonate (4 mL). The reaction mixture was allowed to stir at for 1 hour. The reaction mixture was poured into water and extracted with ethyl acetate. The organic layer was washed with water, brine, and dried over anhydrous magnesium sulfate. The solid was removed by filtration and the filtrate was concentrated under reduced pressure. The material was purified by silica gel column chromatography eluting with a gradient of 0-100% ethyl acetate in hexane to provide product (33, 434 mg). [M+H$^+$]$^+$=329.2.

Step 2—Preparation of tert-butyl 4-[3-[4-[1-(difluoromethyl)pyrazol-4-yl]phenyl]imidazo[1,2-a]pyridin-5-yl]oxypiperidine-1-carboxylate 34

To 3-[4-[1-(difluoromethyl)pyrazol-4-yl]phenyl]-5-fluoro-imidazo[1,2-a]pyridine (33, 300 mg, 0.914 mmol) was added cesium carbonate (500 mg, 1.53 mmol), tert-butyl 4-hydroxypiperidine-1-carboxylate (500 mg, 2.48 mmol) and DMF (3 mL). The reaction mixture was allowed to stir at 150° C. for 1 hour. The solution phase of the reaction mixture was collected by filtration. The volatiles were removed under reduced pressure. The resulting material was purified by silica gel column chromatography eluting with a gradient of 0-100% ethyl acetate in hexane to provide product (34, 466 mg). [M+H$^+$]$^+$=510.2.

Step 3—Preparation of 3-[4-[1-(difluoromethyl)pyrazol-4-yl]phenyl]-5-(4-piperidyloxy)imidazo[1,2-a]pyridine 35

To tert-butyl 4-[3-[4-[1-(difluoromethyl)pyrazol-4-yl]phenyl]imidazo[1,2-a]pyridin-5-yl]oxypiperidine-1-carboxylate (34, 0.31 g, 0.61 mmol) in dichloromethane (30 mL) was added 2 mL of 2,2,2-trifluoroacetic acid. The mixture was allowed to stir at ambient temperature for 4 hours. The volatiles were removed under reduced pressure and dried under high vacuum to provide product (35, 23 mg). [M+H$^+$]$^+$=410.0.

Step 4—Preparation of 1-[4-[3-[4-[1-(difluoromethyl)pyrazol-4-yl]phenyl]imidazo[1,2-a]pyridin-5-yl]oxy-1-piperidyl]ethanone P-0304

To 3-[4-[1-(difluoromethyl)pyrazol-4-yl]phenyl]-5-(4-piperidyloxy)imidazo[1,2-a]pyridine (35, 23 mg, 0.056 mmol) in tetrahydrofuran (1 mL) was added by DIEA (0.2 mL) and acetyl acetate (200 mg). The mixture was allowed to stir at ambient temperature for 1 hour. The reaction mixture was poured into water and extracted with ethyl acetate. The organic layer was washed with water, brine and dried over anhydrous magnesium sulfate. The solid was removed by filtration and the filtrate was concentrated under reduced pressure. The material was purified by prep RP-HPLC to provide product (P-0304). [M+H$^+$]$^+$=452.6.

Example 12

Compound P-0019 is prepared in three steps from 4-(pyrazolo[1,5-a]pyrazin-4-yl)cyclohex-3-ene-1-carbonitrile 16 as shown in Scheme 12.

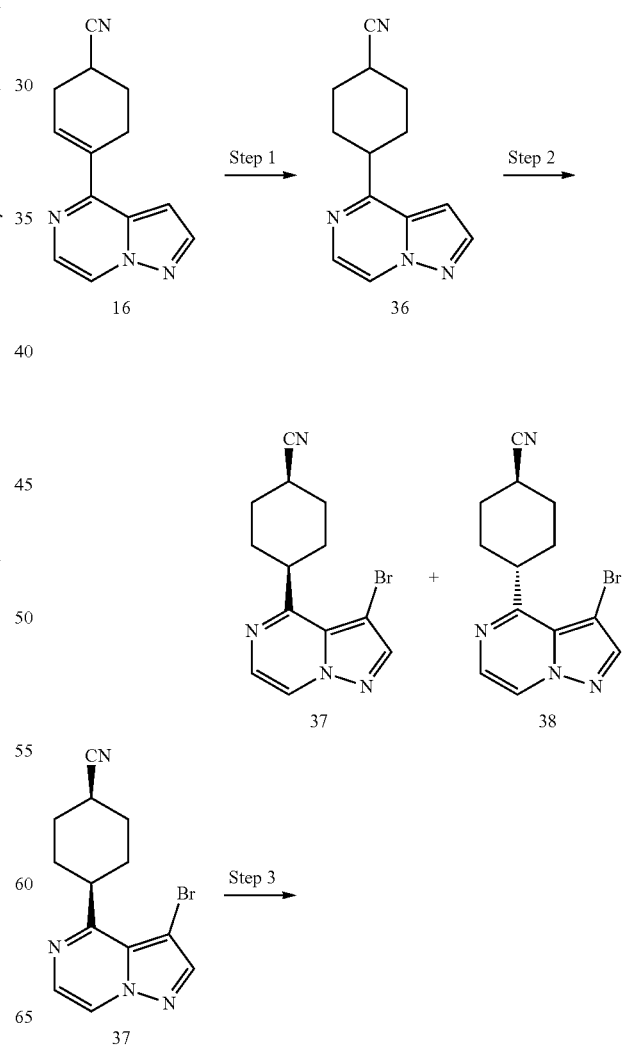

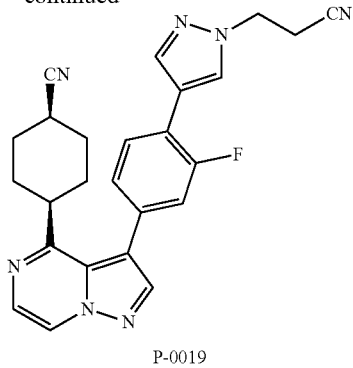

P-0019

Step 1—Preparation of (1s,4s) and (1r,4r)-4-(pyrazolo[1,5-a]pyrazin-4-yl)cyclohexane-1-carbonitrile 36

To a solution of 4-pyrazolo[1,5-a]pyrazin-4-ylcyclohex-3-ene-1-carbonitrile (16, 1.00 g, 4.46 mmol) in methanol (20 mL) and dichloromethane (10 mL) was added palladium on activated carbon (10 wt %, 0.05 g) and palladium hydroxide on carbon (20% wt, 0.07 g). The mixture was degassed and then shaken under 50 psi of hydrogen (Parr shaker) for five hours. The catalyst was filtered off and solvent was removed under reduced pressure. The material was dried under vacuum to provide product (36, 0.97 g). [M+H$^+$]$^+$=227.1.

Step 2—Preparation of (1s,4s)-4-(3-bromopyrazolo[1,5-a]pyrazin-4-yl)cyclohexane-1-carbonitrile 37 and (1r,4r)-4-(3-bromopyrazolo[1,5-a]pyrazin-4-yl)cyclohexane-1-carbonitrile 38

To a stirred solution of 4-pyrazolo[1,5-a]pyrazin-4-ylcyclohexanecarbonitrile (0.91 g, 4.1 mmol) in acetonitrile (10 mL) at 0° C. was added 1-bromopyrrolidine-2,5-dione (0.75 g, 4.24 mmol) in 4 portions over 5 minutes. The reaction was allowed to stir at while for 30 minutes. The reaction mixture was then poured over saturated aqueous sodium thiosulfate and extracted with ethyl acetate. The organic layer was washed with brine, dried over sodium sulfate, filtered and the filtrate was concentrated under reduced pressure. The material was purified by silica gel column chromatography eluting with 35% ethyl acetate in hexane to provide product (37, 0.620 g, cis isomer) and (38, 0.125 g, trans isomer). [M+H$^+$]$^+$=306.9 and 306.9.

Step 3—Preparation of (1s,4s)-4-(3-(4-(1-(2-cyanoethyl)-1H-pyrazol-4-yl)-3-fluorophenyl)pyrazolo[1,5-a]pyrazin-4-yl)cyclohexane-1-carbonitrile P-0019

To (1s,4s)-4-(3-bromopyrazolo[1,5-a]pyrazin-4-yl)cyclohexane-1-carbonitrile (37, 0.20 g, 0.66 mmol) and 3-[4-[2-fluoro-4-(4,4,5,5-tetramethyl-1,3,2-dioxaborolan-2-yl)phenyl]pyrazol-1-yl]propanenitrile (0.34 g, 0.99 mmol) dissolved in 1,4-dioxane (10 mL) was added 1,1'-bis(diphenylphosphino)ferrocene-palladium(II) dichloride dichloromethane complex (0.05 g, 0.07 mmol). The reaction was sealed, purged with nitrogen, and allowed to stir at. Then, 1M aqueous potassium carbonate (1.31 mL) was injected and the reaction was allowed to stir at for 1 hour. The reaction mixture was poured over brine and extracted with ethyl acetate. The organic layer was dried over anhydrous sodium sulfate, filtered, and the filtrate was concentrated under reduced pressure. The material was purified by reverse-phase silica gel column chromatography eluting with 0-50% acetonitrile in water over 30 minutes to give product (P-0019). [M+H$^+$]$^+$=440.2.

Example 13

Compound P-0404 is prepared in three steps from 4-bromopyrazolo[1,5-a]pyridine 27 as shown in Scheme 13.

Scheme 13

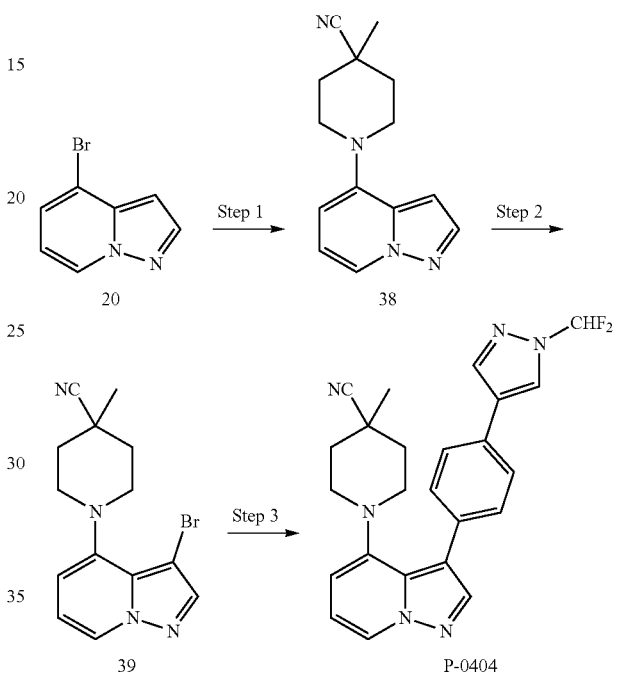

Step 1—Preparation of 4-methyl-1-(pyrazolo[1,5-a]pyridin-4-yl)piperidine-4-carbonitrile 38

To 4-methylpiperidine-4-carbonitrile hydrochloride (1.21 g, 7.53 mmol), 4-bromopyrazolo[1,5-a]pyridine (491 mg, 2.49 mmol), chloro(2-dicyclohexylphosphino-2',4',6'-triisopropyl-1,1'-biphenyl)[2-(2-aminoethylphenyl)]palladium (II) (160 mg, 0.216 mmol) and cesium carbonate (2.44 g, 7.49 mmol) was added 1,4-dioxane (15 mL). The pressure vessel was placed under N$_2$ and the reaction was allowed to stir at for 48 hours. The reaction was added to H$_2$O and extracted with ethyl acetate. The organic layers were combined and washed with H$_2$O and 5 M aqueous sodium chloride and dried over anhydrous sodium sulfate. The solids were filtered and the filtrate was concentrated under reduced pressure. The material was purified by reverse phase flash silica gel column chromatography (C18, 0-100% CH$_3$CN (0.1% HCO$_2$H), H$_2$O (0.1% HCO$_2$H)). The appropriate fractions were combined to yield product that was further purified by normal phase flash silica gel column chromatography eluting with a gradient of 0-10% methanol in dichloromethane to provide product (38). [M+H$^+$]$^+$=241.2.

Step 2—Preparation of 1-(3-bromopyrazolo[1,5-a]pyridin-4-yl)-4-methylpiperidine-4-carbonitrile 39

To 4-methyl-1-pyrazolo[1,5-a]pyridin-4-yl-piperidine-4-carbonitrile (99 mg, 0.41 mmol) in acetonitrile (4 mL) under N₂ and cooled to 0° C. was added N-bromosuccinimide (76 mg, 0.43 mmol, in 1.0 mL acetonitrile) slowly, dropwise, by syringe. The reaction was allowed to stir at 0° C. for 3 hours. The reaction was added to water (100 mL) and extracted with ethyl acetate (3×100 mL). The organic fraction was subsequently dried over anhydrous sodium sulfate, filtered, evaporated, and purified by normal phase flash silica gel column chromatography eluting with a gradient of 0-10% methanol in dichloromethane to provide product (39, 110 mg). [M+H⁺]⁺=321.1.

Step 3—Preparation of 1-[3-[4-[1-(difluoromethyl)pyrazol-4-yl]phenyl]pyrazolo[1,5-a]pyridin-4-yl]-4-methyl-piperidine-4-carbonitrile P-0404

To 1-(3-bromopyrazolo[1,5-a]pyridin-4-yl)-4-methyl-piperidine-4-carbonitrile (55 mg, 0.17 mmol), 1-(difluoromethyl)-4-[4-(4,4,5,5-tetramethyl-1,3,2-dioxaborolan-2-yl)phenyl]pyrazole (61 mg, 0.19 mmol), chloro(2-dicyclohexylphosphino-2',6'-dimethoxy-1,1'-biphenyl)[2-(2-aminoethylphenyl)]palladium(II)methyl-t-butyl ether adduct (14 mg, 0.021 mmol) was added potassium phosphate (0.5 M in water, 1.0 mL) and acetonitrile (3.0 mL). The reaction vial was placed under N₂, sealed, and the reaction was allowed to stir at 120° C. for 2 hours. The reaction was added to ethyl acetate and water. The organic fraction was separated and washed with water and 5 M aqueous sodium chloride, dried over anhydrous sodium sulfate and filtered. The filtrate was concentrated under reduced pressure and purified by reverse phase flash silica gel column chromatography (C18, 0-100% CH₃CN (0.1% HCO₂H), H₂O (0.1% HCO₂H)). The appropriate fractions were combined to yield product that was further purified by normal phase flash silica gel column chromatography eluting with a gradient of 0-10% methanol in dichloromethane to provide product (P-0404). [M+H⁺]⁺=433.3.

Example 14

Compound P-0429 is prepared in three steps from 4-bromopyrazolo[1,5-a]pyridine 20 as shown in Scheme 14.

Scheme 14

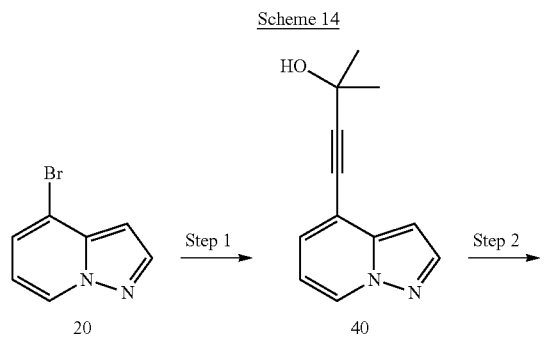

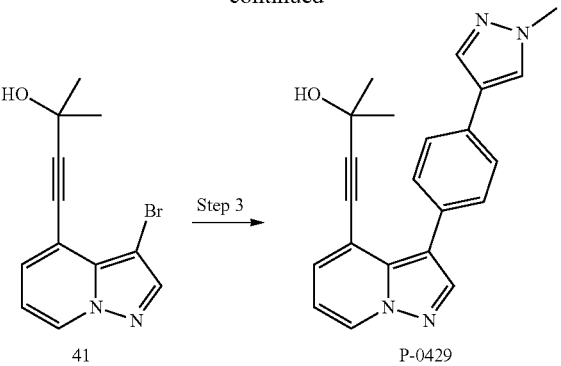

Step 1—Preparation of 2-methyl-4-(pyrazolo[1,5-a]pyridin-4-yl)but-3-yn-2-ol 40

To 4-bromopyrazolo[1,5-a]pyridine (500 mg, 2.54 mmol) in diethylamine (10 mL) was added copper(I) iodide (39 mg, 0.205 mmol), palladium(II) acetate (46 mg, 0.205 mmol), triphenylphosphine (100 mg, 0.381 mmol) and 2-methylbut-3-yn-2-ol (1.49 g, 17.7 mmol). The reaction was allowed to stir at 60° C. for 6 hours. The reaction mixture was added to water and saturated aqueous ammonium chloride solution and extracted with ethyl acetate. The organic layer was washed with water and brine and then dried over anhydrous magnesium sulfate. The solids were removed by filtration and the filtrate was concentrated under reduced pressure. This crude material (40) was used without further purification in the next step.

Step 2—Preparation of 4-(3-bromopyrazolo[1,5-a]pyridin-4-yl)-2-methylbut-3-yn-2-ol 41

To 2-methyl-4-(pyrazolo[1,5-a]pyridin-4-yl)but-3-yn-2-ol (40) from the previous step was added N-bromosuccinimide (680 mg, 3.82 mmol) in acetonitrile (5 mL). The reaction was allowed to stir at ambient temperature for 3 hours. The reaction was then partitioned between ethyl acetate and water. The organic layer was washed with brine, dried over anhydrous magnesium sulfate, and concentrated under reduced pressure. The material was purified by silica gel column chromatography eluting with a gradient of 0-50% ethyl acetate in hexane to provided product (41, 560 mg). [M+H⁺]⁺=279.0.

Step 3—Preparation of 2-methyl-4-[3-[4-(1-methylpyrazol-4-yl)phenyl]pyrazolo[1,5-a]pyridin-4-yl]but-3-yn-2-ol P-0429

To 4-(3-bromopyrazolo[1,5-a]pyridin-4-yl)-2-methylbut-3-yn-2-ol (41, 40 mg, 0.14 mmol), 1-methyl-4-[4-(4,4,5,5-tetramethyl-1,3,2-dioxaborolan-2-yl)phenyl]pyrazole (60 mg, 0.21 mmol) and 1,1'-bis(diphenylphosphino)ferrocene-palladium(II) dichloride dichloromethane complex (16.4 mg, 0.020 mmol) was added 2.5M aqueous potassium carbonate (0.17 mL) and acetonitrile. The reaction was flushed with argon, sealed and allowed to stir at 100° C. for 45 min. The reaction was filtered through celite and the filtrate was concentrated under reduced pressure. The material was purified by silica gel column chromatography eluting with a gradient of 0-5% methanol in dichloromethane to provide product (P-0429). [M+H⁺]⁺=357.3.

Example 15

Compound P-0250 is prepared in three steps from 4-bromo-5-methylpyrazolo[1,5-a]pyridine 42 as shown in Scheme 15.

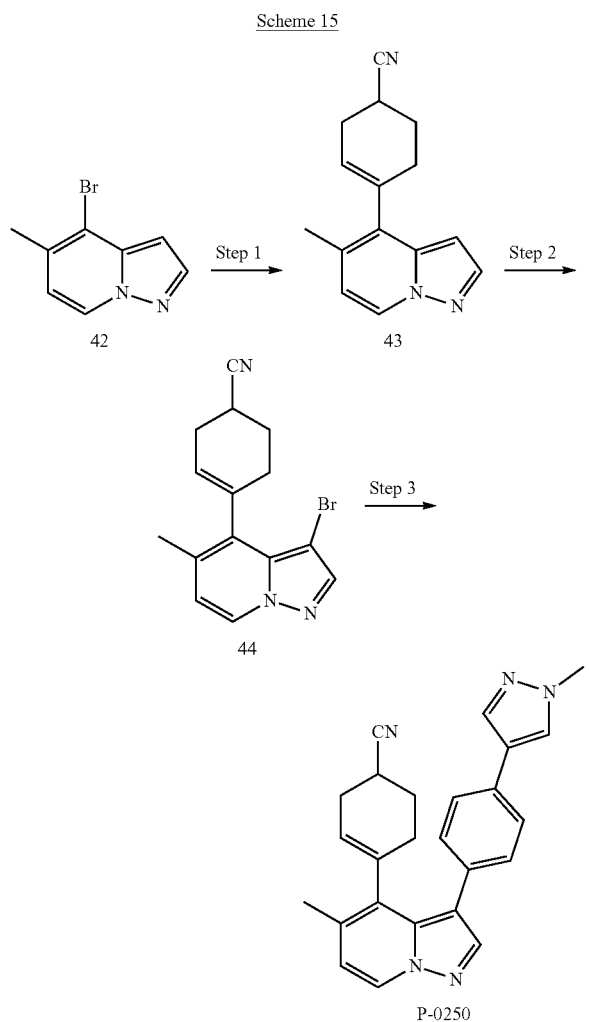

Scheme 15

Step 1—Preparation of 4-(5-methylpyrazolo[1,5-a]pyridin-4-yl)cyclohex-3-ene-1-carbonitrile 43

To 4-bromo-5-methyl-pyrazolo[1,5-a]pyridine (42, 209 mg, 0.992 mmol), 4-(4,4,5,5-tetramethyl-1,3,2-dioxaborolan-2-yl)cyclohex-3-ene-1-carbonitrile (246 mg, 1.06 mmol), chloro(2-dicyclohexylphosphino-2',6'-dimethoxy-1,1'-biphenyl) [2-(2-aminoethylphenyl)]palladium(II)methyl-t-butyl ether adduct (77.5 mg, 0.115 mmol) and potassium phosphate (0.5 M in H$_2$O, 3.0 mL, 1.5 mmol) was added acetonitrile (6.0 mL). The reaction vial was placed under N$_2$, sealed, and allowed to stir at 120° C. for 2 hours. The reaction was added to ethyl acetate and was extracted with water followed by 5 M aqueous sodium chloride. The organic layer was dried over anhydrous sodium sulfate, filtered, and the filtrate was concentrated under reduced pressure. The material was purified by reverse phase flash silica gel column chromatography (C18, 0-100% CH$_3$CN (0.1% HCO$_2$H), H$_2$O (0.1% HCO$_2$H)), to provide product (43, 193 mg). [M+H$^+$]$^+$=238.5.

Step 2—Preparation of 4-(3-bromo-5-methylpyrazolo[1,5-a]pyridin-4-yl)cyclohex-3-ene-1-carbonitrile 44

To 4-(5-methylpyrazolo[1,5-a]pyridin-4-yl)cyclohex-3-ene-1-carbonitrile (43, 193 mg, 0.813 mmol) in acetonitrile (5.0 mL) under an N$_2$ atmosphere and cooled to 0° C., was added a solution of N-bromosuccinimide (145 mg, 0.815 mmol) in THF (5.0 mL). The reaction was allowed to stir at 0° C. for 1 hour. The reaction was added to ethyl acetate and was extracted with water followed by 5 M aqueous sodium chloride. The organic layer was dried over anhydrous sodium sulfate, filtered, and the filtrate was concentrated under reduced pressure to provide product (44, 252 mg). [M+H$^+$]$^+$=318.0.

Step 3—Preparation of 4-[5-methyl-3-[4-(1-methyl-pyrazol-4-yl)phenyl]pyrazolo[1,5-a]pyridin-4-yl]cyclohex-3-ene-1-carbonitrile P-0250

To 4-(3-bromo-5-methyl-pyrazolo[1,5-a]pyridin-4-yl)cyclohex-3-ene-1-carbonitrile (44, 126 mg, 0.398 mmol), 1-methyl-4-[4-(4,4,5,5-tetramethyl-1,3,2-dioxaborolan-2-yl)phenyl]pyrazole (114 mg, 0.401 mmol), chloro(2-dicyclohexylphosphino-2',6'-dimethoxy-1,1'-biphenyl)[2-(2-aminoethylphenyl)]palladium(II)methyl-t-butyl ether adduct (33.1 mg, 0.049 mmol) and potassium phosphate (133 mg, 0.628 mmol) was added water (1.0 mL), and acetonitrile (4.0 mL). The reaction vial was placed under N$_2$, sealed, and allowed to stir at 160° C. for 1 hour. The reaction was added to ethyl acetate and was extracted with water followed by 5 M aqueous sodium chloride. The organic layer was dried over anhydrous sodium sulfate, filtered, and the filtrate was concentrated under reduced pressure. The material was purified by reverse phase flash silica gel column chromatography (C18, 0-100% CH$_3$CN (0.1% HCO$_2$H), H$_2$O (0.1% HCO$_2$H)), to provide product (P-0250). [M+H$^+$]$^+$=394.2.

Example 16

Compound P-0017 is prepared in three steps from 4-(pyrazolo[1,5-a]pyrazin-4-yl)cyclohexane-1-carbonitrile 36 as shown in Scheme 16.

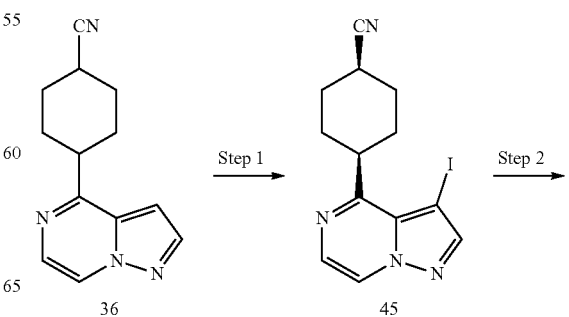

Scheme 16

-continued

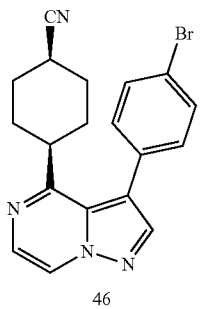

46

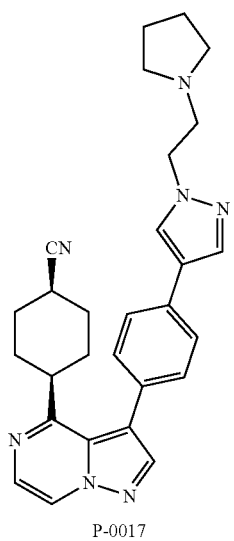

P-0017

Step 1—Preparation of (1s,4s)-4-(3-iodopyrazolo[1,5-a]pyrazin-4-yl)cyclohexane-1-carbonitrile 45

To a mixture of (1s,4s) and (1r,4r)-4-(pyrazolo[1,5-a]pyrazin-4-yl)cyclohexane-1-carbonitrile (36, 505 mg, 2.23 mmol) in acetonitrile (20 mL) was added N-iodosuccinimide (0.75 g, 3.3 mmol). The reaction was allowed to stir at 50° C. for 16 hours and at 85° C. for an additional 8 hours. The reaction mixture was poured into aqueous potassium carbonate, and extracted with dichloromethane. The organic layer was washed with water followed by brine and dried over anhydrous magnesium sulfate. The solids were removed by filtration and the filtrate was concentrated under reduced pressure. The material was purified by silica gel column chromatography eluting with a gradient of 0-20% ethyl acetate in hexane to provide product (45, 255 mg). [M+H$^+$]$^+$=353.0.

Step 3—Preparation of (1s,4s)-4-(3-(4-bromophenyl)pyrazolo[1,5-a]pyrazin-4-yl)cyclohexane-1-carbonitrile 46

To (1s,4s)-4-(3-iodopyrazolo[1,5-a]pyrazin-4-yl)cyclohexane-1-carbonitrile (45, 155 mg, 0.44 mmol), 2-(4-bromophenyl)-4,4,5,5-tetramethyl-1,3,2-dioxaborolane (0.16 g, 0.57 mmol), and 1,1'-bis(diphenylphosphino)ferrocene-palladium(II) dichloride dichloromethane complex (0.04 g, 0.05 mmol) in acetonitrile (4 mL) was added 1M aqueous potassium carbonate (2 mL). The reaction mixture was allowed to stir at for 5 minutes. The reaction mixture was poured into water and extracted with ethyl acetate. The organic layer was washed with water, brine, and then dried over anhydrous magnesium sulfate. The solids were removed by filtration and the filtrate was concentrated under reduced pressure. The material was purified by silica gel column chromatography eluting with a gradient of 0-100% ethyl acetate in hexane to provide product (46, 120 mg). [M+H$^+$]$^+$=381.0.

Step 3—Preparation of (1s,4s)-4-(3-(4-(1-(2-(pyrrolidin-1-yl)ethyl)-1H-pyrazol-4-yl)phenyl)pyrazolo[1,5-a]pyrazin-4-yl)cyclohexane-1-carbonitrile P-0017

To (1s,4s)-4-(3-(4-bromophenyl)pyrazolo[1,5-a]pyrazin-4-yl)cyclohexane-1-carbonitrile (46, 0.12 g, 0.31 mmol), 1-(2-pyrrolidin-1-ylethyl)-4-(4,4,5,5-tetramethyl-1,3,2-dioxaborolan-2-yl)pyrazole (0.10 g, 0.34 mmol) and 1,1'-bis(diphenylphosphino)ferrocene-palladium(II) dichloride dichloromethane complex (0.030 g, 0.037 mmol) in acetonitrile (4 mL) was added 1M aqueous potassium carbonate (2 mL). The reaction mixture was allowed to stir at for 15 minutes. The reaction mixture was poured into water and extracted with ethyl acetate. The organic layer was washed with water, brine and dried over anhydrous magnesium sulfate. The solids were removed by filtration and the filtrate was concentrated under reduced pressure. The material was purified by reverse phase flash silica gel column chromatography (C18, 0-100% CH$_3$CN (0.1% HCO$_2$H), H$_2$O (0.1% HCO$_2$H)), to provide product (P-0017). [M+H$^+$]$^+$= 466.3.

Example 17

Compounds P-0426 and P-0425 are prepared in four steps from 4-bromopyrazolo[1,5-a]pyridine 20 as shown in Scheme 17.

Scheme 17

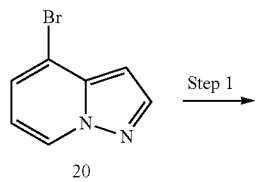

20

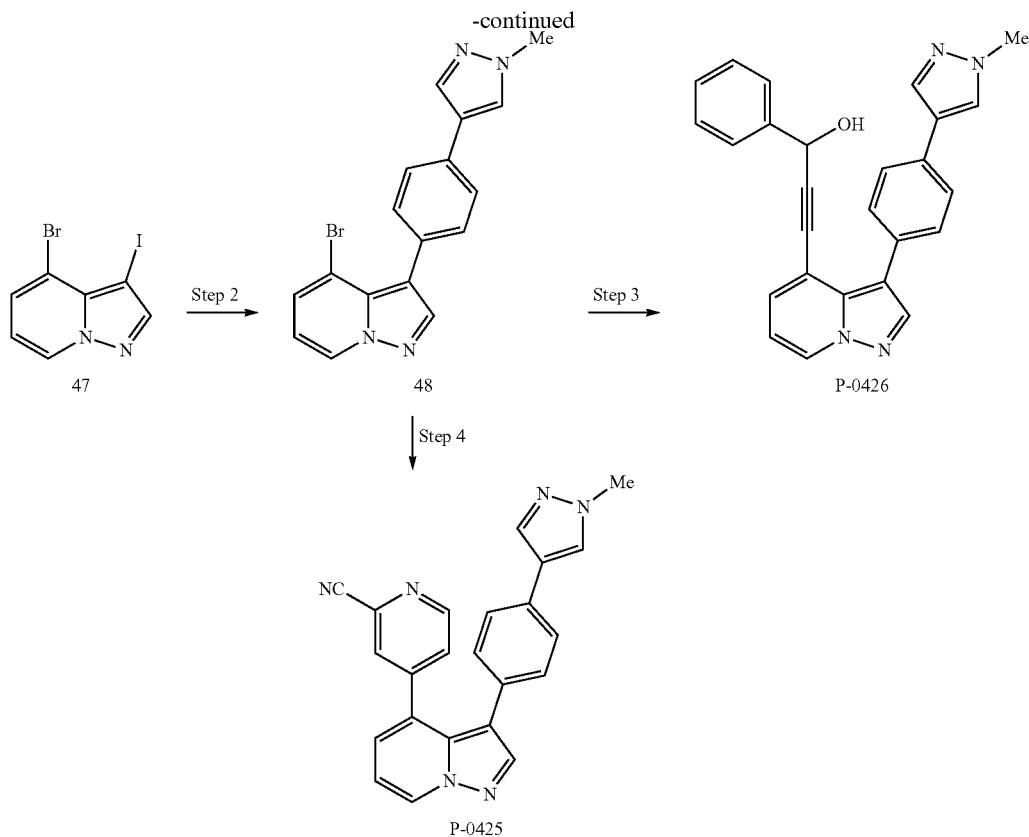

Step 1—Preparation of 4-bromo-3-iodopyrazolo[1,5-a]pyridine 47

To 4-bromopyrazolo[1,5-a]pyridine (0.6 g, 3 mmol) and N-iodosuccinimide (1 g, 4 mmol) was added THF and the reaction was allowed to stir for 6 hours at ambient temperature. The reaction was then partitioned between aqueous ammonium chloride and ethyl acetate. The organic layer was separated, washed with brine and dried over anhydrous magnesium sulfate. The solids were removed by filtration and the filtrate was concentrated under reduced pressure. The material was purified by silica gel column chromatography eluting with a gradient of 0-50% ethyl acetate in hexane to provide product (47, 420 mg). [M+H$^+$]$^+$=322.7 and 324.7.

Step 2—Preparation of 4-bromo-3-(4-(1-methyl-1H-pyrazol-4-yl)phenyl)pyrazolo[1,5-a]pyridine 48

To 4-bromo-3-iodo-pyrazolo[1,5-a]pyridine (47, 420 mg, 1.3 mmol), 1-methyl-4-[4-(4,4,5,5-tetramethyl-1,3,2-dioxaborolan-2-yl)phenyl]pyrazole (462 mg, 1.63 mmol), 1,1'-bis(diphenylphosphino)ferrocene-palladium(II) dichloride dichloromethane complex (149 mg, 0.182 mmol) and 2.5M aqueous potassium carbonate (1.56 mL) was added 1,4-dioxane (5 mL). the reaction was allowed to stir, under an argon atmosphere, at 100° C. for 16 hours. The reaction mixture was then cooled, filtered through celite, and partitioned between ethyl acetate and aqueous ammonium chloride. The organic layer was separated, washed with brine, and then dried over anhydrous magnesium sulfate. The material was purified by silica gel column chromatography eluting with a gradient of 0-100% ethyl acetate in hexane to provide product (48, 280 mg). [M+H$^+$]$^+$=353.1.

Step 3—Preparation of 3-[3-[4-(1-methylpyrazol-4-yl)phenyl]pyrazolo[1,5-a]pyridin-4-yl]-1-phenyl-prop-2-yn-1-ol P-0426

To 4-bromo-3-[4-(1-methylpyrazol-4-yl)phenyl]pyrazolo[1,5-a]pyridine (48, 50 mg, 0.14 mmol), 1-phenylprop-2-yn-1-ol (37 mg, 0.28 mmol), cesium carbonate (161 mg, 0.495 mmol), tris(dibenzylideneacetone)dipalladium(0) (12 mg, 0.013 mmol) and tricyclohexylphosphine (12 mg, 0.043 mmol) was added acetonitrile (1 mL) and the reaction was allowed to stir 80° C. for 3 hours. The reaction was filtered through celite and then partitioned between ethyl acetate and water. The organic layer was dried over anhydrous magnesium sulfate and filtered. The material was purified by silica gel column chromatography eluting with a gradient of 0-5% methanol in dichloromethane to provide product (P-0426). [M+H$^+$]$^+$=405.3.

Step 4—Preparation of 4-[3-[4-(1-methylpyrazol-4-yl)phenyl]pyrazolo[1,5-a]pyridin-4-yl]pyridine-2-carbonitrile P-0425

To a mixture 4-bromo-3-[4-(1-methylpyrazol-4-yl)phenyl]pyrazolo[1,5-a]pyridine (48, 34 mg, 0.096 mmol), 4-(4,4,5,5-tetramethyl-1,3,2-dioxaborolan-2-yl)picolinonitrile (28 mg, 0.12 mmol) and 1,1'-bis(diphenylphosphino)ferrocene-palladium(II) dichloride dichloromethane complex (8 mg, 0.010 mmol) in 1,4-dioxane (3 mL) was added 1M aqueous potassium carbonate. The reaction was allowed to stir at 120° C. for 20 minutes. The reaction mixture was poured into water and extracted with ethyl acetate. The organic layer was separated, washed with brine, and dried over anhydrous sodium sulfate. After removal of drying agent and solvent, the residue was purified by silica gel column chromatography to provide product (P-0425). [M+H+]+=377.0.

Example 18

Compound P-0326 is prepared in three steps from 4-bromopyrazolo[1,5-a]pyrazine 49 as shown in Scheme 18.

Scheme 18

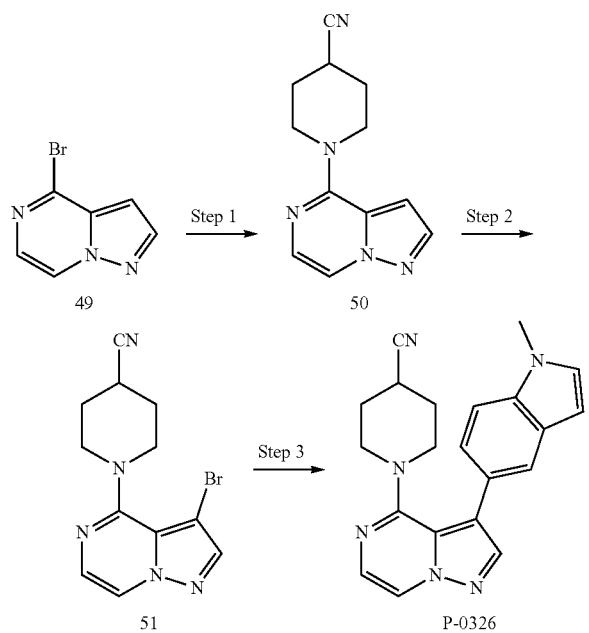

Step 1—Preparation of 1-(pyrazolo[1,5-a]pyrazin-4-yl)piperidine-4-carbonitrile 50

To piperidine-4-carbonitrile (551 mg, 5.00 mmol) and 4-bromopyrazolo[1,5-a]pyrazine (49, 198 mg, 1.00 mmol) was added N-methylpyrrolidinone (3.0 mL). The reaction vial was placed under $N_2$, sealed, and allowed to stir at 200° C. for 2 hours. The reaction was partitioned between water and ethyl acetate. The organic fraction was subsequently washed with water and 5 M aqueous sodium chloride, dried over anhydrous sodium sulfate and filtered. The resulting filtrate was concentrated under reduced pressure and was purified by silica gel column chromatography eluting with a gradient of 0-10% methanol in dichloromethane to provide product (50, 179 mg). [M+H+]+=228.2.

Step 2—Preparation of 1-(3-bromopyrazolo[1,5-a]pyrazin-4-yl)piperidine-4-carbonitrile 51

To 1-pyrazolo[1,5-a]pyrazin-4-ylpiperidine-4-carbonitrile (50, 176 mg, 0.774 mmol) in acetonitrile (6.0 mL), under $N_2$ and cooled to 0° C., was added N-bromosuccinimide (145 mg, 0.815 mmol) in acetonitrile (1.0 mL) dropwise. The reaction was allowed to stir at 0° C. for 1 hour. The reaction was added to ethyl acetate and was extracted with 1.2 M aqueous sodium bicarbonate, water and 5M aqueous sodium chloride. The organic layer was dried over anhydrous sodium sulfate, filtered, and the resulting filtrate was concentrated under reduced pressure. The resulting filtrate was concentrated under reduced pressure and was purified by silica gel column chromatography eluting with a gradient of 0-10% methanol in dichloromethane to provide material that was further purified by reverse phase flash column chromatography (C18, 0-100% $CH_3CN$ (0.1% $HCO_2H$), $H_2O$ (0.1% $HCO_2H$)) to provide product (51, 63 mg). [M+H+]+=306.0.

Step 3—Preparation of 1-[3-(1-methylindazol-5-yl)pyrazolo[1,5-a]pyrazin-4-yl]piperidine-4-carbonitrile P-0326

To 1-(3-bromopyrazolo[1,5-a]pyrazin-4-yl)piperidine-4-carbonitrile (51, 55 mg, 0.18 mmol), (1-methylindazol-5-yl)boronic acid (19 mg, 0.11 mmol), chloro(2-dicyclohexylphosphino-2',6'-dimethoxy-1,1'-biphenyl)[2-(2-aminoethylphenyl)]palladium(II)methyl-t-butyl ether adduct (14 mg, 0.021 mmol) and potassium phosphate (56 mg, 0.26 mmol) was added acetonitrile (3.0 mL). The reaction vial was placed under $N_2$, sealed, and allowed to stir at 120° C. for 2 hours. The reaction was incomplete so additional (1-methylindazol-5-yl)boronic acid (19 mg, 0.11 mmol), chloro(2-dicyclohexylphosphino-2',6'-dimethoxy-1,1'-biphenyl)[2-(2-aminoethylphenyl)]palladium(II)methyl-t-butyl ether adduct (13 mg, 0.019 mmol) and water (0.5 mL) were added. The reaction vial was placed under $N_2$, sealed, and allowed to stir at 120° C. for an additional 2 hours. The reaction was added to ethyl acetate and the organic fraction was washed with water followed by 5 M aqueous sodium chloride. The organic layer was separated and dried over anhydrous sodium sulfate. The solids were removed by filtration and the resulting filtrate was concentrated under reduced pressure. The material was purified by reverse phase flash column chromatography (C18, 0-100% $CH_3CN$ (0.1% $HCO_2H$), $H_2O$ (0.1% $HCO_2H$)), to provide product (P-0326). [M+H+]+=358.2.

Example 19

Compounds P-0011 and P-0010 are prepared in two steps from 4-(3-bromopyrazolo[1,5-a]pyrazin-4-yl)cyclohex-3-ene-1-carbonitrile 17 as shown in Scheme 19.

Scheme 19

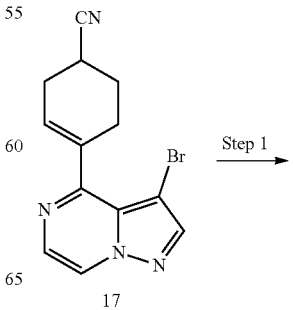

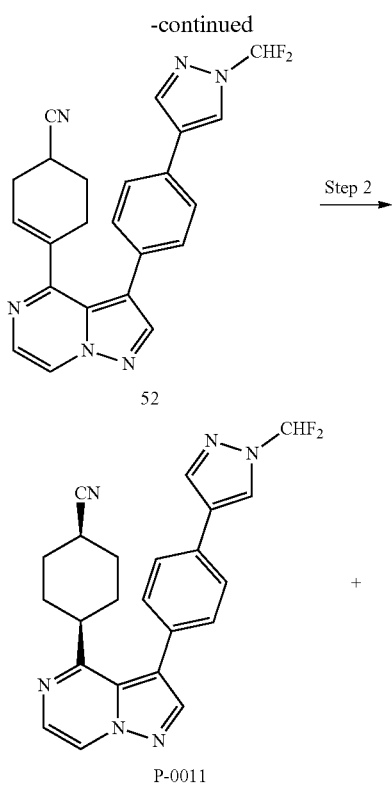

Step 2—Preparation of (1s,4s)-4-(3-(4-(1-(difluoromethyl)-1H-pyrazol-4-yl)phenyl)pyrazolo[1,5-a]pyrazin-4-yl)cyclohexane-1-carbonitrile P-0011 and (1r,4r)-4-(3-(4-(1-(difluoromethyl)-H-pyrazol-4-yl)phenyl)pyrazolo[1,5-a]pyrazin-4-yl) cyclohexane-1-carbonitrile P-0010

To a solution of 4-[3-[4-[1-(difluoromethyl)pyrazol-4-yl]phenyl]pyrazolo[1,5-a]pyrazin-4-yl]cyclohex-3-ene-1-carbonitrile (52, 0.15 g, 0.36 mmol) in methanol (30 mL) and dichloromethane (10 mL) was added palladium hydroxide on carbon, 20% wt (10 mg). The mixture was degassed and then shaken under hydrogen (50 psi, Parr shaker) for five hours. Additional palladium hydroxide on carbon, 20% wt (10 mg) was added and the mixture was shaken under hydrogen (50 psi, Parr shaker) for 15 hours. The catalyst was filtered off and the filtrate was concentrated under reduced pressure. The material was purified by column chromatography to provide products (P-0011, cis isomer) and (P-0010, trans isomer). [M+H$^+$]$^+$=419.0 and 419.1.

Example 20

Compound P-0047 is prepared in three steps from 4-(pyrazolo[1,5-a]pyrazin-4-yl)cyclohex-3-ene-1-carbonitrile 16 as shown in Scheme 20.

Scheme 20

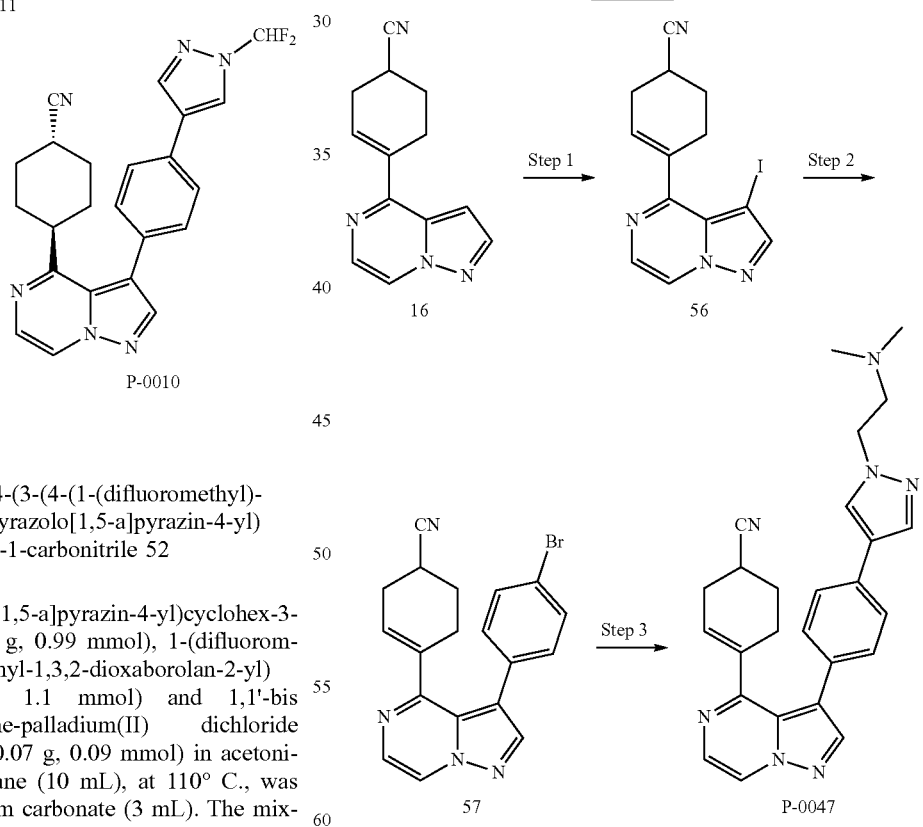

Step 1—Preparation of 4-(3-(4-(1-(difluoromethyl)-H-pyrazol-4-yl)phenyl)pyrazolo[1,5-a]pyrazin-4-yl)cyclohex-3-ene-1-carbonitrile 52

To 4-(3-bromopyrazolo[1,5-a]pyrazin-4-yl)cyclohex-3-ene-1-carbonitrile (17, 0.30 g, 0.99 mmol), 1-(difluoromethyl)-4-[4-(4,4,5,5-tetramethyl-1,3,2-dioxaborolan-2-yl)phenyl]pyrazole (0.35 g, 1.1 mmol) and 1,1'-bis(diphenylphosphino)ferrocene-palladium(II) dichloride dichloromethane complex (0.07 g, 0.09 mmol) in acetonitrile (10 mL) and 1,4-dioxane (10 mL), at 110° C., was added 1M aqueous potassium carbonate (3 mL). The mixture was allowed to stir at 110° C. for four hours. The reaction mixture was poured into water and extracted with ethyl acetate. The organic layer was separated, washed with brine, and dried over anhydrous sodium sulfate. After removal of drying agent and solvent, the residue was purified by silica gel column chromatography to provide product (52, 0.25 g). [M+H$^+$]$^+$=417.5.

Step 1—Preparation of 4-(3-iodopyrazolo[1,5-a]pyrazin-4-yl)cyclohex-3-ene-1-carbonitrile 56

To 4-pyrazolo[1,5-a]pyrazin-4-ylcyclohex-3-ene-1-carbonitrile (16, 505 mg, 2.25 mmol) in acetonitrile (20 mL)

was added N-iodosuccinimide (0.55 g, 2.4 mmol). The reaction was allowed to stir at 50° C. for 4 days. The reaction mixture was poured into aqueous potassium carbonate, and extracted with dichloromethane. The organic layer was washed with water and brine and then dried over anhydrous magnesium sulfate. The solids were removed by filtration and the resulting filtrate was concentrated under reduced pressure. The material was purified by silica gel column chromatography eluting with a gradient of 0-100% ethyl acetate in hexane to provide product (56, 629 mg). [M+H$^+$]$^+$= 350.8.

Step 2—Preparation of 4-(3-(4-bromophenyl)pyrazolo[1,5-a]pyrazin-4-yl)cyclohex-3-ene-1-carbonitrile 57

To 4-(3-iodopyrazolo[1,5-a]pyrazin-4-yl)cyclohex-3-ene-1-carbonitrile (56, 525 mg, 1.50 mmol), 2-(4-bromophenyl)-4,4,5,5-tetramethyl-1,3,2-dioxaborolane (0.420 g, 1.48 mmol), and 1,1'-bis(diphenylphosphino)ferrocene-palladium(II) dichloride dichloromethane complex (200 mg, 0.245 mmol) in acetonitrile (8 mL) was added 1M aqueous potassium carbonate (4 mL). The reaction mixture was allowed to stir at 60° C. for 10 minutes. The reaction mixture was poured into water and extracted with ethyl acetate. The organic layer was washed with water and brine and then dried over anhydrous magnesium sulfate. The solids were removed by filtration and the resulting filtrate was concentrated under reduced pressure. The material was purified by silica gel column chromatography eluting with a gradient of 0-100% ethyl acetate in hexane to provide product (57, 271 mg). [M+H$^+$]$^+$=379.0.

Step 3—Preparation of 4-[3-[4-[1-(2-dimethylaminoethyl)pyrazol-4-yl]phenyl]pyrazolo[1,5-a]pyrazin-4-yl]cyclohex-3-ene-1-carbonitrile P-0047

To 4-[3-(4-bromophenyl)pyrazolo[1,5-a]pyrazin-4-yl]cyclohex-3-ene-1-carbonitrile (57, 68 mg, 0.18 mmol), N,N-dimethyl-2-[4-(4,4,5,5-tetramethyl-1,3,2-dioxaborolan-2-yl)pyrazol-1-yl]ethanamine (75 mg, 0.28 mmol), and 1,1'-bis(diphenylphosphino)ferrocene-palladium(II) dichloride dichloromethane complex (34 mg, 0.042 mmol) in acetonitrile (3 mL) was added 1M aqueous potassium carbonate in water (1.5 mL). The reaction mixture was allowed to stir at 120° C. for 15 minutes. The reaction mixture was poured into water and extracted with ethyl acetate. The organic layer was washed with water and brine and then dried over anhydrous magnesium sulfate. The solids were removed by filtration and the resulting filtrate was concentrated under reduced pressure. The material was purified by RP-HPLC to provide product (P-0047). [M+H$^+$]$^+$=438.6.

Example 21

Compounds P-0447 and P-0434 were prepared in two and three steps from 3-bromo-5-fluoroimidazo[1,2-a]pyridine 10 as shown in Scheme 21.

Scheme 21

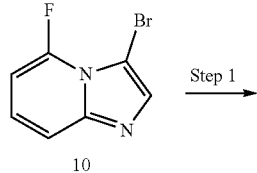

-continued

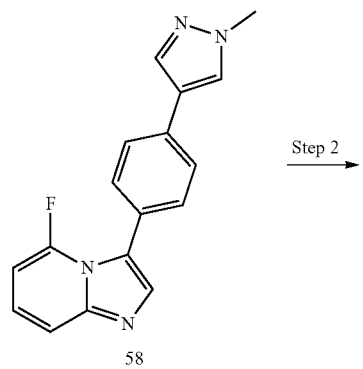

58

Step 2 →

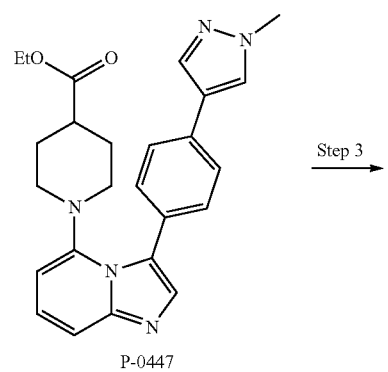

P-0447

Step 3 →

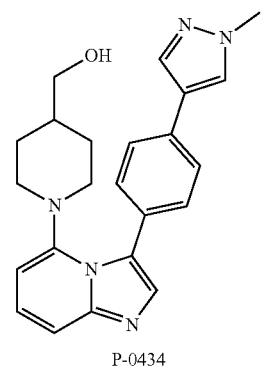

P-0434

Step 1 Preparation of 5-fluoro-3-(4-(1-methyl-1H-pyrazol-4-yl)phenyl)imidazo[1,2-a]pyridine 58

To 1-methyl-4-[4-(4,4,5,5-tetramethyl-1,3,2-dioxaborolan-2-yl)phenyl]pyrazole (3.20 g, 11.3 mmol), 3-bromo-5-fluoro-imidazo[1,2-a]pyridine (10, 2.0 g, 9.3 mmol), and 1,1'-bis(diphenylphosphino)ferrocene-palladium(II) dichloride dichloromethane complex (0.40 g, 0.49 mmol) in THF (100 mL) was added 1M aqueous potassium carbonate (50 mL). The reaction mixture was degassed and purged with nitrogen. The reaction was allowed to stir at 70° C. for 2 hours. The reaction mixture was poured into water and extracted with ethyl acetate. The organic layer was washed with brine, dried over anhydrous sodium sulfate, and filtered. The filtrate was concentrated in the presence of silica the resulting crude material was purified by silica gel column chromatography eluting with a gradient of 0-15% methanol in dichloromethane to provide product (58, 2.3 g). $[M+H^+]^+=293.5$.

Step 2—Preparation of ethyl 1-(3-(4-(1-methyl-1H-pyrazol-4-yl)phenyl)imidazo[1,2-a]pyridin-5-yl)piperidine-4-carboxylate P-0447

To 5-fluoro-3-[4-(1-methylpyrazol-4-yl)phenyl]imidazo[1,2-a]pyridine (58, 200 mg, 0.68 mmol) in N-methylpyrrolidone (2.5 mL) was added N,N-diisopropylethylamine (0.25 mL) followed by ethyl piperidine-4-carboxylate (226 mg, 1.56 mmol). The reaction mixture was allowed to stir at 240° C. for 1 hour. The reaction mixture was poured into water and extracted with ethyl acetate. The organic layer was washed with brine, dried over anhydrous sodium sulfate and filtered. The filtrate was concentrated under reduced pressure and the material was purified by silica gel column chromatography eluting with a gradient of 0-20% methanol in dichloromethane to provide product (P-0447). $[M+H^+]^+=430.1$.

Step 3—Preparation of [1-[3-[4-(1-methylpyrazol-4-yl)phenyl]imidazo[1,2-a]pyridin-5-yl]-4-piperidyl]methanol P-0434

To ethyl 1-(3-(4-(1-methyl-1H-pyrazol-4-yl)phenyl)imidazo[1,2-a]pyridin-5-yl)piperidine-4-carboxylate (P-0447, 30 mg, 0.070 mmol) in THF (6 mL) was added 1M LiAlH₄ in THF (120 µl, 0.12 mmol). The reaction was allowed to stir at ambient temperature for 2 hours. To the reaction was added 1.0 g of sodium sulfate decahydrate. The mixture was allowed to stir for an additional 30 minutes. The mixture was filtered and the filtrate was concentrated under reduced pressure. The material was triturated with dichloromethane/hexane to provide product (P-0434). $[M+H^+]^+=388.3$.

Example 22

Compound P-0010 is prepared in one step from (1r,4r)-4-(3-bromopyrazolo[1,5-a]pyrazin-4-yl)cyclohexane-1-carbonitrile 38 as shown in Scheme 22.

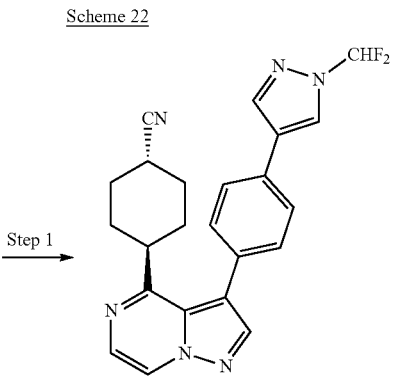

Scheme 22

Step 1—Preparation of (1r,4r)-4-(3-(4-(1-(difluoromethyl)-1H-pyrazol-4-yl)phenyl)pyrazolo[1,5-a]pyrazin-4-yl)cyclohexane-1-carbonitrile P-0010

To (1r,4r)-4-(3-bromopyrazolo[1,5-a]pyrazin-4-yl)cyclohexane-1-carbonitrile (38, 83 mg, 0.27 mmol), 1-(difluoromethyl)-4-[4-(4,4,5,5-tetramethyl-1,3,2-dioxaborolan-2-yl)phenyl]pyrazole (89 mg, 0.28 mmol) and 1,1'-bis(diphenylphosphino)ferrocene-palladium(II) dichloride dichloromethane complex (21 mg, 0.028 mmol) in acetonitrile (2 mL) and 1,4-dioxane (2 mL), was added 1M aqueous potassium carbonate (1 mL). The mixture was allowed to stir at 110° C. for one hour. The reaction mixture was poured into water and extracted with ethyl acetate. The organic layer was separated, washed with brine, and dried over anhydrous sodium sulfate. After removal of drying agent and solvent, the residue was purified by silica gel column chromatography to provide product (P-0010, 65 mg). $[M+H^+]^+=419.5$.

Example 23

Compound P-0458 is prepared in three steps from (1s,4s)-4-(3-bromopyrazolo[1,5-a]pyrazin-4-yl)cyclohexane-1-carbonitrile 37 and 2-methyl-1-(4-(4,4,5,5-tetramethyl-1,3,2-dioxaborolan-2-yl)-1H-pyrazol-1-yl)propan-2-ol 60 as shown in Scheme 23.

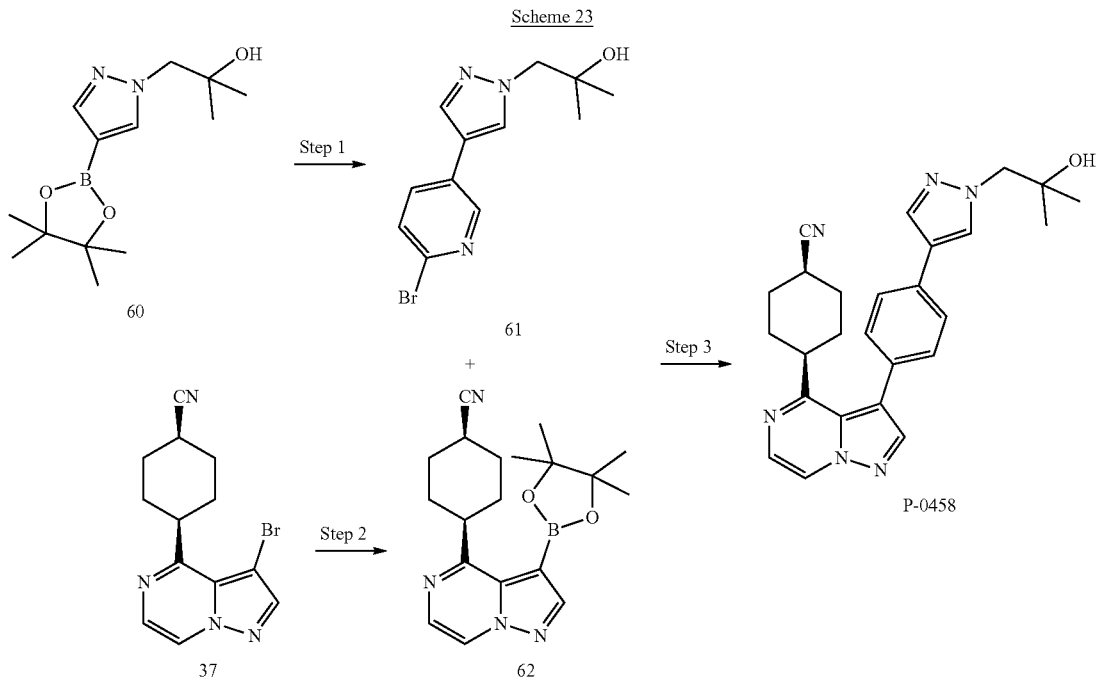 [SMILES: CC(C)(O)Cn1cc(B2OC(C)(C)C(C)(C)O2)cn1 ; N#C[C@H]1CC[C@@H](c2nccn3ncc(Br)c23)CC1 ; CC(C)(O)Cn1cc(-c2ccc(Br)nc2)cn1 ; CC1(C)OB(c2cnn3ccnc([C@H]4CC[C@@H](C#N)CC4)c23)OC1(C)C ; CC(C)(O)Cn1cc(-c2ccc(-c3cnn4ccnc([C@H]5CC[C@@H](C#N)CC5)c34)cc2)cn1]

Scheme 23

Step 1—Preparation of 1-(4-(6-bromopyridin-3-yl)-1H-pyrazol-1-yl)-2-methylpropan-2-ol 61:

To 2-bromo-5-iodo-pyridine (310 mg, 1.09 mmol), 2-methyl-1-[4-(4,4,5,5-tetramethyl-1,3,2-dioxaborolan-2-yl)pyrazol-1-yl]propan-2-ol (60, 280 mg, 1.05 mol) and 1,1'-bis(diphenylphosphino)ferrocene-palladium(II) dichloride dichloromethane complex (70 mg, 0.086 mmol) in acetonitrile (20 mL) was added 1M aqueous potassium carbonate (10 mL). The reaction was allowed to stir at 60° C. for 1 hour. The reaction mixture was poured into water and extracted with ethyl acetate. The organic layer was washed with water and brine, and then dried over anhydrous magnesium sulfate. The solids were removed by filtration and the resulting filtrate was concentrated under reduced pressure. The material purified by silica gel column chromatography eluting with a gradient of 0-100% ethyl acetate in hexane to product (61, 226 mg). [M+H$^+$]+=296.0 and 298.0.

Step 2—Preparation of (1s,4s)-4-(3-(4,4,5,5-tetramethyl-1,3,2-dioxaborolan-2-yl)pyrazolo[1,5-a]pyrazin-4-yl)cyclohexane-1-carbonitrile 62

To (1s,4s)-4-(3-bromopyrazolo[1,5-a]pyrazin-4-yl)cyclohexane-1-carbonitrile (37, 150 mg, 0.49 mmol) in DMF (15 mL) was added potassium acetate (0.26 g, 2.6 mmol) followed by 1,1'-bis(diphenylphosphino)ferrocene-palladium(II) dichloride dichloromethane complex (0.13 g, 0.16 mmol) and 4,4,5,5-tetramethyl-2-(4,4,5,5-tetramethyl-1,3,2-dioxaborolan-2-yl)-1,3,2-dioxaborolane (480 mg, 1.89 mmol). The reaction was allowed to stir at 90° C. for 2 hours. The reaction mixture was filtered through celite and the filtrate was concentrated under reduced pressure. This provided crude material was used in the next step without further purification (62, 173 mg. [M+H$^+$]+=353.15.

Step 3—Preparation of (1s,4s)-4-(3-(5-(1-(2-hydroxy-2-methylpropyl)-1H-pyrazol-4-yl)pyridin-2-yl)pyrazolo[1,5-a]pyrazin-4-yl)cyclohexane-1-carbonitrile P-0458

To (1s,4s)-4-(3-(4,4,5,5-tetramethyl-1,3,2-dioxaborolan-2-yl)pyrazolo[1,5-a]pyrazin-4-yl)cyclohexane-1-carbonitrile (62, 173 mg, 0.123 mmol), 1-[4-(6-bromo-3-pyridyl)pyrazol-1-yl]-2-methyl-propan-2-ol (61, 40 mg, 0.14 mmol) and 1,1'-bis(diphenylphosphino)ferrocene-palladium(II) dichloride dichloromethane complex (30 mg, 0.036 mmol) in acetonitrile (4 mL) was added 1M aqueous potassium carbonate (2 mL). The reaction was allowed to stir at 120° C. for 15 minutes. The reaction mixture was poured into water and extracted with ethyl acetate. The organic layer was washed with water and brine and then dried over anhydrous magnesium sulfate. The solids were filtered and the resulting filtrate was concentrated under reduced pressure. The material was purified by silica gel column chromatography eluting with a gradient of 0-100% ethyl acetate in hexane to provide product that was further purified by RP-HPLC to provide product (P-0458, 6.5 mg). [M+H$^+$]+=442.6.

All compounds in Table 1 listed below can be made according to the synthetic examples described in this disclosure, and by making any necessary substitutions of starting materials that the skilled artisan would be able to obtain either commercially or otherwise.

TABLE 1

| P Number | Structure | Name | MS |
|---|---|---|---|
| P-0001 | 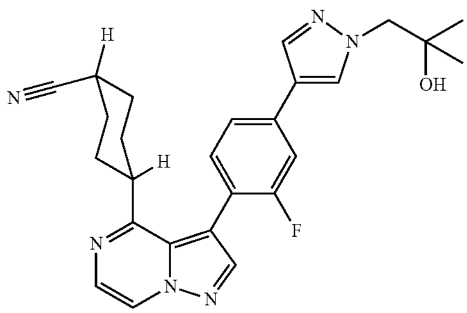 [SMILES: CC(C)(O)Cn1cc(-c2ccc(-c3cnn4ccnc(C5CCC(C#N)CC5)c34)c(F)c2)cn1] | (1s,4s)-4-(3-(2-fluoro-4-(1-(2-hydroxy-2-methylpropyl)-1H-pyrazol-4-yl)phenyl)pyrazolo[1,5-a]pyrazin-4-yl)cyclohexane-1-carbonitrile | 459.6 |
| P-0002 | 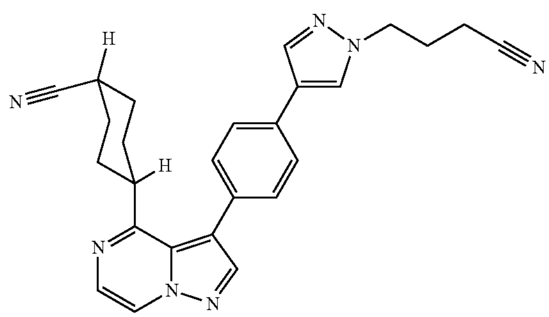 [SMILES: N#CCCCn1cc(-c2ccc(-c3cnn4ccnc(C5CCC(C#N)CC5)c34)cc2)cn1] | (1s,4s)-4-(3-(4-(1-(3-cyanopropyl)-1H-pyrazol-4-yl)phenyl)pyrazolo[1,5-a]pyrazin-4-yl)cyclohexane-1-carbonitrile | 436.2 |
| P-0003 | 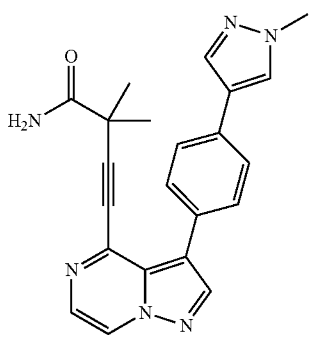 [SMILES: Cn1cc(-c2ccc(-c3cnn4ccnc(C#CC(C)(C)C(N)=O)c34)cc2)cn1] | 2,2-dimethyl-4-(3-(4-(1-methyl-1H-pyrazol-4-yl)phenyl)pyrazolo[1,5-a]pyrazin-4-yl)but-3-ynamide | 385.10 |
| P-0004 | 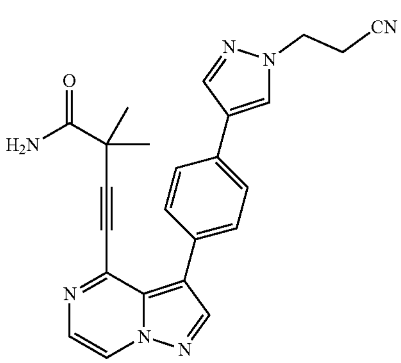 [SMILES: CC(C)(C#Cc1nccn2ncc(-c3ccc(-c4cnn(CCC#N)c4)cc3)c12)C(N)=O] | 4-(3-(4-(1-(2-cyanoethyl)-1H-pyrazol-4-yl)phenyl)pyrazolo[1,5-a]pyrazin-4-yl)-2,2-dimethylbut-3-ynamide | 424.1 |

TABLE 1-continued

| P Number | Structure | Name | MS |
|---|---|---|---|
| P-0005 | 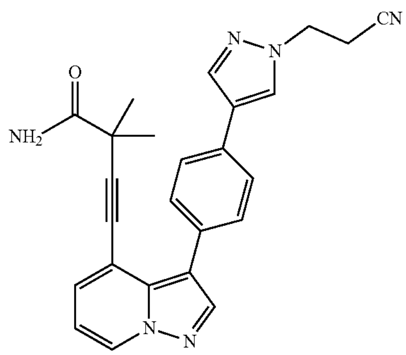 [SMILES: CC(C)(C#Cc1cccn2ncc(-c3ccc(-c4cnn(CCC#N)c4)cc3)c12)C(N)=O] | 4-(3-(4-(1-(2-cyanoethyl)-1H-pyrazol-4-yl)phenyl)pyrazolo[1,5-a]pyridin-4-yl)-2,2-dimethylbut-3-ynamide | 423.2 |
| P-0006 | 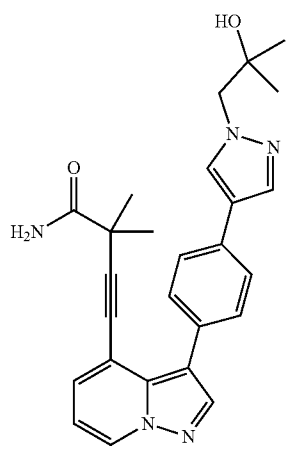 [SMILES: CC(C)(O)Cn1cc(-c2ccc(-c3cnn4cccc(C#CC(C)(C)C(N)=O)c34)cc2)cn1] | 4-(3-(4-(1-(2-hydroxy-2-methylpropyl)-1H-pyrazol-4-yl)phenyl)pyrazolo[1,5-a]pyridin-4-yl)-2,2-dimethylbut-3-ynamide | 442.6 |
| P-0007 | 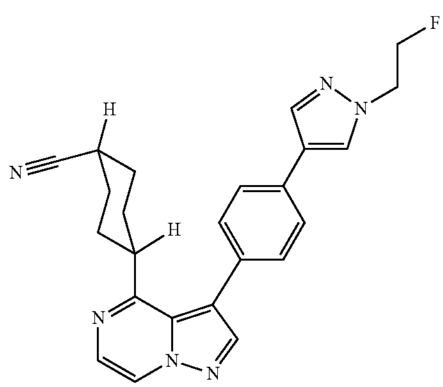 [SMILES: N#CC1CCC(c2nccn3ncc(-c4ccc(-c5cnn(CCF)c5)cc4)c23)CC1] | (1s,4s)-4-(3-(4-(1-(2-fluoroethyl)-1H-pyrazol-4-yl)phenyl)pyrazolo[1,5-a]pyrazin-4-yl)cyclohexane-1-carbonitrile | 415.2 |
| P-0008 | 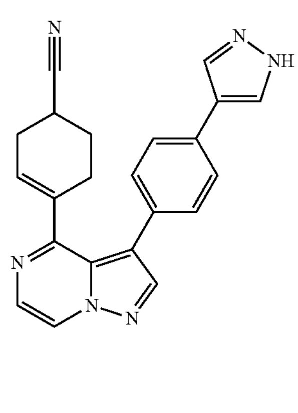 [SMILES: N#CC1CC=C(c2nccn3ncc(-c4ccc(-c5cn[nH]c5)cc4)c23)CC1] | 4-(3-(4-(1H-pyrazol-4-yl)phenyl)pyrazolo[1,5-a]pyrazin-4-yl)cyclohex-3-ene-1-carbonitrile | 367.2 |

TABLE 1-continued

| P Number | Structure | Name | MS |
|---|---|---|---|
| P-0009 | 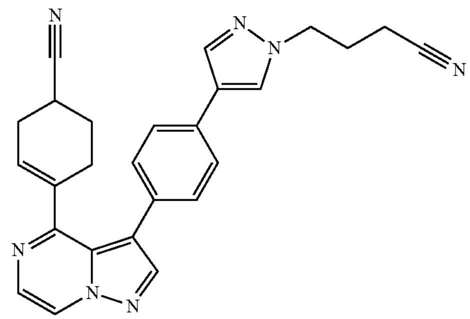 [SMILES: N#CCCCn1cc(-c2ccc(-c3cnn4ccnc(C5=CCC(C#N)CC5)c34)cc2)cn1] | 4-(3-(4-(1-(3-cyanopropyl)-1H-pyrazol-4-yl)phenyl)pyrazolo[1,5-a]pyrazin-4-yl)cyclohex-3-ene-1-carbonitrile | 434.2 |
| P-0010 | 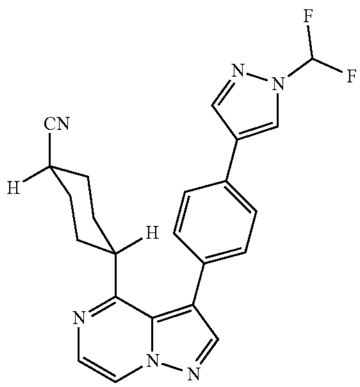 [SMILES: N#CC1CCC(c2nccn3ncc(-c4ccc(-c5cnn(C(F)F)c5)cc4)c23)CC1] | (1r,4r)-4-(3-(4-(1-(difluoromethyl)-1H-pyrazol-4-yl)phenyl)pyrazolo[1,5-a]pyrazin-4-yl)cyclohexane-1-carbonitrile | 419.5 |
| P-0011 | 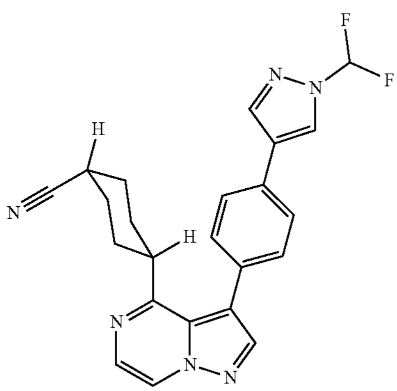 [SMILES: N#CC1CCC(c2nccn3ncc(-c4ccc(-c5cnn(C(F)F)c5)cc4)c23)CC1] | (1s,4s)-4-(3-(4-(1-(difluoromethyl)-1H-pyrazol-4-yl)phenyl)pyrazolo[1,5-a]pyrazin-4-yl)cyclohexane-1-carbonitrile | 419.0 |
| P-0012 | 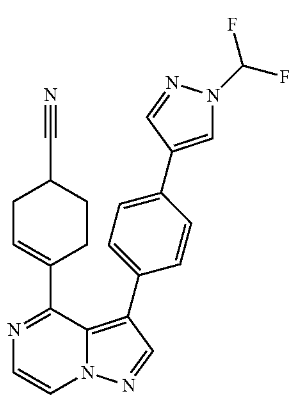 [SMILES: N#CC1CC=C(c2nccn3ncc(-c4ccc(-c5cnn(C(F)F)c5)cc4)c23)CC1] | 4-(3-(4-(1-(difluoromethyl)-1H-pyrazol-4-yl)phenyl)pyrazolo[1,5-a]pyrazin-4-yl)cyclohex-3-ene-1-carbonitrile | 417.5 |

TABLE 1-continued

| P Number | Structure | Name | MS |
|---|---|---|---|
| P-0013 | 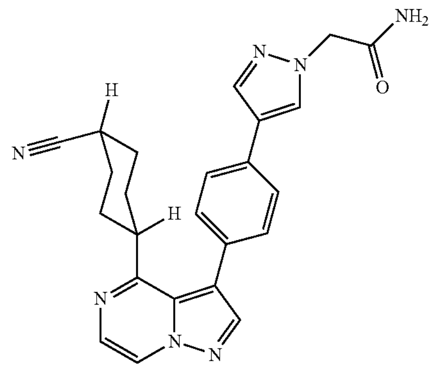 [SMILES: N#CC1CCC(c2nccn3ncc(-c4ccc(-c5cnn(CC(N)=O)c5)cc4)c23)CC1] | 2-(4-(4-(4-((1s,4s)-4-cyanoclohexyl)pyrazolo[1,5-a]pyrazin-3-yl)phenyl)-1H-pyrazol-1-yl)acetamide | 426.2 |
| P-0014 | 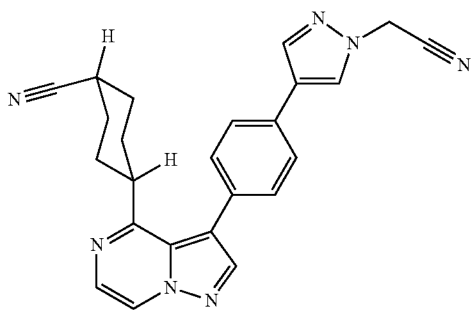 [SMILES: N#CCn1cc(-c2ccc(-c3cnn4ccnc(C5CCC(C#N)CC5)c34)cc2)cn1] | (1s,4s)-4-(3-(4-(1-(cyanomethyl)-1H-pyrazol-4-yl)phenyl)pyrazolo[1,5-a]pyrazin-4-yl)cyclohexane-1-carbonitrile | 408.2 |
| P-0015 | 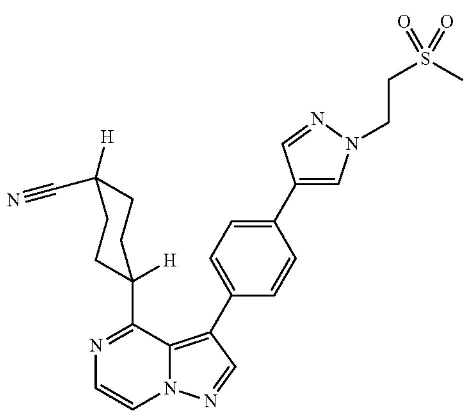 [SMILES: CS(=O)(=O)CCn1cc(-c2ccc(-c3cnn4ccnc(C5CCC(C#N)CC5)c34)cc2)cn1] | (1s,4s)-(3-(4-(1-(2-(methylsulfonyl)ethyl)-1H-pyrazol-4-yl)phenyl)pyrazolo[1,5-a]pyrazin-4-yl)cyclohexane-1-carbonitrile | 475.1 |
| P-0016 | 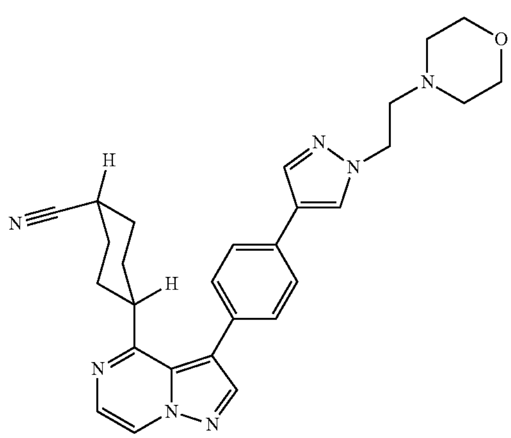 [SMILES: N#CC1CCC(c2nccn3ncc(-c4ccc(-c5cnn(CCN6CCOCC6)c5)cc4)c23)CC1] | (1s,4s)-4-(3-(4-(1-(2-morpholinoethyl)-1H-pyrazol-4-yl)phenyl)pyrazolo[1,5-a]pyrazin-4-yl)cyclohexane-1-carbonitrile | 482.2 |

TABLE 1-continued

| P Number | Structure | Name | MS |
|---|---|---|---|
| P-0017 | 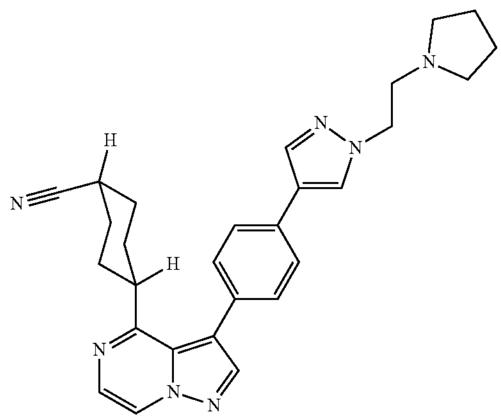 [SMILES: N#CC1CCC(c2nccn3ncc(-c4ccc(-c5cnn(CCN6CCCC6)c5)cc4)c23)CC1] | (1s,4s)-4-(3-(4-(1-(2-(pyrrolidin-1-yl)ethyl)-1H-pyrazol-4-yl)phenyl)pyrazolo[1,5-a]pyrazin-4-yl)cyclohexane-1-carbonitrile | 482.3 |
| P-0018 | 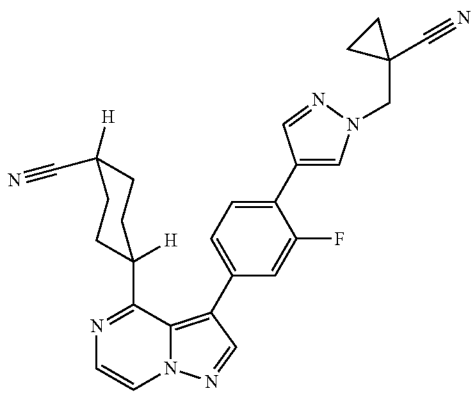 [SMILES: N#CC1CCC(c2nccn3ncc(-c4ccc(-c5cnn(CC6(C#N)CC6)c5)c(F)c4)c23)CC1] | (1s,4s)-4-(3-(4-(1-((1-cyanocyclopropyl)methyl)-1H-pyrazol-4-yl)-3-fluorophenyl)pyrazolo[1,5-a]pyrazin-4-yl)cyclohexane-1-carbonitrile | 466.2 |
| P-0019 | 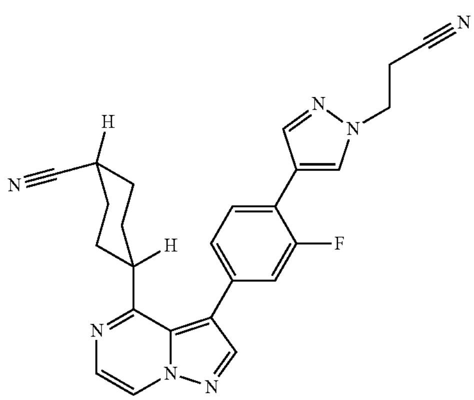 [SMILES: N#CCCn1cc(-c2ccc(-c3cnn4ccnc(C5CCC(C#N)CC5)c34)cc2F)cn1] | (1s,4s)-4-(3-(4-(1-(2-cyanoethyl)-1H-pyrazol-4-yl)-3-fluorophenyl)pyrazolo[1,5-a]pyrazin-4-yl)cyclohexane-1-carbonitrile | 440.2 |
| P-0020 | 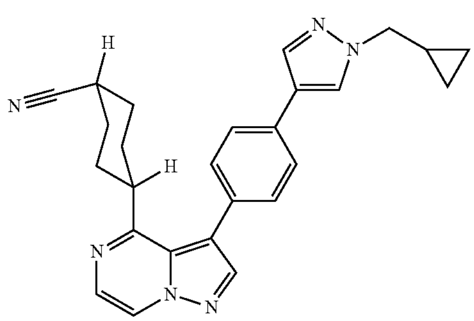 [SMILES: N#CC1CCC(c2nccn3ncc(-c4ccc(-c5cnn(CC6CC6)c5)cc4)c23)CC1] | (1s,4s)-4-(3-(4-(1-(cyclopropylmethyl-1H-pyrazol-4-yl)phenyl)pyrazolo[1,5-a]pyrazin-4-yl)cyclohexane-1-carbonitrile | 423.6 |

TABLE 1-continued

| P Number | Structure | Name | MS |
|---|---|---|---|
| P-0021 | 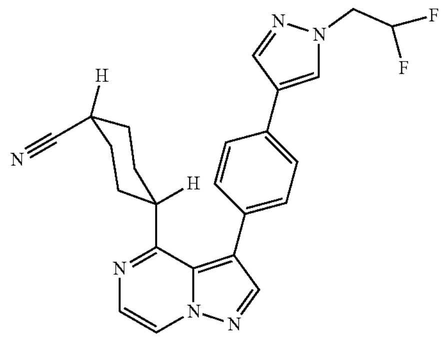 [SMILES: N#CC1CCC(c2nccn3ncc(-c4ccc(-c5cnn(CC(F)F)c5)cc4)c23)CC1] | (1s,4s)-4-(3-(4-(1-(2,2-difluoroethyl)-1H-pyrazol-4-yl)phenyl)pyrazolo[1,5-a]pyrazin-4-yl)cyclohexane-1-carbonitrile | 433.6 |
| P-0022 | 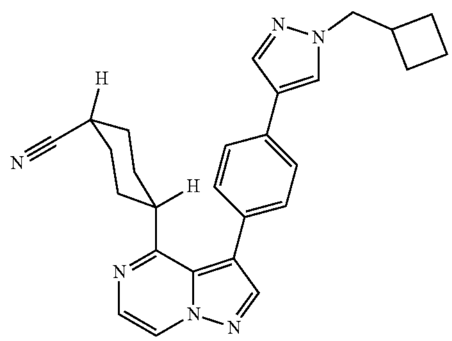 [SMILES: N#CC1CCC(c2nccn3ncc(-c4ccc(-c5cnn(CC6CCC6)c5)cc4)c23)CC1] | (1s,4s)-4-(3-(4-(1-(cyclobutylmethyl)-1H-pyrazol-4-yl)phenyl)pyrazolo[1,5-a]pyrazin-4-yl)cyclohexane-1-carbonitrile | 437.7 |
| P-0023 | 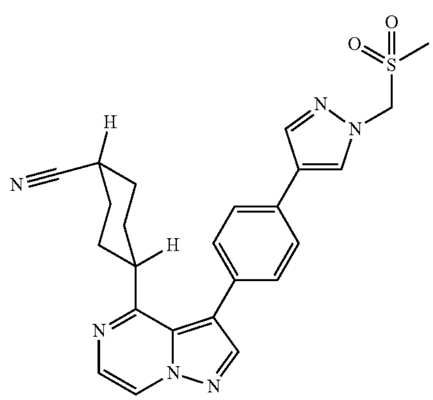 [SMILES: CS(=O)(=O)Cn1cc(-c2ccc(-c3cnn4ccnc(C5CCC(C#N)CC5)c34)cc2)cn1] | (1s,4s)-4-(3-(4-(1-((methylsulfonyl)methyl)-1H-pyrazol-4-yl)phenyl)pyrazolo[1,5-a]pyrazin-4-yl)cyclohexane-1-carbonitrile | 461.2 |
| P-0024 | 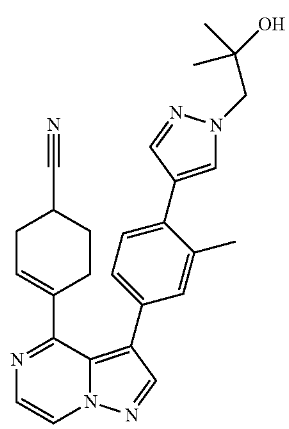 [SMILES: Cc1cc(-c2cnn3ccnc(C4=CCC(C#N)CC4)c23)ccc1-c1cnn(CC(C)(C)O)c1] | 4-(3-(4-(1-(2-hydroxy-2-methylpropyl)-1H-pyrazol-4-yl)-3 methylphenyl)pyrazolo[1,5-a]pyrazin-4-yl)cyclohex-3-ene-1-carbonitrile | 453.2 |

TABLE 1-continued

| P Number | Structure | Name | MS |
|---|---|---|---|
| P-0025 | 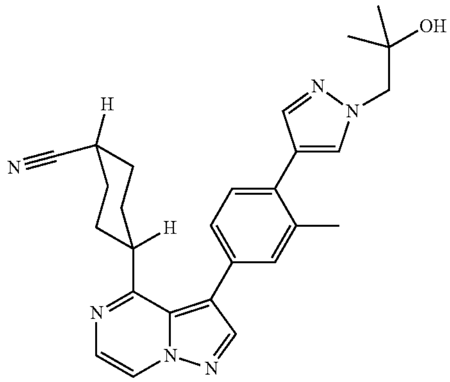 [SMILES: Cc1cc(-c2cnn3ccnc(C4CCC(C#N)CC4)c23)ccc1-c1cnn(CC(C)(C)O)c1] | (1s,4s)-4-(3-(4-(1-(2-hydroxy-2-methylpropyl)-1H-pyrazol-4-yl)-3-methylphenyl)pyrazolo[1,5-a]pyrazin-4-yl)cyclohexane-1-carbonitrile | 455.2 |
| P-0026 | 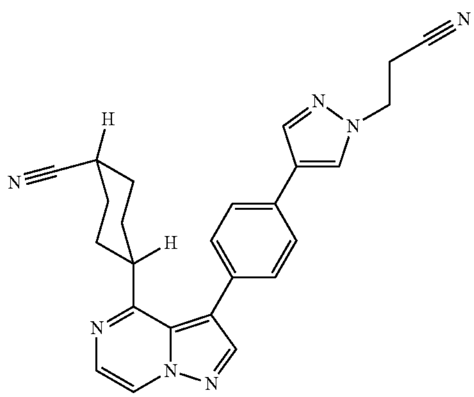 [SMILES: N#CCCn1cc(-c2ccc(-c3cnn4ccnc(C5CCC(C#N)CC5)c34)cc2)cn1] | (1s,4s)-4-(3-(4-(1-(2-cyanoethyl)-1H-pyrazol-4-yl)phenyl)pyrazolo[1,5-a]pyrazin-4-yl)cyclohexane-1-carbonitrile | 422.1 |
| P-0027 | 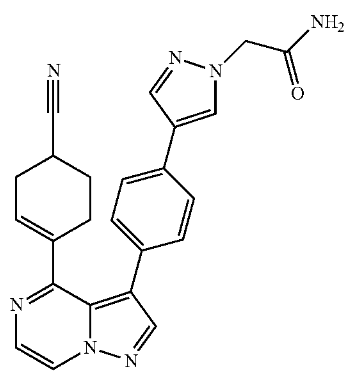 [SMILES: N#CC1CC=C(c2nccn3ncc(-c4ccc(-c5cnn(CC(N)=O)c5)cc4)c23)CC1] | 2-(4-(4-(4-cyanocyclohex-1-en-1-yl)pyrazolo[1,5-a]pyrazin-3-yl)phenyl)-1H-pyrazol-1-yl)acetamide | 424.1 |
| P-0028 | 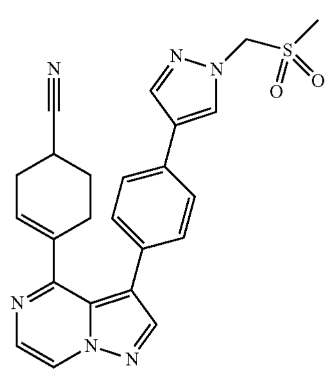 [SMILES: CS(=O)(=O)Cn1cc(-c2ccc(-c3cnn4ccnc(C5=CCC(C#N)CC5)c34)cc2)cn1] | 4-(3-(4-(1-((methylsulfonyl)methyl)-1H-pyrazol-4-yl)phenyl)pyrazolo[1,5-a]pyrazin-4-yl)cyclohex-3-ene-1-carbonitrile | 459.1 |

TABLE 1-continued

| P Number | Structure | Name | MS |
|---|---|---|---|
| P-0029 | 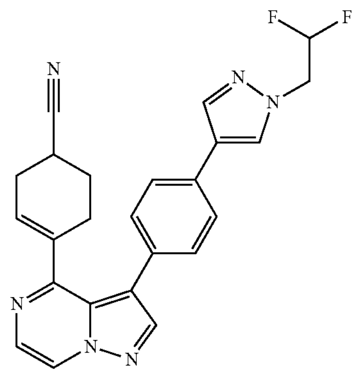 [SMILES: N#CC1CC=C(c2nccn3ncc(-c4ccc(-c5cnn(CC(F)F)c5)cc4)c23)CC1] | 4-(3-(4-(1-(2,2-difluoroethyl)-1H-pyrazol-4-yl)phenyl)pyrazolo[1,5-a]pyrazin-4-yl)cyclohex-3-ene-1-carbonitrile | 431.1 |
| P-0030 | 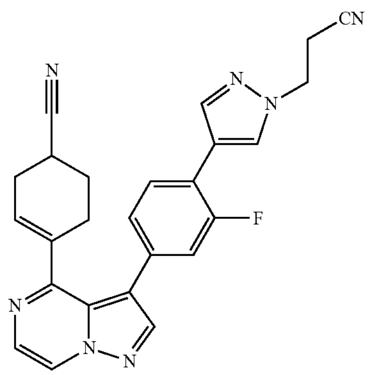 [SMILES: N#CCCn1cc(-c2ccc(-c3cnn4ccnc(C5=CCC(C#N)CC5)c34)cc2F)cn1] | 4-(3-(4-(1-(2-cyanoethyl)-1H-pyrazol-4-yl)-3-fluorophenyl)pyrazolo[1,5-a]pyrazin-4-yl)cyclohex-3-ene-1-carbonitrile | 438.2 |
| P-0031 | 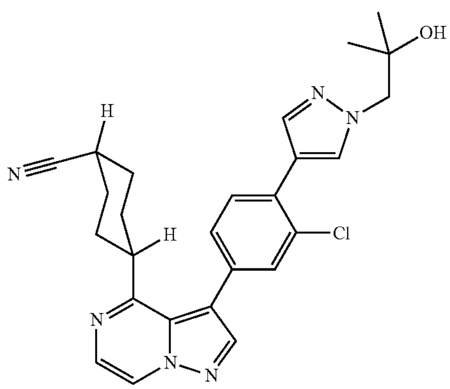 [SMILES: CC(C)(O)Cn1cc(-c2ccc(-c3cnn4ccnc(C5CCC(C#N)CC5)c34)cc2Cl)cn1] | (1s,4s)-4-(3-(3-chloro-4-(1-(2-hydroxy-2-methylpropyl)-1H-pyrazol-4-yl)phenyl)pyrazolo[1,5-a]pyrazin-4-yl)cyclohexane-1-carbonitrile | 475.5 |
| P-0032 | 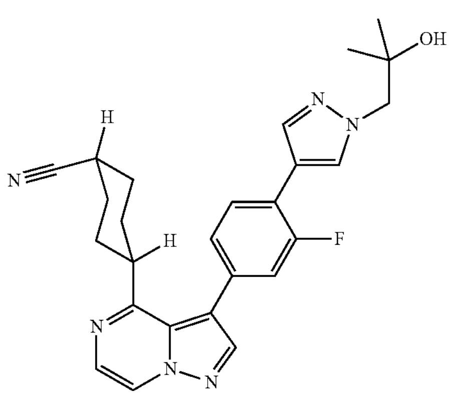 [SMILES: CC(C)(O)Cn1cc(-c2ccc(-c3cnn4ccnc(C5CCC(C#N)CC5)c34)cc2F)cn1] | (1s,4s)-4-(3-(3-fluoro-4-(1-(2-hydroxy-2-methylpropyl)-1H-pyrazol-4-yl)phenyl)pyrazolo[1,5-a]pyrazin-4-yl)cyclohexane-1-carbonitrile | 459.2 |

TABLE 1-continued

| P Number | Structure | Name | MS |
|---|---|---|---|
| P-0033 | 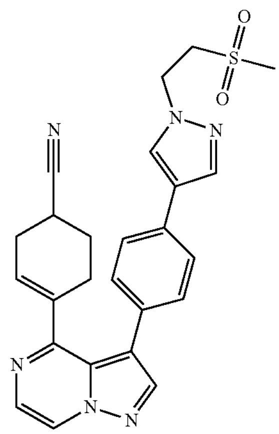 [SMILES: CS(=O)(=O)CCn1cc(-c2ccc(-c3cnn4ccnc(C5=CCC(C#N)CC5)c34)cc2)cn1] | 4-(3-(4-(1-(2-(methylsulfonyl)ethyl)-1H-pyrazol-4-yl)phenyl)pyrazolo[1,5-a]pyrazin-4-yl)cyclohex-3-ene-1-carbonitrile | 473.1 |
| P-0034 | 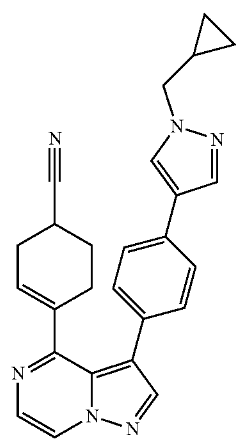 [SMILES: N#CC1CC=C(c2nccn3ncc(-c4ccc(-c5cnn(CC6CC6)c5)cc4)c23)CC1] | 4-(3-(4-(1-(cyclopropylmethyl)-1H-pyrazol-4-yl)phenyl)pyrazolo[1,5-a]pyrazin-4-yl)cyclohex-3-ene-1-carbonitrile | 421.2 |
| P-0035 | 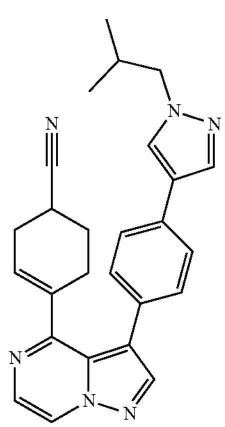 [SMILES: CC(C)Cn1cc(-c2ccc(-c3cnn4ccnc(C5=CCC(C#N)CC5)c34)cc2)cn1] | 4-(3-(4-(1-isobutyl-1H-pyrazol-4-yl)phenyl)pyrazolo[1,5-a]pyrazin-4-yl)cyclohex-3-ene-1-carbonitrile | 423.2 |

TABLE 1-continued

| P Number | Structure | Name | MS |
|---|---|---|---|
| P-0036 | 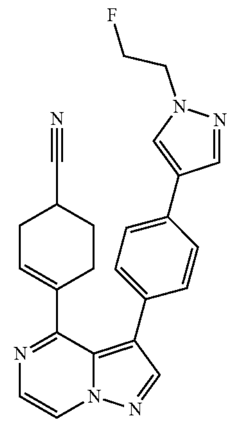 [SMILES: N#CC1CC=C(c2nccn3ncc(-c4ccc(-c5cnn(CCF)c5)cc4)c23)CC1] | 4-(3-(4-(1-(2-fluoroethyl)-1H-pyrazol-4-yl)phenyl)pyrazolo[1,5-a]pyrazin-4-yl)cyclohex-3-ene-1-carbonitrile | 413.6 |
| P-0037 | 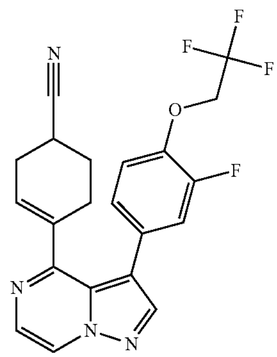 [SMILES: N#CC1CC=C(c2nccn3ncc(-c4ccc(OCC(F)(F)F)c(F)c4)c23)CC1] | 4-(3-(3-fluoro-4-(2,2,2-trifluoroethoxy)phenyl)pyrazolo[1,5-a]pyrazin-4-yl)cyclohex-3-ene-1-carbonitrile | 417.1 |
| P-0038 | 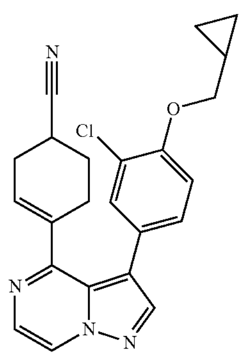 [SMILES: N#CC1CC=C(c2nccn3ncc(-c4ccc(OCC5CC5)c(Cl)c4)c23)CC1] | 4-(3-(3-chloro-4-(cyclopropylmethoxy)phenyl)pyrazolo[1,5-a]pyrazin-4-yl)cyclohex-3-ene-1-carbonitrile | 405.4 |
| P-0039 | 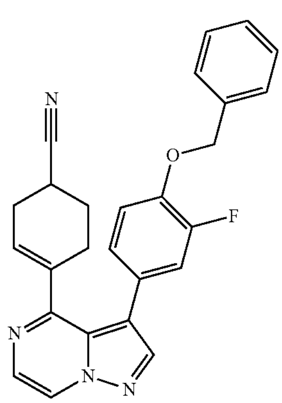 [SMILES: N#CC1CC=C(c2nccn3ncc(-c4ccc(OCc5ccccc5)c(F)c4)c23)CC1] | 4-(3-(4-(benzyloxy)-3-fluorophenyl)pyrazolo[1,5-a]pyrazin-4-yl)cyclohex-3-ene-1-carbonitrile | 425.2 |

TABLE 1-continued

| P Number | Structure | Name | MS |
|---|---|---|---|
| P-0040 | 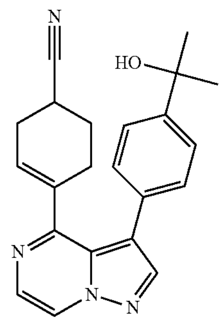 [SMILES: CC(C)(O)c1ccc(-c2cnn3ccnc(C4=CCC(C#N)CC4)c23)cc1] | 4-(3-(4-(2-hydroxypropan-2-yl)phenyl)pyrazolo[1,5-a]pyrazin-4-yl)cyclohex-3-ene-1-carbonitrile | 359.1 |
| P-0041 | 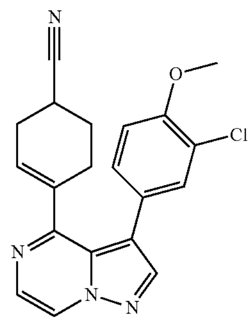 [SMILES: COc1ccc(-c2cnn3ccnc(C4=CCC(C#N)CC4)c23)cc1Cl] | 4-(3-(3-chloro-4-methoxyphenyl)pyrazolo[1,5-a]pyrazin-4-yl)cyclohex-3-ene-1-carbonitrile | 365.1 |
| P-0042 | 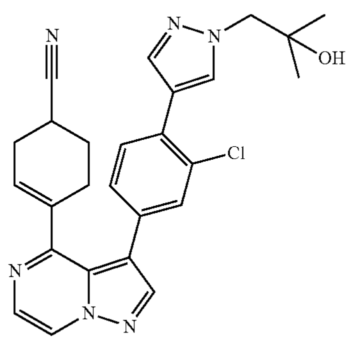 [SMILES: CC(C)(O)Cn1cc(-c2ccc(-c3cnn4ccnc(C5=CCC(C#N)CC5)c34)cc2Cl)cn1] | 4-(3-(3-chloro-4-(1-(2-hydroxy-2-methylpropyl)-1H-pyrazol-4-yl)phenyl)pyrazolo[1,5-a]pyrazin-4-yl)cyclohex-3-ene-1-carbonitrile | 473.1 |
| P-0043 | 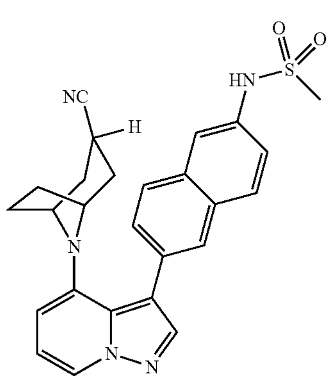 [SMILES: CS(=O)(=O)Nc1ccc2cc(-c3cnn4cccc(N5C6CCC5CC(C#N)C6)c34)ccc2c1] | N-(6-(4-(3-isocyano-8-azabicyclo[3.2.1]octan-8-yl)pyrazolo[1,5-a]pyridin-3-yl)naphthalen-2-yl)methanesulfonamide | 472.2 |

TABLE 1-continued

| P Number | Structure | Name | MS |
|---|---|---|---|
| P-0044 | 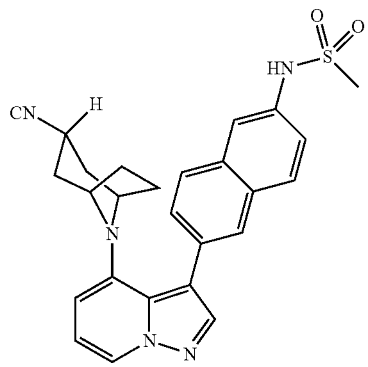 | N-(6-(4-(3-cyano-8-azabicyclo[3.2.1]octan-8-yl)pyrazolo[1,5-a]pyridin-3-yl)naphthalen-2-yl)methanesulfonamide | 472.0 |
| P-0045 | 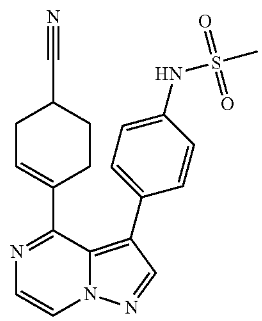 [SMILES: CS(=O)(=O)Nc1ccc(-c2cnn3ccnc(C4=CCC(C#N)CC4)c23)cc1] | N-(4-(4-(4-cyanocyclohex-1-en-1-yl)pyrazolo[1,5-a]pyrazin-3-yl)phenyl)methanesulfonamide | 394.0 |
| P-0046 | 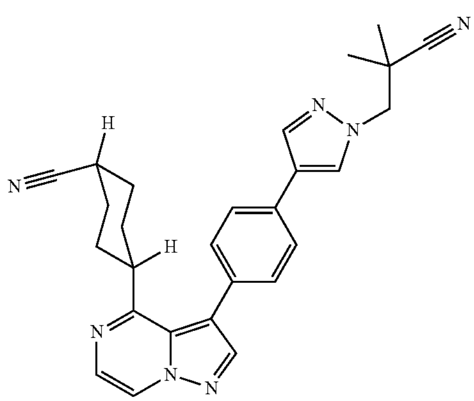 [SMILES: CC(C)(C#N)Cn1cc(-c2ccc(-c3cnn4ccnc(C5CCC(C#N)CC5)c34)cc2)cn1] | (1s,4s)-4-(3-(4-(1-(2-cyano-2-methylpropyl)-1H-pyrazol-4-yl)phenyl)pyrazolo[1,5-a]pyrazin-4-yl)cyclohexane-1-carbonitrile | 450.2 |
| P-0047 | 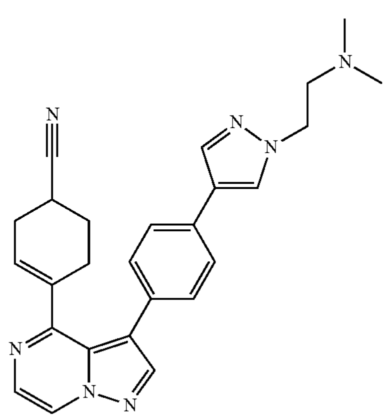 [SMILES: CN(C)CCn1cc(-c2ccc(-c3cnn4ccnc(C5=CCC(C#N)CC5)c34)cc2)cn1] | 4-(3-(4-(1-(2-(dimethylamino)ethyl)-1H-pyrazol-4-yl)phenyl)pyrazolo[1,5-a]pyrazin-4-yl)cyclohex-3-ene-1-carbonitrile | 438.6 |

TABLE 1-continued
| P Number | Structure | Name | MS |
|---|---|---|---|
| P-0048 | 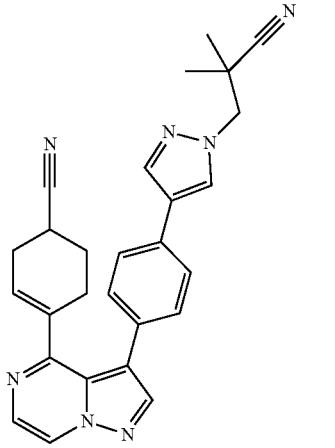 [SMILES: CC(C)(C#N)Cn1cc(-c2ccc(-c3cnn4ccnc(C5=CCC(C#N)CC5)c34)cc2)cn1] | 4-(3-(4-(1-(2-cyano-2-methylpropyl)-1H-pyrazol-4-yl)phenyl)pyrazolo[1,5-a]pyrazin-4-yl)cyclohex-3-ene-1-carbonitrile | 448.2 |
| P-0049 | 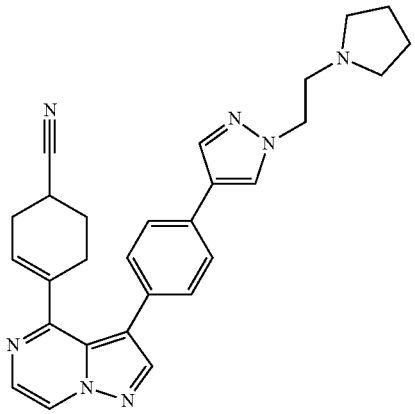 [SMILES: N#CC1CC=C(c2nccn3ncc(-c4ccc(-c5cnn(CCN6CCCC6)c5)cc4)c23)CC1] | 4-(3-(4-(1-(2-(pyrrolidin-1-yl)ethyl)-1H-pyrazol-4-yl)phenyl)pyrazolo[1,5-a]pyrazin-4-yl)cyclohex-3-ene-1-carbonitrile | 464.6 |
| P-0050 | 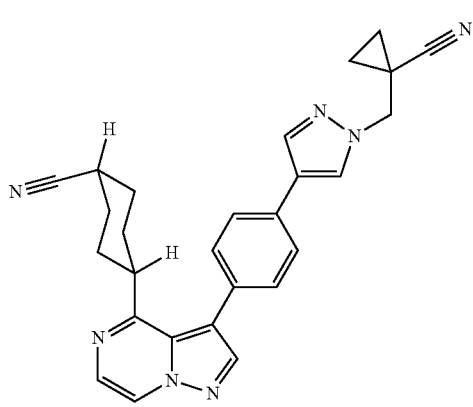 [SMILES: N#CC1CCC(c2nccn3ncc(-c4ccc(-c5cnn(CC6(C#N)CC6)c5)cc4)c23)CC1] | (1s,4s)-4-(3-(4-(1-((1-cyanocyclopropyl)methyl)-1H-pyrazol-4-yl)phenyl)pyrazolo[1,5-a]pyrazin-4-yl)cyclohexane-1-carbonitrile | 448.2 |

TABLE 1-continued

| P Number | Structure | Name | MS |
|---|---|---|---|
| P-0051 | 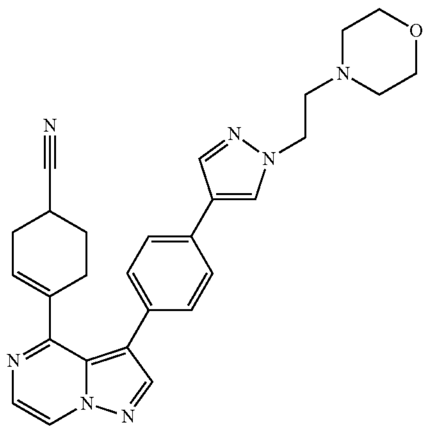 [SMILES: N#CC1CC=C(c2nccn3ncc(-c4ccc(-c5cnn(CCN6CCOCC6)c5)cc4)c23)CC1] | 4-(3-(4-(1-(2-morpholinoethyl)-1H-pyrazol-4-yl)phenyl)pyrazolo[1,5-a]pyrazin-4-yl)cyclohex-3-ene-1-carbonitrile | 480.2 |
| P-0052 | 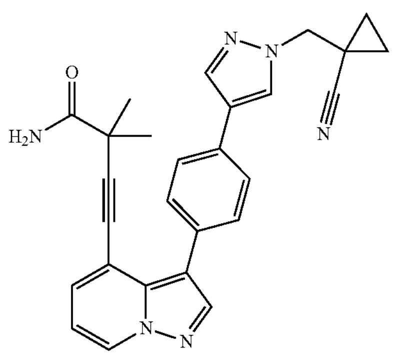 [SMILES: CC(C)(C#Cc1cccn2ncc(-c3ccc(-c4cnn(CC5(C#N)CC5)c4)cc3)c12)C(N)=O] | 4-(3-(4-(1-((1-cyanocyclopropyl)methyl)-1H-pyrazol-4-yl)phenyl)pyrazolo[1,5-a]pyridin-4-yl)-2,2-dimethylbut-3-ynamide | 449.2 |
| P-0053 | 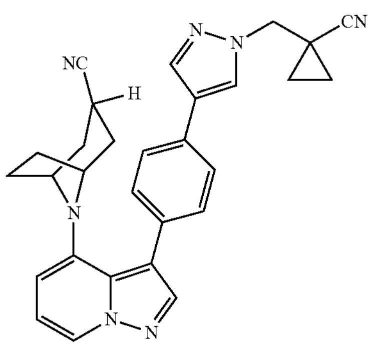 [SMILES: N#CC1CC2CCC(C1)N2c1cccn2ncc(-c3ccc(-c4cnn(CC5(C#N)CC5)c4)cc3)c12] | 1-((4-(4-(4-(3-isocyano-8-azabicyclo[3.2.1]octan-8-yl)pyrazolo[1,5-a]pyridin-3-yl)phenyl)-1H-pyrazol-1-yl)methyl)cyclopropane-1-carbonitrile | 474.2 |
| P-0054 | 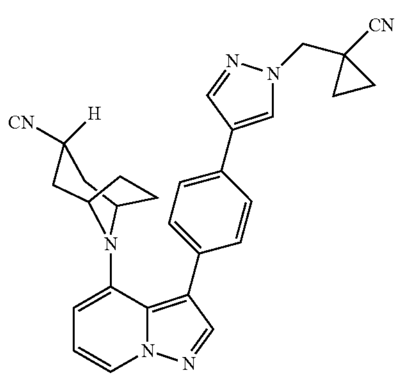 | 8-(3-(4-(1-((1-cyanocyclopropyl)methyl)-1H-pyrazol-4-yl)phenyl)pyrazolo[1,5-a]pyridin-4-yl)-8-azabicyclo[3.2.1]octane-3-carbonitrile | 474.2 |

TABLE 1-continued

| P Number | Structure | Name | MS |
|---|---|---|---|
| P-0055 | 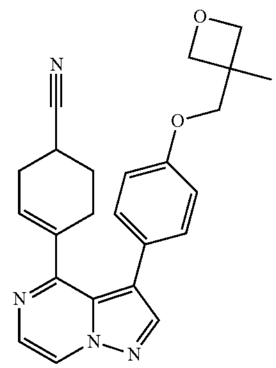 [SMILES: CC1(COc2ccc(-c3cnn4ccnc(C5=CCC(C#N)CC5)c34)cc2)COC1] | 4-(3-(4-((3-methyloxetan-3-yl)methoxy)phenyl)pyrazolo[1,5-a]pyrazin-4-yl)cyclohex-3-ene-1-carbonitrile | 401.5 |
| P-0056 | 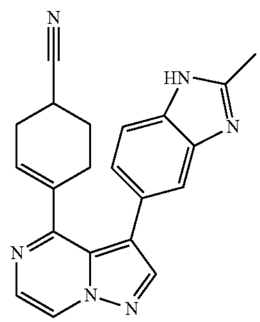 [SMILES: Cc1nc2cc(-c3cnn4ccnc(C5=CCC(C#N)CC5)c34)ccc2[nH]1] | 4-(3-(2-methyl-1H-benzo[d]imidazol-5-yl)pyrazolo[1,5-a]pyrazin-4-yl)cyclohex-3-ene-1-carbonitrile | 355.2 |
| P-0057 | 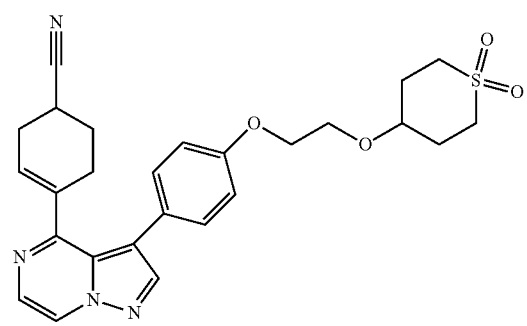 [SMILES: N#CC1CC=C(c2nccn3ncc(-c4ccc(OCCOC5CCS(=O)(=O)CC5)cc4)c23)CC1] | 4-(3-(4-(2-((1,1-dioxidotetrahydro-2H-thiopyran-4-yl)oxy)ethoxy)phenyl)pyrazolo[1,5-a]pyrazin-4-yl)cyclohex-3-ene-1-carbonitrile | 493.2 |
| P-0058 | 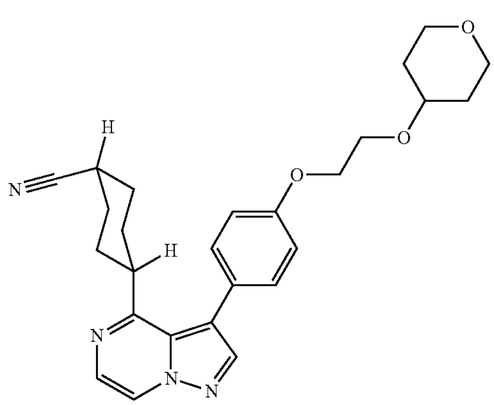 [SMILES: N#CC1CCC(c2nccn3ncc(-c4ccc(OCCOC5CCOCC5)cc4)c23)CC1] | (1s,4s)-4-(3-(4-(2-((tetrahydro-2H-pyran-4-yl)oxy)ethoxy)phenyl)pyrazolo[1,5-a]pyrazin-4-yl)cyclohexane-1-carbonitrile | 447.2 |

TABLE 1-continued

| P Number | Structure | Name | MS |
|---|---|---|---|
| P-0059 | 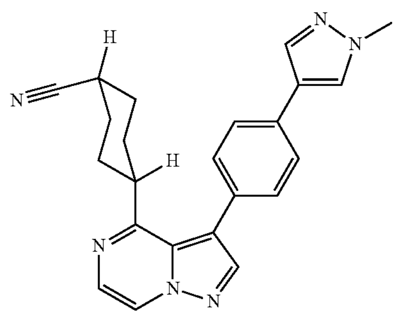 [SMILES: Cn1cc(-c2ccc(-c3cnn4ccnc(C5CCC(C#N)CC5)c34)cc2)cn1] | (1s,4s)-4-(3-(4-(1-methyl-1H-pyrazol-4-yl)phenyl)pyrazolo[1,5-a]pyrazin-4-yl)cyclohexane-1-carbonitrile | 383.1 |
| P-0060 | 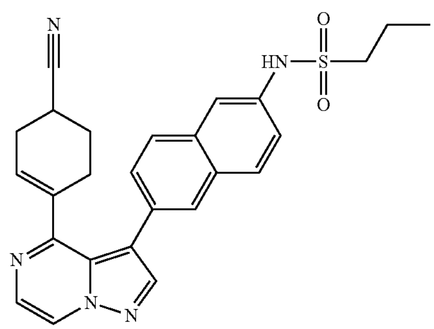 [SMILES: CCCS(=O)(=O)Nc1ccc2cc(-c3cnn4ccnc(C5=CCC(C#N)CC5)c34)ccc2c1] | N-(6-(4-(4-cyanocyclohex-1-en-1-yl)pyrazolo[1,5-a]pyrazin-3-yl)naphthalen-2-yl)propane-1-sulfonamide | 472.2 |
| P-0061 | 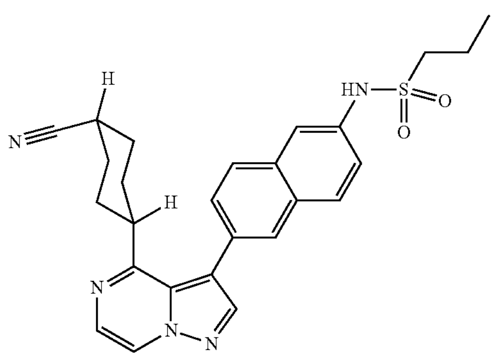 [SMILES: CCCS(=O)(=O)Nc1ccc2cc(-c3cnn4ccnc(C5CCC(C#N)CC5)c34)ccc2c1] | N-(6-(4-((1s,4s)-4-cyanocyclohexyl)pyrazolo[1,5-a]pyrazin-3-yl)naphthalen-2-yl)propane-1-sulfonamide | 474.1 |
| P-0062 | 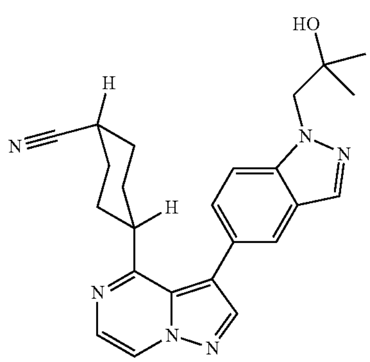 [SMILES: CC(C)(O)Cn1ncc2cc(-c3cnn4ccnc(C5CCC(C#N)CC5)c34)ccc21] | (1s,4s)-4-(3-(1-(2-hydroxy-2-methylpropyl)-1H-indazol-5-yl)pyrazolo[1,5-a]pyrazin-4-yl)cyclohexane-1-carbonitrile | 415.5 |

TABLE 1-continued

| P Number | Structure | Name | MS |
|---|---|---|---|
| P-0063 | 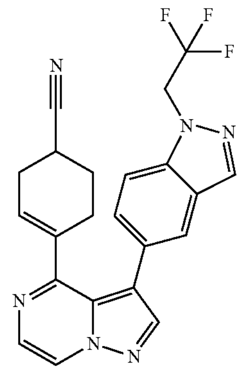 [SMILES: N#CC1CC=C(c2nccn3ncc(-c4ccc5c(cnn5CC(F)(F)F)c4)c23)CC1] | 4-(3-(1-(2,2,2-trifluoroethyl)-1H-indazol-5-yl)pyrazolo[1,5-a]pyrazin-4-yl)cyclohex-3-ene-1-carbonitrile | 423.0 |
| P-0064 | 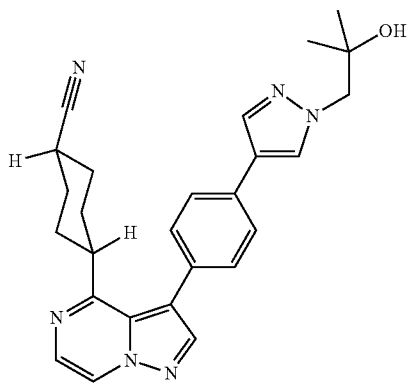 [SMILES: CC(C)(O)Cn1cc(-c2ccc(-c3cnn4ccnc(C5CCC(C#N)CC5)c34)cc2)cn1] | (1r,4r)-4-(3-(4-(1-(2-hydroxy-2-methylpropyl)-1H-pyrazol-4-yl)phenyl)pyrazolo[1,5-a]pyrazin-4-yl)cyclohexane-1-carbonitrile | 441.6 |
| P-0065 | 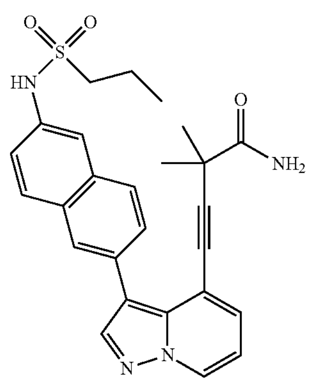 [SMILES: CCCS(=O)(=O)Nc1ccc2cc(-c3cnn4cccc(C#CC(C)(C)C(N)=O)c34)ccc2c1] | 2,2-dimethyl-4-(3-(6-(propylsulfonamido)naphthalen-2-yl)pyrazolo[1,5-a]pyridin-4-yl)but-2-ynamide | |
| P-0066 | 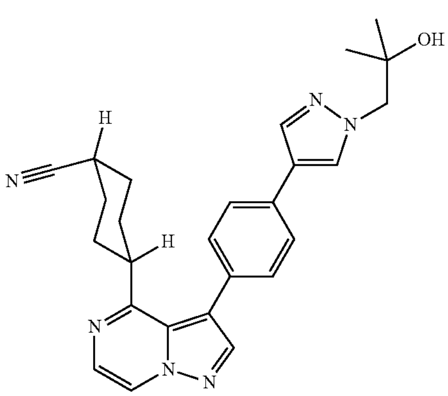 [SMILES: CC(C)(O)Cn1cc(-c2ccc(-c3cnn4ccnc(C5CCC(C#N)CC5)c34)cc2)cn1] | (1s,4s)-4-(3-(4-(1-(2-hydroxy-2-methylpropyl)-1H-pyrazol-4-yl)phenyl)pyrazolo[1,5-a]pyrazin-4-yl)cyclohexane-1-carbonitrile | 441.2 |

TABLE 1-continued

| P Number | Structure | Name | MS |
|---|---|---|---|
| P-0067 | 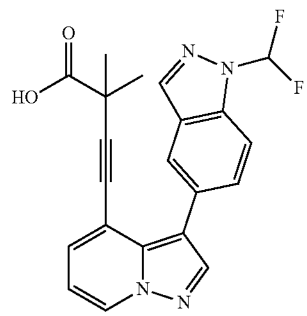 [SMILES: CC(C)(C#Cc1cccn2ncc(-c3ccc4c(cnn4C(F)F)c3)c12)C(=O)O] | 4-(3-(1-(difluoromethyl)-1H-indazol-5-yl)pyrazolo[1,5-a]pyridin-4-yl)-2,2-dimethylbut-3-ynoic acid | 395.1 |
| P-0068 | 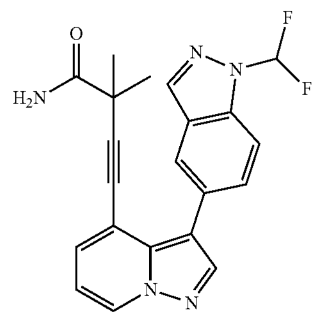 | 4-(3-(1-(difluoromethyl)-1H-indazol-5-yl)pyrazolo[1,5-a]pyridin-4-yl)-2,2-dimethylbut-3-ynamide | 394.3 |
| P-0069 | 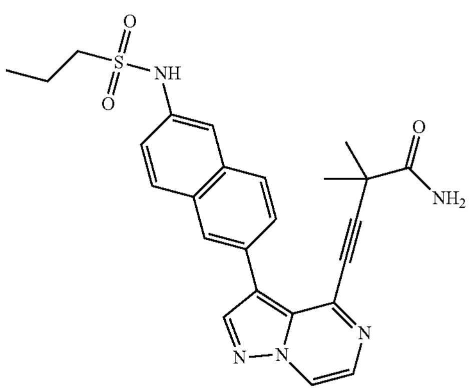 [SMILES: CCCS(=O)(=O)Nc1ccc2cc(-c3cnn4ccnc(C#CC(C)(C)C(N)=O)c34)ccc2c1] | 2,2-dimethyl-4-(3-(6-(propylsulfonamido)naphthalen-2-yl)pyrazolo[1,5-a]pyrazin-4-yl)but-3-ynamide | 476.1 |
| P-0070 | 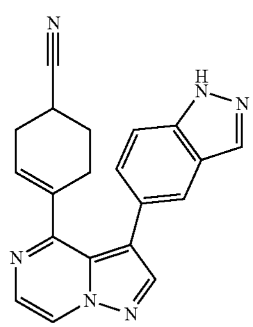 [SMILES: N#CC1CC=C(c2nccn3ncc(-c4ccc5[nH]ncc5c4)c23)CC1] | 4-(3-(1H-indazol-5-yl)pyrazolo[1,5-a]pyrazin-4-yl)cyclohex-3-ene-1-carbonitrile | 341.1 |

TABLE 1-continued

| P Number | Structure | Name | MS |
|---|---|---|---|
| P-0071 | 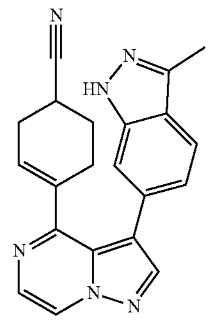 [SMILES: Cc1n[nH]c2cc(-c3cnn4ccnc(C5=CCC(C#N)CC5)c34)ccc12] | 4-(3-(3-methyl-1H-indazol-6-yl)pyrazolo[1,5-a]pyrazin-4-yl)cyclohex-3-ene-1-carbonitrile | 355.2 |
| P-0072 | 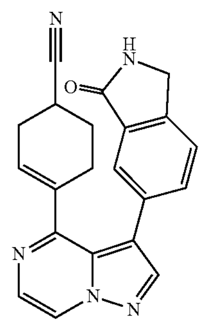 [SMILES: N#CC1CC=C(c2nccn3ncc(-c4ccc5c(c4)C(=O)NC5)c23)CC1] | 4-(3-(3-oxoisoindolin-5-yl)pyrazolo[1,5-a]pyrazin-4-yl)cyclohex-3-ene-1-carbonitrile | 356.4 |
| P-0073 | 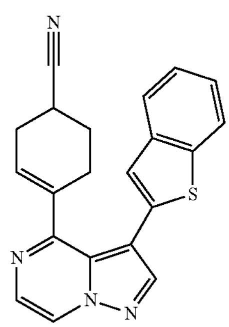 [SMILES: N#CC1CC=C(c2nccn3ncc(-c4cc5ccccc5s4)c23)CC1] | 4-(3-(benzo[b]thiophen-2-yl)pyrazolo[1,5-a]pyrazin-4-yl)cyclohex-3-ene-1-carbonitrile | 357.0 |
| P-0074 | 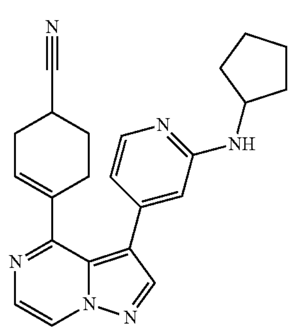 [SMILES: N#CC1CC=C(c2nccn3ncc(-c4ccnc(NC5CCCC5)c4)c23)CC1] | 4-(3-(2-cyclopentylamino)pyridin-4-yl)pyrazolo[1,5-a]pyrazin-4-yl)cyclohex-3-ene-1-carbonitrile | 385.2 |

TABLE 1-continued

| P Number | Structure | Name | MS |
|---|---|---|---|
| P-0075 | 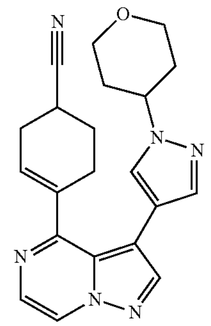 [SMILES: N#CC1CC=C(c2nccn3ncc(-c4cnn(C5CCOCC5)c4)c23)CC1] | 4-(3-(1-tetrahydro-2H-pyran-4-yl)-1H-pyrazol-4-yl)pyrazolo[1,5-a]pyrazin-4-yl)cyclohex-3-ene-1-carbonitrile | 375.0 |
| P-0076 | 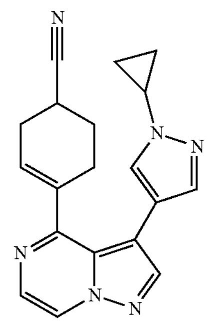 [SMILES: N#CC1CC=C(c2nccn3ncc(-c4cnn(C5CC5)c4)c23)CC1] | 4-(3-(1-cyclopropyl-1H-pyrazol-4-yl)pyrazolo[1,5-a]pyrazin-4-yl)cyclohex-3-ene-1-carbonitrile | 331.2 |
| P-0077 | 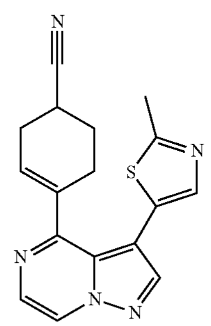 [SMILES: Cc1ncc(-c2cnn3ccnc(C4=CCC(C#N)CC4)c23)s1] | 4-(3-(2-methylthiazol-5-yl)pyrazolo[1,5-a]pyrazin-4-yl)cyclohex-3-ene-1-carbonitrile | 322.2 |
| P-0078 | 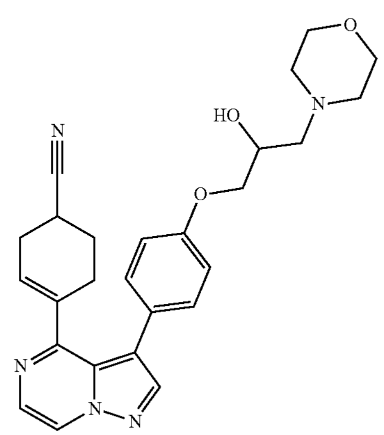 [SMILES: N#CC1CC=C(c2nccn3ncc(-c4ccc(OCC(O)CN5CCOCC5)cc4)c23)CC1] | 4-(3-(4-(2-hydroxy-3-morpholinopropoxy)phenyl)pyrazolo[1,5-a]pyrazin-4-yl)cyclohex-3-ene-1-carbonitrile | 460.3 |

TABLE 1-continued

| P Number | Structure | Name | MS |
|---|---|---|---|
| P-0079 | 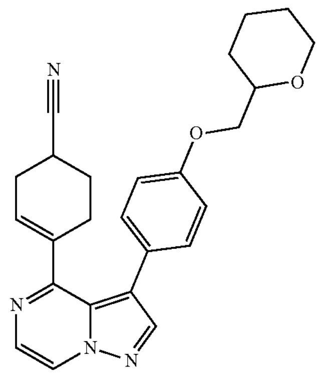 [SMILES: N#CC1CC=C(c2nccn3ncc(-c4ccc(OCC5CCCCO5)cc4)c23)CC1] | 4-(3-(4-((tetrahydro-2H-pyran-2-yl)methoxy)phenyl)pyrazolo[1,5-a]pyrazin-4-yl)cyclohex-3-ene-1-carbonitrile | 415.3 |
| P-0080 | 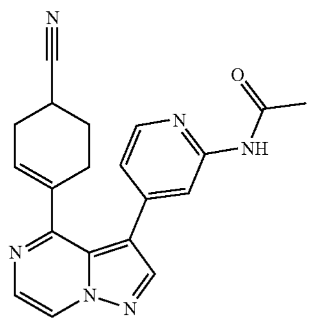 [SMILES: CC(=O)Nc1cc(-c2cnn3ccnc(C4=CCC(C#N)CC4)c23)ccn1] | N-(4-(4-(4-cyanocyclohex-1-ene-1-yl)pyrazolo[1,5-a]pyrazin-3-yl)pyridin-2-yl)acetamide | 359.1 |
| P-0081 | 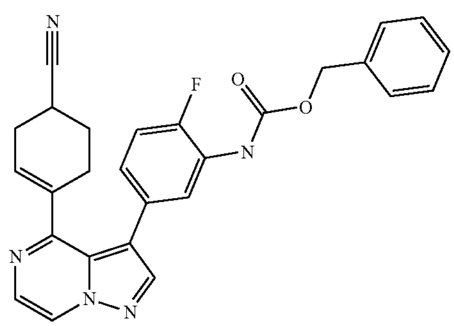 [SMILES: N#CC1CC=C(c2nccn3ncc(-c4ccc(F)c(NC(=O)OCc5ccccc5)c4)c23)CC1] | benzyl (5-(4-(4-cyanocyclohex-1-en-1-yl)pyrazolo[1,5-a]pyrazin-3-yl)-2-fluorophenyl)carbamate | 468.1 |
| P-0082 | 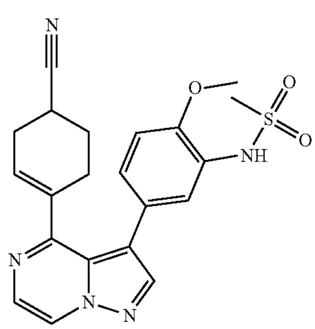 [SMILES: COc1ccc(-c2cnn3ccnc(C4=CCC(C#N)CC4)c23)cc1NS(C)(=O)=O] | N-(5-(4-(4-cyanocyclohex-1-en-1-yl)pyrazolo[1,5-a]pyrazin-3-yl)-2-methoxyphenyl)methane-sulfonamide | 424.0 |

TABLE 1-continued

| P Number | Structure | Name | MS |
|---|---|---|---|
| P-0083 | 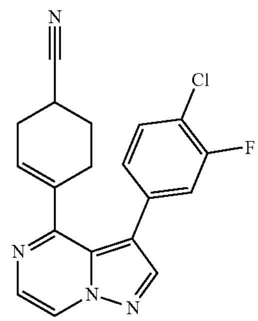 [SMILES: N#CC1CC=C(c2nccn3ncc(-c4ccc(Cl)c(F)c4)c23)CC1] | 4-(3-(4-chloro-3-fluorophenyl)pyrazolo[1,5-a]pyrazin-4-yl)cyclohex-3-ene-1-carbonitrile | 353.1 |
| P-0084 | 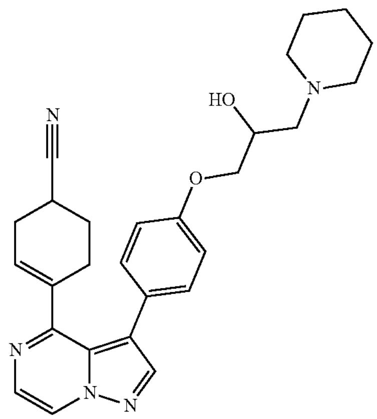 [SMILES: N#CC1CC=C(c2nccn3ncc(-c4ccc(OCC(O)CN5CCCCC5)cc4)c23)CC1] | 4-(3-(4-(2-hydroxy-3-(piperidin-1-yl)propoxy)phenyl)pyrazolo[1,5-a]pyrazin-4-yl)cyclohex-3-ene-1-carbonitrile | 458.2 |
| P-0085 | 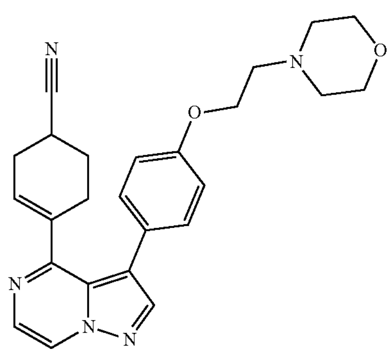 [SMILES: N#CC1CC=C(c2nccn3ncc(-c4ccc(OCCN5CCOCC5)cc4)c23)CC1] | 4-(3-(4-(2-morpholinoethoxy)phenyl)pyrazolo[1,5-a]pyrazin-4-yl)cyclohex-3-ene-1-carbonitrile | 430.3 |
| P-0086 | 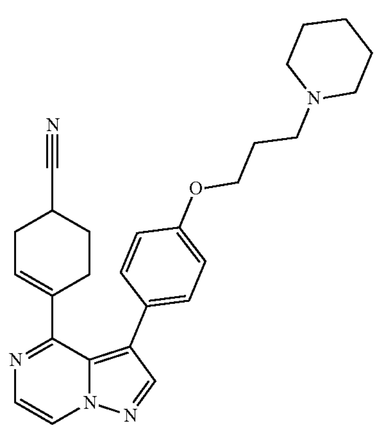 [SMILES: N#CC1CC=C(c2nccn3ncc(-c4ccc(OCCCN5CCCCC5)cc4)c23)CC1] | 4-(3-(4-(3-(piperidin-1-yl)propoxy)phenyl)pyrazolo[1,5-a]pyrazin-4-yl)cyclohex-3-ene-1-carbonitrile | 442.3 |

TABLE 1-continued

| P Number | Structure | Name | MS |
|---|---|---|---|
| P-0087 | 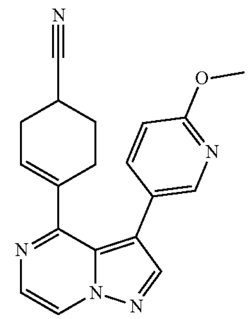 [SMILES: COc1ccc(-c2cnn3ccnc(C4=CCC(C#N)CC4)c23)cn1] | 4-(3-(6-methoxypyridin-3-yl)pyrazolo[1,5-a]pyrazin-4-yl)cyclohex-3-ene-1-carbonitrile | 332.4 |
| P-0088 | 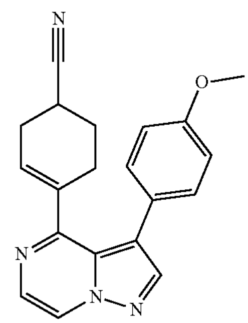 [SMILES: COc1ccc(-c2cnn3ccnc(C4=CCC(C#N)CC4)c23)cc1] | 4-(3-(4-methoxyphenyl)pyrazolo[1,5-a]pyrazin-4-yl)cyclohex-3-ene-1-carbonitrile | |
| P-0089 | 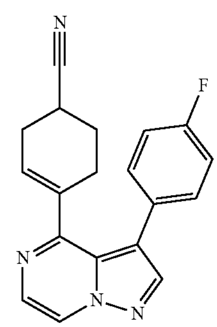 [SMILES: N#CC1CC=C(c2nccn3ncc(-c4ccc(F)cc4)c23)CC1] | 4-(3-(4-fluorophenyl)pyrazolo[1,5-a]pyrazin-4-yl)cyclohex-3-ene-1-carbonitrile | 318.9 |
| P-0090 | 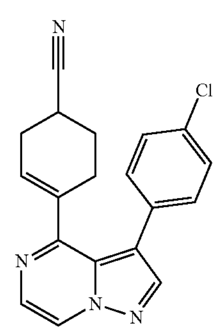 [SMILES: N#CC1CC=C(c2nccn3ncc(-c4ccc(Cl)cc4)c23)CC1] | 4-(3-(4-chlorophenyl)pyrazolo[1,5-a]pyrazin-4-yl)cyclohex-3-ene-1-carbonitrile | 335.1 |

TABLE 1-continued

| P Number | Structure | Name | MS |
|---|---|---|---|
| P-0091 | 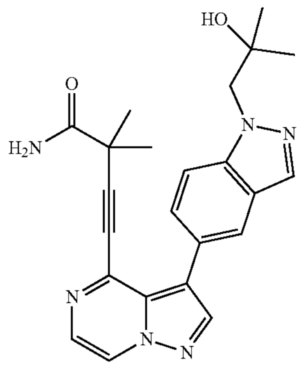 [SMILES: CC(C)(O)Cn1ncc2cc(-c3cnn4ccnc(C#CC(C)(C)C(N)=O)c34)ccc21] | 4-(3-(1-(2-hydroxy-2-methylpropyl)-1H-indazol-5-yl)pyrazolo[1,5-a]pyrazin-4-yl)-2,2-dimethylbut-3-ynamide | 417.2 |
| P-0092 | 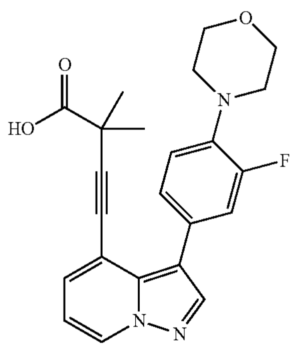 [SMILES: CC(C)(C#Cc1cccn2ncc(-c3ccc(N4CCOCC4)c(F)c3)c12)C(=O)O] | 4-(3-(3-fluoro-4-morpholinophenyl)pyrazolo[1,5-a]pyridin-4-yl)-2,2-dimethylbut-3-ynoic acid | 408.5 |
| P-0093 | 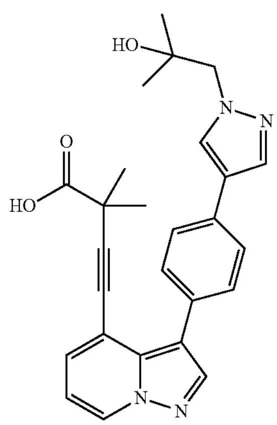 [SMILES: CC(C)(O)Cn1cc(-c2ccc(-c3cnn4cccc(C#CC(C)(C)C(=O)O)c34)cc2)cn1] | 4-(3-(4-(1-(2-hydroxy-2-methylpropyl)-1H-pyrazol-4-yl)phenyl)pyrazolo[1,5-a]pyridin-4-yl)-2,2-dimethylbut-3-ynoic acid | 443.2 |
| P-0094 | 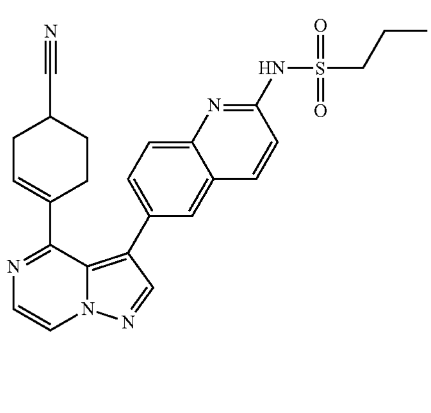 [SMILES: CCCS(=O)(=O)Nc1ccc2cc(-c3cnn4ccnc(C5=CCC(C#N)CC5)c34)ccc2n1] | N-(6-(4-(4-cyanocyclohex-1-en-1-yl)pyrazolo[1,5-a]pyrazin-3-yl)quinolin-2-yl)propane-1-sulfonamide | 473.6 |

TABLE 1-continued

| P Number | Structure | Name | MS |
|---|---|---|---|
| P-0095 | 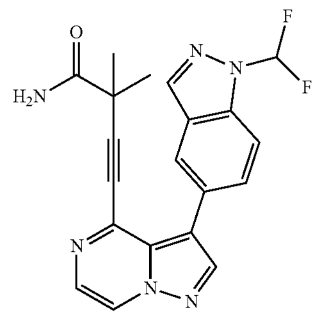 [SMILES: CC(C)(C#Cc1nccn2ncc(-c3ccc4c(cnn4C(F)F)c3)c12)C(N)=O] | 4-(3-(1-(difluoromethyl)-1H-indazol-5-yl)pyrazolo[1,5-a]pyrazin-4-yl)-2,2-dimethylbut-3-ynamide | 395.0 |
| P-0096 | 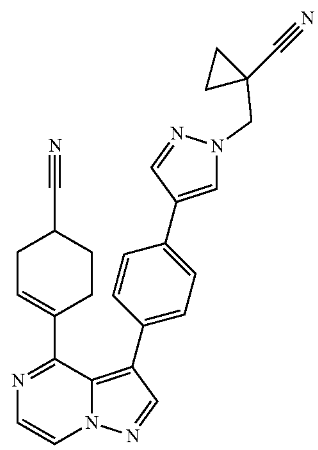 [SMILES: N#CC1CC=C(c2nccn3ncc(-c4ccc(-c5cnn(CC6(C#N)CC6)c5)cc4)c23)CC1] | 4-(3-(4-(1-((1-cyanocyclopropyl)methyl)-1H-pyrazol-4-yl)phenyl)pyrazolo[1,5-a]pyrazin-4-yl)cyclohex-3-ene-1-carbonitrile | 446.2 |
| P-0097 | 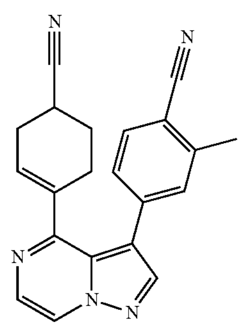 [SMILES: Cc1cc(-c2cnn3ccnc(C4=CCC(C#N)CC4)c23)ccc1C#N] | 4-(4-(4-cyanocyclohex-1-en-1-yl)pyrazolo[1,5-a]pyrazin-3-yl)-2-methylbenzonitrile | 340.1 |
| P-0098 | 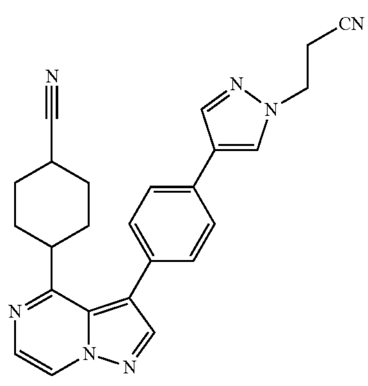 [SMILES: N#CCCn1cc(-c2ccc(-c3cnn4ccnc(C5CCC(C#N)CC5)c34)cc2)cn1] | 4-(3-(4-(1-(2-cyanoethyl)-1H-pyrazol-4-yl)phenyl)pyrazolo[1,5-a]pyrazin-4-yl)cyclohexane-1-carbonitrile | 422.6 |

TABLE 1-continued

| P Number | Structure | Name | MS |
|---|---|---|---|
| P-0099 | 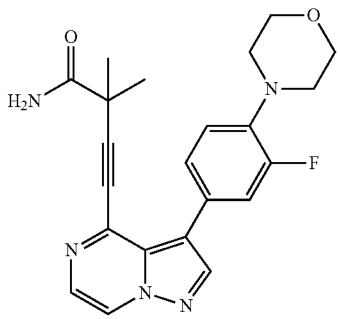 [SMILES: CC(C)(C#Cc1nccn2ncc(-c3ccc(N4CCOCC4)c(F)c3)c12)C(N)=O] | 4-(3-(3-fluoro-4-morpholinophenyl)pyrazolo[1,5-a]pyrazin-4-yl)-2,2-dimethylbut-3-ynamide | 408.2 |
| P-0100 | 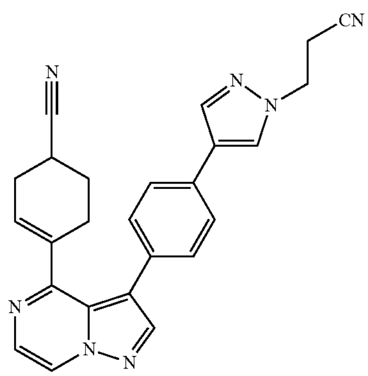 [SMILES: N#CCCn1cc(-c2ccc(-c3cnn4ccnc(C5=CCC(C#N)CC5)c34)cc2)cn1] | 4-(3-(4-(1-(2-cyanoethyl)-1H-pyrazol-4-yl)phenyl)pyrazolo[1,5-a]pyrazin-4-yl)cyclohex-3-ene-1-carbonitrile | 420.6 |
| P-0101 | 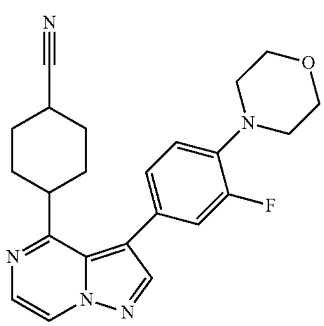 [SMILES: N#CC1CCC(c2nccn3ncc(-c4ccc(N5CCOCC5)c(F)c4)c23)CC1] | 4-(3-(3-fluoro-4-morpholinophenyl)pyrazolo[1,5-a]pyrazin-4-yl)cyclohexane-1-carbonitrile | 406.2 |
| P-0102 | 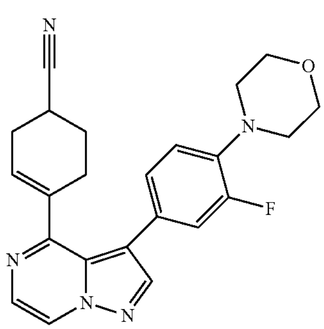 [SMILES: N#CC1CC=C(c2nccn3ncc(-c4ccc(N5CCOCC5)c(F)c4)c23)CC1] | 4-(3-(3-fluoro-4-morpholinophenyl)pyrazolo[1,5-a]pyrazin-4-yl)cyclohex-3-ene-1-carbonitrile | 404.5 |

TABLE 1-continued

| P Number | Structure | Name | MS |
|---|---|---|---|
| P-0103 | 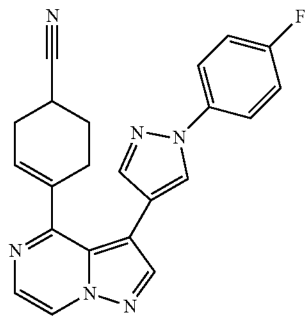 [SMILES: N#CC1CC=C(c2nccn3ncc(-c4cnn(-c5ccc(F)cc5)c4)c23)CC1] | 4-(3-(1-(4-fluorophenyl)-1H-pyrazol-4-yl)pyrazolo[1,5-a]pyrazin-4-yl)cyclohex-3-ene-1-carbonitrile | 385.1 |
| P-0104 | 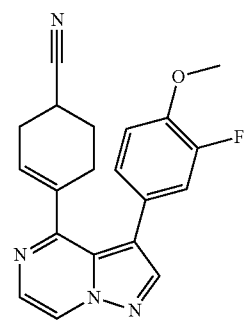 [SMILES: COc1ccc(-c2cnn3ccnc(C4=CCC(C#N)CC4)c23)cc1F] | 4-(3-(3-fluoro-4-methoxyphenyl)pyrazolo[1,5-a]pyrazin-4-yl)cyclohex-3-ene-1-carbonitrile | 349.4 |
| P-0105 | 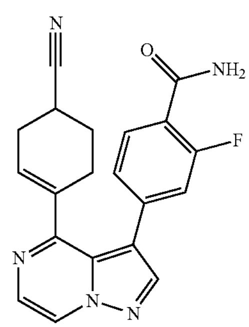 [SMILES: N#CC1CC=C(c2nccn3ncc(-c4ccc(C(N)=O)c(F)c4)c23)CC1] | 4-(4-(4-cyanocyclohex-1-en-1-yl)pyrazolo[1,5-a]pyrazin-3-yl)-2-fluorobenzamide | 361.9 |
| P-0106 | 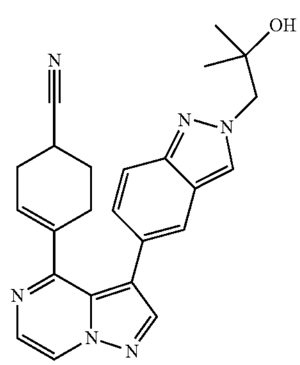 [SMILES: CC(C)(O)Cn1cc2cc(-c3cnn4ccnc(C5=CCC(C#N)CC5)c34)ccc2n1] | 4-(3-(2-(2-hydroxy-2-methylpropyl)-2H-indazol-5-yl)pyrazolo[1,5-a]pyrazin-4-yl)cyclohex-3-ene-1-carbonitrile | 413.1 |

TABLE 1-continued

| P Number | Structure | Name | MS |
|---|---|---|---|
| P-0107 | 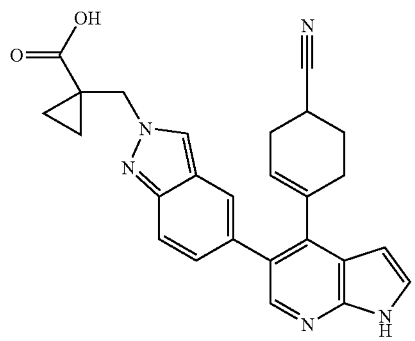 [SMILES: N#CC1CC=C(c2c(-c3ccc4nn(CC5(C(=O)O)CC5)cc4c3)cnc3[nH]ccc23)CC1] | 1-((5-(4-(4-cyanocyclohex-1-en-1-yl)-1H-pyrrolo[2,3-b]pyridin-5-yl)-2H-indazol-2-yl)methyl)cyclopropane-1-carboxylic acid | 438.2 |
| P-0108 | 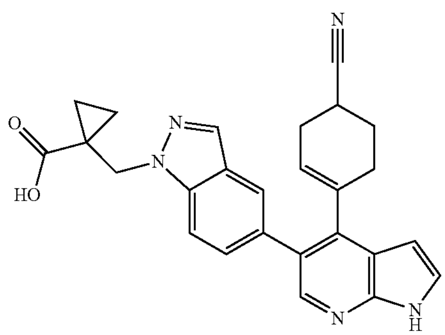 [SMILES: N#CC1CC=C(c2c(-c3ccc4c(cnn4CC4(C(=O)O)CC4)c3)cnc3[nH]ccc23)CC1] | 1-((5-(4-(4-cyanocyclohex-1-en-1-yl)-1H-pyrrolo[2,3-b]pyridin-5-yl)-1H-indazol-1-yl)methyl)cyclopropane-1-carboxylic acid | 438.1 |
| P-0109 | 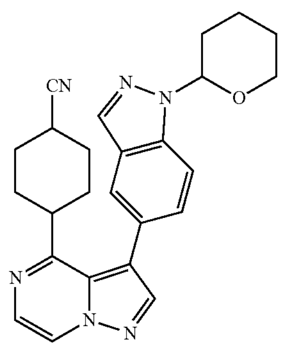 [SMILES: N#CC1CCC(c2nccn3ncc(-c4ccc5c(cnn5C5CCCCO5)c4)c23)CC1] | 4-(3-(1-(tetrahydro-2H-pyran-2-yl)-1H-indazol-5-yl)pyrazolo[1,5-a]pyrazin-4-yl)cyclohexane-1-carbonitrile | 427.6 |
| P-0110 | 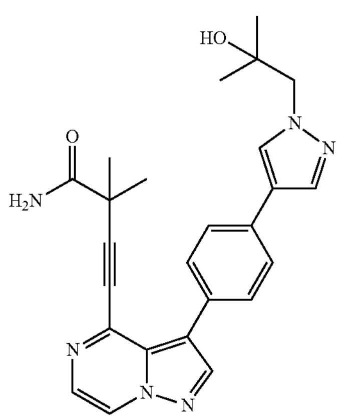 [SMILES: CC(C)(O)Cn1cc(-c2ccc(-c3cnn4ccnc(C#CC(C)(C)C(N)=O)c34)cc2)cn1] | 4-(3-(4-(1-(2-hydroxy-2-methylpropyl)-1H-pyrazol-4-yl)phenyl)pyrazolo[1,5-a]pyrazin-4-yl)-2,2-dimethylbut-3-ynamide | 443.6 |

TABLE 1-continued

| P Number | Structure | Name | MS |
|---|---|---|---|
| P-0111 | 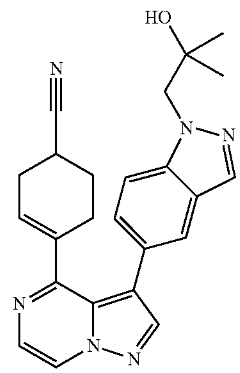 [SMILES: CC(C)(O)Cn1ncc2cc(-c3cnn4ccnc(C5=CCC(C#N)CC5)c34)ccc21] | 4-(3-(1-(2-hydroxy-2-methylpropyl)-1H-indazol-5-yl)pyrazolo[1,5-a]pyrazin-4-yl)cyclohex-3-ene-1-carbonitrile | 413.1 |
| P-0112 | 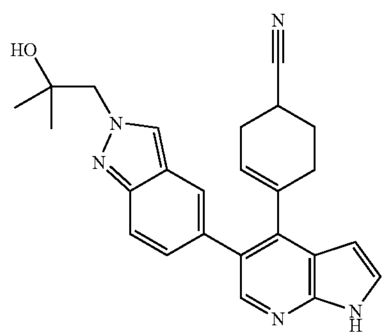 [SMILES: CC(C)(O)Cn1cc2cc(-c3cnc4[nH]ccc4c3C3=CCC(C#N)CC3)ccc2n1] | 4-(5-(2-(2-hydroxy-2-methylpropyl)-2H-indazol-5-yl)-1H-pyrrolo[2,3-b]pyridin-4-yl)cyclohex-3-ene-1-carbonitrile | 412.1 |
| P-0113 | 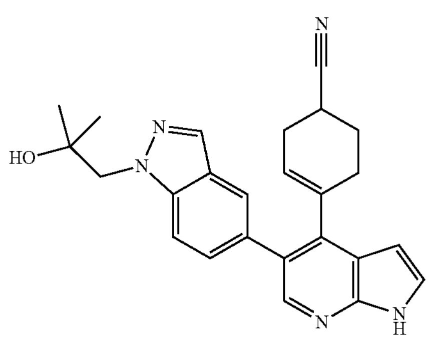 [SMILES: CC(C)(O)Cn1ncc2cc(-c3cnc4[nH]ccc4c3C3=CCC(C#N)CC3)ccc21] | 4-(5-(1-hydroxy-2-methylpropyl)-1H-indazol-5-yl)-1H-pyrrolo[2,3-b]pyridin-4-yl)cyclohex-3-ene-1-carbonitrile | 412.1 |
| P-0114 | 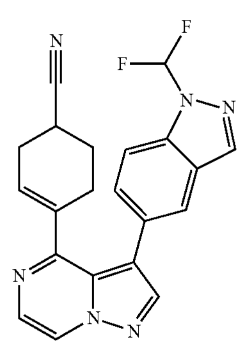 [SMILES: N#CC1CC=C(c2nccn3ncc(-c4ccc5c(cnn5C(F)F)c4)c23)CC1] | 4-(3-(1-(difluoromethyl)-1H-indazol-5-yl)pyrazolo[1,5-a]pyrazin-4-yl)cyclohex-3-ene-1-carbonitrile | 391.5 |

TABLE 1-continued

| P Number | Structure | Name | MS |
|---|---|---|---|
| P-0115 | 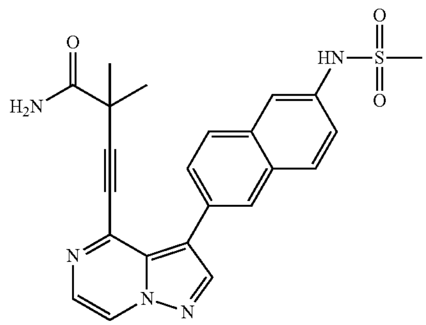 [SMILES: CC(C)(C#Cc1nccn2ncc(-c3ccc4cc(NS(C)(=O)=O)ccc4c3)c12)C(N)=O] | 2,2-dimethyl-4-(3-(6-(methylsulfonamido)naphthalen-2-yl)pyrazolo[1,5-a]pyrazin-4-yl)but-3-ynamide | 448.1 |
| P-0116 | 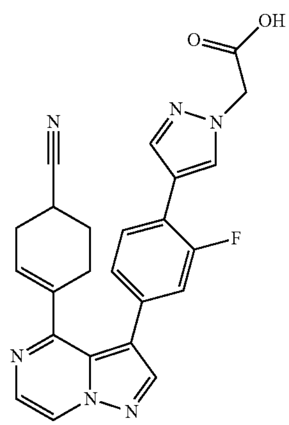 [SMILES: N#CC1CC=C(c2nccn3ncc(-c4ccc(-c5cnn(CC(=O)O)c5)c(F)c4)c23)CC1] | 2-(4-(4-(4-(4-cyanocyclohex-1-en-1-yl)pyrazolo[1,5-a]pyrazin-3-yl)-2-fluorophenyl)-1H-pyrazol-1-yl)acetic acid | 443.1 |
| P-0117 | 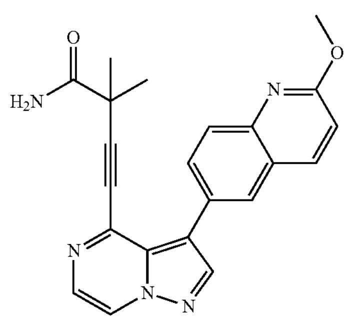 [SMILES: COc1ccc2cc(-c3cnn4ccnc(C#CC(C)(C)C(N)=O)c34)ccc2n1] | 4-(3-(2-methoxyquinolin-6-yl)pyrazolo[1,5-a]pyrazin-4-yl)-2,2-dimethylbut-3-ynamide | 386.5 |
| P-0118 | 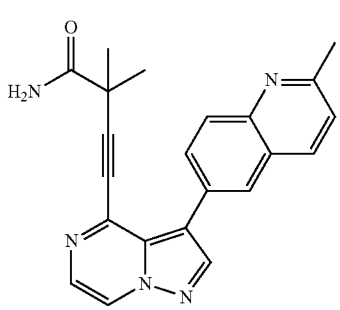 [SMILES: Cc1ccc2cc(-c3cnn4ccnc(C#CC(C)(C)C(N)=O)c34)ccc2n1] | 2,2-dimethyl-4-(3-(2-methylquinolin-6-yl)pyrazolo[1,5-a]pyrazin-4-yl)but-3-ynamide | 370.5 |

TABLE 1-continued

| P Number | Structure | Name | MS |
|---|---|---|---|
| P-0119 | 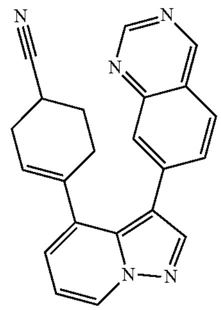 [SMILES: N#CC1CC=C(c2cccn3ncc(-c4ccc5cncnc5c4)c23)CC1] | 4-(3-(quinazolin-7-yl)pyrazolo[1,5-a]pyridin-4-yl)cyclohex-3-ene-1-carbonitrile | 352.2 |
| P-0120 | 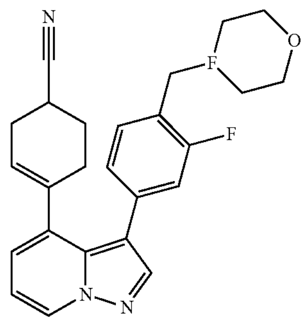 | 4-(3-(3-fluoro-4-(morpholinomethyl)phenyl)pyrazolo[1,5-a]pyridin-4-yl)cyclohex-3-ene-1-carbonitrile | 417.4 |
| P-0121 | 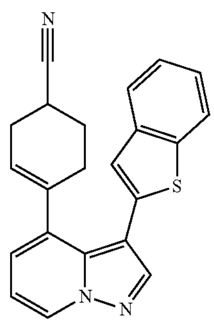 [SMILES: N#CC1CC=C(c2cccn3ncc(-c4cc5ccccc5s4)c23)CC1] | 4-(3-(benzo[b]thiophen-2-yl)pyrazolo[1,5-a]pyridin-4-yl)cyclohex-3-ene-1-carbonitrile | 356.1 |
| P-0122 | 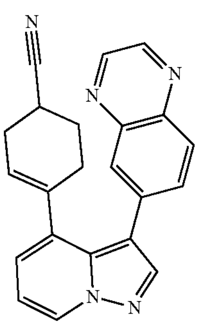 [SMILES: N#CC1CC=C(c2cccn3ncc(-c4ccc5nccnc5c4)c23)CC1] | 4-(3-(quinoxalin-6-yl)pyrazolo[1,5-a]pyridin-4-yl)cyclohex-3-ene-1-carbonitrile | 352.2 |
| P-0123 | 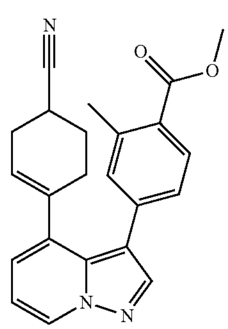 [SMILES: COC(=O)c1ccc(-c2cnn3cccc(C4=CCC(C#N)CC4)c23)cc1C] | methyl 4-(4-(4-cyanocyclohex-1-en-1-yl)pyrazolo[1,5-a]pyridin-3-yl)-2-methylbenzoate | 372.0 |

TABLE 1-continued

| P Number | Structure | Name | MS |
|---|---|---|---|
| P-0124 | 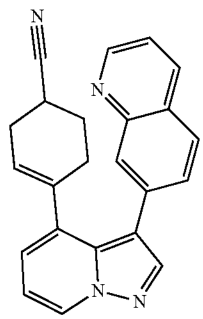 [SMILES: N#CC1CC=C(c2cccn3ncc(-c4ccc5cccnc5c4)c23)CC1] | 4-(3-(quinolin-7-yl)pyrazolo[1,5-a]pyridin-4-yl)cyclohex-3-ene-1-carbonitrile | 351.0 |
| P-0125 | 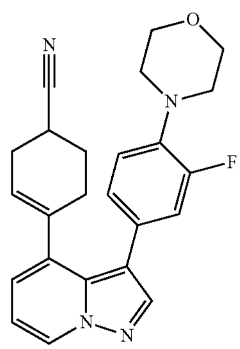 [SMILES: N#CC1CC=C(c2cccn3ncc(-c4ccc(N5CCOCC5)c(F)c4)c23)CC1] | 4-(3-(3-fluoro-4-morpholinophenyl)pyrazolo[1,5-a]pyridin-4-yl)cyclohex-3-ene-1-carbonitrile | 403.3 |
| P-0126 | 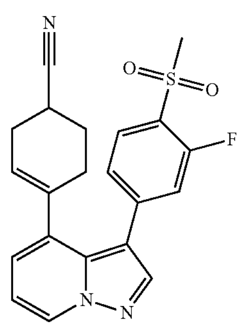 [SMILES: CS(=O)(=O)c1ccc(-c2cnn3cccc(C4=CCC(C#N)CC4)c23)cc1F] | 4-(3-(3-fluoro-4-(methylsulfonyl)phenyl)pyrazolo[1,5-a]pyridin-4-yl)cyclohex-3-ene-1-carbonitrile | 396.4 |
| P-0127 | 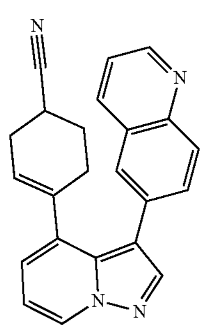 [SMILES: N#CC1CC=C(c2cccn3ncc(-c4ccc5ncccc5c4)c23)CC1] | 4-(3-(quinolin-6-yl)pyrazolo[1,5-a]pyridin-4-yl)cyclohex-3-ene-1-carbonitrile | 351.3 |

TABLE 1-continued

| P Number | Structure | Name | MS |
|---|---|---|---|
| P-0128 | 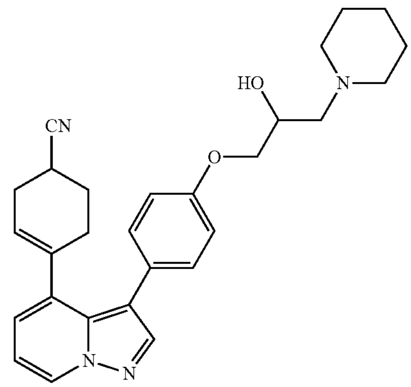 [SMILES: N#CC1CC=C(c2cccn3ncc(-c4ccc(OCC(O)CN5CCCCC5)cc4)c23)CC1] | 4-(3-(4-(2-hydroxy-3-(piperidin-1-yl)propoxy)phenyl)pyrazolo[1,5-a]pyridin-4-yl)cyclohex-3-ene-1-carbonitrile | 457.3 |
| P-0129 | 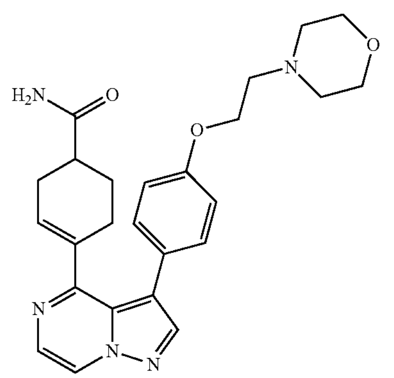 [SMILES: NC(=O)C1CC=C(c2nccn3ncc(-c4ccc(OCCN5CCOCC5)cc4)c23)CC1] | 4-(3-(4-(2-morpholino-ethoxy)phenyl)pyrazolo[1,5-a]pyrazin-4-yl)cyclohex-3-ene-1-carboxamide | 448.2 |
| P-0130 | 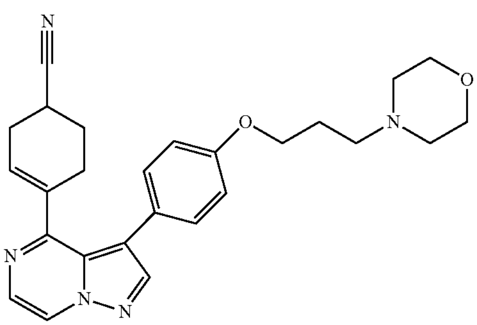 [SMILES: N#CC1CC=C(c2nccn3ncc(-c4ccc(OCCCN5CCOCC5)cc4)c23)CC1] | 4-(3-(4-(3-morpholino-propoxy)phenyl)pyrazolo[1,5-a]pyrazin-4-yl)cyclohex-3-ene-1-carbonitrile | 444.2 |
| P-0131 | 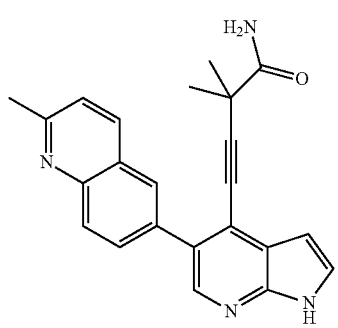 [SMILES: Cc1ccc2cc(-c3cnc4[nH]ccc4c3C#CC(C)(C)C(N)=O)ccc2n1] | 2,2-dimethyl-4-(5-(2-methylquinolin-6-yl)-1H-pyrrolo[2,3-b]pyridin-4-yl)but-3-ynamide | 369.0 |

TABLE 1-continued

| P Number | Structure | Name | MS |
|---|---|---|---|
| P-0132 | 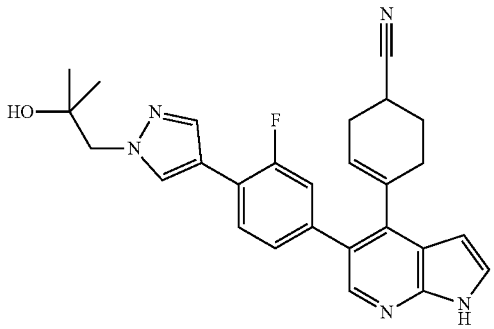 [SMILES: CC(C)(O)Cn1cc(-c2ccc(-c3cnc4[nH]ccc4c3C3=CCC(C#N)CC3)cc2F)cn1] | 4-(5-(3-fluoro-4-(1-(2-hydroxy-2-methylpropyl)-1H-pyrazol-4-yl)phenyl)-1H-pyrrolo[2,3-b]pyridin-4-yl)cyclohex-3-ene-1-carbonitrile | 456.5 |
| P-0133 | 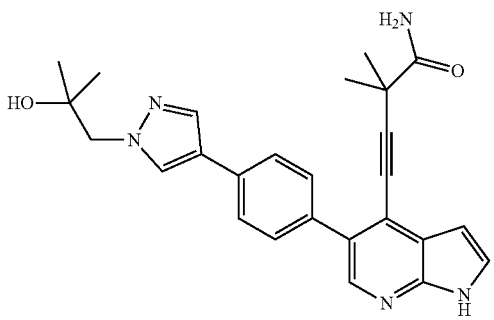 [SMILES: CC(C)(O)Cn1cc(-c2ccc(-c3cnc4[nH]ccc4c3C#CC(C)(C)C(N)=O)cc2)cn1] | 4-(5-(4-(1-(2-hydroxy-2-methylpropyl)-1H-pyrazol-4-yl)phenyl)-1H-pyrrolo[2,3-b]pyridin-4-yl)-2,2-dimethylbut-3-ynamide | 442.1 |
| P-0134 | 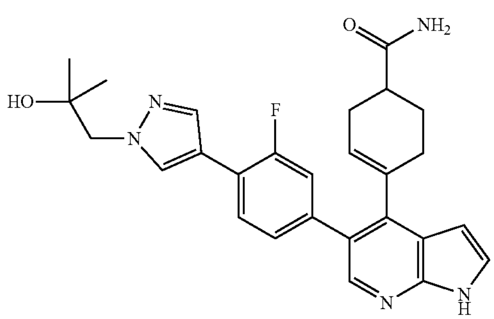 [SMILES: CC(C)(O)Cn1cc(-c2ccc(-c3cnc4[nH]ccc4c3C3=CCC(C(N)=O)CC3)cc2F)cn1] | 4-(5-(3-fluoro-4-(1-(2-hydroxy-2-methylpropyl)-1H-pyrazol-4-yl)phenyl)-1H-pyrrolo[2,3-b]pyridin-4-yl)cyclohex-3-ene-1-carboxamide | 474.2 |
| P-0135 | 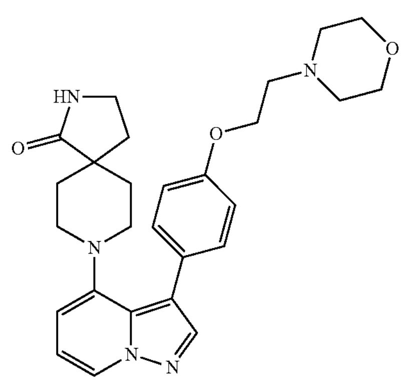 [SMILES: O=C1NCCC12CCN(c1cccn3ncc(-c4ccc(OCCN5CCOCC5)cc4)c13)CC2] | 8-(3-(4-(2-morpholinoethoxy)phenyl)pyrazolo[1,5-a]pyridin-4-yl)-2,8-diazaspiro[4.5]decan-1-one | 476.6 |

TABLE 1-continued

| P Number | Structure | Name | MS |
|---|---|---|---|
| P-0136 | 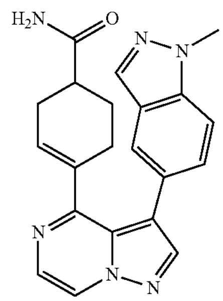 [SMILES: Cn1ncc2cc(-c3cnn4ccnc(C5=CCC(C(N)=O)CC5)c34)ccc21] | 4-(3-(1-methyl-1H-indazol-5-yl)pyrazolo[1,5-a]pyrazin-4-yl)cyclohex-3-ene-1-carboxamide | 373.5 |
| P-0137 | 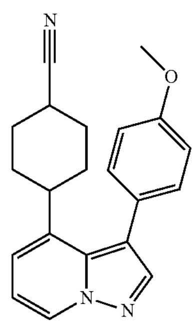 [SMILES: COc1ccc(-c2cnn3cccc(C4CCC(C#N)CC4)c23)cc1] | 4-(3-(4-methoxyphenyl)pyrazolo[1,5-a]pyridin-4-yl)cyclohexane-1-carbonitrile | 332.4 |
| P-0138 | 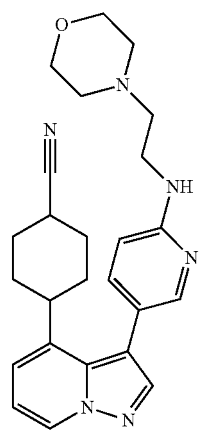 [SMILES: N#CC1CCC(c2cccn3ncc(-c4ccc(NCCN5CCOCC5)nc4)c23)CC1] | 4-(3-(6-((2-morpholinoethyl)amino)pyridin-3-yl)pyrazolo[1,5-a]pyridin-4-yl)cyclohexane-1-carbonitrile | 431.2 |
| P-0139 | 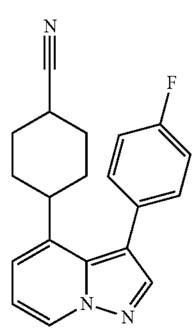 [SMILES: N#CC1CCC(c2cccn3ncc(-c4ccc(F)cc4)c23)CC1] | 4-(3-(4-fluorophenyl)pyrazolo[1,5-a]pyridin-4-yl)cyclohexane-1-carbonitrile | 320.1 |

TABLE 1-continued

| P Number | Structure | Name | MS |
|---|---|---|---|
| P-0140 | 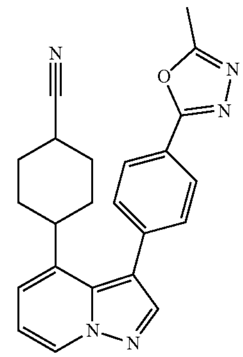 [SMILES: Cc1nnc(-c2ccc(-c3cnn4cccc(C5CCC(C#N)CC5)c34)cc2)o1] | 4-(3-(4-(5-methyl-1,3,4-oxadiazol-2-yl)phenyl)pyrazolo[1,5-a]pyridin-4-yl)cyclohexane-1-carbonitrile | 384.0 |
| P-0141 | 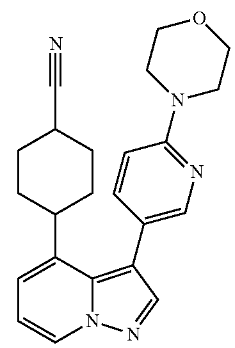 [SMILES: N#CC1CCC(c2cccn3ncc(-c4ccc(N5CCOCC5)nc4)c23)CC1] | 4-(3-(6-morpholinopyridin-3-yl)pyrazolo[1,5-a]pyridin-4-yl)cyclohexane-1-carbonitrile | 388.2 |
| P-0142 | 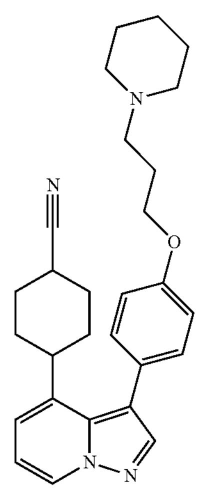 [SMILES: N#CC1CCC(c2cccn3ncc(-c4ccc(OCCCN5CCCCC5)cc4)c23)CC1] | 4-(3-(4-(3-(piperidin-1-yl)propoxy)phenyl)pyrazolo[1,5-a]pyridin-4-yl)cyclohexane-1-carbonitrile | 443.2 |
| P-0143 | 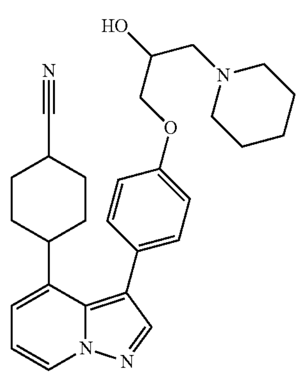 [SMILES: N#CC1CCC(c2cccn3ncc(-c4ccc(OCC(O)CN5CCCCC5)cc4)c23)CC1] | 4-(3-(4-(2-hydroxy-3-(piperidin-1-yl)propoxy)phenyl)pyrazolo[1,5-a]pyridin-4-yl)cyclohexane-1-carbonitrile | 459.4 |

TABLE 1-continued

| P Number | Structure | Name | MS |
|---|---|---|---|
| P-0144 | 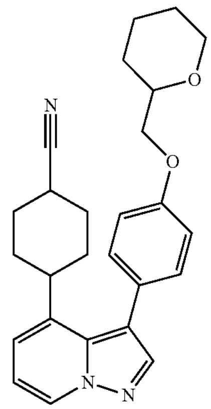 [SMILES: N#CC1CCC(c2cccn3ncc(-c4ccc(OCC5CCCCO5)cc4)c23)CC1] | 4-(3-(4-((tetrahydro-2H-pyran-2-yl)methoxy)phenyl)pyrazolo[1,5-a]pyridin-4-yl)cyclohexane-1-carbonitrile | 416.5 |
| P-0145 | 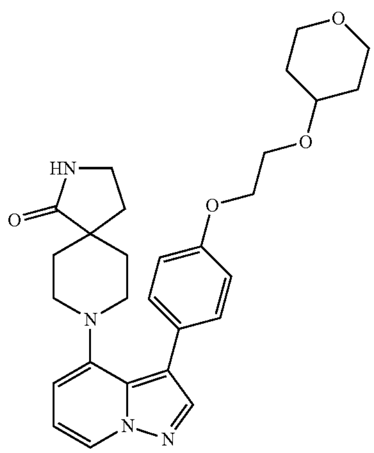 [SMILES: O=C1NCCC12CCN(c1cccn3ncc(-c4ccc(OCCOC5CCOCC5)cc4)c13)CC2] | 8-(3-(4-(2-((tetrahydro-2H-pyran-4-yl)oxy)ethoxy)phenyl)pyrazolo[1,5-a]pyridin-4-yl)-2,8-diazaspiro[4.5]decan-1-one | 491.6 |
| P-0146 | 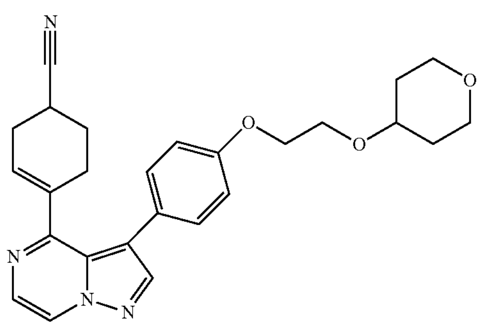 [SMILES: N#CC1CC=C(c2nccn3ncc(-c4ccc(OCCOC5CCOCC5)cc4)c23)CC1] | 4-(3-(4-(2-((tetrahydro-2H-pyran-4-yl)oxy)ethoxy)phenyl)pyrazolo[1,5-a]pyrazin-4-yl)cyclohex-3-ene-1-carbonitrile | 445.6 |
| P-0147 | 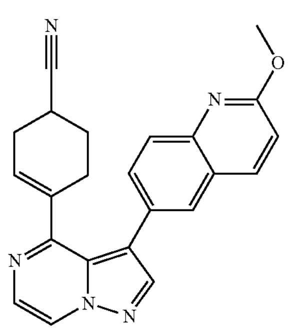 [SMILES: COc1ccc2cc(-c3cnn4ccnc(C5=CCC(C#N)CC5)c34)ccc2n1] | 4-(3-(2-methoxyquinolin-6-yl)pyrazolo[1,5-a]pyrazin-4-yl)cyclohex-3-ene-1-carbonitrile | 382.5 |

TABLE 1-continued

| P Number | Structure | Name | MS |
|---|---|---|---|
| P-0148 | 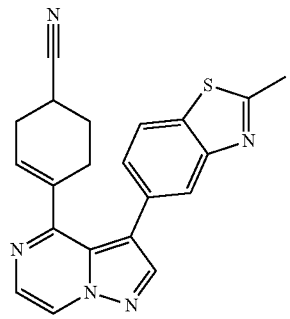 [SMILES: Cc1nc2cc(-c3cnn4ccnc(C5=CCC(C#N)CC5)c34)ccc2s1] | 4-(3-(2-methylbenzo[d]thiazol-5-yl)pyrazolo[1,5-a]pyrazin-4-yl)cyclohex-3-ene-1-carbonitrile | 372.1 |
| P-0149 | 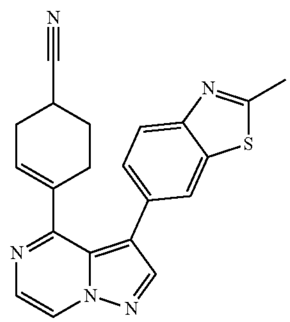 [SMILES: Cc1nc2ccc(-c3cnn4ccnc(C5=CCC(C#N)CC5)c34)cc2s1] | 4-(3-(2-methylbenzo[d]thiazol-6-yl)pyrazolo[1,5-a]pyrazin-4-yl)cyclohex-3-ene-1-carbonitrile | 372.5 |
| P-0150 | 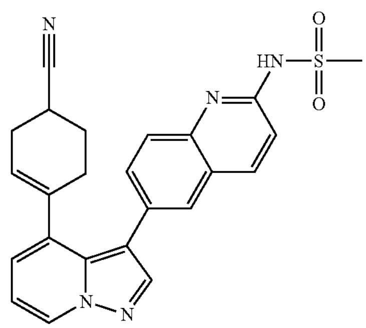 [SMILES: CS(=O)(=O)Nc1ccc2cc(-c3cnn4cccc(C5=CCC(C#N)CC5)c34)ccc2n1] | N-(6-(4-(4-cyanocyclohex-1-en-1-yl)pyrazolo[1,5-a]pyridin-3-yl)quinolin-2-yl)methanesulfonamide | 444.1 |
| P-0151 | 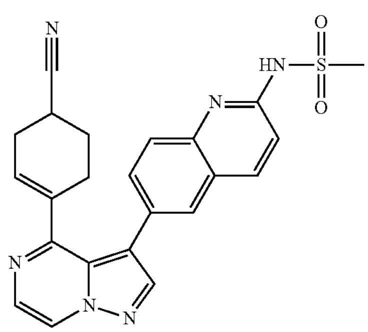 [SMILES: CS(=O)(=O)Nc1ccc2cc(-c3cnn4ccnc(C5=CCC(C#N)CC5)c34)ccc2n1] | N-(6-(4-(4-cyanocyclohex-1-ene-1-yl)pyrazolo[1,5-a]pyrazin-3-yl)quinolin-2-yl)methanesulfonamide | 445.5 |
| P-0152 | 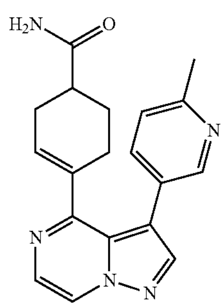 [SMILES: Cc1ccc(-c2cnn3ccnc(C4=CCC(C(N)=O)CC4)c23)cn1] | 4-(3-(6-methylpyridin-3-yl)pyrazolo[1,5-a]pyrazin-4-yl)cyclohex-3-ene-1-carboxamide | 334.2 |

TABLE 1-continued

| P Number | Structure | Name | MS |
|---|---|---|---|
| P-0153 | 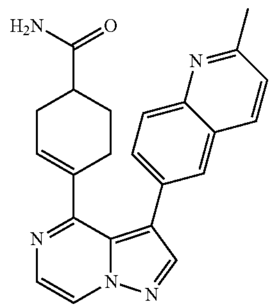 [SMILES: Cc1ccc2cc(-c3cnn4ccnc(C5=CCC(C(N)=O)CC5)c34)ccc2n1] | 4-(3-(2-methylquinolin-6-yl)pyrazolo[1,5-a]pyrazin-4-yl)cyclohex-3-ene-1-carboxamide | 384.2 |
| P-0154 | 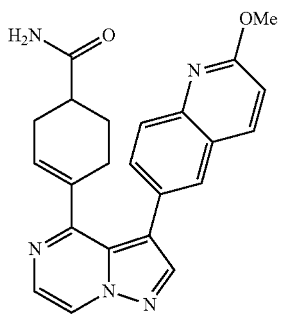 [SMILES: COc1ccc2cc(-c3cnn4ccnc(C5=CCC(C(N)=O)CC5)c34)ccc2n1] | 4-(3-(2-methoxyquinolin-6-yl)pyrazolo[1,5-a]pyrazin-4-yl)cyclohex-3-ene-1-carboxamide | 400.5 |
| P-0155 | 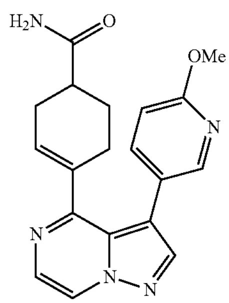 [SMILES: COc1ccc(-c2cnn3ccnc(C4=CCC(C(N)=O)CC4)c23)cn1] | 4-(3-(6-methoxypyridin-3-yl)pyrazolo[1,5-a]pyrazin-4-yl)cyclohex-3-ene-1-carboxamide | 350.5 |
| P-0156 | 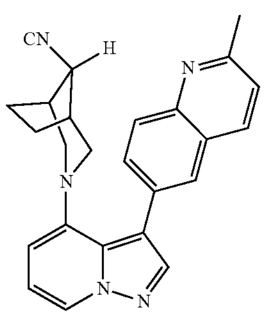 | 3-(3-(2-methylquinolin-6-yl)pyrazolo[1,5-a]pyridin-4-yl)-3-azabicyclo[3.2.1]octane-8-carbonitrile | 394.1 |
| P-0157 | 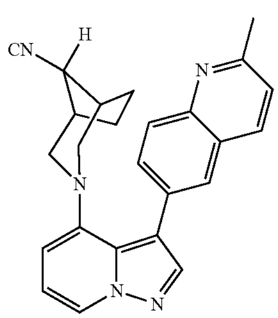 | 3-(3-(2-methylquinolin-6-yl)pyrazolo[1,5-a]pyridin-4-yl)-3-azabicyclo[3.2.1]octane-8-carbonitrile | 394.1 |

TABLE 1-continued

| P Number | Structure | Name | MS |
|---|---|---|---|
| P-0158 | 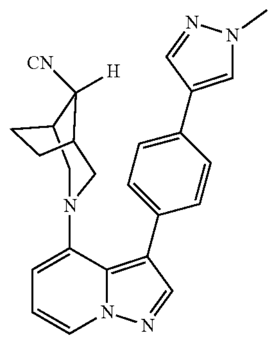 | 3-(3-(4-(1-methyl-1H-pyrazol-4-yl)phenyl)pyrazolo[1,5-a]pyridin-4-yl)-3-azabicyclo[3.2.1]octane-8-carbonitrile | 409.1 |
| P-0159 | 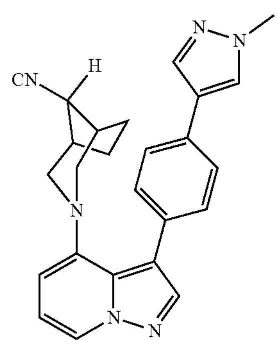 | 3-(3-(4-(1-methyl-1H-pyrazol-4-yl)phenyl)pyrazolo[1,5-a]pyridin-4-yl)-3-azabicyclo[3.2.1]octane-8-carbonitrile | 409.4 |
| P-0160 | 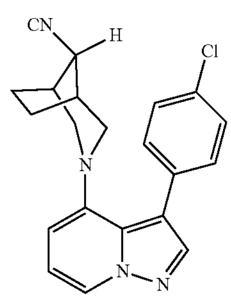 | 3-(3-(4-chlorophenyl)pyrazolo[1,5-a]pyridin-4-yl)-3-azabicyclo[3.2.1]octane-8-carbonitrile | 363.0 |
| P-0161 | 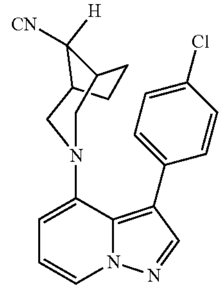 | 3-(3-(4-chlorophenyl)pyrazolo[1,5-a]pyridin-4-yl)-3-azabicyclo[3.2.1]octane-8-carbonitrile | 363.0 |

TABLE 1-continued

| P Number | Structure | Name | MS |
|---|---|---|---|
| P-0162 | 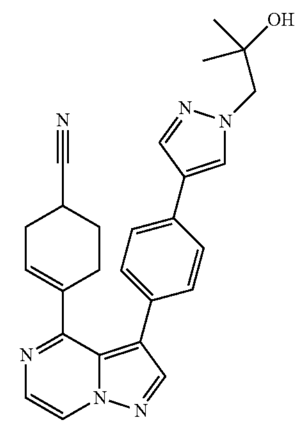 [SMILES: CC(C)(O)Cn1cc(-c2ccc(-c3cnn4ccnc(C5=CCC(C#N)CC5)c34)cc2)cn1] | 4-(3-(4-(1-(2-hydroxy-2-methylpropyl)-1H-pyrazol-4-yl)phenyl)pyrazolo[1,5-a]pyrazin-4-yl)cyclohex-3-ene-1-carbonitrile | 439.1 |
| P-0163 | 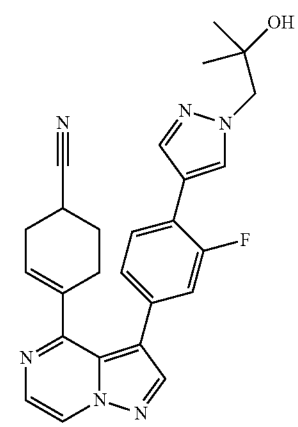 [SMILES: CC(C)(O)Cn1cc(-c2ccc(-c3cnn4ccnc(C5=CCC(C#N)CC5)c34)cc2F)cn1] | 4-(3-(3-fluoro-4-(1-(2-hydroxy-2-methylpropyl)-1H-pyrazol-4-yl)phenyl)pyrazolo[1,5-a]pyrazin-4-yl)cyclohex-3-ene-1-carbonitrile | 457.5 |
| P-0164 | 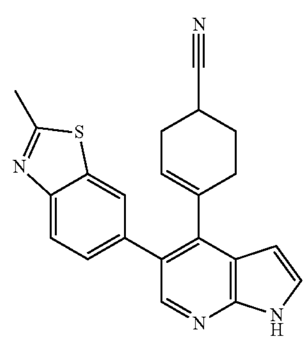 [SMILES: Cc1nc2ccc(-c3cnc4[nH]ccc4c3C3=CCC(C#N)CC3)cc2s1] | 4-(5-(2-methylbenzo[d]thiazol-6-yl)-1H-pyrrolo[2,3-b]pyridin-4-yl)cyclohex-3-ene-1-carbonitrile | 370.9 |
| P-0165 | 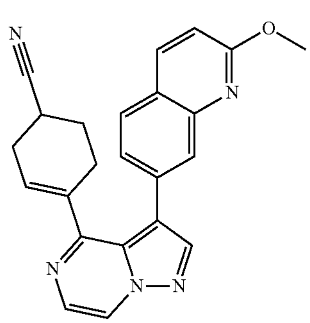 [SMILES: COc1ccc2ccc(-c3cnn4ccnc(C5=CCC(C#N)CC5)c34)cc2n1] | 4-(3-(2-methoxyquinolin-7-yl)pyrazolo[1,5-a]pyrazin-4-yl)cyclohex-3-ene-1-carbonitrile | 382.5 |

TABLE 1-continued

| P Number | Structure | Name | MS |
|---|---|---|---|
| P-0166 | 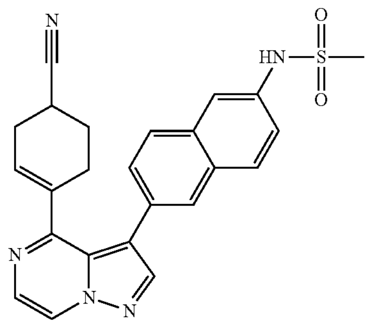 [SMILES: CS(=O)(=O)Nc1ccc2cc(-c3cnn4ccnc(C5=CCC(C#N)CC5)c34)ccc2c1] | N-(6-(4-(4-cyanocyclohex-1-en-1-yl)pyrazolo[1,5-a]pyrazin-3-yl)naphthalen-2-yl)methanesulfonamide | 444.1 |
| P-0167 | 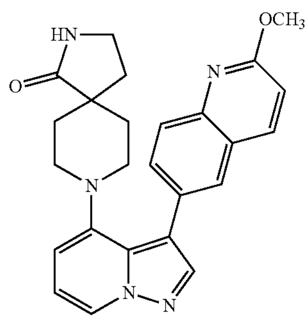 [SMILES: COc1ccc2cc(-c3cnn4cccc(N5CCC6(CCNC6=O)CC5)c34)ccc2n1] | 8-(3-(2-methoxyquinolin-6-yl)pyrazolo[1,5-a]pyridin-4-yl)-2,8-diazaspiro[4.5]decan-1-one | 428.2 |
| P-0168 | 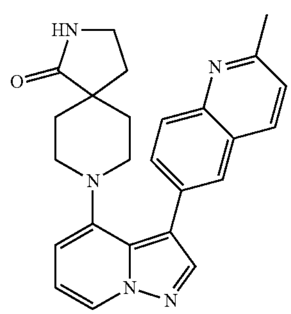 [SMILES: Cc1ccc2cc(-c3cnn4cccc(N5CCC6(CCNC6=O)CC5)c34)ccc2n1] | 8-(3-(2-methylquinolin-6-yl)pyrazolo[1,5-a]pyridin-4-yl)-2,8-diazaspiro[4.5]decan-1-one | 412.2 |
| P-0169 | 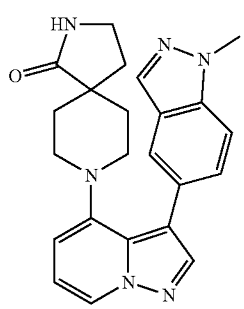 [SMILES: Cn1ncc2cc(-c3cnn4cccc(N5CCC6(CCNC6=O)CC5)c34)ccc21] | 8-(3-(1-methyl-1H-indazol-5-yl)pyrazolo[1,5-a]pyridin-4-yl)-2,8-diazaspiro[4.5]decan-1-one | 401.2 |
| P-0170 | 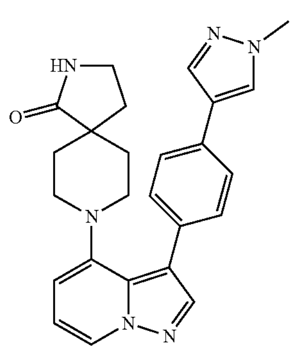 [SMILES: Cn1cc(-c2ccc(-c3cnn4cccc(N5CCC6(CCNC6=O)CC5)c34)cc2)cn1] | 8-(3-(4-(1-methyl-1H-pyrazol-4-yl)phenyl)pyrazolo[1,5-a]pyridin-4-yl)-2,8-diazaspiro[4.5]decan-1-one | 427.3 |

TABLE 1-continued

| P Number | Structure | Name | MS |
|---|---|---|---|
| P-0171 | 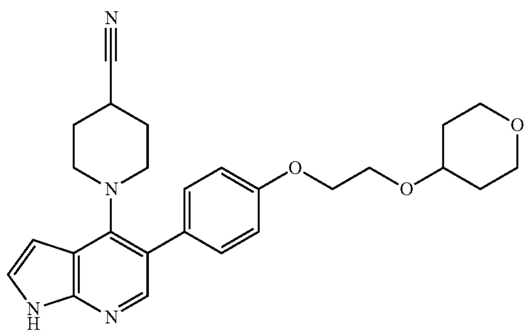 [SMILES: N#CC1CCN(c2c(-c3ccc(OCCOC4CCOCC4)cc3)cnc3[nH]ccc23)CC1] | 1-(5-(4-(2-((tetrahydro-2H-pyran-4-yl)oxy)ethoxy)phenyl-1H-pyrrolo[2,3-b]pyridin-4-yl)piperidine-4-carbonitrile | 447.6 |
| P-0172 | 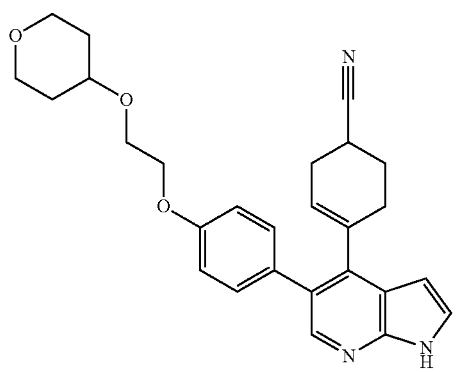 [SMILES: N#CC1CC=C(c2c(-c3ccc(OCCOC4CCOCC4)cc3)cnc3[nH]ccc23)CC1] | 4-(5-(4-(2-((tetrahydro-2H-pyran-4-yl)oxy)ethoxy)phenyl)-1H-pyrrolo[2,3-b]pyridin-4-yl)cyclohex-3-ene-1-carbonitrile | 444.2 |
| P-0173 | 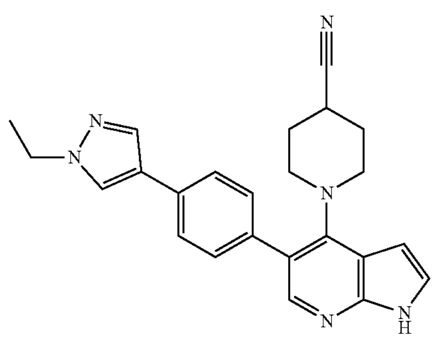 [SMILES: CCn1cc(-c2ccc(-c3cnc4[nH]ccc4c3N3CCC(C#N)CC3)cc2)cn1] | 1-(5-(4-(1-ethyl-1H-pyrazol-4-yl)phenyl)-1H-pyrrolo[2,3-b]pyridin-4-yl)piperidine-4-carbonitrile | 397.1 |
| P-0174 | 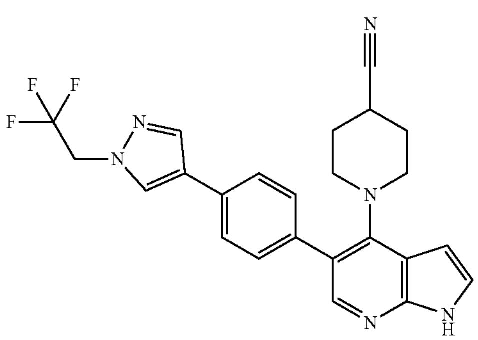 [SMILES: N#CC1CCN(c2c(-c3ccc(-c4cnn(CC(F)(F)F)c4)cc3)cnc3[nH]ccc23)CC1] | 1-(5-(4-(1-(2,2,2-trifluoroethyl)-1H-pyrazol-4-yl)phenyl)-1H-pyrrolo[2,3-b]pyridin-4-yl)piperidine-4-carbonitrile | 451.0 |

TABLE 1-continued

| P Number | Structure | Name | MS |
|---|---|---|---|
| P-0175 | 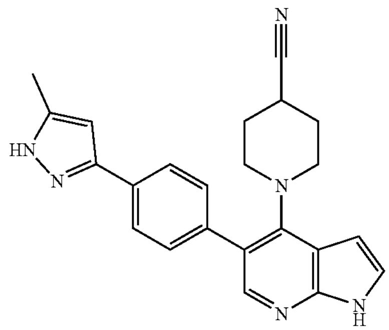 [SMILES: Cc1cc(-c2ccc(-c3cnc4[nH]ccc4c3N3CCC(C#N)CC3)cc2)n[nH]1] | 1-(5-(4-(5-methyl-1H-pyrazol-3-yl)phenyl)-1H-pyrrolo[2,3-b]pyridin-4-yl)piperidine-4-carbonitrile | 383.0 |
| P-0176 | 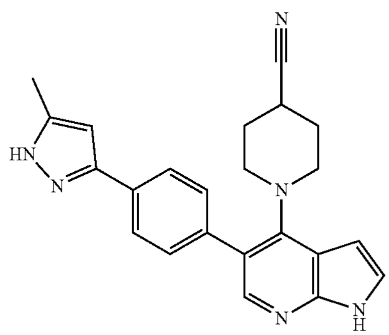 [SMILES: Cc1cc(-c2ccc(-c3cnc4[nH]ccc4c3N3CCC(C#N)CC3)cc2)n[nH]1] | 1-(5-(4-(5-methyl-1H-pyrazol-3-yl)phenyl)-1H-pyrrolo[2,3-b]pyridin-4-yl)piperidine-4-carbonitrile | 359.0 |
| P-0177 | 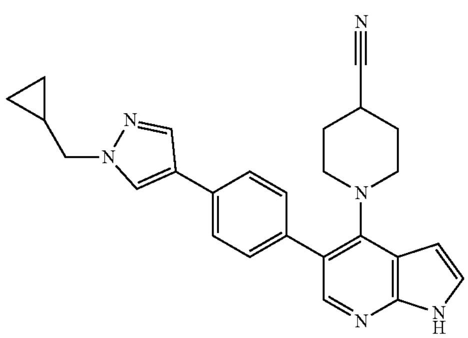 [SMILES: N#CC1CCN(c2c(-c3ccc(-c4cnn(CC5CC5)c4)cc3)cnc3[nH]ccc23)CC1] | 1-(5-(4-(1-(cyclopropylmethyl)-1H-pyrazol-4-yl)phenyl)-1H-pyrrolo[2,3-b]pyridin-4-yl)piperidine-4-carbonitrile | 423.1 |
| P-0178 | 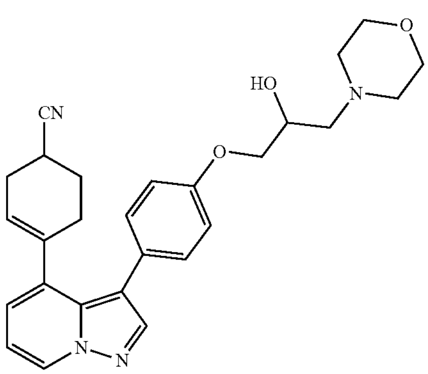 [SMILES: N#CC1CC=C(c2cccn3ncc(-c4ccc(OCC(O)CN5CCOCC5)cc4)c23)CC1] | 4-(3-(4-(2-hydroxy-3-morpholinopropoxy)phenyl)pyrazolo[1,5-a]pyridin-4-yl)cyclohex-3-ene-1-carbonitrile | 459.4 |

TABLE 1-continued

| P Number | Structure | Name | MS |
|---|---|---|---|
| P-0179 | 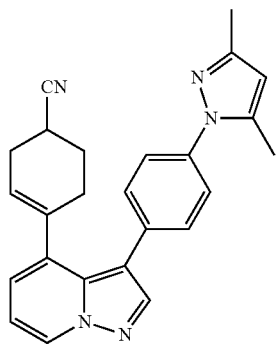 [SMILES: Cc1cc(C)n(-c2ccc(-c3cnn4cccc(C5=CCC(C#N)CC5)c34)cc2)n1] | 4-(3-(4-(3,5-dimethyl-1H-pyrazol-1-yl)phenyl)pyrazolo[1,5-a]pyridin-4-yl)cyclohex-3-ene-1-carbonitrile | 394.0 |
| P-0180 | 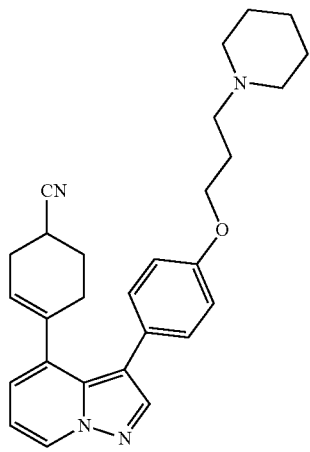 [SMILES: N#CC1CC=C(c2cccn3ncc(-c4ccc(OCCCN5CCCCC5)cc4)c23)CC1] | 4-(3-(4-(3-(piperidin-1-yl)propoxy)phenyl)pyrazolo[1,5-a]pyridin-4-yl)cyclohex-3-ene-1-carbonitrile | 441.4 |
| P-0181 | 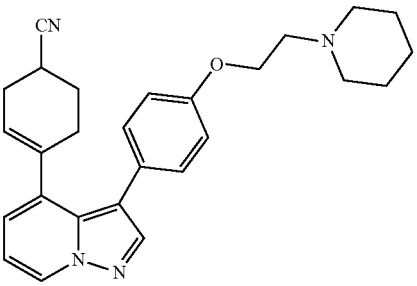 [SMILES: N#CC1CC=C(c2cccn3ncc(-c4ccc(OCCN5CCCCC5)cc4)c23)CC1] | 4-(3-(4-(2-(piperidin-1-yl)ethoxy)phenyl)pyrazolo[1,5-a]pyridin-4-yl)cyclohex-3-ene-1-carbonitrile | 427.3 |
| P-0182 | 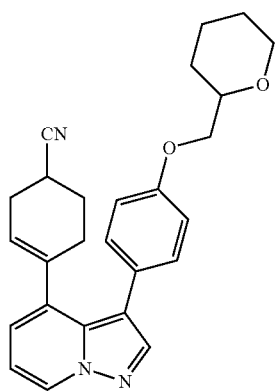 [SMILES: N#CC1CC=C(c2cccn3ncc(-c4ccc(OCC5CCCCO5)cc4)c23)CC1] | 4-(3-(4-((tetrahydro-2H-pyran-2-yl)methoxy)phenyl)pyrazolo[1,5-a]pyridin-4-yl)cyclohex-3-ene-1-carbonitrile | 414.1 |

TABLE 1-continued

| P Number | Structure | Name | MS |
|---|---|---|---|
| P-0183 | 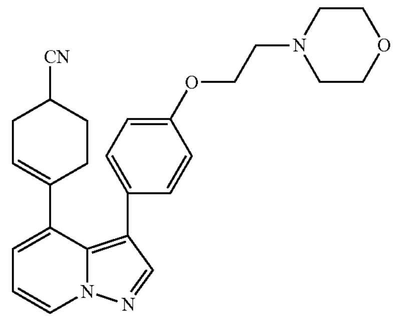 [SMILES: N#CC1CC=C(c2cccn3ncc(-c4ccc(OCCN5CCOCC5)cc4)c23)CC1] | 4-(3-(4-(2-morpholino-ethoxy)phenyl)pyrazolo[1,5-a]pyridin-4-yl)cyclohex-3-ene-1-carbonitrile | 429.4 |
| P-0184 | 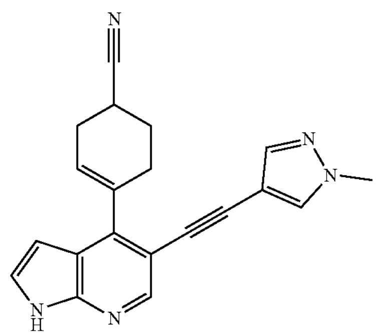 [SMILES: Cn1cc(C#Cc2cnc3[nH]ccc3c2C2=CCC(C#N)CC2)cn1] | 4-(5-((1-methyl-1H-pyrazol-4-yl)ethynyl)-1H-pyrrolo[2,3-b]pyridin-4-yl)cyclohex-3-ene-1-carbonitrile | 328.2 |
| P-0185 | 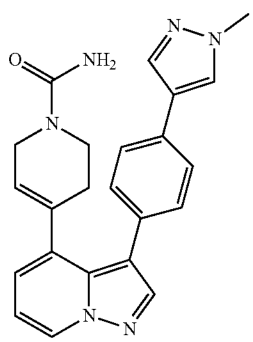 [SMILES: Cn1cc(-c2ccc(-c3cnn4cccc(C5=CCN(C(N)=O)CC5)c34)cc2)cn1] | 4-(3-(4-(1-methyl-1H-pyrazol-4-yl)phenyl)pyrazolo[1,5-a]pyridin-4-yl)-3,6-dihydropyridine-1(2H)-carboxamide | 399.1 |
| P-0186 | 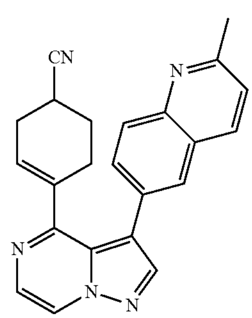 [SMILES: Cc1ccc2cc(-c3cnn4ccnc(C5=CCC(C#N)CC5)c34)ccc2n1] | 4-(3-(2-methylquinolin-6-yl)pyrazolo[1,5-a]pyrazin-4-yl)cyclohex-3-ene-1-carbonitrile | 366.1 |

TABLE 1-continued

| P Number | Structure | Name | MS |
|---|---|---|---|
| P-0187 | 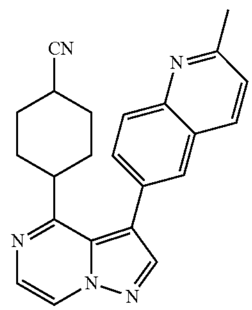 [SMILES: Cc1ccc2cc(-c3cnn4ccnc(C5CCC(C#N)CC5)c34)ccc2n1] | 4-(3-(2-methylquinolin-6-yl)pyrazolo[1,5-a]pyrazin-4-yl)cyclohexane-1-carbonitrile | 368.0 |
| P-0188 | 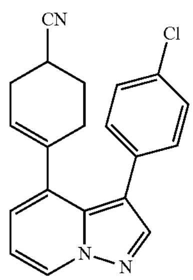 [SMILES: N#CC1CC=C(c2cccn3ncc(-c4ccc(Cl)cc4)c23)CC1] | 4-(3-(4-chlorophenyl)pyrazolo[1,5-a]pyridin-4-yl)cyclohex-3-ene-1-carbonitrile | 334.5 |
| P-0189 | 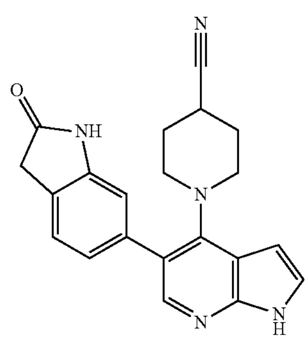 [SMILES: N#CC1CCN(c2c(-c3ccc4c(c3)NC(=O)C4)cnc3[nH]ccc23)CC1] | 1-(5-(2-oxoindolin-6-yl)-1H-pyrrolo[2,3-b]pyridin-4-yl)piperidine-4-carbonitrile | 358.0 |
| P-0190 | 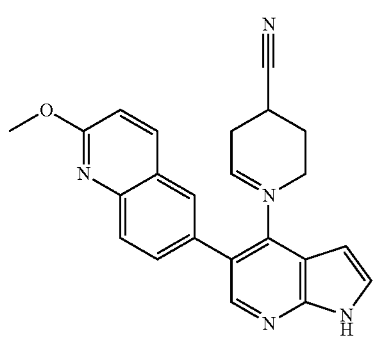 | 4-(5-(2-methoxyquinolin-6-yl)-1H-pyrrolo[2,3-b]pyridin-4-yl)cyclohex-3-ene-1-carbonitrile | 381.1 |

TABLE 1-continued

| P Number | Structure | Name | MS |
|---|---|---|---|
| P-0191 | 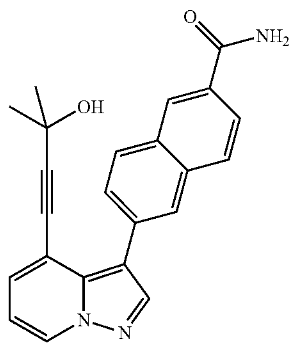 [SMILES: CC(C)(O)C#Cc1cccn2ncc(-c3ccc4cc(C(N)=O)ccc4c3)c12] | 6-(4-(3-hydroxy-3-methylbut-1-yn-1-yl)pyrazolo[1,5-a]pyridin-3-yl)-2-naphthamide | 370.0 |
| P-0193 | 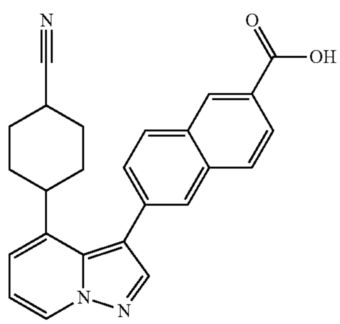 [SMILES: N#CC1CCC(c2cccn3ncc(-c4ccc5cc(C(=O)O)ccc5c4)c23)CC1] | 6-(4-(4-cyanocyclohexyl)pyrazolo[1,5-a]pyridin-3-yl)-2-naphthoic acid | 396.2 |
| P-0194 | 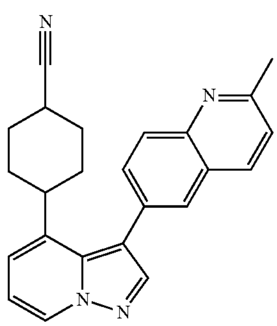 [SMILES: Cc1ccc2cc(-c3cnn4cccc(C5CCC(C#N)CC5)c34)ccc2n1] | 4-(3-(2-methylquinolin-6-yl)pyrazolo[1,5-a]pyridin-4-yl)cyclohexane-1-carbonitrile | 367.6 |
| P-0195 | 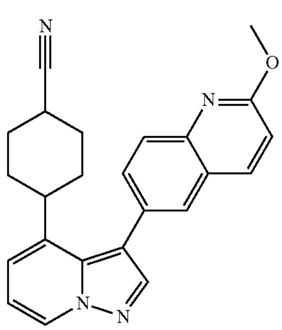 [SMILES: COc1ccc2cc(-c3cnn4cccc(C5CCC(C#N)CC5)c34)ccc2n1] | 4-(3-(2-methoxyquinolin-6-yl)pyrazolo[1,5-a]pyridin-4-yl)cyclohexane-1-carbonitrile | 383.6 |

TABLE 1-continued
| P Number | Structure | Name | MS |
|---|---|---|---|
| P-0196 | 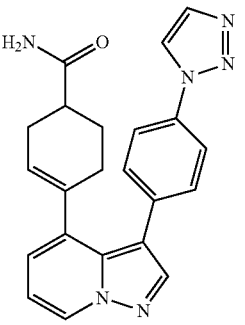 [SMILES: NC(=O)C1CC=C(c2cccn3ncc(-c4ccc(-n5ccnn5)cc4)c23)CC1] | 4-(3-(4-(1H-1,2,3-triazol-1-yl)phenyl)pyrazolo[1,5-a]pyridin-4-yl)cyclohex-3-ene-1-carboxamide | 385.2 |
| P-0197 | 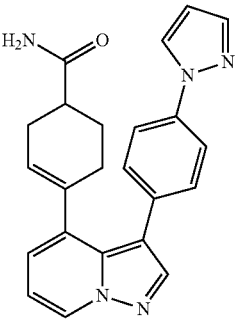 | 4-(3-(4-(1H-pyrazol-1-yl)phenyl)pyrazolo[1,5-a]pyridin-4-yl)cyclohex-3-ene-1-carboxamide | 384.1 |
| P-0198 | 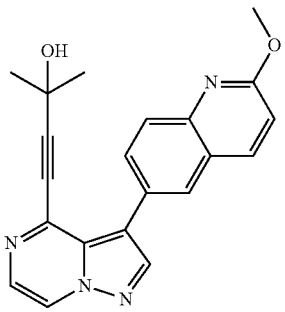 [SMILES: COc1ccc2cc(-c3cnn4ccnc(C#CC(C)(C)O)c34)ccc2n1] | 4-(3-(2-methoxyquinolin-6-yl)pyrazolo[1,5-a]pyrazin-4-yl)-2-methylbut-3-yn-2-ol | 359.1 |
| P-0199 | 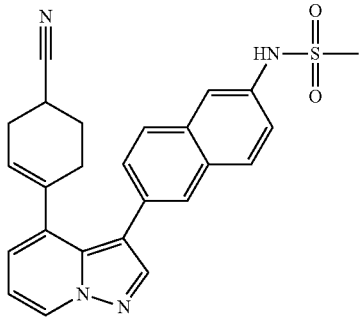 [SMILES: CS(=O)(=O)Nc1ccc2cc(-c3cnn4cccc(C5=CCC(C#N)CC5)c34)ccc2c1] | N-(6-(4-(4-cyanocyclohex-1-en-1-yl)pyrazolo[1,5-a]pyridin-3-yl)naphthalen-2-yl)methanesulfonamide | 443.1 |

TABLE 1-continued
| P Number | Structure | Name | MS |
|---|---|---|---|
| P-0200 | 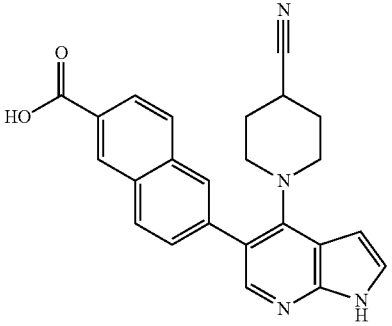 [SMILES: N#CC1CCN(c2c(-c3ccc4cc(C(=O)O)ccc4c3)cnc3[nH]ccc23)CC1] | 6-(4-(4-cyanopiperidin-1-yl)-1H-pyrrolo[2,3-b]pyridin-5-yl)-2-naphthoic acid | 397.2 |
| P-0201 | 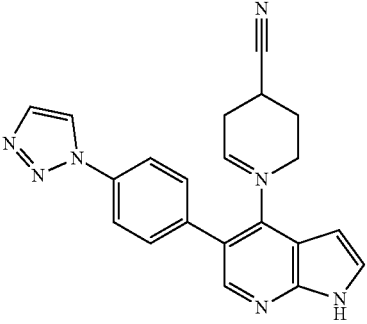 | 4-(5-(4-(1H-1,2,3-triazol-1-yl)phenyl)-1H-pyrrolo[2,3-b]pyridin-4-yl)cyclohex-3-ene-1-carbonitrile | 367.0 |
| P-0202 | 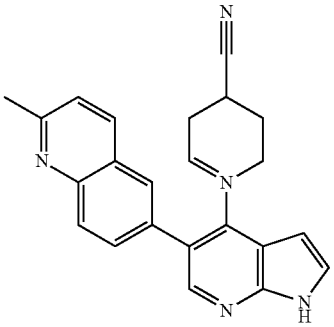 | 4-(5-(2-methylquinolin-6-yl)-1H-pyrrolo[2,3-b]pyridin-4-yl)cyclohex-3-ene-1-carbonitrile | 365.0 |
| P-0203 | 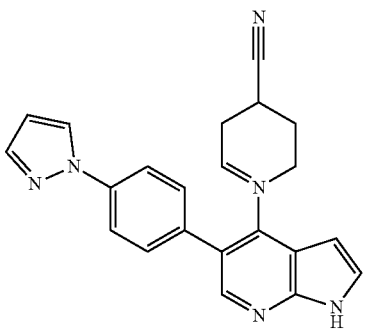 | 4-(5-(4-(1H-pyrazol-1-yl)phenyl)-1H-pyrrolo[2,3-b]pyridin-4-yl)cyclohex-3-ene-1-carbonitrile | 366.0 |

TABLE 1-continued

| P Number | Structure | Name | MS |
|---|---|---|---|
| P-0204 | 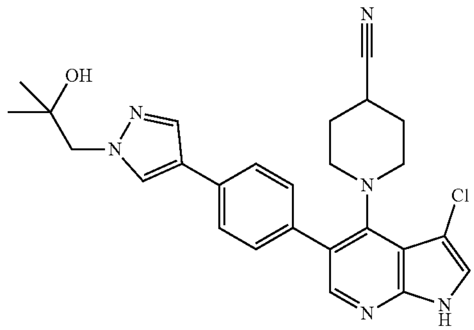 [SMILES: CC(C)(O)Cn1cc(-c2ccc(-c3cnc4[nH]cc(Cl)c4c3N3CCC(C#N)CC3)cc2)cn1] | 1-(3-chloro-5-(4-(1-(2-hydroxy-2-methylpropyl)-1H-pyrazol-4-yl)phenyl)-1H-pyrrolo[2,3-b]pyridin-4-yl)piperidine-4-carbonitrile | 475.1 |
| P-0205 | 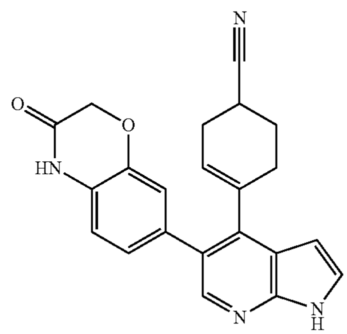 [SMILES: N#CC1CC=C(c2c(-c3ccc4c(c3)OCC(=O)N4)cnc3[nH]ccc23)CC1] | 4-(5-(3-oxo-3,4-dihydro-2H-benzo[b][1,4]oxazin-7-yl)-1H-pyrrolo[2,3-b]pyridin-4-yl)cyclohex-3-ene-1-carbonitrile | 371.0 |
| P-0206 | 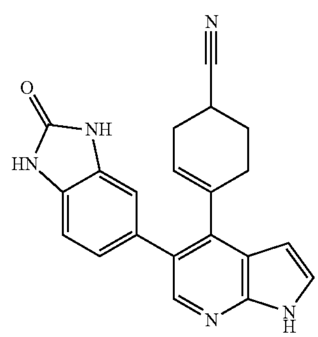 [SMILES: N#CC1CC=C(c2c(-c3ccc4[nH]c(=O)[nH]c4c3)cnc3[nH]ccc23)CC1] | 4-(5-(2-oxo-2,3-dihydro-1H-benzo[d]imidazol-5-yl)-1H-pyrrolo[2,3-b]pyridin-4-yl)cyclohex-3-ene-1-carbonitrile | 356.0 |
| P-0207 | 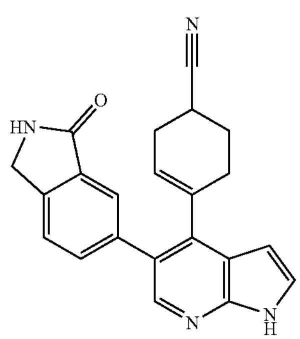 [SMILES: N#CC1CC=C(c2c(-c3ccc4c(c3)C(=O)NC4)cnc3[nH]ccc23)CC1] | 4-(5-(3-oxoisoindolin-5-yl)-1H-pyrrolo[2,3-b]pyridin-4-yl)cyclohex-3-ene-1-carbonitrile | 355.0 |

TABLE 1-continued

| P Number | Structure | Name | MS |
|---|---|---|---|
| P-0208 | 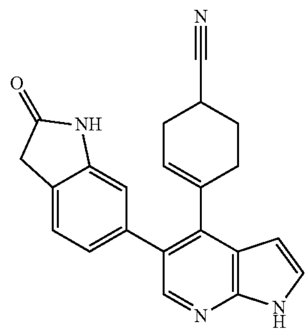 [SMILES: N#CC1CC=C(c2c(-c3ccc4c(c3)NC(=O)C4)cnc3[nH]ccc23)CC1] | 4-(5-(2-oxoindolin-6-yl)-1H-pyrrolo[2,3-b]pyridin-4-yl)cyclohex-3-ene-1-carbonitrile | 355.0 |
| P-0209 | 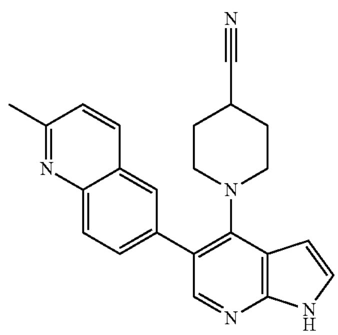 [SMILES: Cc1ccc2cc(-c3cnc4[nH]ccc4c3N3CCC(C#N)CC3)ccc2n1] | 1-(5-(2-methylquinolin-6-yl)-1H-pyrrolo[2,3-b]pyridin-4-yl)piperidine-4-carbonitrile | 368.1 |
| P-0210 | 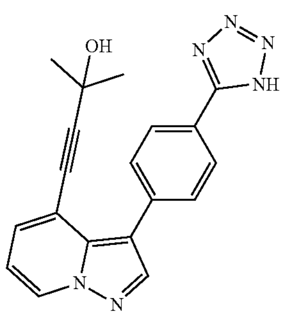 [SMILES: CC(C)(O)C#Cc1cccn2ncc(-c3ccc(-c4nnn[nH]4)cc3)c12] | 4-(3-(4-(1H-tetrazol-5-yl)phenyl)pyrazolo[1,5-a]pyridin-4-yl)-2-methylbut-3-yn-2-ol | 342.9 |
| P-0211 | 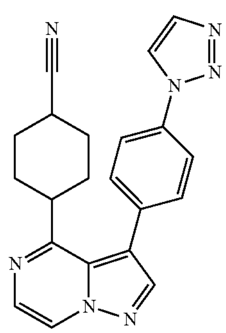 [SMILES: N#CC1CCC(c2nccn3ncc(-c4ccc(-n5ccnn5)cc4)c23)CC1] | 4-(3-(4-(1H-1,2,3-triazol-1-yl)phenyl)pyrazolo[1,5-a]pyrazin-4-yl)cyclohexane-1-carbonitrile | 370.2 |

TABLE 1-continued
| P Number | Structure | Name | MS |
|---|---|---|---|
| P-0212 | 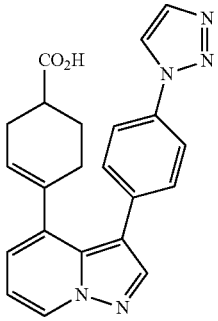 [SMILES: O=C(O)C1CC=C(c2cccn3ncc(-c4ccc(-n5ccnn5)cc4)c23)CC1] | 4-(3-(4-(1H-1,2,3-triazol-1-yl)phenyl)pyrazolo[1,5-a]pyridin-4-yl)cyclohex-3-ene-1-carboxylic acid | 386.1 |
| P-0213 | 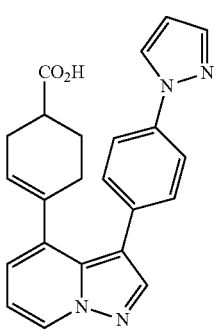 [SMILES: O=C(O)C1CC=C(c2cccn3ncc(-c4ccc(-n5cccn5)cc4)c23)CC1] | 4-(3-(4-(1H-pyrazol-1-yl)phenyl)pyrazolo[1,5-a]pyridin-4-yl)cyclohex-3-ene-1-carboxylic acid | 385.2 |
| P-0214 | 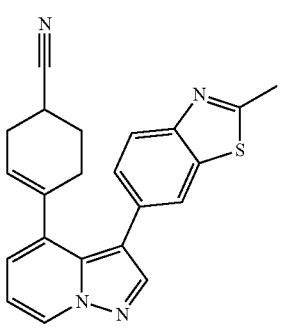 [SMILES: Cc1nc2ccc(-c3cnn4cccc(C5=CCC(C#N)CC5)c34)cc2s1] | 4-(3-(2-methylbenzo[d]thiazol-6-yl)pyrazolo[1,5-a]pyridin-4-yl)cyclohex-3-ene-1-carbonitrile | 371.1 |
| P-0215 | 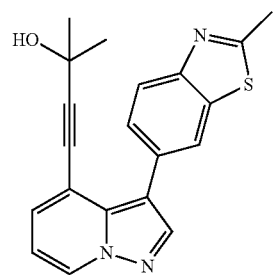 [SMILES: Cc1nc2ccc(-c3cnn4cccc(C#CC(C)(C)O)c34)cc2s1] | 2-methyl-4-(3-(2-methylbenzo[d]thiazol-6-yl)pyrazolo[1,5-a]pyridin-4-yl)but-3-yn-2-ol | 347.9 |

TABLE 1-continued

| P Number | Structure | Name | MS |
|---|---|---|---|
| P-0216 | 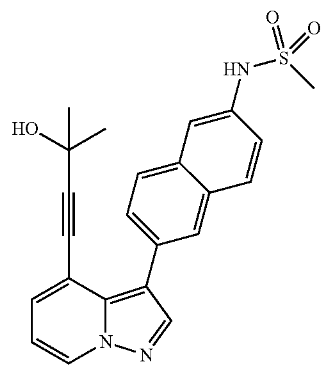 [SMILES: CC(C)(O)C#Cc1cccn2ncc(-c3ccc4cc(NS(C)(=O)=O)ccc4c3)c12] | N-(6-(4-(3-hydroxy-3-methylbut-1-yn-1-yl)pyrazolo[1,5-a]pyridin-3-yl)naphthalen-2-yl)methanesulfonamide | 417.9 |
| P-0217 | 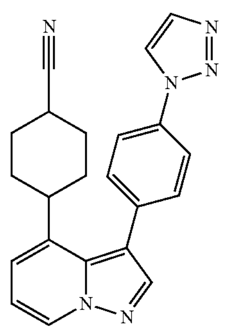 [SMILES: N#CC1CCC(c2cccn3ncc(-c4ccc(-n5ccnn5)cc4)c23)CC1] | 4-(3-(4-(1H-1,2,3-triazol-1-yl)phenyl)pyrazolo[1,5-a]pyridin-4-yl)cyclohexane-1-carbonitrile | 369.5 |
| P-0218 | 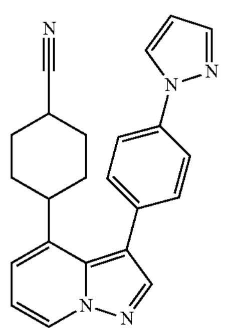 [SMILES: N#CC1CCC(c2cccn3ncc(-c4ccc(-n5cccn5)cc4)c23)CC1] | 4-(3-(4-(1H-pyrazol-1-yl)phenyl)pyrazolo[1,5-a]pyridin-4-yl)cyclohexane-1-carbonitrile | 368.6 |
| P-0219 | 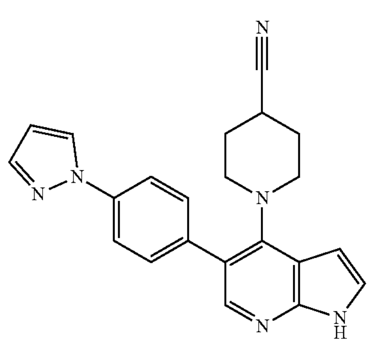 [SMILES: N#CC1CCN(c2c(-c3ccc(-n4cccn4)cc3)cnc3[nH]ccc23)CC1] | 1-(5-(4-(1H-pyrazol-1-yl)phenyl)-1H-pyrrolo[2,3-b]pyridin-4-yl)piperidine-4-carbonitrile | 369.1 |

TABLE 1-continued

| P Number | Structure | Name | MS |
|---|---|---|---|
| P-0220 | 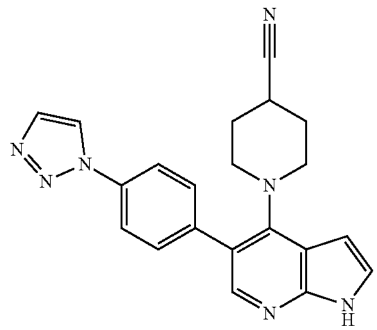 [SMILES: N#CC1CCN(c2c(-c3ccc(-n4ccnn4)cc3)cnc3[nH]ccc23)CC1] | 1-(5-(4-(1H-1,2,3-triazol-1-yl)phenyl)-1H-pyrrolo[2,3-b]pyridin-4-yl)piperidine-4-carbonitrile | 370.0 |
| P-0221 | 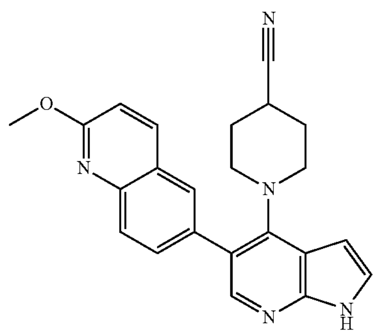 [SMILES: COc1ccc2cc(-c3cnc4[nH]ccc4c3N3CCC(C#N)CC3)ccc2n1] | 1-(5-(2-methoxyquinolin-6-yl)-1H-pyrrolo[2,3-b]pyridin-4-yl)piperidine-4-carbonitrile | 384.2 |
| P-0222 | 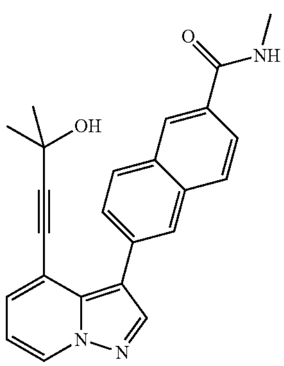 [SMILES: CNC(=O)c1ccc2cc(-c3cnn4cccc(C#CC(C)(C)O)c34)ccc2c1] | 6-(4-(3-hydroxy-3-methylbut-1-yn-1-yl)pyrazolo[1,5-a]pyridin-3-yl)-N-methyl-2-naphthamide | 384.2 |
| P-0223 | 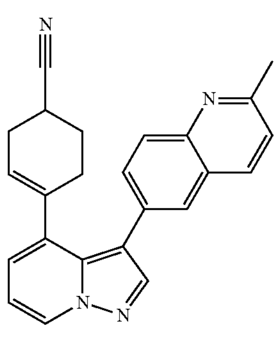 [SMILES: Cc1ccc2cc(-c3cnn4cccc(C5=CCC(C#N)CC5)c34)ccc2n1] | 4-(3-(2-methylquinolin-6-yl)pyrazolo[1,5-a]pyridin-4-yl)cyclohex-3-ene-1-carbonitrile | 365.2 |

TABLE 1-continued
| P Number | Structure | Name | MS |
|---|---|---|---|
| P-0224 | 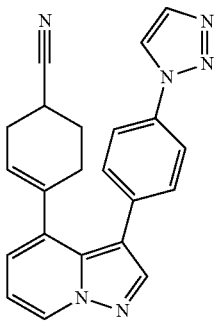 [SMILES: N#CC1CC=C(c2cccn3ncc(-c4ccc(-n5ccnn5)cc4)c23)CC1] | 4-(3-(4-(1H-1,2,3-triazol-1-yl)phenyl)pyrazolo[1,5-a]pyridin-4-yl)cyclohex-3-ene-1-carbonitrile | 367.5 |
| P-0225 | 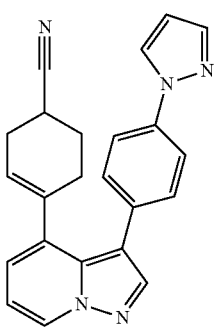 | 4-(3-(4-(1H-pyrazol-1-yl)phenyl)pyrazolo[1,5-a]pyridin-4-yl)cyclohex-3-ene-1-carbonitrile | 366.3 |
| P-0226 | 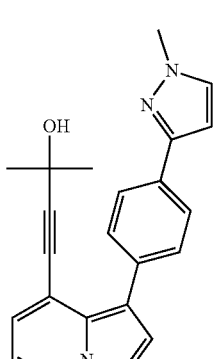 | 2-methyl-4-(3-(4-(1-methyl-1H-pyrazol-3-yl)phenyl)pyrazolo[1,5-a]pyridin-4-yl)but-3-yn-2-ol | 339.0 |
| P-0227 | 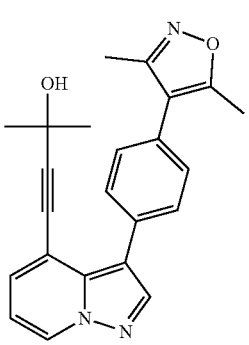 [SMILES: Cc1noc(C)c1-c1ccc(-c2cnn3cccc(C#CC(C)(C)O)c23)cc1] | 4-(3-(4-(3,5-dimethylisoxazol-4-yl)phenyl)pyrazolo[1,5-a]pyridin-4-yl)-2-methylbut-3-yn-2-ol | 372.0 |

TABLE 1-continued

| P Number | Structure | Name | MS |
|---|---|---|---|
| P-0228 | 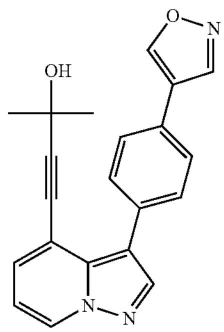 [SMILES: CC(C)(O)C#Cc1cccn2ncc(-c3ccc(-c4cnoc4)cc3)c12] | 4-(3-(4-(isoxazol-4-yl)phenyl)pyrazolo[1,5-a]pyridin-4-yl)-2-methylbut-3-yn-2-ol | 344.1 |
| P-0229 | 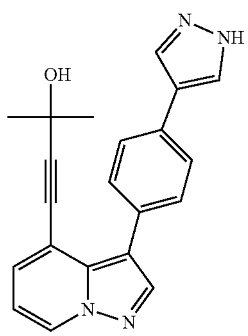 [SMILES: CC(C)(O)C#Cc1cccn2ncc(-c3ccc(-c4cn[nH]c4)cc3)c12] | 4-(3-(4-(1H-pyrazol-4-yl)phenyl)pyrazolo[1,5-a]pyridin-4-yl)-2-methylbut-3-yn-2-ol | 342.9 |
| P-0230 | 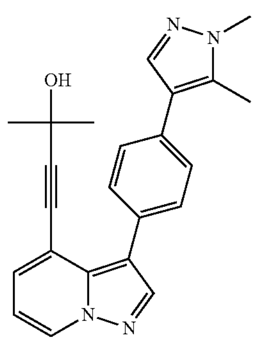 [SMILES: Cc1c(-c2ccc(-c3cnn4cccc(C#CC(C)(C)O)c34)cc2)cnn1C] | 4-(3-(4-(1,5-dimethyl-1H-pyrazol-4-yl)phenyl)pyrazolo[1,5-a]pyridin-4-yl)-2-methylbut-3-yn-2-ol | 371.1 |
| P-0231 | 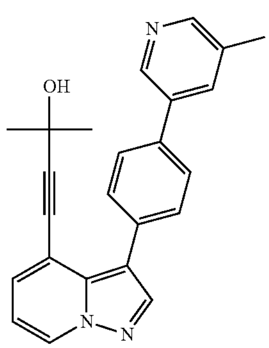 [SMILES: Cc1cncc(-c2ccc(-c3cnn4cccc(C#CC(C)(C)O)c34)cc2)c1] | 2-methyl-4-(3-(4-(5-methylpyridin-3-yl)phenyl)pyrazolo[1,5-a]pyridin-4-yl)but-3-yn-2-ol | 368.1 |

TABLE 1-continued

| P Number | Structure | Name | MS |
|---|---|---|---|
| P-0232 | 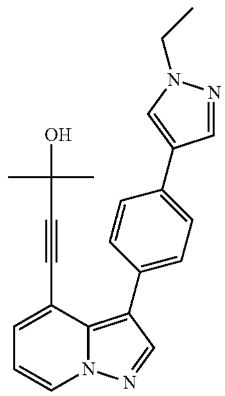 [SMILES: CCn1cc(-c2ccc(-c3cnn4cccc(C#CC(C)(C)O)c34)cc2)cn1] | 4-(3-(4-(1-ethyl-1H-pyrazol-4-yl)phenyl)pyrazolo[1,5-a]pyridin-4-yl)-2-methylbut-3-yn-2-ol | 371.1 |
| P-0233 | 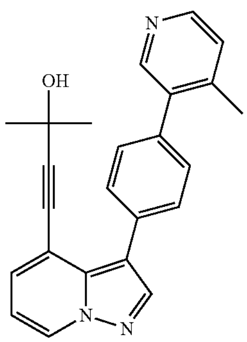 [SMILES: Cc1ccncc1-c1ccc(-c2cnn3cccc(C#CC(C)(C)O)c23)cc1] | 2-methyl-4-(3-(4-(4-methylpyridin-3-yl)phenyl)pyrazolo[1,5-a]pyridin-4-yl)but-3-yl-2-ol | 368.1 |
| P-0234 | 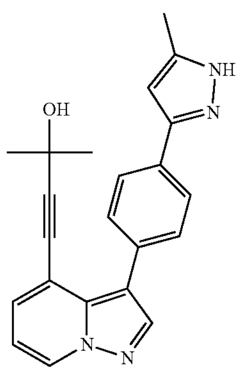 [SMILES: Cc1cc(-c2ccc(-c3cnn4cccc(C#CC(C)(C)O)c34)cc2)n[nH]1] | 2-methyl-4-(3-(4-(5-methyl-1H-pyrazol-3-yl)phenyl)pyrazolo[1,5-a]pyridin-4-yl)but-3-yl-2-ol | 339.0 |
| P-0235 | 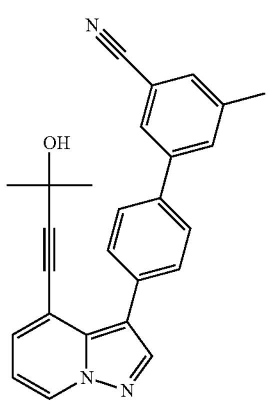 [SMILES: Cc1cc(C#N)cc(-c2ccc(-c3cnn4cccc(C#CC(C)(C)O)c34)cc2)c1] | 4'-(4-(3-hydroxy-3-methylbut-1-yn-1-yl)pyrazolo[1,5-a]pyridin-3-yl)-5-methyl-[1,1'-biphenyl]-3-carbonitrile | 392.2 |

TABLE 1-continued
| P Number | Structure | Name | MS |
|---|---|---|---|
| P-0236 | 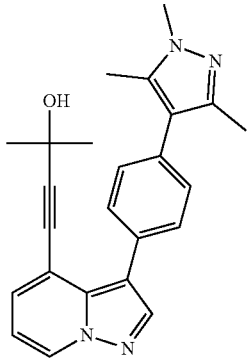 [SMILES: Cc1nn(C)c(C)c1-c1ccc(-c2cnn3cccc(C#CC(C)(C)O)c23)cc1] | 2-methyl-4-(3-(4-(1,3,5-trimethyl-1H-pyrazol-4-yl)phenyl)pyrazolo[1,5-a]pyridin-4-yl)but-3-yn-2-ol | 385.2 |
| P-0237 | 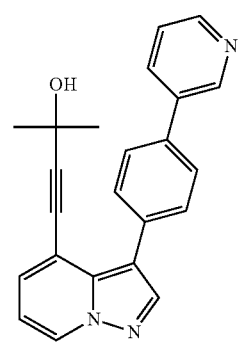 [SMILES: CC(C)(O)C#Cc1cccn2ncc(-c3ccc(-c4cccnc4)cc3)c12] | 2-methyl-4-(3-(4-(pyridin-3-yl)phenyl)pyrazolo[1,5-a]pyridin-4-yl)but-3-yn-2-ol | 354.3 |
| P-0238 | 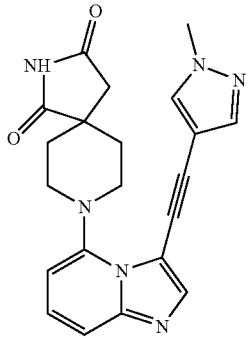 [SMILES: Cn1cc(C#Cc2cnc3cccc(N4CCC5(CC4)CC(=O)NC5=O)n23)cn1] | 8-(3-((1-methyl-1H-pyrazol-4-yl)ethynyl)imidazo[1,2-a]pyridin-5-yl)-2,8-diazaspiro[4.5]decane-1,3-dione | 389.4 |
| P-0239 | 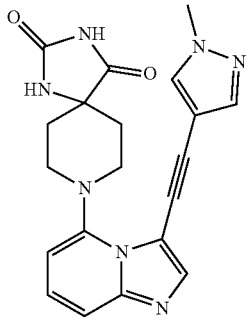 [SMILES: Cn1cc(C#Cc2cnc3cccc(N4CCC5(CC4)NC(=O)NC5=O)n23)cn1] | 8-(3-((1-methyl-1H-pyrazol-4-yl)ethynyl)imidazo[1,2-a]pyridin-5-yl)-1,3,8-triazaspiro[4.5]decane-2,4-dione | 390.4 |

TABLE 1-continued

| P Number | Structure | Name | MS |
|---|---|---|---|
| P-0240 | 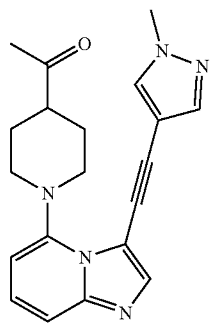 [SMILES: CC(=O)C1CCN(c2cccc3ncc(C#Cc4cnn(C)c4)n23)CC1] | 1-(1-(3-((1-methyl-1H-pyrazol-4-yl)ethynyl)imidazo[1,2-a]pyridin-5-yl)piperidin-4-yl)ethan-1-one | 348.3 |
| P-0241 | 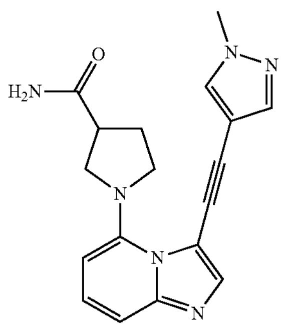 [SMILES: Cn1cc(C#Cc2cnc3cccc(N4CCC(C(N)=O)C4)n23)cn1] | 1-(3-((1-methyl-1H-pyrazol-4-yl)ethynyl)imidazo[1,2-a]pyridin-5-yl)pyrrolidine-3-carboxamide | 335.4 |
| P-0242 | 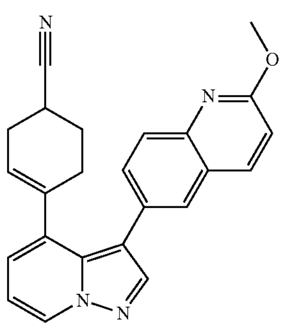 [SMILES: COc1ccc2cc(-c3cnn4cccc(C5=CCC(C#N)CC5)c34)ccc2n1] | 4-(3-(2-methoxyquinolin-6-yl)pyrazolo[1,5-a]pyridin-4-yl)cyclohex-3-ene-1-carbonitrile | 381.5 |
| P-0243 | 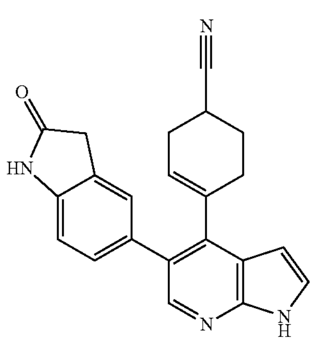 [SMILES: N#CC1CC=C(c2c(-c3ccc4c(c3)CC(=O)N4)cnc3[nH]ccc23)CC1] | 4-(5-(2-oxoindolin-5-yl)-1H-pyrrolo[2,3-b]pyridin-1-yl)cyclohex-3-ene-1-carbonitrile | 355.5 |

TABLE 1-continued
| P Number | Structure | Name | MS |
|---|---|---|---|
| P-0244 | 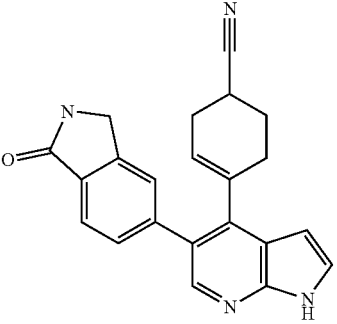 [SMILES: N#CC1CC=C(c2c(-c3ccc4c(c3)CNC4=O)cnc3[nH]ccc23)CC1] | 4-(5-(1-oxoisoindolin-5-yl)-1H-pyrrolo[2,3-b]pyridin-4-yl)cyclohex-3-ene-1-carbonitrile | 355.1 |
| P-0245 | 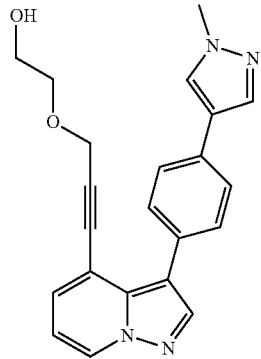 [SMILES: Cn1cc(-c2ccc(-c3cnn4cccc(C#CCOCCO)c34)cc2)cn1] | 2-((3-(3-(4-(1-methyl-1H-pyrazol-4-yl)phenyl)pyrazolo[1,5-a]pyridin-4-yl)prop-2-yn-1-yl)oxy)ethan-1-ol | 373.1 |
| P-0246 | 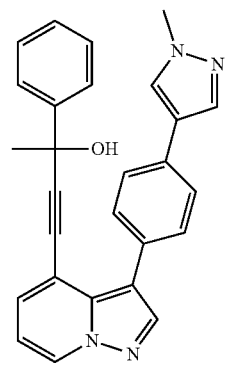 [SMILES: Cn1cc(-c2ccc(-c3cnn4cccc(C#CC(C)(O)c5ccccc5)c34)cc2)cn1] | (S)-4-(3-(4-(1-methyl-1H-pyrazol-4-yl)phenyl)pyrazolo[1,5-a]pyridin-4-yl)-2-phenylbut-3-yn-2-ol | 419.6 |
| P-0247 | 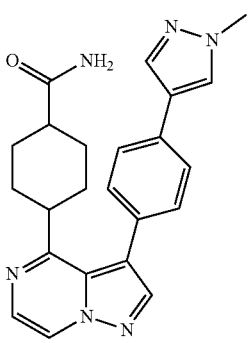 [SMILES: Cn1cc(-c2ccc(-c3cnn4ccnc(C5CCC(C(N)=O)CC5)c34)cc2)cn1] | 4-(3-(4-(1-methyl-1H-pyrazol-4-yl)phenyl)pyrazolo[1,5-a]pyrazin-4-yl)cyclohexane-1-carboxamide | 401.0 |

TABLE 1-continued

| P Number | Structure | Name | MS |
|---|---|---|---|
| P-0248 | 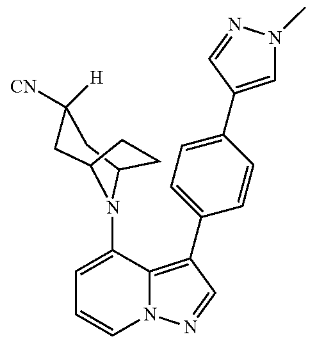 | 8-(3-(4-(1-methyl-1H-pyrazol-4-yl)phenyl)pyrazolo[1,5-a]pyridin-4-yl)-8-azabicyclo[3.2.1]octane-3-carbonitrile | 409.1 |
| P-0249 | 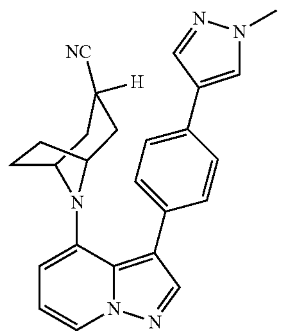 [SMILES: Cn1cc(-c2ccc(-c3cnn4cccc(N5C6CCC5CC(C#N)C6)c34)cc2)cn1] | 4-(3-isocyano-8-azabicyclo[3.2.1]octan-8-yl)-3-(4-(1-methyl-1H-pyrazol-4-yl)phenyl)pyrazolo[1,5-a]pyridine | 409.1 |
| P-0250 | 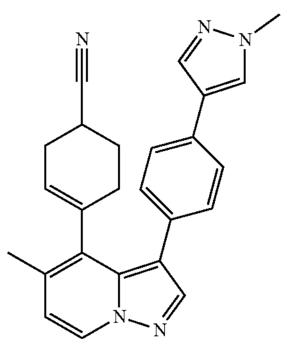 | 4-(5-methyl-3-(4-(1-methyl-1H-pyrazol-4-yl)phenyl)pyrazolo[1,5-a]pyridin-4-yl)cyclohex-3-ene-1-carbonitrile | 394.2 |
| P-0251 | 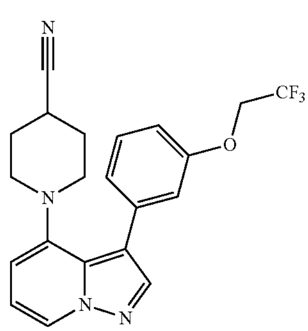 [SMILES: N#CC1CCN(c2cccn3ncc(-c4cccc(OCC(F)(F)F)c4)c23)CC1] | 1-(3-(3-(2,2,2-trifluoro-ethoxy)phenyl)pyrazolo[1,5-a]pyridin-4-yl)piperidine-4-carbonitrile | 401.2 |

TABLE 1-continued
| P Number | Structure | Name | MS |
|---|---|---|---|
| P-0252 | 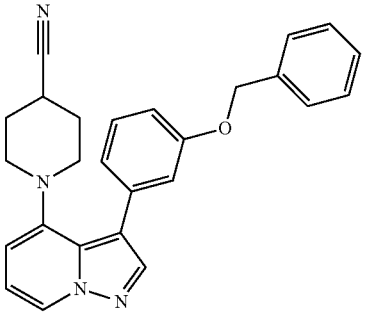 [SMILES: N#CC1CCN(c2cccn3ncc(-c4cccc(OCc5ccccc5)c4)c23)CC1] | 1-(3-(3-(benzyloxy)phenyl)pyrazolo[1,5-a]pyridin-4-yl)piperidine-4-carbonitrile | 409.3 |
| P-0253 | 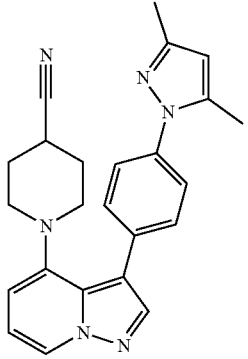 [SMILES: Cc1cc(C)n(-c2ccc(-c3cnn4cccc(N5CCC(C#N)CC5)c34)cc2)n1] | 1-(3-(4-(3,5-dimethyl-1H-pyrazol-1-yl)phenyl)pyrazolo[1,5-a]pyridin-4-yl)piperidine-4-carbonitrile | 397.3 |
| P-0254 | 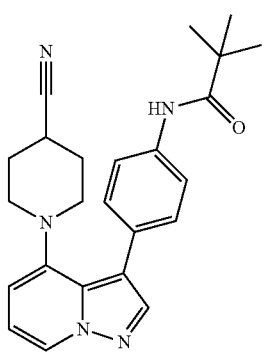 [SMILES: CC(C)(C)C(=O)Nc1ccc(-c2cnn3cccc(N4CCC(C#N)CC4)c23)cc1] | N-(4-(4-(4-cyanopiperidin-1-yl)pyrazolo[1,5-a]pyridin-3-yl)phenyl)pivalamide | 402.4 |
| P-0255 | 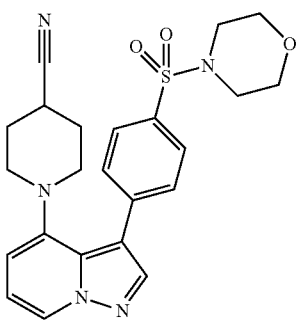 [SMILES: N#CC1CCN(c2cccn3ncc(-c4ccc(S(=O)(=O)N5CCOCC5)cc4)c23)CC1] | 1-(3-(4-(morpholinosulfonyl)phenyl)pyrazolo[1,5-a]pyridin-4-yl)piperidine-4-carbonitrile | 452.2 |

TABLE 1-continued

| P Number | Structure | Name | MS |
|---|---|---|---|
| P-0256 | 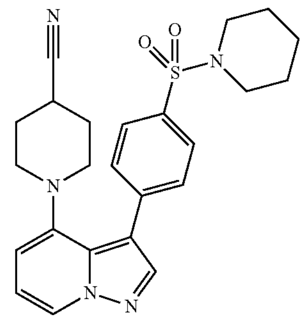 [SMILES: N#CC1CCN(c2cccn3ncc(-c4ccc(S(=O)(=O)N5CCCCC5)cc4)c23)CC1] | 1-(3-(4-(piperidin-1-ylsulfonyl)phenyl)pyrazolo[1,5-a]pyridin-4-yl)piperidine-4-carbonitrile | 450.1 |
| P-0257 | 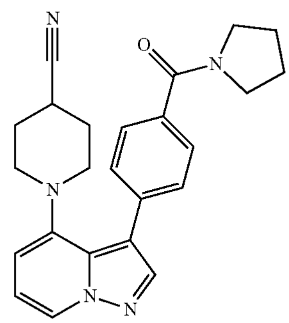 [SMILES: N#CC1CCN(c2cccn3ncc(-c4ccc(C(=O)N5CCCC5)cc4)c23)CC1] | 1-(3-(4-(pyrrolidine-1-carbonyl)phenyl)pyrazolo[1,5-a]pyridin-4-yl)piperidine-4-carbonitrile | 400.3 |
| P-0258 | 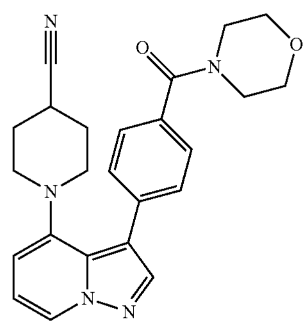 [SMILES: N#CC1CCN(c2cccn3ncc(-c4ccc(C(=O)N5CCOCC5)cc4)c23)CC1] | 1-(3-(4-(morpholine-4-carbonyl)phenyl)pyrazolo[1,5-a]pyridin-4-yl)piperidine-4-carbonitrile | 416.2 |
| P-0259 | 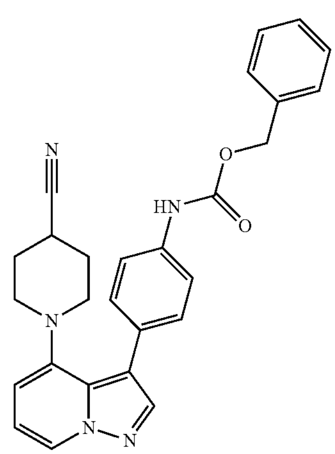 [SMILES: N#CC1CCN(c2cccn3ncc(-c4ccc(NC(=O)OCc5ccccc5)cc4)c23)CC1] | benzyl (4-(4-(4-cyanopiperidin-1-yl)pyrazolo[1,5-a]pyridin-3-yl)phenyl)carbamate | 452.2 |

TABLE 1-continued

| P Number | Structure | Name | MS |
|---|---|---|---|
| P-0260 | 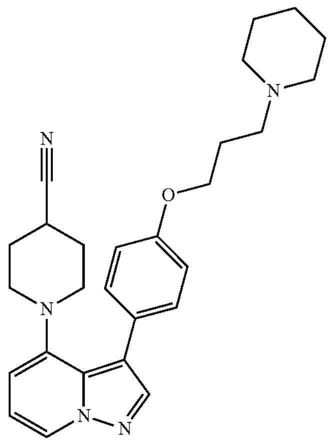 [SMILES: N#CC1CCN(c2cccn3ncc(-c4ccc(OCCCN5CCCCC5)cc4)c23)CC1] | 1-(3-(4-(3-(piperidin-1-yl)propoxy)phenyl)pyrazolo[1,5-a]pyridin-4-yl)piperidine-4-carbonitrile | 444.4 |
| P-0261 | 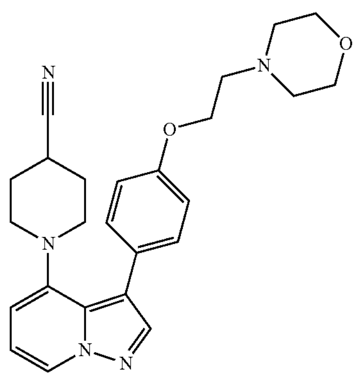 [SMILES: N#CC1CCN(c2cccn3ncc(-c4ccc(OCCN5CCOCC5)cc4)c23)CC1] | 1-(3-(4-(2-morpholino-ethoxy)phenyl)pyrazolo[1,5-a]pyridin-4-yl)piperidine-4-carbonitrile | 432.4 |
| P-0262 | 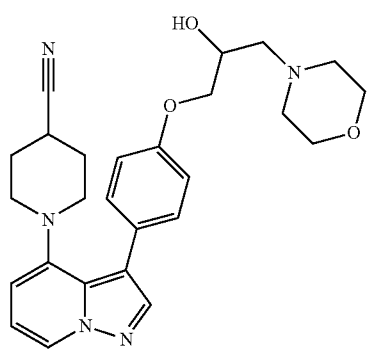 [SMILES: N#CC1CCN(c2cccn3ncc(-c4ccc(OCC(O)CN5CCOCC5)cc4)c23)CC1] | 1-(3-(4-(2-hydroxy-3-morpholino-propoxy)phenyl)pyrazolo[1,5-a]pyridin-4-yl)piperidine-4-carbonitrile | 462.4 |
| P-0263 | 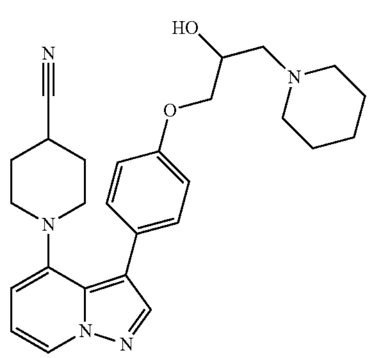 [SMILES: N#CC1CCN(c2cccn3ncc(-c4ccc(OCC(O)CN5CCCCC5)cc4)c23)CC1] | 1-(3-(4-(2-hydroxy-3-(piperidin-1-yl)propoxy)phenyl)pyrazolo[1,5-a]pyridin-4-yl)piperidine-4-carbonitrile | 460.3 |

TABLE 1-continued

| P Number | Structure | Name | MS |
|---|---|---|---|
| P-0264 | 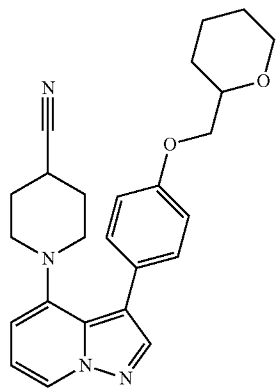 [SMILES: N#CC1CCN(c2cccn3ncc(-c4ccc(OCC5CCCCO5)cc4)c23)CC1] | 1-(3-(4-((tetrahydro-2H-pyran-2-yl)methoxy)phenyl)pyrazolo[1,5-a]pyridin-4-yl)piperidine-4-carbonitrile | 417.4 |
| P-0265 | 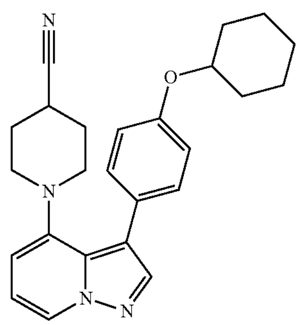 [SMILES: N#CC1CCN(c2cccn3ncc(-c4ccc(OC5CCCCC5)cc4)c23)CC1] | 1-(3-(4-(cyclohexyloxy)phenyl)pyrazolo[1,5-a]pyridin-4-yl)piperidine-4-carbonitrile | 401.2 |
| P-0266 | 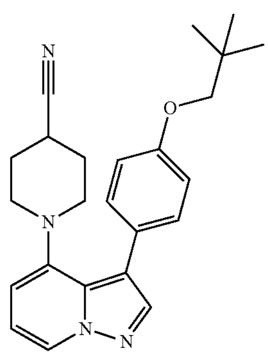 [SMILES: CC(C)(C)COc1ccc(-c2cnn3cccc(N4CCC(C#N)CC4)c23)cc1] | 1-(3-(4-(neopentyloxy)phenyl)pyrazolo[1,5-a]pyridin-4-yl)piperidine-4-carbonitrile | 389.4 |
| P-0267 | 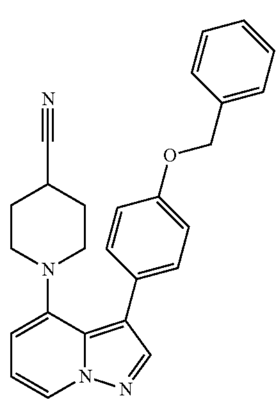 [SMILES: N#CC1CCN(c2cccn3ncc(-c4ccc(OCc5ccccc5)cc4)c23)CC1] | 1-(3-(4-(benzyloxy)phenyl)pyrazolo[1,5-a]pyridin-4-yl)piperidine-4-carbonitrile | 409.3 |

TABLE 1-continued

| P Number | Structure | Name | MS |
|---|---|---|---|
| P-0268 | 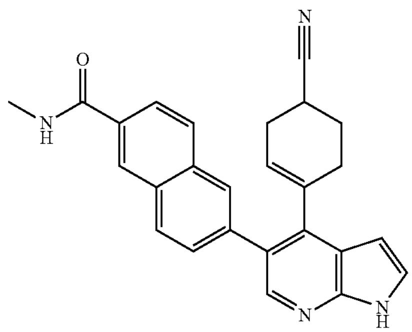 [SMILES: CNC(=O)c1ccc2cc(-c3cnc4[nH]ccc4c3C3=CCC(C#N)CC3)ccc2c1] | 6-(4-(4-cyanocyclohex-1-en-1-yl)-1H-pyrrolo[2,3-b]pyridin-5-yl)-N-methyl-2-naphthamide | 407.1 |
| P-0269 | 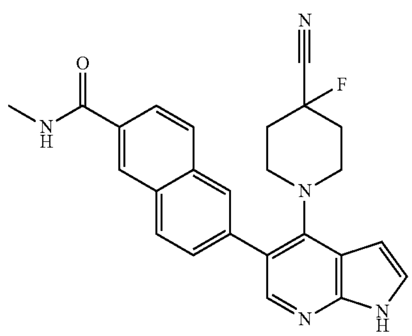 [SMILES: CNC(=O)c1ccc2cc(-c3cnc4[nH]ccc4c3N3CCC(F)(C#N)CC3)ccc2c1] | 6-(4-(4-cyano-4-fluoropiperidin-1-yl)-1H-pyrrolo[2,3-b]pyridin-5-yl)-N-methyl-2-naphthamide | 428.1 |
| P-0270 | 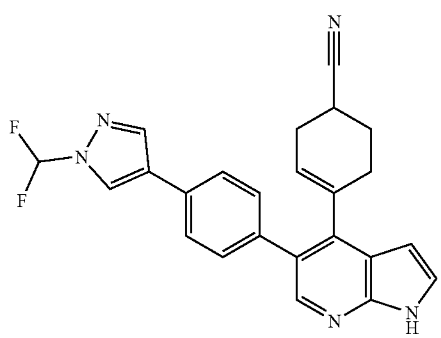 [SMILES: N#CC1CC=C(c2c(-c3ccc(-c4cnn(C(F)F)c4)cc3)cnc3[nH]ccc23)CC1] | 4-(5-(4-(1-(difluoromethyl)-1H-pyrazol-4-yl)phenyl)-1H-pyrrolo[2,3-b]pyridin-4-yl)cyclohex-3-ene-1-carbonitrile | 416.0 |
| P-0271 | 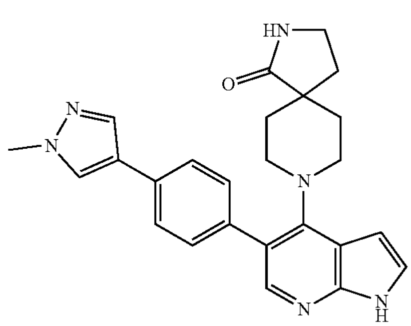 [SMILES: Cn1cc(-c2ccc(-c3cnc4[nH]ccc4c3N3CCC4(CCNC4=O)CC3)cc2)cn1] | 8-(5-(4-(1-methyl-1H-pyrazol-4-yl)phenyl)-1H-pyrrolo[2,3-b]pyridin-4-yl)-2,8-diazaspiro[4.5]decan-1-one | 427.1 |

TABLE 1-continued

| P Number | Structure | Name | MS |
|---|---|---|---|
| P-0272 | 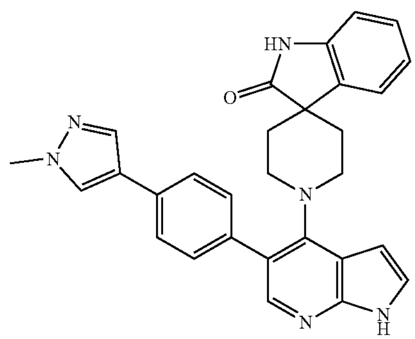 [SMILES: Cn1cc(-c2ccc(-c3cnc4[nH]ccc4c3N3CCC4(CC3)C(=O)Nc3ccccc34)cc2)cn1] | 1'-(5-(4-(1-methyl-1H-pyrazol-4-yl)phenyl)-1H-pyrrolo[2,3-b]pyridin-4-yl)spiro[indoline-3,4'-piperidin]-2-one | 475.1 |
| P-0273 | 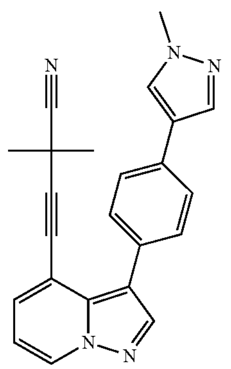 [SMILES: Cn1cc(-c2ccc(-c3cnn4cccc(C#CC(C)(C)C#N)c34)cc2)cn1] | 2,2-dimethyl-4-(3-(4-(1-methyl-1H-pyrazol-4-yl)phenyl)pyrazolo[1,5-a]pyridin-4-yl)but-3-ynenitrile | 366.6 |
| P-0274 | 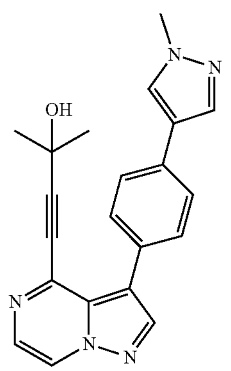 [SMILES: Cn1cc(-c2ccc(-c3cnn4ccnc(C#CC(C)(C)O)c34)cc2)cn1] | 2-methyl-4-(3-(4-(1-methyl-1H-pyrazol-4-yl)phenyl)pyrazolo[1,5-a]pyrazin-4-yl)but-3-yn-2-ol | 358.2 |
| P-0275 | 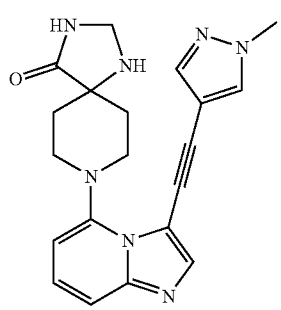 [SMILES: Cn1cc(C#Cc2cnc3cccc(N4CCC5(CC4)NCNC5=O)n23)cn1] | 8-(3-((1-methyl-1H-pyrazol-4-yl)ethynyl)imidazo[1,2-a]pyridin-5-yl)-1,3,8-triazaspiro[4.5]decan-4-one | 376.2 |

TABLE 1-continued

| P Number | Structure | Name | MS |
|---|---|---|---|
| P-0276 | 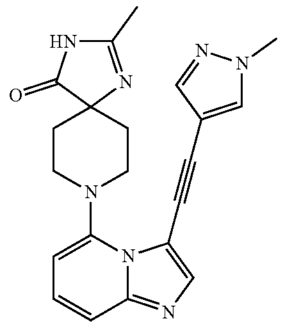 [SMILES: CC1=NC2(CCN(c3cccc4ncc(C#Cc5cnn(C)c5)n34)CC2)C(=O)N1] | 2-methyl-8-(3-((1-methyl-1H-pyrazol-4-yl)ethynyl)imidazo[1,2-a]pyridin-5-yl)-1,3,8-triazaspiro[4.5]dec-1-en-4-one | 388.2 |
| P-0277 | 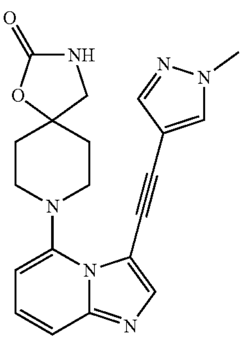 [SMILES: Cn1cc(C#Cc2cnc3cccc(N4CCC5(CC4)CNC(=O)O5)n23)cn1] | 8-(3-((1-methyl-1H-pyrazol-4-yl)ethynyl)imidazo[1,2-a]pyridin-5-yl)-1-oxa-3,8-diazaspiro[4.5]decan-2-one | 377.1 |
| P-0278 | 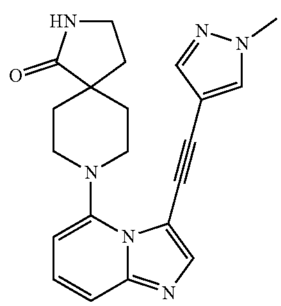 [SMILES: Cn1cc(C#Cc2cnc3cccc(N4CCC5(CCNC5=O)CC4)n23)cn1] | 8-(3-((1-methyl-1H-pyrazol-4-yl)ethynyl)imidazo[1,2-a]pyridin-5-yl)-2,8-diazaspiro[4.5]decan-1-one | 375.5 |
| P-0280 | 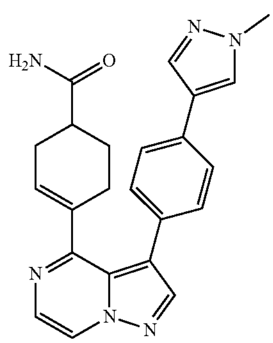 [SMILES: Cn1cc(-c2ccc(-c3cnn4ccnc(C5=CCC(C(N)=O)CC5)c34)cc2)cn1] | 4-(3-(4-(1-methyl-1H-pyrazol-4-yl)phenyl)pyrazolo[1,5-a]pyrazin-4-yl)cyclohex-3-ene-1-carboxamide | 399.2 |
| P-0281 | 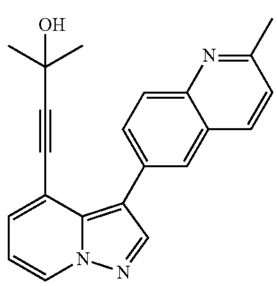 [SMILES: Cc1ccc2cc(-c3cnn4cccc(C#CC(C)(C)O)c34)ccc2n1] | 2-methyl-4-(3-(2-methylquinolin-6-yl)pyrazolo[1,5-a]pyridin-4-yl)but-3-yn-2-ol | 342.5 |

TABLE 1-continued

| P Number | Structure | Name | MS |
|---|---|---|---|
| P-0282 | 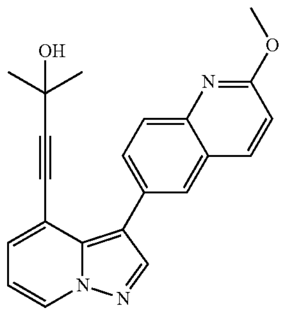 [SMILES: COc1ccc2cc(-c3cnn4cccc(C#CC(C)(C)O)c34)ccc2n1] | 4-(3-(2-methoxyquinolin-6-yl)pyrazolo[1,5-a]pyridin-4-yl)-2-methylbut-3-yn-2-ol | 358.5 |
| P-0283 | 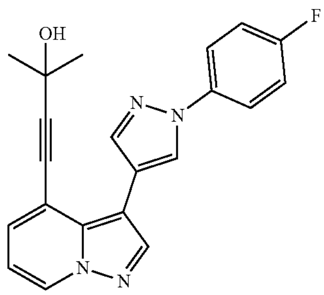 [SMILES: CC(C)(O)C#Cc1cccn2ncc(-c3cnn(-c4ccc(F)cc4)c3)c12] | 4-(3-(1-(4-fluorophenyl)-1H-pyrazol-4-yl)pyrazolo[1,5-a]pyridin-4-yl)-2-methylbut-3-yn-2-ol | 361.1 |
| P-0284 | 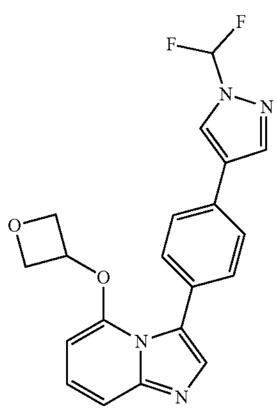 [SMILES: FC(F)n1cc(-c2ccc(-c3cnc4cccc(OC5COC5)n34)cc2)cn1] | 3-(4-(1-(difluoromethyl)-1H-pyrazol-4-yl)phenyl)-5-(oxetan-3-yloxy)imidazo[1,2-a]pyridine | 383.5 |
| P-0285 | 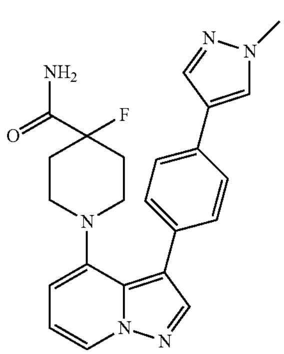 [SMILES: Cn1cc(-c2ccc(-c3cnn4cccc(N5CCC(F)(C(N)=O)CC5)c34)cc2)cn1] | 4-fluoro-1-(3-(4-(1-methyl-1H-pyrazol-4-yl)phenyl)pyrazolo[1,5-a]pyridin-4-yl)piperidine-4-carboxamide | 419.6 |

TABLE 1-continued

| P Number | Structure | Name | MS |
|---|---|---|---|
| P-0286 | 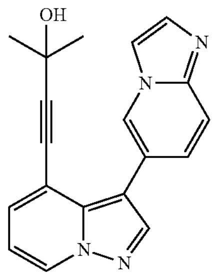 [SMILES: CC(C)(O)C#Cc1cccn2ncc(-c3ccc4nccn4c3)c12] | 4-(3-(imidazo[1,2-a]pyridin-6-yl)pyrazolo[1,5-a]pyridin-4-yl)-2-methylbut-3-yn-2-ol | 317.5 |
| P-0287 | 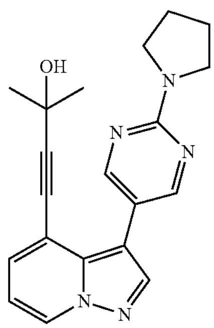 [SMILES: CC(C)(O)C#Cc1cccn2ncc(-c3cnc(N4CCCC4)nc3)c12] | 2-methyl-4-(3-(2-(pyrrolidin-1-yl)pyrimidin-5-yl)pyrazolo[1,5-a]pyridin-4-yl)but-3-yn-2-ol | 348.5 |
| P-0288 | 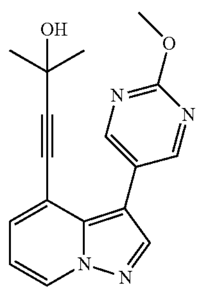 [SMILES: COc1ncc(-c2cnn3cccc(C#CC(C)(C)O)c23)cn1] | 4-(3-(2-methoxypyrimidin-5-yl)pyrazolo[1,5-a]pyridin-4-yl)-2-methylbut-3-yn-2-ol | 309.1 |
| P-0289 | 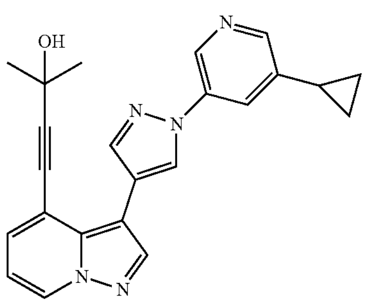 [SMILES: CC(C)(O)C#Cc1cccn2ncc(-c3cnn(-c4cncc(C5CC5)c4)c3)c12] | 4-(3-(1-(5-cyclopropylpyridin-3-yl)-1H-pyrazol-4-yl)pyrazolo[1,5-a]pyridin-4-yl)-2-methylbut-3-yn-2-ol | 384.6 |
| P-0290 | 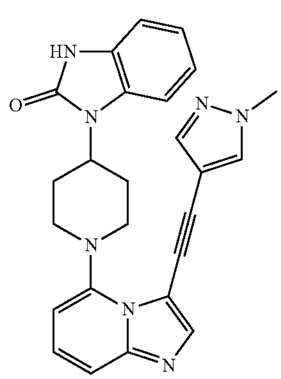 [SMILES: Cn1cc(C#Cc2cnc3cccc(N4CCC(n5c(=O)[nH]c6ccccc65)CC4)n23)cn1] | 1-(1-(3-((1-methyl-1H-pyrazol-4-yl)ethynyl)imidazo[1,2-a]pyridin-5-yl)piperidin-4-yl)-1,3-dihydro-2H-benzo[d]imidazol-2-one | 438.2 |

TABLE 1-continued

| P Number | Structure | Name | MS |
|---|---|---|---|
| P-0291 | 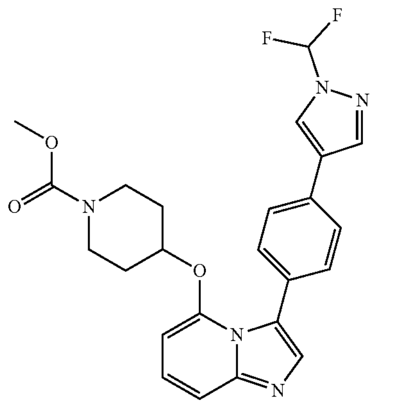 [SMILES: COC(=O)N1CCC(Oc2cccc3ncc(-c4ccc(-c5cnn(C(F)F)c5)cc4)n23)CC1] | methyl 4-((3-(4-(1-(difluoromethyl)-1H-pyrazol-4-yl)phenyl)imidazo[1,2-a]pyridin-5-yl)oxy)piperidine-1-carboxylate | 468.2 |
| P-0292 | 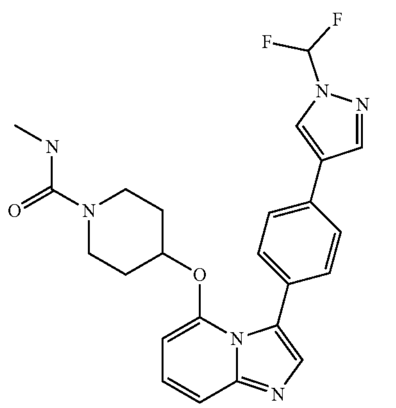 [SMILES: CNC(=O)N1CCC(Oc2cccc3ncc(-c4ccc(-c5cnn(C(F)F)c5)cc4)n23)CC1] | 4-((3-(4-(1-(difluoromethyl)-1H-pyrazol-4-yl)phenyl)imidazo[1,2-a]pyridin-5-yl)oxy)-N-methylpiperidine-1-carboxamide | 467.6 |
| P-0293 | 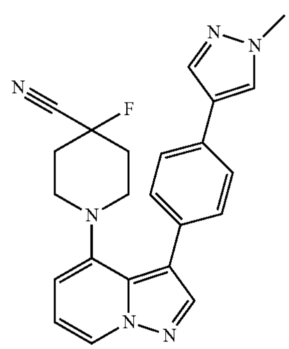 [SMILES: Cn1cc(-c2ccc(-c3cnn4cccc(N5CCC(F)(C#N)CC5)c34)cc2)cn1] | 4-fluoro-1-(3-(4-(1-methyl-1H-pyrazol-4-yl)phenyl)pyrazolo[1,5-a]pyridin-4-yl)piperidine-4-carbonitrile | 401.2 |
| P-0294 | 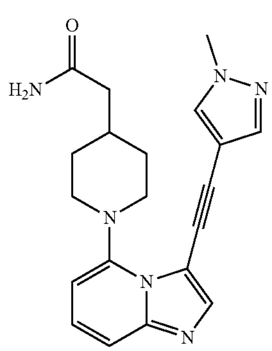 [SMILES: Cn1cc(C#Cc2cnc3cccc(N4CCC(CC(N)=O)CC4)n23)cn1] | 2-(1-(3-((1-methyl-1H-pyrazol-4-yl)ethynyl)imidazo[1,2-a]pyridin-5-yl)piperidin-4-yl)acetamide | 363.5 |

TABLE 1-continued

| P Number | Structure | Name | MS |
|---|---|---|---|
| P-0295 | 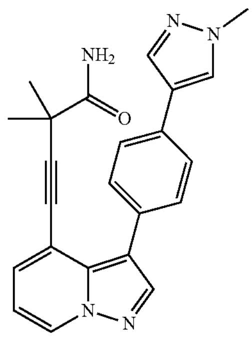 [SMILES: Cn1cc(-c2ccc(-c3cnn4cccc(C#CC(C)(C)C(N)=O)c34)cc2)cn1] | 2,2-dimethyl-4-(3-(4-(1-methyl-1H-pyrazol-4-yl)phenyl)pyrazolo[1,5-a]pyridin-4-yl)but-3-ynamide | 384.1 |
| P-0296 | 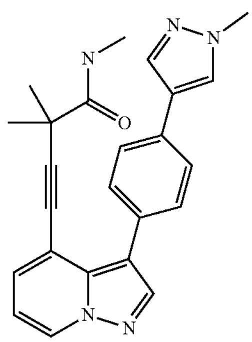 [SMILES: CNC(=O)C(C)(C)C#Cc1cccn2ncc(-c3ccc(-c4cnn(C)c4)cc3)c12] | N,2,2-trimethyl-4-(3-(4-(1-methyl-1H-pyrazol-4-yl)phenyl)pyrazolo[1,5-a]pyridin-4-yl)but-3-ynamide | 398.5 |
| P-0297 | 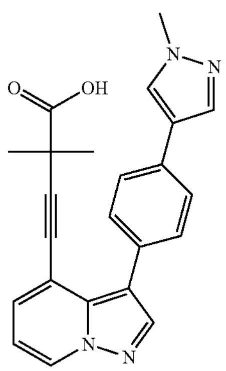 [SMILES: Cn1cc(-c2ccc(-c3cnn4cccc(C#CC(C)(C)C(=O)O)c34)cc2)cn1] | 2,2-dimethyl-4-(3-(4-(1-methyl-1H-pyrazol-4-yl)phenyl)pyrazolo[1,5-a]pyridin-4-yl)but-3-ynoic acid | 385.5 |
| P-0298 | 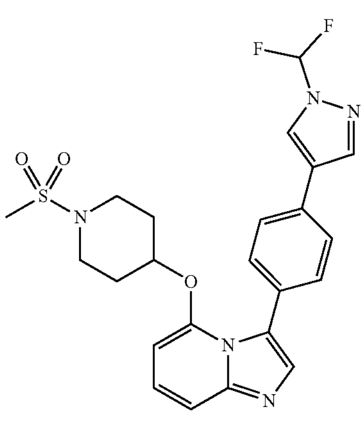 [SMILES: CS(=O)(=O)N1CCC(Oc2cccc3ncc(-c4ccc(-c5cnn(C(F)F)c5)cc4)n23)CC1] | 3-(4-(1-(difluoromethyl)-1H-pyrazol-4-yl)phenyl)-5-((1-(methylsulfonyl)piperidin-4-yl)oxy)imidazo[1,2-a]pyridine | 488.5 |

TABLE 1-continued

| P Number | Structure | Name | MS |
|---|---|---|---|
| P-0299 | 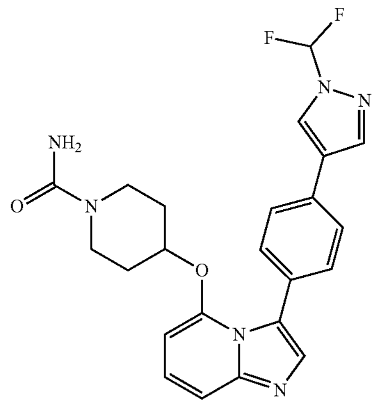 [SMILES: NC(=O)N1CCC(Oc2cccc3ncc(-c4ccc(-c5cnn(C(F)F)c5)cc4)n23)CC1] | 4-((3-(4-(1-(difluoromethyl)-1H-pyrazol-4-yl)phenyl)imidazo[1,2-a]pyridin-5-yl)oxy)piperidine-1-carboxamide | 453.1 |
| P-0300 | 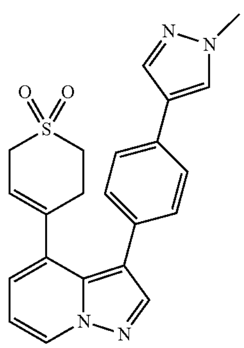 [SMILES: Cn1cc(-c2ccc(-c3cnn4cccc(C5=CCS(=O)(=O)CC5)c34)cc2)cn1] | 4-(3-(4-(1-methyl-1H-pyrazol-4-yl)phenyl)pyrazolo[1,5-a]pyridin-4-yl)-3,6-dihydro-2H-thiopyran 1,1-dioxide | 405.1 |
| P-0301 | 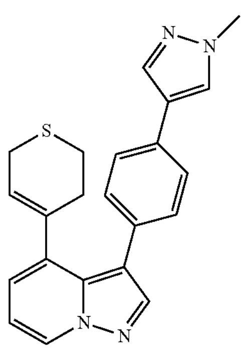 [SMILES: Cn1cc(-c2ccc(-c3cnn4cccc(C5=CCSCC5)c34)cc2)cn1] | 4-(3,6-dihydro-2H-thiopyran-4-yl)-3-(4-(1-methyl-1H-pyrazol-4-yl)phenyl)pyrazolo[1,5-a]pyridine | 373.1 |
| P-0302 | 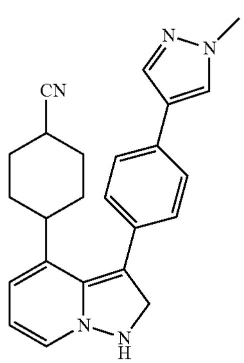 [SMILES: Cn1cc(-c2ccc(C3=C4C(C5CCC(C#N)CC5)=CC=CN4NC3)cc2)cn1] | 4-(3-(4-(1-methyl-1H-pyrazol-4-yl)phenyl)-1,2-dihydropyrazolo[1,5-a]pyridin-4-yl)cyclohexane-1-carbonitrile | 384.1 |

TABLE 1-continued

| P Number | Structure | Name | MS |
|---|---|---|---|
| P-0303 | 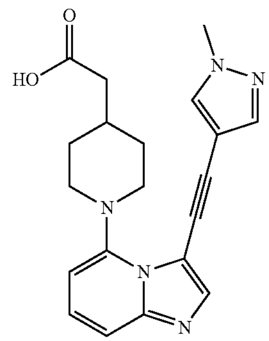 [SMILES: Cn1cc(C#Cc2cnc3cccc(N4CCC(CC(=O)O)CC4)n23)cn1] | 2-(1-(3-((1-methyl-1H-pyrazol-4-yl)ethynyl)imidazo[1,2-a]pyridin-5-yl)piperidin-4-yl)acetic acid | 364.6 |
| P-0304 | 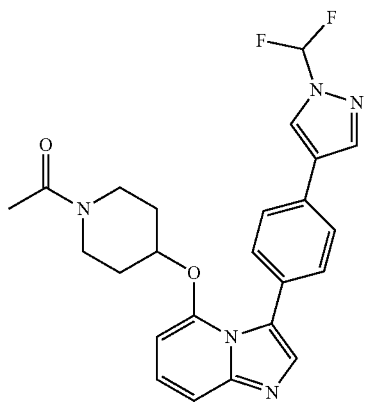 [SMILES: CC(=O)N1CCC(Oc2cccc3ncc(-c4ccc(-c5cnn(C(F)F)c5)cc4)n23)CC1] | 1-(4-((3-(4-(1-(difluoromethyl)-1H-pyrazol-4-yl)phenyl)imidazo[1,2-a]pyridin-5-yl)oxy)piperidin-1-yl)ethan-1-one | 452.6 |
| P-0305 | 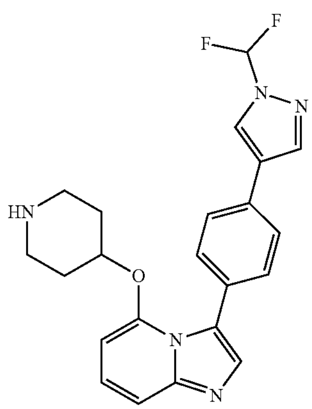 [SMILES: FC(F)n1cc(-c2ccc(-c3cnc4cccc(OC5CCNCC5)n34)cc2)cn1] | 3-(4-(1-(difluoromethyl)-1H-pyrazol-4-yl)phenyl)-5-(piperidin-4-yloxy)imidazo[1,2-a]pyridine | 410.0 |
| P-0306 | 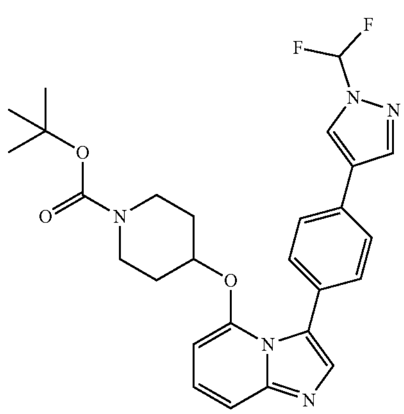 [SMILES: CC(C)(C)OC(=O)N1CCC(Oc2cccc3ncc(-c4ccc(-c5cnn(C(F)F)c5)cc4)n23)CC1] | tert-butyl 4-((3-(4-(1-(difluoromethyl)-1H-pyrazol-4-yl)phenyl)imidazo[1,2-a]pyridin-5-yl)oxy)piperidine-1-carboxylate | 510.2 |

TABLE 1-continued

| P Number | Structure | Name | MS |
|---|---|---|---|
| P-0307 | 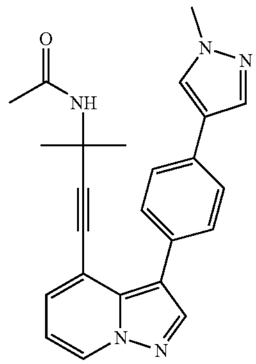 [SMILES: CC(=O)NC(C)(C)C#Cc1cccn2ncc(-c3ccc(-c4cnn(C)c4)cc3)c12] | N-(2-methyl-4-(3-(4-(1-methyl-1H-pyrazol-4-yl)phenyl)pyrazolo[1,5-a]pyridin-4-yl)but-3-yn-2-yl)acetamide | 398.1 |
| P-0308 | 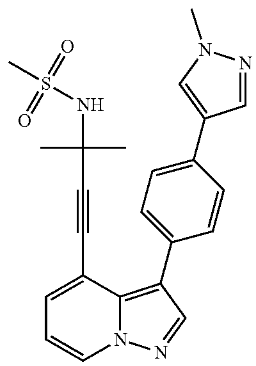 [SMILES: Cn1cc(-c2ccc(-c3cnn4cccc(C#CC(C)(C)NS(C)(=O)=O)c34)cc2)cn1] | N-(2-methyl-4-(3-(4-(1-methyl-1H-pyrazol-4-yl)phenyl)pyrazolo[1,5-a]pyridin-4-yl)but-3-yn-2-yl)methanesulfonamide | 434.2 |
| P-0309 | 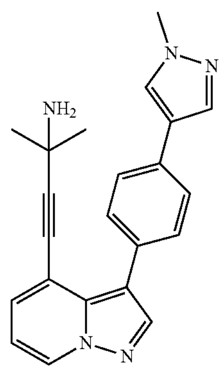 [SMILES: Cn1cc(-c2ccc(-c3cnn4cccc(C#CC(C)(C)N)c34)cc2)cn1] | 2-methyl-4-(3-(4-(1-methyl-1H-pyrazol-4-yl)phenyl)pyrazolo[1,5-a]pyridin-4-yl)but-3-yn-2-amine | 357.2 |
| P-0310 | 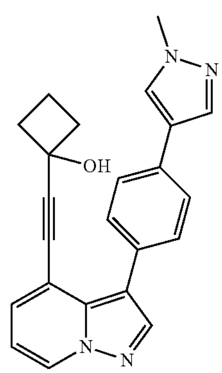 [SMILES: Cn1cc(-c2ccc(-c3cnn4cccc(C#CC5(O)CCC5)c34)cc2)cn1] | 1-((3-(4-(1-methyl-1H-pyrazol-4-yl)phenyl)pyrazolo[1,5-a]pyridin-4-yl)ethynyl)cyclobutan-1-ol | 369.5 |

TABLE 1-continued

| P Number | Structure | Name | MS |
|---|---|---|---|
| P-0311 | 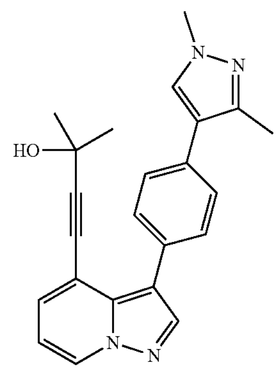 [SMILES: Cc1nn(C)cc1-c1ccc(-c2cnn3cccc(C#CC(C)(C)O)c23)cc1] | 4-(3-(4-(1,3-dimethyl-1H-pyrazol-4-yl)phenyl)pyrazolo[1,5-a]pyridin-4-yl)-2-methylbut-3-yn-2-ol | 371.6 |
| P-0312 | 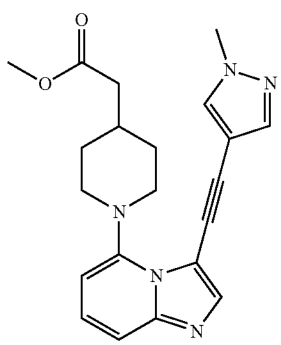 [SMILES: COC(=O)CC1CCN(c2cccc3ncc(C#Cc4cnn(C)c4)n23)CC1] | methyl 2-(1-(3-((1-methyl-1H-pyrazol-4-yl)ethynyl)imidazo[1,2-a]pyridin-5-yl)piperidin-4-yl)acetate | 378.6 |
| P-0313 | 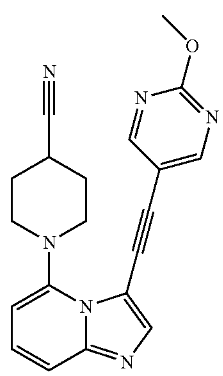 [SMILES: COc1ncc(C#Cc2cnc3cccc(N4CCC(C#N)CC4)n23)cn1] | 1-(3-((2-methoxypyrimidin-5-yl)ethynyl)imidazo[1,2-a]pyridin-5-yl)piperidine-4-carbonitrile | 359.2 |
| P-0314 | 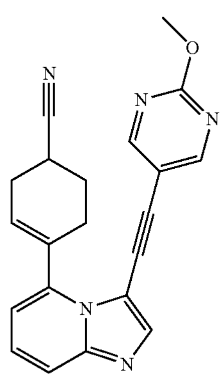 [SMILES: COc1ncc(C#Cc2cnc3cccc(C4=CCC(C#N)CC4)n23)cn1] | 4-(3-((2-methoxypyrimidin-5-yl)ethynyl)imidazo[1,2-a]pyridin-5-yl)cyclohex-3-ene-1-carbonitrile | 356.6 |

TABLE 1-continued

| P Number | Structure | Name | MS |
|---|---|---|---|
| P-0315 | 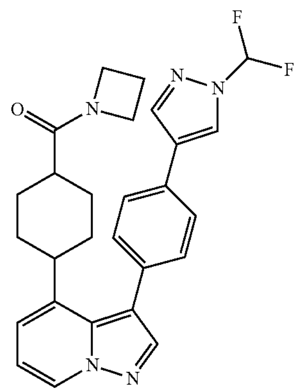 [SMILES: O=C(C1CCC(c2cccn3ncc(-c4ccc(-c5cnn(C(F)F)c5)cc4)c23)CC1)N1CCC1] | azetidin-1-yl(4-(3-(4-(1-(difluoromethyl)-1H-pyrazol-4-yl)phenyl)pyrazolo[1,5-a]pyridin-4-yl)cyclohexyl)methanone | 476.1 |
| P-0316 | 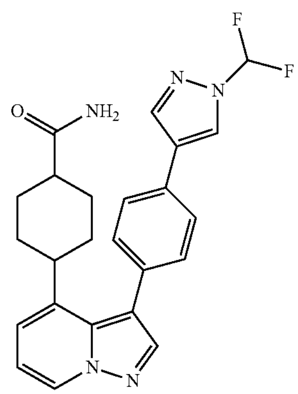 [SMILES: NC(=O)C1CCC(c2cccn3ncc(-c4ccc(-c5cnn(C(F)F)c5)cc4)c23)CC1] | 4-(3-(4-(1-(difluoromethyl)-1H-pyrazol-4-yl)phenyl)pyrazolo[1,5-a]pyridin-4-yl)cyclohexane-1-carboxamide | 436.0 |
| P-0317 | 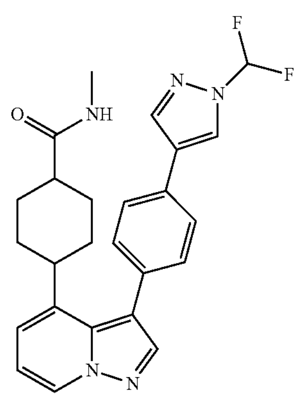 [SMILES: CNC(=O)C1CCC(c2cccn3ncc(-c4ccc(-c5cnn(C(F)F)c5)cc4)c23)CC1] | 4-(3-(4-(1-(difluoromethyl)-1H-pyrazol-4-yl)phenyl)pyrazolo[1,5-a]pyridin-4-yl)-N-methylcyclohexane-1-carboxamide | 450.1 |
| P-0318 | 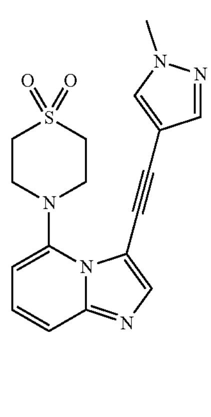 [SMILES: Cn1cc(C#Cc2cnc3cccc(N4CCS(=O)(=O)CC4)n23)cn1] | 4-(3-((1-methyl-1H-pyrazol-4-yl)ethynyl)imidazo[1,2-a]pyridin-5-yl)thiomorpholine 1,1-dioxide | 356.5 |

TABLE 1-continued

| P Number | Structure | Name | MS |
|---|---|---|---|
| P-0319 | 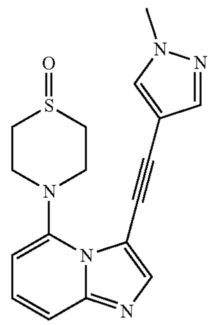 [SMILES: Cn1cc(C#Cc2cnc3cccc(N4CCS(=O)CC4)n23)cn1] | 4-(3-((1-methyl-1H-pyrazol-4-yl)ethynyl)imidazo[1,2-a]pyridin-5-yl)thiomorpholine 1-oxide | 340.1 |
| P-0321 | 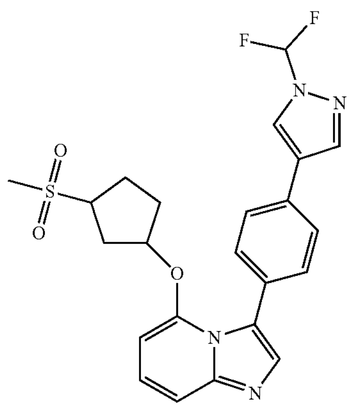 [SMILES: CS(=O)(=O)C1CCC(Oc2cccc3ncc(-c4ccc(-c5cnn(C(F)F)c5)cc4)n23)C1] | 3-(4-(1-(difluoromethyl)-1H-pyrazol-4-yl)phenyl)-5-((3-(methylsulfonyl)cyclopentyl)oxy)imidazo[1,2-a]pyridine | 473.5 |
| P-0322 | 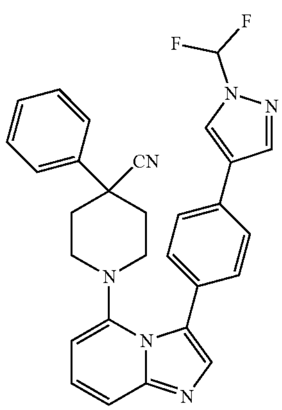 [SMILES: N#CC1(c2ccccc2)CCN(c2cccc3ncc(-c4ccc(-c5cnn(C(F)F)c5)cc4)n23)CC1] | 1-(3-(4-(1-(difluoromethyl)-1H-pyrazol-4-yl)phenyl)imidazo[1,2-a]pyridin-5-yl)-4-phenylpiperidine-4-carbonitrile | 495.2 |
| P-0323 | 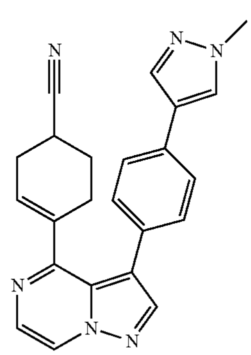 [SMILES: Cn1cc(-c2ccc(-c3cnn4ccnc(C5=CCC(C#N)CC5)c34)cc2)cn1] | 4-(3-(4-(1-methyl-1H-pyrazol-4-yl)phenyl)pyrazolo[1,5-a]pyrazin-4-yl)cyclohex-3-ene-1-carbonitrile | 381.5 |

TABLE 1-continued

| P Number | Structure | Name | MS |
|---|---|---|---|
| P-0324 | 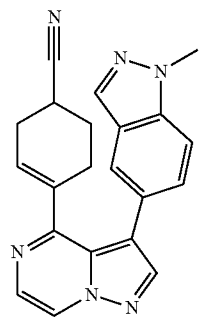 [SMILES: Cn1ncc2cc(-c3cnn4ccnc(C5=CCC(C#N)CC5)c34)ccc21] | 4-(3-(1-methyl-1H-indazol-5-yl)pyrazolo[1,5-a]pyrazin-4-yl)cyclohex-3-ene-1-carbonitrile | 355.1 |
| P-0325 | 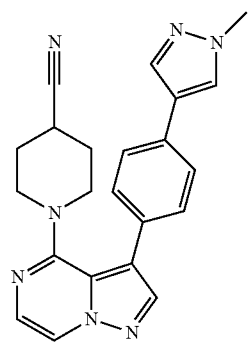 [SMILES: Cn1cc(-c2ccc(-c3cnn4ccnc(N5CCC(C#N)CC5)c34)cc2)cn1] | 1-(3-(4-(1-methyl-1H-pyrazol-4-yl)phenyl)pyrazolo[1,5-a]pyrazin-4-yl)piperidine-4-carbonitrile | 384.2 |
| P-0326 | 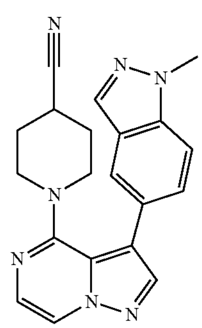 [SMILES: Cn1ncc2cc(-c3cnn4ccnc(N5CCC(C#N)CC5)c34)ccc21] | 1-(3-(1-methyl-1H-indazol-5-yl)pyrazolo[1,5-a]pyrazin-4-yl)piperidine-4-carbonitrile | 358.2 |
| P-0327 | 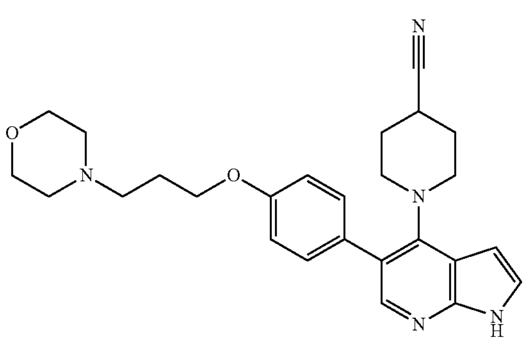 [SMILES: N#CC1CCN(c2c(-c3ccc(OCCCN4CCOCC4)cc3)cnc3[nH]ccc23)CC1] | 1-(5-(4-(3-morpholinopropoxy)phenyl)-1H-pyrrolo[2,3-b]pyridin-4-yl)piperidine-4-carbonitrile | 446.1 |

TABLE 1-continued

| P Number | Structure | Name | MS |
|---|---|---|---|
| P-0328 | 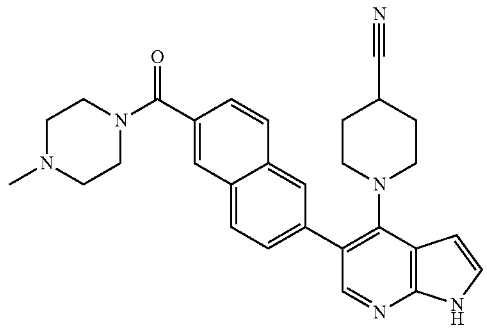 [SMILES: CN1CCN(C(=O)c2ccc3cc(-c4cnc5[nH]ccc5c4N4CCC(C#N)CC4)ccc3c2)CC1] | 1-(5-(6-(4-methylpiperazine-1-carbonyl)naphthalen-2-yl)-1H-pyrrolo[2,3-b]pyridin-4-yl)piperidine-4-carbonitrile | 477.1 |
| P-0329 | 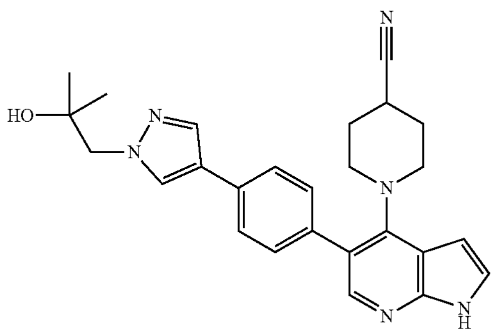 [SMILES: CC(C)(O)Cn1cc(-c2ccc(-c3cnc4[nH]ccc4c3N3CCC(C#N)CC3)cc2)cn1] | 1-(5-(4-(1-(2-hydroxy-2-methylpropyl)-1H-pyrazol-4-yl)phenyl)-1H-pyrrolo[2,3-b]pyridin-4-yl)piperidine-4-carbonitrile | 441.1 |
| P-0330 | 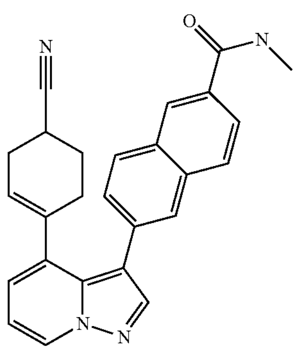 [SMILES: CNC(=O)c1ccc2cc(-c3cnn4cccc(C5=CCC(C#N)CC5)c34)ccc2c1] | 6-(4-(4-cyanocyclohex-1-en-1-yl)pyrazolo[1,5-a]pyridin-3-yl)-N-methyl-2-naphthamide | 407.1 |
| P-0331 | 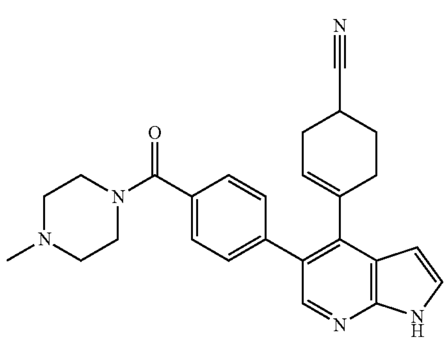 [SMILES: CN1CCN(C(=O)c2ccc(-c3cnc4[nH]ccc4c3C3=CCC(C#N)CC3)cc2)CC1] | 4-(5-(4-(4-methylpiperazine-1-carbonyl)phenyl)-1H-pyrrolo[2,3-b]pyridin-4-yl)cyclohex-3-ene-1-carbonitrile | 424.1 |

TABLE 1-continued

| P Number | Structure | Name | MS |
|---|---|---|---|
| P-0332 | 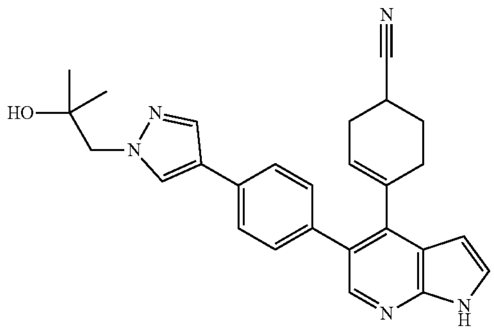 [SMILES: CC(C)(O)Cn1cc(-c2ccc(-c3cnc4[nH]ccc4c3C3=CCC(C#N)CC3)cc2)cn1] | 4-(5-(4-(1-(2-hydroxy-2-methylpropyl)-1H-pyrazol-4-yl)phenyl)-1H-pyrrolo[2,3-b]pyridin-4-yl)cyclohex-3-ene-1-carbonitrile | 438.1 |
| P-0333 | 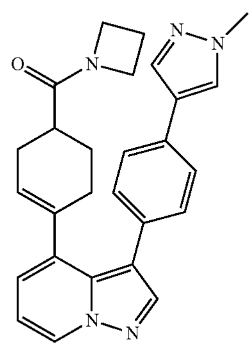 [SMILES: Cn1cc(-c2ccc(-c3cnn4cccc(C5=CCC(C(=O)N6CCC6)CC5)c34)cc2)cn1] | azetidin-1-yl(4-(3-(4-(1-methyl-1H-pyrazol-4-yl)phenyl)pyrazolo[1,5-a]pyridin-4-yl)cyclohex-3-en-1-yl)methanone | 438.2 |
| P-0334 | 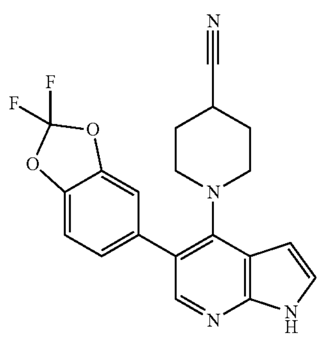 [SMILES: N#CC1CCN(c2c(-c3ccc4c(c3)OC(F)(F)O4)cnc3[nH]ccc23)CC1] | 1-(5-(2,2-difluorobenzo[d][1,3]dioxol-5-yl)-1H-pyrrolo[2,3-b]pyridin-4-yl)piperidine-4-carbonitrile | 383.0 |
| P-0335 | 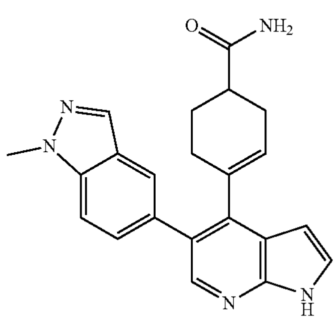 [SMILES: Cn1ncc2cc(-c3cnc4[nH]ccc4c3C3=CCC(C(N)=O)CC3)ccc21] | 4-(5-(1-methyl-1H-indazol-5-yl)-1H-pyrrolo[2,3-b]pyridin-4-yl)cyclohex-3-ene-1-carboxamide | 372.0 |
| P-0336 | 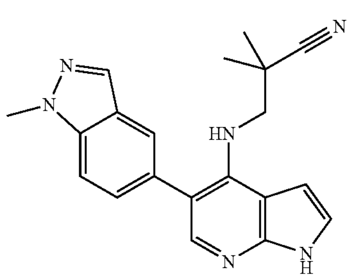 [SMILES: Cn1ncc2cc(-c3cnc4[nH]ccc4c3NCC(C)(C)C#N)ccc21] | 2,2-dimethyl-3-((5-(1-methyl-1H-indazol-5-yl)-1H-pyrrolo[2,3-b]pyridin-4-yl)amino)propanenitrile | 345.0 |

TABLE 1-continued

| P Number | Structure | Name | MS |
|---|---|---|---|
| P-0337 | 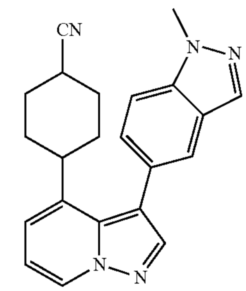 [SMILES: Cn1ncc2cc(-c3cnn4cccc(C5CCC(C#N)CC5)c34)ccc21] | 4-(3-(1-methyl-1H-indazol-5-yl)pyrazolo[1,5-a]pyridin-4-yl)cyclohexane-1-carbonitrile | 356.0 |
| P-0338 | 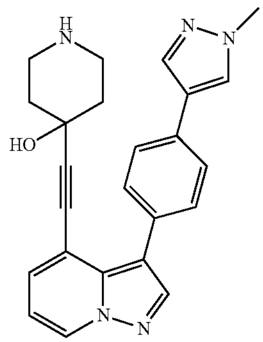 [SMILES: Cn1cc(-c2ccc(-c3cnn4cccc(C#CC5(O)CCNCC5)c34)cc2)cn1] | 4-((3-(4-(1-methyl-1H-pyrazol-4-yl)phenyl)pyrazolo[1,5-a]pyridin-4-yl)ethynyl)piperidin-4-ol | 398.3 |
| P-0339 | 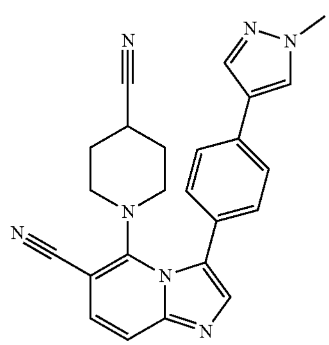 [SMILES: Cn1cc(-c2ccc(-c3cnc4ccc(C#N)c(N5CCC(C#N)CC5)n34)cc2)cn1] | 5-(4-cyanopiperidin-1-yl)-3-(4-(1-methyl-1H-pyrazol-4-yl)phenyl)imidazo[1,2-a]pyridine-6-carbonitrile | 408.4 |
| P-0340 | 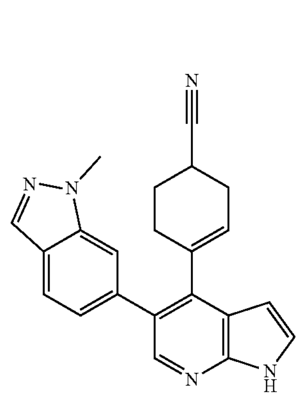 [SMILES: Cn1ncc2ccc(-c3cnc4[nH]ccc4c3C3=CCC(C#N)CC3)cc21] | 4-(5-(1-methyl-1H-indazol-6-yl)-1H-pyrrolo[2,3-b]pyridin-4-yl)cyclohex-3-ene-1-carbonitrile | 354.0 |

TABLE 1-continued

| P Number | Structure | Name | MS |
|---|---|---|---|
| P-0341 | 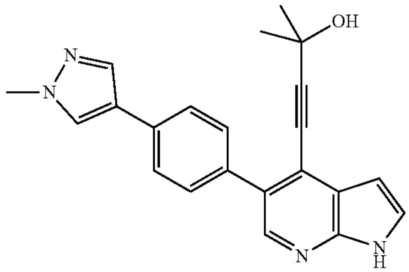 [SMILES: Cn1cc(-c2ccc(-c3cnc4[nH]ccc4c3C#CC(C)(C)O)cc2)cn1] | 2-methyl-4-(5-(4-(1-methyl-1H-pyrazol-4-yl)phenyl)-1H-pyrrolo[2,3-b]pyridin-4-yl)but-3-yn-2-ol | 357.0 |
| P-0342 | 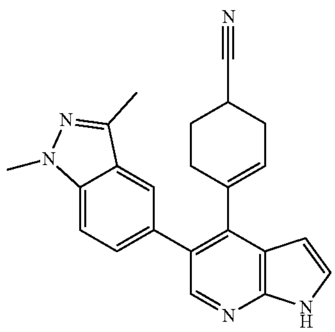 [SMILES: Cc1nn(C)c2ccc(-c3cnc4[nH]ccc4c3C3=CCC(C#N)CC3)cc12] | 4-(5-(1,3-dimethyl-1H-indazol-5-yl)-1H-pyrrolo[2,3-b]pyridin-4-yl)cyclohex-3-ene-1-carbonitrile | 368.1 |
| P-0343 | 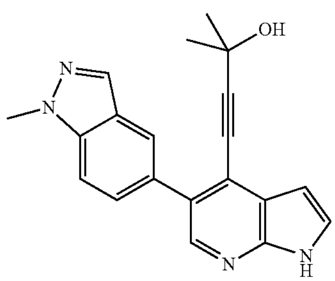 [SMILES: Cn1ncc2cc(-c3cnc4[nH]ccc4c3C#CC(C)(C)O)ccc21] | 2-methyl-4-(5-(1-methyl-1H-indazol-5-yl)-1H-pyrrolo[2,3-b]pyridin-4-yl)but-3-yn-2-ol | 331.0 |
| P-0344 | 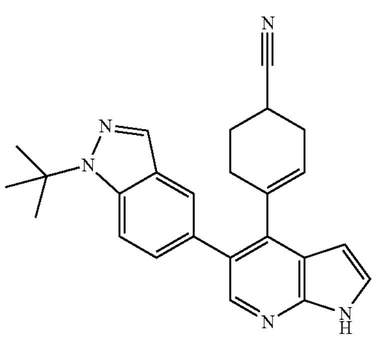 [SMILES: CC(C)(C)n1ncc2cc(-c3cnc4[nH]ccc4c3C3=CCC(C#N)CC3)ccc21] | 4-(5-(1-(tert-butyl)-1H-indazol-5-yl)-1H-pyrrolo[2,3-b]pyridin-4-yl)cyclohex-3-ene-1-carbonitrile | 396.1 |
| P-0345 | 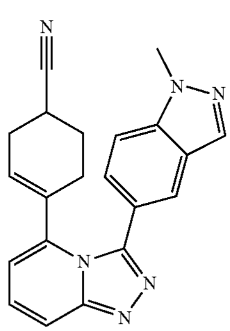 [SMILES: Cn1ncc2cc(-c3nnc4cccc(C5=CCC(C#N)CC5)n34)ccc21] | 4-(3-(1-methyl-1H-indazol-5-yl)-[1,2,4]triazolo[4,3-a]pyridin-5-yl)cyclohex-3-ene-1-carbonitrile | 355.0 |

TABLE 1-continued

| P Number | Structure | Name | MS |
|---|---|---|---|
| P-0346 | 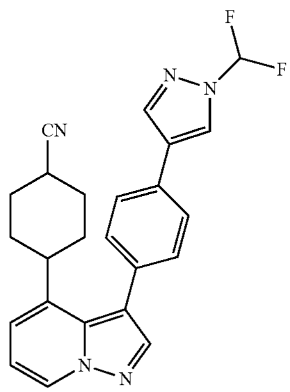 [SMILES: N#CC1CCC(c2cccn3ncc(-c4ccc(-c5cnn(C(F)F)c5)cc4)c23)CC1] | 4-(3-(4-(1-(difluoromethyl)-1H-pyrazol-4-yl)phenyl)pyrazolo[1,5-a]pyridin-4-yl)cyclohexane-1-carbonitrile | 418.3 |
| P-0347 | 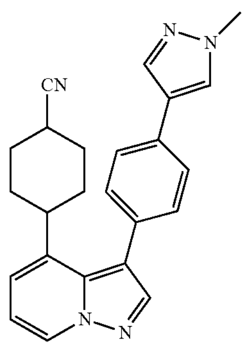 [SMILES: Cn1cc(-c2ccc(-c3cnn4cccc(C5CCC(C#N)CC5)c34)cc2)cn1] | 4-(3-(4-(1-methyl-1H-pyrazol-4-yl)phenyl)pyrazolo[1,5-a]pyridin-4-yl)cyclohexane-1-carbonitrile | 382.1 |
| P-0348 | 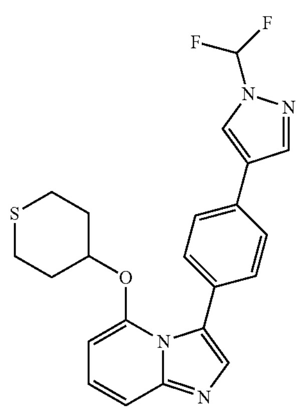 [SMILES: FC(F)n1cc(-c2ccc(-c3cnc4cccc(OC5CCSCC5)n34)cc2)cn1] | 3-(4-(1-(difluoromethyl)-1H-pyrazol-4-yl)phenyl)-5-((tetrahydro-2H-thiopyran-4-yl)oxy)imidazo[1,2-a]pyridine | 427.3 |
| P-0349 | 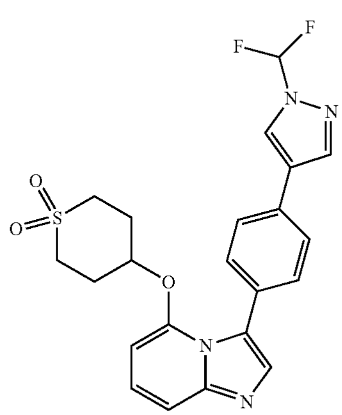 [SMILES: O=S1(=O)CCC(Oc2cccc3ncc(-c4ccc(-c5cnn(C(F)F)c5)cc4)n23)CC1] | 4-((3-(4-(1-(difluoromethyl)-1H-pyrazol-4-yl)phenyl)imidazo[1,2-a]pyradin-5-yl)oxy)tetrahydro-2H-thiopyran 1,1-dioxide | 459.0 |

TABLE 1-continued

| P Number | Structure | Name | MS |
|---|---|---|---|
| P-0350 | 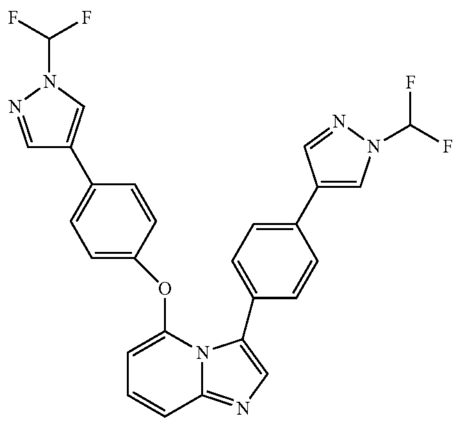 [SMILES: FC(F)n1cc(-c2ccc(Oc3cccc4ncc(-c5ccc(-c6cnn(C(F)F)c6)cc5)n34)cc2)cn1] | 5-(4-(1-(difluoromethyl)-1H-pyrazol-4-yl)phenoxy)-3-(4-(1-(difluoromethyl)-1H-pyrazol-4-yl)phenyl)imidazo[1,2-a]pyridine | 519.3 |
| P-0351 | 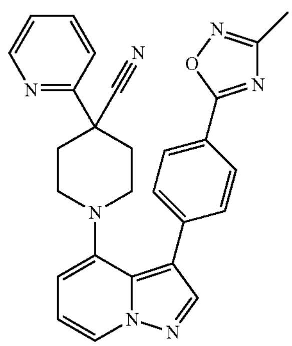 [SMILES: Cc1noc(-c2ccc(-c3cnn4cccc(N5CCC(C#N)(c6ccccn6)CC5)c34)cc2)n1] | 1-(3-(4-(3-methyl-1,2,4-oxadiazol-5-yl)phenyl)pyrazolo[1,5-a]pyridin-4-yl)-4-(pyridin-2-yl)piperidine-4-carbonitrile | 462.4 |
| P-0352 | 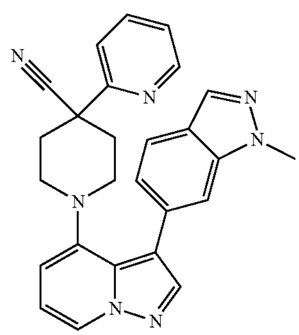 [SMILES: Cn1ncc2ccc(-c3cnn4cccc(N5CCC(C#N)(c6ccccn6)CC5)c34)cc21] | 1-(3-(1-methyl-1H-indazol-6-yl)pyrazolo[1,5-a]pyridin-4-yl)-4-(pyridin-2-yl)piperidine-4-carbonitrile | 434.4 |
| P-0353 | 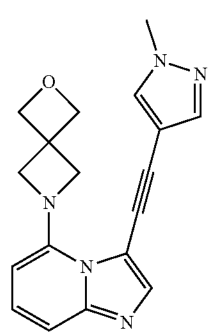 [SMILES: Cn1cc(C#Cc2cnc3cccc(N4CC5(COC5)C4)n23)cn1] | 6-(3-((1-methyl-1H-pyrazol-4-yl)ethynyl)imidazo[1,2-a]pyridin-5-yl)-2-oxa-6-azaspiro[3.3]heptane | 320.2 |

TABLE 1-continued

| P Number | Structure | Name | MS |
|---|---|---|---|
| P-0354 | 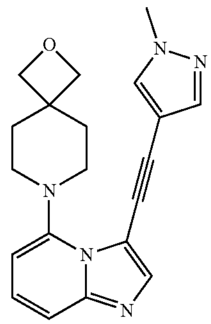 [SMILES: Cn1cc(C#Cc2cnc3cccc(N4CCC5(CC4)COC5)n23)cn1] | 7-(3-((1-methyl-1H-pyrazol-4-yl)ethynyl)imidazo[1,2-a]pyridin-5-yl)-2-oxa-7-azaspiro[3.5]nonane | 348.3 |
| P-0355 | 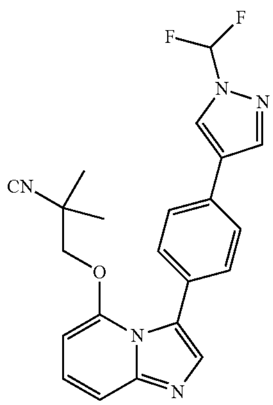 | 3-((3-(4-(1-(difluoromethyl)-1H-pyrazol-4-yl)phenyl)imidazo[1,2-a]pyridin-5-yl)oxy)-2,2-dimethylpropanenitrile | 408.3 |
| P-0356 | 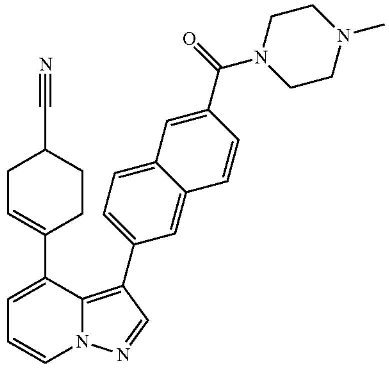 [SMILES: CN1CCN(C(=O)c2ccc3cc(-c4cnn5cccc(C6=CCC(C#N)CC6)c45)ccc3c2)CC1] | 4-(3-(6-(4-methylpiperazine-1-carbonyl)naphthalen-2-yl)pyrazolo[1,5-a]pyridin-4-yl)cyclohex-3-ene-1-carbonitrile | 476.2 |
| P-0357 | 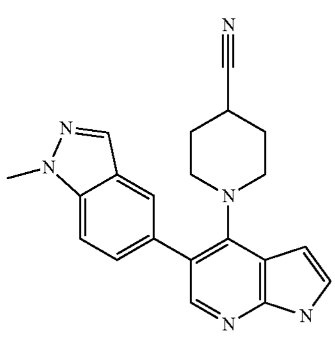 [SMILES: Cn1ncc2cc(-c3cnc4[nH]ccc4c3N3CCC(C#N)CC3)ccc21] | 1-(5-(1-methyl-1H-indazol-5-yl)-1H-pyrrolo[2,3-b]pyridin-4-yl)piperidine-4-carbonitrile | 357.0 |

TABLE 1-continued

| P Number | Structure | Name | MS |
|---|---|---|---|
| P-0358 | 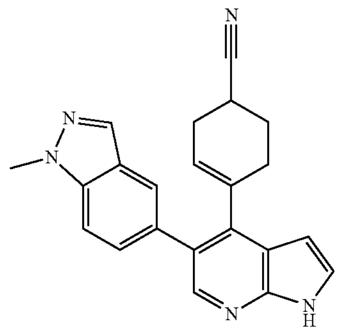 [SMILES: Cn1ncc2cc(-c3cnc4[nH]ccc4c3C3=CCC(C#N)CC3)ccc21] | 4-(5-(1-methyl-1H-indazol-5-yl)-1H-pyrrolo[2,3-b]pyridin-4-yl)cyclohex-3-ene-1-carbonitrile | 354.0 |
| P-0359 | 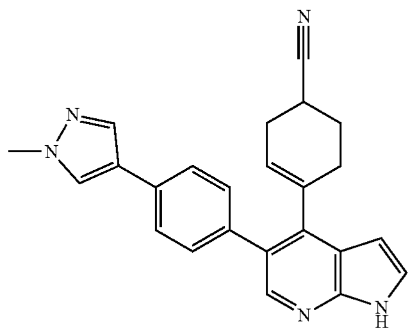 [SMILES: Cn1cc(-c2ccc(-c3cnc4[nH]ccc4c3C3=CCC(C#N)CC3)cc2)cn1] | 4-(5-(4-(1-methyl-1H-pyrazol-4-yl)phenyl)-1H-pyrrolo[2,3-b]pyridin-4-yl)cyclohex-3-ene-1-carbonitrile | 380.5 |
| P-0360 | 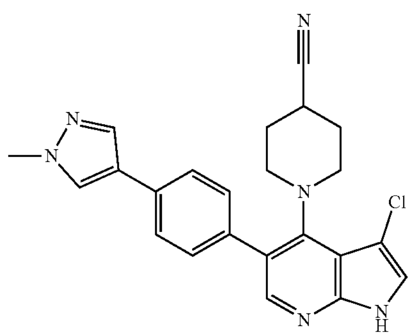 [SMILES: Cn1cc(-c2ccc(-c3cnc4[nH]cc(Cl)c4c3N3CCC(C#N)CC3)cc2)cn1] | 1-(3-chloro-5-(4-(1-methyl-1H-pyrazol-4-yl)phenyl)-1H-pyrrolo[2,3-b]pyridin-4-yl)piperidine-4-carbonitrile | 417.0 |
| P-0361 | 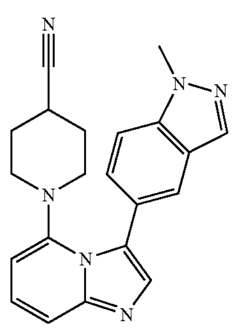 [SMILES: Cn1ncc2cc(-c3cnc4cccc(N5CCC(C#N)CC5)n34)ccc21] | 1-(3-(1-methyl-1H-indazol-5-yl)imidazo[1,2-a]pyridin-5-yl)piperidine-4-carbonitrile | 357.3 |

TABLE 1-continued

| P Number | Structure | Name | MS |
|---|---|---|---|
| P-0362 | 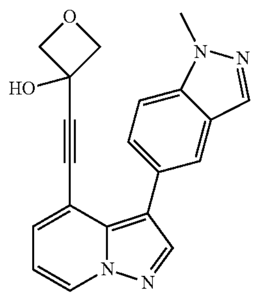 [SMILES: Cn1ncc2cc(-c3cnn4cccc(C#CC5(O)COC5)c34)ccc21] | 3-((3-(1-methyl-1H-indazol-5-yl)pyrazolo[1,5-a]pyridin-4-yl)ethynyl)oxetan-3-ol | 345.0 |
| P-0363 | 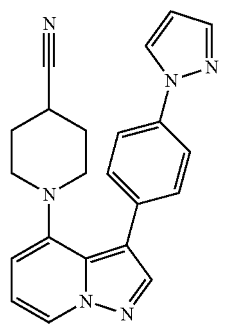 | 1-(3-(4-(1H-pyrazol-1-yl)phenyl)pyrazolo[1,5-a]pyridin-4-yl)piperidine-4-carbonitrile | 369.0 |
| P-0364 | 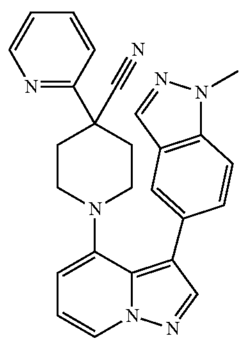 [SMILES: Cn1ncc2cc(-c3cnn4cccc(N5CCC(C#N)(c6ccccn6)CC5)c34)ccc21] | 1-(3-(1-methyl-1H-indazol-5-yl)pyrazolo[1,5-a]pyridin-4-yl)-4-(pyridin-2-yl)piperidine-4-carbonitrile | 434.4 |
| P-0365 | 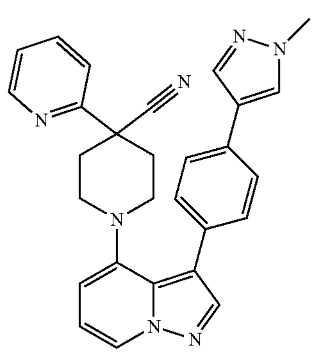 [SMILES: Cn1cc(-c2ccc(-c3cnn4cccc(N5CCC(C#N)(c6ccccn6)CC5)c34)cc2)cn1] | 1-(3-(4-(1-methyl-1H-pyrazol-4-yl)phenyl)pyrazolo[1,5-a]pyridin-4-yl)-4-(pyridin-2-yl)piperidine-4-carbonitrile | 460.3 |

TABLE 1-continued

| P Number | Structure | Name | MS |
|---|---|---|---|
| P-0366 | 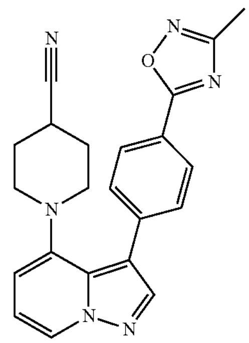 [SMILES: Cc1noc(-c2ccc(-c3cnn4cccc(N5CCC(C#N)CC5)c34)cc2)n1] | 1-(3-(4-(3-methyl-1,2,4-oxadiazol-5-yl)phenyl)pyrazolo[1,5-a]pyridin-4-yl)piperidine-4-carbonitrile | 385.3 |
| P-0367 | 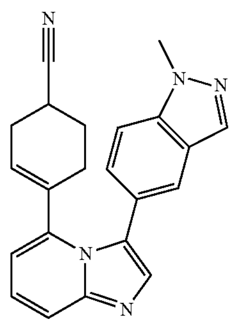 [SMILES: Cn1ncc2cc(-c3cnc4cccc(C5=CCC(C#N)CC5)n34)ccc21] | 4-(3-(1-methyl-1H-indazol-5-yl)imidazo[1,2-a]pyridin-5-yl)cyclohex-3-ene-1-carbonitrile | 354.0 |
| P-0368 | 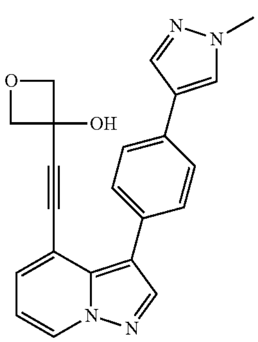 [SMILES: Cn1cc(-c2ccc(-c3cnn4cccc(C#CC5(O)COC5)c34)cc2)cn1] | 3-((3-(4-(1-methyl-1H-pyrazol-4-yl)phenyl)pyrazolo[1,5-a]pyridin-4-yl)ethynyl)oxetan-3-ol | 371.2 |
| P-0369 | 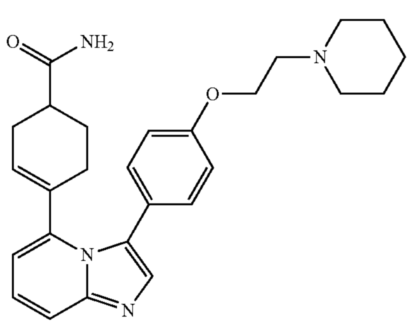 [SMILES: NC(=O)C1CC=C(c2cccc3ncc(-c4ccc(OCCN5CCCCC5)cc4)n23)CC1] | 4-(3-(4-(2-(piperidin-1-yl)ethoxy)phenyl)imidazo[1,2-a]pyridin-5-yl)cyclohex-3-ene-1-carboxamide | 445.4 |

TABLE 1-continued

| P Number | Structure | Name | MS |
|---|---|---|---|
| P-0370 | 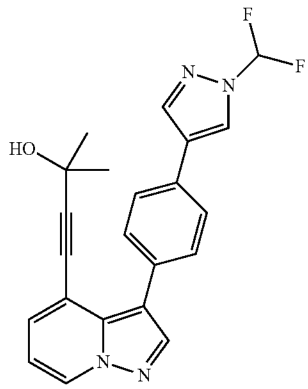 [SMILES: CC(C)(O)C#Cc1cccn2ncc(-c3ccc(-c4cnn(C(F)F)c4)cc3)c12] | 4-(3-(4-(1-(difluoromethyl)-1H-pyrazol-4-yl)phenyl)pyrazolo[1,5-a]pyridin-4-yl)-2-methylbut-3-yn-2-ol | 393.3 |
| P-0371 | 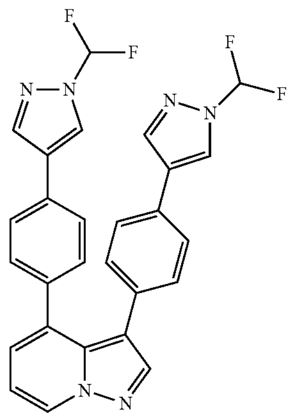 [SMILES: FC(F)n1cc(-c2ccc(-c3cccn4ncc(-c5ccc(-c6cnn(C(F)F)c6)cc5)c34)cc2)cn1] | 3,4-bis(4-(1-(difluoromethyl)-1H-pyrazol-4-yl)phenyl)pyrazolo[1,5-a]pyridine | 503.3 |
| P-0372 | 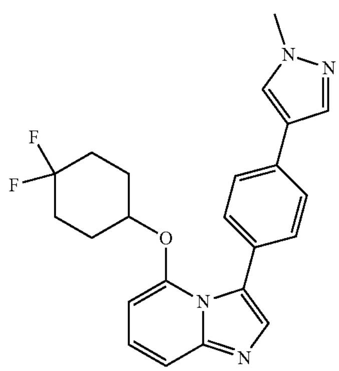 [SMILES: Cn1cc(-c2ccc(-c3cnc4cccc(OC5CCC(F)(F)CC5)n34)cc2)cn1] | 5-((4,4-difluorocyclohexyl)oxy)-3-(4-(1-methyl-1H-pyrazol-4-yl)phenyl)imidazo[1,2-a]pyridine | 409.3 |
| P-0373 | 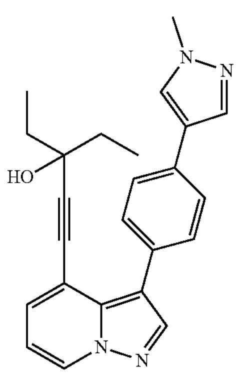 [SMILES: CCC(O)(C#Cc1cccn2ncc(-c3ccc(-c4cnn(C)c4)cc3)c12)CC] | 3-ethyl-1-(3-(4-(1-methyl-1H-pyrazol-4-yl)phenyl)pyrazolo[1,5-a]pyridin-4-yl)pent-1-yn-3-ol | 385.3 |

TABLE 1-continued

| P Number | Structure | Name | MS |
|---|---|---|---|
| P-0374 | 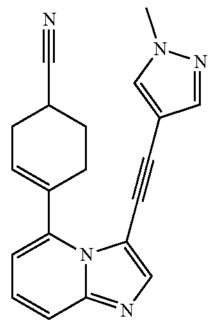 [SMILES: Cn1cc(C#Cc2cnc3cccc(C4=CCC(C#N)CC4)n23)cn1] | 4-(3-((1-methyl-1H-pyrazol-4-yl)ethynyl)imidazo[1,2-a]pyridin-5-yl)cyclohex-3-ene-1-carbonitrile | 328.3 |
| P-0375 | 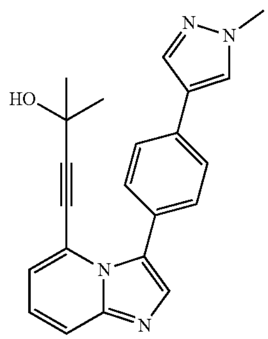 [SMILES: Cn1cc(-c2ccc(-c3cnc4cccc(C#CC(C)(C)O)n34)cc2)cn1] | 2-methyl-4-(3-(4-(1-methyl-1H-pyrazol-4-yl)phenyl)imidazo[1,2-a]pyridin-5-yl)but-3-yn-2-ol | 357.4 |
| P-0376 | 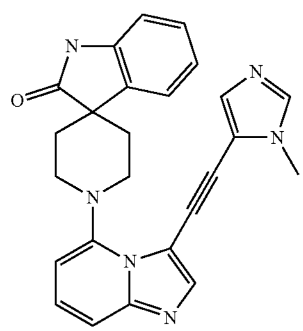 [SMILES: Cn1cncc1C#Cc1cnc2cccc(N3CCC4(CC3)C(=O)Nc3ccccc34)n12] | 1'-(3-((1-methyl-1H-imidazol-5-yl)ethynyl)imidazo[1,2-a]pyridin-5-yl)spiro[indoline-3,4'-piperidin]-2-one | 423.3 |
| P-0377 | 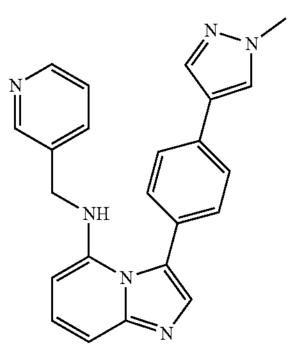 [SMILES: Cn1cc(-c2ccc(-c3cnc4cccc(NCc5cccnc5)n34)cc2)cn1] | 3-(4-(1-methyl-1H-pyrazol-4-yl)phenyl)-N-(pyridin-3-ylmethyl)imidazo[1,2-a]pyridin-5-amine | 381.0 |

TABLE 1-continued

| P Number | Structure | Name | MS |
|---|---|---|---|
| P-0378 | 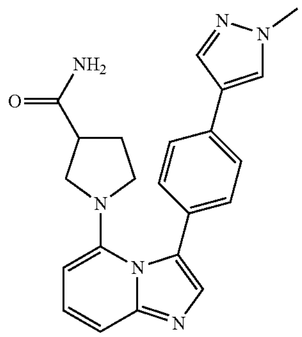 [SMILES: Cn1cc(-c2ccc(-c3cnc4cccc(N5CCC(C(N)=O)C5)n34)cc2)cn1] | 1-(3-(4-(1-methyl-1H-pyrazol-4-yl)phenyl)imidazo[1,2-a]pyridin-5-yl)pyrrolidine-3-carboxamide | 387.0 |
| P-0379 | 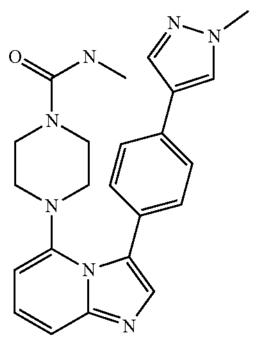 [SMILES: CNC(=O)N1CCN(c2cccc3ncc(-c4ccc(-c5cnn(C)c5)cc4)n23)CC1] | N-methyl-4-(3-(4-(1-methyl-1H-pyrazol-4-yl)phenyl)imidazo[1,2-a]pyridin-5-yl)piperazine-1-carboxamide | 416.5 |
| P-0380 | 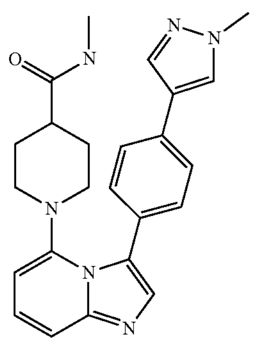 [SMILES: CNC(=O)C1CCN(c2cccc3ncc(-c4ccc(-c5cnn(C)c5)cc4)n23)CC1] | N-methyl-1-(3-(4-(1-methyl-1H-pyrazol-4-yl)phenyl)imidazo[1,2-a]pyridin-5-yl)piperidine-4-carboxamide | 415.3 |
| P-0381 | 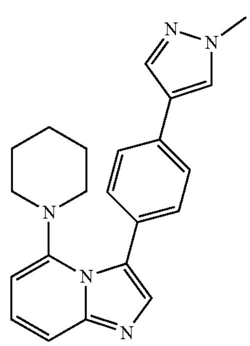 | 3-(4-(1-methyl-1H-pyrazol-4-yl)phenyl)-5-(piperidin-1-yl)imidazo[1,2-a]pyridine | 358.2 |

TABLE 1-continued

| P Number | Structure | Name | MS |
|---|---|---|---|
| P-0382 | 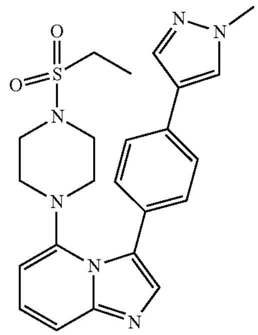 [SMILES: CCS(=O)(=O)N1CCN(c2cccc3ncc(-c4ccc(-c5cnn(C)c5)cc4)n23)CC1] | 5-(4-(ethylsulfonyl)piperazin-1-yl)-3-(4-(1-methyl-1H-pyrazol-4-yl)phenyl)imidazo[1,2-a]pyridine | 451.3 |
| P-0383 | 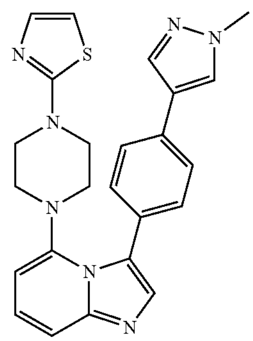 [SMILES: Cn1cc(-c2ccc(-c3cnc4cccc(N5CCN(c6nccs6)CC5)n34)cc2)cn1] | 2-(4-(3-(4-(1-methyl-1H-pyrazol-4-yl)phenyl)imidazo[1,2-a]pyridin-5-yl)piperazin-1-yl)thiazole | 442.3 |
| P-0384 | 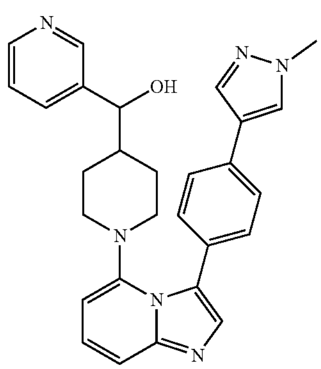 [SMILES: Cn1cc(-c2ccc(-c3cnc4cccc(N5CCC(C(O)c6cccnc6)CC5)n34)cc2)cn1] | (1-(3-(4-(1-methyl-1H-pyrazol-4-yl)phenyl)imidazo[1,2-a]pyridin-5-yl)piperidin-4-yl)(pyridin-3-yl)methanol | 465.4 |
| P-0385 | 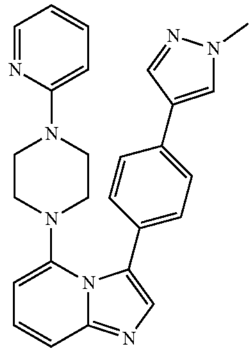 [SMILES: Cn1cc(-c2ccc(-c3cnc4cccc(N5CCN(c6ccccn6)CC5)n34)cc2)cn1] | 3-(4-(1-methyl-1H-pyrazol-4-yl)phenyl)-5-(4-(pyridin-2-yl)piperazin-1-yl)imidazo[1,2-a]pyridine | 436.3 |

TABLE 1-continued

| P Number | Structure | Name | MS |
| --- | --- | --- | --- |
| P-0386 | 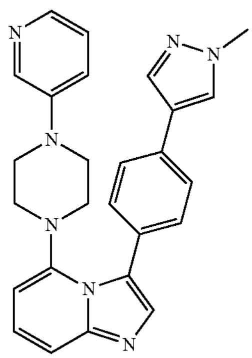 [SMILES: Cn1cc(-c2ccc(-c3cnc4cccc(N5CCN(c6cccnc6)CC5)n34)cc2)cn1] | 3-(4-(1-methyl-1H-pyrazol-4-yl)phenyl)-5-(4-(pyridin-3-yl)piperazin-1-yl)imidazo[1,2-a]pyridine | 436.3 |
| P-0387 | 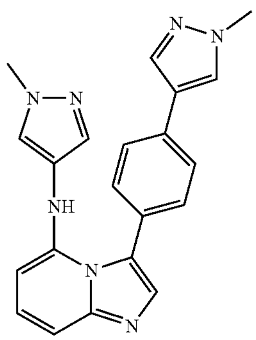 | N-(1-methyl-1H-pyrazol-4-yl)-3-(4-(1-methyl-1H-pyrazol-4-yl)phenyl)imidazo[1,2-a]pyridin-5-amine | 369.9 |
| P-0388 | 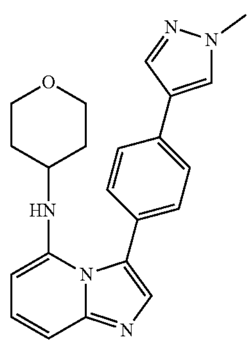 [SMILES: Cn1cc(-c2ccc(-c3cnc4cccc(NC5CCOCC5)n34)cc2)cn1] | 3-(4-(1-methyl-1H-pyrazol-4-yl)phenyl)-N-(tetrahydro-2H-pyran-4-yl)imidazo[1,2-a]pyridin-5-amine | 374.1 |
| P-0389 | 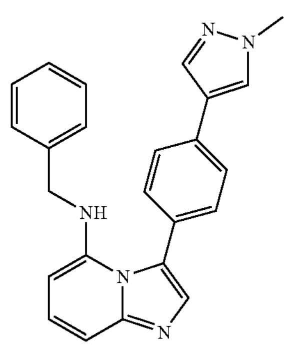 [SMILES: Cn1cc(-c2ccc(-c3cnc4cccc(NCc5ccccc5)n34)cc2)cn1] | N-benzyl-3-(4-(1-methyl-1H-pyrazol-4-yl)phenyl)imidazo[1,2-a]pyridin-5-amine | 380.1 |

TABLE 1-continued

| P Number | Structure | Name | MS |
|---|---|---|---|
| P-0390 | 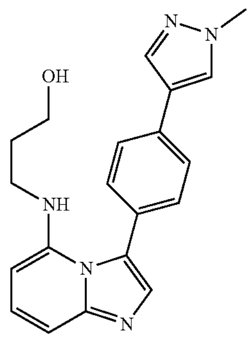 [SMILES: Cn1cc(-c2ccc(-c3cnc4cccc(NCCCO)n34)cc2)cn1] | 3-((3-(4-(1-methyl-1H-pyrazol-4-yl)phenyl)imidazo[1,2-a]pyridin-5-yl)amino)propan-1-ol | 348.3 |
| P-0391 | 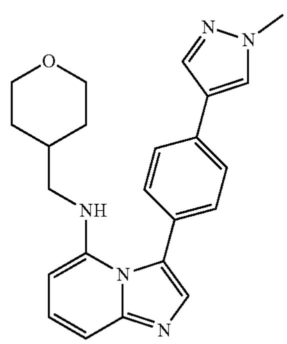 [SMILES: Cn1cc(-c2ccc(-c3cnc4cccc(NCC5CCOCC5)n34)cc2)cn1] | 3-(4-(1-methyl-1H-pyrazol-4-yl)phenyl)-N-((tetrahydro-2H-pyran-4-yl)methyl)imidazo[1,2-a]pyridin-5-amine | 388.2 |
| P-0392 | 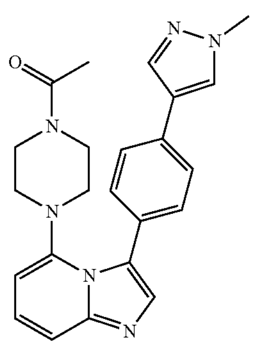 [SMILES: CC(=O)N1CCN(c2cccc3ncc(-c4ccc(-c5cnn(C)c5)cc4)n23)CC1] | 1-(4-(3-(4-(1-methyl-1H-pyrazol-4-yl)phenyl)imidazo[1,2-a]pyridin-5-yl)piperazin-1-yl)ethan-1-one | 401.2 |
| P-0393 | 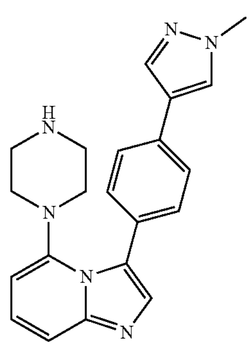 [SMILES: Cn1cc(-c2ccc(-c3cnc4cccc(N5CCNCC5)n34)cc2)cn1] | 3-(4-(1-methyl-1H-pyrazol-4-yl)phenyl)-5-(piperazin-1-yl)imidazo[1,2-a]pyridine | 359.4 |

TABLE 1-continued

| P Number | Structure | Name | MS |
|---|---|---|---|
| P-0394 | 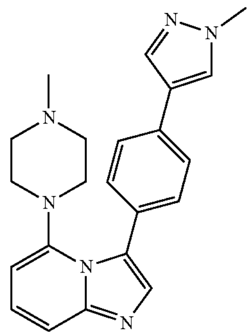 [SMILES: CN1CCN(c2cccc3ncc(-c4ccc(-c5cnn(C)c5)cc4)n23)CC1] | 3-(4-(1-methyl-1H-pyrazol-4-yl)phenyl)-5-(4-methylpiperazin-1-yl)imidazo[1,2-a]pyridine | 373.2 |
| P-0395 | 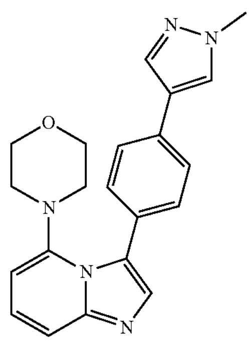 [SMILES: Cn1cc(-c2ccc(-c3cnc4cccc(N5CCOCC5)n34)cc2)cn1] | 4-(3-(4-(1-methyl-1H-pyrazol-4-yl)phenyl)imidazo[1,2-a]pyridin-5-yl)morpholine | 360.0 |
| P-0396 | 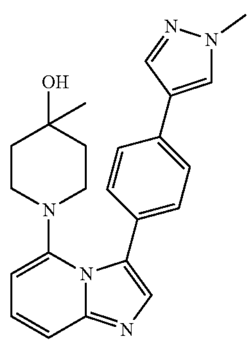 [SMILES: Cn1cc(-c2ccc(-c3cnc4cccc(N5CCC(C)(O)CC5)n34)cc2)cn1] | 4-methyl-1-(3-(4-(1-methyl-1H-pyrazol-4-yl)phenyl)imidazo[1,2-a]pyridin-5-yl)piperidin-4-ol | 388.2 |
| P-0397 | 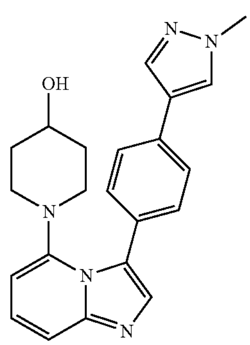 [SMILES: Cn1cc(-c2ccc(-c3cnc4cccc(N5CCC(O)CC5)n34)cc2)cn1] | 1-(3-(4-(1-methyl-1H-pyrazol-4-yl)phenyl)imidazo[1,2-a]pyridin-5-yl)piperidin-4-ol | 374.1 |

TABLE 1-continued

| P Number | Structure | Name | MS |
|---|---|---|---|
| P-0398 | 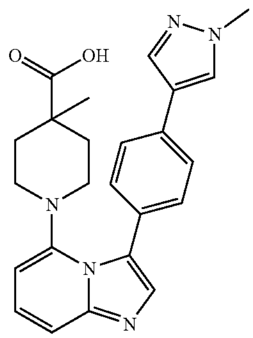 [SMILES: Cn1cc(-c2ccc(-c3cnc4cccc(N5CCC(C)(C(=O)O)CC5)n34)cc2)cn1] | 4-methyl-1-(3-(4-(1-methyl-1H-pyrazol-4-yl)phenyl)imidazo[1,2-a]pyridin-5-yl)piperidine-4-carboxylic acid | 416.4 |
| P-0399 | 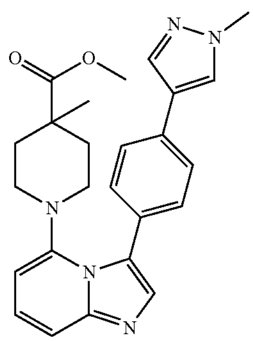 [SMILES: COC(=O)C1(C)CCN(c2cccc3ncc(-c4ccc(-c5cnn(C)c5)cc4)n23)CC1] | methyl 4-methyl-1-(3-(4-(1-methyl-1H-pyrazol-4-yl)phenyl)imidazo[1,2-a]pyridin-5-yl)piperidine-4-carboxylate | 430.3 |
| P-0400 | 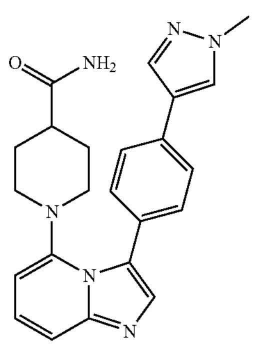 [SMILES: Cn1cc(-c2ccc(-c3cnc4cccc(N5CCC(C(N)=O)CC5)n34)cc2)cn1] | 1-(3-(4-(1-methyl-1H-pyrazol-4-yl)phenyl)imidazo[1,2-a]pyridin-5-yl)piperidine-4-carboxamide | 401.2 |
| P-0401 | 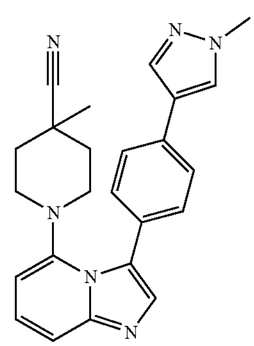 [SMILES: Cn1cc(-c2ccc(-c3cnc4cccc(N5CCC(C)(C#N)CC5)n34)cc2)cn1] | 4-methyl-1-(3-(4-(1-methyl-1H-pyrazol-4-yl)phenyl)imidazo[1,2-a]pyridin-5-yl)piperidine-4-carbonitrile | 397.0 |

TABLE 1-continued

| P Number | Structure | Name | MS |
|---|---|---|---|
| P-0402 | 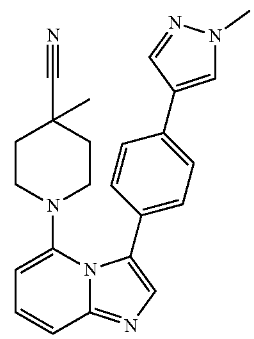 [SMILES: Cn1cc(-c2ccc(-c3cnc4cccc(N5CCC(C)(C#N)CC5)n34)cc2)cn1] | 4-methyl-1-(3-(4-(1-methyl-1H-pyrazol-4-yl)phenyl)imidazo[1,2-a]pyridin-5-yl)piperidine-4-carbonitrile | 383.4 |
| P-0403 | 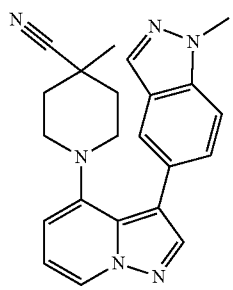 [SMILES: Cn1ncc2cc(-c3cnn4cccc(N5CCC(C)(C#N)CC5)c34)ccc21] | 4-methyl-1-(3-(1-methyl-1H-indazol-5-yl)pyrazolo[1,5-a]pyridin-4-yl)piperidine-4-carbonitrile | 371.3 |
| P-0404 | 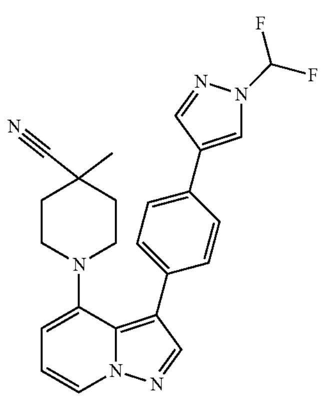 [SMILES: CC1(C#N)CCN(c2cccn3ncc(-c4ccc(-c5cnn(C(F)F)c5)cc4)c23)CC1] | 1-(3-(4-(1-(difluoromethyl)-1H-pyrazol-4-yl)phenyl)pyrazolo[1,5-a]pyridin-4-yl)-4-methylpiperidine-4-carbonitrile | 433.3 |
| P-0405 | 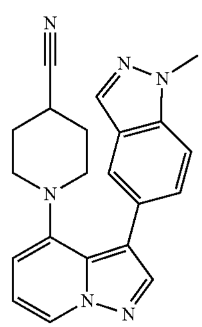 [SMILES: Cn1ncc2cc(-c3cnn4cccc(N5CCC(C#N)CC5)c34)ccc21] | 1-(3-(1-methyl-1H-indazol-5-yl)pyrazolo[1,5-a]pyridin-4-yl)piperidine-4-carbonitrile | 357.3 |

TABLE 1-continued

| P Number | Structure | Name | MS |
|---|---|---|---|
| P-0406 | 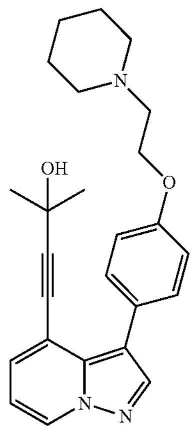 [SMILES: CC(C)(O)C#Cc1cccn2ncc(-c3ccc(OCCN4CCCCC4)cc3)c12] | 2-methyl-4-(3-(4-(2-(piperidin-1-yl)ethoxy)phenyl)pyrazolo[1,5-a]pyridin-4-yl)but-3-yn-2-ol | 404.3 |
| P-0407 | 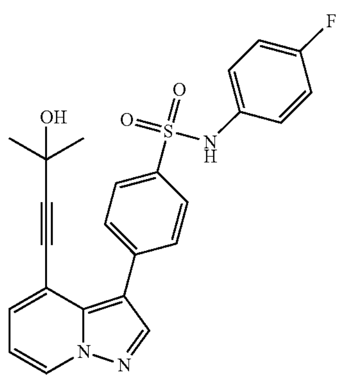 [SMILES: CC(C)(O)C#Cc1cccn2ncc(-c3ccc(S(=O)(=O)Nc4ccc(F)cc4)cc3)c12] | N-(4-fluorophenyl)-4-(4-(3-hydroxy-3-methylbut-1-yn-1-yl)pyrazolo[1,5-a]pyridin-3-yl)benzenesulfonamide | 450.3 |
| P-0409 | 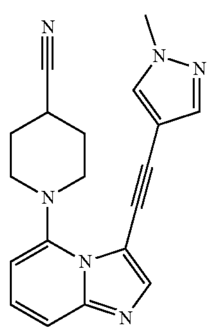 [SMILES: Cn1cc(C#Cc2cnc3cccc(N4CCC(C#N)CC4)n23)cn1] | 1-(3-((1-methyl-1H-pyrazol-4-yl)ethynyl)imidazo[1,2-a]pyridin-5-yl)piperidine-4-carbonitrile | 331.3 |
| P-0410 | 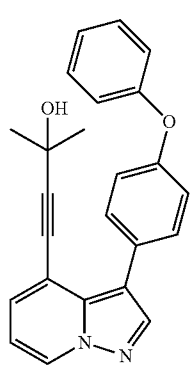 [SMILES: CC(C)(O)C#Cc1cccn2ncc(-c3ccc(Oc4ccccc4)cc3)c12] | 2-methyl-4-(3-(4-phenoxyphenyl)pyrazolo[1,5-a]pyridin-4-yl)but-3-yn-2-ol | 369.3 |

TABLE 1-continued

| P Number | Structure | Name | MS |
|---|---|---|---|
| P-0411 | 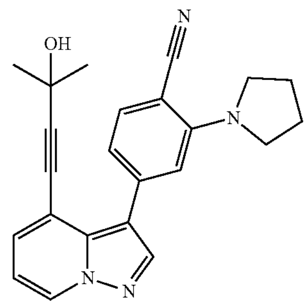 [SMILES: CC(C)(O)C#Cc1cccn2ncc(-c3ccc(C#N)c(N4CCCC4)c3)c12] | 4-(4-(3-hydroxy-3-methylbut-1-yn-1-yl)pyrazolo[1,5-a]pyridin-3-yl)-2-(pyrrolidin-1-yl)benzonitrile | 371.3 |
| P-0412 | 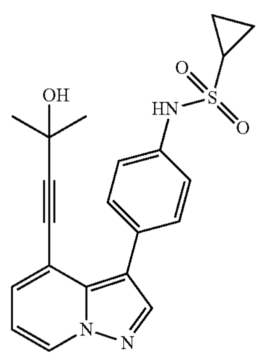 [SMILES: CC(C)(O)C#Cc1cccn2ncc(-c3ccc(NS(=O)(=O)C4CC4)cc3)c12] | N-(4-(4-(3-hydroxy-3-methylbut-1-yn-1-yl)pyrazolo[1,5-a]pyridin-3-yl)phenyl)cyclopropane-sulfonamide | 396.2 |
| P-0413 | 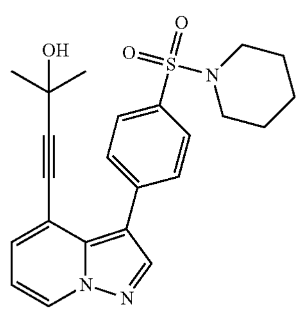 [SMILES: CC(C)(O)C#Cc1cccn2ncc(-c3ccc(S(=O)(=O)N4CCCCC4)cc3)c12] | 2-methyl-4-(3-(4-(piperidin-1-ylsulfonyl)phenyl)pyrazolo[1,5-a]pyridin-4-yl)but-3-yn-2-ol | 424.3 |
| P-0414 | 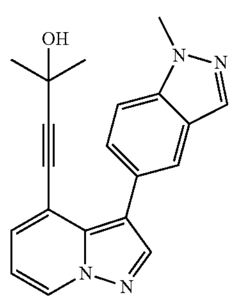 [SMILES: Cn1ncc2cc(-c3cnn4cccc(C#CC(C)(C)O)c34)ccc21] | 2-methyl-4-(3-(1-methyl-1H-indazol-5-yl)pyrazolo(1,5-a]pyridin-4-yl)but-3-yn-2-ol | 331.2 |

TABLE 1-continued

| P Number | Structure | Name | MS |
|---|---|---|---|
| P-0415 | 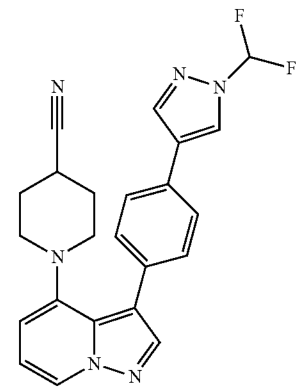 [SMILES: N#CC1CCN(c2cccn3ncc(-c4ccc(-c5cnn(C(F)F)c5)cc4)c23)CC1] | 1-(3-(4-(1-(difluoromethyl)-1H-pyrazol-4-yl)phenyl)pyrazolo[1,5-a]pyridin-4-yl)piperidine-4-carbonitrile | 419.3 |
| P-0416 | 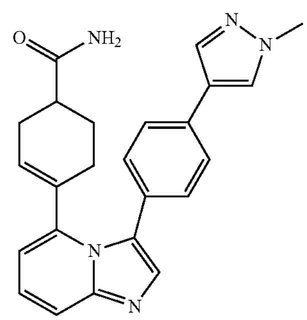 [SMILES: Cn1cc(-c2ccc(-c3cnc4cccc(C5=CCC(C(N)=O)CC5)n34)cc2)cn1] | 4-(3-(4-(1-methyl-1H-pyrazol-4-yl)phenyl)imidazo[1,2-a]pyridin-5-yl)cyclohex-3-ene-1-carboxamide | 398.3 |
| P-0417 | 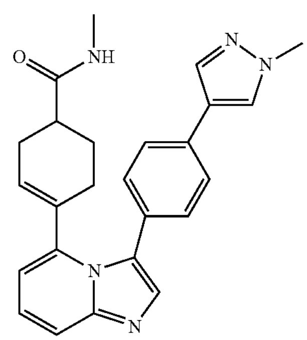 [SMILES: CNC(=O)C1CC=C(c2cccc3ncc(-c4ccc(-c5cnn(C)c5)cc4)n23)CC1] | N-methyl-4-(3-(4-(1-methyl-1H-pyrazol-4-yl)phenyl)imidazo[1,2-a]pyridin-5-yl)cyclohex-3-ene-1-carboxamide | 412.3 |
| P-0418 | 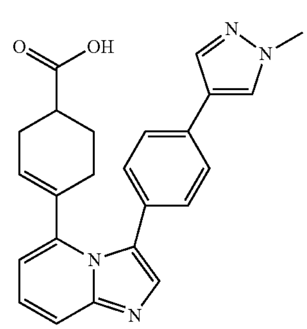 [SMILES: Cn1cc(-c2ccc(-c3cnc4cccc(C5=CCC(C(=O)O)CC5)n34)cc2)cn1] | 4-(3-(4-(1-methyl-1H-pyrazol-4-yl)phenyl)imidazo[1,2-a]pyridin-5-yl)cyclohex-3-ene-1-carboxylic acid | 399.3 |

TABLE 1-continued

| P Number | Structure | Name | MS |
|---|---|---|---|
| P-0419 | 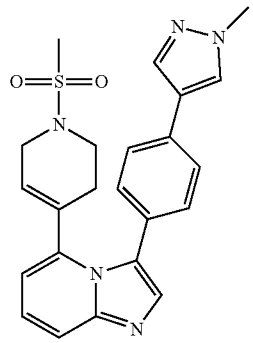 [SMILES: Cn1cc(-c2ccc(-c3cnc4cccc(C5=CCN(S(C)(=O)=O)CC5)n34)cc2)cn1] | 3-(4-(1-methyl-1H-pyrazol-4-yl)phenyl)-5-(1-(methylsulfonyl)-1,2,3,6-tetrahydropyridin-4-yl)imidazo[1,2-a]pyridine | 434.3 |
| P-0420 | 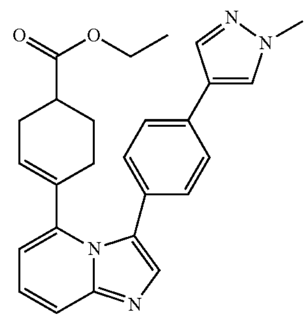 [SMILES: CCOC(=O)C1CC=C(c2cccc3ncc(-c4ccc(-c5cnn(C)c5)cc4)n23)CC1] | ethyl 4-(3-(4-(1-methyl-1H-pyrazol-4-yl)phenyl)imidazo[1,2-a]pyridin-5-yl)cyclohex-3-ene-1-carboxylate | 427.3 |
| P-0421 | 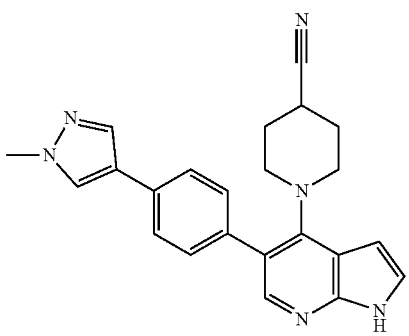 [SMILES: Cn1cc(-c2ccc(-c3cnc4[nH]ccc4c3N3CCC(C#N)CC3)cc2)cn1] | 1-(5-(4-(1-methyl-1H-pyrazol-4-yl)phenyl)-1H-pyrrolo[2,3-b]pyridin-4-yl)piperidine-4-carbonitrile | 383.1 |
| P-0422 | 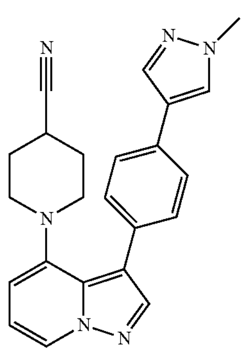 [SMILES: Cn1cc(-c2ccc(-c3cnn4cccc(N5CCC(C#N)CC5)c34)cc2)cn1] | 1-(3-(4-(1-methyl-1H-pyrazol-4-yl)phenyl)pyrazolo[1,5-a]pyridin-4-yl)piperidine-4-carbonitrile | 383.3 |

TABLE 1-continued

| P Number | Structure | Name | MS |
|---|---|---|---|
| P-0423 | 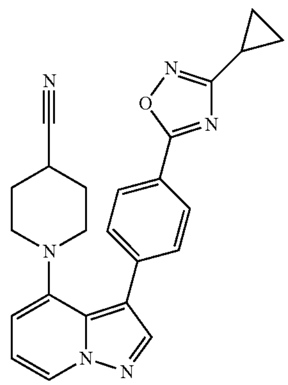 [SMILES: N#CC1CCN(c2cccn3ncc(-c4ccc(-c5nc(C6CC6)no5)cc4)c23)CC1] | 1-(3-(4-(3-cyclopropyl-1,2,4-oxadiazol-5-yl)phenyl)pyrazolo[1,5-a]pyridin-4-yl)piperidine-4-carbonitrile | 411.3 |
| P-0424 | 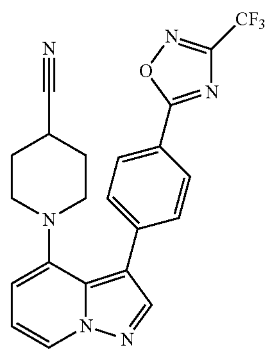 [SMILES: N#CC1CCN(c2cccn3ncc(-c4ccc(-c5nc(C(F)(F)F)no5)cc4)c23)CC1] | 1-(3-(4-(3-(trifluoromethyl)-1,2,4-oxadiazol-5-yl)phenyl)pyrazolo[1,5-a]pyridin-4-yl)piperidine-4-carbonitrile | 439.3 |
| P-0425 | 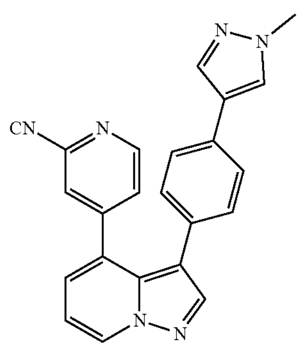 | 4-(3-(4-(1-methyl-1H-pyrazol-4-yl)phenyl)pyrazolo[1,5-a]pyridin-4-yl)picolinonitrile | 377.0 |
| P-0426 | 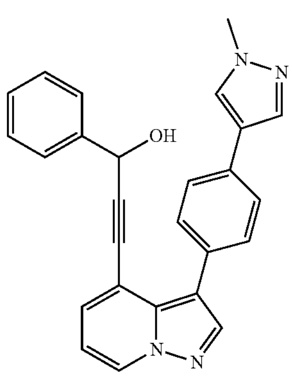 [SMILES: Cn1cc(-c2ccc(-c3cnn4cccc(C#CC(O)c5ccccc5)c34)cc2)cn1] | 3-(3-(4-(1-methyl-1H-pyrazol-4-yl)phenyl)pyrazolo[1,5-a]pyridin-4-yl)-1-phenylprop-2-yn-1-ol | 405.3 |

TABLE 1-continued

| P Number | Structure | Name | MS |
|---|---|---|---|
| P-0427 | 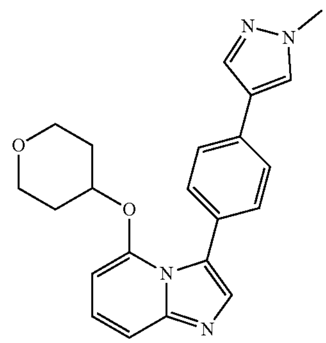 [SMILES: Cn1cc(-c2ccc(-c3cnc4cccc(OC5CCOCC5)n34)cc2)cn1] | 3-(4-(1-methyl-1H-pyrazol-4-yl)phenyl)-5-((tetrahydro-2H-pyran-4-yl)oxy)imidazo[1,2-a]pyridine | 375.3 |
| P-0428 | 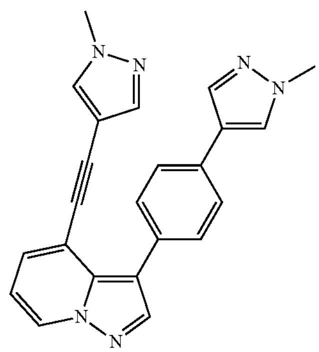 [SMILES: Cn1cc(C#Cc2cccn3ncc(-c4ccc(-c5cnn(C)c5)cc4)c23)cn1] | 4-((1-methyl-1H-pyrazol-4-yl)ethynyl)-3-(4-(1-methyl-1H-pyrazol-4-yl)phenyl)pyrazolo[1,5-a]pyridine | 379.3 |
| P-0429 | 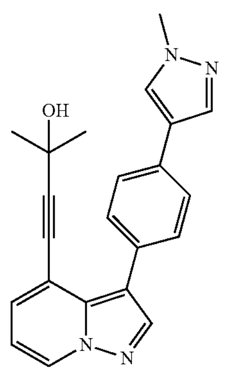 [SMILES: Cn1cc(-c2ccc(-c3cnn4cccc(C#CC(C)(C)O)c34)cc2)cn1] | 2-methyl-4-(3-(4-(1-methyl-1H-pyrazol-4-yl)phenyl)pyrazolo[1,5-a]pyridin-4-yl)but-3-yn-2-ol | 357.0 |
| P-0430 | 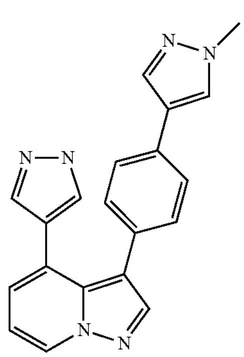 [SMILES: Cn1cc(-c2ccc(-c3cnn4cccc(-c5cn[nH]c5)c34)cc2)cn1] | 3-(4-(1-methyl-1H-pyrazol-4-yl)phenyl)-4-(1H-pyrazol-4-yl)pyrazolo[1,5-a]pyridine | 341.0 |

TABLE 1-continued

| P Number | Structure | Name | MS |
|---|---|---|---|
| P-0431 | 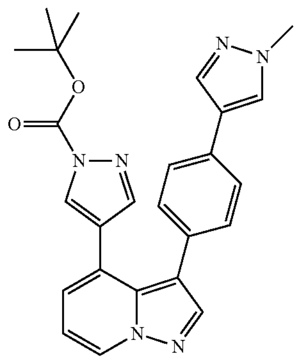 [SMILES: Cn1cc(-c2ccc(-c3cnn4cccc(-c5cnn(C(=O)OC(C)(C)C)c5)c34)cc2)cn1] | tert-butyl 4-(3-(4-(1-methyl-1H-pyrazol-4-yl)phenyl)pyrazolo[1,5-a]pyridin-4-yl)-1H-pyrazole-1-carboxylate | 441.1 |
| P-0432 | 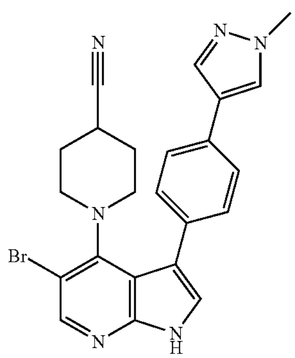 [SMILES: Cn1cc(-c2ccc(-c3c[nH]c4ncc(Br)c(N5CCC(C#N)CC5)c34)cc2)cn1] | 1-(5-bromo-3-(4-(1-methyl-1H-pyrazol-4-yl)phenyl)-1H-pyrrolo[2,3-b]pyridin-4-yl)piperidine-4-carbonitrile | 463.0 |
| P-0433 | 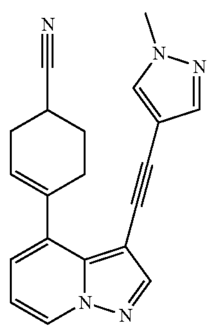 [SMILES: Cn1cc(C#Cc2cnn3cccc(C4=CCC(C#N)CC4)c23)cn1] | 4-(3-((1-methyl-1H-pyrazol-4-yl)ethynyl)pyrazolo[1,5-a]pyridin-4-yl)cyclohex-3-ene-1-carbonitrile | 328.2 |
| P-0434 | 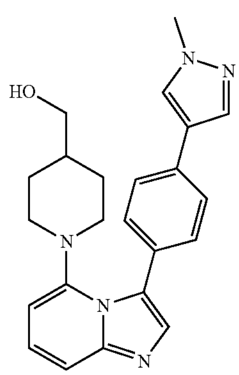 [SMILES: Cn1cc(-c2ccc(-c3cnc4cccc(N5CCC(CO)CC5)n34)cc2)cn1] | (1-(3-(4-(1-methyl-1H-pyrazol-4-yl)phenyl)imidazo[1,2-a]pyridin-5-yl)piperidin-4-yl)methanol | 388.2 |

TABLE 1-continued

| P Number | Structure | Name | MS |
|---|---|---|---|
| P-0435 | 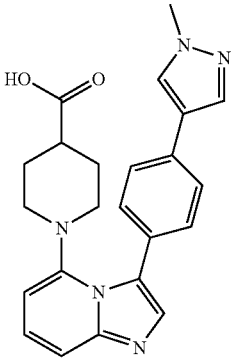 [SMILES: Cn1cc(-c2ccc(-c3cnc4cccc(N5CCC(C(=O)O)CC5)n34)cc2)cn1] | 1-(3-(4-(1-methyl-1H-pyrazol-4-yl)phenyl)imidazo[1,2-a]pyridin-5-yl)piperidine-4-carboxylic acid | 402.3 |
| P-0436 | 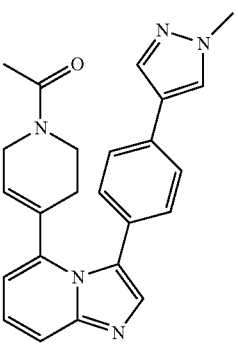 [SMILES: CC(=O)N1CC=C(c2cccc3ncc(-c4ccc(-c5cnn(C)c5)cc4)n23)CC1] | 1-(4-(3-(4-(1-methyl-1H-pyrazol-4-yl)phenyl)imidazo[1,2-a]pyridin-5-yl)-3,6-dihydropyridin-1(2H)-yl)ethan-1-one | 398.1 |
| P-0437 | 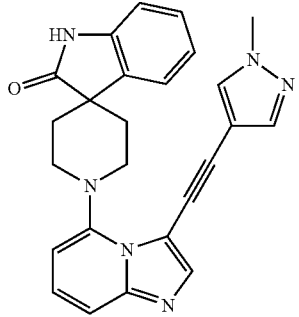 [SMILES: Cn1cc(C#Cc2cnc3cccc(N4CCC5(CC4)C(=O)Nc4ccccc45)n23)cn1] | 1'-(3-((1-methyl-1H-pyrazol-4-yl)ethynyl)imidazo[1,2-a]pyridin-5-yl)spiro[indoline-3,4'-piperidin]-2-one | 423.3 |
| P-0438 | 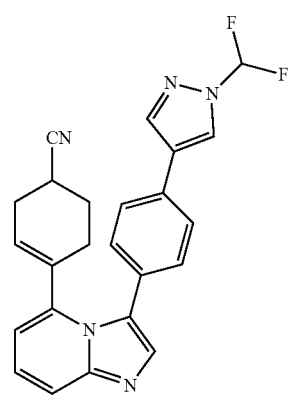 [SMILES: N#CC1CC=C(c2cccc3ncc(-c4ccc(-c5cnn(C(F)F)c5)cc4)n23)CC1] | 4-(3-(4-(1-(difluoromethyl)-1H-pyrazol-4-yl)phenyl)imidazo[1,2-a]pyridin-5-yl)cyclohex-3-ene-1-carbonitrile | 416.3 |

TABLE 1-continued

| P Number | Structure | Name | MS |
|---|---|---|---|
| P-0439 | 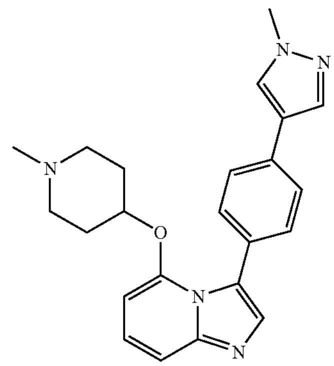 [SMILES: CN1CCC(Oc2cccc3ncc(-c4ccc(-c5cnn(C)c5)cc4)n23)CC1] | 3-(4-(1-methyl-1H-pyrazol-4-yl)phenyl)-5-((1-methylpiperidin-4-yl)oxy)imidazo[1,2-a]pyridine | 388.3 |
| P-0440 | 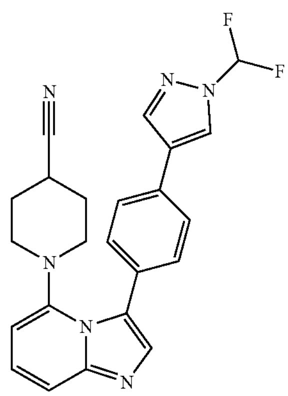 [SMILES: N#CC1CCN(c2cccc3ncc(-c4ccc(-c5cnn(C(F)F)c5)cc4)n23)CC1] | 1-(3-(4-(1-(difluoromethyl)-1H-pyrazol-4-yl)phenyl)imidazo[1,2-a]pyridin-5-yl)piperidine-4-carbonitrile | 419.1 |
| P-0441 | 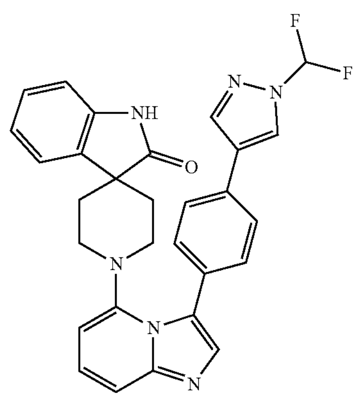 [SMILES: O=C1Nc2ccccc2C12CCN(c1cccc3ncc(-c4ccc(-c5cnn(C(F)F)c5)cc4)n13)CC2] | 1'-(3-(4-(1-(difluoromethyl)-1H-pyrazol-4-yl)phenyl)imidazo[1,2-a]pyridin-5-yl)spiro[indoline-3,4'-piperidin]-2-one | 511.1 |
| P-0442 | 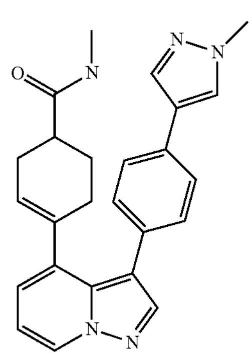 [SMILES: CNC(=O)C1CC=C(c2cccn3ncc(-c4ccc(-c5cnn(C)c5)cc4)c23)CC1] | N-methyl-4-(3-(4-(1-methyl-1H-pyrazol-4-yl)phenyl)pyrazolo[1,5-a]pyridin-4-yl)cyclohex-3-ene-1-carboxamide | 412.1 |

TABLE 1-continued

| P Number | Structure | Name | MS |
|---|---|---|---|
| P-0443 | 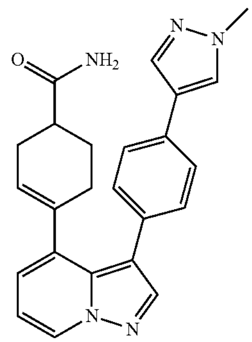 [SMILES: Cn1cc(-c2ccc(-c3cnn4cccc(C5=CCC(C(N)=O)CC5)c34)cc2)cn1] | 4-(3-(4-(1-methyl-1H-pyrazol-4-yl)phenyl)pyrazolo[1,5-a]pyridin-4-yl)cyclohex-3-ene-1-carboxamide | 398.3 |
| P-0444 | 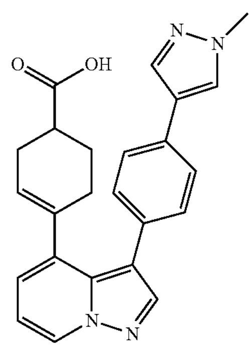 [SMILES: Cn1cc(-c2ccc(-c3cnn4cccc(C5=CCC(C(=O)O)CC5)c34)cc2)cn1] | 4-(3-(4-(1-methyl-1H-pyrazol-4-yl)phenyl)pyrazolo[1,5-a]pyridin-4-yl)cyclohex-3-ene-1-carboxylic acid | 399.3 |
| P-0445 | 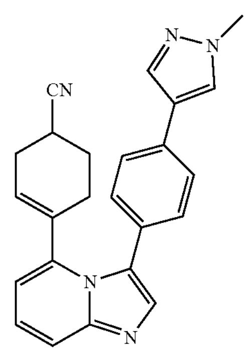 [SMILES: Cn1cc(-c2ccc(-c3cnc4cccc(C5=CCC(C#N)CC5)n34)cc2)cn1] | 4-(3-(4-(1-methyl-1H-pyrazol-4-yl)phenyl)imidazo[1,2-a]pyridin-5-yl)cyclohex-3-ene-1-carbonitrile | 380.3 |
| P-0446 | 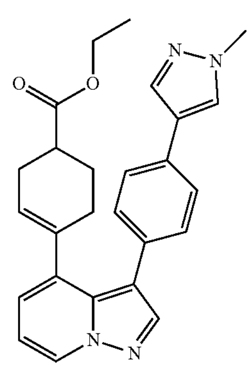 [SMILES: CCOC(=O)C1CC=C(c2cccn3ncc(-c4ccc(-c5cnn(C)c5)cc4)c23)CC1] | ethyl 4-(3-(4-(1-methyl-1H-pyrazol-4-yl)phenyl)pyrazolo[1,5-a]pyridin-4-yl)cyclohex-3-ene-1-carboxylate | 427.3 |

TABLE 1-continued

| P Number | Structure | Name | MS |
|---|---|---|---|
| P-0447 | 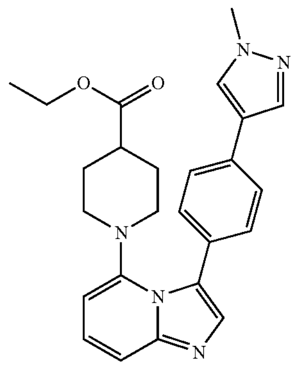 [SMILES: CCOC(=O)C1CCN(c2cccc3ncc(-c4ccc(-c5cnn(C)c5)cc4)n23)CC1] | ethyl 1-(3-(4-(1-methyl-1H-pyrazol-4-yl)phenyl)imidazo[1,2-a]pyridin-5-yl)piperidine-4-carboxylate | 430.1 |
| P-0448 | 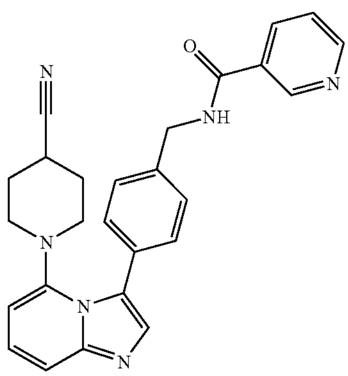 [SMILES: N#CC1CCN(c2cccc3ncc(-c4ccc(CNC(=O)c5cccnc5)cc4)n23)CC1] | N-(4-(5-(4-cyanopiperidin-1-yl)imidazo[1,2-a]pyridin-3-yl)benzyl)nicotinamide | 437.4 |
| P-0449 | 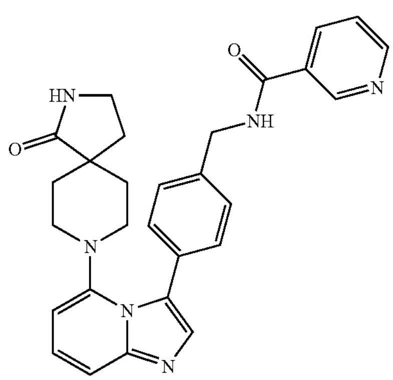 [SMILES: O=C(NCc1ccc(-c2cnc3cccc(N4CCC5(CCNC5=O)CC4)n23)cc1)c1cccnc1] | N-(4-(5-(1-oxo-2,8-diazaspiro[4.5]decan-8-yl)imidazo[1,2-a]pyridin-3-yl)benzyl)nicotinamide | 481.4 |
| P-0450 | 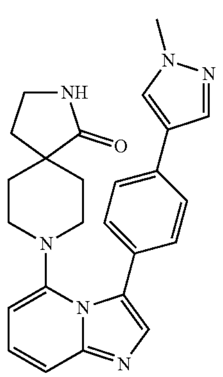 [SMILES: Cn1cc(-c2ccc(-c3cnc4cccc(N5CCC6(CCNC6=O)CC5)n34)cc2)cn1] | 8-(3-(4-(1-methyl-1H-pyrazol-4-yl)phenyl)imidazo[1,2-a]pyridin-5-yl)-2,8-diazaspiro[4.5]decan-1-one | 427.1 |

TABLE 1-continued

| P Number | Structure | Name | MS |
|---|---|---|---|
| P-0451 | 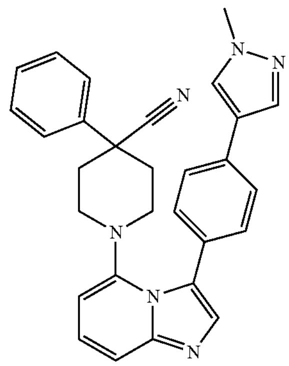 [SMILES: Cn1cc(-c2ccc(-c3cnc4cccc(N5CCC(C#N)(c6ccccc6)CC5)n34)cc2)cn1] | 1-(3-(4-(1-methyl-1H-pyrazol-4-yl)phenyl)imidazo[1,2-a]pyridin-5-yl)-4-phenylpiperidine-4-carbonitrile | 459.3 |
| P-0452 | 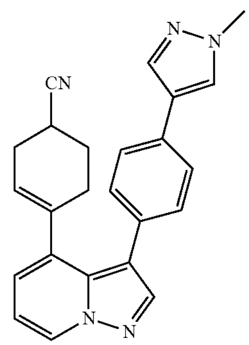 [SMILES: Cn1cc(-c2ccc(-c3cnn4cccc(C5=CCC(C#N)CC5)c34)cc2)cn1] | 4-(3-(4-(1-methyl-1H-pyrazol-4-yl)phenyl)pyrazolo[1,5-a]pyridin-4-yl)cyclohex-3-ene-1-carbonitrile | 380.3 |
| P-0453 | 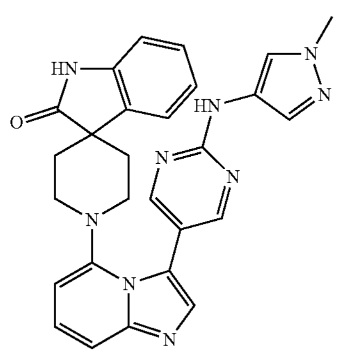 [SMILES: Cn1cc(Nc2ncc(-c3cnc4cccc(N5CCC6(CC5)C(=O)Nc5ccccc56)n34)cn2)cn1] | 1'-(3-(2-((1-methyl-1H-pyrazol-4-yl)amino)pyrimidin-5-yl)imidazo[1,2-a]pyridin-5-yl)spiro[indoline-3,4'-piperidin]-2-one | 492.2 |
| P-0454 | 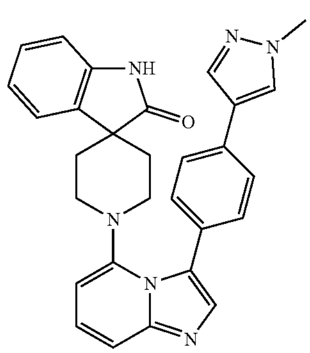 [SMILES: Cn1cc(-c2ccc(-c3cnc4cccc(N5CCC6(CC5)C(=O)Nc5ccccc56)n34)cc2)cn1] | 1'-(3-(4-(1-methyl-1H-pyrazol-4-yl)phenyl)imidazo[1,2-a]pyridin-5-yl)spiro[indoline-3,4'-piperidin]-2-one | 475.2 |

TABLE 1-continued

| P Number | Structure | Name | MS |
|---|---|---|---|
| P-0455 | 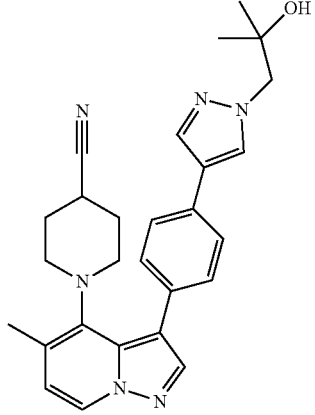 [SMILES: Cc1ccn2ncc(-c3ccc(-c4cnn(CC(C)(C)O)c4)cc3)c2c1N1CCC(C#N)CC1] | 1-(3-(4-(1-(2-hydroxy-2-methylpropyl)-1H-pyrazol-4-yl)phenyl)-5-methylpyrazolo[1,5-a]pyridin-4-yl)piperidine-4-carbonitrile | 455.3 |
| P-0456 | 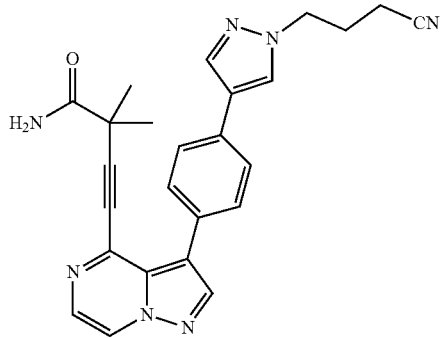 [SMILES: CC(C)(C#Cc1nccn2ncc(-c3ccc(-c4cnn(CCCC#N)c4)cc3)c12)C(N)=O] | 4-(3-(4-(1-(3-cyanopropyl)-1H-pyrazol-4-yl)phenyl)pyrazolo[1,5-a]pyrazin-4-yl)-2,2-dimethylbut-3-ynamide | 438.2 |
| P-0457 | 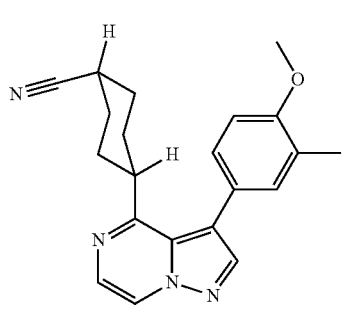 [SMILES: COc1ccc(-c2cnn3ccnc(C4CCC(C#N)CC4)c23)cc1C] | (1s,4s)-4-(3-(4-methoxy-3-methylphenyl)pyrazolo[1,5-a]pyrazin-4-yl)cyclohexane-1-carbonitrile | 347.0 |
| P-0458 | 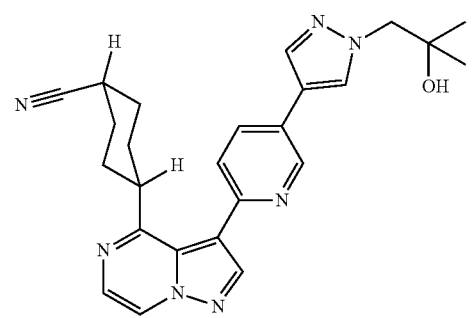 [SMILES: CC(C)(O)Cn1cc(-c2ccc(-c3cnn4ccnc(C5CCC(C#N)CC5)c34)nc2)cn1] | (1s,4s)-4-(3-(5-(1-(2-hydroxy-2-methylpropyl)-1H-pyrazol-4-yl)pyridin-2-yl)pyrazolo[1,5-a]pyrazin-4-yl)cyclohexane-1-carbonitrile | 442.6 |

TABLE 1-continued

| P Number | Structure | Name | MS |
|---|---|---|---|
| P-0459 | 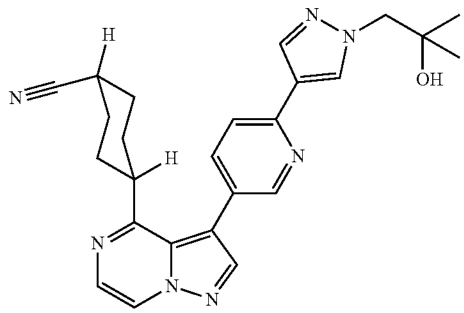 [SMILES: CC(C)(O)Cn1cc(-c2ccc(-c3cnn4ccnc(C5CCC(C#N)CC5)c34)cn2)cn1] | (1s,4s)-4-(3-(6-(1-(2-hydroxy-2-methylpropyl)-1H-pyrazol-4-yl)pyridin-3-yl)pyrazolo[1,5-a]pyrazin-4-yl)cyclohexane-1-carbonitrile | 442.1 |
| P-0460 | 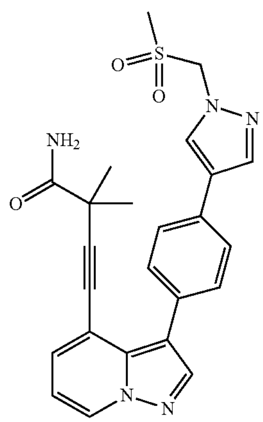 [SMILES: CC(C)(C#Cc1cccn2ncc(-c3ccc(-c4cnn(CS(C)(=O)=O)c4)cc3)c12)C(N)=O] | 2,2-dimethyl-4-(3-(4-(1-((methylsulfonyl)methyl)-1H-pyrazol-4-yl)phenyl)pyrazolo[1,5-a]pyridin-4-yl)but-3-ynamide | 462.0 |
| P-0461 | 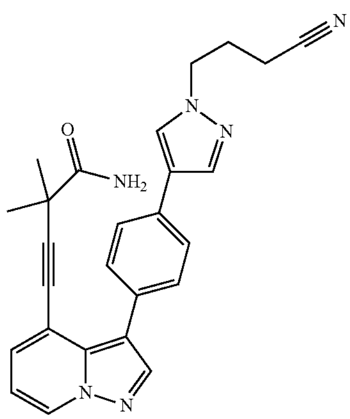 [SMILES: CC(C)(C#Cc1cccn2ncc(-c3ccc(-c4cnn(CCCC#N)c4)cc3)c12)C(N)=O] | 4-(3-(4-(1-(3-cyanopropyl)-1H-pyrazol-4-yl)phenyl)pyrazolo[1,5-a]pyridin-4-yl)-2,2-dimethylbut-3-ynamide | 437.2 |
| P-0462 | 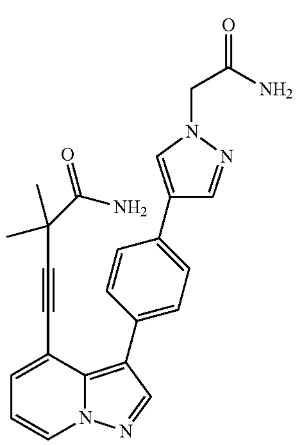 [SMILES: CC(C)(C#Cc1cccn2ncc(-c3ccc(-c4cnn(CC(N)=O)c4)cc3)c12)C(N)=O] | 4-(3-(4-(1-(2-amino-2-oxoethyl)-1H-pyrazol-4-yl)phenyl)pyrazolo[1,5-a]pyridin-4-yl)-2,2-dimethylbut-3-ynamide | 427.3 |

TABLE 1-continued

| P Number | Structure | Name | MS |
|---|---|---|---|
| P-0463 | 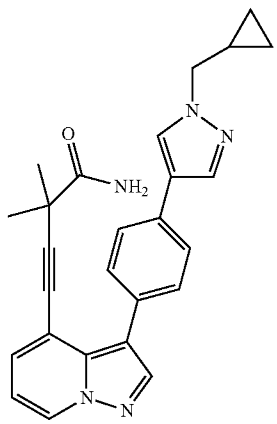 [SMILES: CC(C)(C#Cc1cccn2ncc(-c3ccc(-c4cnn(CC5CC5)c4)cc3)c12)C(N)=O] | 4-(3-(4-(1-(cyclopropylmethyl)-1H-pyrazol-4-yl)phenyl)pyrazolo[1,5-a]pyridin-4-yl)-2,2-dimethylbut-3-ynamide | 424.3 |
| P-0464 | 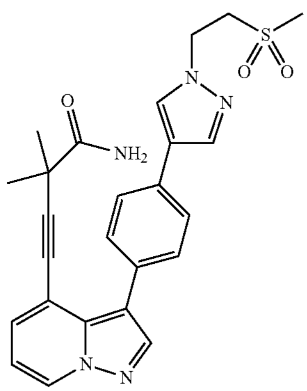 [SMILES: CC(C)(C#Cc1cccn2ncc(-c3ccc(-c4cnn(CCS(C)(=O)=O)c4)cc3)c12)C(N)=O] | 2,2-dimethyl-4-(3-(4-(1-(2-(methylsulfonyl)ethyl)-1H-pyrazol-4-yl)phenyl)pyrazolo[1,5-a]pyridin-4-yl)but-3-ynamide | 476.2 |
| P-0465 | 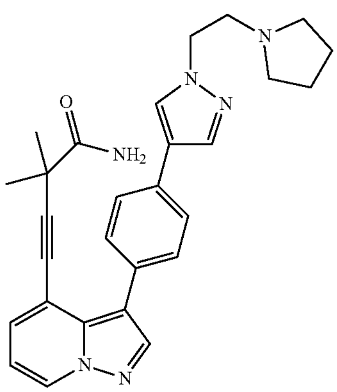 [SMILES: CC(C)(C#Cc1cccn2ncc(-c3ccc(-c4cnn(CCN5CCCC5)c4)cc3)c12)C(N)=O] | 2,2-dimethyl-4-(3-(4-(1-(2-(pyrrolidin-1-yl)ethyl)-1H-pyrazol-4-yl)phenyl)pyrazolo[1,5-a]pyridin-4-yl)but-3-ynamide | 467.2 |
| P-0466 | 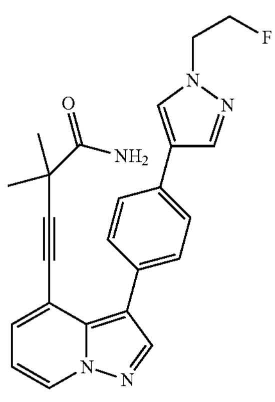 [SMILES: CC(C)(C#Cc1cccn2ncc(-c3ccc(-c4cnn(CCF)c4)cc3)c12)C(N)=O] | 4-(3-(4-(1-(2-fluoroethyl)-1H-pyrazol-4-yl)phenyl)pyrazolo[1,5-a]pyridin-4-yl)-2,2-dimethylbut-3-ynamide | 416.2 |

TABLE 1-continued

| P Number | Structure | Name | MS |
|---|---|---|---|
| P-0467 | 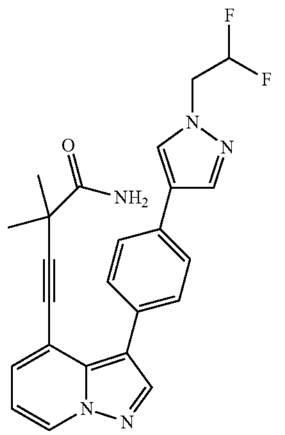 [SMILES: CC(C)(C#Cc1cccn2ncc(-c3ccc(-c4cnn(CC(F)F)c4)cc3)c12)C(N)=O] | 4-(3-(4-(1-(2,2-difluoroethyl)-1H-pyrazol-4-yl)phenyl)pyrazolo[1,5-a]pyridin-4-yl)-2,2-dimethylbut-3-ynamide | 434.2 |
| P-0468 | 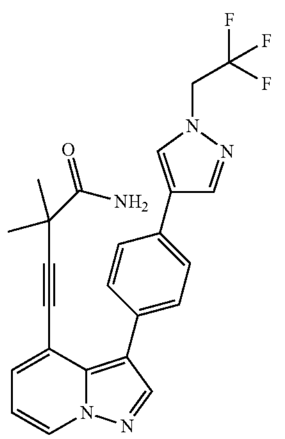 [SMILES: CC(C)(C#Cc1cccn2ncc(-c3ccc(-c4cnn(CC(F)(F)F)c4)cc3)c12)C(N)=O] | 2,2-dimethyl-4-(3-(4-(1-(2,2,2-trifluoroethyl)-1H-pyrazol-4-yl)phenyl)pyrazolo[1,5-a]pyridin-4-yl)but-3-ynamide | 452.2 |
| P-0469 | 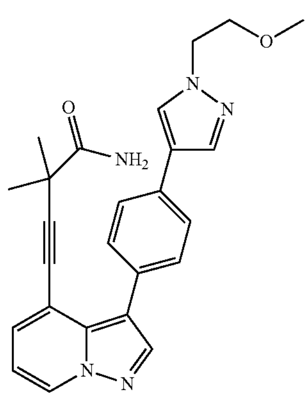 [SMILES: COCCn1cc(-c2ccc(-c3cnn4cccc(C#CC(C)(C)C(N)=O)c34)cc2)cn1] | 4-(3-(4-(1-(2-methoxyethyl)-1H-pyrazol-4-yl)phenyl)pyrazolo[1,5-a]pyridin-4-yl)-2,2-dimethylbut-3-ynamide | 428.2 |

TABLE 1-continued

| P Number | Structure | Name | MS |
|---|---|---|---|
| P-0470 | 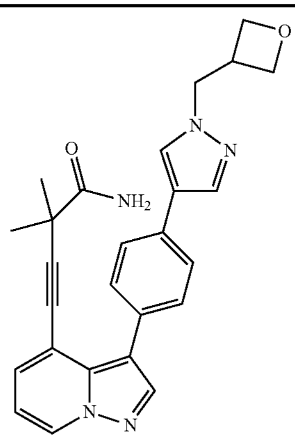 | 2,2-dimethyl-4-(3-(4-(1-(oxetan-3-ylmethyl)-1H-pyrazol-4-yl)phenyl)pyrazolo[1,5-a]pyridin-4-yl)but-3-ynamid | 440.2 |

Biological Examples

Biological Test Methods
The Compounds of Disclosure were Tested Using the Following Assays:
Human CDK8/CyclinC enzymatic assay This assay measures the ability of CDK8 to phosphorylate its direct substrate STAT1 at serine 727 in vitro[1,2]. The recombinant human CDK8/CyclinC enzyme complex is purchased from ProQinase. Biotinylated STAT1 is purified from E. coli. The CDK8/CyclinC enzyme assay is performed using 2 nM CDK8/CyclinC and 0.8 nM STAT1 in the presence of 50 mM Hepes buffer (pH 7.5), 10 mM MgCl$_2$, 1 mM EGTA, 0.01% Tween 20, 2 mM DTT, and 100 µM ATP. A 19 µL volume of the above reaction mixture is added to wells of 384-well AlphaPlate (PerkinElmer GA, USA) containing 1 µL of various concentrations of test compound or DMSO vehicle and incubated for 60 minutes at room temperature. 16 wells containing all the components of reaction mixture and 5% DMSO serve as high control. 16 wells containing all the components except ATP of reaction mixture and 5% DMSO serves as low control. The enzymatic reaction is stopped by the addition of 5 µL stop/detection mixture containing 50 mM Hepes buffer (pH 7.5), 100 mM EDTA, 0.1% BSA, 0.16 nM Phospho-STAT1 (Ser727) rabbit monoclonal antibody (Cell Signaling Technology), 10 µg/mL streptavidin-coated AlphaScreen donor beads (PerkinElmer GA, USA), and 10 µg/mL Protein A-coated AlphaScreen acceptor beads (PerkinElmer GA, USA) and incubated for 3 hours at room temperature. The Phospho-STAT1 (Ser727) antibody binds to STAT1 substrate that has been phosphorylated by active CDK8/CyclinC. The streptavidin donor beads bind to the biotinylated STAT1 substrate, and the Protein A acceptor beads bind to the Phospho-STAT1 (Ser727) antibody. Upon excitation of these beads with laser light at 680 nm, singlet oxygen is produced. This singlet oxygen is rapidly quenched, unless the AlphaScreen Protein A acceptor beads are in close proximity, in which case a proximity signal can be measured at 580 nm. In the presence of catalytic activity, there is a very strong proximity signal. Selective CDK8 inhibitors affect a decrease in this proximity signal through a decrease in phosphorylation of the STAT1 substrate at serine 727. The percentage inhibition at individual concentrations relative to high and low controls is calculated. The data are analyzed by using nonlinear regression to generate IC50 values.

Determine Inhibitor Activity Against CDK8 in Cell Based Phospho-STAT1 Assay

This assay measures the phosphorylation of the CDK8 substrate STAT1 following Interferon-gamma (IFNγ) stimulation[1]. The lung carcinoma cell line A549 is seeded in a 96 well plate in 50 µL of culture media at 5×10$^4$ cells/well and incubated at 37° C. overnight. Serial dilutions of compounds (in total volume of 50 µL culture media) are added to the cells and incubated at 37° C. for one hour. Human IFNγ (R&D Systems) is added to the cells at a 10 ng/mL final concentration. 4 wells containing DMSO treated cells stimulated with IFNγ serve as high controls and 4 wells containing DMSO treated unstimulated cells serve as low controls. After 30 minute IFNγ stimulation at 37° C., the culture media is removed and 50 µL of 1×AlphaLISA lysis buffer (PerkinElmer GA, USA) is added to each well. 5 µL cell lysate is transferred to a 384 well AlphaPlate (PerkinElmer GA, USA) and 5 µL containing 0.156 nM Phospho-STAT1 (Ser727) rabbit monoclonal antibody (Cell Signaling Technology), 0.156 nM Mouse Anti-STAT1 antibody (BD Transduction Laboratories), and 10 µg/mL Anti-rabbit IgG AlphaLISA acceptor beads (PerkinElmer GA, USA) diluted in 1× AlphaLISA immunoassay buffer (PerkinElmer GA, USA) is added to the cell lysates and incubated at room temperature for 90 minutes. 5 µL Anti-Mouse IgG Alpha donor beads diluted in 1× AlphaLISA immunoassay buffer (PerkinElmer GA, USA) is added to the reaction mixture and incubated at room temperature for 90 minutes. Upon excitation of these beads with laser light at 680 nm, singlet oxygen is produced. This singlet oxygen is rapidly quenched, unless the AlphaLISA Anti-Rabbit IgG acceptor beads are in close proximity, in which case a proximity signal can be measured at 580 nm. In the presence of cellular CDK8 catalytic activity, there is a very strong proximity signal. Selective CDK8 inhibitors affect a decrease in this proximity signal through a decrease in phosphorylation of STAT1 at serine 727. The percentage inhibition at individual concentrations relative to high and low controls is calculated. The data are analyzed by using nonlinear regression to generate IC$_{50}$ values.

Determine Inhibitor Activity Against CDK8 in Cell Based TCF/LEF Reporter Assay

The colorectal carcinoma cell line HCT116 was stably transduced with lentivirus encoding the TCF/LEF promoter upstream of a luciferase reporter gene (Qiagen) and single cell clones expressing this construct (referred to as HCT116+TCF/LEF) were isolated. HCT116 express endogenous mutant β-catenin[3], resulting in up-regulation of transcription through the TCF/LEF promoter. Expression of the TCF/LEF reporter construct in HCT116 results in constitutive expression of luciferase. Treatment of the cells with inhibitors of components of the β-catenin signaling pathway (such as CDK8) results in decreased expression of luciferase. The assay is performed as follows. The HCT116+ TCF/LEF cell line is seeded in a 96 well plate in 50 μL of culture media at $1 \times 10^4$ cells/well and incubated at 37° C. overnight. Serial dilutions of compounds (in total volume of 50 μL culture media) are added to the cells and incubated at 37° C. for 24 hours. 4 wells of DMSO treated cells serve as high controls and cells treated with 10 uM of the reference compound CCT251545 (a known CDK8 inhibitor)[4] serve as low controls. The viability of the cells is assayed by the addition of L CellTiter-Fluor reagent (Promega) followed by 30 minute incubation at 37° C. and quantification of the fluorescent signal (Ex400/Em505). The luciferase expression is then assayed by the addition of 25 μL ONE-Glo reagent (Promega) followed by 10 minute incubation at room temperature and quantification of the luminescence signal. The luminescence signal is normalized to the fluorescence signal to correct for any loss in cell viability over the 24 hour compound incubation period. The percentage inhibition at individual concentrations relative to high and low controls is calculated. The data are analyzed by using nonlinear regression to generate $IC_{50}$ values.

REFERENCES

1. Bancerek, J. et al. CDK8 kinase phosphorylates transcription factor STAT1 to selectively regulate the interferon response. *Immunity* 38, 250-62 (2013).
2. Putz, E. M. et al. CDK8-mediated STAT1-S727 phosphorylation restrains NK cell cytotoxicity and tumor surveillance. *Cell Rep.* 4, 437-44 (2013).
3. El-Bahrawy, M. et al. Characterization of the E-cadherin/catenin complex in colorectal carcinoma cell lines. *Int. J. Exp. Pathol.* 85, 65-74 (2004).
4. Dale, T. et al. A selective chemical probe for exploring the role of CDK8 and CDK19 in human disease. *Nat. Chem. Biol.* 11, 973-80 (2015).
5, Rzymski et al. SEL120-34A is a novel CDK8 inhibitor active in AML cells with high levels of serine phosphorylation of STAT1 and STAT5 transactivation domain; Oncotarget. 2017 May 16; 8(20): 33779-33795
6. Johannessen et al. Published Online: 14 Aug. 2017; DOI: 10.1038/NCHEMBIO.2458 Small-molecule studies identifiy CDK8 as a regulator of IL-10 in myeloid cells.
7. MingHua Li et al. Abberrant expression of CDK8 regulates the malignant phenotype and associated with poor prognosis in human larygeal squamous cell carcinoma. Eur Arch Otorhinolaryngol (Feb. 20, 2017).

The following Table 2 provides data indicating biochemical and/or cell inhibitory activity for exemplary compounds as described herein in Table 1. In Table 2 below, activity is provided as follows: +++=0.0001 μM<$IC_{50}$<100 μM; ++=100 μM<$IC_{50}$<1,000 μM, +=1,000 μM<$IC_{50}$<10,000 μM.

TABLE 2

| P # | CDK8 $IC_{50}$ (μM) | A549 $IC_{50}$ (μM) | HCT116 $IC_{50}$ (μM) |
|---|---|---|---|
| P-0001 | +++ | +++ | +++ |
| P-0002 | +++ | +++ | +++ |
| P-0003 | +++ | +++ | +++ |
| P-0004 | +++ | +++ | +++ |
| P-0005 | +++ | +++ | +++ |
| P-0006 | +++ | +++ | +++ |
| P-0007 | +++ | +++ | +++ |
| P-0008 | +++ | +++ | +++ |
| P-0009 | +++ | +++ | +++ |
| P-0010 | +++ | ++ | ++ |
| P-0011 | +++ | +++ | +++ |
| P-0012 | +++ | +++ | +++ |
| P-0013 | +++ | +++ | +++ |
| P-0014 | +++ | +++ | +++ |
| P-0015 | +++ | +++ | +++ |
| P-0016 | +++ | +++ | +++ |
| P-0017 | +++ | +++ | +++ |
| P-0018 | +++ | +++ | +++ |
| P-0019 | +++ | +++ | +++ |
| P-0020 | +++ | +++ | +++ |
| P-0021 | +++ | +++ | +++ |
| P-0022 | +++ | +++ | +++ |
| P-0023 | +++ | +++ | +++ |
| P-0024 | +++ | +++ | +++ |
| P-0025 | +++ | +++ | +++ |
| P-0026 | +++ | +++ | +++ |
| P-0027 | +++ | +++ | +++ |
| P-0028 | +++ | +++ | +++ |
| P-0029 | +++ | +++ | +++ |
| P-0030 | +++ | +++ | +++ |
| P-0031 | +++ | +++ | +++ |
| P-0032 | +++ | +++ | +++ |
| P-0033 | +++ | +++ | +++ |
| P-0034 | +++ | +++ | +++ |
| P-0035 | +++ | +++ | +++ |
| P-0036 | +++ | +++ | +++ |
| P-0037 | ++ | | ++ |
| P-0038 | +++ | +++ | +++ |
| P-0039 | +++ | ++ | ++ |
| P-0040 | +++ | +++ | +++ |
| P-0041 | +++ | +++ | +++ |
| P-0042 | +++ | +++ | +++ |
| P-0043 | +++ | ++ | +++ |
| P-0044 | + | | |
| P-0045 | +++ | ++ | +++ |
| P-0046 | +++ | +++ | +++ |
| P-0047 | +++ | +++ | +++ |
| P-0048 | +++ | +++ | +++ |
| P-0049 | +++ | +++ | +++ |
| P-0050 | +++ | +++ | +++ |
| P-0051 | +++ | +++ | +++ |
| P-0052 | +++ | +++ | +++ |
| P-0053 | +++ | ++ | +++ |
| P-0054 | + | | |
| P-0055 | +++ | +++ | +++ |
| P-0056 | +++ | +++ | +++ |
| P-0057 | +++ | +++ | +++ |
| P-0058 | +++ | +++ | +++ |
| P-0059 | +++ | +++ | +++ |
| P-0060 | +++ | +++ | +++ |
| P-0061 | +++ | +++ | +++ |
| P-0062 | +++ | +++ | +++ |
| P-0063 | +++ | +++ | +++ |
| P-0064 | ++ | +++ | +++ |
| P-0065 | +++ | +++ | ++ |
| P-0066 | +++ | +++ | +++ |
| P-0067 | +++ | ++ | +++ |
| P-0068 | +++ | +++ | +++ |
| P-0069 | +++ | +++ | +++ |
| P-0070 | +++ | +++ | +++ |
| P-0071 | +++ | +++ | +++ |
| P-0072 | + | | |
| P-0073 | +++ | +++ | +++ |
| P-0074 | +++ | ++ | ++ |
| P-0075 | +++ | | |
| P-0076 | +++ | ++ | ++ |
| P-0077 | +++ | ++ | ++ |

TABLE 2-continued

| P # | CDK8 IC$_{50}$ (μM) | A549 IC$_{50}$ (μM) | HCT116 IC$_{50}$ (μM) |
| --- | --- | --- | --- |
| P-0078 | +++ | +++ | +++ |
| P-0079 | +++ | +++ | +++ |
| P-0080 | +++ | +++ | +++ |
| P-0081 | +++ | | |
| P-0082 | ++ | | |
| P-0083 | +++ | ++ | ++ |
| P-0084 | +++ | +++ | +++ |
| P-0085 | +++ | +++ | +++ |
| P-0086 | +++ | +++ | ++ |
| P-0087 | +++ | ++ | ++ |
| P-0088 | +++ | +++ | +++ |
| P-0089 | +++ | +++ | ++ |
| P-0090 | +++ | +++ | +++ |
| P-0091 | +++ | +++ | +++ |
| P-0092 | +++ | | ++ |
| P-0093 | +++ | | ++ |
| P-0094 | +++ | +++ | +++ |
| P-0095 | +++ | +++ | +++ |
| P-0096 | +++ | +++ | +++ |
| P-0097 | +++ | +++ | ++ |
| P-0098 | +++ | +++ | +++ |
| P-0099 | +++ | +++ | ++ |
| P-0100 | +++ | +++ | +++ |
| P-0101 | +++ | +++ | ++ |
| P-0102 | +++ | +++ | +++ |
| P-0103 | +++ | +++ | ++ |
| P-0104 | +++ | +++ | +++ |
| P-0105 | +++ | +++ | ++ |
| P-0106 | +++ | +++ | ++ |
| P-0107 | +++ | | |
| P-0108 | +++ | | ++ |
| P-0109 | +++ | +++ | ++ |
| P-0110- | +++ | +++ | +++ |
| P-0111 | +++ | +++ | +++ |
| P-0112 | +++ | +++ | ++ |
| P-0113 | +++ | +++ | +++ |
| P-0114 | +++ | +++ | +++ |
| P-0115 | +++ | +++ | +++ |
| P-0116 | +++ | ++ | ++ |
| P-0117 | +++ | +++ | +++ |
| P-0118 | +++ | +++ | +++ |
| P-0119 | +++ | +++ | ++ |
| P-0120 | +++ | +++ | ++ |
| P-0121 | +++ | +++ | +++ |
| P-0122 | +++ | +++ | +++ |
| P-0123 | +++ | +++ | +++ |
| P-0124 | +++ | +++ | ++ |
| P-0125 | +++ | +++ | +++ |
| P-0126 | +++ | +++ | ++ |
| P-0127 | +++ | +++ | +++ |
| P-0128 | +++ | +++ | +++ |
| P-0129 | +++ | +++ | +++ |
| P-0130 | +++ | +++ | +++ |
| P-0131 | +++ | ++ | + |
| P-0132 | +++ | +++ | +++ |
| P-0133 | +++ | ++ | ++ |
| P-0134 | +++ | ++ | +++ |
| P-0135 | +++ | ++ | ++ |
| P-0136 | +++ | +++ | +++ |
| P-0137 | +++ | +++ | +++ |
| P-0138 | +++ | +++ | +++ |
| P-0139 | +++ | +++ | +++ |
| P-0140 | +++ | +++ | +++ |
| P-0141 | +++ | +++ | +++ |
| P-0142 | +++ | +++ | +++ |
| P-0143 | +++ | +++ | +++ |
| P-0144 | +++ | +++ | +++ |
| P-0145 | +++ | +++ | +++ |
| P-0146 | +++ | +++ | +++ |
| P-0147 | +++ | +++ | +++ |
| P-0148 | +++ | ++ | +++ |
| P-0149 | +++ | +++ | +++ |
| P-0150 | +++ | +++ | +++ |
| P-0151 | +++ | +++ | +++ |
| P-0152 | +++ | ++ | +++ |
| P-0153 | +++ | +++ | +++ |
| P-0154 | +++ | +++ | +++ |
| P-0155 | +++ | ++ | ++ |
| P-0156 | +++ | + | + |
| P-0157 | +++ | ++ | ++ |
| P-0158 | + | | |
| P-0159 | +++ | ++ | ++ |
| P-0160 | + | | |
| P-0161 | ++ | + | + |
| P-0162 | +++ | +++ | +++ |
| P-0163 | +++ | +++ | +++ |
| P-0164 | +++ | +++ | +++ |
| P-0165 | +++ | ++ | + |
| P-0166 | +++ | +++ | +++ |
| P-0167 | +++ | +++ | +++ |
| P-0168 | +++ | +++ | +++ |
| P-0169 | +++ | +++ | +++ |
| P-0170 | +++ | +++ | +++ |
| P-0171 | +++ | +++ | +++ |
| P-0172 | +++ | +++ | +++ |
| P-0173 | +++ | +++ | +++ |
| P-0174 | +++ | +++ | +++ |
| P-0175 | +++ | +++ | +++ |
| P-0176 | +++ | ++ | +++ |
| P-0177 | +++ | +++ | +++ |
| P-0178 | +++ | +++ | +++ |
| P-0179 | + | | |
| P-0180 | +++ | +++ | +++ |
| P-0181 | +++ | +++ | +++ |
| P-0182 | +++ | +++ | +++ |
| P-0183 | +++ | +++ | +++ |
| P-0184 | +++ | +++ | ++ |
| P-0185 | +++ | ++ | + |
| P-0186 | +++ | +++ | +++ |
| P-0187 | +++ | +++ | +++ |
| P-0188 | +++ | +++ | +++ |
| P-0189 | +++ | +++ | +++ |
| P-0190 | +++ | +++ | +++ |
| P-0191 | +++ | +++ | ++ |
| P-0193 | +++ | ++ | + |
| P-0194 | +++ | +++ | +++ |
| P-0195 | +++ | +++ | +++ |
| P-0196 | +++ | +++ | ++ |
| P-0197 | +++ | +++ | ++ |
| P-0198 | +++ | ++ | ++ |
| P-0199 | +++ | +++ | +++ |
| P-0200 | +++ | + | ++ |
| P-0201 | +++ | ++ | +++ |
| P-0202 | +++ | +++ | +++ |
| P-0203 | +++ | +++ | +++ |
| P-0204 | +++ | +++ | +++ |
| P-0205 | +++ | ++ | +++ |
| P-0206 | +++ | +++ | +++ |
| P-0207 | ++ | + | ++ |
| P-0208 | +++ | +++ | +++ |
| P-0209 | +++ | +++ | +++ |
| P-0210 | ++ | | |
| P-0211 | +++ | +++ | ++ |
| P-0212 | ++ | | ++ |
| P-0213 | ++ | + | + |
| P-0214 | +++ | +++ | +++ |
| P-0215 | +++ | ++ | ++ |
| P-0216 | +++ | +++ | ++ |
| P-0217 | +++ | +++ | +++ |
| P-0218 | +++ | +++ | +++ |
| P-0219 | +++ | +++ | +++ |
| P-0220 | +++ | +++ | +++ |
| P-0221 | +++ | +++ | +++ |
| P-0222 | +++ | +++ | +++ |
| P-0223 | +++ | +++ | +++ |
| P-0224 | +++ | +++ | +++ |
| P-0225 | +++ | +++ | +++ |
| P-0226 | +++ | +++ | +++ |
| P-0227 | ++ | + | |
| P-0228 | +++ | + | + |
| P-0229 | +++ | +++ | +++ |
| P-0230 | +++ | +++ | +++ |
| P-0231 | +++ | ++ | ++ |
| P-0232 | +++ | +++ | +++ |

TABLE 2-continued

| P # | CDK8 IC$_{50}$ (μM) | A549 IC$_{50}$ (μM) | HCT116 IC$_{50}$ (μM) |
|---|---|---|---|
| P-0233 | +++ | + | ++ |
| P-0234 | +++ | ++ | +++ |
| P-0235 | +++ | ++ | ++ |
| P-0236 | +++ | + | |
| P-0237 | +++ | +++ | +++ |
| P-0238 | +++ | +++ | +++ |
| P-0239 | ++ | | |
| P-0240 | ++ | + | + |
| P-0241 | ++ | ++ | ++ |
| P-0242 | +++ | +++ | +++ |
| P-0243 | +++ | +++ | +++ |
| P-0244 | +++ | ++ | ++ |
| P-0245 | +++ | +++ | ++ |
| P-0246 | +++ | +++ | ++ |
| P-0247 | +++ | +++ | +++ |
| P-0248 | +++ | +++ | +++ |
| P-0249 | +++ | + | ++ |
| P-0250 | +++ | +++ | +++ |
| P-0251 | +++ | + | + |
| P-0252 | ++ | + | + |
| P-0253 | +++ | ++ | ++ |
| P-0254 | +++ | ++ | ++ |
| P-0255 | ++ | + | + |
| P-0256 | + | | + |
| P-0257 | +++ | ++ | ++ |
| P-0258 | + | ++ | ++ |
| P-0259 | +++ | ++ | ++ |
| P-0260 | +++ | ++ | ++ |
| P-0261 | +++ | +++ | +++ |
| P-0262 | +++ | +++ | +++ |
| P-0263 | +++ | +++ | +++ |
| P-0264 | +++ | +++ | +++ |
| P-0265 | ++ | + | + |
| P-0266 | ++ | + | + |
| P-0267 | +++ | ++ | ++ |
| P-0268 | +++ | +++ | +++ |
| P-0269 | +++ | ++ | ++ |
| P-0270 | +++ | +++ | +++ |
| P-0271 | +++ | ++ | ++ |
| P-0272 | +++ | ++ | +++ |
| P-0273 | +++ | +++ | +++ |
| P-0274 | +++ | +++ | +++ |
| P-0275 | +++ | ++ | ++ |
| P-0276 | ++ | + | + |
| P-0277 | ++ | + | + |
| P-0278 | +++ | ++ | ++ |
| P-0280 | +++ | +++ | +++ |
| P-0281 | +++ | ++ | ++ |
| P-0282 | +++ | ++ | ++ |
| P-0283 | +++ | ++ | ++ |
| P-0284 | +++ | + | + |
| P-0285 | +++ | ++ | ++ |
| P-0286 | +++ | +++ | ++ |
| P-0287 | + | | |
| P-0288 | + | ++ | |
| P-0289 | +++ | + | + |
| P-0290 | +++ | | |
| P-0291 | +++ | ++ | |
| P-0292 | ++ | + | |
| P-0293 | +++ | +++ | + |
| P-0294 | ++ | + | |
| P-0295 | +++ | +++ | +++ |
| P-0296 | +++ | ++ | + |
| P-0297 | +++ | ++ | +++ |
| P-0298 | +++ | + | |
| P-0299 | +++ | + | |
| P-0300 | +++ | ++ | |
| P-0301 | +++ | ++ | |
| P-0302 | ++ | + | |
| P-0303 | + | | |
| P-0304 | +++ | + | + |
| P-0305 | +++ | + | |
| P-0306 | ++ | + | |
| P-0307 | +++ | ++ | |
| P-0308 | +++ | ++ | ++ |
| P-0309 | +++ | +++ | ++ |
| P-0310 | +++ | +++ | +++ |
| P-0311 | +++ | +++ | ++ |
| P-0312 | + | + | |
| P-0313 | ++ | ++ | ++ |
| P-0314 | +++ | +++ | +++ |
| P-0315 | +++ | ++ | ++ |
| P-0316 | +++ | +++ | +++ |
| P-0317 | +++ | +++ | ++ |
| P-0318 | + | | |
| P-0319 | + | | |
| P-0321 | ++ | + | + |
| P-0322 | +++ | ++ | ++ |
| P-0323 | +++ | +++ | +++ |
| P-0324 | +++ | +++ | +++ |
| P-0325 | + | | |
| P-0326 | ++ | + | |
| P-0327 | +++ | +++ | +++ |
| P-0328 | +++ | +++ | +++ |
| P-0329 | +++ | +++ | +++ |
| P-0330 | +++ | +++ | +++ |
| P-0331 | +++ | ++ | ++ |
| P-0332 | +++ | +++ | +++ |
| P-0333 | +++ | ++ | ++ |
| P-0334 | ++ | ++ | |
| P-0335 | +++ | +++ | |
| P-0336 | ++ | ++ | |
| P-0337 | +++ | +++ | +++ |
| P-0338 | +++ | ++ | |
| P-0339 | ++ | ++ | |
| P-0340 | +++ | +++ | |
| P-0341 | +++ | +++ | +++ |
| P-0342 | +++ | +++ | |
| P-0343 | +++ | ++ | |
| P-0344 | ++ | ++ | |
| P-0345 | + | + | |
| P-0346 | +++ | ++ | |
| P-0347 | +++ | ++ | |
| P-0348 | ++ | + | |
| P-0349 | ++ | ++ | |
| P-0350 | + | | |
| P-0351 | +++ | ++ | |
| P-0352 | +++ | ++ | |
| P-0353 | + | | |
| P-0354 | ++ | + | |
| P-0355 | ++ | ++ | |
| P-0356 | +++ | +++ | |
| P-0357 | +++ | +++ | |
| P-0358 | +++ | +++ | +++ |
| P-0359 | +++ | +++ | +++ |
| P-0360 | +++ | +++ | |
| P-0361 | +++ | +++ | |
| P-0362 | +++ | +++ | ++ |
| P-0363 | +++ | +++ | +++ |
| P-0364 | +++ | +++ | |
| P-0365 | +++ | +++ | |
| P-0366 | +++ | +++ | +++ |
| P-0367 | +++ | +++ | |
| P-0368 | +++ | +++ | |
| P-0369 | ++ | + | |
| P-0370 | +++ | +++ | |
| P-0371 | +++ | + | |
| P-0372 | +++ | + | |
| P-0373 | +++ | ++ | |
| P-0374 | +++ | +++ | |
| P-0375 | +++ | +++ | |
| P-0376 | +++ | ++ | |
| P-0377 | + | + | |
| P-0378 | +++ | ++ | |
| P-0379 | + | | |
| P-0380 | ++ | + | |
| P-0381 | ++ | + | |
| P-0382 | + | | |
| P-0383 | + | + | |
| P-0384 | + | + | |
| P-0385 | + | + | |
| P-0386 | +++ | +++ | |
| P-0387 | + | | |
| P-0388 | ++ | ++ | |

TABLE 2-continued

| P # | CDK8 IC$_{50}$ ($\mu$M) | A549 IC$_{50}$ ($\mu$M) | HCT116 IC$_{50}$ ($\mu$M) |
|---|---|---|---|
| P-0389 | ++ | + | |
| P-0390 | ++ | ++ | |
| P-0391 | ++ | ++ | |
| P-0392 | + | | |
| P-0393 | + | + | |
| P-0394 | + | ++ | |
| P-0395 | + | + | |
| P-0396 | +++ | ++ | |
| P-0397 | ++ | ++ | |
| P-0398 | ++ | | |
| P-0399 | ++ | + | |
| P-0400 | ++ | ++ | |
| P-0401 | +++ | +++ | |
| P-0402 | +++ | +++ | |
| P-0403 | +++ | +++ | |
| P-0404 | +++ | +++ | |
| P-0405 | +++ | +++ | |
| P-0406 | ++ | ++ | |
| P-0407 | + | | |
| P-0409 | +++ | ++ | |
| P-0410 | +++ | + | |
| P-0411 | ++ | | |
| P-0412 | +++ | ++ | |
| P-0413 | ++ | + | |
| P-0414 | +++ | +++ | |
| P-0415 | +++ | +++ | +++ |
| P-0416 | +++ | ++ | ++ |
| P-0417 | +++ | ++ | |
| P-0418 | +++ | | |
| P-0419 | ++ | ++ | |
| P-0420 | +++ | + | |
| P-0421 | +++ | +++ | +++ |
| P-0422 | +++ | +++ | |
| P-0423 | +++ | +++ | |
| P-0424 | ++ | + | |
| P-0425 | ++ | + | |
| P-0426 | +++ | +++ | |
| P-0427 | +++ | ++ | |
| P-0428 | +++ | ++ | |
| P-0429 | +++ | +++ | +++ |
| P-0430 | +++ | + | |
| P-0431 | ++ | + | |
| P-0432 | ++ | + | |
| P-0433 | +++ | +++ | |
| P-0434 | ++ | + | |
| P-0435 | ++ | | |
| P-0436 | + | + | |
| P-0437 | +++ | +++ | +++ |
| P-0438 | +++ | +++ | +++ |
| P-0439 | +++ | +++ | |
| P-0440 | +++ | +++ | |
| P-0441 | +++ | +++ | |
| P-0442 | +++ | +++ | |
| P-0443 | +++ | +++ | +++ |
| P-0444 | +++ | ++ | ++ |
| P-0445 | +++ | +++ | +++ |
| P-0446 | +++ | ++ | |
| P-0447 | ++ | +++ | |
| P-0448 | ++ | + | |
| P-0449 | +++ | + | |
| P-0450 | +++ | +++ | |
| P-0451 | +++ | +++ | |
| P-0452 | +++ | +++ | +++ |
| P-0453 | +++ | ++ | |
| P-0454 | +++ | +++ | +++ |
| P-0455 | + | | |
| P-0456 | +++ | +++ | +++ |
| P-0457 | +++ | +++ | +++ |
| P-0458 | +++ | +++ | +++ |
| P-0459 | +++ | +++ | +++ |
| P-0460 | | +++ | +++ |
| P-0461 | +++ | +++ | +++ |
| P-0462 | +++ | +++ | +++ |
| P-0463 | +++ | +++ | +++ |
| P-0464 | +++ | +++ | +++ |
| P-0465 | +++ | +++ | +++ |
| P-0466 | +++ | +++ | +++ |
| P-0467 | +++ | +++ | +++ |
| P-0468 | +++ | +++ | +++ |
| P-0469 | +++ | +++ | +++ |
| P-0470 | +++ | +++ | +++ |

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of the compounds of this disclosure and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

What is claimed is:

1. A compound of Formula II(b), II(c), or II(d):

II(b)

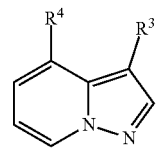
II(c)

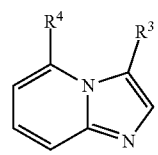
II(d)

or a pharmaceutically acceptable salt, a tautomer, a stereoisomer, or a deuterated analog thereof, wherein:

$R^3$ is —B-L-T;

$R^4$ is one of (a1), (a2), (b1), (b2), (c) or (d):
- (a1) saturated heterocycloalkyl substituted with 0-3 $R^7$ groups, wherein the saturated heterocycloalkyl is further optionally substituted with one $R^8$ group;
- (a2) heterocycloalkenyl substituted with 0-3 $R^7$ groups, wherein the heterocycloalkenyl is further optionally substituted with one $R^8$ group;
- (b1) saturated $C_3$-$C_6$ cycloalkyl substituted with 0-3 $R^7$ groups, wherein the saturated $C_3$-$C_6$ cycloalkyl is further optionally substituted with one $R^8$ group;
- (b2) $C_5$-$C_6$ cycloalkenyl substituted with 0-3 $R^7$ groups, wherein the $C_5$-$C_6$ cycloalkenyl is further optionally substituted with one $R^8$ group;
- (c) aryl or heteroaryl substituted with one $R^{10}$ group, wherein the aryl or heteroaryl is further optionally substituted with one $R^1$ group; or
- (d) —$C_2$-$C_3$ alkynylene substituted with $R^{12}$;

$R^6$ is H, -$C_1$-$C_6$ alkyl, -$C_1$-$C_6$ haloalkyl, —$C_1$-$C_6$ alkylene-CN, —$C_3$-$C_6$ cycloalkyl, 4-6 membered heterocycloalkyl, 5-6 membered heteroaryl, or phenyl;

each $R^7$ is independently —$C_1$-$C_6$ alkyl, halogen, CN, hydroxyl, —$C_1$-$C_6$ haloalkyl, —$C_1$-$C_6$ cyanoalkyl, or —$C_1$-$C_6$ hydroxyalkyl optionally substituted with heteroaryl, provided that halogen and CN are not bonded to a heteroatom;

$R^8$ is CN, phenyl, 5-6 membered heterocycloalkyl or heteroaryl, —(CH$_2$)$_{0-2}$—C(O)—N(H)—$R^6$, —C(O)$R^6$, —(CH$_2$)$_{0-2}$C(O)OR$^6$, —(CH$_2$)$_{0-2}$S(O)$_2$R$^6$; or

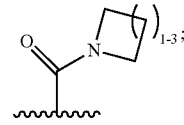

or $R^7$ and $R^8$, when both are attached to the same carbon atom of the saturated heterocycloalkyl, join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 —$C_1$-$C_6$ alkyl groups, and wherein the oxoheterocycloalkyl is optionally fused to a phenyl or 5-6 membered heteroaryl;

B is a bond, arylene, heteroarylene, or heterocycloalkylene, wherein the arylene, heteroarylene, or heterocycloalkylene are each substituted with 0-3 G1 groups and 0-1 G2 groups;

L is a bond, —O—, —C(O)—, —N(H)—, —N(H)S(O)$_2$—, —S(O)$_2$—N(H)—, —S(O)$_2$—, —S(O)$_2$—C$_1$-C$_4$ alkylene, —N(H)C(O)—C$_1$-C$_4$ alkylene, —N(H)C(O)O—C$_1$-C$_4$ alkylene, C$_1$-C$_4$ alkylene-N(H)—C(O)—, —N(H)—(CH$_2$)$_{0-4}$—, —C$_1$-C$_6$ alkylene, —O—C$_1$-C$_6$ alkylene, —O—C$_1$-C$_6$ haloalkylene, —O—C$_1$-C$_6$ alkylene-O—, or —O—C$_1$-C$_6$ hydroxyalkylene;

T is heteroaryl, aryl, cycloalkyl, or heterocycloalkyl, wherein the heteroaryl, cycloalkyl, or heterocycloalkyl are each substituted with 0-3 G3 groups and 0-1 G4 groups;

or B-L is ethynylene and T is heteroaryl substituted with 0-3 G3 or G4 groups;

each G1 is independently halogen, —C$_1$-C$_4$ alkyl, alkoxy, —C$_1$-C$_4$haloalkyl, hydroxyl, or —C$_1$-C$_4$ hydroxyalkyl;

G2 is —C$_0$-C$_4$ alkylene-S(O)$_2$—C$_1$-C$_4$alkyl, —C$_0$-C$_4$ alkylene-C(O)—NH$_2$, or —N(H)C(O)—C$_1$-C$_4$ alkyl;

each G3 is independently halogen, —C$_1$-C$_6$alkyl, —C$_1$-C$_6$ alkoxy, —C$_1$-C$_6$ haloalkyl, hydroxyl, C$_1$-C$_6$ hydroxyalkyl, or —C$_0$-C$_6$ alkylene-CN;

G4, when attached to a carbon atom, is halogen, —C$_1$-C$_6$alkyl, —C$_1$-C$_6$ alkoxy, —C$_1$-C$_6$ haloalkyl, hydroxyl, —C$_1$-C$_6$ hydroxyalkyl, —C$_0$-C$_6$ alkylene-CN, —C$_0$-C$_4$ alkylene-S(O)$_2$—C$_1$-C$_6$ alkyl, —C$_0$-C$_4$ alkylene-N(H)—S(O)$_2$—C$_1$-C$_4$ alkyl, —C$_0$-C$_4$ alkylene-C(O)—NH$_2$, —C$_0$-C$_4$ alkylene-C(O)—N(H)—C$_1$-C$_4$ alkyl, —N(H)—C(O)—C$_1$-C$_4$ alkyl, —C$_0$-C$_4$ alkylene-C(O)—N(C$_1$-C$_4$ alkyl)$_2$, —C$_1$-C$_6$ alkylene-N—(C$_1$-C$_4$ alkyl)$_2$, —C$_1$-C$_6$ alkylene-N(H)—(C$_1$-C$_4$ alkyl), —C$_1$-C$_6$ alkylene-NH$_2$, —C$_0$-C$_4$ alkylene-heterocycloalkyl, —C$_0$-C$_4$ alkylene-C(O)O—C$_1$-C$_6$ alkyl, or —C$_0$-C$_6$ alkylene-cycloalkyl optionally substituted with CN, OH, —C$_1$-C$_4$alkyl, —C(O)O—C$_1$-C$_4$ alkyl, —C(O)OH, or halogen;

or G4, when attached to a nitrogen atom, is —C$_1$-C$_6$alkyl, —C$_1$-C$_6$alkylene-C$_1$-C$_6$ alkoxy, —C$_1$-C$_6$ haloalkyl, —C$_1$-C$_6$ hydroxyalkyl, —C$_1$-C$_6$ alkylene-CN, —C$_1$-C$_4$ alkylene-S(O)$_2$—C$_1$-C$_6$ alkyl, —C$_1$-C$_3$ alkylene-N(H)—S(O)$_2$—C$_1$-C$_4$ alkyl, —C$_1$-C$_4$ alkylene-C(O)—NH$_2$, —C$_1$-C$_4$ alkylene-C(O)—N(H)—C$_1$-C$_4$ alkyl, —C$_1$-C$_4$ alkylene-C(O)—N(C$_1$-C$_4$ alkyl)$_2$, —C$_1$-C$_6$ alkylene-N—(C$_1$-C$_4$ alkyl)$_2$, —C$_1$-C$_6$ alkylene-N(H)—(C$_1$-C$_4$ alkyl), —C$_1$-C$_6$ alkylene-NH$_2$, —C$_0$-C$_4$ alkylene-heterocycloalkyl, —C$_0$-C$_4$ alkylene-C(O)O—C$_1$-C$_6$ alkyl, —C$_0$-C$_4$ alkylene-C(O)OH, or —C$_1$-C$_6$ alkylene-cycloalkyl optionally substituted with CN, OH, C$_1$-C$_4$ alkyl, —C(O)O—C$_1$-C$_4$ alkyl, —C(O)OH, or halogen;

$R^{10}$ is —NHS(O)$_2$—C$_1$-C$_5$ alkyl, —S(O)$_2$—C$_1$-C$_5$ alkyl, —S(O)$_2$-5-6 membered heterocycloalkyl, —S(O)$_2$—N(H) C$_1$-C$_5$alkyl, —(CH$_2$)$_{0-1}$—C(O)NH$_2$, —(CH$_2$)$_{0-1}$—O-phenyl, —(CH$_2$)$_{0-1}$—O-(5-6 membered)heteroaryl, —(CH$_2$)$_{0-1}$—NHC(O)O—C$_1$-C$_2$-alkylene-phenyl, —(CH$_2$)$_{0-1}$—NHC(O)-5-6 membered heteroaryl, —(CH$_2$)$_{0-1}$—NHC(O)-phenyl, —C$_1$-C$_5$ alkylene-(5-6 membered)heterocycloalkyl, —C$_2$-C$_4$alkenyl, or CN;

$R^{11}$ is H, C3-C$_7$ cycloalkyl, C$_5$-C$_6$ cycloalkenyl or 5-6 membered heterocycloalkyl;

R$^{12}$ is 3-6 membered cycloalkylene-R$^{13a}$, —C(O)NHR$^6$, —Z$^1$—(CH$_2$)$_{1-2}$—Z$^2$, —Z$^1$—(C$_1$-C$_2$)haloalkylene-Z$^2$, or —Z$^1$—(C$_1$-C$_2$)hydroxyalkylene-Z$^2$;

each R$^{13a}$ is halogen, hydroxyl, —C$_1$-C$_3$ alkyl, —C$_1$-C$_3$ hydroxyalkyl, —C$_1$-C$_3$ haloalkyl or CN;

Z$^1$ is absent, —C$_1$-C$_3$ alkylene, or —C$_1$-C$_3$ haloalkylene; and

Z$^2$ is —C$_1$-C$_3$ alkoxyl optionally substituted with hydroxyl, —N(H)—S(O)$_2$—C$_1$-C$_3$ alkyl, —N(H)—C(O)—C$_1$-C$_3$ alkyl, —N(H)—C(O)—C$_1$-C$_3$ haloalkyl, —C(O)—N(H)—C$_1$-C$_3$ alkyl, —C(O)—N(H)—C$_1$-C$_3$ haloalkyl or phenyl.

2. The compound according to claim 1, wherein:

R$^4$ is one of (a1), (a2), (b1), (b2), (c), or (d):
(a1) saturated 5-6 membered heterocycloalkyl substituted with 0-1 R$^7$ groups, wherein the saturated heterocycloalkyl is further optionally substituted with one R$^8$ group;
(a2) 5-6 membered N-substituted heterocycloalkenyl substituted with 0-1 R$^7$ groups, wherein the six-membered N-substituted heterocycloalkenyl is further optionally substituted with one R$^8$ group;
(b1) cyclohexyl substituted with 1 R$^7$ group, wherein the cyclohexyl is further optionally substituted with one R$^8$ group;
(b2) cyclohexenyl substituted with 1 R$^7$ group, wherein the cyclohexenyl is further optionally substituted with one R$^8$ group;
(c) phenyl, pyridyl or pyrazolyl, wherein the phenyl, pyridyl or pyrazolyl is substituted with one R$^{10}$ group, and wherein the phenyl, pyridyl or pyrazolyl is further optionally substituted with one R$^{11}$ group; or
(d) ethynylene substituted with R$^{12}$;

R$^6$ is H, —C$_1$-C$_4$ alkyl, —C$_1$-C$_4$ haloalkyl, —C$_3$-C$_4$ cycloalkyl, 4-6 membered heterocycloalkyl, 5-6 membered heteroaryl, or phenyl;

each R$^7$ is independently —C$_1$-C$_4$ alkyl, fluoro, chloro, bromo, CN, hydroxyl, —C$_1$-C$_4$ haloalkyl, —C$_1$-C$_4$ cyanoalkyl, or —C$_1$-C$_4$ hydroxyalkyl optionally substituted with heteroaryl, provided that fluoro, chloro, bromo, and CN are not bonded to a heteroatom;

R$^8$ is CN, phenyl, 5-6 membered heteroaryl, —C(O)—N(H)—R$^6$, —C(O)OR$^6$, —(CH$_2$)$_{0-1}$—S(O)$_2$R$^6$; or

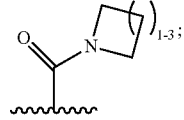

or R$^7$ and R$^8$, when both are attached to the same carbon atom of the saturated heterocycloalkyl, join to form a heterocycloalkyl, oxoheterocycloalkyl, or dioxoheterocycloalkyl, wherein the heterocycloalkyl, oxoheterocycloalkyl, or dioxoheterocycloalkyl is optionally substituted with 1-2 —C$_1$-C$_4$ alkyl groups, and wherein the oxoheterocycloalkyl is optionally fused to a phenyl or 5-6 membered heteroaryl;

R$^{10}$ is —NHS(O)$_2$—C$_1$-C$_4$alkyl, —S(O)$_2$—C$_1$-C$_4$alkyl, —S(O)$_2$-5-6 membered heterocycloalkyl, —S(O)$_2$—N(H) C$_1$-C$_4$alkyl, —(CH$_2$)$_{0-1}$—C(O)NH$_2$, —(CH$_2$)$_{0-1}$—O-phenyl, —(CH$_2$)$_{0-1}$—O-(5-6 membered)heteroaryl, —(CH$_2$)$_{0-1}$—NHC(O)O—CH$_2$-phenyl, —(CH$_2$)$_{0-1}$—NHC(O)-5-6 membered heteroaryl, —(CH$_2$)$_{0-1}$—NHC(O)-phenyl, —C$_1$-C$_4$ alkylene-(5-6 membered)heterocycloalkyl, —C$_2$-C$_4$alkenyl, or CN;

R$^{11}$ is C$_3$-C$_6$ cycloalkyl, C$_5$-C$_6$ cycloalkenyl or 5-6 membered heterocycloalkyl;

R$^{12}$ is 4-6 membered cycloalkylene-R$^{13a}$, —C(O)NHR$^6$, —Z$^1$—(CH$_2$)$_{1-2}$—Z$^2$, —Z$^1$—(C$_1$-C$_2$)haloalkylene-Z$^2$, or —Z$^1$—(C$_1$-C$_2$)hydroxyalkylene-Z$^2$;

each R$^{13a}$ is F, Cl, hydroxyl, —C$_1$-C$_3$ alkyl, —C$_1$-C$_3$ hydroxyalkyl, —C$_1$-C$_3$ haloalkyl or CN;

Z$^1$ is absent, —C$_1$-C$_3$ alkylene, or —C$_1$-C$_3$ fluoroalkylene;

Z$^2$ is —C$_1$-C$_3$ alkoxyl optionally substituted with hydroxyl, —N(H)—S(O)$_2$—C$_1$-C$_3$ alkyl, —N(H)—C(O)—C$_1$-C$_3$ alkyl, —N(H)—C(O)—C$_1$-C$_3$ haloalkyl, —C(O)—N(H)—C$_1$-C$_3$ alkyl, —C(O)—N(H)—C$_1$-C$_3$ haloalkyl, or phenyl;

B is a bond, phenylene, 5-6 membered heteroarylene, or 4-6 membered heterocycloalkylene, wherein the phenylene, 5-6 membered heteroarylene, or 4-6 membered heterocycloalkylene are each substituted with 0-2 G1 groups and 0-1 G2 groups;

L is a bond, —C(O)—, —N(H)—, —N(H)S(O)$_2$—, —S(O)$_2$—N(H)—, —S(O)$_2$—, —S(O)$_2$—C$_1$-C$_3$ alkylene, —N(H)C(O)—C$_1$-C$_3$ alkylene, —N(H)C(O)O—C$_1$-C$_3$ alkylene, C$_1$-C$_4$ alkylene-N(H)—C(O)—, —N(H)—(CH$_2$)$_{0-3}$, —C$_1$-C$_5$ alkylene, —O—C$_1$-C$_5$ alkylene, —O—C$_1$-C$_5$haloalkylene, —O—C$_1$-C$_5$ alkylene-O—, or —O—C$_1$-C$_5$ hydroxyalkylene;

T is 5-10 membered heteroaryl, 6-10 membered aryl, 3-6 membered cycloalkyl, or 4-6 membered heterocycloalkyl; wherein the 5-10 membered heteroaryl, 3-6 membered cycloalkyl, or 4-6 membered heterocycloalkyl are each substituted with 0-3 G3 groups and 0-1 G4 groups;

or B-L is ethynylene and T is 5-10 membered heteroaryl substituted with 0-3 G3 groups;

each G1 is independently halogen, —C$_1$-C$_3$ alkyl, —C$_1$-C$_3$ alkoxy, —C$_1$-C$_3$ haloalkyl, hydroxyl, or C$_1$-C$_3$ hydroxyalkyl;

G2 is —C$_0$-C$_3$ alkylene-S(O)$_2$—C$_1$-C$_3$ alkyl, —C$_0$-C$_3$ alkylene-C(O)—NH$_2$, or —N(H)C(O)—C$_1$-C$_3$ alkyl;

each G3 is independently halogen, —C$_1$-C$_5$ alkyl, —C$_1$-C$_5$ alkoxy, —C$_1$-C$_5$ haloalkyl, hydroxyl, —C$_1$-C$_5$ hydroxyalkyl, or —C$_0$-C$_5$ alkylene-CN; and G4, when attached to a carbon atom, is halogen, —C$_1$-C$_5$ alkyl, —C$_1$-C$_5$ alkoxy, —C$_1$-C$_5$ haloalkyl, hydroxyl, —C$_1$-C$_5$ hydroxyalkyl, —C$_0$-C$_5$ alkylene-CN, —C$_0$-C$_3$ alkylene-S(O)$_2$—C$_1$-C$_3$ alkyl, —C$_0$-C$_3$ alkylene-N(H)—S(O)$_2$—C$_1$-C$_4$ alkyl, —C$_0$-C$_3$ alkylene-C(O)—NH$_2$, —C$_0$-C$_4$ alkylene-C(O)—N(H)—C$_1$-C$_2$ alkyl, —C$_1$-C$_4$ alkylene-N—(C$_1$-C$_3$ alkyl)$_2$, —C$_1$-C$_4$ alkylene-N(H)—(C$_1$-C$_3$ alkyl), —C$_1$-C$_4$ alkylene-NH$_2$, —C$_0$-C$_3$ alkylene-heterocycloalkyl, —C$_0$-C$_3$ alkylene-C(O)O—C$_1$-C$_4$ alkyl, or —C$_0$-C$_3$ alkylene-cycloalkyl optionally substituted with CN, OH, —C$_1$-C$_3$alkyl, —C(O)O—C$_1$-C$_3$ alkyl, —C(O)OH, or halogen;

or G4, when attached to a nitrogen atom, is —C$_1$-C$_6$alkyl, —C$_1$-C$_6$alkylene-C$_1$-C$_6$ alkoxy, —C$_1$-C$_6$ haloalkyl, —C$_1$-C$_6$ hydroxyalkyl, —C$_1$-C$_6$ alkylene-CN, —C$_1$-C$_3$ alkylene-S(O)$_2$—C$_1$-C$_3$ alkyl, —C$_1$-C$_3$ alkylene-N(H)—S(O)$_2$—C$_1$-C$_3$ alkyl, —C$_1$-C$_3$ alkylene-C(O)—NH$_2$, —C$_1$-C$_3$ alkylene-C(O)—N(H)C$_1$-C$_3$ alkyl, or —C$_1$-C$_5$ alkylene-cycloalkyl optionally substituted with CN, OH, C$_1$-C$_3$alkyl, —C(O)O—C$_1$-C$_3$ alkyl, —C(O)OH, or halogen.

3. The compound according to claim 1, wherein:
B is a bond, phenylene, 5-6 membered heteroarylene, or 4-6 membered heterocycloalkylene, wherein the phenylene, 5-6 membered heteroarylene, or 4-6 membered heterocycloalkylene are each substituted with 0-2 G1 groups and 0-1 G2 groups;
L is a bond, —C(O)—, —N(H)—, —N(H)S(O)$_2$—, —S(O)$_2$—C$_1$-C$_3$ alkylene, —N—(H)C(O)—C$_1$-C$_3$ alkylene, —N(H)C(O)O—C$_1$-C$_3$ alkylene, —N(H)—(CH$_2$)$_{0-3}$—, —C$_1$-C$_4$ alkylene, —O—C$_1$-C$_4$ alkylene, —O—C$_1$-C$_4$haloalkylene, —O—C$_1$-C$_4$ alkylene-O—, or —O—C$_1$-C$_4$ hydroxyalkylene;
T is 5-10 membered heteroaryl, 6-10 membered aryl, 3-6 membered cycloalkyl, or 4-6 membered heterocycloalkyl; wherein the 5-10 membered heteroaryl, 3-6 membered cycloalkyl, or 4-6 membered heterocycloalkyl are each substituted with 0-2 G3 groups and 0-1 G4 groups;
each G1 is independently halogen, —C$_1$-C$_2$ alkyl, C$_1$-C$_2$ alkoxy, —C$_1$-C$_2$ fluoroalkyl, hydroxyl, or —C$_1$-C$_2$ hydroxyalkyl;
G2 is —S(O)$_2$—C$_1$-C$_2$ alkyl, —C$_0$-C$_2$ alkylene-C(O)—NH$_2$, or —N(H)C(O)—C$_1$-C$_2$ alkyl;
each G3 is independently halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, or —C$_0$-C$_4$ alkylene-CN; and
G4, when attached to a carbon atom, is halogen, —C$_1$-C$_4$ alkyl, —C$_1$-C$_4$ alkoxy, —C$_0$-C$_4$ fluoroalkyl, hydroxyl, —C$_1$-C$_4$ hydroxyalkyl, —C$_0$-C$_4$ alkylene-CN, —C$_0$-C$_2$ alkylene-S(O)$_2$—C$_1$-C$_2$ alkyl, —N(H)—S(O)$_2$—C$_1$-C$_3$ alkyl, —C$_0$-C$_2$ alkylene-C(O)—NH$_2$, —C$_0$-C$_2$ alkylene-C(O)—N(H)—CH$_3$, —C$_1$-C$_3$alkylene-N—(C$_1$-C$_2$ alkyl)$_2$, —C$_1$-C$_3$ alkylene-N(H)—(C$_1$-C$_2$ alkyl), —C$_1$-C$_3$ alkylene-NH$_2$, —C$_0$-C$_4$ alkylene-pyrrolidinyl, —C$_0$-C$_4$ alkylene-cyclopropyl, —C$_0$-C$_2$ alkylene-C(O)O—C$_1$-C$_3$ alkyl, —C$_0$-C$_2$ alkylene-cyclopropylene-OH, —C$_0$-C$_2$ alkylene-cyclopropylene-C(O)O—C$_1$-C$_4$ alkyl, —C$_0$-C$_2$ alkylene-cyclopropylene-C(O)OH, or —C$_0$-C$_2$ alkylene-cyclopropylene-CN;
or G4, when attached to a nitrogen atom, is —C$_1$-C$_5$ alkyl, —C$_1$-C$_5$alkylene-C$_1$-C$_5$ alkoxy, —C$_1$-C$_5$ haloalkyl, —C$_1$-C$_5$ hydroxyalkyl, —C$_1$-C$_5$ alkylene-CN, —C$_1$-C$_2$ alkylene-S(O)$_2$—C$_1$-C$_2$ alkyl, —C$_1$-C$_3$ alkylene-C(O)—NH$_2$, —C$_1$-C$_3$ alkylene-C(O)—N(H)—C$_1$-C$_2$ alkyl, —C$_1$-C$_4$ alkylene-cyclopropyl, or —C$_1$-C$_4$ alkylene-cyclopropylene-CN.

4. The compound according to claim 1, wherein:
B and L are bonds, and T is a 9-10 membered bicyclic fused aryl or a 9-10 membered bicyclic fused heteroaryl, wherein the bicyclic fused aryl or the bicyclic fused heteroaryl are each optionally substituted with 1-3 substituents, each independently C$_1$-C$_2$ alkyl, halogen, C$_1$-C$_2$ haloalkyl, hydroxyl and C$_1$-C$_2$ hydroxyalkyl.

5. The compound according to claim 1, wherein:
B and L are bonds, and T is a naphthalenyl, isoquinolinyl, quinolinyl, isoindolyl, 1H-indazolyl, 2H-indazolyl, 1H-benzimidazolyl, 1,3-dihydro-2H-inden-2-one-5-yl, 2,3-dihydrobenzofuranyl, 2,3-dihydrobenzo[d]thiazolyl, benzothiophenyl, or imidazo[1,2-a]pyridinyl, indolin-2-one, each optionally substituted with 1-2 substituents, each independently —C$_1$-C$_2$ alkyl, halogen, —C$_1$-C$_2$ haloalkyl, hydroxyl and —C$_1$-C$_2$ hydroxyalkyl.

6. The compound according to claim 1, wherein:
R$^4$ is:

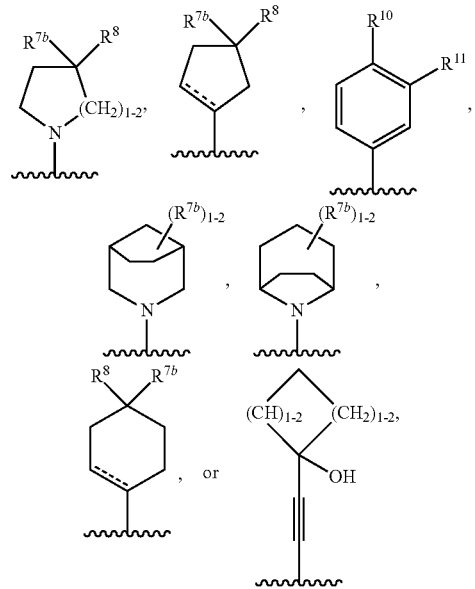

˭˭˭˭˭ is a single or double bond;
R$^6$ is H, —(C$_1$-C$_4$)alkyl, —(C$_1$-C$_4$)haloalkyl, or —(C$_3$-C$_6$)cycloalkyl;
each R$^{7b}$ is independently H, —C$_1$-C$_4$ alkyl, fluoro, chloro, CN, hydroxyl, —C$_1$-C$_3$ haloalkyl, or —C$_1$-C$_3$ cyanoalkyl;
R$^8$ is CN, —(CH$_2$)$_{0-1}$—C(O)—N(H)—R$^6$, —(CH$_2$)$_{0-1}$C(O)OR$^6$, or

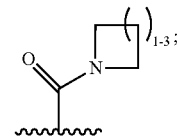

or R$^{7b}$ and R$^8$ join together, with the carbon to which they are attached, to form a 5-6 membered heterocycloalkyl, wherein the 5-6 membered heterocycloalkyl is substituted with one or two oxo groups, and further optionally substituted with 1-2 —C$_1$-C$_6$ alkyl groups, wherein the 5-6 membered heterocycloalkyl is optionally fused to phenyl when the 5-6 membered heterocycloalkyl is a six membered ring and substituted with one oxo group;
R$^{10}$ is —S(O)$_2$—N(H)—C$_1$-C$_5$ alkyl, —O-phenyl, —(CH$_2$)$_2$-piperidine, or CN; and
R$^{11}$ is H or 5-6 membered heterocycloalkyl.

7. The compound according to claim 6, wherein R$^4$ is:

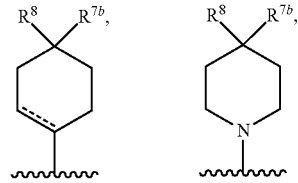

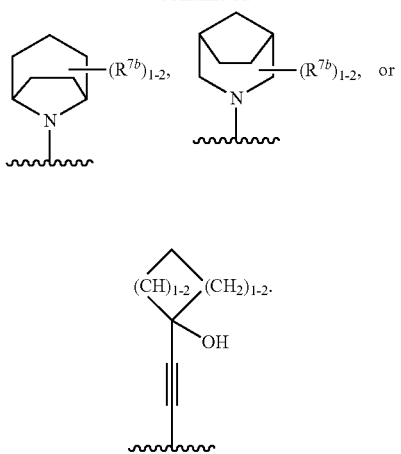
8. The compound according to claim 6, wherein $R^4$ is:
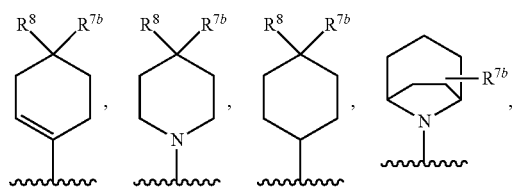
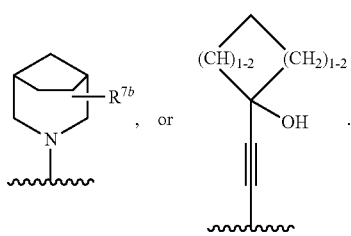
9. The compound according to claim 6, wherein $R^4$ is:
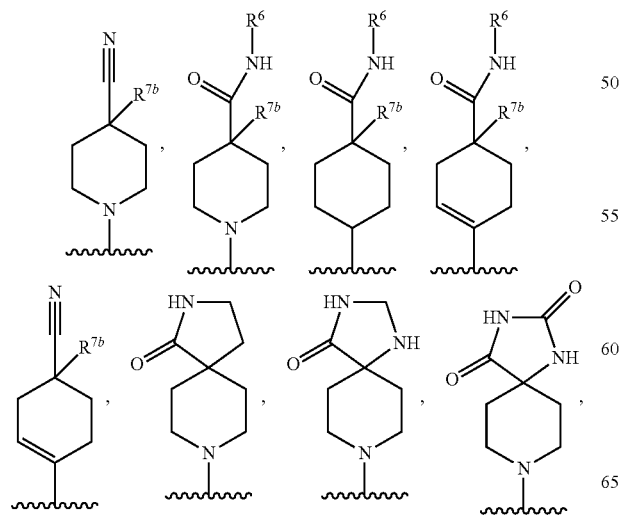
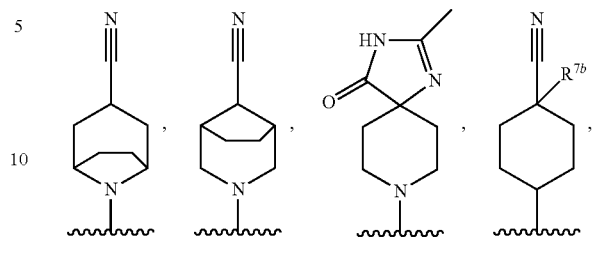
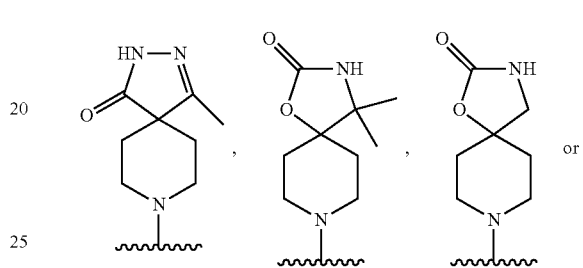
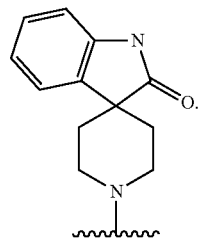
10. The compound according to claim 1, wherein $R^4$ is:
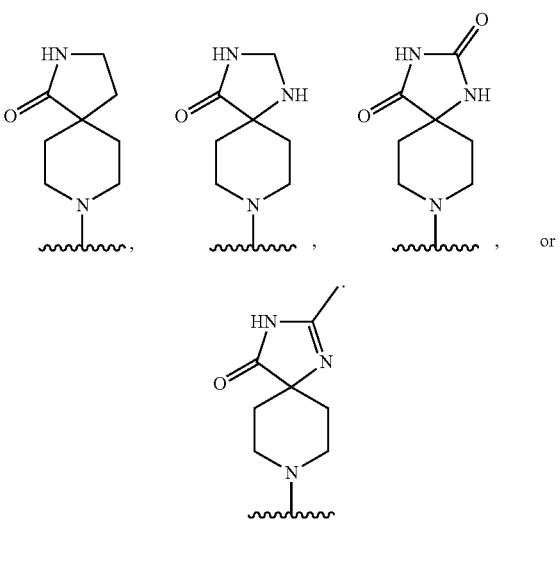

11. The compound according to claim 1, wherein $R^4$ is:
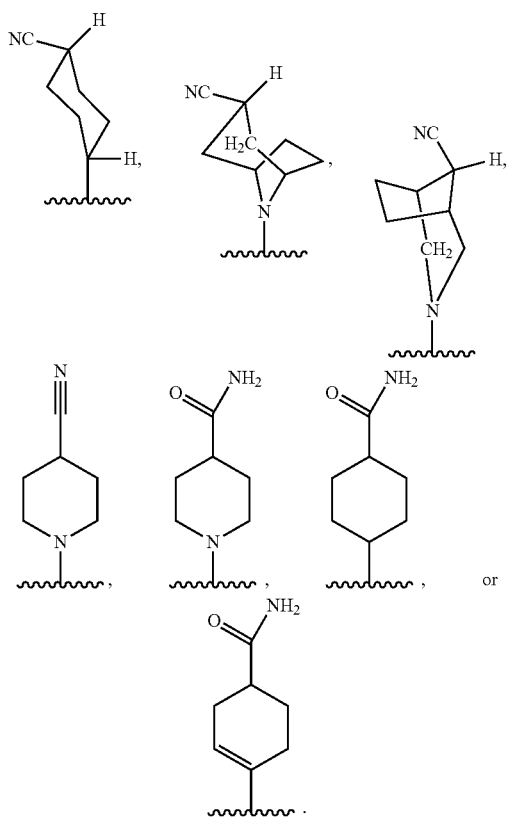
12. The compound according to claim 1, wherein $R^4$ is:
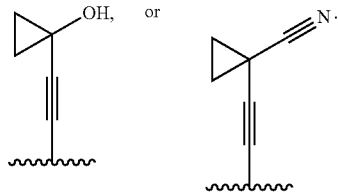 [SMILES: *C#CC1(O)CC1 ; "or" ; *C#CC1(C#N)CC1]
13. The compound according to claim 1, wherein $R^3$ is:
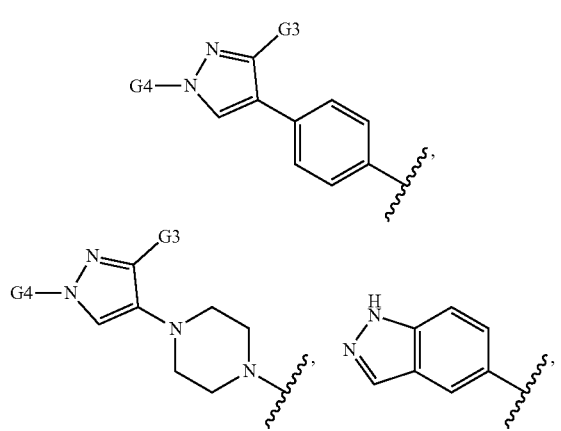
-continued
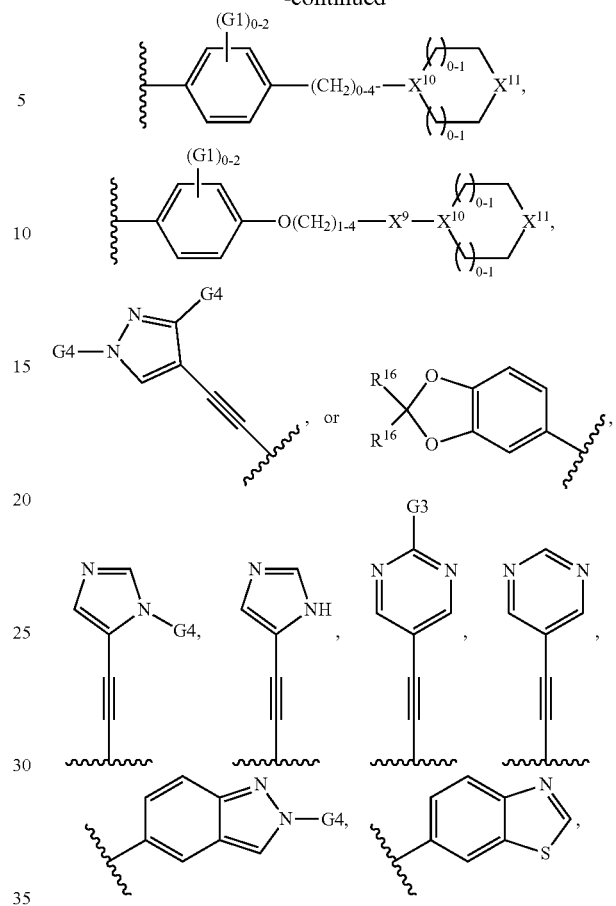
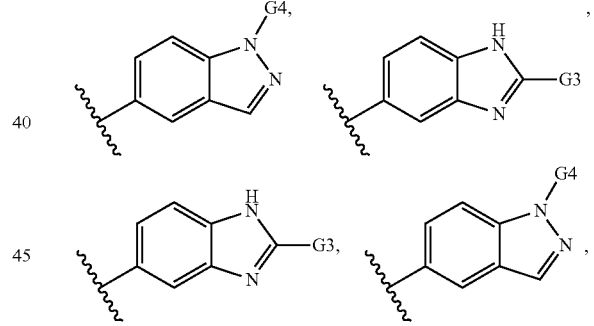
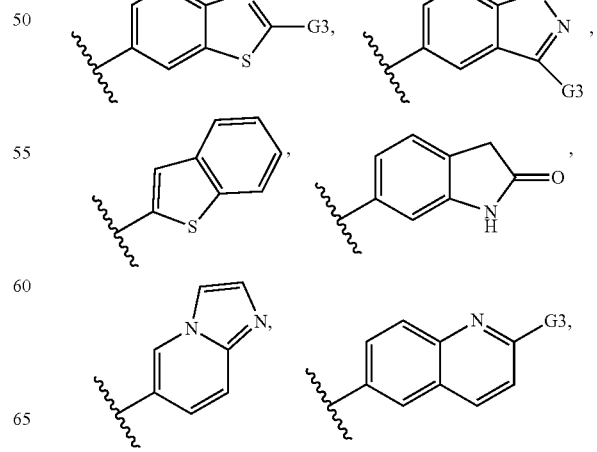

-continued

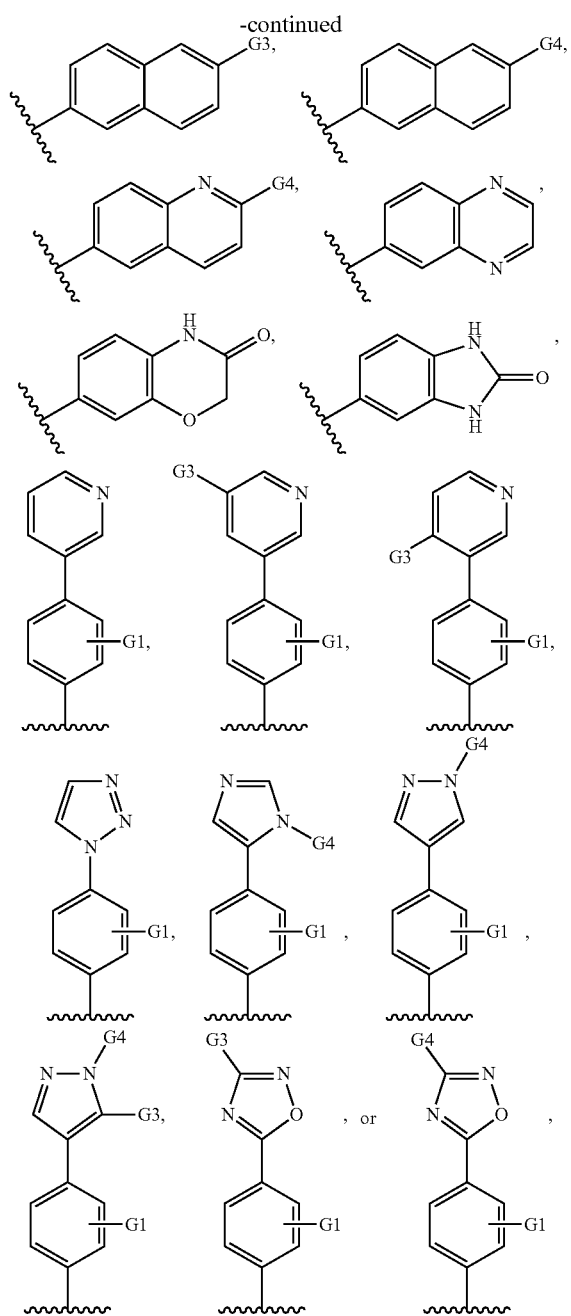

wherein:
G1 is H, —CH₃, or F;
G3 is —CH₃, —CH₂F, —CHF₂, —CF₃, —OCH₃, —CH₂—CH₂F, —(CH₂)₂—CN, —(CH₂)₃—CN, —(CH₂)₁₋₂C(CH₃)₂—CN, or —(CH₂)₁₋₂C(CH₃)₂—OH;
G4 is —CH₃, —CH₂F, —CHF₂, —CF₃, —CH₂—CH₂F, —CH₂—CH₃, —CH₂—CHF₂, —CH₂—CF₃, —CH₂—CH₂—CH₂F, —(CH₂)₁₋₂C(CH₃)₂—OH—, $C_1$-$C_4$ alkylene-cyclopropyl, —$C_1$-$C_4$ alkylene-cyclopropylene-CN, —$C_1$-$C_4$ alkylene-cyclopropylene-OH, —$C_1$-$C_5$ alkylene-CN, or —(CH₂)₁₋₃N(CH₃)₂;
each $R^{16}$ is H, halogen, or —$C_1$-$C_4$alkyl optionally substituted with halogen;
$X^9$ is a bond or O;
$X^{10}$ is CH, —C(CH₃)—, N; and
$X^{11}$ is CH₂, NH, O, S, S(O), or S(O)₂.

14. The compound according to claim 1, wherein $R^3$ is:

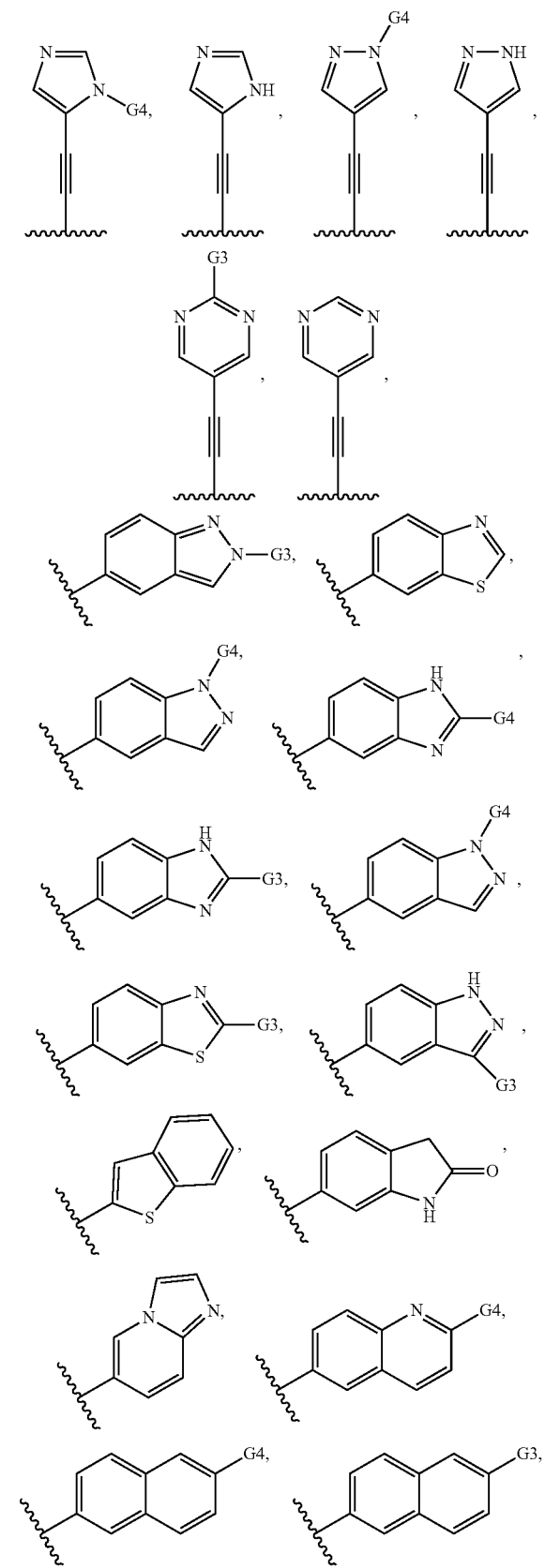

-continued

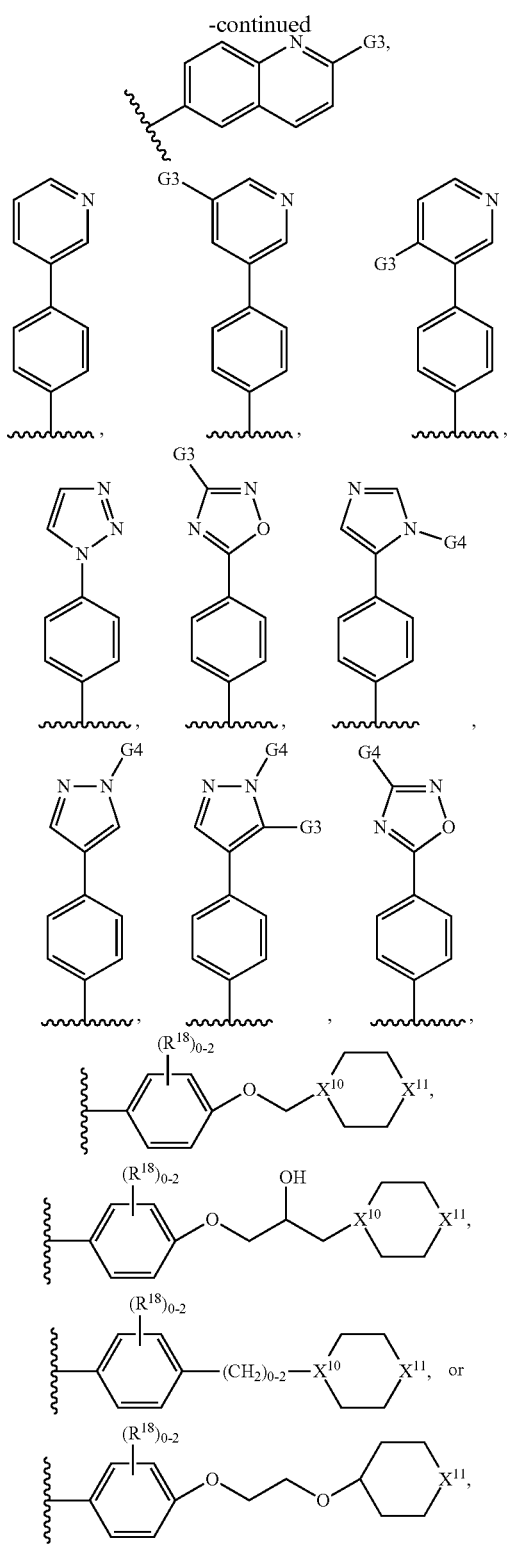

wherein:
X[10] is CH, —C(CH$_3$)—, N;
X[11] is CH$_2$, NH, O, S, S(O), or S(O)$_2$;
G3 is —CH$_3$, —CH$_2$F, —CHF$_2$, —CF$_3$, —CH$_3$, —OCH$_3$, —CH$_2$—CH$_2$F, —(CH$_2$)$_2$—CN, —(CH$_2$)$_3$—CN, —(CH$_2$)$_{1-2}$C(CH$_3$)$_2$—CN, or —(CH$_2$)$_{1-2}$C(CH$_3$)$_2$—OH;

G4 is —CH$_3$, —CH$_2$F, —CHF$_2$, —CF$_3$, —CH$_2$—CH$_2$F, —CH$_2$—CH$_3$, —CH$_2$—CHF$_2$, —CH$_2$—CF$_3$, —CH$_2$—CH$_2$—CH$_2$F, —(CH$_2$)$_2$—CN, —(CH$_2$)$_3$—CN, —(CH$_2$)$_{1-2}$C(CH$_3$)$_2$—CN, —(CH$_2$)$_{1-2}$C(CH$_3$)$_2$—OH, —CH$_2$—CH$_2$OH, —CH$_2$—S(O)$_2$—CH$_3$, —CH$_2$—CH$_2$—S(O)$_2$—CH$_3$, —CH$_2$—C(O)—NH$_2$, —CH$_2$—CH$_2$-morpholinyl, —CH$_2$—CH$_2$-pyrrolidinyl, —CH$_2$-morpholinyl, —CH$_2$-pyrrolidinyl, —CH$_2$—CH$_2$-cyclobutyl, —CH$_2$-cyclobutyl, —C$_1$-C$_3$ alkylene-cyclopropyl, —C$_1$-C$_3$ alkylene-cyclopropylene-OH, or —C$_1$-C$_3$ alkylene-cyclopropylene-CN; and
R[18] is H or F.

15. The compound according to claim 1, wherein R$^3$ is:

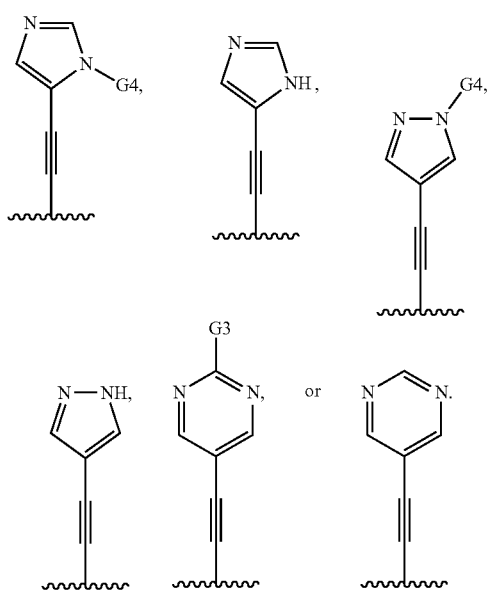

16. The compound according to claim 1, wherein R$^3$ is:

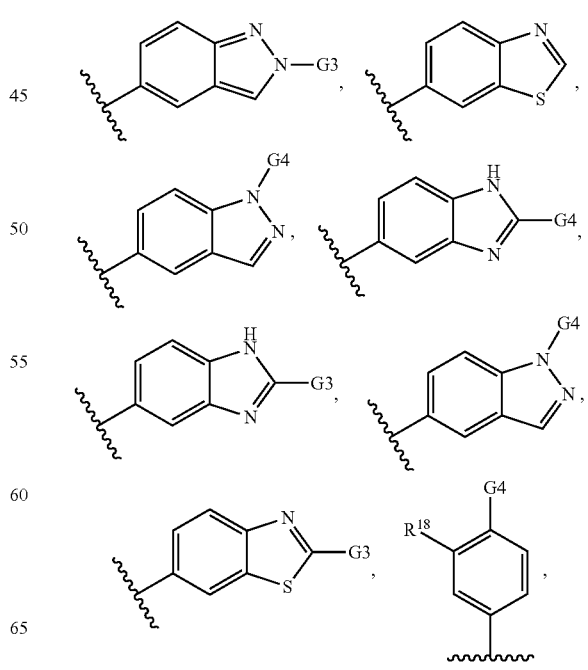

-continued
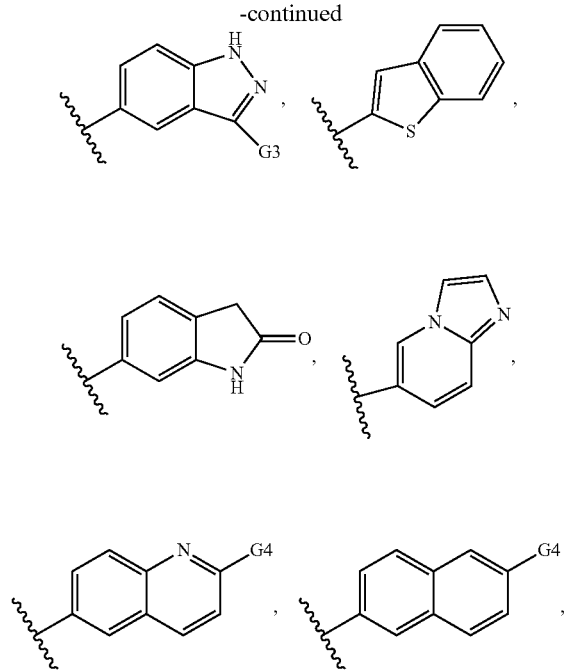
wherein R[18] is H or F.
17. The compound according to claim 1, wherein R[3] is:
-continued
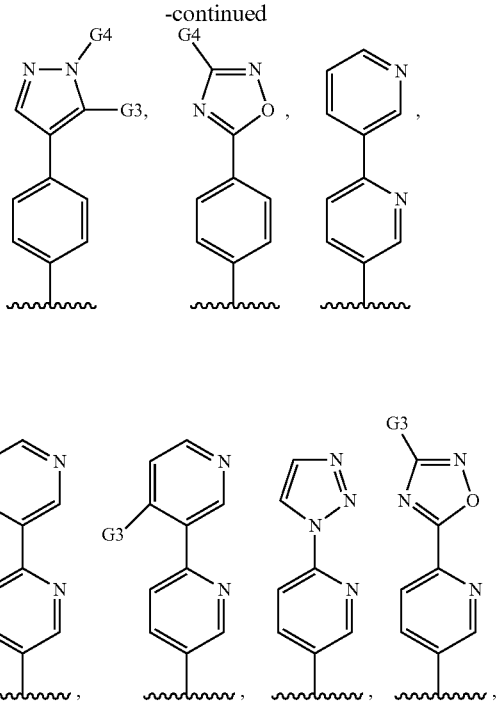
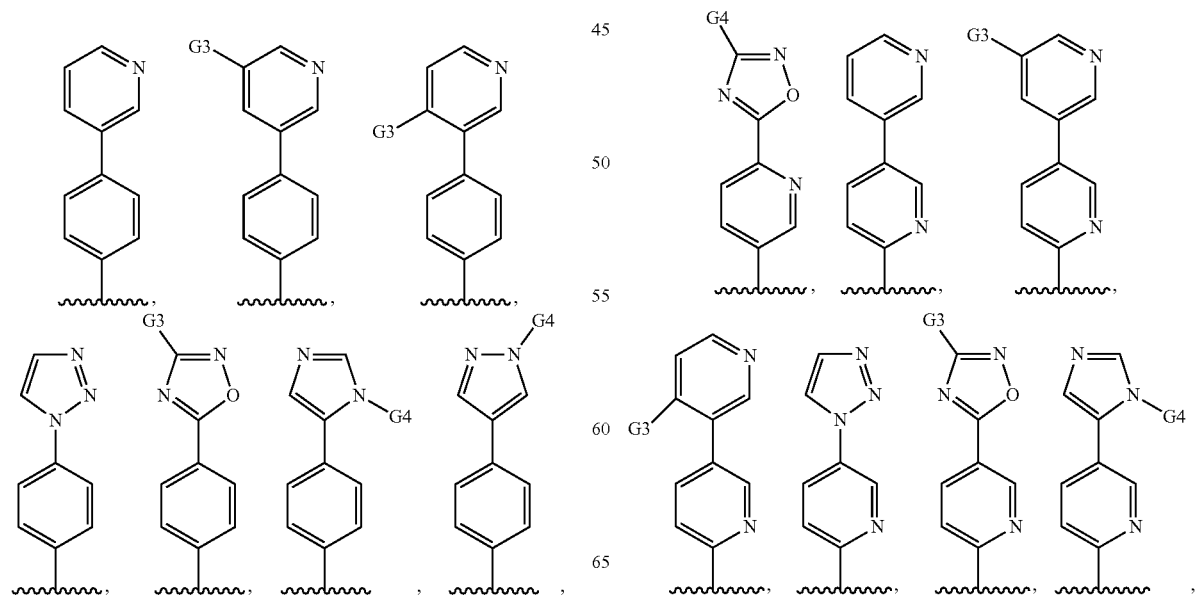

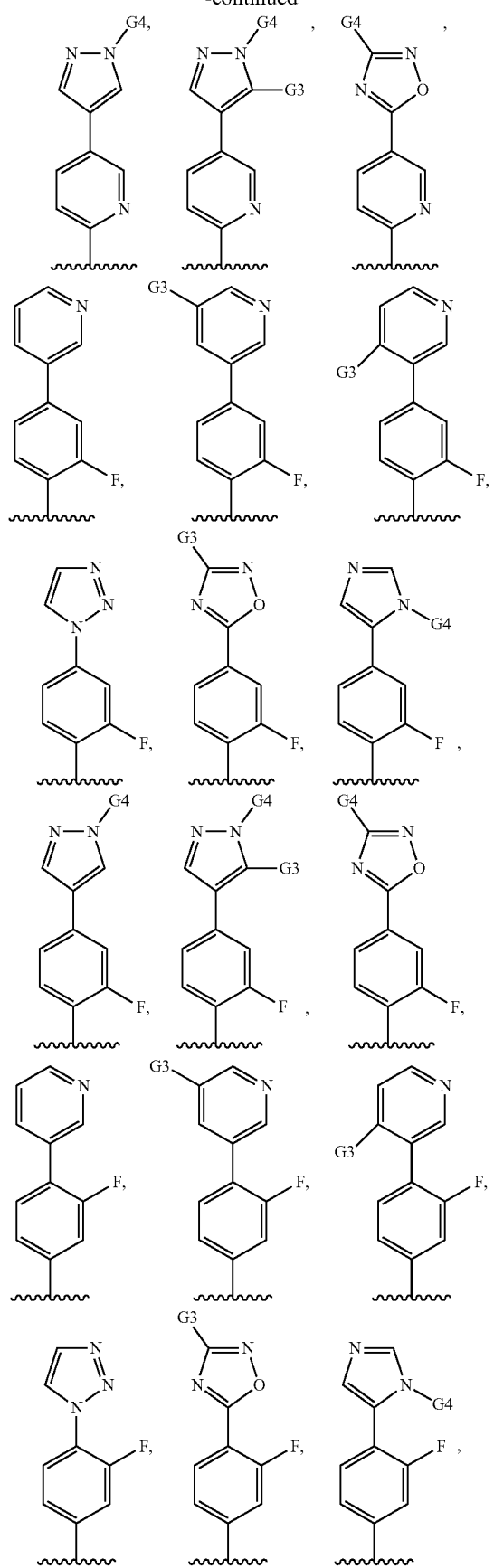
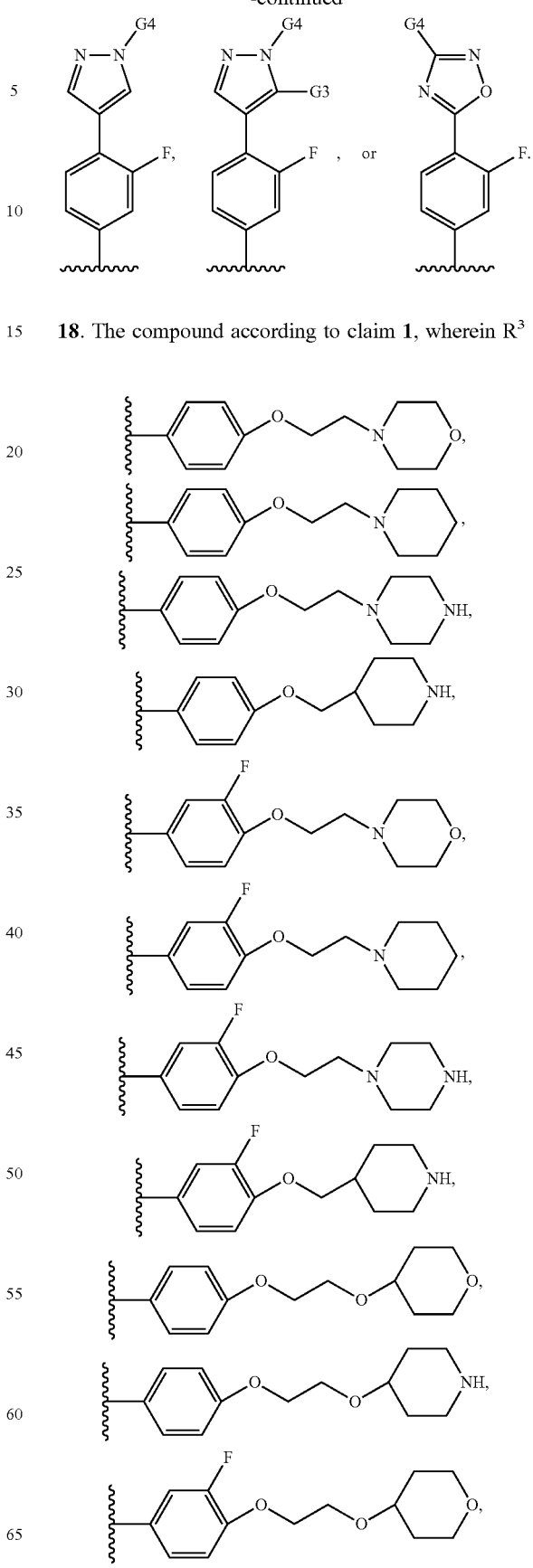
18. The compound according to claim 1, wherein $R^3$ is

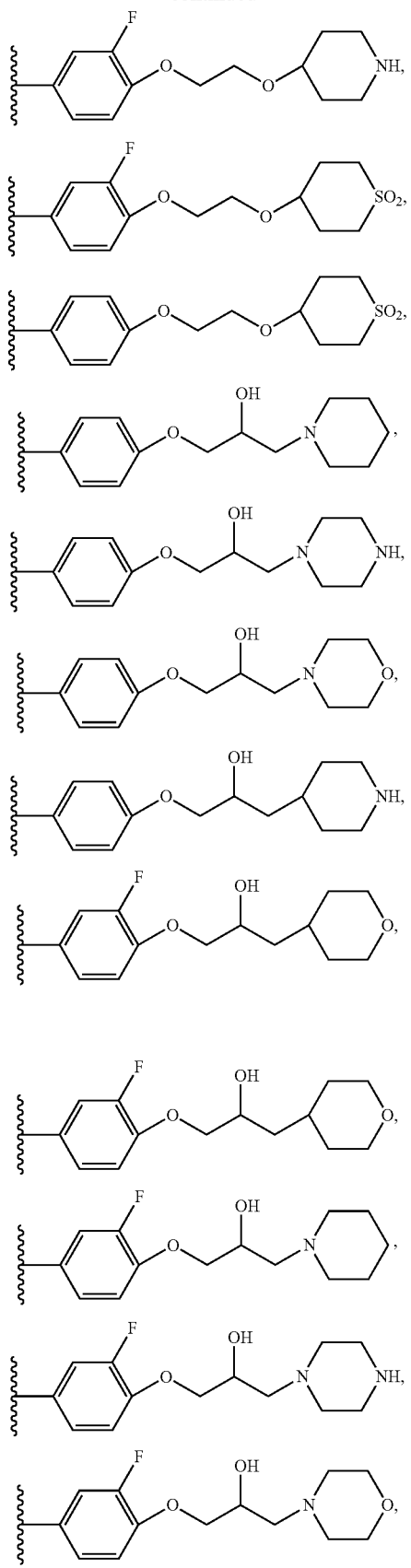
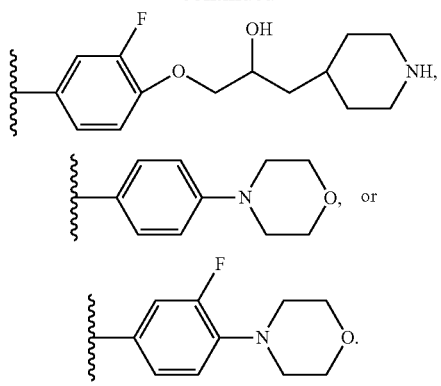
19. The compound according to claim 1, G4 is —CH$_3$, —CH$_2$F, —CHF$_2$, —CF$_3$, —CH$_2$—CH$_2$—CH$_2$F, —(CH$_2$)$_2$—CN, —(CH$_2$)$_3$—CN, —(CH$_2$)C(CH$_3$)$_2$—CN, —CH$_2$—C(CH$_3$)$_2$—OH, —C$_1$-C$_3$ alkylene-cyclopropyl, —CH$_2$-cyclopropylene-OH, or —CH$_2$-cyclopropylene-CN.
20. A compound selected from:
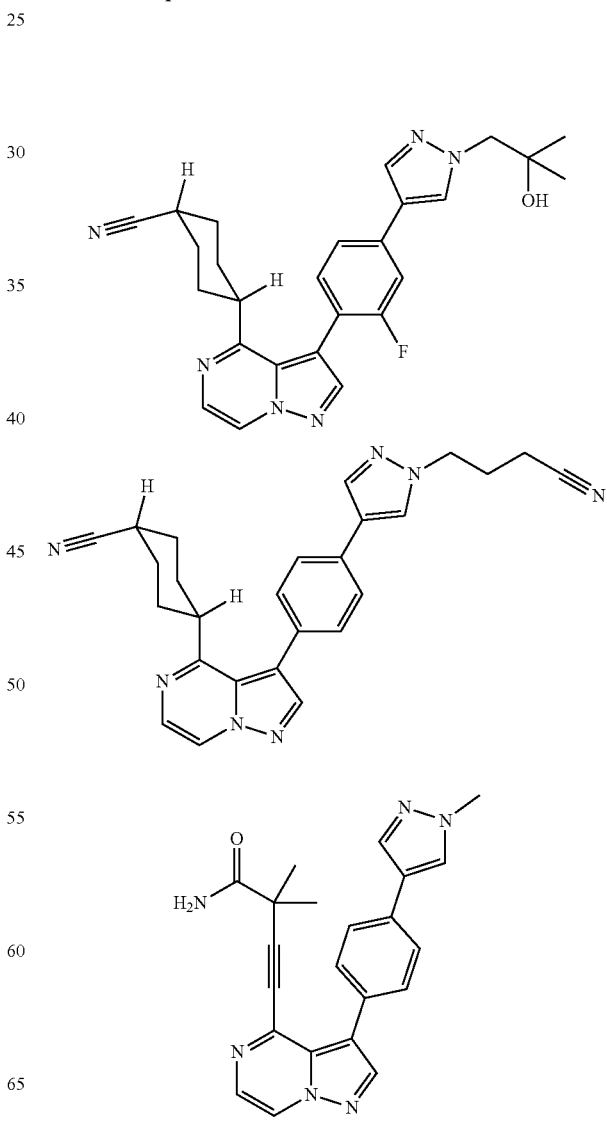

389
-continued
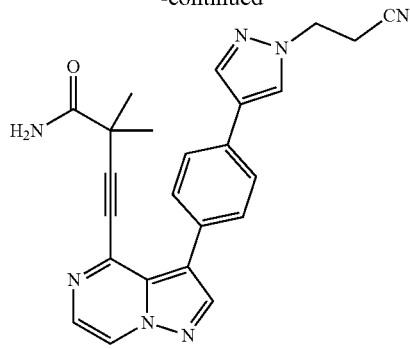
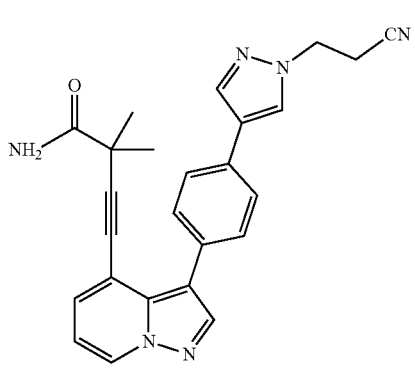
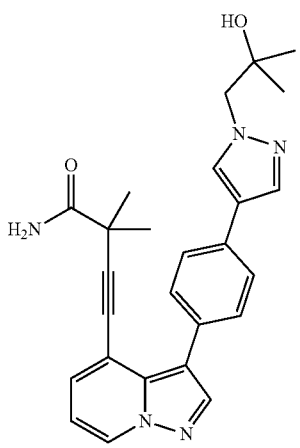
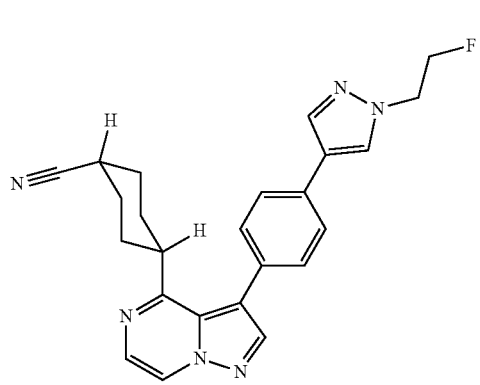
390
-continued
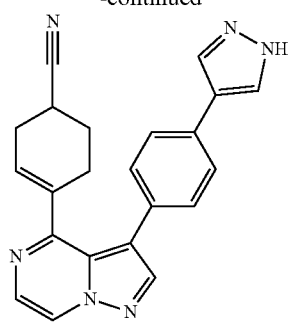
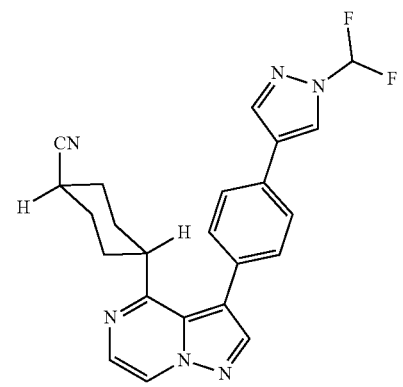
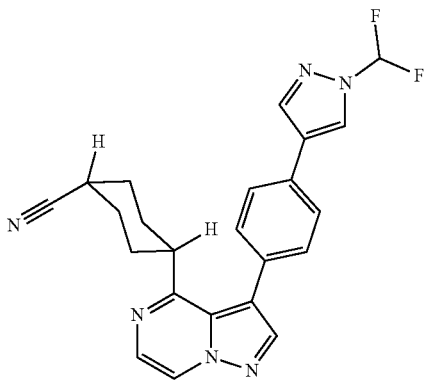

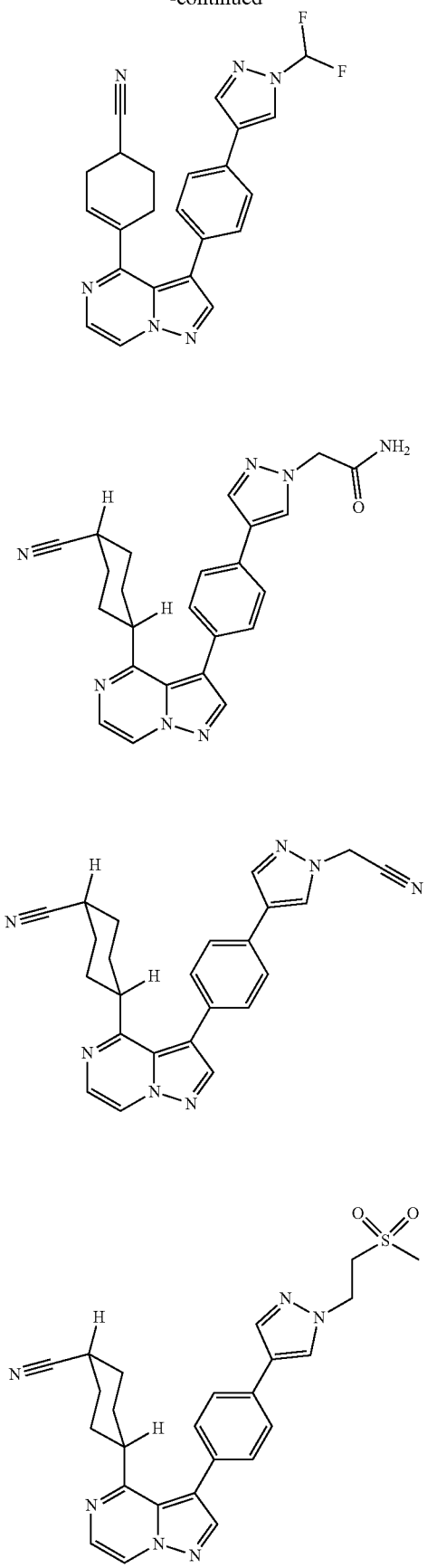
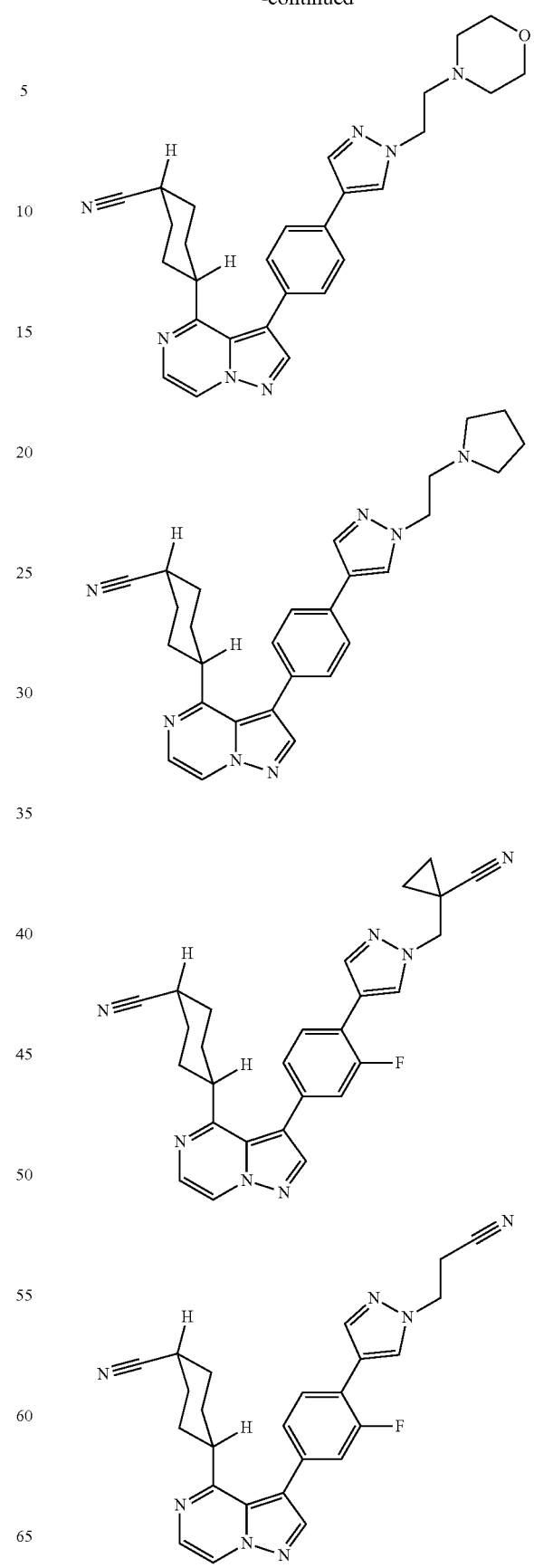

393
-continued
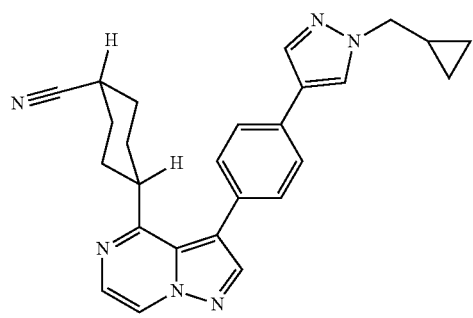
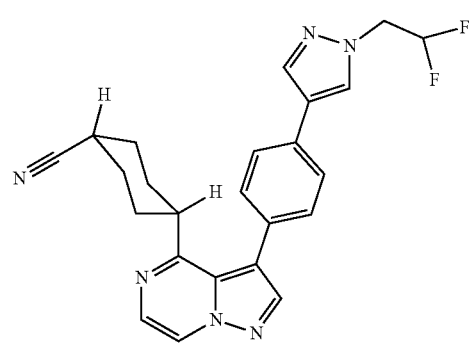
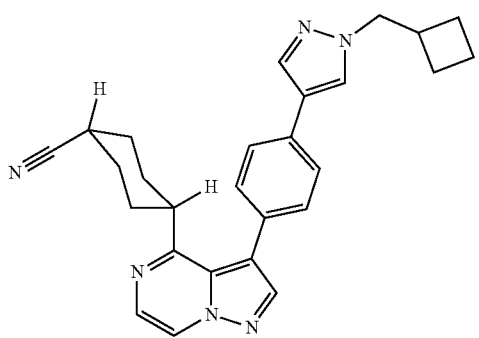
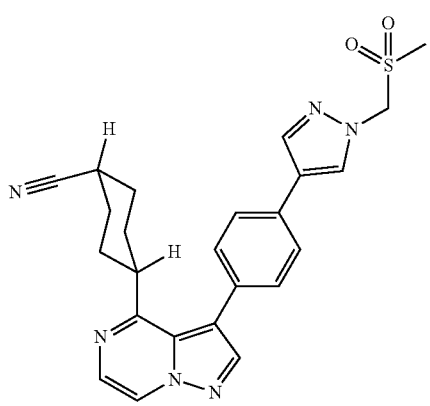
394
-continued
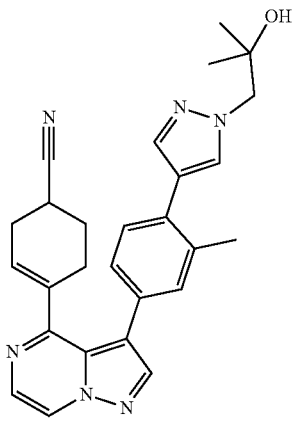
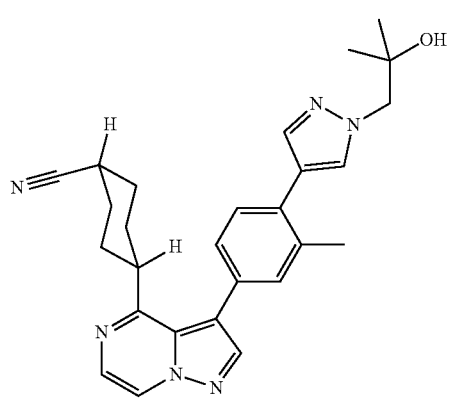
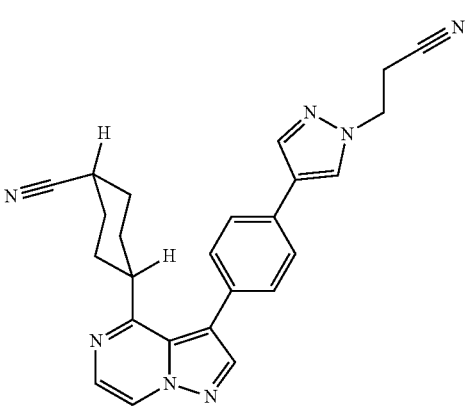
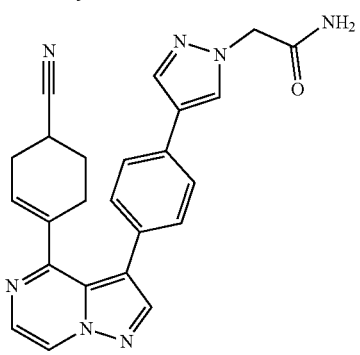

395
-continued
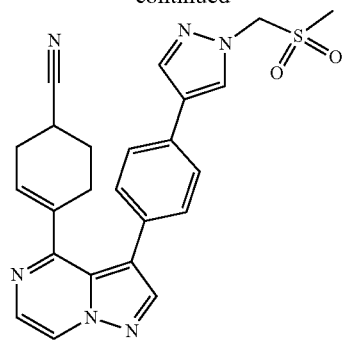
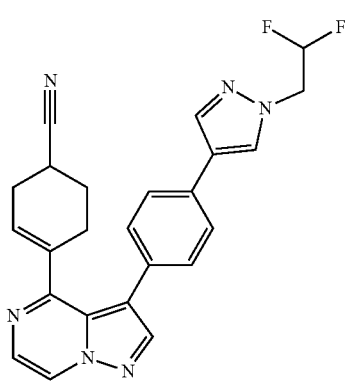
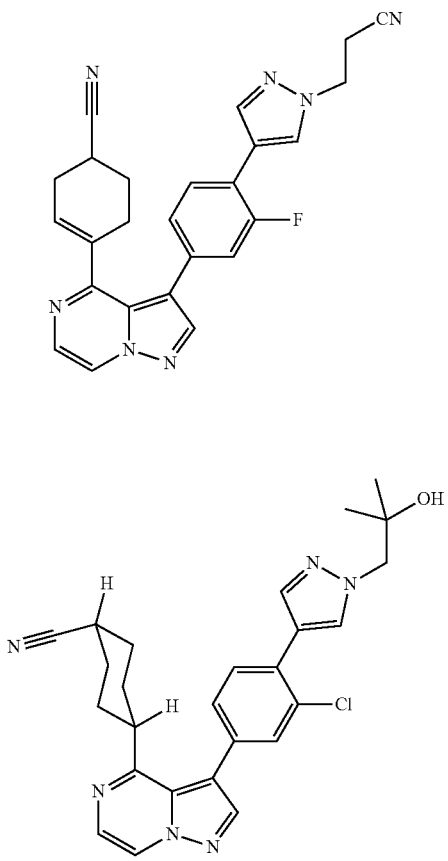
396
-continued
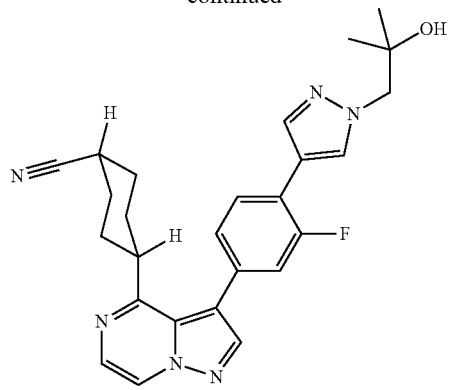
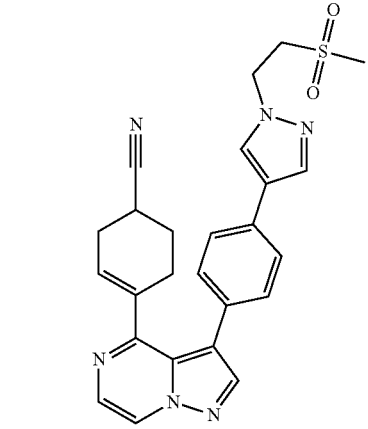
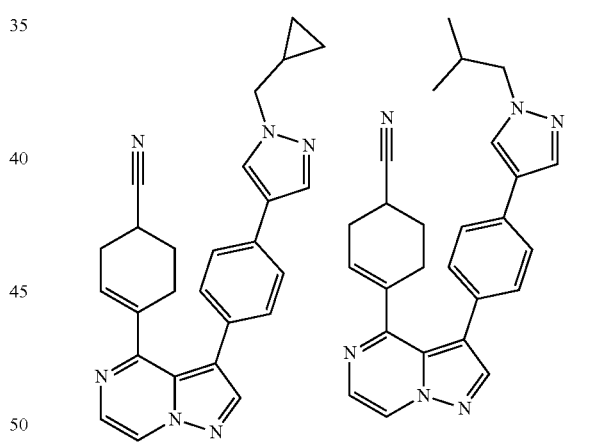
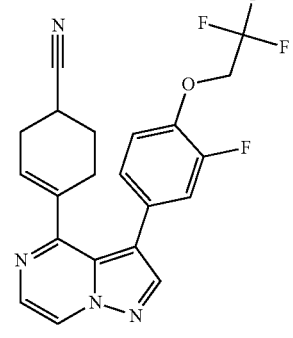

397
-continued
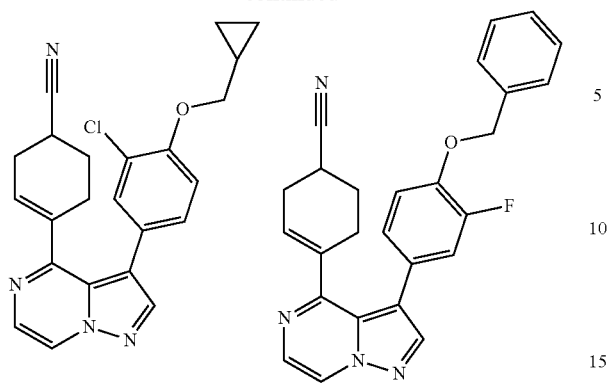
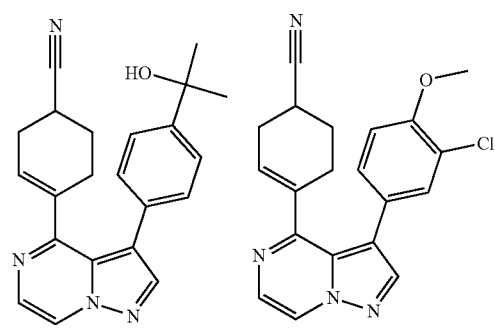
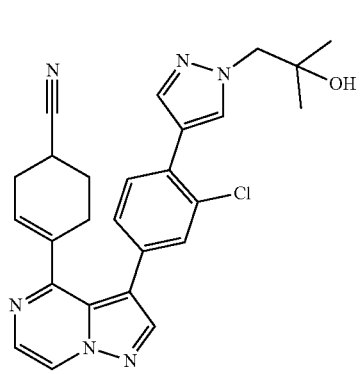
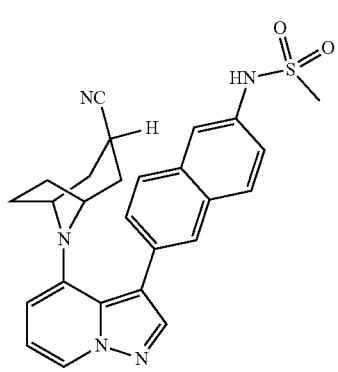
398
-continued
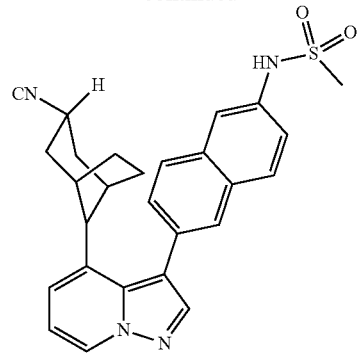
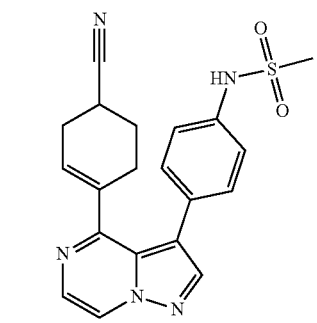
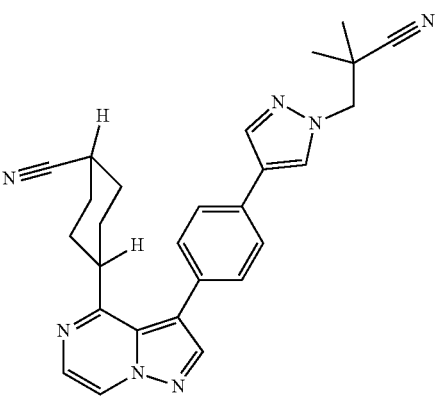
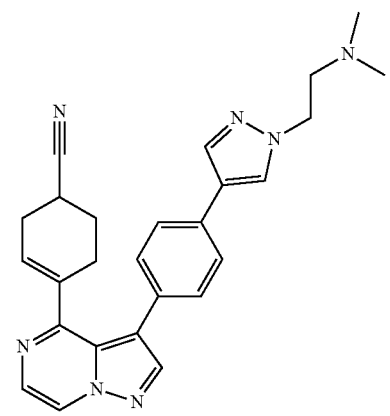

399
-continued
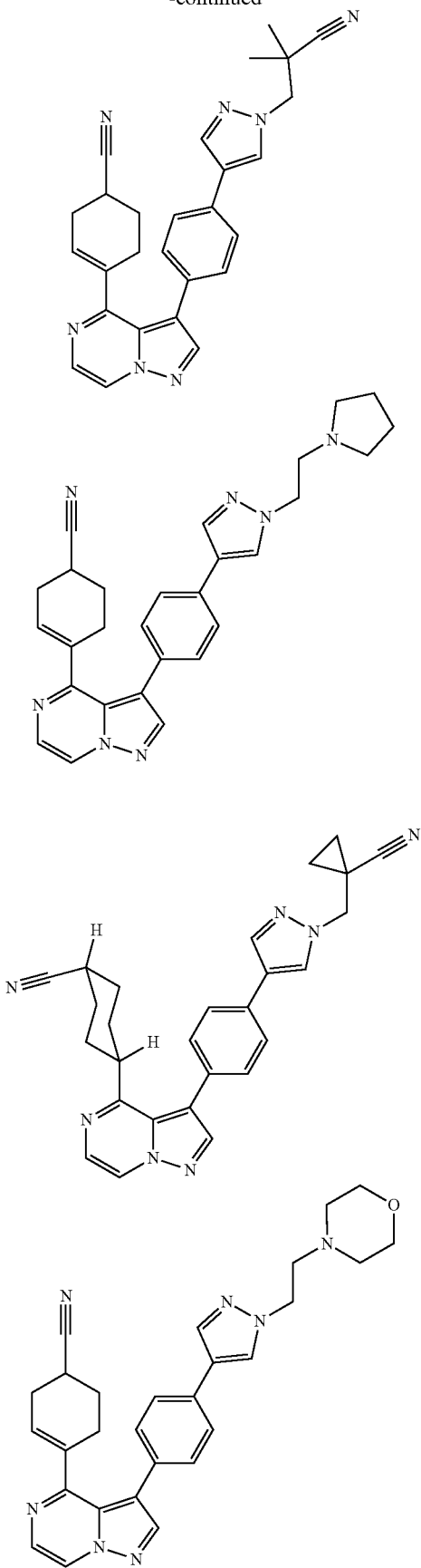
400
-continued
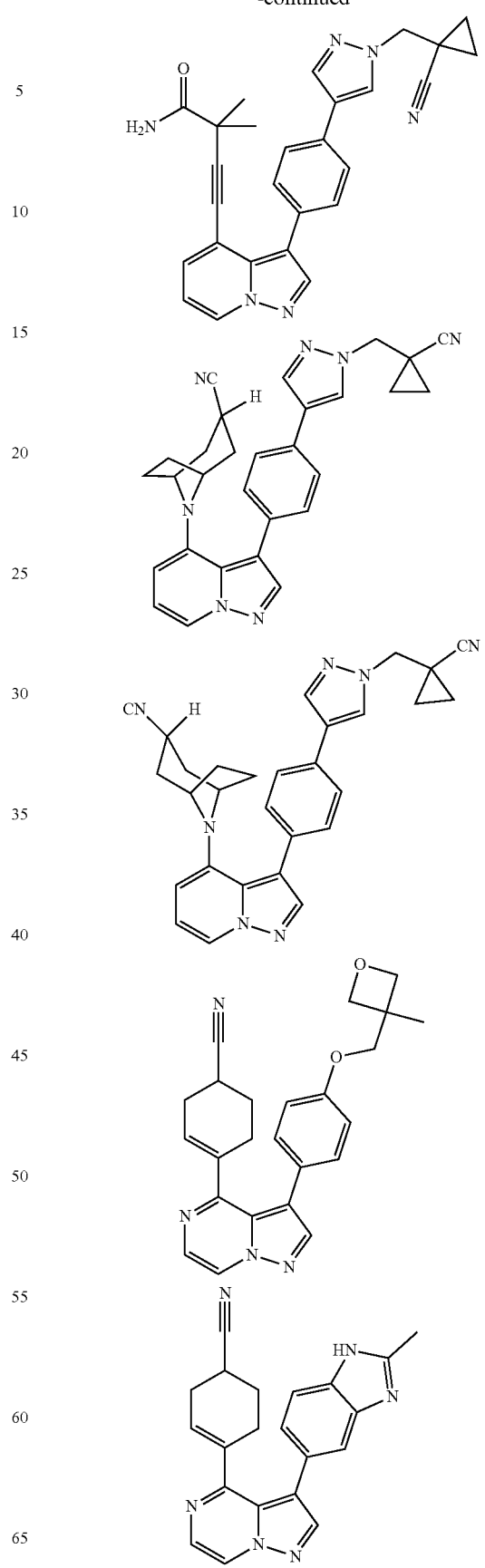

401
-continued
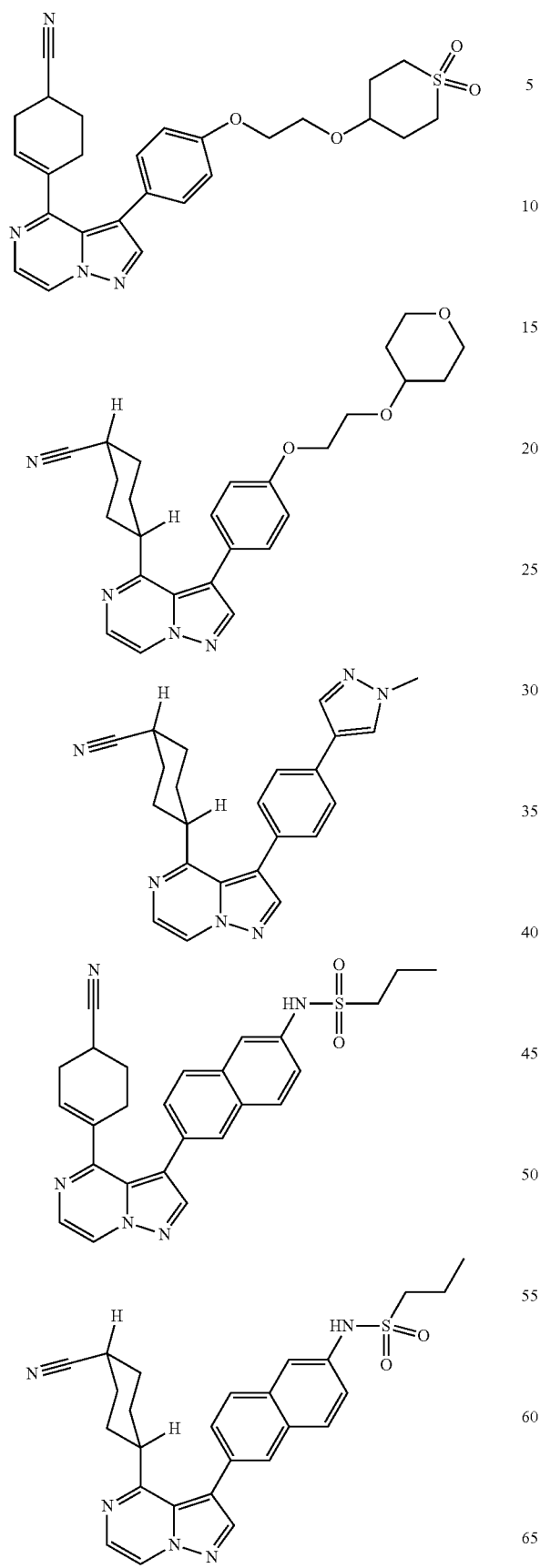
402
-continued
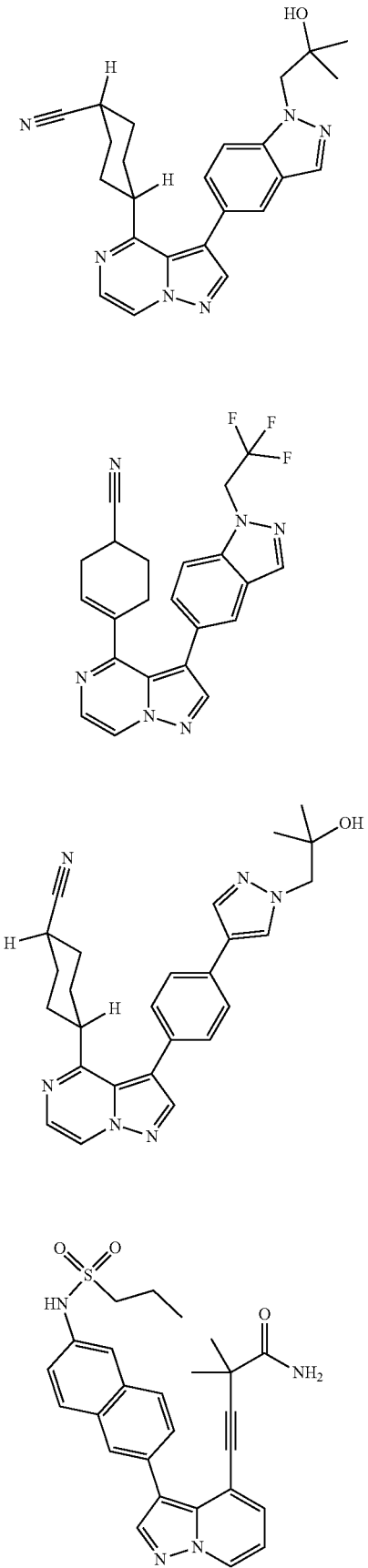

403
-continued
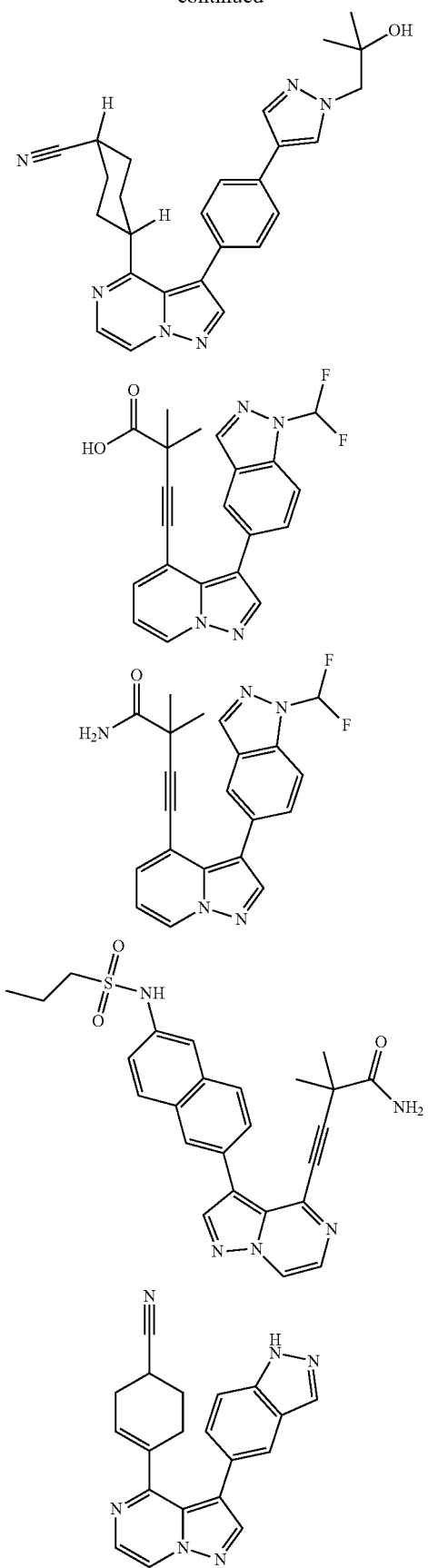
404
-continued
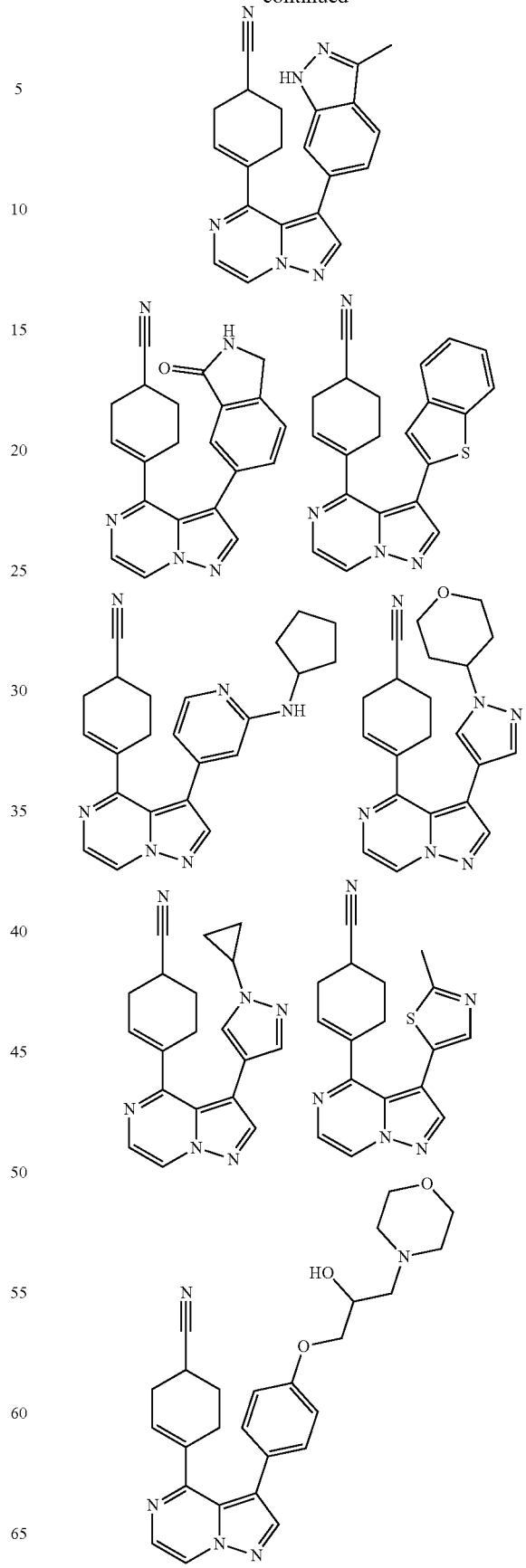

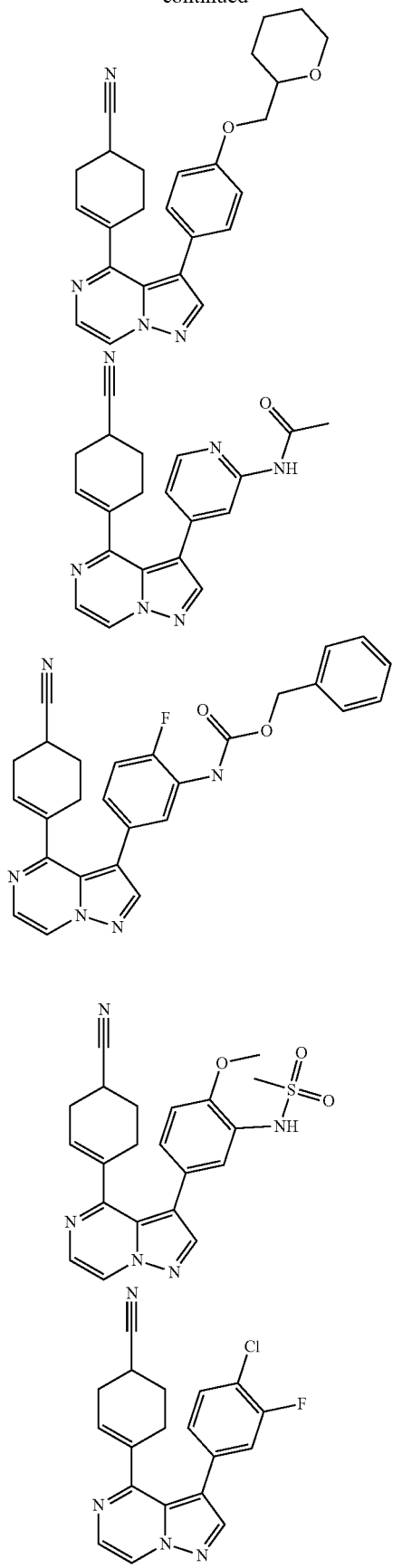
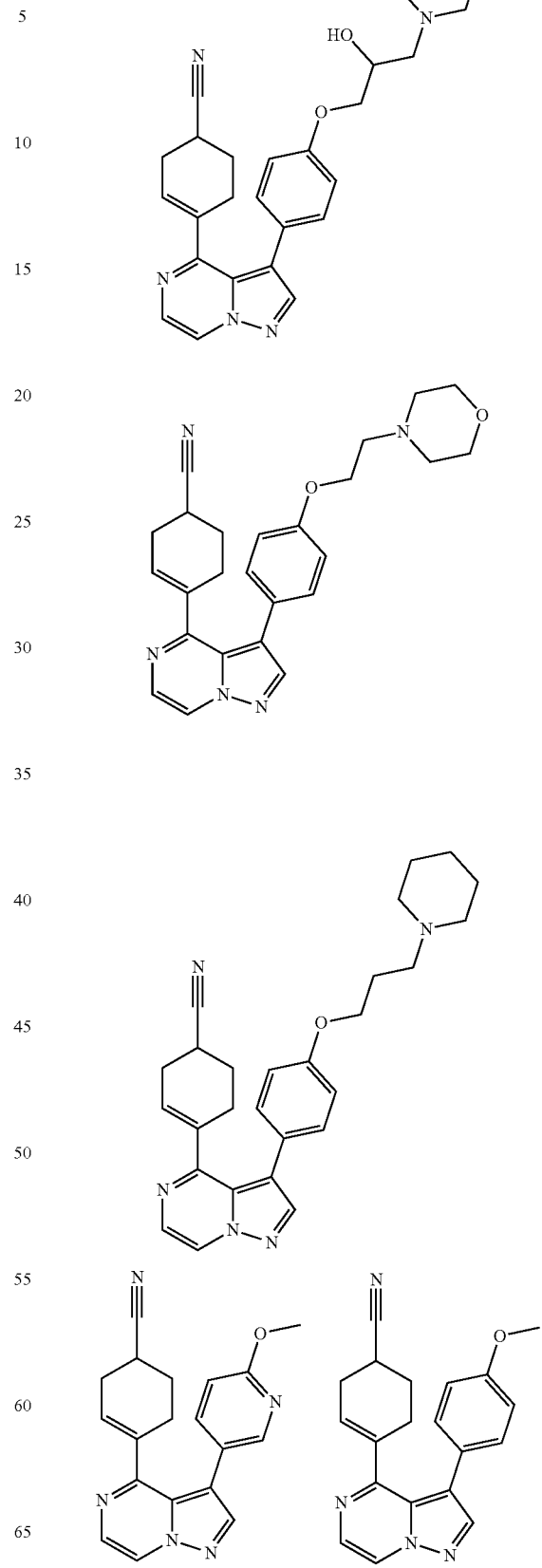

407
-continued
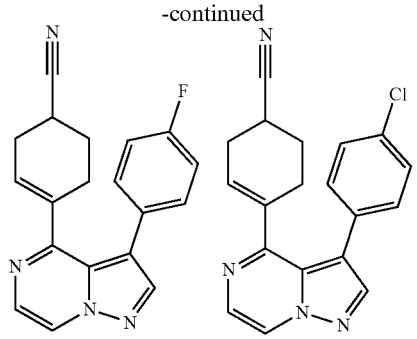
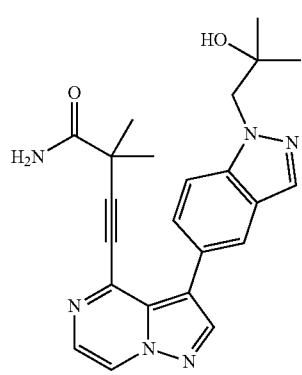
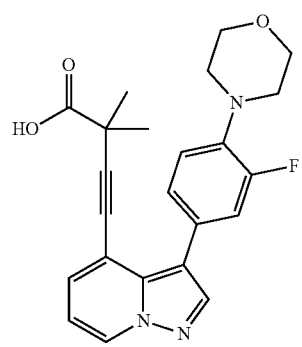
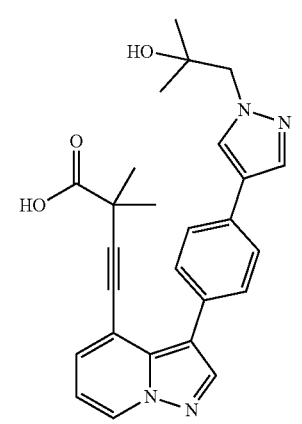
408
-continued
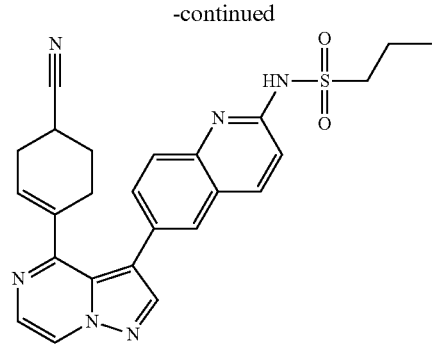
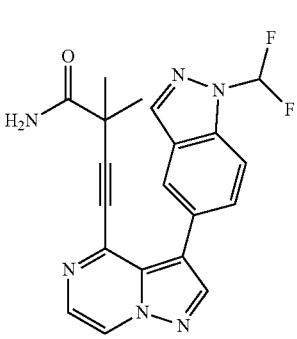
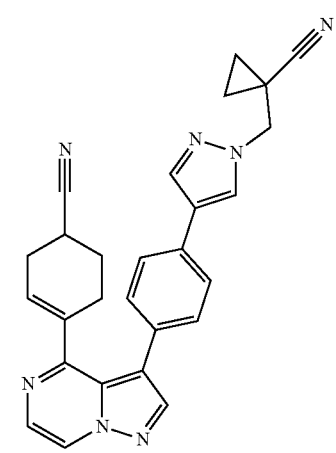
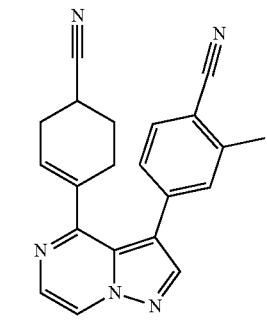

409
-continued
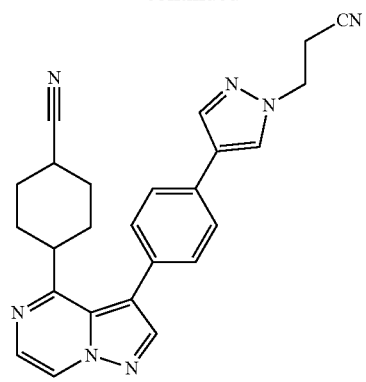
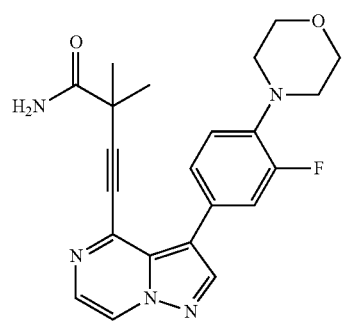
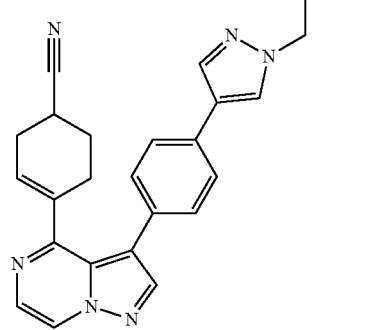
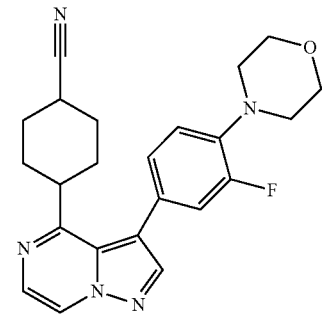
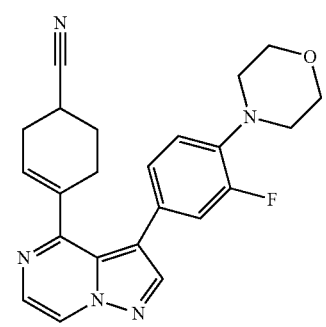
410
-continued
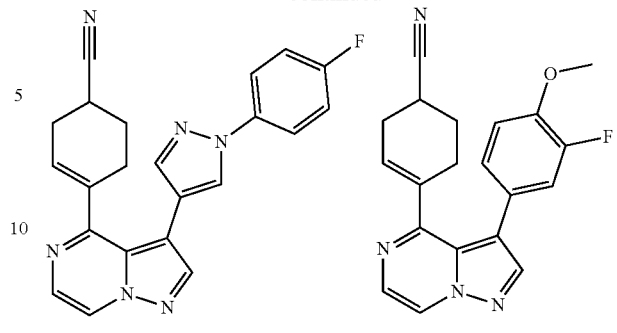
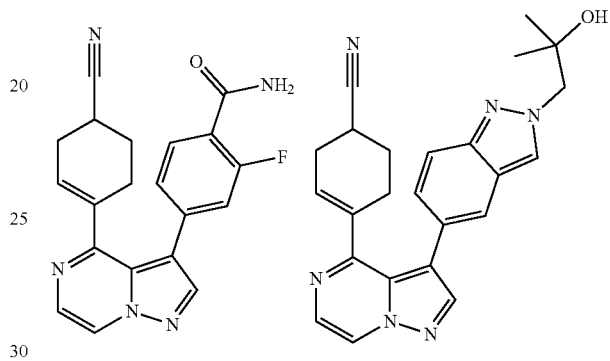
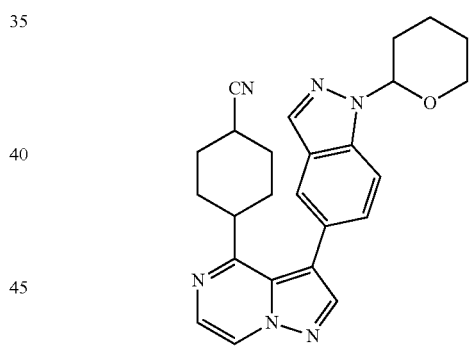
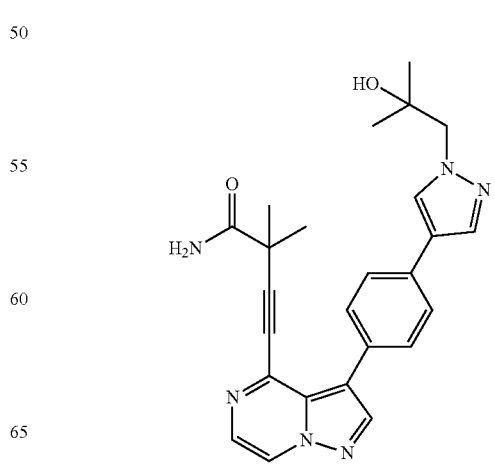

411
-continued
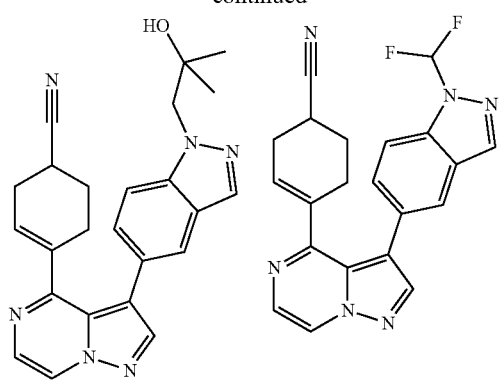
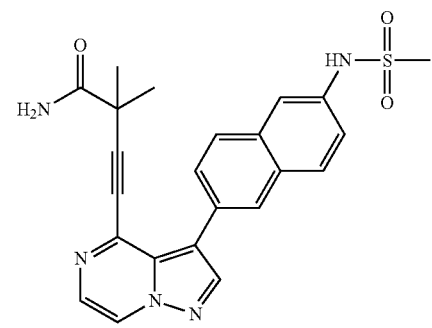
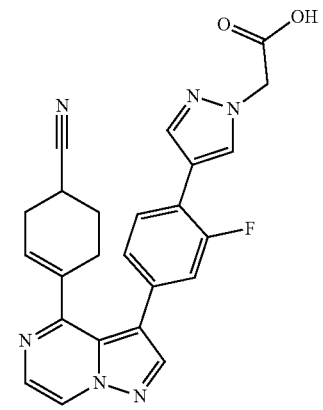
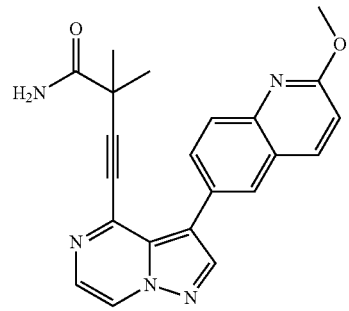
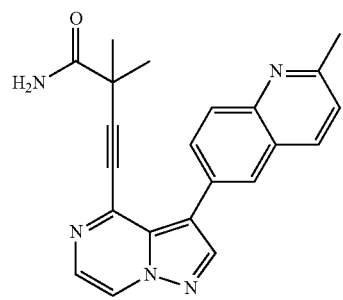
412
-continued
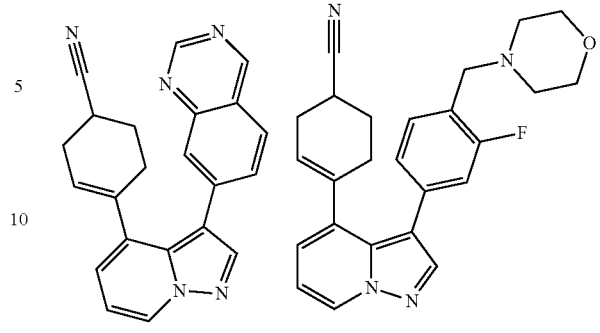
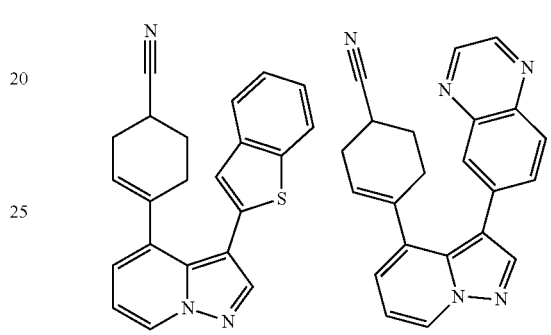
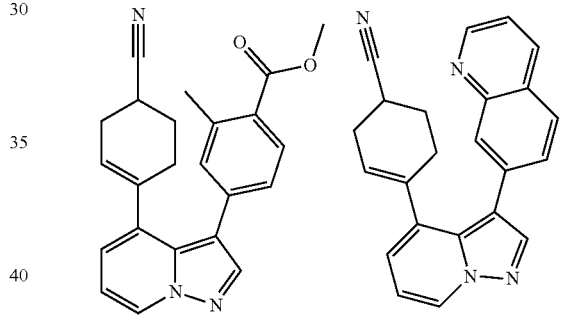
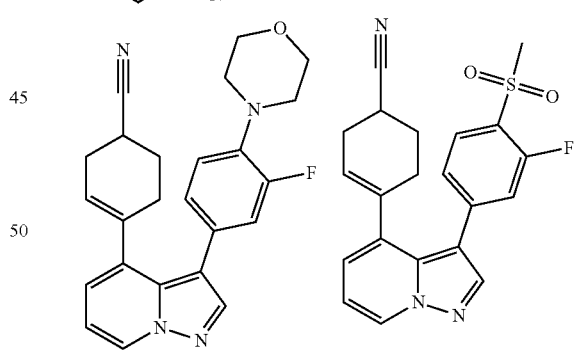
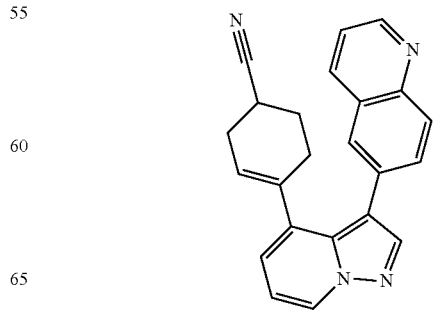

413
-continued
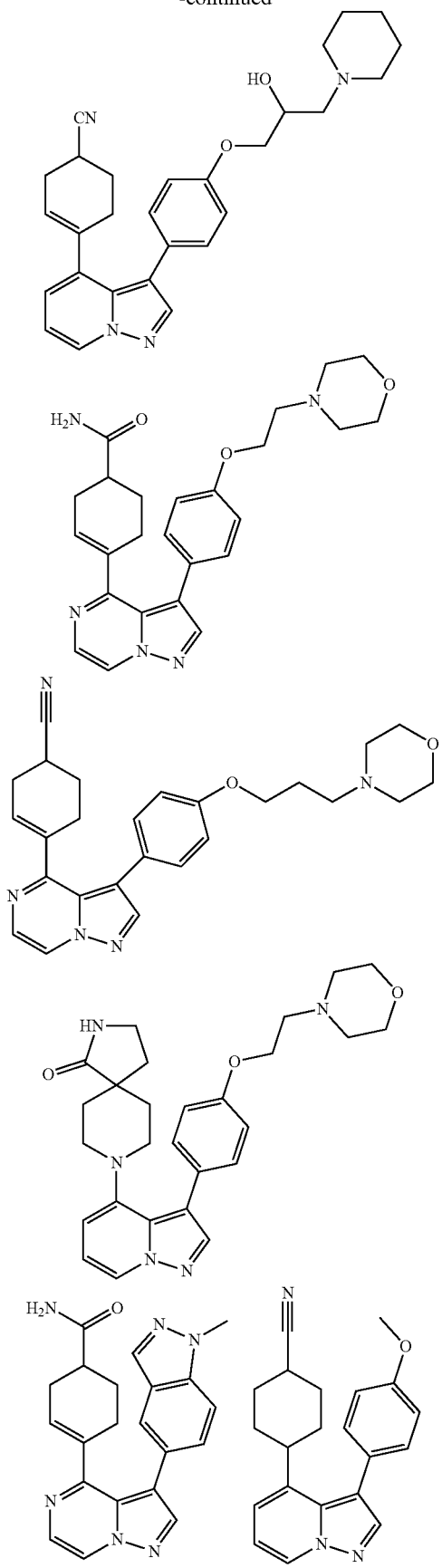
414
-continued
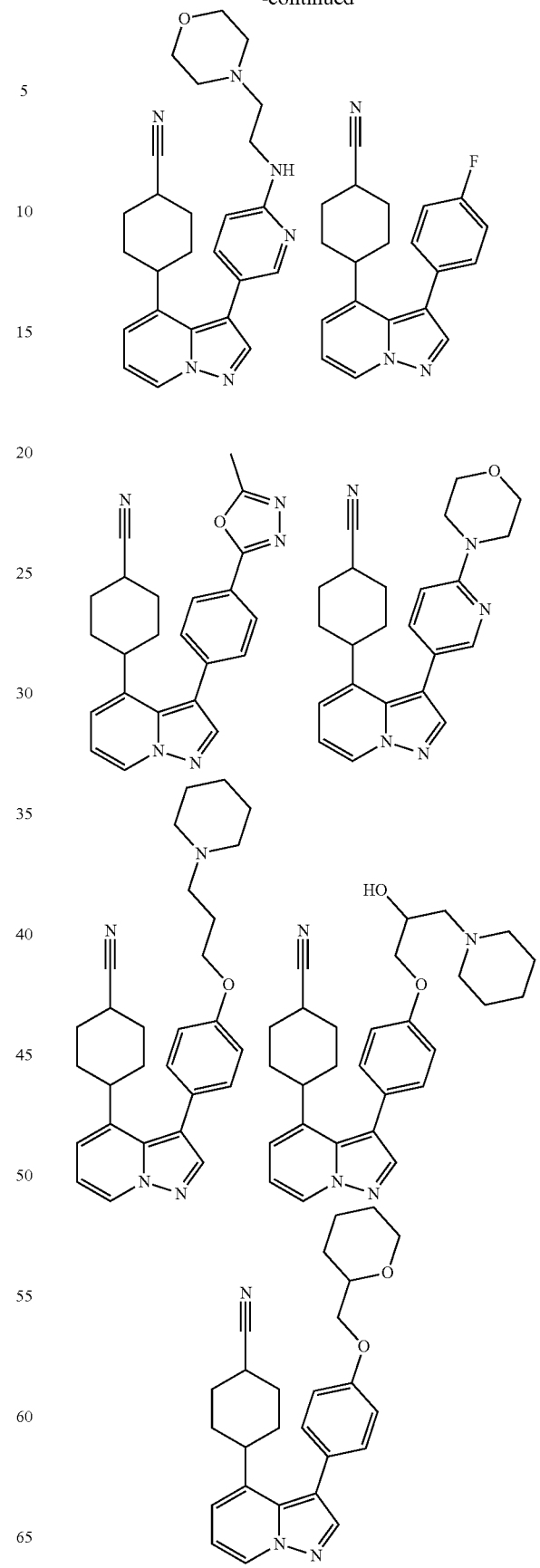

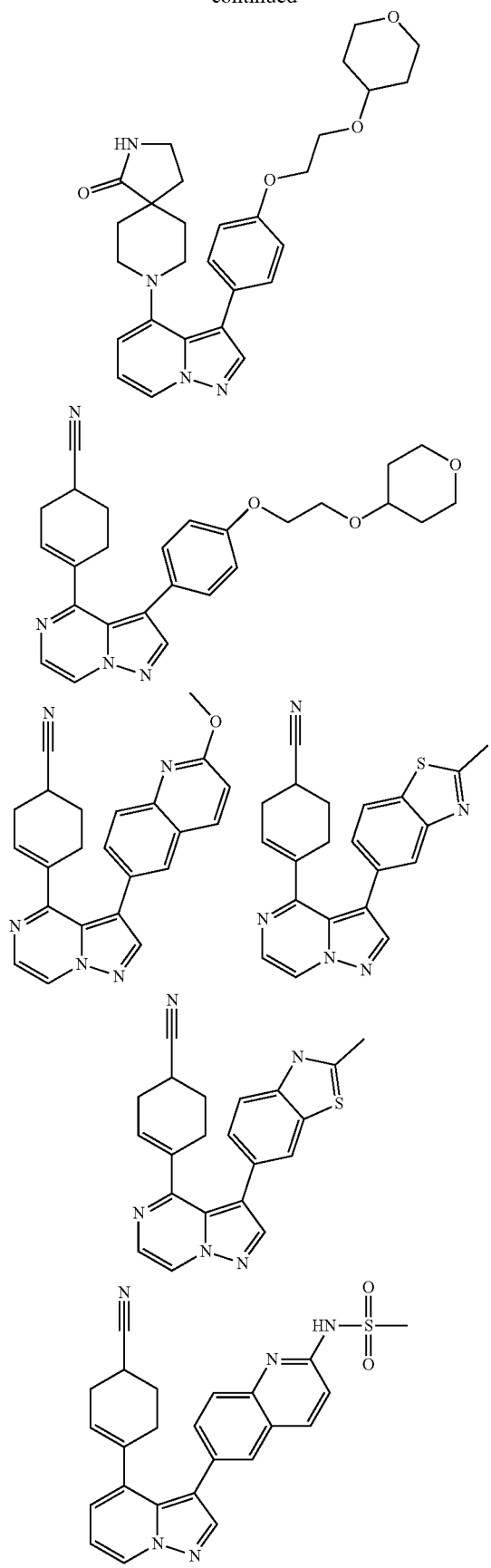
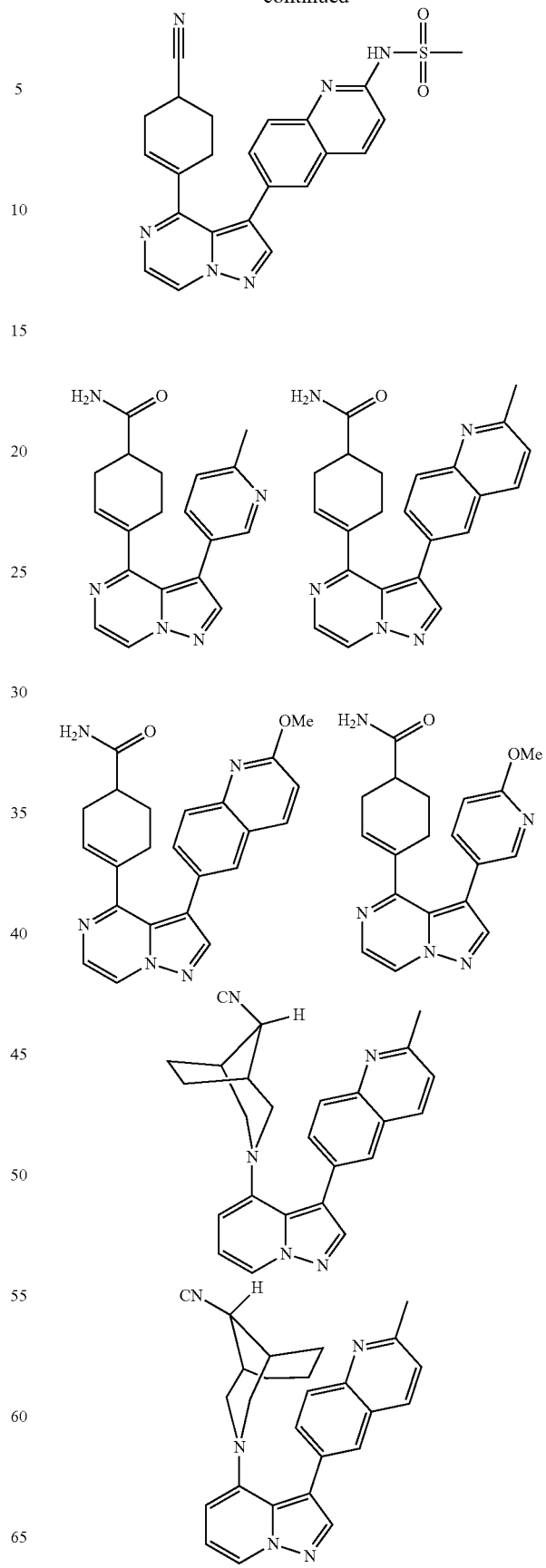

417
-continued
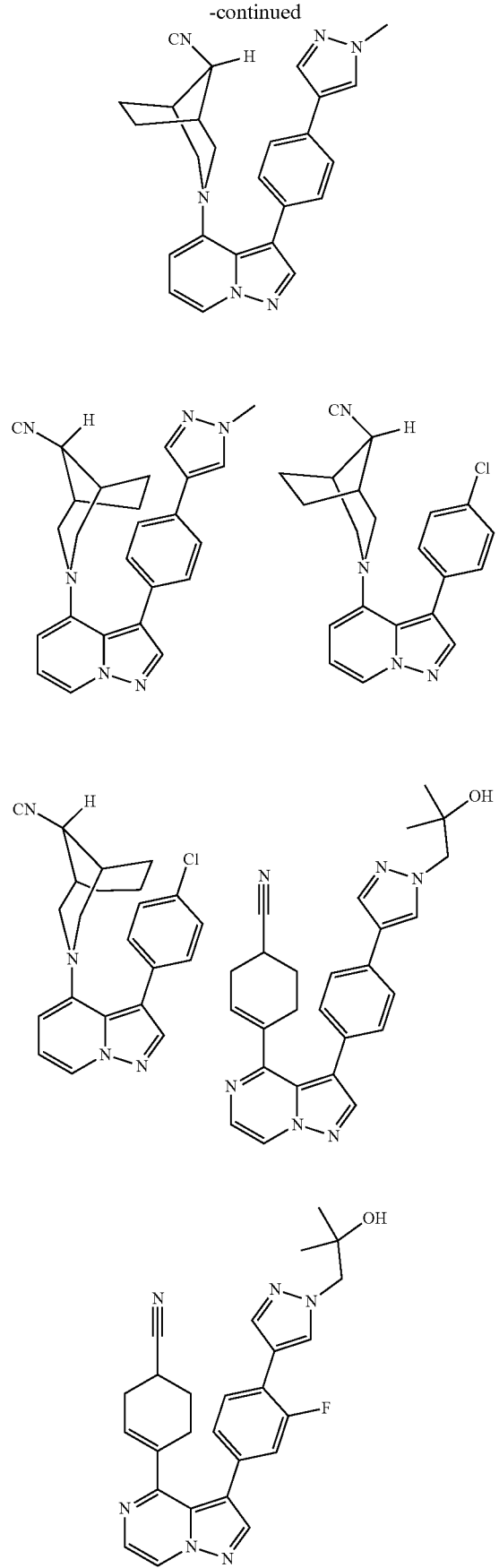
418
-continued
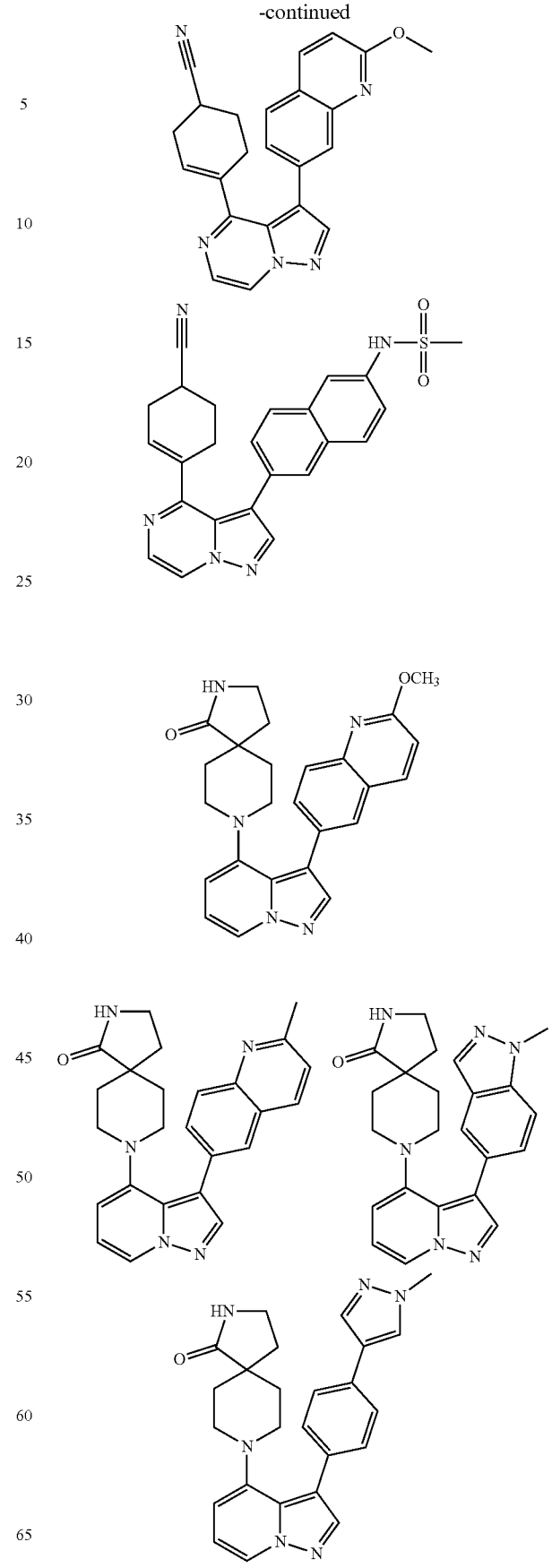

419
-continued
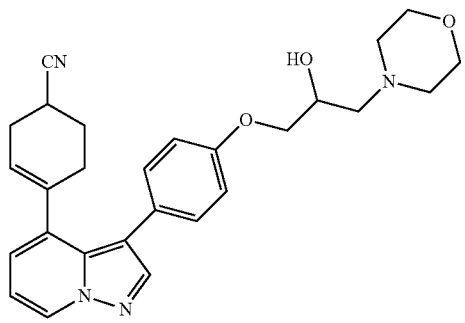
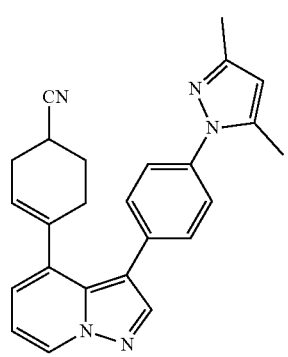
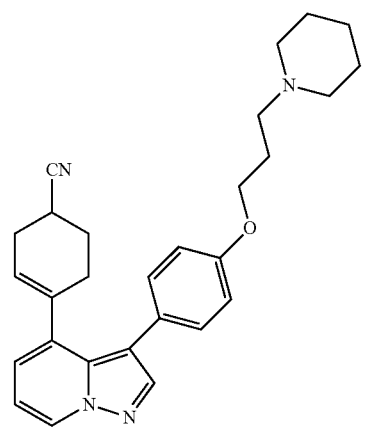
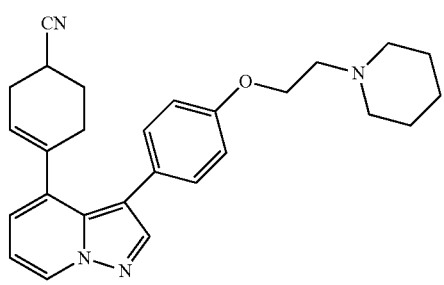
420
-continued
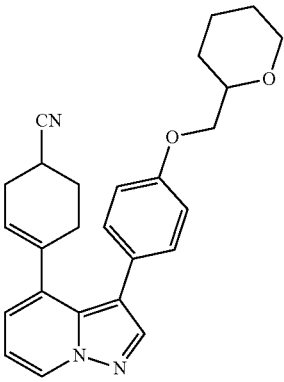
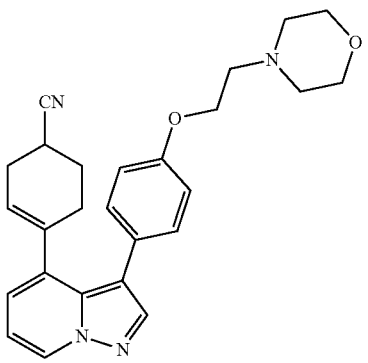
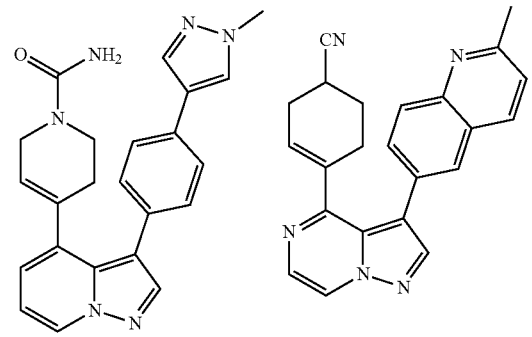
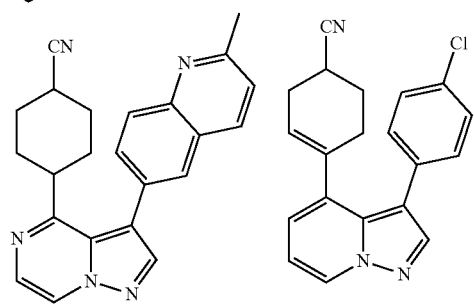
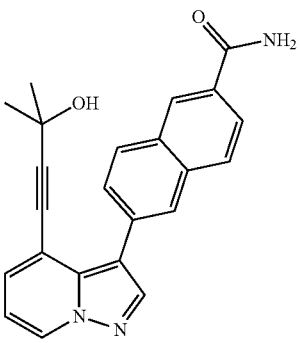

421
-continued
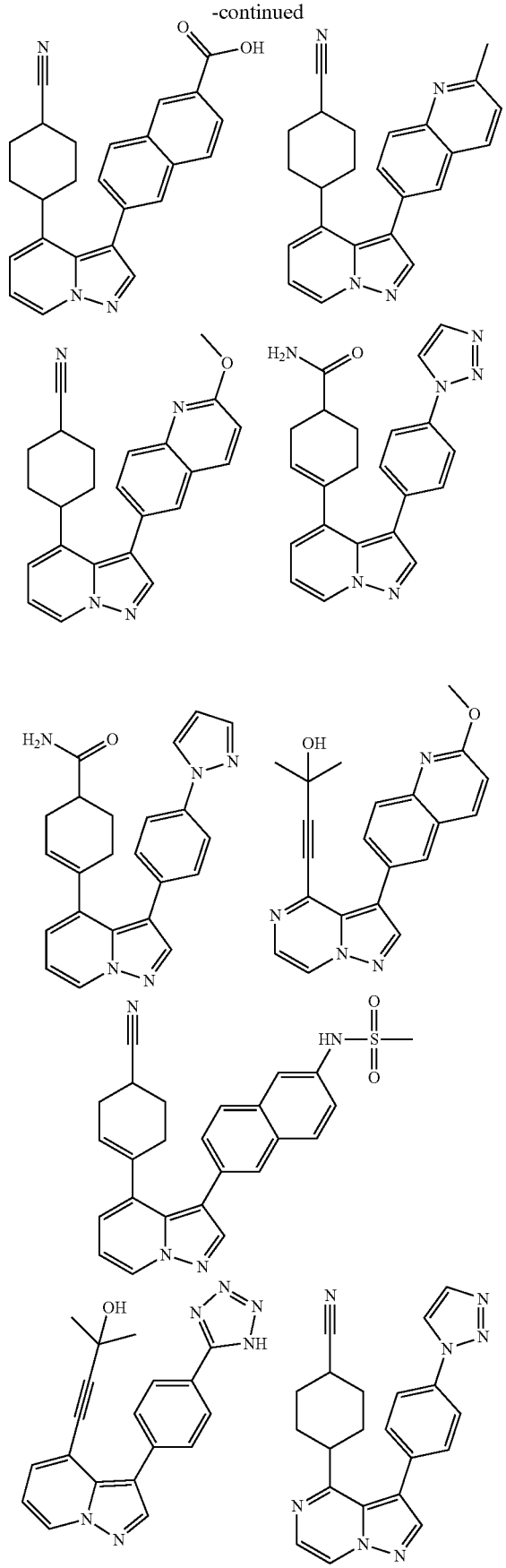
422
-continued
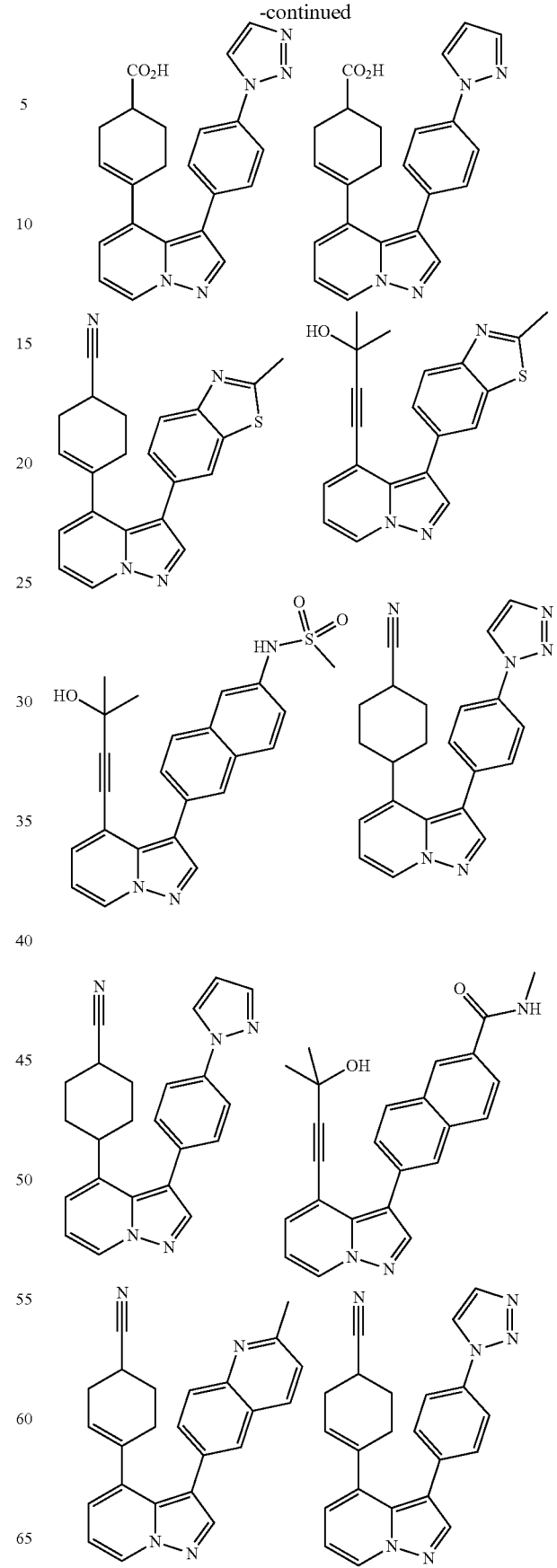

423
-continued
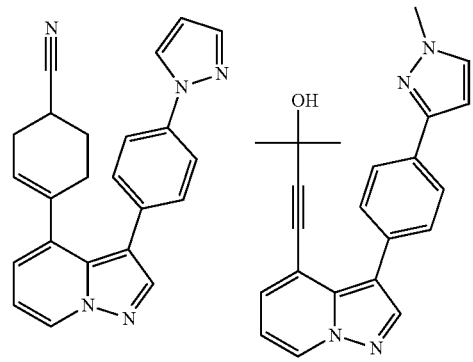
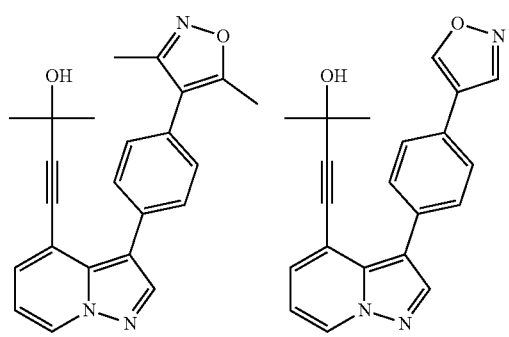
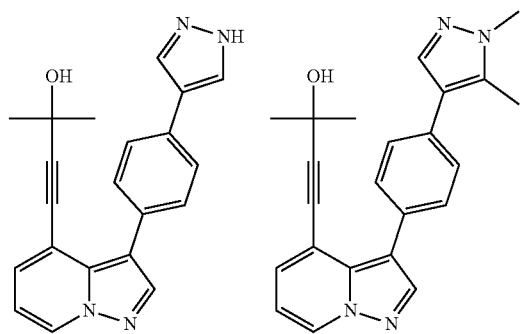
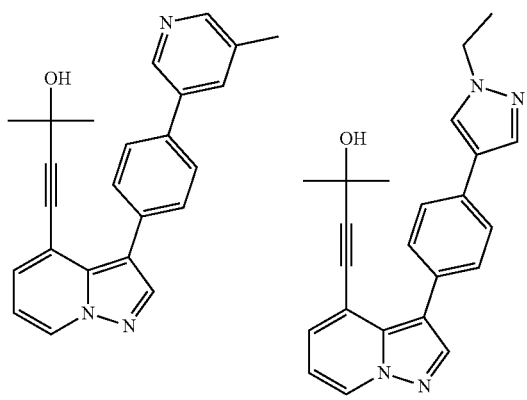
424
-continued
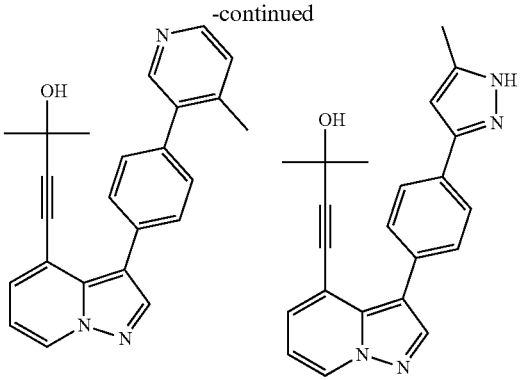
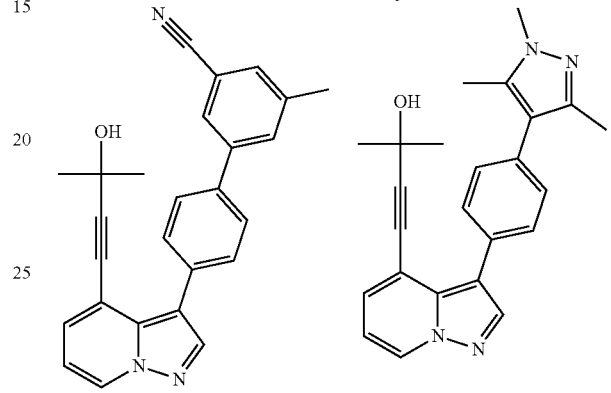
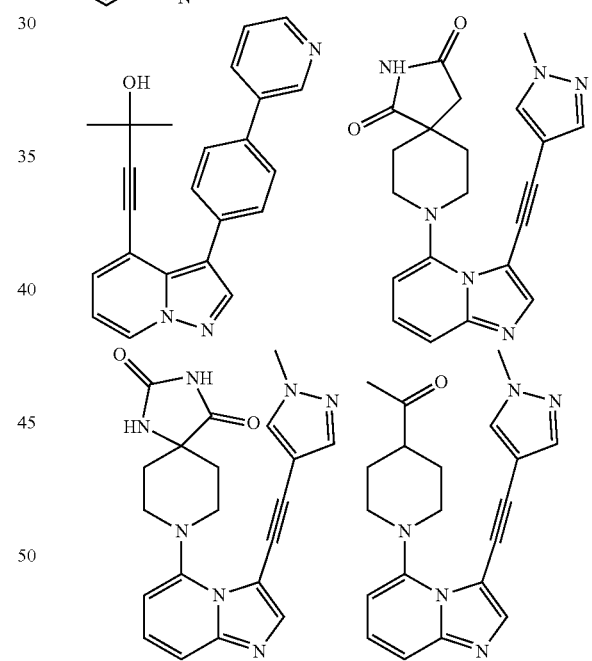
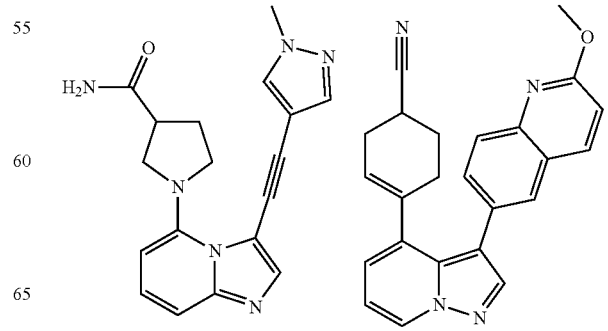

425
-continued
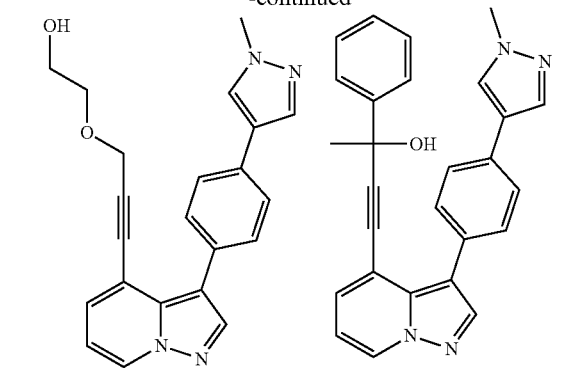
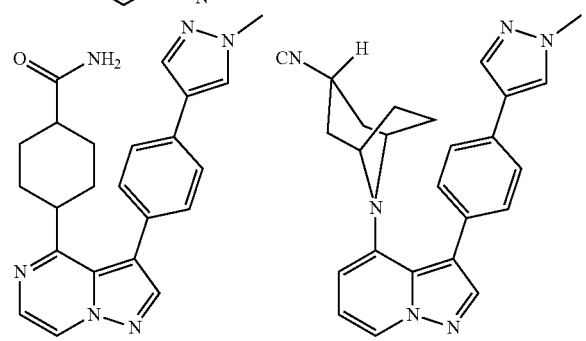
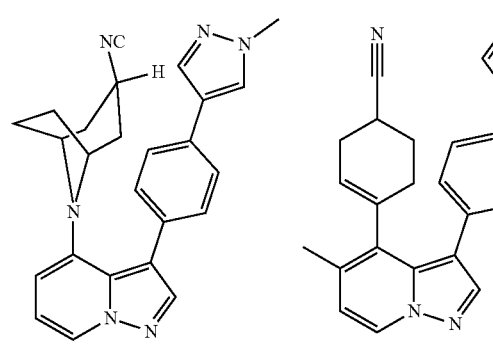
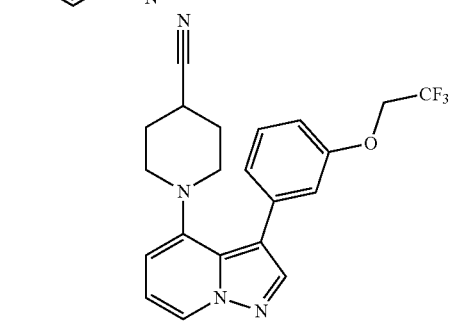
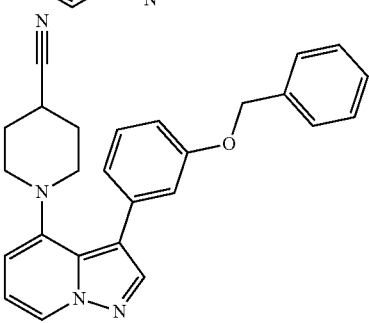
426
-continued
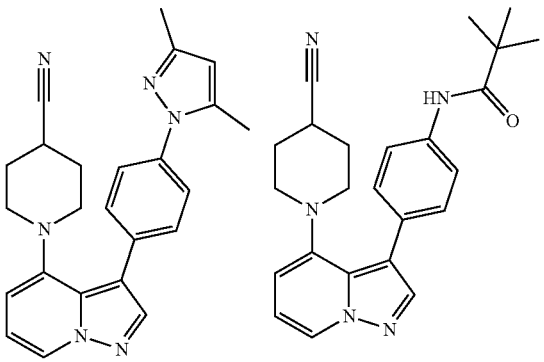
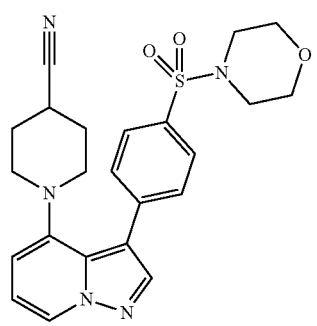
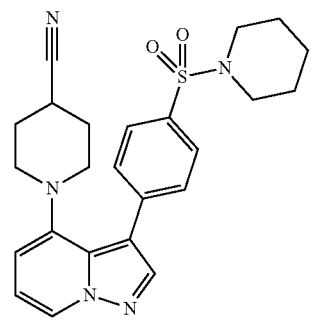
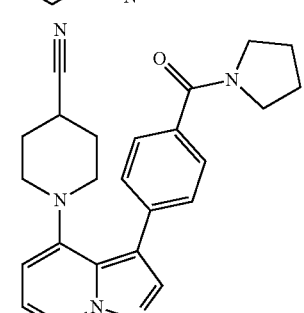
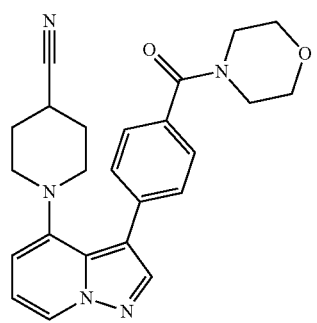

427
-continued
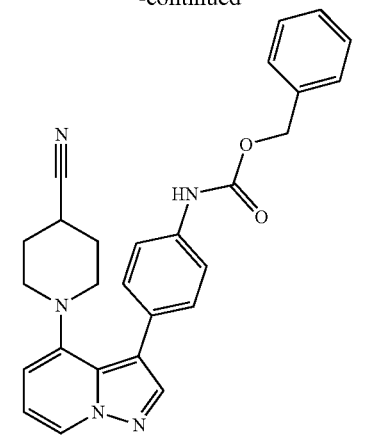
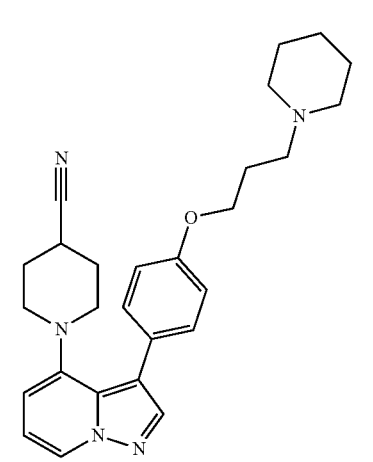
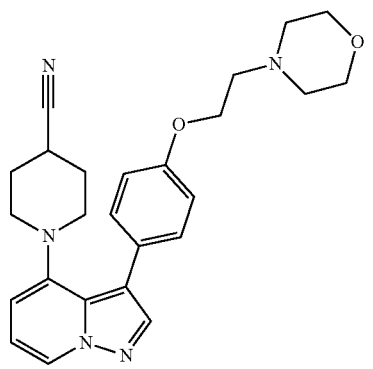
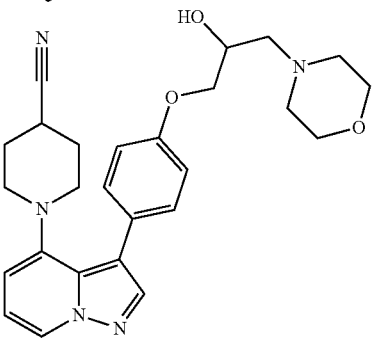
428
-continued
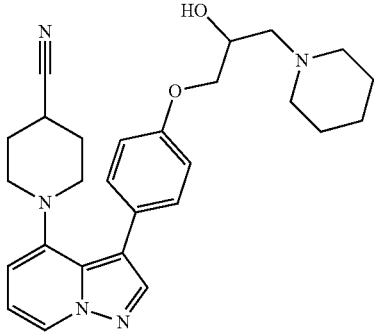
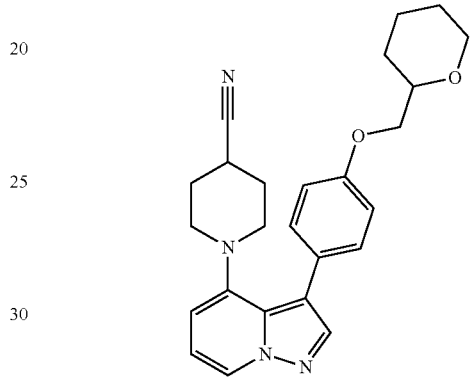
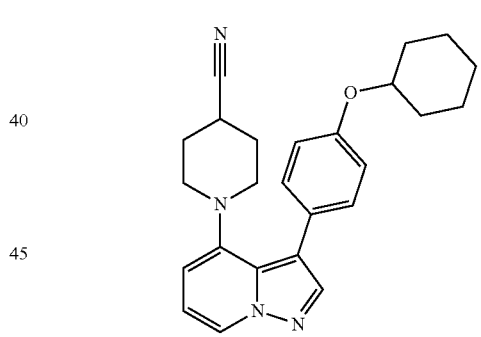
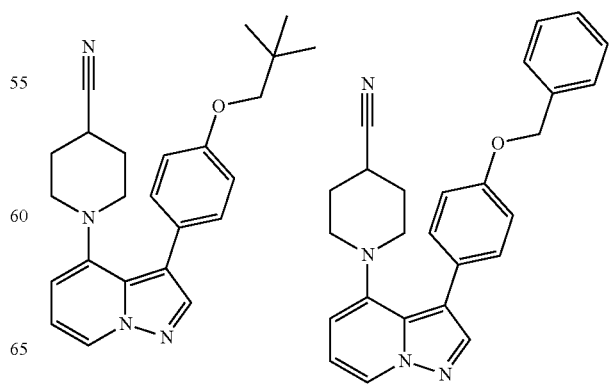

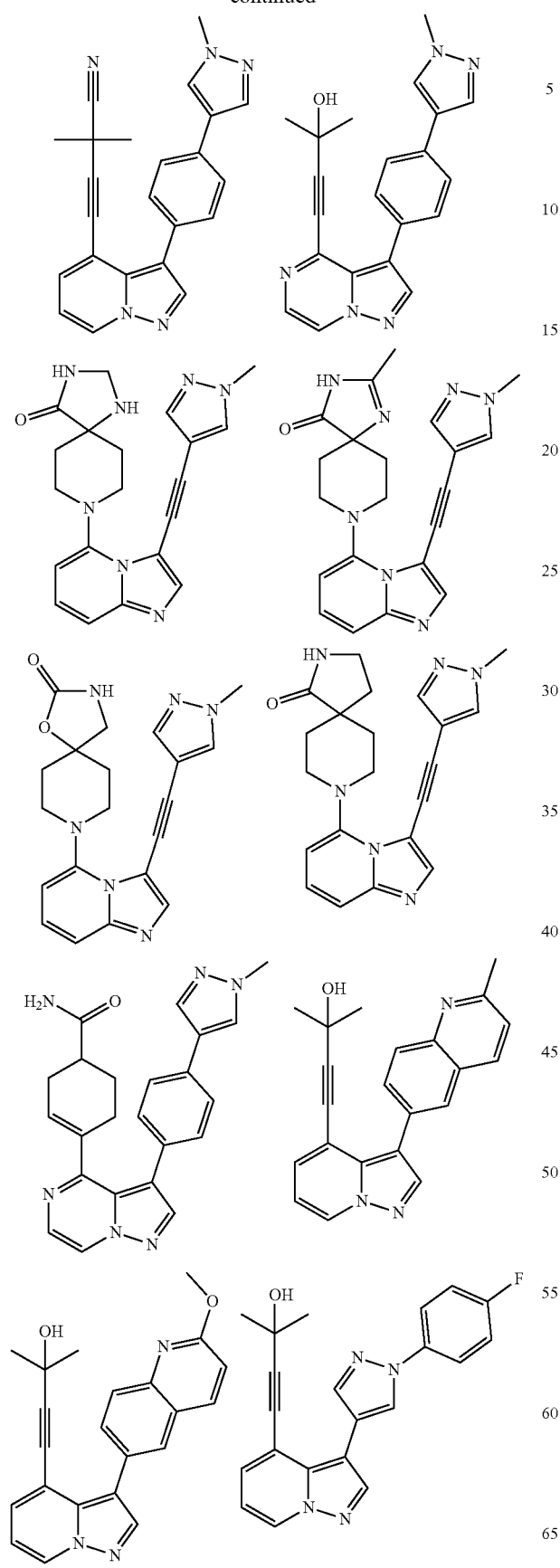
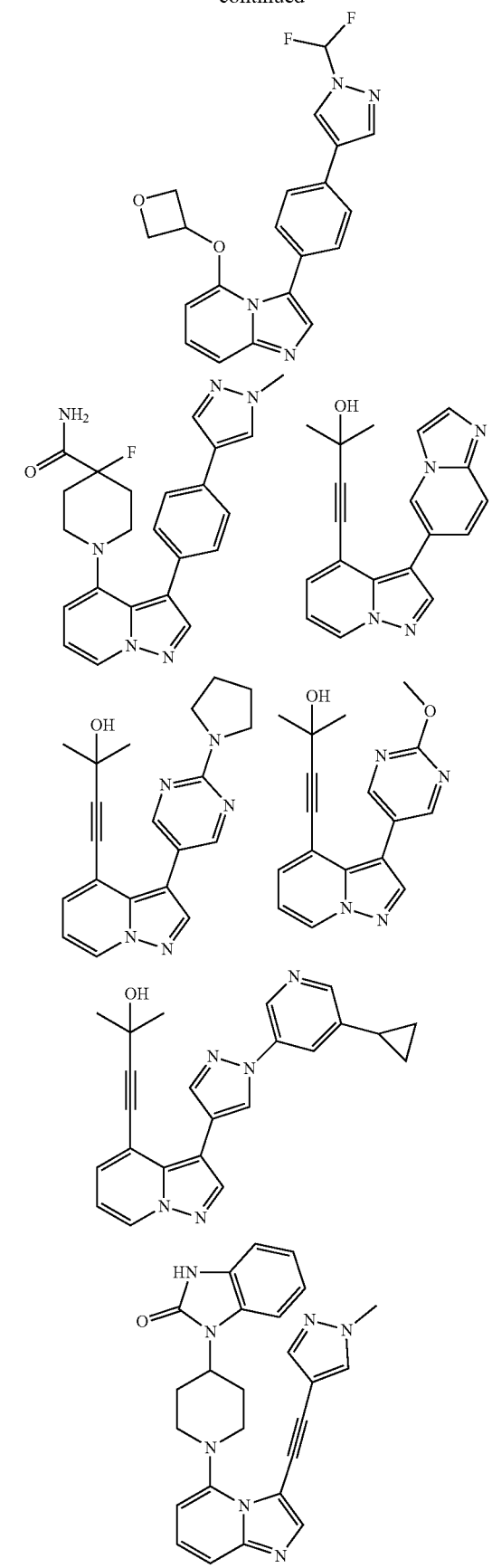

431
-continued
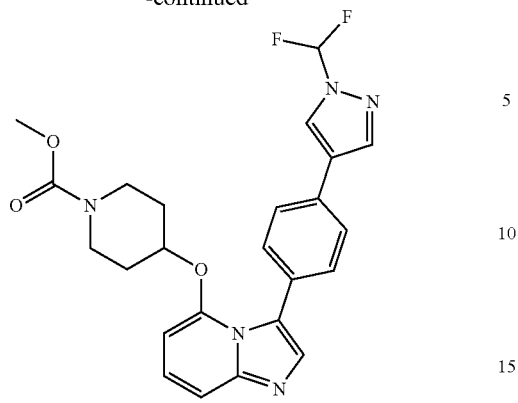
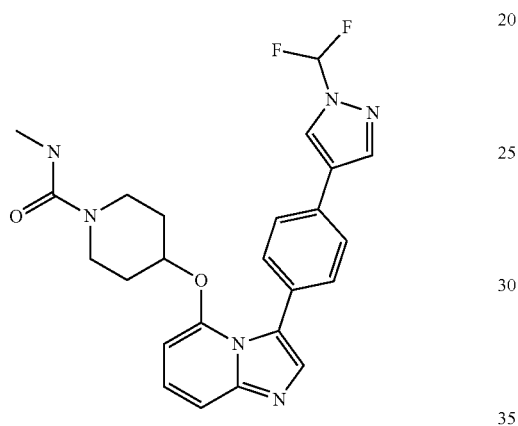
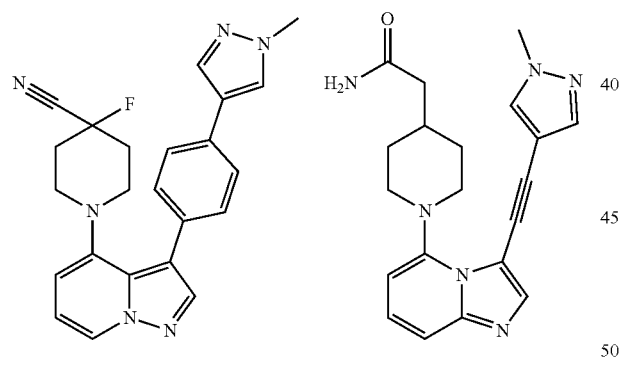
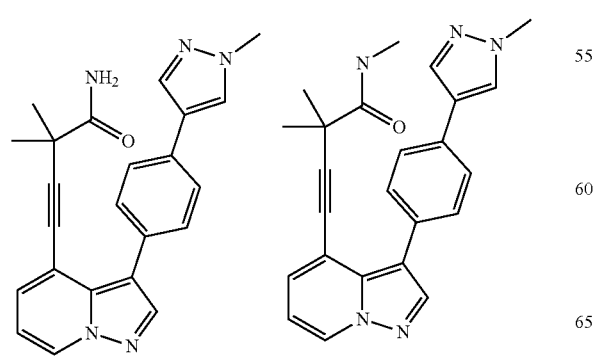
432
-continued
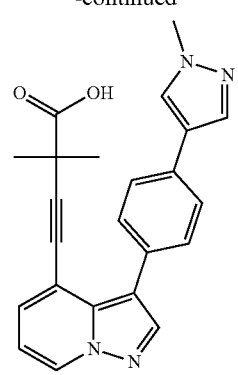
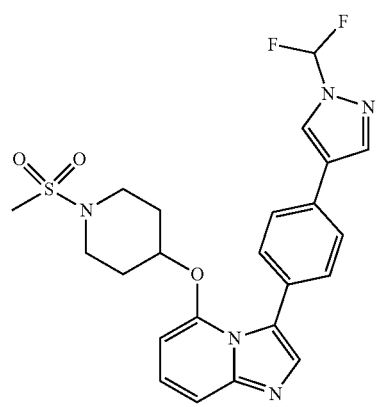
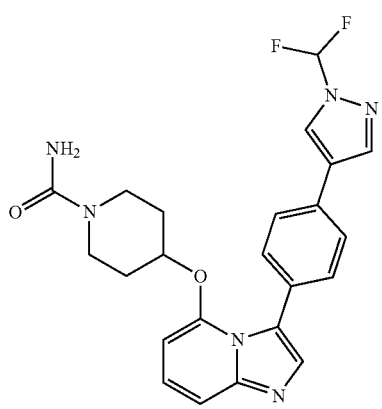
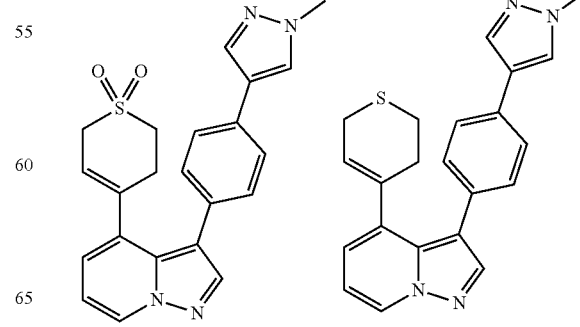

433
-continued
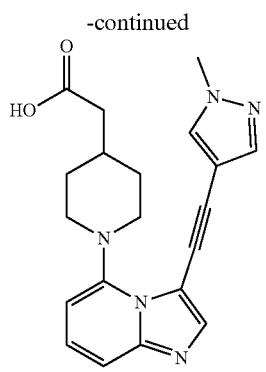
434
-continued
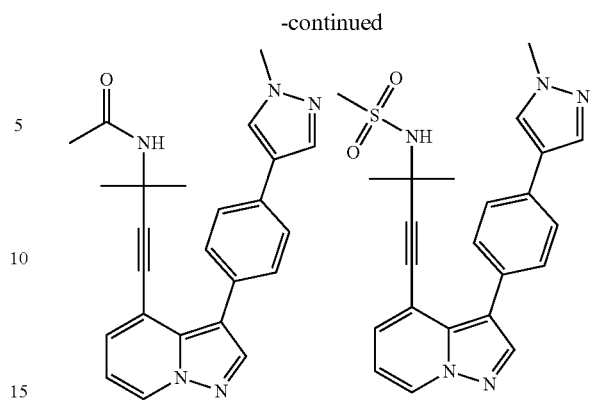
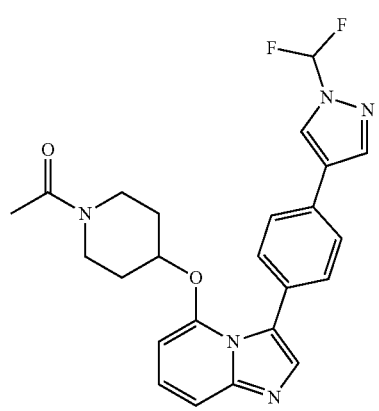
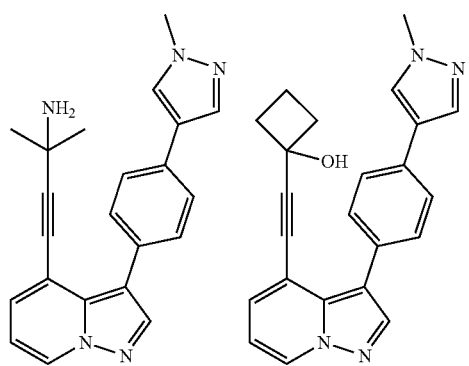
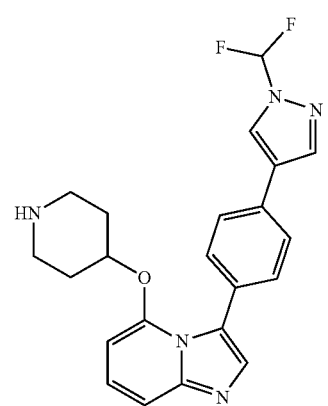
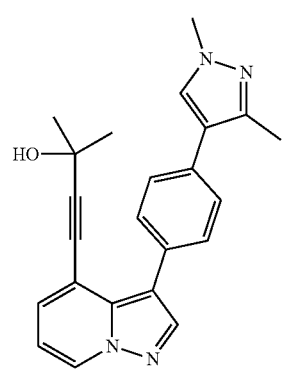
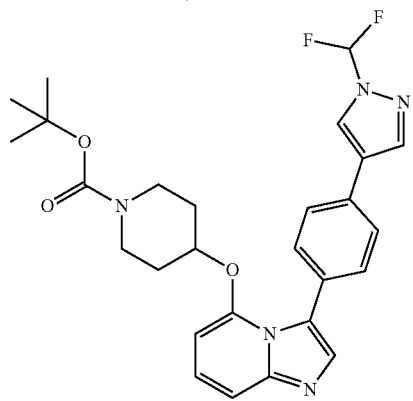
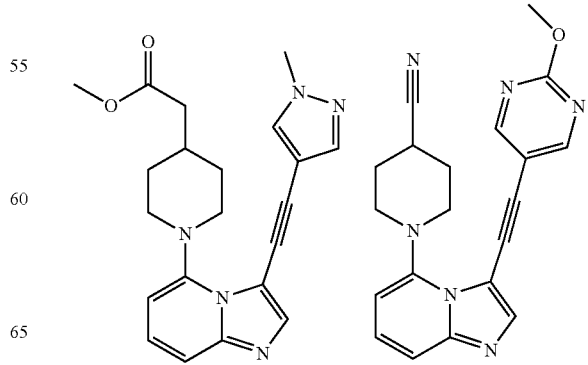

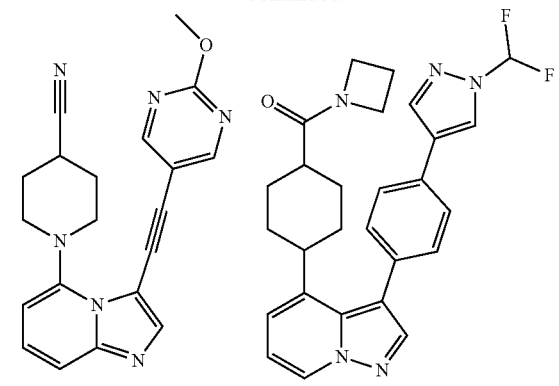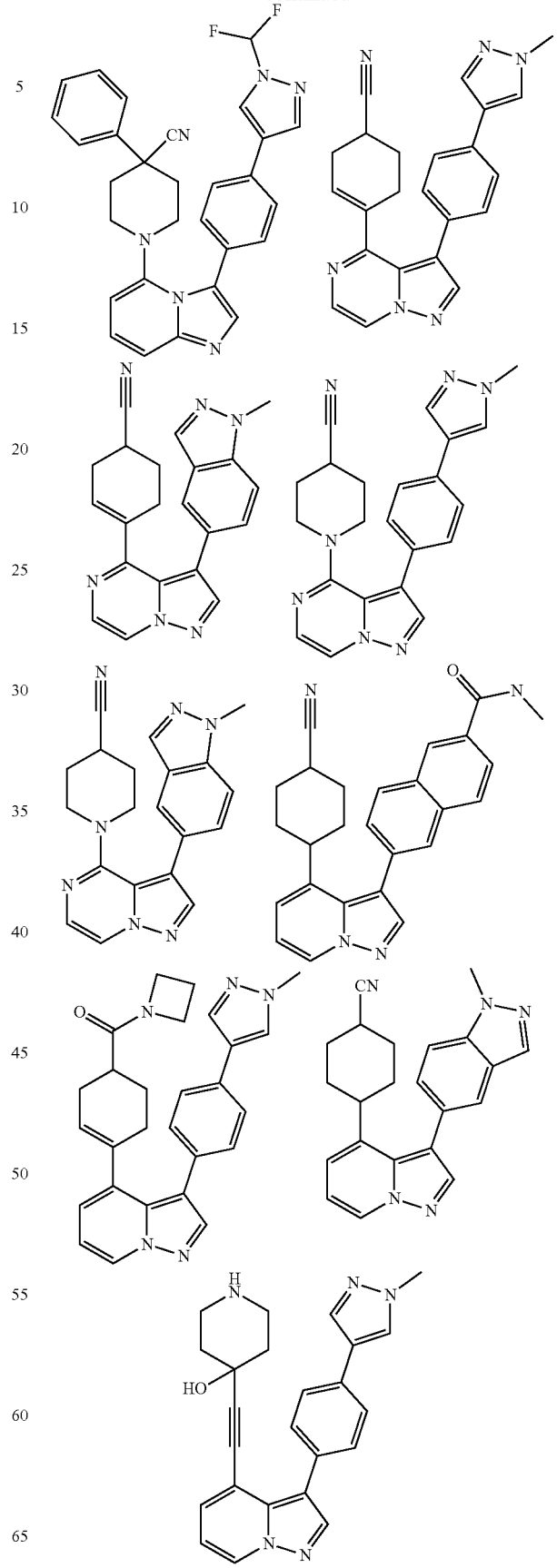

437
-continued
438
-continued
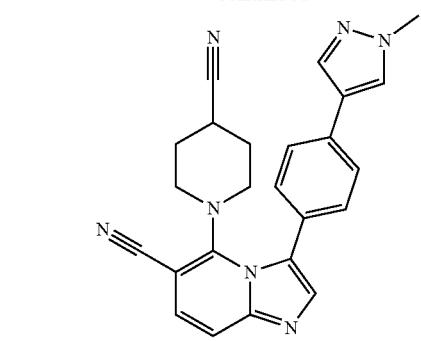
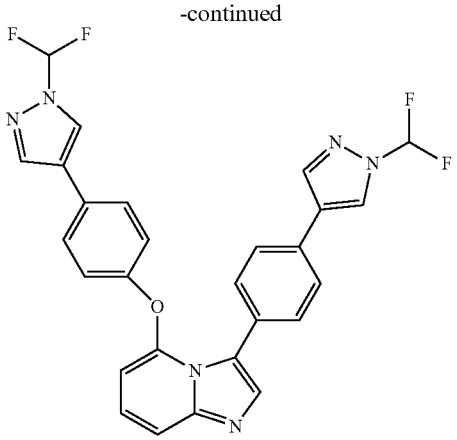
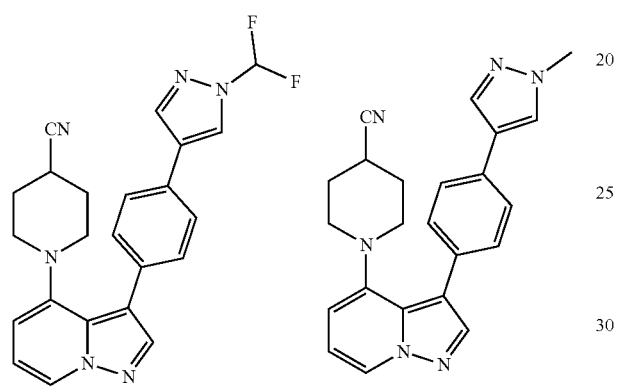
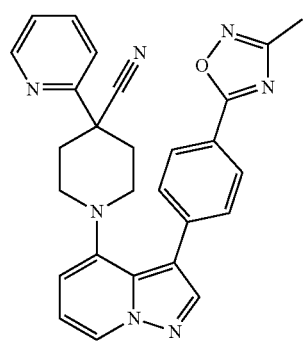
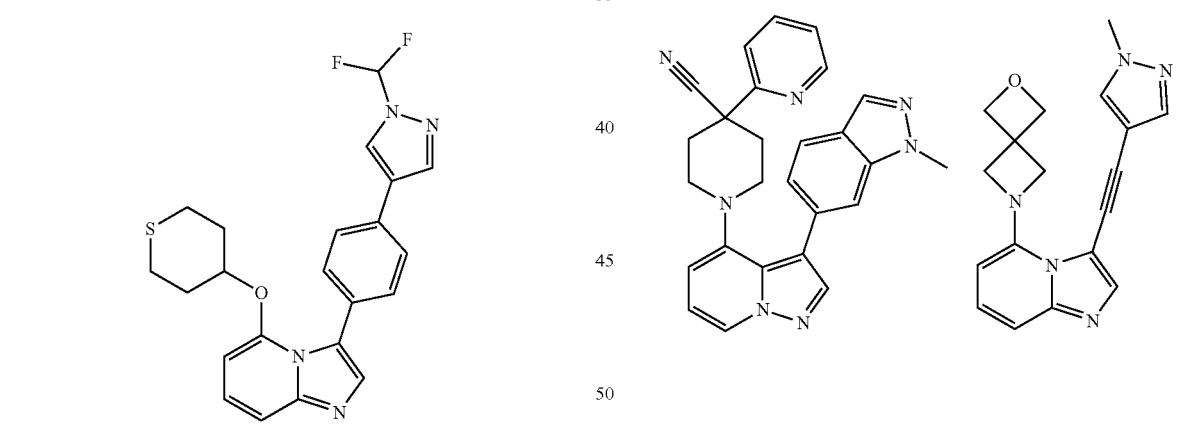
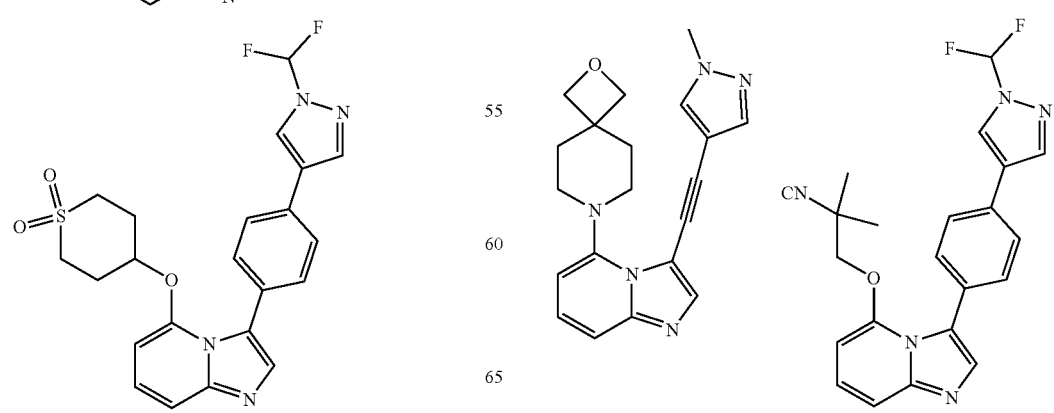

439
-continued
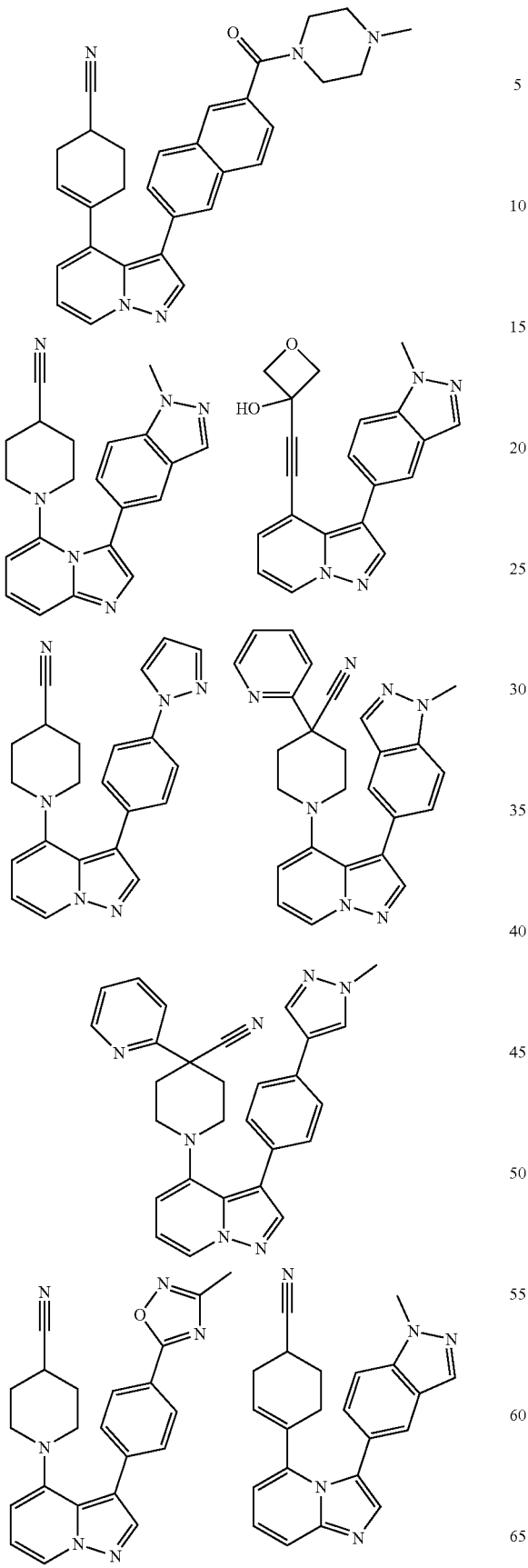
440
-continued
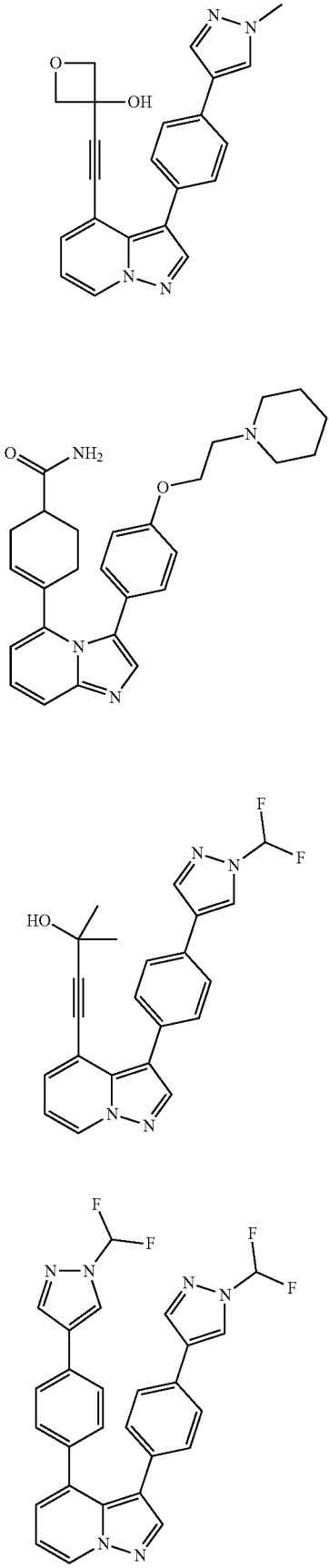

-continued
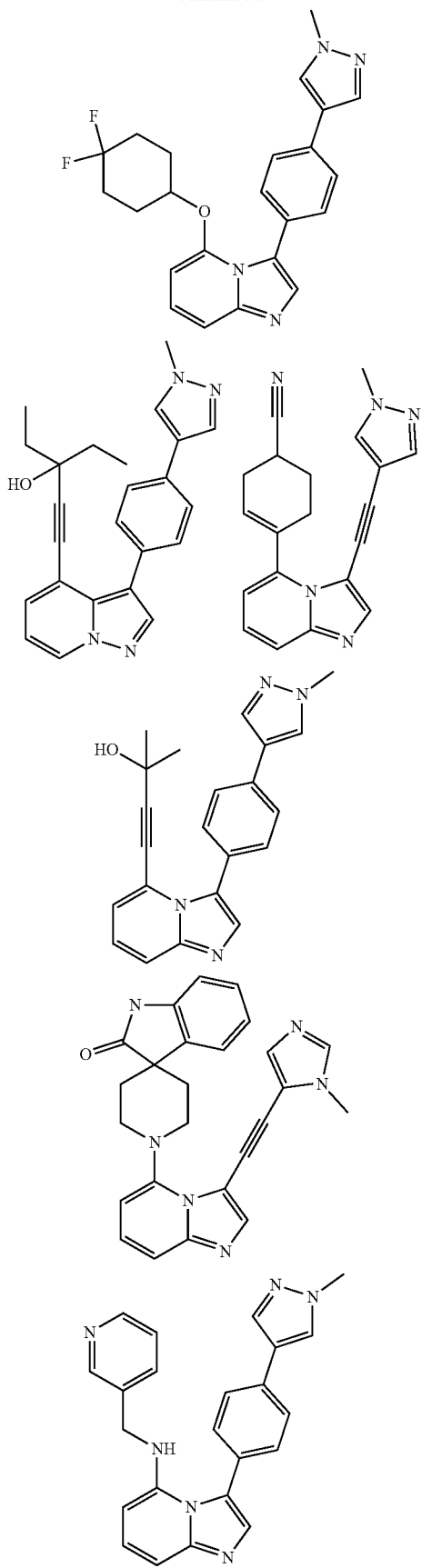
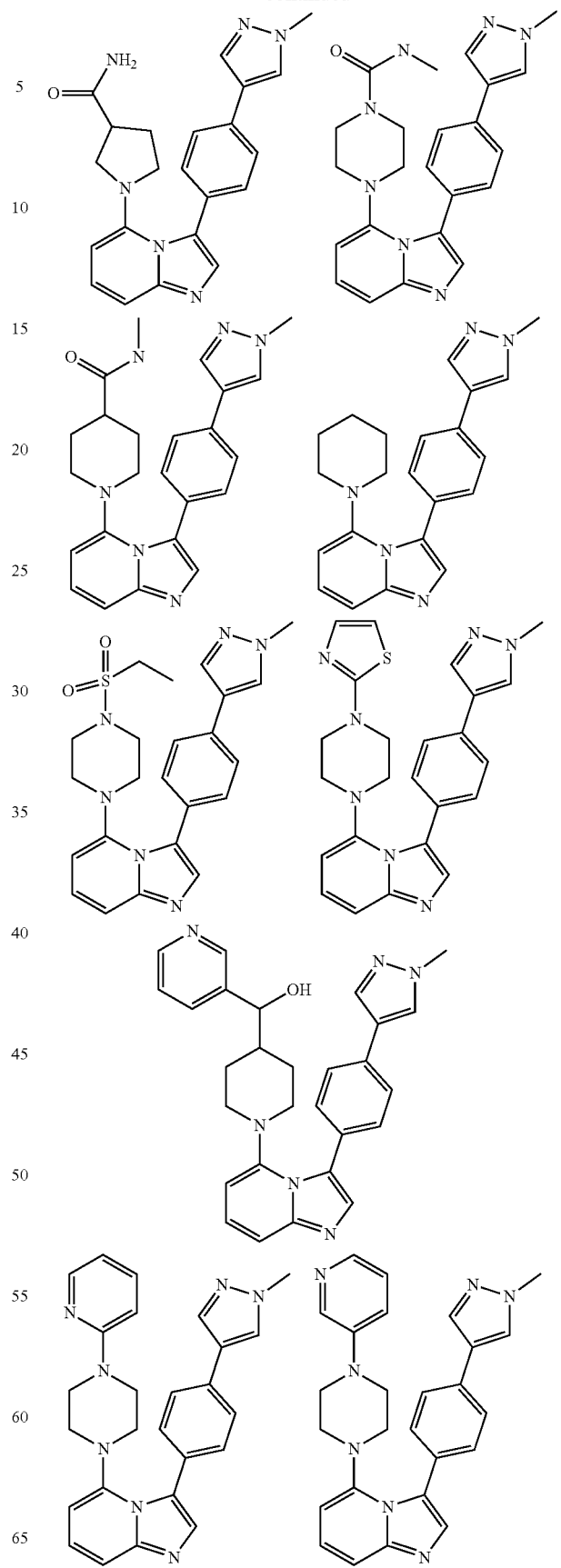

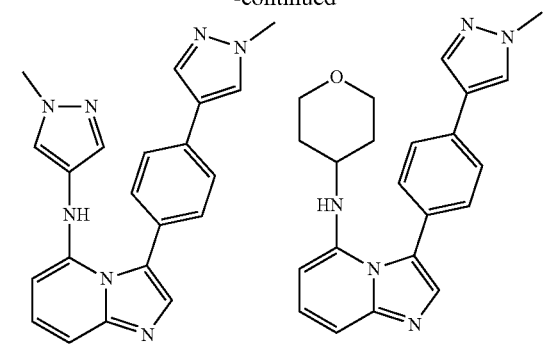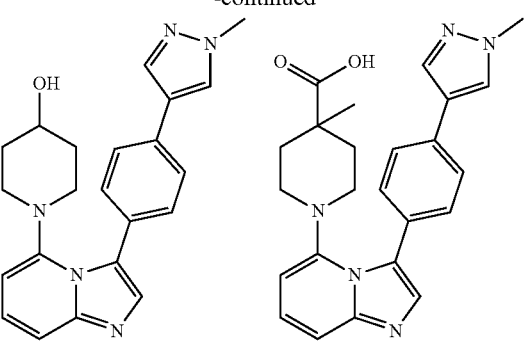

445
-continued
446
-continued
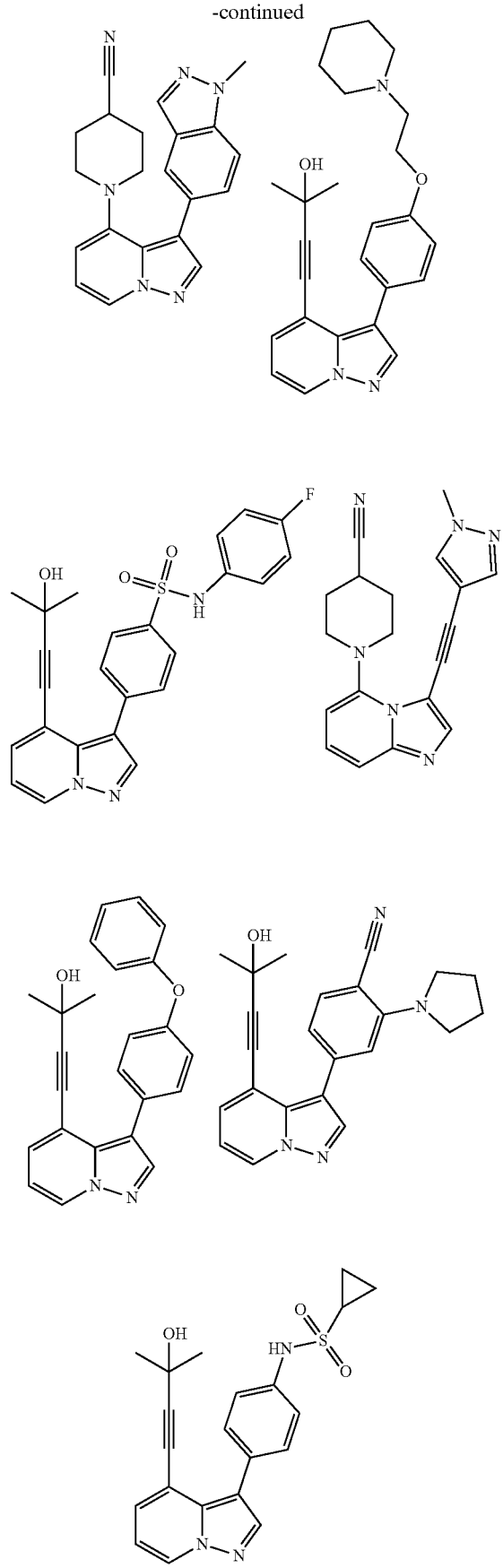
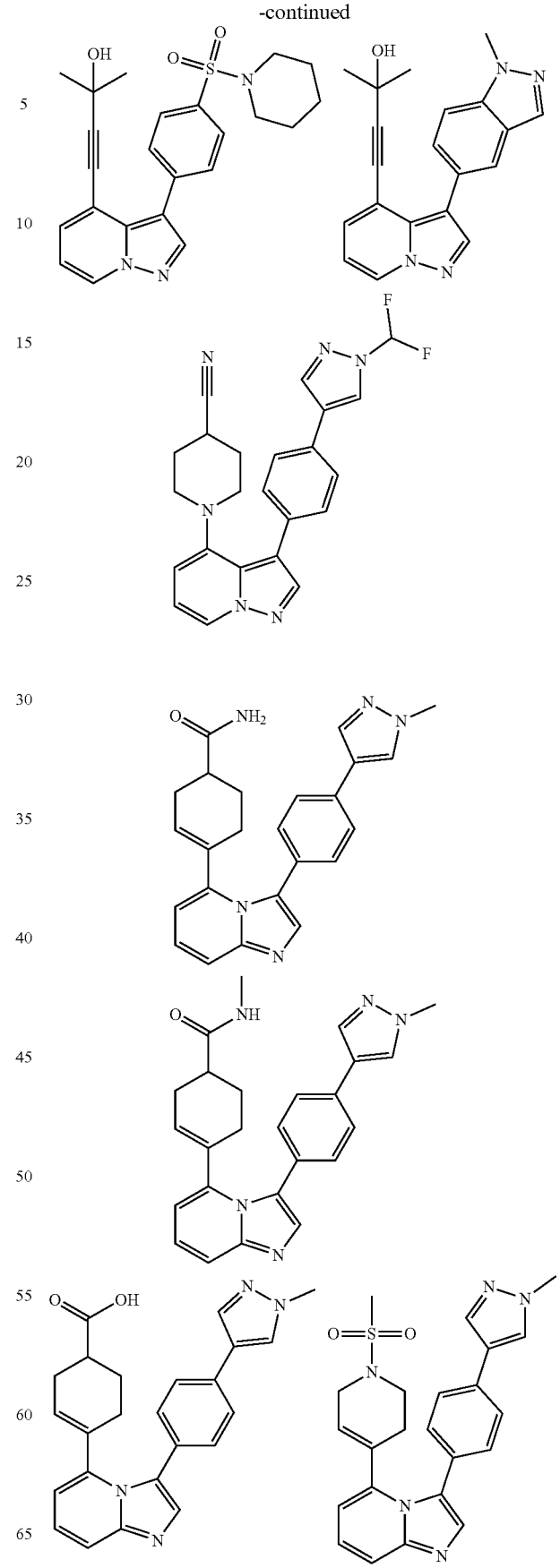

447
-continued
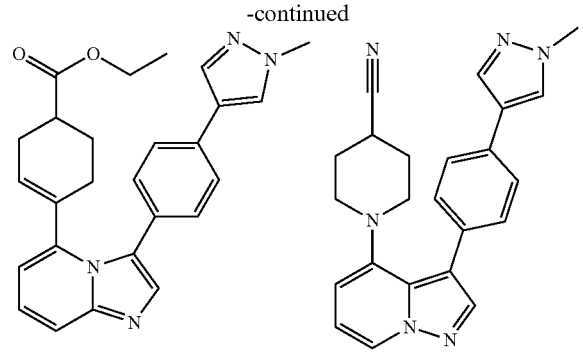
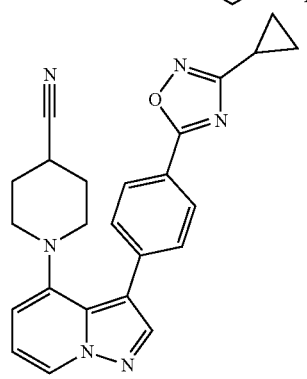
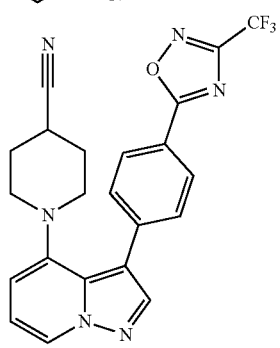
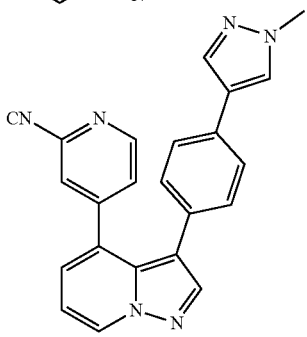
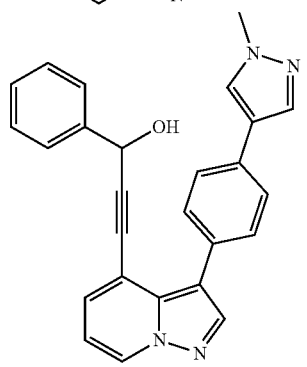
448
-continued
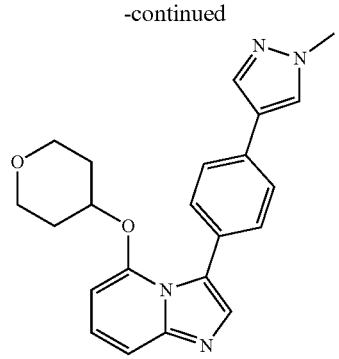
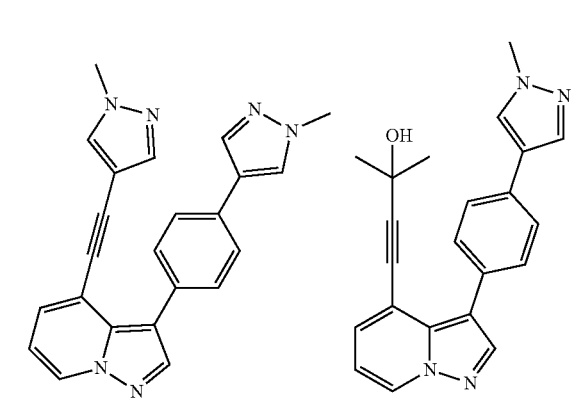
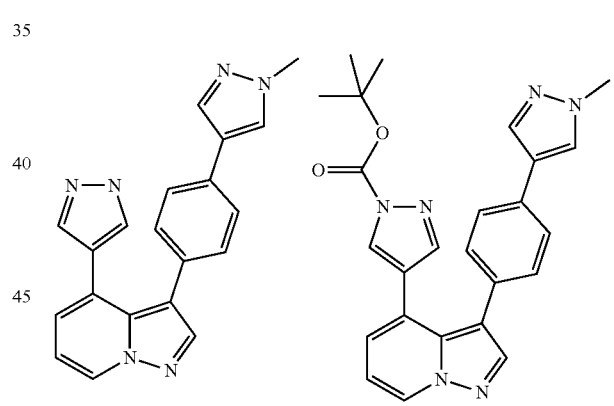
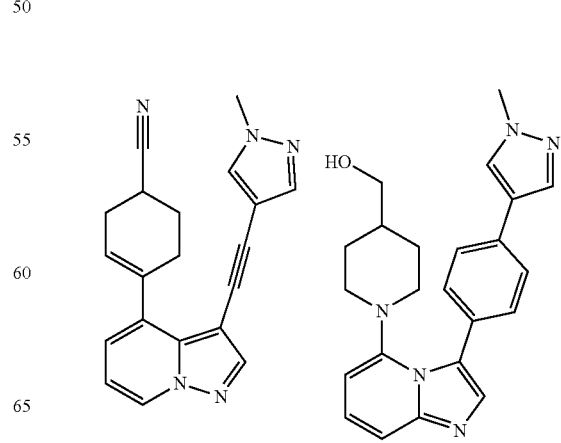

449
-continued
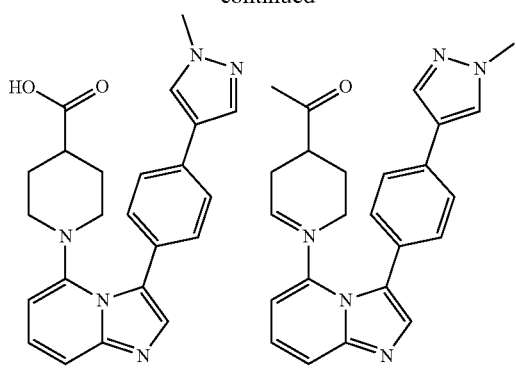
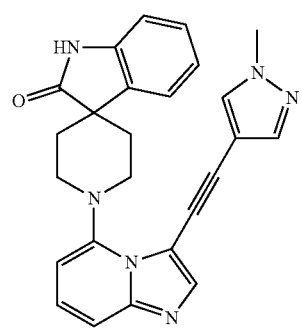
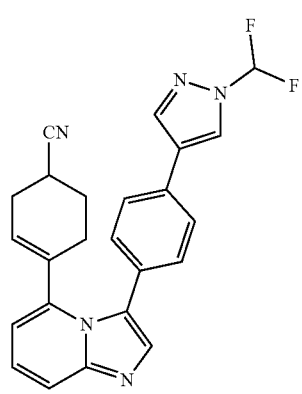
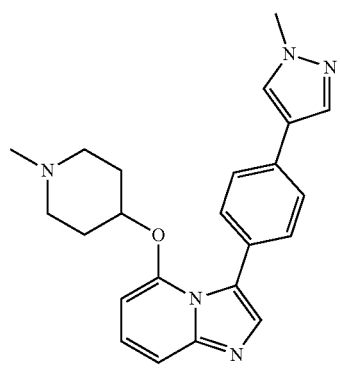
450
-continued
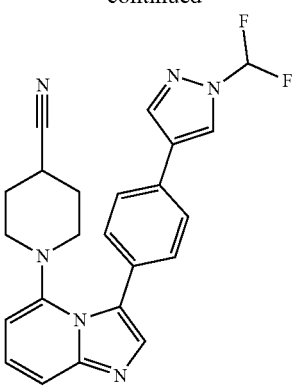
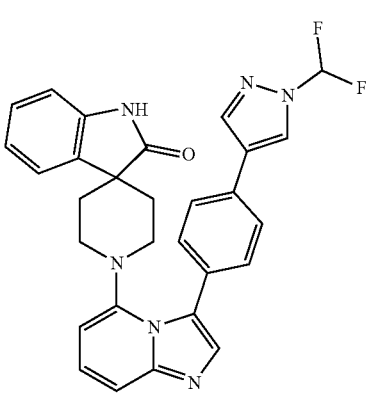
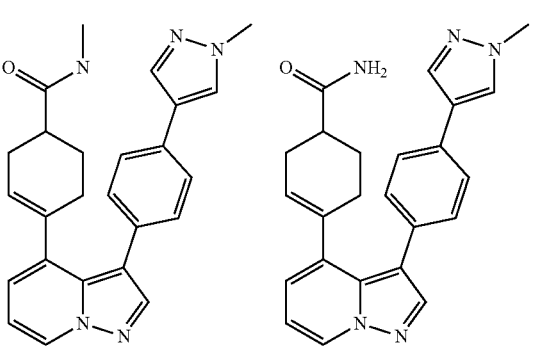
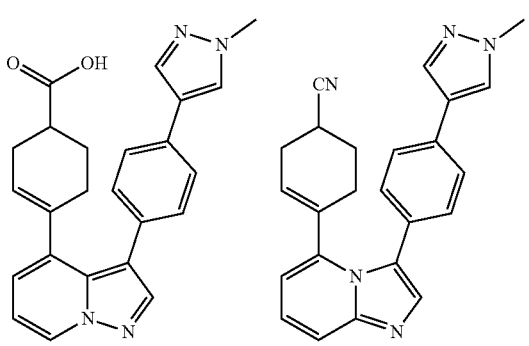

451
-continued
452
-continued
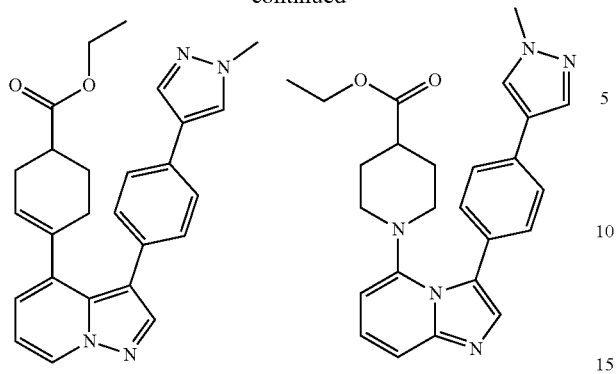
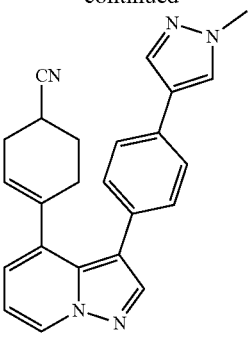
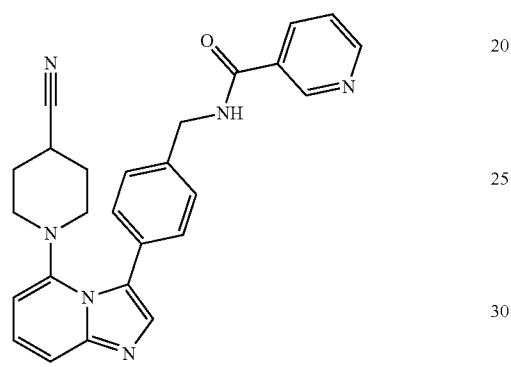
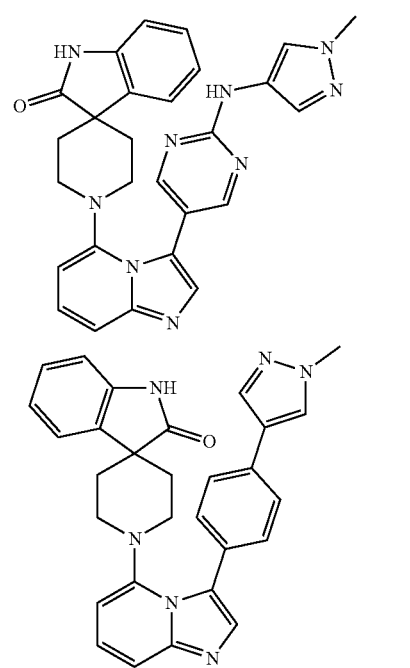
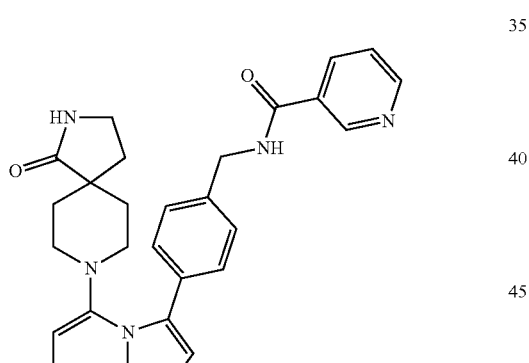
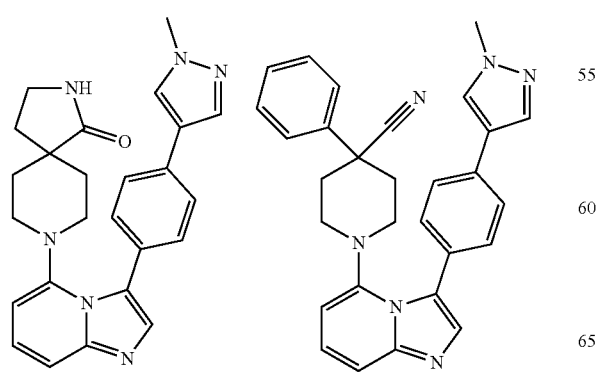
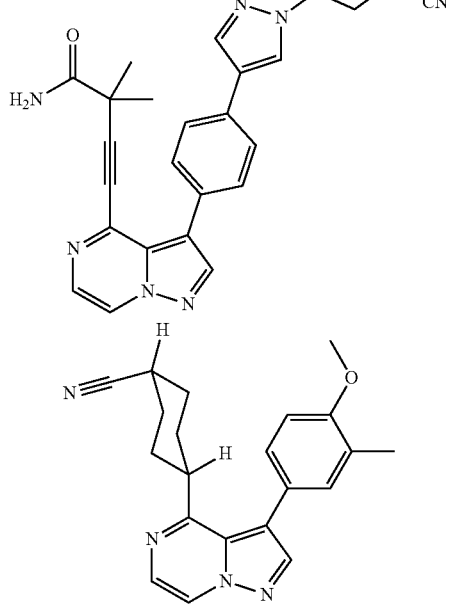

453
-continued
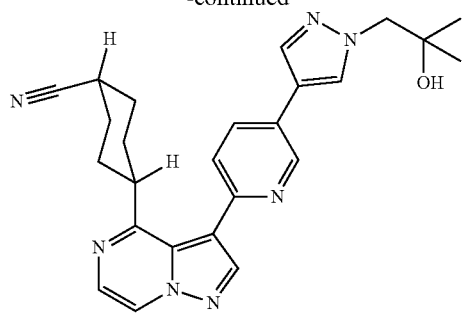
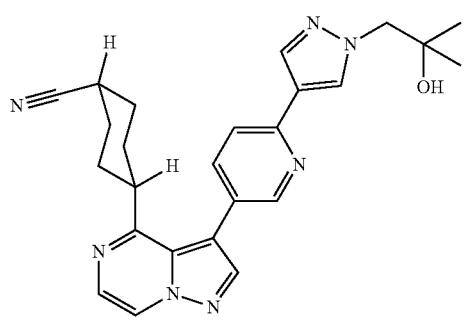
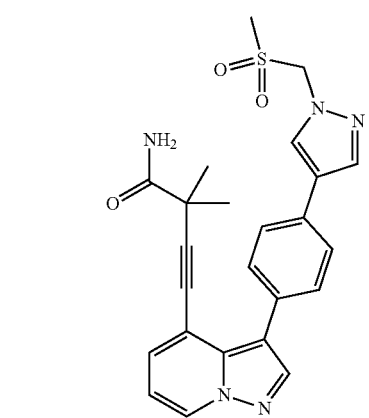
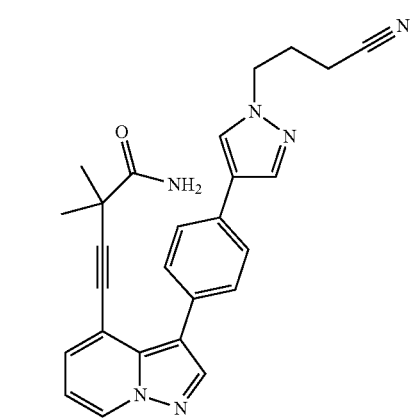
454
-continued
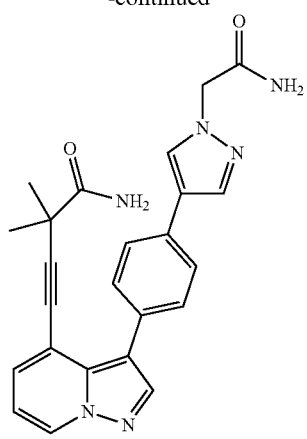
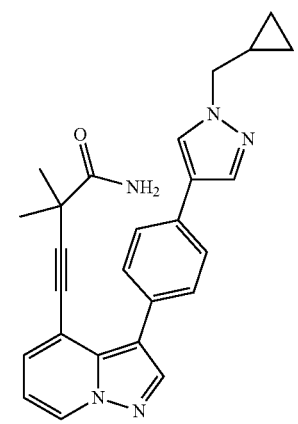
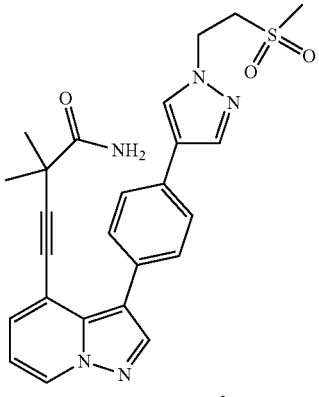
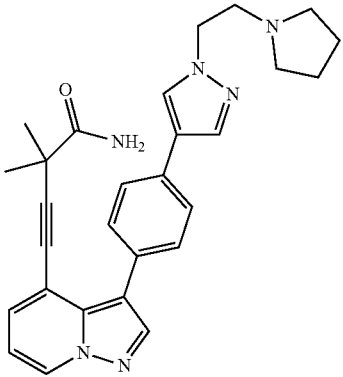

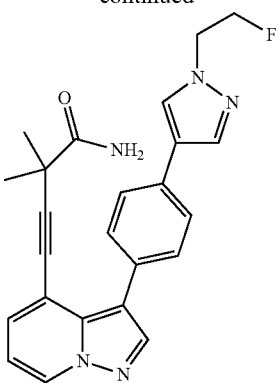

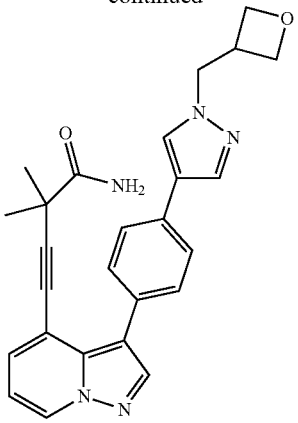

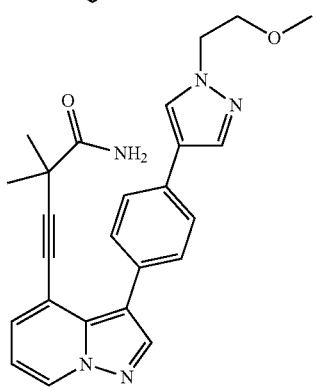

and or a pharmaceutically acceptable salt, a tautomer, a stereoisomer, or a deuterated analog thereof.

21. A pharmaceutical composition comprising a compound of claim 1, and a pharmaceutically acceptable carrier.

22. The pharmaceutical composition of claim 21, further comprising a second pharmaceutical agent.

23. The pharmaceutical composition according to claim 22, wherein the second pharmaceutical agent is: i) an alkylating agent, ii) an antibiotic; iii) an antimetabolite; iv) an antibody therapy agent; v) a hormone or hormone antagonist; vi) a taxane; vii) a retinoid; viii) an alkaloid; ix) an antiangiogenic agent; x) a topoisomerase inhibitor; xi) a kinase inhibitor; xii) a targeted signal transduction; xiii) a biological response modifier; xiv) a chemotherapeutic agent; xv) an Hsp90 inhibitor; xvi) a farnesyltransferase inhibitors; xvii) an aromatase inhibitor; xviii) an IDO inhibitor; xix) a histone acetyltransferase (HAT) inhibitor; a xx) histone deacetylase (HDAC) inhibitor; xxi) a sirtuin (SIRT) inhibitor; xxii) a BET inhibitor; or xxiii) an antiangiogenic agent.

24. A method for treating a subject with a disease or condition mediated by CDK8, said method comprising administering to the subject an effective amount of a compound of claim 1, or a pharmaceutically acceptable salt, a tautomer, a stereoisomer, or a deuterated analog thereof, wherein the disease or condition is brain cancer, lung cancer, colon cancer, epidermoid cancel, squamous cell cancer, bladder cancer, gastric cancer, pancreatic cancer, breast cancer, head cancer, neck cancer, renal cancer, kidney cancer, liver cancer, ovarian cancer, prostate cancer, colorectal cancer, uterine cancer, rectal cancer, oesophageal cancer, testicular cancer, thyroid cancer, melanoma, uveal melanoma, acute myeloid leukemia, multiple myeloma, chronic myelogneous leukemia, myeloid cell leukemia, glioma, Kaposi's sarcoma, human laryngeal squamous cell carcinoma, inflammation, Alzheimer's disease, Parkinson's disease, dementia, amyloidosis, atherosclerosis, stroke/ischemia, pain, traumatic brain injury, kidney disease, inflammation pathologies, type 2 diabetes, or a viral infection.

25. The method according to claim 24, wherein the disease or condition is colorectal cancer, gastric cancer, pancreatic cancer, melanoma, breast cancer, ovarian cancer, lung cancer, lung cancer metastasis, breast cancer metastasis, or acute myeloid leukemia.

26. The method according to claim 24, wherein the viral infection is HSV, HCMV, HPV, or HIV.

27. The method according to claim 24, wherein the disease or condition is FLT3-ITD acute myeloid leukemia, and wherein the method further comprises administering one or more FLT3 inhibitors.

28. The method according to claim 27, wherein the FLT3 inhibitor is quizartinib.

29. The method according to claim 27, wherein the FLT3 inhibitor is gilteritinib.

30. The compound of claim 1, wherein the compound is:

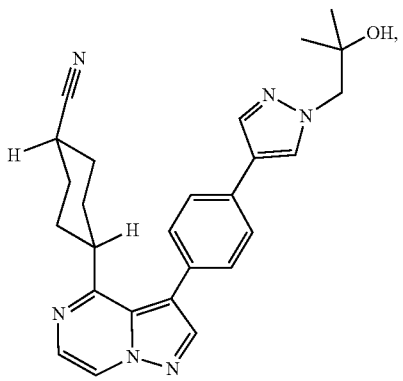 [SMILES: CC(C)(O)Cn1cc(-c2ccc(-c3cnn4ccnc(C5CCC(C#N)CC5)c34)cc2)cn1]

or a pharmaceutically acceptable salt thereof.

31. The compound of claim 1, wherein the compound is:

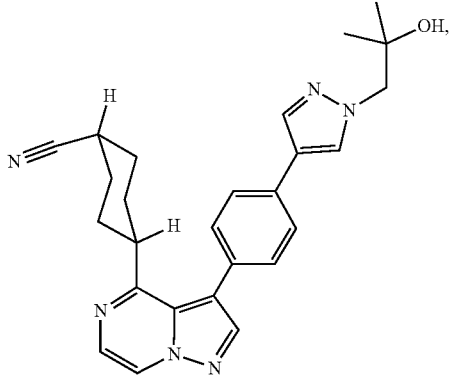 [SMILES: CC(C)(O)Cn1cc(-c2ccc(-c3cnn4ccnc(C5CCC(C#N)CC5)c34)cc2)cn1]

or a pharmaceutically acceptable salt thereof.

32. The compound of claim 1, wherein the compound is:

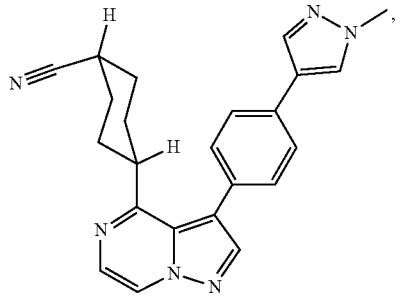 [SMILES: Cn1cc(-c2ccc(-c3cnn4ccnc(C5CCC(C#N)CC5)c34)cc2)cn1]

or a pharmaceutically acceptable salt thereof.

33. The compound of claim 1, wherein the compound is:

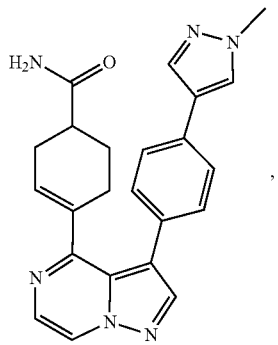 [SMILES: Cn1cc(-c2ccc(-c3cnn4ccnc(C5=CCC(C(N)=O)CC5)c34)cc2)cn1]

or a pharmaceutically acceptable salt thereof.

34. The compound of claim 1, wherein the compound is:

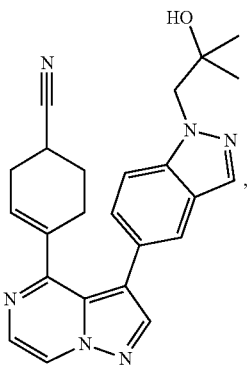 [SMILES: CC(C)(O)Cn1ncc2cc(-c3cnn4ccnc(C5=CCC(C#N)CC5)c34)ccc21]

or a pharmaceutically acceptable salt thereof.

35. The compound of claim 1, wherein the compound is:

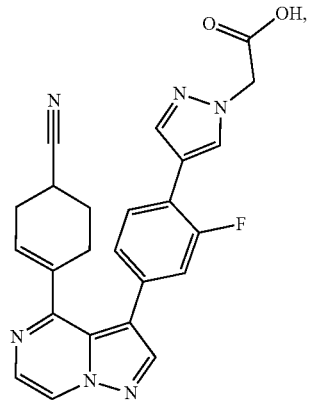 [SMILES: N#CC1CC=C(c2nccn3ncc(-c4ccc(-c5cnn(CC(=O)O)c5)c(F)c4)c23)CC1]

or a pharmaceutically acceptable salt thereof.

36. The compound of claim 1, wherein the compound is:

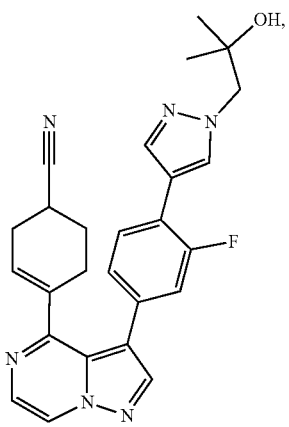 [SMILES: CC(C)(O)Cn1cc(-c2ccc(-c3cnn4ccnc(C5=CCC(C#N)CC5)c34)cc2F)cn1]

or a pharmaceutically acceptable salt thereof.

37. The compound of claim 1, wherein the compound is:

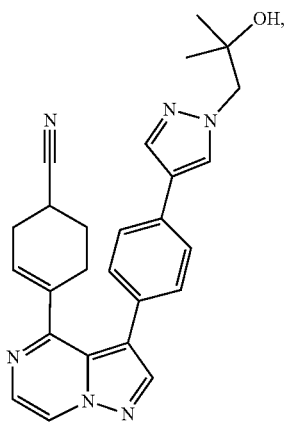 [SMILES: CC(C)(O)Cn1cc(-c2ccc(-c3cnn4ccnc(C5=CCC(C#N)CC5)c34)cc2)cn1]

or a pharmaceutically acceptable salt thereof.

38. The compound according to claim 1, wherein:
$R^4$ is:

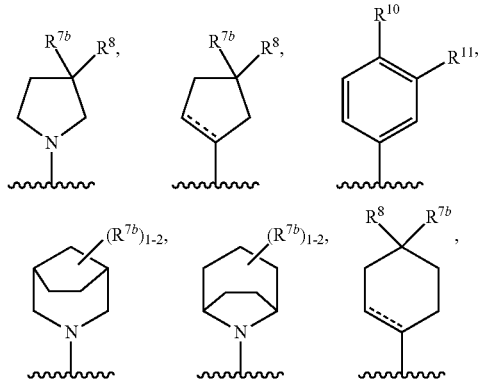

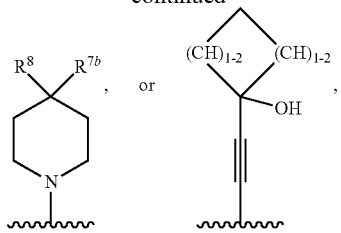

------ is a single or double bond;

$R^6$ is H, —$C_1$-$C_4$ alkyl, —$C_1$-$C_4$haloalkyl, or —$C_3$-$C_6$cycloalkyl;

each $R^{7b}$ is independently H, —$C_1$-$C_4$ alkyl, fluoro, chloro, CN, hydroxyl, —$C_1$-$C_3$ haloalkyl, or —$C_1$-$C_3$ cyanoalkyl;

$R^8$ is CN, —$(CH_2)_{0-1}$—C(O)—N(H)—$R^6$, —$(CH_2)_{0-1}$C(O)OR$^6$, or

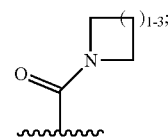

or $R^{7b}$ and $R^8$ join together, with the carbon to which they are attached, to form a 5-6 membered heterocycloalkyl, wherein the 5-6 membered heterocycloalkyl is substituted with one or two oxo groups, and further optionally substituted with 1-2 —$C_1$-$C_6$ alkyl groups, wherein the 5-6 membered heterocycloalkyl is optionally fused to phenyl when the 5-6 membered heterocycloalkyl is a six membered ring and substituted with one oxo group;

$R^{10}$ is —S(O)$_2$—N(H)—$C_1$-$C_5$ alkyl, —O-phenyl, —(CH$_2$)$_2$-piperidine, or CN;

$R^{11}$ is H or 5-6 membered heterocycloalkyl; and $R^3$ is:

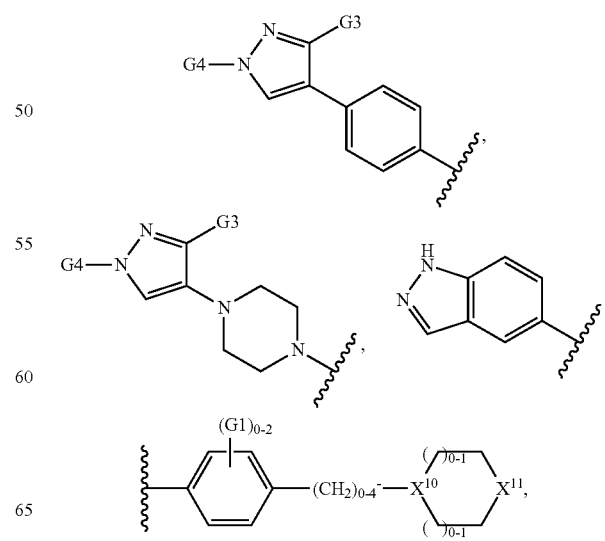

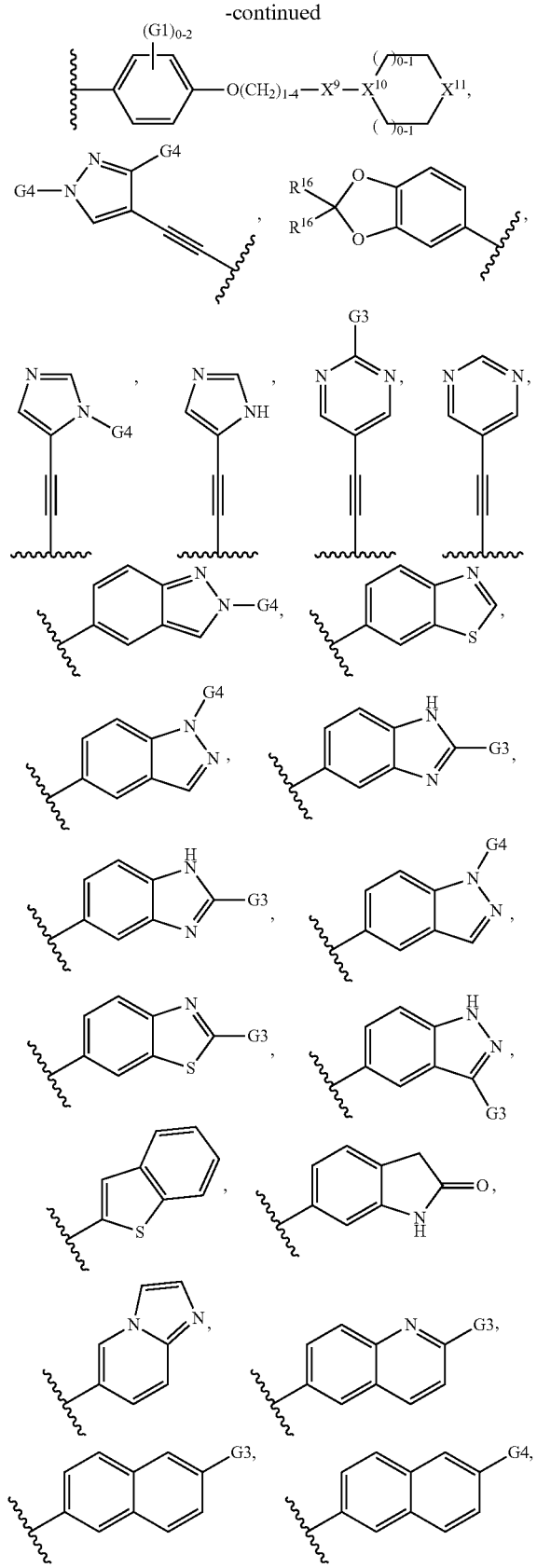
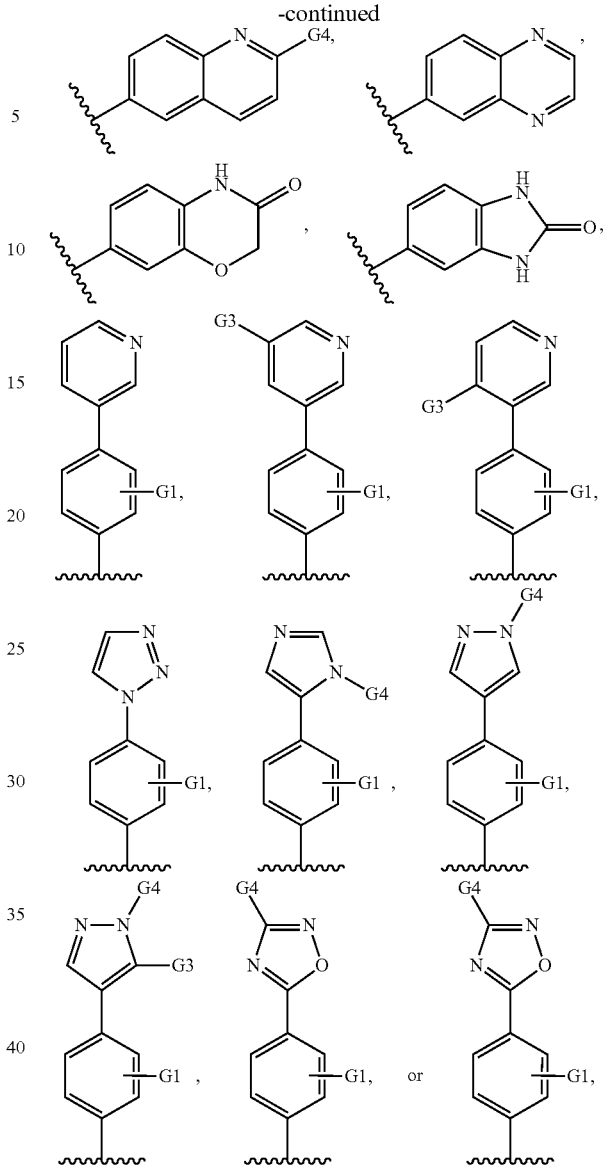

wherein:
G1 is H, —CH₃, or F;
G3 is —CH₃, —CH₂F, —CHF₂, —CF₃, —OCH₃, —CH₂—CH₂F, —(CH₂)₂—CN, —(CH₂)₃—CN, —(CH₂)₁₋₂C(CH₃)₂—CN, or —(CH₂)₁₋₂C(CH₃)₂—OH;
G4 is —CH₃, —CH₂F, —CHF₂, —CF₃, —CH₂—CH₂F, —CH₂—CH₃, —CH₂—CHF₂, —CH₂—CF₃, —CH₂—CH₂—CH₂F, —(CH₂)₁₂C(CH₃)₂—OH—, C₁-C₄ alkylene-cyclopropyl, —C₁-C₄ alkylene-cyclopropylene-CN, —C₁-C₄ alkylene-cyclopropylene-OH, —C₁-C₅ alkylene-CN, or —(CH₂)₁₋₃N(CH₃)₂;
each R¹⁶ is H, halogen, or —C₁-C₄alkyl optionally substituted with halogen;
X⁹ is a bond or O;
X¹⁰ is CH, —C(CH₃)—, N; and
X¹ is CH₂, NH, O, S, S(O), or S(O)₂.

* * * * *